(12) United States Patent
Backer et al.

(10) Patent No.: US 7,169,777 B2
(45) Date of Patent: Jan. 30, 2007

(54) MELANOCORTIN RECEPTOR AGONISTS

(75) Inventors: Ryan Thomas Backer, Indianapolis, IN (US); Karin Briner, Indianapolis, IN (US); Ivan Collado Caño, Madrid (ES); Oscar De Frutos Garcia, Madrid (ES); Christopher William Doecke, Indianapolis, IN (US); Matthew Joseph Fisher, Mooresville, IN (US); Cristina Garcia-Paredes, Madrid (ES); Steven Lee Kuklish, Fishers, IN (US); Vincent Mancuso, Thy-Le Chateau (BE); Michael John Martinelli, Zionsville, IN (US); Ana Isabel Mateo Herranz, Madrid (ES); Jeffrey Thomas Mullaney, Indianapolis, IN (US); Paul Leslie Ornstein, Carmel, IN (US); Zhipei Wu, Noblesville, IN (US); Chaoyu Xie, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 315 days.

(21) Appl. No.: 10/466,250

(22) PCT Filed: Jan. 23, 2002

(86) PCT No.: PCT/US02/00518

§ 371 (c)(1),
(2), (4) Date: Jul. 11, 2003

(87) PCT Pub. No.: WO02/059095

PCT Pub. Date: Aug. 1, 2002

(65) Prior Publication Data

US 2004/0116699 A1 Jun. 17, 2004

Related U.S. Application Data

(60) Provisional application No. 60/263,380, filed on Jan. 23, 2001.

(51) Int. Cl.
| | | |
|---|---|---|
| *A61K 31/496* | (2006.01) | |
| *A61K 31/5377* | (2006.01) | |
| *C07D 401/12* | (2006.01) | |
| *C07D 401/14* | (2006.01) | |
| *C07D 403/12* | (2006.01) | |
| *C07D 403/14* | (2006.01) | |
| *C07D 413/14* | (2006.01) | |
| *A61K 31/551* | (2006.01) | |

(52) U.S. Cl. .......................... 514/233.5; 514/253.05; 514/254.09; 514/218; 544/121; 544/363; 544/373; 540/575

(58) Field of Classification Search ................ 544/121, 544/363, 373; 514/233.5, 253.05, 254.09
See application file for complete search history.

(56) References Cited

U.S. PATENT DOCUMENTS 6,294,534 B1  9/2001  Nargund et al. ......... 514/233.5

FOREIGN PATENT DOCUMENTS

| WO | WO 94 13696 A1 | 6/1994 |
|---|---|---|
| WO | WO 99 55679 A1 | 11/1999 |
| WO | WO 99 64002 A1 | 12/1999 |
| WO | WO 00 74679 A1 | 12/2000 |
| WO | WO 01 70337 A1 | 9/2001 |
| WO | WO 01 70708 A1 | 9/2001 |
| WO | WO 02 15909 A1 | 2/2002 |
| WO | WO 02 059107 A1 | 8/2002 |
| WO | WO 02 059108 A1 | 8/2002 |
| WO | WO 02 059117 A1 | 8/2002 |
| WO | WO 02 070511 A1 | 9/2002 |

OTHER PUBLICATIONS

Sebhat et al. Annual Reports in Medicinal Chemistry, vol. 38, p. 31-40 (2003).*
Campfield et al. Science, vol. 280, p. 1383-1387 (1998).*

* cited by examiner

*Primary Examiner*—Emily Bernhardt
(74) *Attorney, Agent, or Firm*—Soonhee Jang; James B. Myers

(57) ABSTRACT

The present invention relates to melanocortin receptor agonist of the formula I useful in the treatment of obesity, diabetes, and male and/or female sexual dysfunction

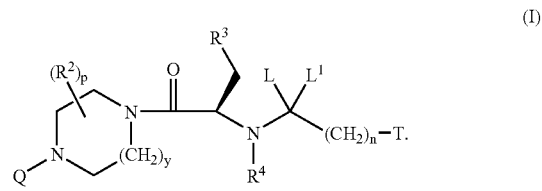

(I)

32 Claims, No Drawings

MELANOCORTIN RECEPTOR AGONISTS

REFERENCE TO RELATED APPLICATION

This is the national stage application, under 35 USC 371, for PCT/US02/00518, filed Jan. 23, 2002, which claims the benefit of U.S. Provisional Application Ser. No. 60/263,380, filed Jan. 23, 2001.

The present invention relates to melanocortin receptor agonists, and as such is useful in the treatment of disorders responsive to the activation of melanocortin receptors, such as obesity, diabetes, and male and/or female sexual dysfunction.

Pro-opiomelanocortin (POMC) derived peptides are known to affect food intake. Several lines of evidence support the notion that the G-protein coupled receptors (GPCRs) of the melanocortin receptor (MC-R) family, several of which are expressed in the brain, are targets of POMC derived peptides involved in the control of food intake and metabolism.

Evidence for the involvement of MC-R in obesity includes: i) the agouti ($A^{vy}$) mouse which ectopically expresses an antagonist of the MC-1R, -3R and -4R is obese, indicating that blocking the action of these three MC-Rs can lead to hyperphagia and metabolic disorders; ii) MC-4R knockout mice (Huszar et al., Cell, 88:131–141, 1997) recapitulate the phenotype of the agouti mouse and these mice are obese; iii) the cyclic heptapeptide MC-1R, -3R, -4R, and -5R agonist melanotanin-II (MT-II) injected intracerebroventricularly (ICV) in rodents, reduces food intake in several animal feeding models (NPY, ob/ob, agouti, fasted) while ICV injected SHU-9119 (MC-3R, -4R antagonist; MC-1R and -5R agonist) reverses this effect and can induce hyperphagia; iv) chronic intraperitoneal treatment of Zucker fatty rats with an α-NDP-MSH derivative (HP228) has been reported to activate MC-1R, -3R, -4R and 5R and to attenuate food intake and body weight gain over a 12 week period.

Five MC-Rs have thus far been identified, and these are expressed in different tissues. MC-1R was initially characterized by dominant gain of function mutations at the extension locus, affecting coat-color by controlling phaeomelanin to eumelanin conversion through control of tyrosinase. MC-1R is mainly expressed in melanocytes. MC-2R is expressed in the adrenal gland and represents the ACTH receptor. MC-3R is expressed in the brain, gut and placenta and may be involved in the control of food intake and thermogenesis. MC-4R is uniquely expressed in the brain and its inactivation was shown to cause obesity. MC-5R is expressed in many tissues including white fat, placenta and exocrine glands. A low level of expression is also observed in the brain. MC-5R knock out mice reveal reduced sebaceous gland lipid production (Chen et al., Cell, 91:789–798, 1997).

Evidence for the involvement of MC-R in male and/or female sexual disfunction is detailed in WO 00/74670.

Melanocortin receptor agonist compounds were disclosed in WO 99/64002.

The present invention relates to compound of formula I:

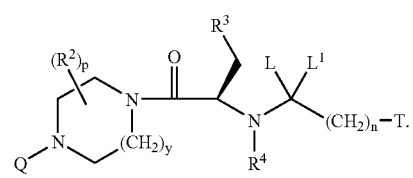

(I)

or a pharmaceutically acceptable salt, solvate or stereoisomer thereof, wherein

L and $L^1$ are both hydrogen, or combine together to form an oxo group;

$R^2$ is:
  Hydrogen, $C_1$–$C_8$ alkyl, $CONHC_1$–$C_4$ alkyl, (D)phenyl, oxo, or (D) $C_3$–$C_7$ cycloalkyl, provided that when $R^2$ is oxo, $R^2$ is on one of the ring carbon atoms adjacent to Q bearing nitrogen atom;

$R^3$ is: phenyl, aryl or thienyl;

wherein phenyl, aryl and thienyl are optionally substituted with one to three substituents independently selected from the group consisting of:
  cyano, perfluoroalkoxy, halo, $C_1$–$C_8$ alkyl, (D)$C_3$–$C_7$ cycloalkyl, $C_1$–$C_4$ alkoxy, $C_1$–$C_4$ haloalkyl;

$R^4$ is hydrogen, $C_1$–$C_8$ alkyl, $C_3$–$C_8$ alkenyl, $C(O)C_1$–$C_8$ alkyl, or (D)phenyl;

Q is: —$C(R^{a1})(R^{a2})(R^{a3})$
  Wherein $R^{a1}$ is $C_1$–$C_8$ alkyl, $C_1$–$C_8$ alkenyl, $C_1$–$C_8$ alkynyl, $C_3$–$C_8$ alkoxy, (D)$C_3$–$C_7$ cycloalkyl, heterocyclic, alkylheterocyclic, (D)phenyl, aryl, 5 to 7 member benzofused bicyclic ring, or heteroaryl, and wherein $C_1$–$C_8$ alkyl, $C_1$–$C_8$ alkenyl, $C_1$–$C_8$ alkynyl, (D)$C_3$–$C_7$ cycloalkyl, heterocyclic, alkylheterocyclic, phenyl, aryl, 5- or 7-membered benzofused bicyclic ring, and heteroaryl, are each optionally substituted with one to five substituents independently selected from R;

R is:
  hydroxy,
  halo,
  $C_1$–$C_8$ alkyl,
  $C_2$–$C_8$ alkenyl,
  $C_1$–$C_8$ alkoxy,
  $C_1$–$C_4$ haloalkyl,
  (D)$C_3$–$C_7$ cycloalkyl,
  (D)aryl,
  (D)heteroaryl;
  (D)$C(O)C_1$–$C_4$ alkyl,
  (D)$C(O)OC_1$–$C_4$ alkyl,
  (D)$C(O)$heteroaryl,
  $(CH_2)_m N(R^8)_2$,
  $(CH_2)_m NR^8 C(O)C_1$–$C_4$ alkyl,
  $(CH_2)_m NR^8 SO_2(C_1$–$C_4$ alkyl),
  (D)$OC_1$–$C_4$ alkyl,
  (D)$OC(O)C_1$–$C_4$ alkyl,
  (D)heterocyclic,
  (D)$SC_1$–$C_4$ alkyl, or
  (D)$SO_2N(R^8)_2$;

wherein $C_1$–$C_8$ alkyl, $C_1$–$C_8$ alkoxy, $C_3$–$C_7$ cycloalkyl, phenyl, aryl, heterocyclic, and heteroaryl are optionally substituted with one to five substituents independently selected from R⁸; and provided that when R is halo or hydroxy it is not substituted on a carbon adjacent to a heteroatom;

$R^{a2}$ is
  $C_1$–$C_8$ alkyl,
  $C_2$–$C_8$ alkenyl,
  C2–C8 alkynyl,
  (D)$C_3$–$C_7$ cycloalkyl,
  phenyl,
  aryl,
  $(CH_2)_m N(R^8)_2$,
  $(CH_2)_m NR^8 C(O)C_1$–$C_4$ alkyl,
  $(CH_2)_m NR^8 C(O)O$ $C_1$–$C_4$ alkyl,
  $(CH_2)_m NR^8 SO_2(C_1$–$C_4$ alkyl),
  $(CH_2)_m OC_1$–$C_4$ alkyl,
  $(CH_2)_m OC(O)C_1$–$C_4$ alkyl,
  $CON(R^8)_2$,
  wherein for the group or subgroup —$N(R^8)_2$, each $R^8$ may combine with the other to form a 5, 6, or 7-membered saturated or unsaturated, optionally substituted nitrogen containing heterocycle;

$R^{a3}$ is selected from the group consisting of hydrogen, methyl, ethyl and propyl;

each $R^8$ is independently:
  hydrogen,
  oxo,
  $C_1$–$C_8$ alkyl,
  $C_2$–$C_8$ alkenyl,
  (D)$C_3$–$C_7$ cycloalkyl,
  phenyl,
  aryl or
  heteroaryl,
  wherein $C_1$–$C_8$ alkyl, $C_1$–$C_8$ alkenyl, $C_3$–$C_7$ cycloalkyl, phenyl, aryl and heteroaryl are optionally substituted with one to three substituents selected from the group consisting of $C_1$–$C_8$ alkyl, halo, and hydroxy; provided that the halo and hydroxy groups are not substituted on a carbon adjacent to a heteroatom;

T is:

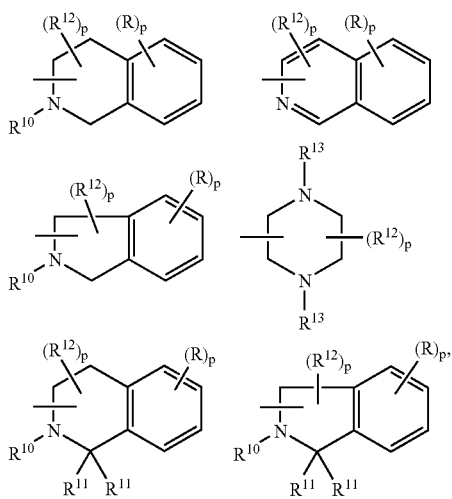

$R^{10}$ is hydrogen, $(C_1$–$C_8)$alkyl, $C_3$–$C_8$ alkenyl, $C(O)C_1$–$C_8$ alkyl, $C_2$–$C_8$ alkynyl, phenyl, aryl, or heteroaryl;

$R^{11}$ is independently hydrogen, $(C_1$–$C_8)$alkyl, or (D)phenyl, or aryl;

$R^{12}$ is independently:
  $C_1$–$C_8$ alkyl,
  phenyl,
  aryl,
  heteroaryl,
  $(CH_2)_n N(R^8)_2$,
  $(CH_2)_n NR^8 C(O)C_1$–$C_4$ alkyl,
  $(CH_2)_n NR^8 C(O)OC_1$–$C_4$ alkyl,
  $(CH_2)_n[O]_q(CH_2)_n N(R^8)_2$,
  $(CH_2)_n[O]_q(CH_2)_n NR^8 C(O)C_1$–$C_4$ alkyl,
  $(CH_2)_n[O]_q(CH_2)_n NR^8 SO_2(C_1$–$C_4$ alkyl),
  $(CH_2)_n[O]_q$-heterocyclic,
  $(CH_2)_n[O]_q(C_1$–$C_8)$alkyl-heterocyclic; and wherein for $R^{12}$ n is 2–8;

$R^{13}$ is independently:
  hydrogen,
  $C_1$–$C_8$ alkyl,
  (D)$C_3$–$C_7$ cycloalkyl,
  (D)phenyl,
  $C(O)C_1$–$C_8$ alkyl,
  $SO_2 C_1$–$C_8$ alkyl, or
  $SO_2$-phenyl;

D is a bond or $C_1$–$C_4$ alkyl;
y is 1 or 2;
m is 1–4;
n is 0–8;
p is 0–4; and
q is 0–1, and wherein,
  aryl is defined as benzylic or naphthyl;
  heteroaryl is defined as a monocyclic or bicyclic aromatic ring of 5 to 10 carbon atoms containing from one to three heteroatoms selected from O, N, or S; and
  heterocyclic is defined as a monocyclic, bicyclic, or tricyclic ring of 5 to 14 carbon atoms which can be aromatic or nonaromatic and containing from one to three heteroatoms selected from N, O, or S.

The present invention also relates to a compound of formula II:

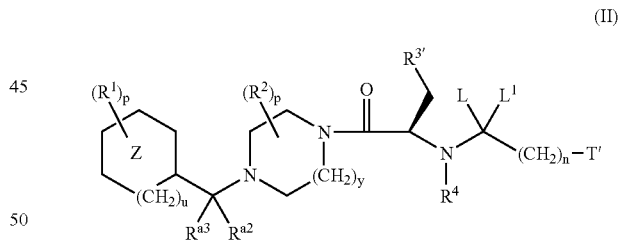

(II)

or a pharmaceutically acceptable salt, solvate or stereoisomer thereof, wherein

L and $L^1$ are both hydrogen, or combine together to form an oxo group;

$R^1$ is selected from the group consisting of:
  Hydrogen,
  Halo,
  $C_1$–$C_8$ alkyl,
  $C_1$–$C_4$ haloalkyl
  $C_2$–$C_8$ alkenyl,
  C2–C8 alkynyl,
  (D)$C_3$–$C_7$ cycloalkyl,
  phenyl,
  aryl, (D)N(R$^8$)$_2$,
(D)NR$^8$C(O)C$_1$–C$_4$ alkyl,
(D)NR$^8$C(O)OC$_1$–C$_4$ alkyl,
(D)OC$_1$–C$_4$ alkyl,
wherein for the group or subgroup —N(R$^8$)$_2$, each R$^8$ may combine with the other to form a 5, 6, or 7-membered saturated or unsaturated, optionally substituted nitrogen containing heterocycle;

R$^2$ is:
Hydrogen, C$_1$–C$_8$ alkyl, CONHC$_1$–C$_4$ alkyl, (D)phenyl, oxo, or (D)C$_3$–C$_7$ cycloalkyl, provided that when R$^2$ is oxo, R$^2$ is on one of the ring carbon atoms adjacent to the nitrogen atom bearing the group CR$^{a2}$;

R$^{3'}$ is: phenyl, aryl; wherein phenyl, and aryl are each optionally substituted with one to three substituents independently selected from the group consisting of: cyano, halo, C$_1$–C$_8$ alkyl, (D)C$_3$–C$_7$ cycloalkyl, C$_1$–C$_4$ alkoxy, C$_1$–C$_4$ haloalkyl and perfluoroalkoxy;

R$^4$ is hydrogen, C$_1$–C$_8$ alkyl, C$_3$–C$_8$ alkenyl, or (D)phenyl;

R$^{a2}$ is:
C$_1$–C$_8$ alkyl,
C$_2$–C$_8$ alkenyl,
C2–C8 alkynyl,
(D)C$_3$–C$_7$ cycloalkyl,
phenyl,
aryl,
(CH$_2$)$_m$N(R$^8$)$_2$,
(CH$_2$)$_m$NR$^8$C(O)C$_1$–C$_4$ alkyl,
(CH$_2$)$_m$NR$^8$C(O)OC$_1$–C$_4$ alkyl,
(CH$_2$)$_m$NR$^8$SO$_2$(C$_1$–C$_4$ alkyl),
(CH$_2$)$_m$OC$_1$–C$_4$ alkyl,
(CH$_2$)$_m$OC(O)C$_1$–C$_4$ alkyl,
CON(R$^8$)$_2$,
wherein for the group or subgroup —N(R$^8$)$_2$, each R$^8$ may combine with the other to form a 4, 5, 6, or 7-membered saturated or unsaturated, optionally substituted nitrogen containing heterocycle;

R$^{a3}$ is selected from the group consisting of hydrogen, methyl, ethyl and propyl;

T' is:

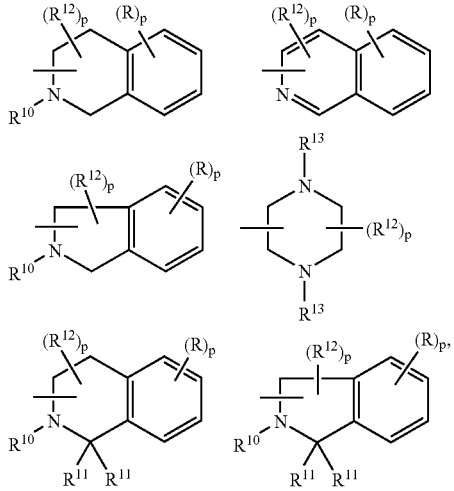

R is:
hydroxy,
halo,
C$_1$–C$_8$ alkyl,
C$_2$–C$_8$ alkenyl,
C$_1$–C$_8$ alkoxy,
C$_1$–C$_4$ haloalkyl,
(D)C$_3$–C$_7$ cycloalkyl,
(D)aryl,
(D)heteroaryl;
(D)C(O)C$_1$–C$_4$ alkyl,
(D)C(O)OC$_1$–C$_4$ alkyl,
(D)C(O) heteroaryl,
(CH$_2$)$_m$N(R$^8$)$_2$,
(CH$_2$)$_m$NR$^8$C(O)C$_1$–C$_4$ alkyl,
(CH$_2$)$_m$NR$^8$SO$_2$(C$_1$–C$_4$ alkyl),
(D)OC$_1$–C$_4$ alkyl,
(D)OC(O)C$_1$–C$_4$ alkyl,
(D)heterocyclic,
(D)SC$_1$–C$_4$ alkyl, or
(D)SO$_2$N (R$^8$)$_2$;

wherein C$_1$–C$_8$ alkyl, C$_1$–C$_8$ alkoxy, C$_3$–C$_7$ cycloalkyl, phenyl, aryl, heterocyclic, and heteroaryl are optionally substituted with one to five substituents independently selected from R$^8$; and provided that when R is halo or hydroxy it is not substituted on a carbon adjacent to a heteroatom;

each R$^8$ is independently:
hydrogen,
oxo,
C$_1$–C$_8$ alkyl,
C$_2$–C$_8$ alkenyl,
(D)C$_3$–C$_7$ cycloalkyl,
phenyl,
aryl or
heteroaryl, wherein C$_1$–C$_8$ alkyl, C$_1$–C$_8$ alkenyl, C$_3$–C$_7$ cycloalkyl, phenyl, aryl and heteroaryl are optionally substituted with one to three substituents selected from the group consisting of C$_1$–C$_8$ alkyl, halo, and hydroxy; provided that the halo and hydroxy groups are not substituted on a carbon adjacent to a heteroatom;

R$^{10}$ is hydrogen, (C$_1$–C$_8$)alkyl, C$_3$–C$_8$ alkenyl, C$_2$–C$_8$ alkynyl, phenyl, aryl, or heteroaryl;

R$^{11}$ is independently hydrogen, (C$_1$–C$_8$)alkyl, or phenyl, aryl;

R$^{12}$ is independently:
C$_3$–C$_8$ alkyl,
phenyl,
aryl,
heteroaryl,
(CH$_2$)$_n$N(R$^8$)$_2$,
(CH$_2$)$_n$NR$^8$C(O)C$_1$–C$_4$ alkyl,
(CH$_2$)$_n$NR$^8$C(O)OC$_1$–C$_4$ alkyl,
(CH$_2$)$_n$[O]$_q$(CH$_2$)$_n$N(R$^8$)$_2$,
(CH$_2$)$_n$[O]$_q$(CH$_2$)$_n$NR$^8$C(O)C$_1$–C$_4$ alkyl,
(CH$_2$)$_n$[O]$_q$(CH$_2$)$_n$NR$^8$SO$_2$(C$_1$–C$_4$ alkyl),
(CH$_2$)$_n$[O]$_q$-heterocyclic,
(CH$_2$)$_n$[O]$_q$(C$_1$–C$_8$)alkyl-heterocyclic; and wherein for R$^{12}$
n is 2–8;

R$^{13}$ is independently:
hydrogen,
C$_1$–C$_8$ alkyl,
(D)C$_3$–C$_7$ cycloalkyl,
(D)phenyl,
C(O)C$_1$–C$_8$ alkyl,
SO$_2$C$_1$–C$_8$ alkyl, or
SO$_2$-phenyl;

D is a bond or C$_1$–C$_4$ alkyl;
y is 1 or 2;
u is 0, 1, or 2;

m is 1–4;
n is 0–8;
p is 0–4; and
q is 0–1; and wherein,
aryl is defined as benzyl or naphthyl;
heteroaryl is defined as a monocyclic or bicyclic aromatic ring of 5 to 10 carbon atoms containing from one to three heteroatoms selected from O, N, or S; and
heterocyclic is defined as a monocyclic, bicyclid, or tricyclic ring of 5 to 14 carbon atoms which can be aromatic or non-aromatic and containing from one to three heteroatoms selected from N, O or S.

Another aspect of the present invention relates to a method for treating obesity or diabetes mellitus in a patient which comprises administering to said patient an effective amount of a compound of formula I or II, or a pharmaceutical salt, solvate, enantiomer or prodrug thereof, wherein said compound is an agonist of the melanocortin-4 receptor.

Another aspect of the present invention relates to a method for treating male or female sexual dysfunction, including erectile dysfunction, which comprises administering to said male or female an effective amount of a compound of formula I or II, or a pharmaceutical salt thereof, wherein said compound is an agonist of the melanocortin-4 receptor.

In addition, the present invention relates to a compound of formula I or II for use in treating obesity or diabetes as well as a compound of formula I or II for use in male or female sexual dysfunction, including erectile dysfunction wherein said compound is an agonist of the melanocortin-4 receptor.

In addition, the present invention relates to a compound of formula I or II for use in treating obesity and/or diabetes in companion animals i.e. dogs, cats and the like wherein said compound is an agonist of the melanocortin-4 receptor.

Yet another aspect of the present invention relates to a pharmaceutical composition comprising a compound of formula I or II or a pharmaceutically acceptable salt thereof, and a pharmaceutical carrier.

The present invention also relates to the use of a compound of formula I:

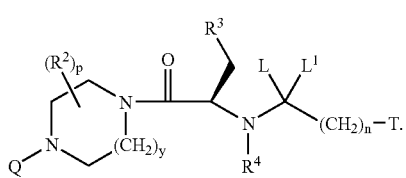

(I)

or a pharmaceutically acceptable salt, solvate or stereoisomer thereof, wherein
L and $L^1$ are both hydrogen, or combine together to form an oxo group;
$R^2$ is:
Hydrogen, $C_1$–$C_8$ alkyl, CONH$C_1$–$C_4$ alkyl, (D)phenyl, oxo, or (D)$C_3$–$C_7$ cycloalkyl, provided that when $R^2$ is oxo, $R^2$ is on one of the ring carbon atoms adjacent to Q bearing nitrogen atom;
$R^3$ is: phenyl, aryl or thienyl;

wherein phenyl, aryl and thienyl are optionally substituted with one to three substituents independently selected from the group consisting of:
cyano, perfluoroalkoxy, halo, $C_1$–$C_8$ alkyl, (D)$C_3$–$C_7$ cycloalkyl, $C_1$–$C_4$ alkoxy, $C_1$–$C_4$ haloalkyl;

$R^4$ is hydrogen, $C_1$–$C_8$ alkyl, $C_3$–$C_8$ alkenyl, C(O)$C_1$–$C_8$ alkyl, or (D)phenyl;
Q is: —C($R^{a1}$)($R^{a2}$)($R^{a3}$)
Wherein $R^{a1}$ is $C_1$–$C_8$ alkyl, $C_1$–$C_8$ alkenyl, $C_1$–$C_8$ alkynyl, $C_3$–$C_8$ alkoxy, (D)$C_3$–$C_7$ cycloalkyl, heterocyclic, alkylheterocyclic, (D)phenyl, aryl, 5 to 7 member benzofused bicyclic ring, or heteroaryl, and wherein $C_1$–$C_8$ alkyl, $C_1$–$C_8$ alkenyl, $C_1$–$C_8$ alkynyl, (D)$C_3$–$C_7$ cycloalkyl, heterocyclic, alkylheterocyclic, phenyl, aryl, 5- or 7-membered benzofused bicyclic ring, and heteroaryl, are each optionally substituted with one to five substituents independently selected from R;
R is:
hydroxy,
halo,
$C_1$–$C_8$ alkyl,
$C_2$–$C_8$ alkenyl,
$C_1$–$C_8$ alkoxy,
$C_1$–$C_4$ haloalkyl,
(D)$C_3$–$C_7$ cycloalkyl,
(D)aryl,
(D)heteroaryl;
(D)C(O)$C_1$–$C_4$ alkyl,
(D)C(O)O$C_1$–$C_4$ alkyl,
(D)C(O)heteroaryl,
(CH$_2$)$_m$N($R^8$)$_2$,
(CH$_2$)$_m$N$R^8$C(O)$C_1$–$C_4$ alkyl,
(CH$_2$)$_m$N$R^8$SO$_2$($C_1$–$C_4$ alkyl),
(D)O$C_1$–$C_4$ alkyl,
(D)OC(O)$C_1$–$C_4$ alkyl,
(D)heterocyclic,
(D)S$C_1$–$C_4$ alkyl, or
(D)SO$_2$N($R^8$)$_2$;
wherein $C_1$–$C_8$ alkyl, $C_1$–$C_8$ alkoxy, $C_3$–$C_7$ cycloalkyl, phenyl, aryl, heterocyclic, and heteroaryl are optionally substituted with one to five substituents independently selected from $R^8$; and provided that when R is halo or hydroxy it is not substituted on a carbon adjacent to a heteroatom;
$R^{a2}$ is
$C_1$–$C_8$ alkyl,
$C_2$–$C_8$ alkenyl,
$C_2$–$C_8$ alkynyl,
(D)$C_3$–$C_7$ cycloalkyl,
phenyl,
aryl,
(CH$_2$)$_m$N($R^8$)$_2$,
(CH$_2$)$_m$N$R^8$C(O)$C_1$–$C_4$ alkyl,
(CH$_2$)$_m$N$R^8$C(O)O$C_1$–$C_4$ alkyl,
(CH$_2$)$_m$N$R^8$SO$_2$($C_1$–$C_4$ alkyl),
(CH$_2$)$_m$O$C_1$–$C_4$ alkyl,
(CH$_2$)$_m$OC(O)$C_1$–$C_4$ alkyl,
CON($R^8$)$_2$,
wherein for the group or subgroup —N($R^8$)$_2$, each $R^8$ may combine with the other to form a 5, 6, or 7-membered saturated or unsaturated, optionally substituted nitrogen containing heterocycle;
$R^{a3}$ is selected from the group consisting of hydrogen, methyl, ethyl and propyl;
each $R^8$ is independently:
hydrogen,
oxo, $C_1$–$C_8$ alkyl,
$C_2$–$C_8$ alkenyl,
(D)$C_3$–$C_7$ cycloalkyl,
phenyl,
aryl or
heteroaryl,
wherein $C_1$–$C_8$ alkyl, $C_1$–$C_8$ alkenyl, $C_3$–$C_7$ cycloalkyl, phenyl, aryl and heteroaryl are optionally substituted with one to three substituents selected from the group consisting of $C_1$–$C_8$ alkyl, halo, and hydroxy; provided that the halo and hydroxy groups are not substituted on a carbon adjacent to a heteroatom;

T is:

[chemical structures depicting various ring systems with substituents $(R^{12})_p$, $(R)_p$, $R^{10}$, $R^{11}$, $R^{13}$]

$R^{10}$ is hydrogen, ($C_1$–$C_8$) alkyl, $C_3$–$C_8$ alkenyl, C(O)$C_1$–$C_8$ alkyl, $C_2$–$C_8$ alkynyl, phenyl, aryl, or heteroaryl;
$R^{11}$ is independently hydrogen, ($C_1$–$C_8$) alkyl, or (D)phenyl, or aryl;
$R^{12}$ is independently:
  $C_1$–$C_8$ alkyl,
  phenyl,
  aryl,
  heteroaryl,
  $(CH_2)_nN(R^8)_2$,
  $(CH_2)_nNR^8C(O)C_1$–$C_4$ alkyl,
  $(CH_2)_nNR^8C(O)OC_1$–$C_4$ alkyl,
  $(CH_2)_n[O]_q(CH_2)_nN(R^8)_2$,
  $(CH_2)_n[O]_q(CH_2)_nNR^8C(O)C_1$–$C_4$ alkyl,
  $(CH_2)_n[O]_q(CH_2)_nNR^8 SO_2(C_1$–$C_4$ alkyl),
  $(CH_2)_n[O]_q$-heterocyclic,
  $(CH_2)_n[O]_q(C_1$–$C_8)$alkyl-heterocyclic; and wherein for $R^{12}$
n is 2–8;
$R^{13}$ is independently:
hydrogen,
$C_1$–$C_8$ alkyl,
(D)$C_3$–$C_7$ cycloalkyl,
(D)phenyl,
C(O)$C_1$–$C_8$ alkyl,
$SO_2C_1$–$C_8$ alkyl, or
$SO_2$-phenyl;
D is a bond or $C_1$–$C_4$ alkyl;
y is 1 or 2;
m is 1–4;
n is 0–8;
p is 0–4; and
q is 0–1,
useful in the manufacture of a medicament for treating obesity and/or diabetes.

The present invention also provides a process for preparing a compound of formula I:

[chemical structure of formula (I) showing piperazine-containing compound with substituents $(R^2)_p$, $R^3$, $R^4$, Q, L, $L^1$, $(CH_2)_y$, $(CH_2)_n$–T]

(I)

or a pharmaceutically acceptable salts or stereoisomers thereof, wherein
—CLL'—$(CH_2)_n$—T is:

[chemical structure showing a bicyclic indoline-type structure with carbonyl, $NR^{10}$, $R^{11}$, $(R)_p$]

wherein $R^{10}$ is a CBz or Boc protecting group, hydrogen, ($C_1$–$C_8$)alkyl, $C_3$–$C_8$ alkenyl, C(O)$C_1$–$C_8$ alkyl, $C_2$–$C_8$ alkynyl, phenyl, aryl, or heteroaryl;
$R^2$ is:
  Hydrogen, $C_1$–$C_8$ alkyl, CONH$C_1$–$C_4$ alkyl, (D)phenyl, oxo, or (D)$C_3$–$C_7$ cycloalkyl, provided that when $R^2$ is oxo, $R^2$ is on one of the ring carbon atoms adjacent to Q bearing nitrogen atom;
$R^3$ is: phenyl, aryl or thienyl;
wherein phenyl, aryl and thienyl are optionally substituted with one to three substituents independently selected from the group consisting of:
  cyano, perfluoroalkoxy, halo, $C_1$–$C_8$ alkyl, (D)$C_3$–$C_7$ cycloalkyl, $C_1$–$C_4$ alkoxy, $C_1$–$C_4$ haloalkyl;
$R^4$ is hydrogen, $C_1$–$C_8$ alkyl, $C_3$–$C_8$ alkenyl, C(O)$C_3$–$C_8$ alkyl, or (D)phenyl;
Q is: —C($R^{a1}$)($R^{a2}$)($R^{a3}$)
  Wherein $R^{a1}$ is $C_1$–$C_8$ alkyl, $C_1$–$C_8$ alkenyl, $C_1$–$C_8$ alkynyl, $C_3$–$C_8$ alkoxy, (D)$C_3$–$C_7$ cycloalkyl, heterocyclic, alkylheterocyclic, (D)phenyl, aryl, 5 to 7 member benzofused bicyclic ring, or hetero6aryl, and wherein $C_1$–$C_8$ alkyl, $C_1$–$C_8$ alkenyl, $C_1$–$C_8$ alkynyl, (D)$C_3$–$C_7$ cycloalkyl, heterocyclic, alkylheterocyclic, phenyl, aryl, 5- or 7-membered benzofused bicyclic ring, and heteroaryl, are each optionally substituted with one to five substituents independently selected from R;
R is:
  hydroxy,
  halo,
  $C_1$–$C_8$ alkyl,
  $C_2$–$C_8$ alkenyl,
  $C_1$–$C_8$ alkoxy,
  $C_1$–$C_4$ haloalkyl,
  (D)$C_3$–$C_7$ cycloalkyl, (D)aryl,
(D)heteroaryl;
(D)C(O)C$_1$–C$_4$ alkyl,
(D)C(O)OC$_1$–C$_4$ alkyl,
(D)C(O)heteroaryl,
(CH$_2$)$_m$N(R$^8$)$_2$,
(CH$_2$)$_m$NR$^8$C(O)C$_1$–C$_4$ alkyl,
(CH$_2$)$_m$NR$^8$SO$_2$(C$_1$–C$_4$ alkyl),
(D)OC$_1$–C$_4$ alkyl,
(D)OC(O)C$_1$–C$_4$ alkyl,
(D)heterocyclic,
(D)SC$_1$–C$_4$ alkyl, or
(D)SO$_2$N(R$^8$)$_2$;
wherein C$_1$–C$_8$ alkyl, C$_1$–C$_8$ alkoxy, C$_3$–C$_7$ cycloalkyl, phenyl, aryl, heterocyclic, and heteroaryl are optionally substituted with one to five substituents independently selected from R$^8$; and provided that when R is halo or hydroxy it is not substituted on a carbon adjacent to a heteroatom;

R$^{a2}$ is
C$_1$–C$_8$ alkyl,
C$_2$–C$_8$ alkenyl,
C2–C8 alkynyl,
(D)C$_3$–C$_7$ cycloalkyl,
phenyl,
aryl,
(CH$_2$)$_m$N(R$^8$)$_2$,
(CH$_2$)$_m$NR$^8$C(O)C$_1$–C$_4$ alkyl,
(CH$_2$)$_m$NR$^8$C(O)OC$_1$–C$_4$ alkyl,
(CH$_2$)$_m$NR$^8$SO$_2$(C$_1$–C$_4$ alkyl),
(CH$_2$)$_m$OC$_1$–C$_4$ alkyl,
(CH$_2$)$_m$OC(O)C$_1$–C$_4$ alkyl,
CON(R$^8$)$_2$,
wherein for the group or subgroup —N(R$^8$)$_2$, each R$^8$ may combine with the other to form a 5, 6, or 7-membered saturated or unsaturated, optionally substituted nitrogen containing heterocycle;

R$^{a3}$ is selected from the group consisting of hydrogen, methyl, ethyl and propyl;

each R$^8$ is independently:
hydrogen,
oxo,
C$_1$–C$_8$ alkyl,
C$_2$–C$_8$ alkenyl,
(D)C$_3$–C$_7$ cycloalkyl,
phenyl,
aryl or
heteroaryl,
wherein C$_1$–C$_8$ alkyl, C$_1$–C$_8$ alkenyl, C$_3$–C$_7$ cycloalkyl, phenyl, aryl and heteroaryl are optionally substituted with one to three substituents selected from the group consisting of C$_1$–C$_8$ alkyl, halo, and hydroxy; provided that the halo and hydroxy groups are not substituted on a carbon adjacent to a heteroatom;

R$^{11}$ is independently hydrogen, (C$_1$–C$_8$)alkyl, or (D)phenyl, or aryl;

D is a bond or C$_1$–C$_4$ alkyl;
y is 1 or 2;
m is 1–4;
n is 0–8; and
p is 0–4;

comprising the steps of:
a) reacting a compound having a structural formula 1:

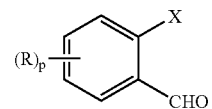

(1)

with CH$_2$CH=C(O)OR$^a$ wherein R$^a$ is hydrogen or C$_1$–C$_8$ alkyl and X is halo, in the presence of a catalyst and a base in a suitable organic solvent to give the compound of formula 2

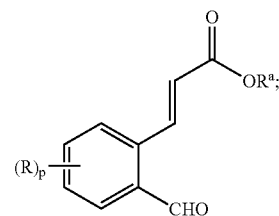

(2)

b) reductively aminating the compound of formula 2 in the presence of amine to give a compound of formula 3

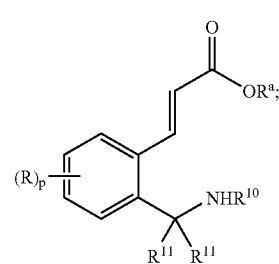

(3)

c) cyclizing the compound of formula 3 by Michael addition to give a compound of formula 4 or stereoisomers thereof

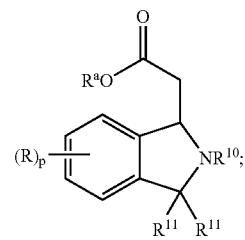

(4)

d) coupling the compound of formula 4 or stereoisomers thereof wherein R$^a$ is H, with a compound of formula 5

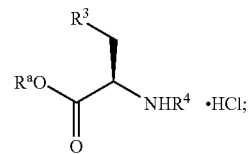

(5)

wherein $R^a$ is $C_1$–$C_8$ alkyl, to give a compound of formula 6

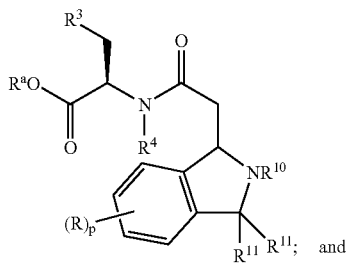

(6)

e) coupling the compound of formula 6 wherein $R^a$ is H, with a compound having a structural formula

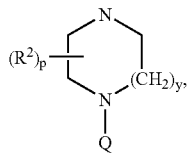

to afford the compound of formula 1.

The present invention also provides a process for preparing a compound of formula I:

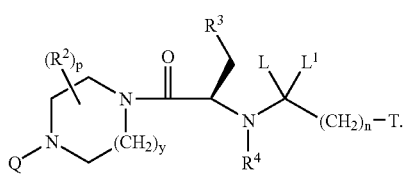

(I)

wherein —LL' $(CH_2)_n$—T is represented by the group:

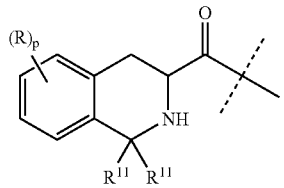

$R^2$ is:
Hydrogen, $C_1$–$C_8$ alkyl, CONH$C_1$–$C_4$ alkyl, (D)phenyl, oxo, or (D)$C_3$–$C_7$ cycloalkyl, provided that when $R^2$ is oxo, $R^2$ is on one of the ring carbon atoms adjacent to Q bearing nitrogen atom;

$R^3$ is: phenyl, aryl or thienyl;

wherein phenyl, aryl and thienyl are optionally substituted with one to three substituents independently selected from the group consisting of:
cyano, perfluoroalkoxy, halo, $C_1$–$C_8$ alkyl, (D)$C_3$–$C_7$ cycloalkyl, $C_1$–$C_4$ alkoxy, $C_1$–$C_4$ haloalkyl;

$R^4$ is hydrogen, $C_1$–$C_8$ alkyl, $C_3$–$C_8$ alkenyl, C(O)$C_1$–$C_8$ alkyl, or (D)phenyl;

Q is: —C($R^{a1}$)($R^{a2}$)($R^{a3}$)

Wherein $R^{a1}$ is $C_1$–$C_8$ alkyl, $C_1$–$C_8$ alkenyl, $C_1$–$C_8$ alkynyl, $C_3$–$C_8$ alkoxy, (D)$C_3$–$C_7$ cycloalkyl, heterocyclic, alkylheterocyclic, (D)phenyl, aryl, 5 to 7 member benzofused bicyclic ring, or heteroaryl, and wherein $C_1$–$C_8$ alkyl, $C_1$–$C_8$ alkenyl, $C_1$–$C_8$ alkynyl, (D)$C_3$–$C_7$ cycloalkyl, heterocyclic, alkylheterocyclic, phenyl, aryl, 5- or 7-membered benzofused bicyclic ring, and heteroaryl, are each optionally substituted with one to five substituents independently selected from R;

R is:
hydroxy,
halo,
$C_1$–$C_8$ alkyl,
$C_2$–$C_8$ alkenyl,
$C_1$–$C_8$ alkoxy,
$C_1$–$C_4$ haloalkyl,
(D)$C_3$–$C_7$ cycloalkyl,
(D)aryl,
(D)heteroaryl;
(D)C(O)$C_1$–$C_4$ alkyl,
(D)C(O)O$C_1$–$C_4$ alkyl,
(D)C(O)heteroaryl,
$(CH_2)_m N(R^8)_2$,
$(CH_2)_m NR^8C(O)C_1$–$C_4$ alkyl,
$(CH_2)_m NR^8SO_2(C_1$–$C_4$ alkyl),
(D)O$C_1$–$C_4$ alkyl,
(D)OC(O)$C_1$–$C_4$ alkyl,
(D)heterocyclic,
(D)S$C_1$–$C_4$ alkyl, or
(D)SO$_2$N($R^8$)$_2$;
wherein $C_1$–$C_8$ alkyl, $C_1$–$C_8$ alkoxy, $C_3$–$C_7$ cycloalkyl, phenyl, aryl, heterocyclic, and heteroaryl are optionally substituted with one to five substituents independently selected from $R^8$; and provided that when R is halo or hydroxy it is not substituted on a carbon adjacent to a heteroatom;

$R^{a2}$ is
$C_1$–$C_8$ alkyl,
$C_2$–$C_8$ alkenyl,
C2–C8 alkynyl,
(D)$C_3$–$C_7$ cycloalkyl,
phenyl,
aryl,
$(CH_2)_m N(R^8)_2$,
$(CH_2)_m NR^8C(O)C_1$–$C_4$ alkyl,
$(CH_2)_m NR^8C(O)OC_1$–$C_4$ alkyl,
$(CH_2)_m NR^8SO_2(C_1$–$C_4$ alkyl),
$(CH_2)_m OC_1$–$C_4$ alkyl,
$(CH_2)_m OC(O)C_1$–$C_4$ alkyl,
CON($R^8$)$_2$,
wherein for the group or subgroup —N($R^8$)$_2$, each $R^8$ may combine with the other to form a 5, 6, or 7-membered saturated or unsaturated, optionally substituted nitrogen containing heterocycle;

$R^{a3}$ is selected from the group consisting of hydrogen, methyl, ethyl and propyl;

each $R^8$ is independently:
hydrogen,
oxo,
$C_1$–$C_8$ alkyl,
$C_2$–$C_8$ alkenyl,
(D)$C_3$–$C_7$ cycloalkyl,
phenyl,
aryl or
heteroaryl,
wherein $C_1$–$C_8$ alkyl, $C_1$–$C_8$ alkenyl, $C_3$–$C_7$ cycloalkyl, phenyl, aryl and heteroaryl are optionally substituted with one to three substituents selected from the group consisting of $C_1$–$C_8$ alkyl, halo, and hydroxy; provided that the halo and hydroxy groups are not substituted on a carbon adjacent to a heteroatom;

$R^{10}$ is hydrogen, $(C_1$–$C_8)$alkyl, $C_3$–$C_8$ alkenyl, $C(O)C_1$–$C_8$ alkyl, $C_2$–$C_8$ alkynyl, phenyl, aryl, or heteroaryl;

$R^{11}$ is independently hydrogen, $(C_1$–$C_8)$alkyl, or (D)phenyl, or aryl;

D is a bond or $C_1$–$C_4$ alkyl;

y is 1 or 2;

m is 1–4;

n is 0–8; and p is 0–4;

comprising the steps of:

a) esterifying a compound of formula 1 with an alcohol $R^aOH$

![Formula 1: HO-phenyl(R)p-CH2-CH(NH2)-CO2H]

1 to form a compound of formula 2:

![Formula 2: HO-phenyl(R)p-CH2-CH(NH2·HCl)-CO2Ra]

2 wherein $R^a$ is a group selected from $C_1$–$C_4$ alkyl, and (D) phenyl;

b) reacting a compound of formula 2 with $R^{11}COR^{11}$ to form a compound of formula ![Formula 3: HO-tetrahydroisoquinoline with CO2Ra, NH·HCl, R11, R11, (R)p]

3 wherein $R^{11}$ is independently hydrogen, $C_1$–$C_4$ alkyl;

c) reacting a compound of formula 3 with an activating group to form a compound of formula 4

![Formula 4: A-O-tetrahydroisoquinoline with CO2Ra, NH, R11, R11, (R)p]

4 wherein A is an activating group;

d) deoxygenating the compound of formula 4 by hydrogenation to afford a compound of formula 5

![Formula 5: tetrahydroisoquinoline with CO2Ra, NH·HA, R11, R11, (R)p]

5 e) optionally reacting the compound of formula 5 wherein HA is an acidic, with an inorganic base to form a compound of formula 6

![Formula 6: tetrahydroisoquinoline with CO2M, NH, R11, R11, (R)p]

6 wherein M is a univalent cation;

f) resolving the compound of formula 5 or the compound of formula 6 wherein M is hydrogen to afford a chiral compound of formula 7

![Formula 7: tetrahydroisoquinoline with CO2Ra', NH, R11, R11, (R)p, chiral center *]

7 wherein Ra' is H or $R^a$;

g) coupling the compound of formula 7 with a compound of formula 8

![Formula 8: HCl·R4NH-CH(CO2Ra)-CH2-R3]

8 to afford a compound of formula 9:

![Formula 9: tetrahydroisoquinoline-C(O)-N(R4)-CH(CO2Ra)-CH2-R3 with NH, R11, R11, (R)p]

9 h) coupling the compound of formula 9 with a compound of formula 10:

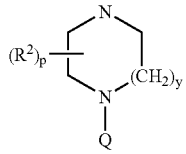

to afford a compound of formula I:

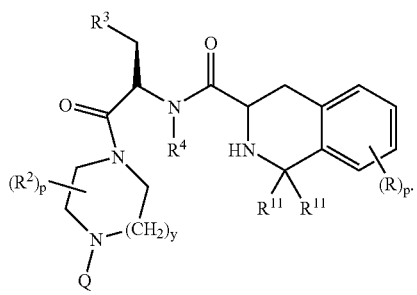

Throughout the instant application, the following terms have the indicated meanings:

The term "$C_1$–$C_8$ alkyl" refers to a straight or branched saturated hydrocarbon moiety containing from 1 to 8 carbon atoms. The term "$C_1$–$C_4$ alkyl" refers specifically to methyl, ethyl, n-propyl, isopropyl, n-butyl, isobutyl, sec-butyl and t-butyl. A "$C_1$–$C_8$ haloalkyl" is a $C_1$–$C_8$ alkyl moiety that is substituted with one or more halo atoms. One example of a haloalkyl group is trifluoromethyl. A "$C_1$–$C_8$ alkoxy" group or "$C_1$–$C_8$ alkoxy alkyl" group is a $C_1$–$C_8$ alkyl group attached through an oxygen linker.

The term "bezofused bicyclic" as used herein refers to a bicyclic ring system or radical wherein one of the rings is the benzene ring and wherein the point of attachment to the backbone of the compound the invention is at other than the benzene ring. Unless otherwise specified it is to be understood that each ring of the benzofused bicyclcic is optionally substituted with 1 to 3 substituents selected from alky, alkenyl, alkynyl, halo, haloalkyl, cyano, alkoxy, alkoxyalkyl, amino, substituted amino, thiol, formyl, carboxy alkyl, carboxyester, carbxamide, and sulfonamido groups.

The term "perfluoroalkoxy" as used herein refers to $C_1$–$C_4$ alkoxy groups having from 1 to 5 fluorine atoms, and includes for example, trifluoromethoxy, and pentafluoroethoxy.

The term "$C_3$–$C_7$ cycloalkyl" refers to cyclopropyl, cyclobutyl, cyclopentyl, cyclohexyl and cycloheptyl.

The term "hydrocarbon diradical" refers to a straight or branched chain of carbon atoms that may optionally be unsaturated at two or more carbons. Thus, a hydrocarbon diradical according to the present invention includes alkylene, alkenylene and alkylidene moieties. Examples include but are not intended to be limited to methylene, ethylene, propylene, butylene, —CH(CH$_3$)CH(CH$_3$)—, —CH$_2$C(CH$_3$)$_2$—, —CH$_2$CH(CH$_3$)CH$_2$—, —CH═CHCH$_2$—, —CH═CH—, —CH$_2$—C═CCH$_2$—, and the like.

The term "halo" refers to fluoro, chloro, bromo and iodo.

The term haloalkyl refers to a group having at least one carbon atom and as many halogen atoms as chemically sensible with or without hydrogen atoms, and positional isomers thereof. The term haloalkyl, therefore, includes but is not limited to groups such as trifluoromethytl, methylchloride, dichloromethyl, pentylchloride, butyl chloride, isopropyl chloride and the like.

As used herein a line "_____" attached to a structure, partial structure of a molecule or fragment thereof, without a group attached at the end represents a point of attachment to another molecule, fragment or radical unless otherwise indicated. For example, the group:

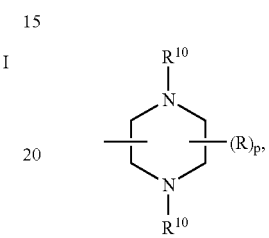

shows the piperazine groups as being attachable to another molecule or fragment at any position of the piperazine ring where the valency allows i.e. the carbon atoms.

Unless otherwise specified, a "heterocycle" or "heterocyclic" or "heterocyclyl" group is a 5, 6 or 7 membered saturated, or partially unsaturated, or aromatic mono-cyclic ring containing 1–5 heteroatoms selected from N, S or O, wherein said heterocycle is optionally substituted 1–4 times with: $C_1$–$C_8$ alkyl, $C_1$–$C_4$ haloalkyl, (D)($C_3$–$C_7$ cycloalkyl), (D)NR$^8$R$^8$, (D)NR$^8$C(O)C$_1$–$C_8$ alkyl, (D)NR$^8$SO$_2$($C_1$–$C_8$ alkyl), (D)SO($C_1$–$C_8$ alkyl), (CH$_2$)$_m$SO$_2$R$^8$, (CH$_2$)$_m$SO$^2$NR$^8$R$^8$ or (D)phenyl wherein:

R$^8$ is as described herein; or when two R$^8$ groups are attached to the same nitrogen atom, said R$^8$ groups, together with the nitrogen to which they are attached, may combine to form a nitrogen containing heterocycle.

The variable "D" at each occurrence is independently a bond or a $C_1$–$C_4$ hydrocarbon diradical.

Unless otherwise specified, a "nitrogen containing heterocycle" is a heterocycle that contains 1–4 nitrogen atoms and optionally contains 1 other heteroatom selected from O or S. Examples of nitrogen containing heterocylces includes but is not limited to 1,1-dioxo-1λ$^6$-isothiazolidin-2-yl, pyrrole, thiazole, oxazolyl, imidazolyl, imidazolidinyl, 1,2,3-oxadiazolyl, piperidynyl, poiperazinyl, pyrazinyl, pyrimidinyl, 1,3,5-triazinyl, morpholinyl, thiomorpholinyl, pyridazinyl, 1,3–4 thiadiazolyl, isothiazolyl, each optionally substituted with 1 to 3 substituents including for example halo, oxo, carboxy esters, carboxyamides, $C_1$–$C_8$ alkyl.

The term "oxo" as used herein refers to an oxygen atom formed by the combination of single bonds resulting in a double bond to oxygen. For example an "oxo" group formed by geminal substituents on a carbon atom depicts a carbonyl group ie., an oxo group bonded to carbon.

The term "composition", as in pharmaceutical composition, is intended to encompass a product comprising the active ingredient(s), and the inert ingredient(s) that make up the carrier. Accordingly, the pharmaceutical compositions of the present invention encompass any composition made by admixing a compound of the present invention and a pharmaceutically acceptable carrier.

The term "pharmaceutical" when used herein as an adjective means substantially non-deleterious to the recipient patient.

The term "unit dosage form" refers to physically discrete units suitable as unitary dosages for human subjects and other non-human animals, each unit containing a predetermined quantity of active material calculated to produce the desired therapeutic effect, in association with a suitable pharmaceutical carrier.

The terms "treating" and "treat", as used herein, include their generally accepted meanings, i.e., preventing, prohibiting, restraining, alleviating, ameliorating, slowing, stopping, or reversing the progression or severity of a pathological condition, or sequela thereof, described herein.

"Erectile dysfunction" is a disorder involving the failure of a male mammal to achieve erection, ejaculation, or both. Symptoms of erectile dysfunction include an inability to achieve or maintain an erection, ejaculatory failure, premature ejaculation, and inability to achieve an orgasm. An increase in erectile dysfunction is often associated with age and is generally caused by a physical disease or as a side effect of drug treatment.

"Female sexual dysfunction" encompasses, without limitation, conditions such as a lack of sexual desire and related arousal disorders, inhibited orgasm, lubrication difficulties, and vaginismus.

Because certain compounds of the invention contain an acidic moiety (e.g., carboxy), the compound of formula I may exist as a pharmaceutical base addition salt thereof. Such salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like.

Because certain compounds of the invention contain a basic moiety (e.g., amino), the compound of formula I can also exist as a pharmaceutical acid addition salt. Such salts include sulfate, pyrosulfate, bisulfate, sulfite, bisulfite, phosphate, mono-hydrogenphosphate, dihydrogenphosphate, metaphosphate, pyrophosphate, chloride, bromide, iodide, acetate, propionate, decanoate, caprylate, acrylate, formate, isobutyrate, heptanoate, propiolate, oxalate, malonate, succinate, suberate, sebacate, fumarate, maleate, 2-butyne-1,4 dioate, 3-hexyne-2, 5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, beta-hydroxybutyrate, glycollate, maleate, tartrate, methanesulfonate, propanesulfonate, naphthalene-1-sulfonate, naphthalene-2-sulfonate, mandelate and the like salts. Preferred acid addition salts include the hydrochloride.

It will be understood that, as used herein, references to the compounds of formula I or II are meant to also include the pharmaceutical salts.

Some of the compounds described herein may exist as tautomers such as keto-enol tautomers. The individual tautomers as well as mixtures thereof are encompassed within the scope of the present invention.

When describing various aspects of the present compounds, the terms "A domain", "B domain" and "C domain" are used below. This domain concept is illustrated below:

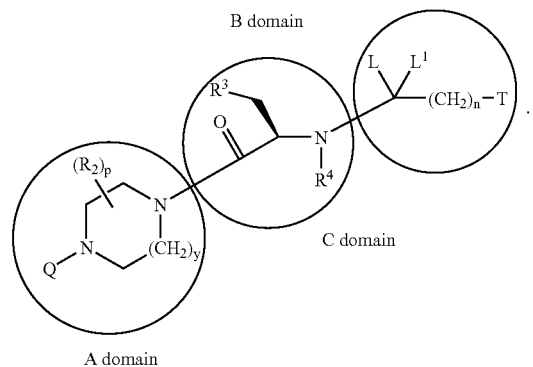

Utility

Compounds of formula I or II are effective as mnelanocortin receptor agonists, particularly as agonists of the human MC-4 receptor. As melanocortin receptor agonists, the compounds of formula I or II are useful in the treatment of diseases, disorders or conditions responsive to the activation of one or more of the melanocortin receptors including, but not limited to, MC-1, MC-2, MC-3, MC-4, or MC-5. Diseases, disorders or conditions receptive to treatment with a MC-4 agonist include those mentioned supra and those described in WO 00/74679, the teachings of which are herein incorporated by reference.

One embodiment of the invention, provides a novel process for preparing compounds of formula I:

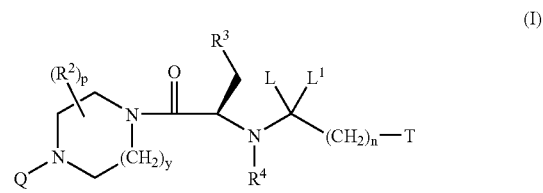

(I)

wherein —LL' $(CH_2)_n$—T represents the group:

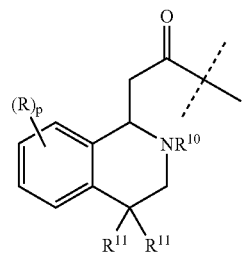

wherein $R^{10}$ is a CBz or Boc protecting group, hydrogen, $(C_1–C_8)$alkyl, $C_3–C_8$ alkenyl, $C(O)C_1–C_8$ alkyl, $C_2–C_8$ alkynyl, phenyl, aryl, or heteroaryl;

$R^2$ is:

Hydrogen, $C_1–C_8$ alkyl, $CONHC_1–C_4$ alkyl, (D)phenyl, oxo, or (D)$C_3–C_7$ cycloalkyl, provided that when $R^2$ is oxo, $R^2$ is on one of the ring carbon atoms adjacent to Q bearing nitrogen atom;

R³ is: phenyl, aryl or thienyl;

wherein phenyl, aryl and thienyl are optionally substituted with one to three substituents independently selected from the group consisting of:
cyano, perfluoroalkoxy, halo, $C_1-C_8$ alkyl, (D)$C_3-C_7$ cycloalkyl, $C_1-C_4$ alkoxy, $C_1-C_4$ haloalkyl;

R⁴ is hydrogen, $C_1-C_8$ alkyl, $C_3-C_8$ alkenyl, C(O)$C_1-C_8$ alkyl, or (D)phenyl;

Q is: —C(R^{a1})(R^{a2})(R^{a3})

Wherein R^{a1} is $C_1-C_8$ alkyl, $C_1-C_8$ alkenyl, $C_1-C_8$ alkynyl, $C_3-C_8$ alkoxy, (D)$C_3-C_7$ cycloalkyl, heterocyclic, alkylheterocyclic, (D)phenyl, aryl, 5 to 7 member benzofused bicyclic ring, or heteroaryl, and wherein $C_1-C_8$ alkyl, $C_1-C_8$ alkenyl, $C_1-C_8$ alkynyl, (D)$C_3-C_7$ cycloalkyl, heterocyclic, alkylheterocyclic, phenyl, aryl, 5- or 7-membered benzofused bicyclic ring, and heteroaryl, are each optionally substituted with one to five substituents independently selected from R;

R is:
hydroxy,
halo,
$C_1-C_8$ alkyl,
$C_2-C_8$ alkenyl,
$C_1-C_8$ alkoxy,
$C_1-C_4$ haloalkyl,
(D)$C_3-C_7$ cycloalkyl,
(D)aryl,
(D)heteroaryl;
(D)C(O)$C_1-C_4$ alkyl,
(D)C(O)O$C_1-C_4$ alkyl,
(D)C(O)heteroaryl,
$(CH_2)_m N(R^8)_2$,
$(CH_2)_m NR^8 C(O)C_1-C_4$ alkyl,
$(CH_2)_m N^8 SO_2(C_1-C_4$ alkyl),
(D)O$C_1-C_4$ alkyl,
(D)OC(O)$C_1-C_4$ alkyl,
(D)heterocyclic,
(D)S$C_1-C_4$ alkyl, or
(D)SO$_2$N(R^8)$_2$;
wherein $C_1-C_8$ alkyl, $C_1-C_8$ alkoxy, $C_3-C_7$ cycloalkyl, phenyl, aryl, heterocyclic, and heteroaryl are optionally substituted with one to five substituents independently selected from R⁸; and provided that when R is halo or hydroxy it is not substituted on a carbon adjacent to a heteroatom;

R^{a2} is
$C_1-C_8$ alkyl,
$C_2-C_8$ alkenyl,
C2–C8 alkynyl,
(D)$C_3-C_7$ cycloalkyl,
phenyl,
aryl,
$(CH_2)_m N(R^8)_2$,
$(CH_2)_m NR^8 C(O)C_1-C_4$ alkyl,
$(CH_2)_m NR^8 C(O)OC_1-C_4$ alkyl,
$(CH_2)_m NR^8 SO_2(C_1-C_4$ alkyl),
$(CH_2)_m OC_1-C_4$ alkyl,
$(CH_2)_m OC(O)C_1-C_4$ alkyl,
CON(R^8)$_2$,
wherein for the group or subgroup —N(R^8)$_2$, each R⁸ may combine with the other to form a 5, 6, or 7-membered saturated or unsaturated, optionally substituted nitrogen containing heterocycle;

R^{a3} is selected from the group consisting of hydrogen, methyl, ethyl and propyl;

each R⁸ is, independently:
hydrogen,
oxo,
$C_1-C_8$ alkyl,
$C_2-C_8$ alkenyl,
(D)$C_3-C_7$ cycloalkyl,
phenyl,
aryl or
heteroaryl,
wherein $C_1-C_8$ alkyl, $C_1-C_8$ alkenyl, $C_3-C_7$ cycloalkyl, phenyl, aryl and heteroaryl are optionally substituted with one to three substituents selected from the group consisting of $C_1-C_8$ alkyl, halo, and hydroxy; provided that the halo and hydroxy groups are not substituted on a carbon adjacent to a heteroatom;

R¹¹ is independently hydrogen, $(C_1-C_8)$alkyl, or (D)phenyl, or aryl;

D is a bond or $C_1-C_4$ alkyl;

y is 1 or 2;

m is 1–4;

n is 0–8; and p is 0–4; and comprising the steps of:

a) reacting a compound formula 1:

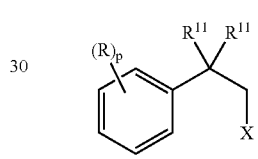

wherein X is halo and R¹¹ is independently, hydrogen or $C_1-C_4$ alkyl, with CNCH$_2$CO$_2$R^a wherein R^a is $C_1-C_8$ alkyl, or benzyl to afford a compound of formula 2:

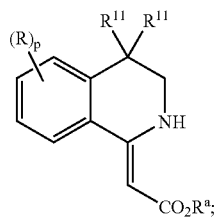

b) protecting the compound of formula 2 to form the compound of formula 3:

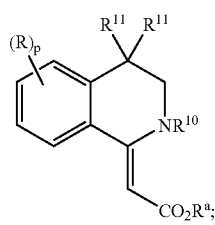

c) hydrogenating the compound of formula 3 to afford a compound of formula 4:

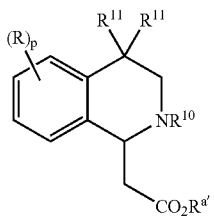

4 wherein $R^{a'}$ is H or $R^a$;

d) coupling the compound of formula 4 wherein $R^{a'}$ is hydrogen with a compound of formula 5:

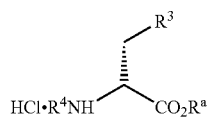

5 to afford a compound of formula 6:

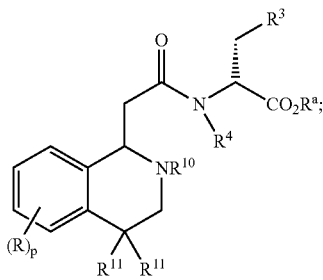

6 e) coupling the compound of formula 6 with a compound of formrula 7:

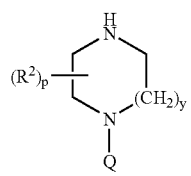

7 to afford a compound of formula I:

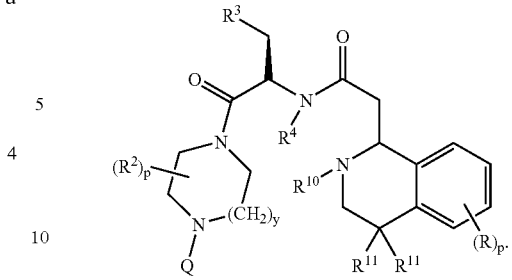

I

Preferred Compounds of the Invention

The following listing sets out several groups of preferred compounds organized by domains. It will be understood that each of the listings may be combined with other listings to create additional groups of preferred compounds.

A Domains

Q is: —C($R^{a1}$)($R^{a2}$)($R^{a3}$)

Wherein $R^{a1}$ is $C_1$–$C_8$ alkyl, $C_1$–$C_8$ alkenyl, cycloalkyl, heterocyclic, phenyl, aryl, or heteroaryl, and wherein $C_1$–$C_8$ alkyl, $C_1$–$C_8$ alkenyl, cycloalkyl, heterocyclic, phenyl, aryl, or heteroaryl are each optionally substituted with one to five substituents independently selected from R, wherein R has been described supra.

a) Q is: —C($R^{a1}$)($R^{a2}$)($R^{a3}$)

Wherein $R^{a1}$ is phenyl, benzyl, cyclohexane, cyclopentane or cycloheptane each optionally substituted with one to three substituents (R) selected from the group consisting of $C_1$–$C_8$ alkyl, halo, and haloalkyl;

b) Wherein $R^{a2}$ is $C_1$–$C_8$ alkyl, $C_1$–$C_8$ alkenyl, (D)$C_3$–$C_7$ cycloalkyl, (D)N($R^8$)$_2$, (D)$NR^8$C(O)$C_1$–$C_4$ alkyl, (D)$NR^8$COO$R^8$, (D)$NR^8$SO$_2$($C_1$–$C_4$ alkyl), (D)CON($R^8$)$_2$, wherein for the group or subgroup —N($R^8$)$_2$, each $R^8$ may combine with the other to form a nitrogen containing heterocycle;

c) $R^{a3}$ is selected from the group consisting of hydrogen, methyl ethyl and propyl.

d) $R^{a3}$ is hydrogen.

e) For the compounds of formula II, the Z ring is a saturated ring or Z is phenyl.

f) the A domain is selected from those exemplified below in the Preparations and Examples sections;

g) $R^2$ is hydrogen, $C_1$–$C_8$ alkyl, (D)phenyl, CONH$C_1$–$C_4$ alkyl, oxo, or (D)$C_3$–$C_7$ cycloalkyl;

B Domains h) $R^3$ is phenyl optionally para-substituted with halo, trifluoromethyl, benzyl, benzyloxy, $C_1$–$C_2$ alkyl or $C_1$–$C_2$ alkoxy;

i) $R^3$ is phenyl para-substituted with chloro;

j) the B domain is a diradical with the C-terminus attaching to the A-domain and the N-terminus attaching to the C domain and is selected from the group consisting of:

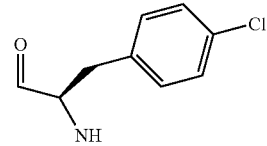

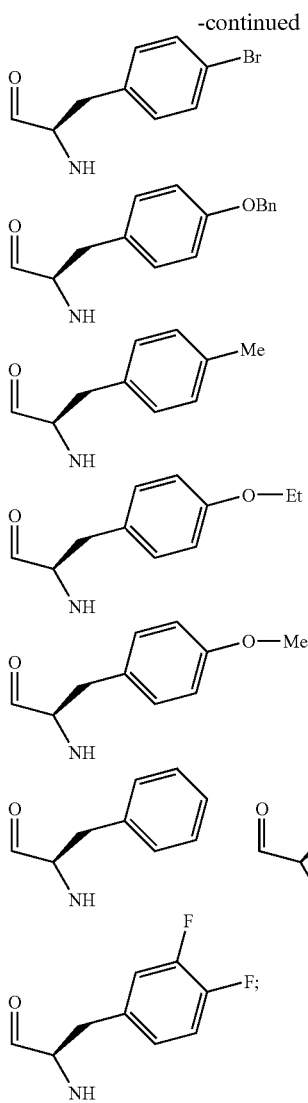

k) the B domain is a diradical with the C-terminus attaching to the A-domain and the N-terminus attaching to the C domain and is selected from the group consisting of:

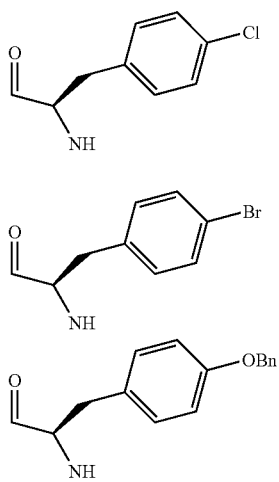

C Domains

The C-domain is represented by the formula —CLL¹—(CH₂)ₙ—T or —CLL¹—(CH₂)ₙ—T'. Preferred embodiments of the C-domain or aspects thereof include:

1) the C domain wherein T or T' is a moiety of the formula:

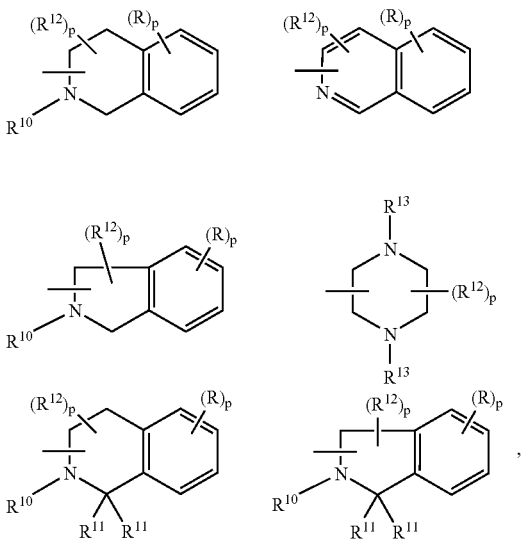

wherein R, $R^{10}$, $R^{11}$, $R^{12}$ and $R^{13}$ are as described previously;

m) T or T' for the C domain is a moiety of the formula:

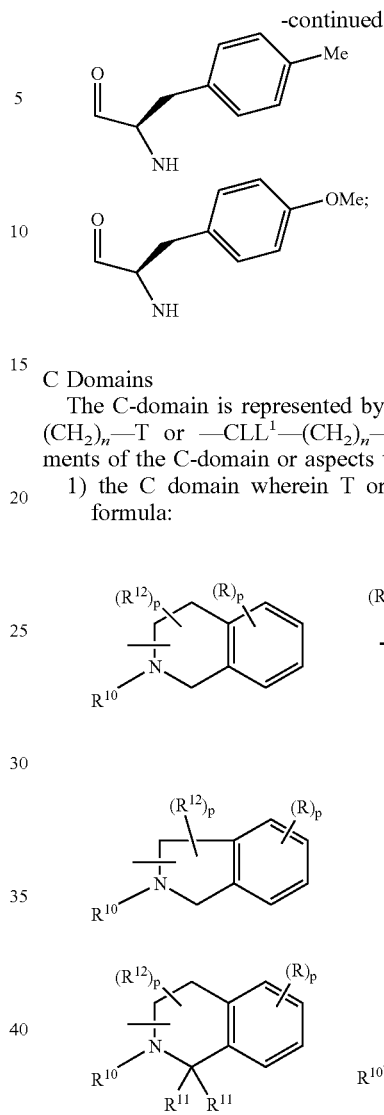

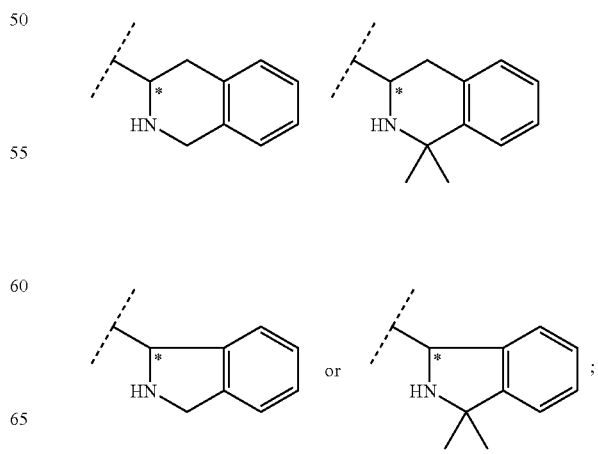

n) the C domain is a moiety selected from the group consisting of:

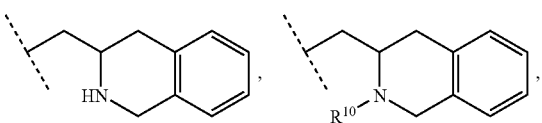

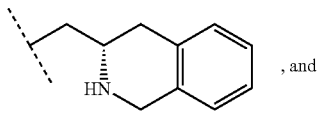, and

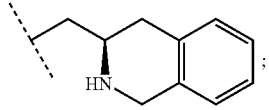;

Most preferred R⁴ groups include hydrogen, and $C_1$–$C_8$ alkyl.

For the "C" domain it is preferred that both L and L' are hydrogen or combine to form an oxo group.

Salt Forms o) the compound of formula I is an acid addition salt;

p) the compound of formula I is the hydrochloride salt.

A preferred compound of the invention is a compound selected from the group consisting of those in Table A below:

TABLE A

| Structure | Additional Information | NAME |
|---|---|---|
| 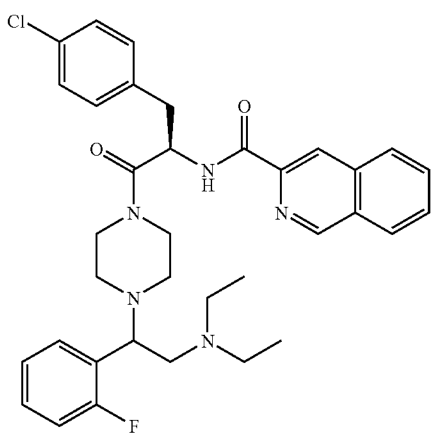 | "A" isomer #2 | Isoquinoline-3-carboxylic acid (1-(4-chloro-benzyl)-2-{4-[2-diethylamino-1-(2-fluoro-phenyl)-ethyl]-piperazin-1-yl}-2-oxo-ethyl)-amide |
| 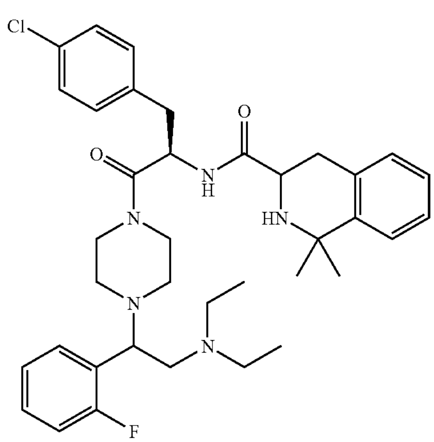 | "isomer #2 for "A" and "C" | 1,1-Dimethyl-1,2,3,4-tetrahydro-isoquinoline-3-carboxylic acid (1-(4-chloro-benzyl)-2-{4-[2-diethylamino-1-(2-fluoro-phenyl)-ethyl]-piperazin-1-yl}-2-oxo-ethyl)-amide |

TABLE A-continued

| Structure | Additional Information | NAME |
|---|---|---|
| | "A" isomer #2 | N-(1-(4-Chloro-benzyl)-2-{4-[1-(2-chloro-phenyl)-2-diethylemino-ethyl]-piperazin-1-yl}-2-oxo-ethyl)-2-(2-methyl-2,3-dihydro-1H-isoindol-1-yl)-acetamide |
| | "A" isomer #2 | N-(1-(4-Chloro-benzyl)-2-{4-[2-diethylamino-1-(2-fluoro-phenyl)-ethyl]-piperazin-1-yl}-2-oxo-ethyl)-2-(2-methyl-2,3-dihydro-1H-isoindol-1-yl)-acetamide |
| | | 1,2,3,4-Tetrahydro-isoquinoline-3-carboxylic acid (1-(4-chloro-benzyl)-2-{4-[1-(2-chloro-phenyl)-2-dimethylamino-ethyl]-piperazin-1-yl}-2-oxo-ethyl)-amide |

TABLE A-continued

| Structure | Additional Information | NAME |
|---|---|---|
| | | 1,2,3,4-Tetrahydro-isoquinoline-3-carboxylic acid (1-(4-chloro-benzyl)-2-{4-[2-diethylamino-1-(2-trifluoromethyl-phenyl)-ethyl]-piperazin-1-yl}-2-oxo-ethyl)-amide |
| | isomer #1 (of 2 - HPLC) | 1,2,3,4-Tetrahydro-isoquinoline-3-carboxylic acid (1-(4-chloro-benzyl)-2-{4-[2-diethylamino-1-(2-trifluoromethyl-phenyl)-ethyl]-piperazin-1-yl}-2-oxo-ethyl)-amide |
| 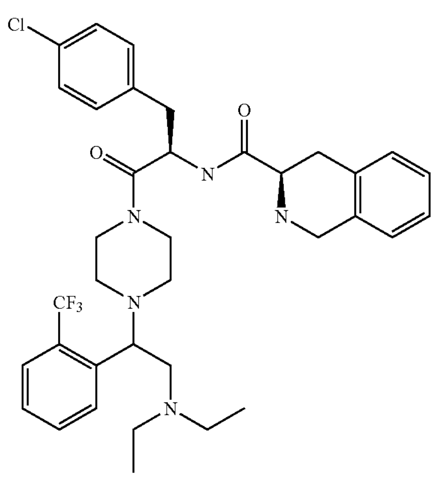 | isomer #2 (of 2 - HPLC) | 1,2,3,4-Tetrahydro-isoquinoline-3-carboxylic acid (1-(4-chloro-benzyl)-2-{4-[2-diethylamino-1-(2-trifluoromethyl-phenyl)-ethyl]-piperazin-1-yl}-2-oxo-ethyl)-amide |

TABLE A-continued

| Structure | Additional Information | NAME |
|---|---|---|
| 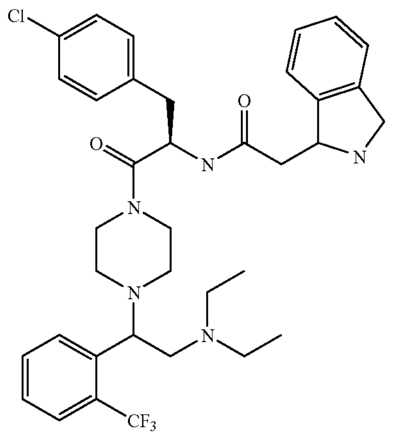 | isomer #2-UNK (of 4 - HPLC) | N-(1-(4-Chloro-benzyl)-2-{4-[2-diethylamino-1-(2-trifluoromethyl-phenyl)-ethyl]-piperazin-1-yl}-2-oxo-ethyl)-2-(2,3-dihydro-1H-isoindol-1-yl)-acetamide |
| 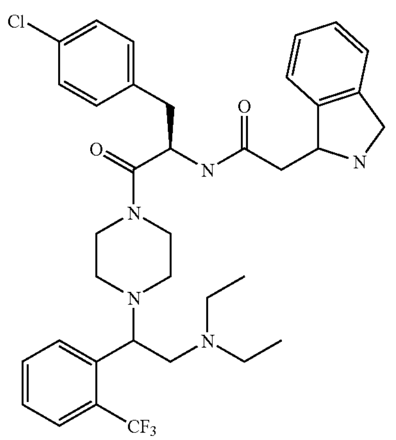 | isomer #4-UNK (of 4 - HPLC) | N-(1-(4-Chloro-benzyl)-2-{4-[2-diethylamino-1-(2-trifluoromethyl-phenyl)-ethyl]-piperazin-1-yl}-2-isoindol-1-yl)-acetamide |
| 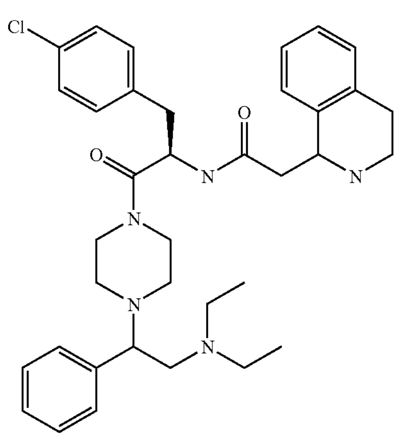 | isomer #2 (of 4 - HPLC) | N-{1-[4-(2-Diethylamino-1-phenyl-ethyl)-piperazine-1-carbonyl]-3-methylene-hex-4-enyl}-2-(4-methyl-3-vinyl-1,2,5,6-tetrahydro-pyridin-2-yl)-acetamide |

TABLE A-continued

| Structure | Additional Information | NAME |
|---|---|---|
| | isomer #1 (of 2 - HPLC) | N-(1-(4-chloro-benzyl)-2-{4-[2-diethylamino-1-(2-trifluoromethyl-phenyl)-ethyl]-piperazin-1-yl}-2-oxo-ethyl)-2-(2,3-dihydro-1H-isoindol-1-yl)-acetamide |
| 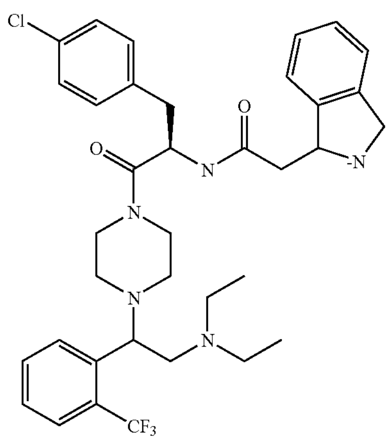 | isomer #2 (of 2 - HPLC) | N-(1-(4-chloro-benzyl)-2-{4-[2-diethylamino-1-(2-trifluoromethyl-phenyl)-ethyl]-piperazin-1-yl}-2-oxo-ethyl)-2-(2,3-dihydro-1H-isoindol-1-yl)-acetamide |
| | isomer #1 (of 2 - HPLC) | N-(1-(4-Chloro-benzyl)-2-{4-[2-diethylamino-1-(2-trifluoromethyl-phenyl)-ethyl]-piperazin-1-yl}-2-oxo-ethyl)-2-(2,3-dihydro-1H-isoindol-1-yl)-acetamide |

TABLE A-continued

| Structure | Additional Information | NAME |
|---|---|---|
| 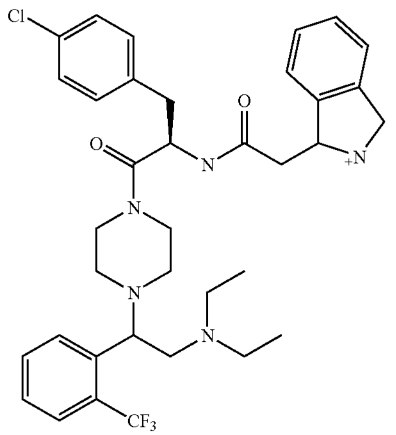 | isomer #2 (of 2 - HPLC) | N-(1-(4-Chloro-benzyl)-2-{4-[2-diethylamino-1-(2-trifluoromethyl-phenyl)-ethyl]-piperazin-1-yl}-2-oxo-ethyl)-2-(2,3-dihydro-1H-isoindol-1-yl)-acetamide |
| | | 1,2,3,4-Tetrahydro-isoquinoline-3-carboxylic acid (1-(4-chloro-benzyl)-2-{4-[2-diethylamino-1-(2-fluoro-phenyl)-ethyl]-piperazin-1-yl}-2-oxo-ethyl)-amide |
| | | 1,2,3,4-Tetrahydro-isoquinoline-3-carboxylic acid (1-(4-chloro-benzyl)-2-(4-[1-(2-fluoro-phenyl)-2-methanesulfonylamino-ethyl]-piperazin-1-yl}-2-oxo-ethyl)-amide |

TABLE A-continued

| Structure | Additional Information | NAME |
|---|---|---|
| | | N-(1-(4-chloro-beazyl)-2-{4-[2-diethylamino-1-(2-fluoro-phenyl)-ethyl]-piperazin-1-yl}-2-oxo-ethyl)-2-(2,3-dihydro-1H-isoindol-1-yl)-acetamide |
| | | N-(1-(4-chloro-benzyl)-2-{4-[2-diethylamino-1-(2-fluoro-phenyl)-ethyl]-piperazin-1-yl}-2-oxo-ethyl)-2-(2,3-dihydro-1H-isoindol-1-yl)-acetamide |
| | | N-(1-(4-Chloro-benzyl)-2-{4-[2-(ethyl-methanesulfonyl-amino)-1-(2-fluoro-phenyl)-ethyl]-piperazin-1-yl}-2-oxo-ethyl)-2-(2,3-dihydro-1H-isoindol-1-yl)-acetamide |

TABLE A-continued

| Structure | Additional Information | NAME |
|---|---|---|
| | | 3-(4-Chloro-phenyl)-1-{4-[2-diethylamino-1-(2-fluoro-phenyl)-ethyl]-piperazin-1-yl}-2-[(1,2,3,4-tetrahydro-isoquinolin-3-ylmethyl)-amino]-propan-1-one |
| | | N-[2-(4-{3-(4-Chloro-phenyl)-2-[(1,2,3,4-tetrahydro-isoquinolin-3-ylmethyl)-amino]-propionyl}-phenyl)-ethyl]-methanesulfonamide |
| | | N-[2-(4-{3-(4-Chloro-phenyl)-2-[(1,2,3,4-tetrahydro-isoquinolin-3-ylmethyl)-amino]-propionyl}-piperazin-1-yl)-2-(2-fluoro-phenyl)-ethyl]-N-ethyl-methanesulfonamide |

TABLE A-continued

| Structure | Additional Information | NAME |
|---|---|---|
| | | 1,2,3,4-Tetrahydro-isoquinoline-3-carboxylic acid (1-(4-chloro-benzyl)-2-{4-[2-diethylamino-1-(2,4-difluoro-phenyl)-ethyl]-piperazin-1-yl}-2-oxo-ethyl)-amide |
| | | 1,2,3,4-Tetrahydro-isoquinoline-3-carboxylic acid (1-(4-chloro-benzyl)-2-{4-[2-diethylamino-1-(2,6-difluoro-phenyl)-ethyl]-piperazin-1-yl}-2-oxo-ethyl)-amide |
| | | 1,2,3,4-Tetrahydro-isoquinoline-3-carboxylic acid (1-(4-chloro-benzyl)-2-{4-[2-diethylamino-1-(2-fluoro-4-trifluoromethyl-phenyl)-ethyl]-piperazin-1-yl}-2-oxo-ethyl)-amide |

TABLE A-continued

| Structure | Additional Information | NAME |
|---|---|---|
| | "A" isomer #2 | N-(1-(4-Chloro-benzyl)-2-{4-[2-diethylamino-1-(2-fluoro-phenyl)-ethyl]-piperazin-1-yl}-2-oxo-ethyl)-2-(2,3-dihydro-1H-isoindol-1-yl)-acetamide |
| | "A" isomer #2 | 1,2,3,4-Tetrahydro-isoquinoline-3-carboxylic acid (1-(4-chloro-benzyl)-2-{4-[2-diethylamino-1-(2-fluoro-phenyl)-ethyl]-piperazin-1-yl}-2-oxo-ethyl)-amide |
| | "A" isomer #2 | 1,2,3,4-Tetrahydro-isoquinline-3-carboxylic acid (1-(4-chloro-benzyl)-2-{4-[1-(2-chloro-phenyl)-2-diethylamino-ethyl]-piperazin-1-yl}-2-oxo-ethyl)-amide |

TABLE A-continued

| Structure | Additional Information | NAME |
|---|---|---|
| | "A" isomer #2 | 1,2,3,4-Tetrahydro-isoquinoline-3-carboxylic acid (1-(4-chloro-benzyl)-2-{4-[1-(2-chloro-phenyl)-ethyl]-piperazin-1-yl}-2-oxo-ethyl)-amide |
| | | [2-(4-{3-(4-Chloro-phenyl)-2-[(1,2,3,4-tetrahydro-isoquinoline-3-carbonyl)-amino]-propionyl}-piperazin-1-yl)-2-(2,4-difluoro-phenyl)-ethyl]-carbamic acid methyl ester |
| | "A" isomer #2 | N-(1-(4-Chloro-benzyl)-2-{4-[1-(2-chloro-phenyl)-2-diethylamino-ethyl]-piperazin-1-yl}-2-oxo-ethyl)-2-(2,3-dihydro-1H-isoindol-1-yl)-acetamide |

TABLE A-continued

| Structure | Additional Information | NAME |
|---|---|---|
| 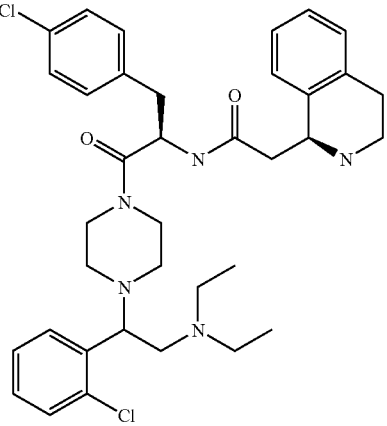 | "A" isomer #2 | N-(1-(4-Chloro-benzyl)-2-{4-[1-(2-chloro-phenyl)-2-diethylamino-ethyl]-piperazine-1-yl}-2-oxo-ethyl)-2-(1,2,3,4-tetrahydro-isoquinolin-1-yl)-acetamide |
| 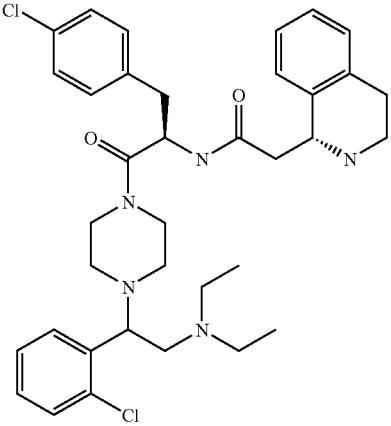 | "A" isomer #2 | N-(1-(4-Chloro-benzyl)-2-{4-[1-(2-chloro-phenyl)-2-diethylamino-ethyl]-piperazine-1-yl}-2-oxo-ethyl)-2-(1,2,3,4-tetrahydro-isoquinolin-1-yl)-acetamide |
| 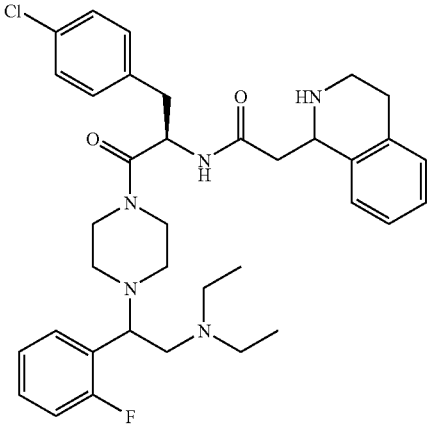 | "A" isomer #2, "C" isomer #1 | N-(1-(4-Chloro-benzyl)-2-{4-[2-diethylamino-1-(2-fluoro-phenyl)-ethyl]piperazin-1-yl}-2-oxo-ethyl)-2-(1,2,3,4-tetrahydro-isoquinolin-1-yl)-acetamide |

TABLE A-continued

| Structure | Additional Information | NAME |
|---|---|---|
| 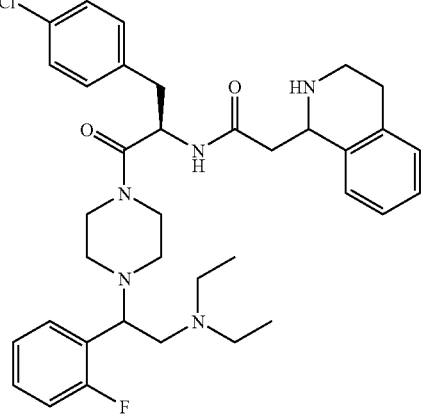 | "A" isomer #2, "C" isomer #1 | N-(1-(4-Chloro-benzyl)-2-{4-[2-diethylamino-1-(2-fluoro-phenyl)-ethyl]piperazin-1-yl}-2-oxo-ethyl)-2-(1,2,3,4-tetrahydro-isoquinolin-1-yl)-acetamide |
| 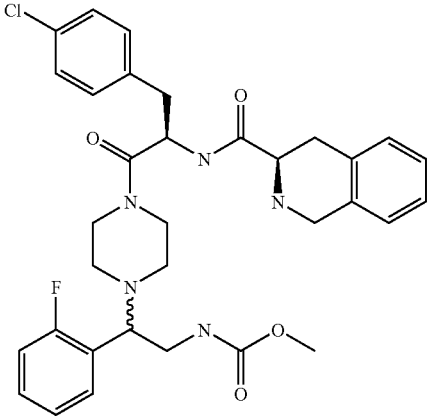 | | [2-(4-{3-(4-Chloro-phenyl)-2-[(1,2,3,4-tetrahydro-isoquinoline-3-carbonyl)-amino]-propionyl}-piperazin-1-yl)-2-(2-fluoro-phenyl)-ethyl]-carbamic acid methyl ester |
| 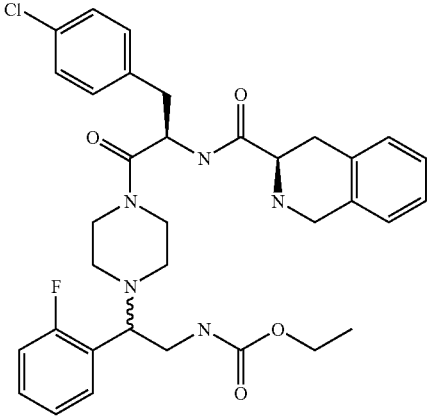 | | [2-(4-{3-(4-Chloro-phenyl)-2-[(1,2,3,4-tetrahydro-isoquinoline-3-carbonyl)-amino]-propionyl}-piperazin-1-yl)-2-(2-fluoro-phenyl)-ethyl]-carbamic acid ethyl ester |

TABLE A-continued

| Structure | Additional Information | NAME |
|---|---|---|
| | | [2-(4-{3-(4-Chloro-phenyl)-2-[(1,2,3,4-tetrahydro-isoquinoline-3-carbonyl)-amino]-propionyl}-piperazin-1-yl)-2-(2-fluoro-phenyl)-ethyl]-carbamic acid isopropyl ester |
| | | 1,2,3,4-Tetrahydro-isoquinoline-3-carboxylic acid [2-{4-[2-(acetyl-methyl-amino)-1-(2-fluoro-phenyl)-ethyl]-piperazin-1-(4-chloro-benzyl)-2-oxo-ethyl]-amide |
| | | 1,2,3,4-Tetrahydro-isoquinoline-3-carboxylic acid {1-(4-chloro-benzyl)-2-[4-(2-dipropylamino-1-phenyl-ethyl)-piperazin-1-yl]-2-oxo-ethyl}-amide |

TABLE A-continued

| Structure | Additional Information | NAME |
|---|---|---|
| | | 1,2,3,4-Tetrahydro-isoquinoline-3-carboxylic acid {1-(4-chloro-benzyl)-2-[4-(2-dipropylamino-1-phenyl-ethyl-piperazin-1-yl]-2-oxo-ethyl}-amide |
| | | 1,2,3,4-Tetrahydro-isoquinoline-3-carboxylic acid (1-(4-chloro-benzyl)-2-oxo-2-[4-(1-phenyl-2-yl]-ethyl}-amide |
| | | 7-Fluoro-1,2,3,4-tetrahydro-isoquinoline-3-carboxylic acid {1-(4-chloro-benzyl)-2-[4-(2-diethylamino-1-phenyl-ethyl)-piperazin-1-yl]-2-oxo-ethyl}-amide |

TABLE A-continued

| Structure | Additional Information | NAME |
|---|---|---|
| 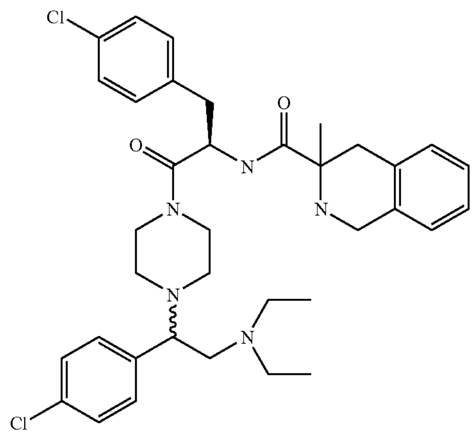 | "C" isomer #1 | 3-Methyl-1,2,3,4-tetrahydro-isoquinoline-3-carboxylic acid (1-(4-chloro-benzyl)-2-{4-[1-(4-chloro-phenyl)-2-diethylamino-ethyl]-piperazin-1-yl}-2-oxo-ethyl)-amide |
| | | 1,2,3,4-Tetrahydro-isoquinoline-3-carboxylic acid [2-{4-[2-(acetyl-ethyl-amino)-1-(2-fluoro-phenyl)-ethyl]piperazin-1-yl}-1-(4-chloro-benzyl)-2-oxo-ethyl]-amide |
| | | 1,2,3,4-Tetrahydro-isoquinoline-3-carboxylic acid (1-(4-chloro-benzyl)-2-{4-[2-(ethyl-propionyl-amino)-1-(2-fluoro-phenyl)-ethyl]-piperazin-1-yl}-2-oxo-ethyl)-amide |

TABLE A-continued

| Structure | Additional Information | NAME |
|---|---|---|
| | | 1,2,3,4-Tetrahydro-isoquinoline-3-carboxylic acid (1-(4-chloro-benzyl)-2-{4-[2-(ethyl-isobutyryl-amino)-1-(2-fluoro-phenyl)-ethyl]piperazin-1-yl}-2-oxo-ethyl)-amide |
| | | [2-(4-{3-(4-Chloro-phenyl)-2-[(1,2,3,4-tetrahydro-isoquinoline-3-carbonyl)-amino]-propionyl}-piperazin-1-yl)-2-(2-fluoro-phenyl)-ethyl}-ethyl-carbamic acid methyl ester |
| | | [2-(4-{3-(4-Chloro-phenyl)-2-[(1,2,3,4-tetrahydro-isoquinoline-3-carbonyl)-amino]-propionyl}-piperazin-1-yl)-2-(2-fluoro-phenyl)-ethyl}-ethyl-carbamic acid ethyl ester |

TABLE A-continued

| Structure | Additional Information | NAME |
|---|---|---|
| | | [2-(4-{3-(4-Chloro-phenyl)-2-[(1,2,3,4-tetrahydro-isoquinoline-3-carbonyl)-amino]-propionyl}-piperazin-1-yl)-2-(2-fluoro-phenyl)-ethyl]-ethyl-carbamic acid isopropyl ester |
| | | N-[2-{4-[2-[Acetyl-(2-ethyl-butyl)-amino]-1-(2-fluoro-phenyl)-ethyl]-piperazine-1-yl}-1-(4-chloro-benzyl)-2-oxo-ethyl]-2-(2,3-dihydro-1H-isoindol-1-yl)-acetamide |
| | | N-[2-{4-[2-(Acetyl-cyclohexylmethyl-amino)-1-(2-fluoro-phenyl)-ethyl]-piperazin-1-yl}-1-(4-chloro-benzyl)-2-oxo-ethyl]-2-(2,3-dihydro-1H-isoindol-1-yl)-acetamide |

TABLE A-continued

| Structure | Additional Information | NAME |
|---|---|---|
| | "A" isomer #2 | N-(1-(4-Chloro-benzyl)-2-{4-[1-(2-chloro-phenyl)-2-(ethyl-methanesulfonyl-amino)-ethyl]-piperazin-1-yl}-2-oxo-ethyl)-2-(2,3-dihydro-1H-isoindol-1-yl)-acetamide |
| | "A" isomer #2 | N-(1-(4-Chloro-benzyl)-2-{4-[1-(2-chloro-phenyl)-2-(ethyl-methanesulfonyl-amino)-ethyl]-piperazin-1-yl}-2-oxo-ethyl)-2-(1,2,3,4-tetrahydro-isoquinolin-1-yl)-acetamide |
| | "A" isomer #2 | N-(1-(4-Chloro-benzyl)-2-{4-[2-diethylamino-1-(2-trifluoromethyl-phenyl)-ethyl]-piperazin-1-yl}-2-oxo-ethy)-2-(1,2,3,4-tetrahydro-isoquinolin-1-yl)-acetamide |

TABLE A-continued

| Structure | Additional Information | NAME |
|---|---|---|
| 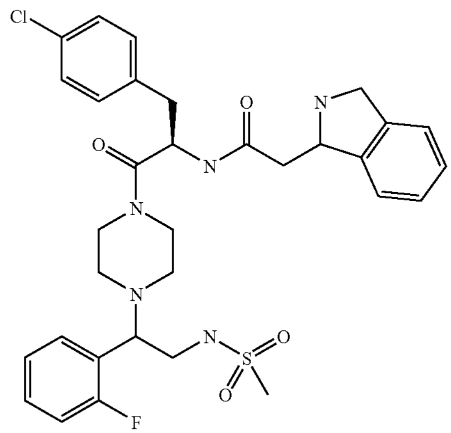 | "A" isomer #2 | N-(1-(4-Chloro-benzyl)-2-{4-[1-(2-fluoro-phenyl)-2-methanesulfonylamino-ethyl]-piperazin-1-yl}-2-oxo-ethyl)-2-(2,3-dihydro-1H-isoindol-1-yl)-acetamide |
|  | | 3-(4-Chloro-phenyl)-1-[4-(2-diethylamino-1-phenyl-ethyl)-piperazin-1-yl ]-2-[(1,2,3,4-tetrahydro-isoquinolin-3-ylmethyl)-amino]-propan-1-one |
| 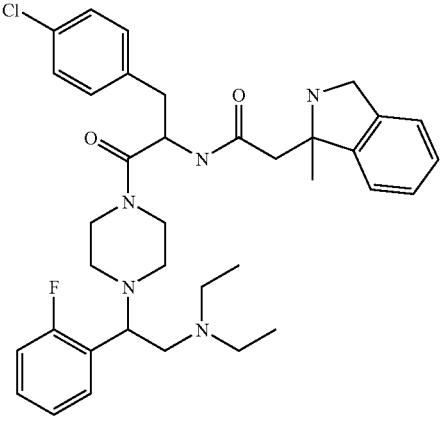 | "A" isomer #2, "C" isomer #1 | N-(1-(4-Chloro-benzyl)-2-{4-[2-diethylamino-1-(2-fluoro-phenyl)-ethyl]-piperazin-1-yl}-2-oxo-ethyl)-2-(1-methyl-2,3-dihydro-1H-isoindol-1-yl)-acetamide |

TABLE A-continued

| Structure | Additional Information | NAME |
|---|---|---|
| 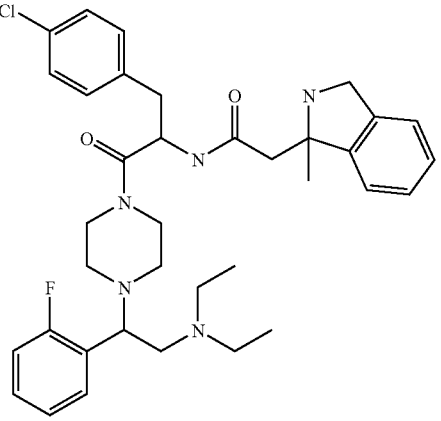 | "A" isomer #2, "C" isomer #1 | N-(1-(4-Chloro-benzyl)-2-{4-[2-diethylamino-1-(2-fluoro-phenyl)-ethyl]-piperazin-1-yl}-2-oxo-ethyl)-2-(1-methyl-2,3-dihydro-1H-isoindol-1-yl)-acetamide |
| 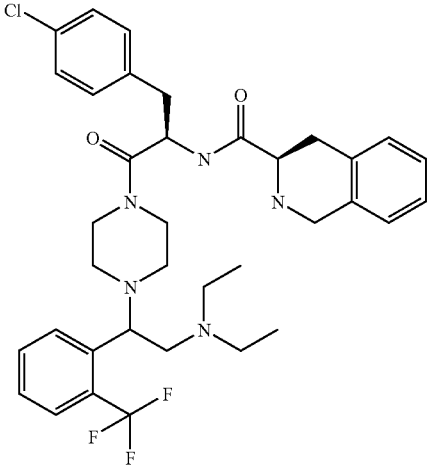 | "A" isomer #2 | 1,2,3,4-Tetrahydro-isoquinoline-3-carboxylic acid (1-(4-chloro-benzyl)-2-{4-[2-diethylamino-1-(2-trifluoromethyl-phenyl)-ethyl]-piperazin-1-yl}-2-oxo-ethyl)-amide |
| 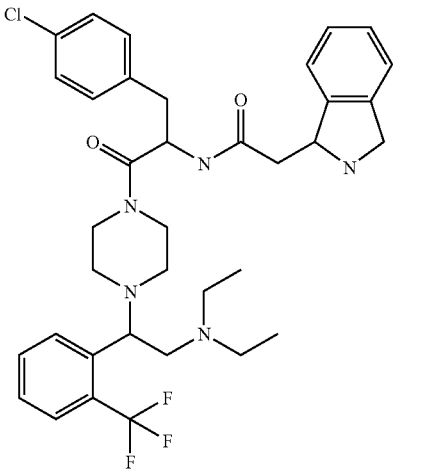 | "A" isomer #2 | 1,2,3,4-Tetrahydro-isoquinoline-3-carboxylic acid (1-(4-chloro-benzyl)-2-{4-[2-diethylamino-1-(2-trifluoromethyl-phenyl)-ethyl]-piperazin-1-yl}-2-oxo-ethyl)-amide |

TABLE A-continued

| Structure | Additional Information | NAME |
|---|---|---|
| 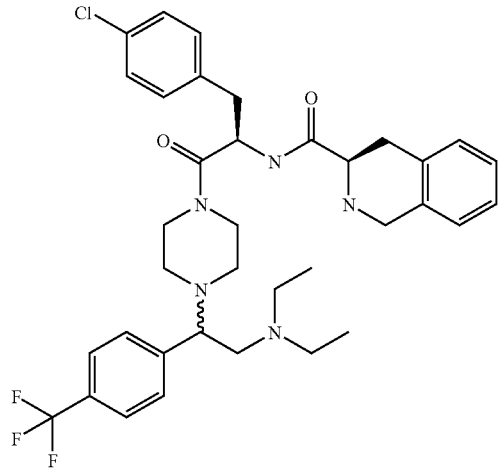 | | 1,2,3,4-Tetrahydro-isoquinoline-3-carboxylic acid (1-(4-chloro-benzyl)-2-{4-[2-diethylamino-1-(4-trifluoromethyl-phenyl)-ethyl]-piperazin-1-yl}-2-oxo-ethyl)-amide |
| 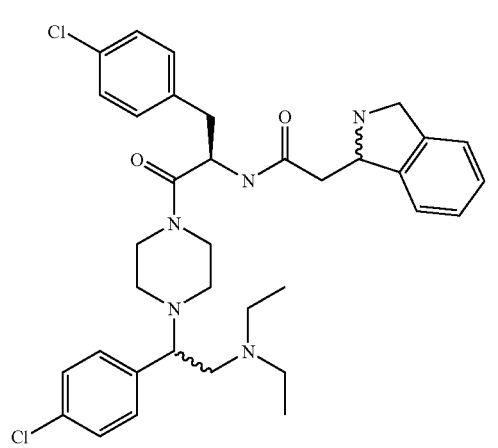 | | N-(1-(4-Chloro-benzyl)-2-{4-[1-(4-chloro-phenyl)-2-diethylamino-ethyl]-piperazin-1-yl}-2-oxo-ethyl)-2-(2,3-dihydro-1H-isoindol-1-yl)-acetamide |
| 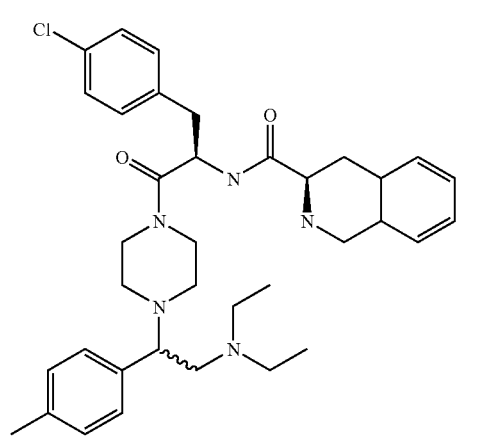 | | 1,2,3,4,4a,8a,-Hexahydro-isoquinoline-3-carboxylic acid [2-[4-(2-diethylamino-1-p-tolyl-ethyl)-piperazin-1-yl]-1-(4-methyl-benzyl)-2-oxo-ethyl]-amide |

TABLE A-continued

| Structure | Additional Information | NAME |
|---|---|---|
| | | N-[2-[4-(2-Diethylamino-1-p-tolyl-ethyl)-piperazin-1-yl]-1-(4-methyl-benzyl)-2-oxo-ethyl]-2-(2,3-dihydro-1H-isoindol-1-yl)-acetamide |
| | "A" isomer #1 | N-[2-{4-[1-(2-Chloro-phenyl)-2-diethylamino-ethyl]-piperazin-1-yl}-1-(4-methyl-benzyl)-2-oxo-ethyl]-2-(2,3-dihydro-1H-isoindol-1-yl)-acetamide |
| | "A" isomer #2 | N-[2-{4-[1-(2-Chloro-phenyl)-2-diethylamino-ethyl]-piperazin-1-yl}-1-(4-methyl-benzyl)-2-oxo-ethyl]-2-(2,3-dihydro-1H-isoindol-1-yl)-acetamide |

TABLE A-continued

| Structure | Additional Information | NAME |
|---|---|---|
| 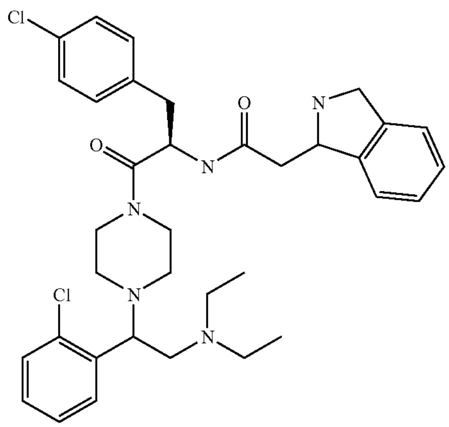 | "A" isomer #1 | N-[2-{4-[1-(2-Chloro-phenyl)-2-diethylamino-ethyl]-piperazin-1-yl}-1-(4-methyl-benzyl)-2-oxo-ethyl]-2-(2,3-dihydro-1H-isoindol-1-yl)-acetamide |
| 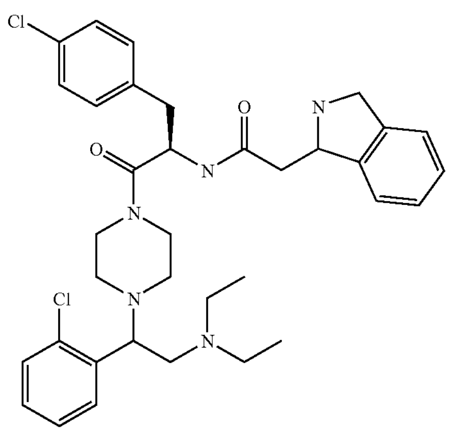 | "A" isomer #2 | N-[2-{4-[1-(2-Chloro-phenyl)-2-diethylamino-ethyl]-piperazin-1-yl}-1-(4-methyl-benzyl)-2-oxo-ethyl]-2-(2,3-dihydro-1H-isoindol-1-yl)-acetamide |
| | | 1,2,3,4-Tetrahydro-isoquinoline-3-carboxylic acid [2-{4-[2-diethylamino-1-(2-methoxy-phenyl)-ethyl]-piperazin-1-yl}-1-(4-methyl-benzyl)-2-oxo-ethyl]-amide |

TABLE A-continued

| Structure | Additional Information | NAME |
|---|---|---|
| | | N-[2-{4-[2-Diethylamino-1-(2-methoxy-phenyl)-ethyl]-piperazin-1-yl}-1-(4-methyl-benzyl)-2-oxo-ethyl]-2-(2,3-dihydro-1H-isoindol-1-yl)-acetamide |
| 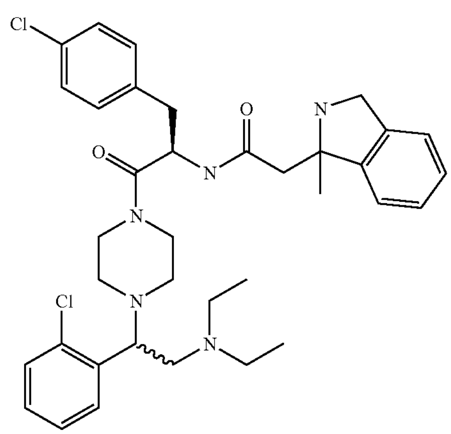 | "C" ]isomer #1 | N-[2-{4-[1-(2-Chloro-phenyl)-2-diethylamino-ethyl]-piperazin-1-yl}-1-(4-methyl-benzyl)-2-oxo-ethyl]-2-(1-methyl-2,3-dihydro-1H-isoindol-1-yl)-acetamide |
| 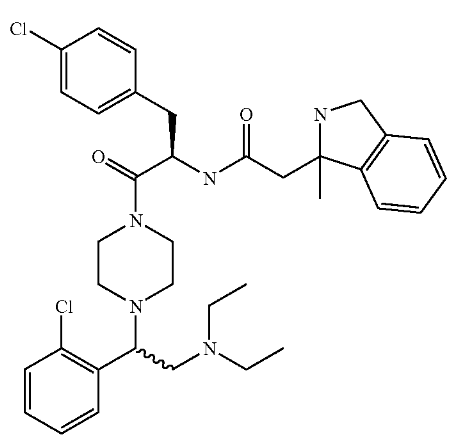 | "C" ]isomer #2 | N-[2-{4-[1-(2-Chloro-phenyl)-2-diethylamino-ethyl]-piperazin-1-yl}-1-(4-methyl-benzyl)-2-oxo-ethyl]-2-(1-methyl-2,3-dihydro-1H-isoindol-1-yl)-acetamide |

TABLE A-continued

| Structure | Additional Information | NAME |
|---|---|---|
| | | 1,2,3,4-Tetrahydro-isoquinoline-3-carboxylic acid [2-{4-[1-(2-chloro-phenyl)-2-methanesulfonylamino-ethyl]-benzyl)-2-oxo-ethyl]-amide |
| | | 1,2,3,4-Tetrahydro-isoquinoline-3-carboxylic acid [2-{4-[1-(2-chloro-phenyl)-2-diethylamino-ethyl]-piperazin-1-yl}-1-(4-methyl-benzyl)-2-oxo-ethyl]-amide |
| | | 1,2,3,4-Tetrahydro-isoquinoline-3-carboxylic acid {1-(4-chloro-benzyl)-2-[4-(diethylamino-1-phenyl-ethyl)-piperazin-1-yl]-2-oxo-ethyl}-amide |

TABLE A-continued

| Structure | Additional Information | NAME |
|---|---|---|
| 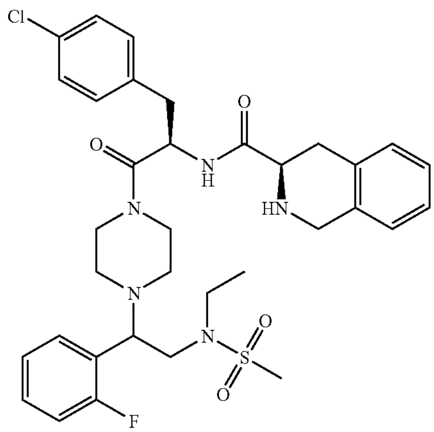 | "A" isomer #2 | 1,2,3,4-Tetrahydro-isoquinoline-3-carboxylic acid (1-(4-chloro-benzyl)-2-{4-[2-(ethyl-methanesulfonyl-amino)-1-(2-fluoro-phenyl)-ethyl]-piperazin-1-yl}-2-oxo-ethyl)-amide |
| 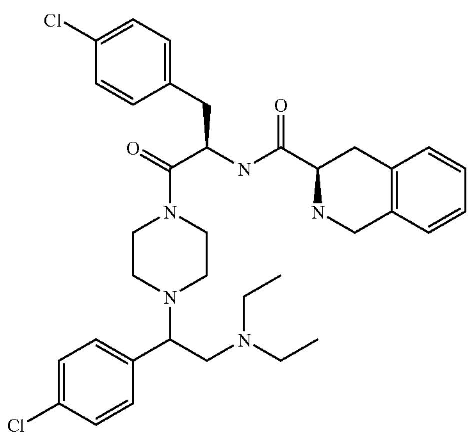 | "A" isomer #1 | 1,2,3,4-Tetrahydro-isoquinoline-3-carboxylic acid (1-(4-chloro-benzyl)-2-{4-[1-(4-chloro-phenyl)-2-diethylamino-ethyl]-piperazin-1-yl}-2-oxo-ethyl)-amide |
| | | 1,2,3,4-Tetrahydro-isoquinoline-3-carboxylic acid {1-(4-chloro-benzyl)-2-[4-(2-diethylamino-1-o-tolyl-ethyl)-piperazin-1-yl]-2-oxo-ethyl}-amide |

TABLE A-continued

| Structure | Additional Information | NAME |
|---|---|---|
| 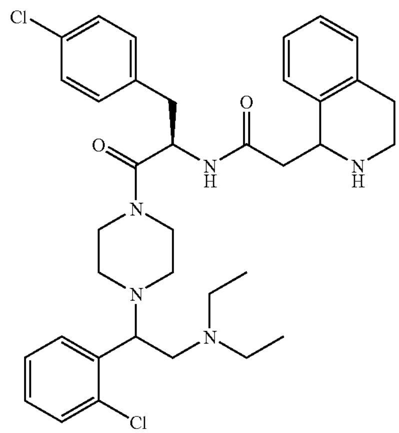 | "A" isomer #2, "C" isomer #2 | N-(1-(4-Chloro-benzy)-2-{4-[1-(2-chloro-phenyl)-2-diethylamino-ethyl]-piperazin-1-yl}-2-oxo-ethyl)-2-(1,2,3,4-tetrahydro-isoquinolin-1-yl)-acetamide |
| | | 1,2,3,4-Tetrahydro-isoquinoline-3-carboxylic acid {1-(4-chloro-benzyl)-2-[4-(2-diethylamino-1-phenyl-ethyl)-[1,4]diazepan-1-yl]-2-oxo-ethyl}-amide |
| | | N-{1-(4-Chloro-benzyl)-2-[4-(2-diethylamino-1-phenyl-ethyl)-piperazin-1-yl]-2-oxo-ethyl}-2-(2,3-dihydro-1H-isoindol-1-yl)-acetamide |

TABLE A-continued

| Structure | Additional Information | NAME |
|---|---|---|
| | | 1,2,3,4-Tetrahydro-isoquinoline-3-carboxylic acid {1-(4-chloro-benzyl)-2-[4-(1-cyclohexyl-2-diethylamino-ethyl)-piperazin-1-yl]-2-oxo-ethyl}-amide |
| | | 1,2,3,4-Tetrahydro-isoquinoline-3-carboxylic acid {1-(4-chloro-benzyl)-2-[4-(1-cyclopentyl-2-diethylamino-ethyl)-piperazin-1-yl]-2-oxo-ethyl}-amide |
| | | 1,2,3,4-Tetrahydro-isoquinoline-3-carboxylic acid {1-(4-chloro-benzyl)-2-[4-(1-cycloheptyl-2-diethylamino-ethyl)-piperazin-1-yl]-2-oxo-ethyl}-amide |

TABLE A-continued

| Structure | Additional Information | NAME |
|---|---|---|
| | | 1,2,3,4-Tetrahydro-isoquinoline-3-carboxylic acid {1-(4-chloro-benzyl)-2-[4-(1-cyclohexylmethyl-2-diethylamino-ethyl)-piperazin-1-yl]-2-oxo-ethyl}-amide |
| | | 1,2,3,4-Tetrahydro-isoquinoline-3-carboxylic acid (1-(4-chloro-benzyl)-2-{4-[1-cyclohexyl-2-(ethyl-methanesulfonyl-amino)-ethyl]-piperazin-1-yl}-2-oxo-ethyl)-amide |
| | | 1,2,3,4-Tetrahydro-isoquinoline-3-carboxylic acid (1-(4-chloro-benzyl)-2-{4-[1-cyclopentyl-2-(ethyl-methanesulfonyl-amino)-ethyl]-piperazin-1-yl}-2-oxo-ethyl)-amide |

TABLE A-continued

| Structure | Additional Information | NAME |
|---|---|---|
| | | 1,2,3,4-Tetrahydro-isoquinoline-3-carboxylic acid (1-(4-chloro-benzyl)-2-{4-[1-cyclohexylmethyl-2-(ethyl-methanesulfonyl-amino)-ethyl]-piperazin-1-yl}-2-oxo-ethyl)-amide |
| | | 1,2,3,4-Tetrahydro-isoquinoline-3-carboxylic acid {1-(4-chloro-benzyl)-2-[4-[1-cyclohexyl-2-methanesulfonylamino-ethyl)-piperazin-1-yl]-2-oxo-ethyl}-amide |
| | | 1,2,3,4-Tetrahydro-isoquinoline-3-carboxylic acid {1-(4-chloro-benzyl)-2-[4-(1-cyclohexyl-2-pyrrolidin-1-yl-ethyl)-piperazin-1-yl]-2-oxo-ethyl}-amide |

TABLE A-continued

| Structure | Additional Information | NAME |
|---|---|---|
| | | 1,2,3,4-Tetrahydro-isoquinoline-3-carboxylic acid [2-{4-[2-(benzyl-methanesulfonyl-amino)-1-cyclohexyl-ethyl]-piperazin-1-yl}-1-(4-chloro-benzyl)-2-oxo-ethyl]-amide |
| | | 1,2,3,4-Tetrahydro-isoquinoline-3-carboxylic acid [2-[4-[(2-acetylamino-1-cyclohexyl-ethyl)-piperazin-1-yl]-1-(4-chloro-benzyl)-2-oxo-ethyl]-amide |
| | | 1,2,3,4-Tetrahydro-isoquinoline-3-carboxylic acid {1-(4-chloro-benzyl)-2-[4-[1-cyclohexylmethyl-2-methanesulfonylamino-ethyl]-piperazin-1-yl]-2-oxo-ethyl}-amide |

TABLE A-continued

| Structure | Additional Information | NAME |
|---|---|---|
| | | 1,2,3,4-Tetrahydro-isoquinoline-3-carboxylic acid {1-(4-chloro-benzyl)-2-[4-[1-cyclohexylmethyl-2-morpholin-4-yl-ethyl)-piperazin-1-yl]-2-oxo-ethyl}-amide |
| | | 1,2,3,4-Tetrahydro-isoquinoline-3-carboxylic acid {1-(4-chloro-benzyl)-2-[4-[1-cyclohexylmethyl-2-pyrrolidin-1-yl-ethyl)-piperazin-1-yl]-2-oxo-ethyl}-amide |
| | | 1,2,3,4-Tetrahydro-isoquinoline-3-carboxylic acid {1-(4-chloro-benzyl)-2-[4-[1-cyclohexylmethyl-2-piperidin-1-ethyl)-piperazin-1-yl]-2-oxo-ethyl}-amide |
| | | N-{1-(4-chloro-benzyl)-2-[4-(1-cycohexyl-2-diethylamino-ethyl)-piperazin-1-yl]-2-oxo-ethyl}-2-(2,3-dihydro-1H-isoindol-1-yl)-acetamide |

TABLE A-continued

| Structure | Additional Information | NAME |
|---|---|---|
| | | N-{1-(4-chloro-benzyl)-2-[4-(1-cyclohexyl-2-diethylamino-ethyl)-piperazin-1-yl]-2-oxo-ethyl}-2-(2,3-dihydro-1H-isoindol-1-yl)-acetamide |
| | | N-{1-(4-chloro-benzyl)-2-[4-(1-cyclohexyl-2-diethylamino-ethyl)-piperazin-1-yl]-2-oxo-ethyl}-2-(2,3-dihydro-1H-isoindol-1-yl)-acetamide |
| | | N-{1-(4-chloro-benzyl)-2-{4-[1-cyclohexyl-2-(ethyl-methanesulfonyl-amino)-ethyl]-piperazin-1-yl}-2-oxo-ethyl)-2-(2,3-dihydro-1H-isoindol-1-yl)-acetamide |

TABLE A-continued

| Structure | Additional Information | NAME |
|---|---|---|
| 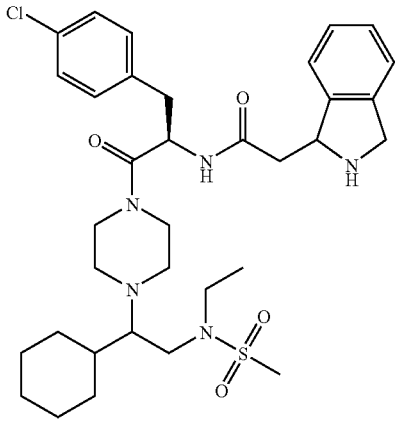 | | N-{1-(4-chloro-benzyl)-2-{4-[1-cyclohexyl-2-(ethyl-methanesulfonyl-amino)-ethyl]-piperazin-1-yl}-2-oxo-ethyl)-2-(2,3-dihydro-1H-isoindol-1-yl)-acetamide |
|  | | N-{1-(4-chloro-benzyl)-2-{4-[1-cyclohexyl-2-(ethyl-methanesulfonyl-amino)-ethyl]-piperazin-1-yl}-2-oxo-ethyl)-2-(2,3-dihydro-1H-isoindol-1-yl)-acetamide |
| 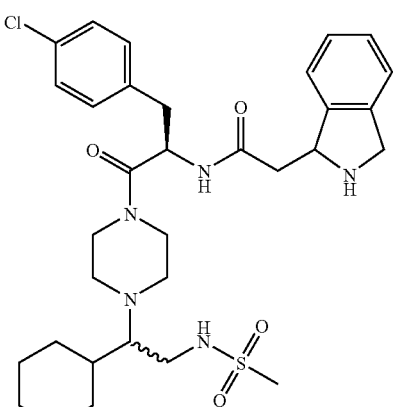 | | N-{1-(4-chloro-benzyl)-2-[4-(1-cyclohexyl-2-methanesulfonylamino-ethyl)-piperazin-1-yl]-2-oxo-ethyl}-2-(2,3-dihydro-1H-isoindol-1-yl)-acetamide |

TABLE A-continued

| Structure | Additional Information | NAME |
|---|---|---|
| 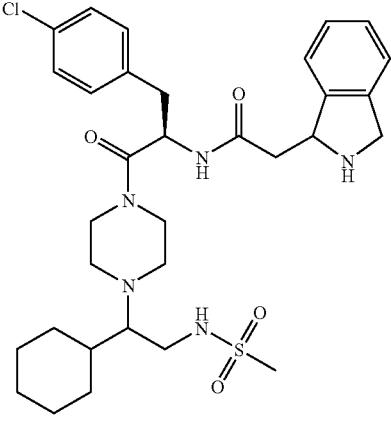 | | N-{1-(4-chloro-benzyl)-2-[4-(1-cyclohexyl-2-methanesulfonylamino-ethyl)-piperazin-1-yl]-2-oxo-ethyl}-2-(2,3-dihydro-1H-isoindol-1-yl)-acetamide |
| 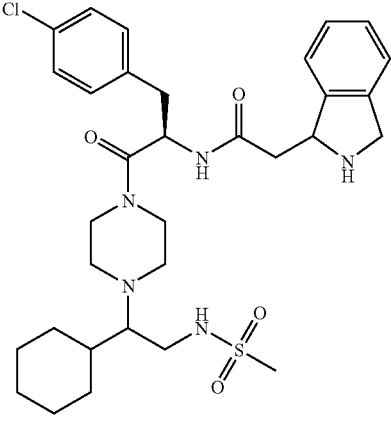 | | N-{1-(4-chloro-benzyl)-2-[4-(1-cyclohexyl-2-methanesulfonylamino-ethyl)-piperazin-1-yl]-2-oxo-ethyl}-2-(2,3-dihydro-1H-isoindol-1-yl)-acetamide |
| 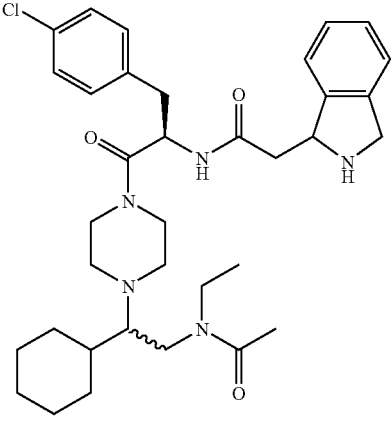 | | N-[2-{4-(Acethyl-ethyl-amino)-1-cyclohexyl-ethyl]-piperazin-1-yl}-1-(4-chloro-benzyl)-2-oxo-ethyl]-2-(2,3-dihydro-1H-isoindol-1-yl)-acetamide |

TABLE A-continued

| Structure | Additional Information | NAME |
|---|---|---|
| | | N-[2-{4-(Acethyl-ethyl-amino)-1-cyclohexyl-ethyl]-piperazin-1-yl}-1-(4-chloro-benzyl)-2-oxo-ethyl]-2-(2,3-dihydro-1H-isoindol-1-yl)-acetamide |
| | | N-[2-{4-(Acethyl-ethyl-amino)-1-cyclohexyl-ethyl]-piperazin-1-yl}-1-(4-chloro-benzyl)-2-oxo-ethyl]-2-(2,3-dihydro-1H-isoindol-1-yl)-acetamide |
| | | N-(1-(4-chloro-benzyl)2-{4-[1-cyclohexyl-2-(2,5-dioxo-pyrrolidin-yl)-ethyl]-piperazin-1-yl}-2-oxo-ethyl]-2-(2,3-dihydro-1H-isoindol-1-yl)-acetamide |

TABLE A-continued

| Structure | Additional Information | NAME |
|---|---|---|
| | | N-(1-(4-chloro-benzyl)2-{4-[1-cyclohexyl-2-(2,5-dioxo-pyrrolidin-yl)-ethyl]-piperazin-1-yl}-2-oxo-ethyl]-2-(2,3-dihydro-1H-isoindol-1-yl)-acetamide |
| | | N-(1-(4-chloro-benzyl)2-{4-[1-cyclohexyl-2-(2,5-dioxo-pyrrolidin-yl)-ethyl]-piperazin-1-yl}-2-oxo-ethyl]-2-(2,3-dihydro-1H-isoindol-1-yl)-acetamide |
| | | N-(1-(4-chloro-benzyl)2-{4-[1-cyclohexyl-2-(2-oxo-pyrrolidin-yl)-ethyl]-piperazin-1-yl}-2-oxo-ethyl]-2-(2,3-dihydro-1H-isoindol-1-yl)-acetamide |

TABLE A-continued

| Structure | Additional Information | NAME |
|---|---|---|
| | | N-(1-(4-chloro-benzyl)2-{4-[1-cyclohexyl-2-(2-oxo-pyrrolidin-yl)-ethyl]-piperazin-1-yl}-2-oxo-ethyl]-2-(2,3-dihydro-1H-isoindol-1-yl)-actamide |
| | | 2-{4-[3-(4-Chloro-benzyl)2-(2-2,3-dihydro-1H-isoindol-1-yl-acetylamino)-propionyl]-piperazin-1-yl}-3-cyclohexyl-N,N-diethyl-propionamide |
| | | 2-{4-[3-(4-Chloro-benzyl)2-(2-2,3-dihydro-1H-isoindol-1-yl-acetylamino)-propionyl]-piperazin-1-yl}-3-cyclohexyl-N,N-diethyl-propionamide |

TABLE A-continued

| Structure | Additional Information | NAME |
|---|---|---|
| 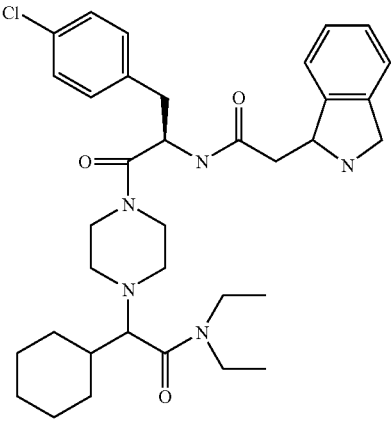 | | 2-{4-[3-(4-Chloro-benzyl)2-(2-2,3-dihydro-1H-isoindol-1-yl-acetylamino)-propionyl]-piperazin-1-yl}-3-cyclohexyl-N,N-diethyl-propionamide |
| 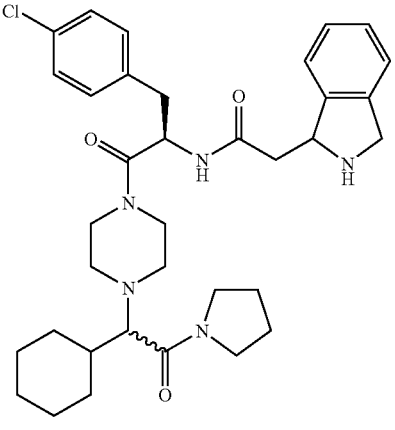 | | N-(1-(4-chloro-benzyl)2-[4-(1-cyclohexyl-2-oxo-2-pyrrolidin-yl-ethyl)-piperazin-1-yl]-2-oxo-ethyl}-2-(2,3-dihydro-1H-isoindol-1-yl)-acetamide |
| 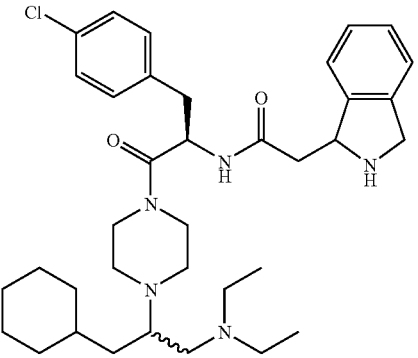 | | N-{1-(4-chloro-benzyl)-2-[4-(1-cyclohexylmethyl-2-diethylamino-ethyl)-piperazin-1-yl]-2-oxo-ethyl}-2-(2,3-dihydro-1H-isoindol-1-yl)-acetamide |

TABLE A-continued

| Structure | Additional Information | NAME |
|---|---|---|
| | | N-{1-(4-chloro-benzyl)-2-[4-(1-cyclohexylmethyl-2-morpholine-4-yl-ethyl)-piperazin-1-yl]-2-oxo-ethyl}-2-(2,3-dihydro-1H-isoindol-1-yl)-acetamide |
| | | N-{1-(4-chloro-benzyl)-2-[4-(1-cyclohexylmethyl-2-piperidin-1-yl-ethyl)-piperazin-1-yl]-2-oxo-ethyl}-2-(2,3-dihydro-1H-isoindol-1-yl)-acetamide |
| | | N-{1-(4-chloro-benzyl)-2-[4-(1-cyclohexylmethyl-2-pyrrolidin-1-yl-ethyl)-piperazin-1-yl]-2-oxo-ethyl}-2-(2,3-dihydro-1H-isoindol-1-yl)-acetamide |
| | | N-{1-(4-chloro-benzyl)-2-{4-[1-cyclohexylmethyl-2-(ethyl-methanesulfonyl-amino)-ethyl]-piperazin-1-yl}-2-oxo-ethyl}-2-(2,3-dihydro-1H-isoindol-1-yl)-acetamide |

TABLE A-continued

| Structure | Additional Information | NAME |
|---|---|---|
| | | N-{1-(4-chloro-benzyl)-2-[4-(1-cyclohexylmethyl-2-methanesulfonylamino-ethyl)-piperazin-1-yl]-2-oxo-ethyl}-2-(2,3-dihydro-1H-isoindol-1-yl)-acetamide |
| | | N-{1-(4-chloro-benzyl)-2-[4-(1-cyclohexyl-2-diethylamino-ethyl)-piperazin-1-yl]-2-oxo-ethyl}-2-(1,2,3,4-tetrahydro-isoquinolin-1-yl)-acetamide |
| | | N-{1-(4-chloro-benzyl)-2-[4-(1-cyclohexyl-2-diethylamino-ethyl)-piperazin-1-yl]-2-oxo-ethyl}-2-(1,2,3,4-tetrahydro-isoquinolin-1-yl)-acetamide |

TABLE A-continued

| Structure | Additional Information | NAME |
|---|---|---|
| | | N-{1-(4-chloro-benzyl)-2-[4-(1-cyclohexyl-2-diethylamino-ethyl)-piperazin-1-yl]-2-oxo-ethyl}-2-(2-methyl-2,3-dihydro-1H-isoindol-1-yl)-acetamide |
| | | 1,1,-Dimethyl-1,2,3,4-tetrahydro-isoquinoline-3-carboxylic acid {1-(4-chloro-benzyl)-2-[4-(1-cyclohexyl-2-diethlamino-ethyl)-piperazin-1-yl]-2-oxo-ethyl}-amide |
| | | 1,1,-Dimethyl-1,2,3,4-tetrahydro-isoquinoline-3-carboxylic acid {1-(4-chloro-benzyl)-2-[4-(1-cyclohexyl-2-diethlamino-ethyl)-piperazin-1-yl]-2-oxo-ethyl}-amide |

TABLE A-continued

| Structure | Additional Information | NAME |
|---|---|---|
| | | Isoquinoline-3-carboxylic acid {1-(4-chloro-benzyl)-2-[4-(1-cyclohexyl-2-diethylamino-ethyl)-piperazin-1-yl]-2-oxo-ethyl}-amide |
| | | N-{1-(4-chloro-benzyl)-2-[4-(1-cyclohexyl-2-(ethyl-methanesulfonyl-amino)-ethyl]-piperazin-1-yl]-2-oxo-ethyl}-2-(1,2,3,4-tetrahydro-isoquinolin-1-yl)-acetamide |
| | | N-{1-(4-chloro-benzyl)-2-[4-(1-cyclohexyl-2-(ethyl-methanesulfonyl-amino)-ethyl]-piperazin-1-yl]-2-oxo-ethyl}-2-(1,2,3,4-tetrahydro-isoquinolin-1-yl)-acetamide |

TABLE A-continued

| Structure | Additional Information | NAME |
|---|---|---|
| | | N-{1-(4-chloro-benzyl)-2-{4-[1-cyclohexyl-2-(ethyl-methanesulfonyl-amino)-ethyl]-piperazin-1-yl}-2-oxo-ethyl)-2-(2-methyl-2,3-dihydro-1H-isoindol-1-yl)-acetamide |
| | | Isoquinoline-3-carboxylic acid {1-(4-chloro-benzyl)-2-{4-[1-cyclohexyl-2-(ethyl-methanesulfonyl-amino)-ethyl]-piperazin-1-yl}-2-oxo-ethyl}-amide |
| | | 1,1-Dimethyl-1,2,3,4-Tetrahydro-isoquinoline-3-carboxylic acid (1-(4-chloro-benzyl)-2-{4-[1-cyclohexylmethyl-2-(ethyl-methanesulfonyl-amino)-ethyl]-piperazin-1-yl}-2-oxo-ethyl)-amide |

TABLE A-continued

| Structure | Additional Information | NAME |
|---|---|---|
| | | 1,1-Dimethyl-1,2,3,4-Tetrahydro-isoquinoline-3-carboxylic acid (1-(4-chloro-benzyl)-2-{4-[1-cyclohexylmethyl-2-(ethyl-methanesulfonyl-amino)-ethyl]-piperazin-1-yl}-2-oxo-ethyl)-amide |
| | | 1,1-Dimethyl-1,2,3,4-Tetrahydro-isoquinoline-3-carboxylic acid (1-(4-chloro-benzyl)-2-{4-[1-cyclohexylmethyl-2-(ethyl-methanesulfonyl-amino)-ethyl]-piperazin-1-yl}-2-oxo-ethyl)-amide |
| | | N-{1-(4-chloro-benzyl)-2-[4-(1-cyclohexyl-2-methanesulfonyl-amino-ethyl]-piperazin-1-yl]-2-oxo-ethyl}-2-(1,2,3,4-tetrahydro-isoquinolin-1-yl)-acetamide |

TABLE A-continued

| Structure | Additional Information | NAME |
|---|---|---|
| | | N-{1-(4-chloro-benzyl)-2-[4-(1-cyclohexyl-2-methanesulfonyl-amino-ethyl]-piperazin-1-yl]-2-oxo-ethyl}-2-(1,2,3,4-tetrahydro-isoquinolin-1-yl)-acetamide |
| | | N-{1-(4-chloro-benzyl)-2-[4-(1-cyclohexyl-2-methanesulfonyl-amino-ethyl]-piperazin-1-yl]-2-oxo-ethyl}-2-(1,2,3,4-tetrahydro-isoquinolin-1-yl)-acetamide |
| | | N-{1-(4-chloro-benzyl)-2-[4-(1-cyclohexyl-2-methanesulfonyl-amino-ethyl]-piperazin-1-yl]-2-oxo-ethyl}-2-(1,2,3,4-tetrahydro-isoquinolin-1-yl)-acetamide |

TABLE A-continued

| Structure | Additional Information | NAME |
|---|---|---|
| | | N-{1-(4-chloro-benzyl)-2-{4-[1-cyclohexyl-2-methanesulfonyl-amino-ethyl]-piperazin-1-yl}-2-oxo-ethyl)-2-(2-methyl-2,3-dihydro-1H-isoindol-1-yl)-acetamide |
| | | 1,1-Dimethyl-1,2,3,4-tetrahydro-isoquinoline-3-carboxylic acid {1-(4-chloro-benzyl)-2-[4-[1-cyclohexyl-2-methanesulfonylamino-ethyl)-piperazin-1-yl]-2-oxo-ethyl}-amide |
| | | 1,1-Dimethyl-1,2,3,4-tetrahydro-isoquinoline-3-carboxylic acid {1-(4-chloro-benzyl)-2-[4-[1-cyclohexyl-2-methanesulfonylamino-ethyl)-piperazin-1-yl]-2-oxo-ethyl}-amide |

TABLE A-continued

| Structure | Additional Information | NAME |
|---|---|---|
| | | 1,1-Dimethyl-1,2,3,4-tetrahydro-isoquinoline-3-carboxylic acid {1-(4-chloro-benzyl)-2-[4-[1-cyclohexyl-2-methanesulfonylamino-ethyl)-piperazin-1-yl]-2-oxo-ethyl}-amide |
| | | 1,2,3,4-Tetrahydro-isoquinoline-3-carboxylic acid [2-[4-(1-benzyl-2-diethylamino-ethyl)-piperazin-1-yl]-1-(4-chloro-benzyl)-2-oxo-ethyl]-amide |
| | | N-{1-(4-Chloro-benzyl)-2-[4-(1-cyclohexy-3-methyl-butyl)-piperazin-1-yl]-2-oxo-ethyl}-2-(2,3-dihydro-1H-isoindol-1-yl)-acetamide |

TABLE A-continued

| Structure | Additional Information | NAME |
|---|---|---|
| | | N-{1-(4-Chloro-benzyl)-2-[4-(2-cyclohexyl-1-cyclohexylmethyl-ethyl)-piperazin-1-yl]-2-oxo-ethyl}-2-(2,3-dihydro-1H-isoindol-1-yl)-acetamide |
| | | N-(1-(4-Chloro-benzyl)-2-{4-[1-cyclohexyl-2-(isobutyl-methanesulfonyl-amino)-ethyl]-piperazin-1-yl}-2-oxo-ethyl)-2-(2,3-dihydro-1H-isoindol-1-yl)-acetamide |
| | | N-(1-(4-Chloro-benzyl)-2-{4-[1-cyclohexyl-2-(isobutyl-methanesulfonyl-amino)ethyl]-piperazin-1-yl}-2-oxo-ethyl)-2-(2,3-dihydro-1H-isoindol-1-yl)-acetamide |

TABLE A-continued

| Structure | Additional Information | NAME |
|---|---|---|
| | | N-[2-{4-[2-(Acetyl-isobutyl-amino)-1-cyclohexyl-ethyl]-piperazin-1-yl}-1-(4-chloro-benzyl)-2-oxo-ethyl]-2-(2,3-dihydro-1H-isoindol-1-yl)-acetamide |
| | | N-[2-{4-[2-(Acetyl-isobutyl-amino)-1-cyclohexyl-ethyl]-piperazin-1-yl}-1-(4-chloro-benzyl)-2-oxo-ethyl]-2-(2,3-dihydro-1H-isoindol-1-yl)-acetamide |
| | | N-[1-(4-Chloro-benzyl)-2-(4-dicyclohexylmethyl-piperazin-1-yl)-2-oxo-ethyl]-2-(2,3-dihydro-1H-isoindol-1-yl)-acetamide |

More preferred is a compound selected from the group consisting of:

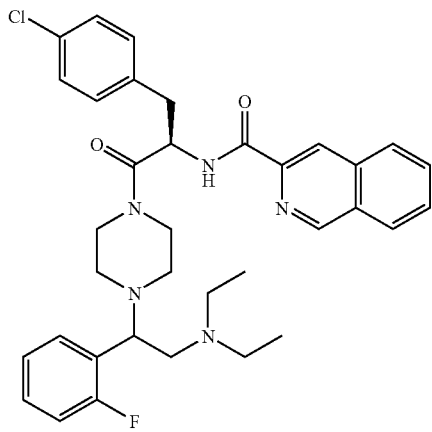

"A" isomer#2

Isoquinoline-3-carboxylic acid (1-(4-chloro-benzyl)-2-{4-[2diethylamino-1-(2-fluoro-phenyl)-ethyl]-piperazin-1-yl}-2-oxo-ethyl)-amide,

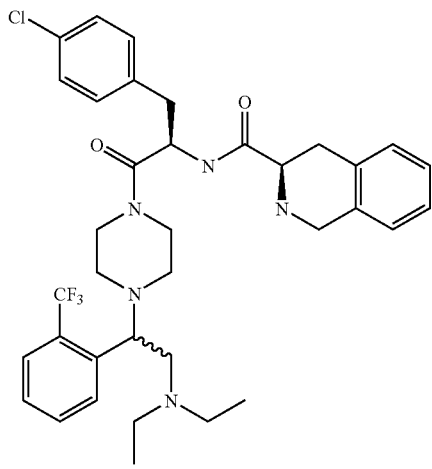

1,2,3,4-Tetrahydro-isoquinoline-3-carboxylic acid (1-(4-chloro-benzyl)-2-{4-[2-diethylamino-1-(2-trifluoromethyl-phenyl)-ethyl]-piperazin-1-yl}-2-oxo-ethyl)-amide,

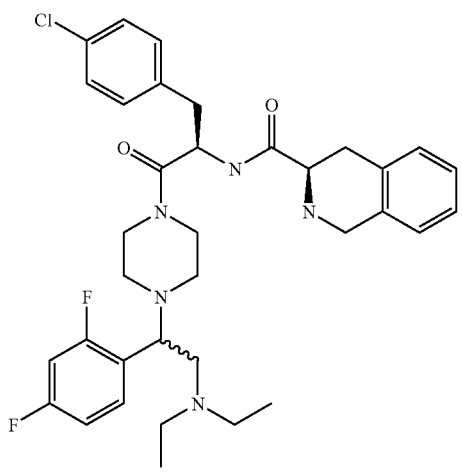

1,2,3,4-Tetrahydro-isoquinoline-3-carboxylic acid (1-(4-chloro-benzyl)-2-{4-[2-diethylamino-1-(2,4-difluoro-phenyl)-ethyl]-piperazin-1-yl}-2-oxo-ethyl)-amide,

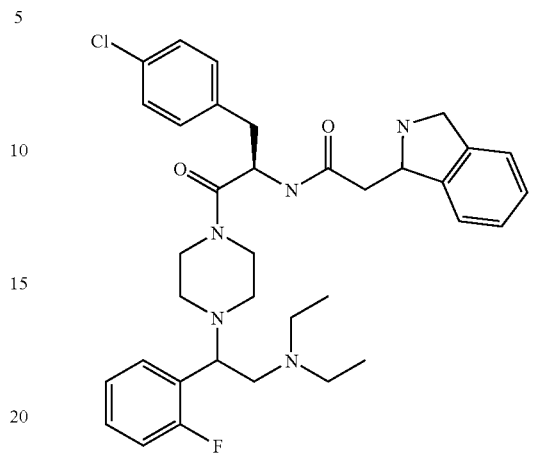

"A" isomer#2

N-(1-(4-Chloro-benzyl)-2-{4-[2-diethylamino-1-(2-fluoro-phenyl)-ethyl]-piperazin-1-yl}-2-oxo-ethyl)-2-(2,3-dihydro-1H-isoindol-1-yl)-acetamide,

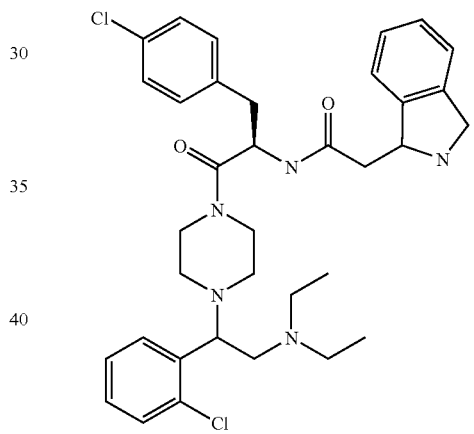

"A" isomer#2

N-(1-(4-Chloro-benzyl)-2-{4-[1-(2-chloro-phenyl)-2-diethylamino-ethyl]-piperazin-1-yl}-2-oxo-ethyl)-2-(2,3-dihydro-1H-isoindol-1-yl)-acetamide,

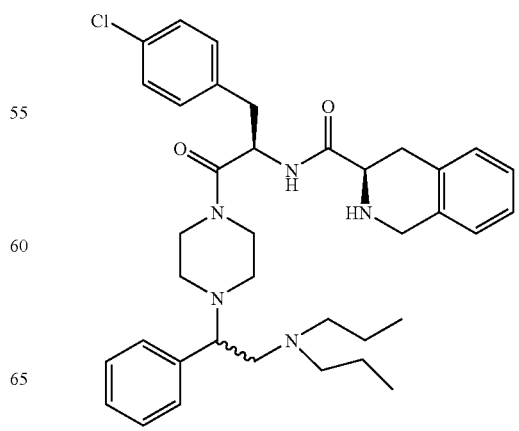

1,2,3,4-Tetrahydro-isoquinoline-3-carboxylic acid {1-(4-chloro-benzyl)-2-[4-(2-dipropylamino-1-phenyl-ethyl)-piperazin-1-yl]-2-oxo-ethyl}-amide,

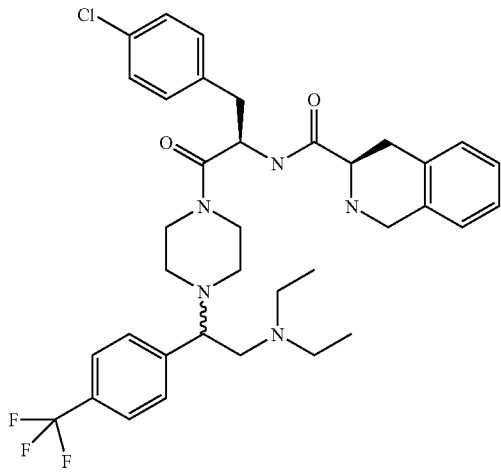

1,2,3,4-Tetrahydro-isoquinoline-3-carboxylic acid (1-(4-chloro-benzyl)-2-{4-[2-diethylamino-1-(4-trifluoromethyl-phenyl)-ethyl]-piperazin-1-yl}-2-oxo-ethyl)-amide, "A" isomer #2
2-{4-[3-(4-Chloro-phenyl)-2-(2-2,3-dihydro-1H-isoindol-1-yl-acetylamino)-propionyl]-piperazin-1-yl}-N,N-diethyl-2-(2-fluoro-phenyl)-acetamide,

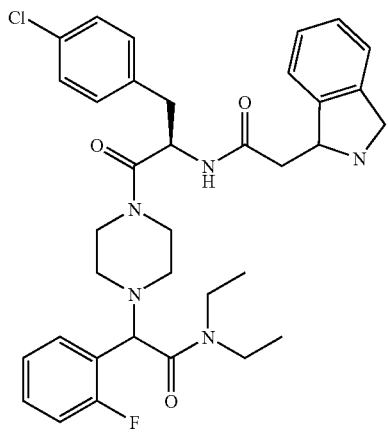

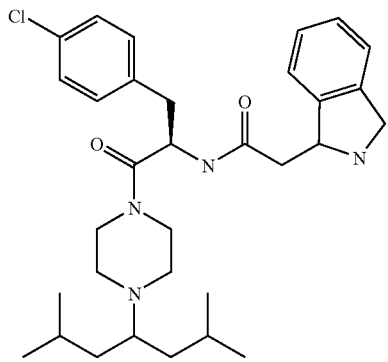

N-{1-(4-Chloro-benzyl)-2-[4-(1-isobutyl-3-methyl-butyl)-piperazin-1-yl]-2-oxo-ethyl}-2-(2,3-dihydro-1H-isoindol-1-yl)-acetamide,

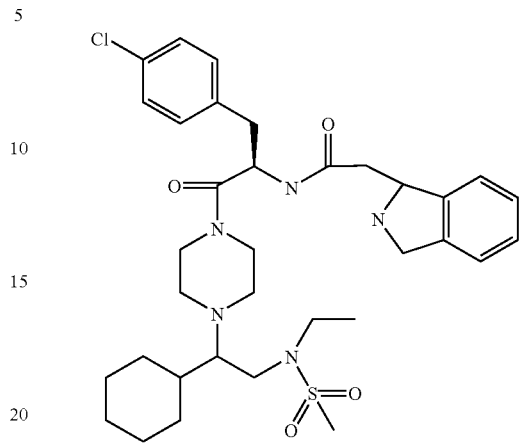

N-(1-(4-Chloro-benzyl)-2-{4-[1-cyclohexyl-2-(ethyl-methanesulfonyl-amino)-ethyl]-piperazin-1-yl}-2-oxo-ethyl)-2-(2,3-dihydro-1H-isoindol-1-yl)-acetamide,

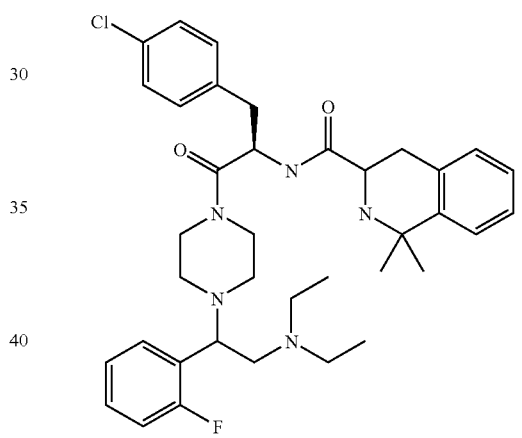

"A" isomer#2, "C" isomer#2
1,1-Dimethyl-1,2,3,4-tetrahydro-isoquinoline-3-carboxylic acid(1-(4-chloro-benzyl)-2-{4-[2-diethylamino-1-(2-fluoro-phenyl)-ethyl]-piperazin-1-yl}-2-oxo-ethyl)-amide,

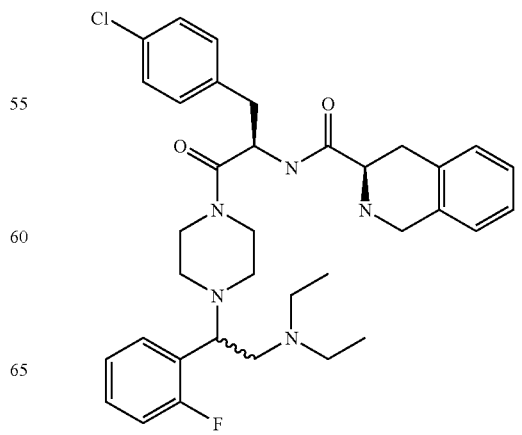

3-(4-Chloro-phenyl)-1-{4-[2-diethylamino-1-(2-fluoro-phenyl)-ethyl]-piperazin-1-yl}-2-[(1,2,3,4-tetrahydro-isoquinolin-3-ylmethyl)-amino]-propan-1-one,

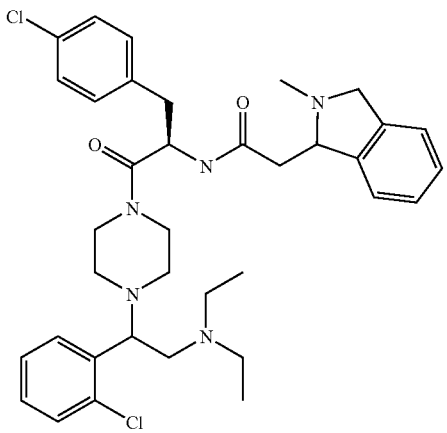

"A" isomer#2, "C" isomer#2
N-(1-(4-Chloro-benzyl)-2-{4-[1-(2-chloro-phenyl)-2-diethylamino-ethyl]-piperazin-1-yl}-2-oxo-ethyl)-2-(2-methyl-2,3-dihydro-1H-isoindol-1-yl)-acetamide,

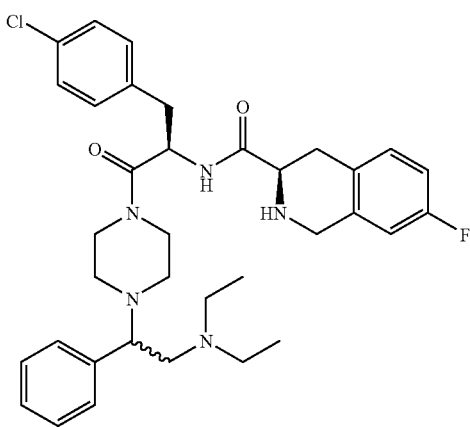

7-Fluoro-1,2,3,4-tetrahydro-isoquinoline-3-carboxylic acid{1-(4-chloro-benzyl)-2-[4-(2-diethylamino-1-phenyl-ethyl)-piperazin-1-yl]-2-oxo-ethyl}-amide,

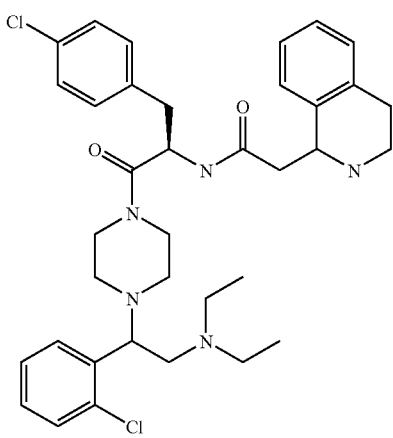

"A" isomer#2, "C" isomer#2
N-(1-(4-Chloro-benzyl)-2-{4-[1-(2-chloro-phenyl)-2-diethylamino-ethyl]-piperazin-1-yl}-2-oxo-ethyl)-2-(1,2,3,4-tetrahydro-isoquinolin-1-yl)-acetamide,

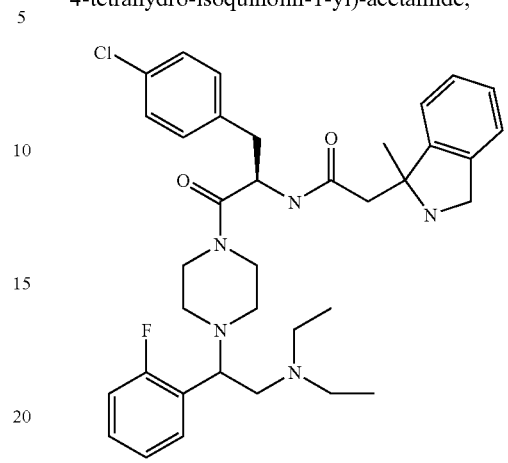

"A" isomer#2, "C" isomer#1
N-(1-(4-Chloro-benzyl)-2-{4-[2-diethylamino-1-(2-fluorophenyl)-ethyl]-piperazin-1-yl}-2-oxo-ethyl)-2-(1-methyl-2,3-dihydro-1H-isoindol-1-yl)-acetamide,

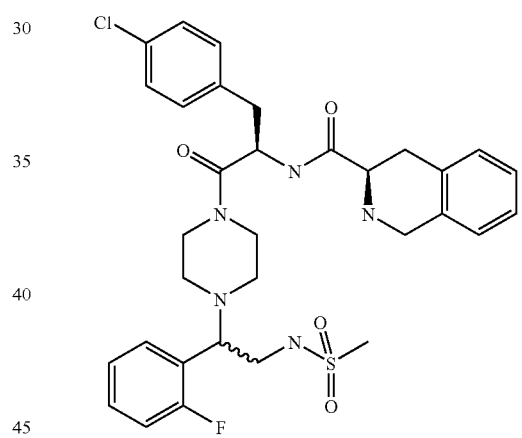

1,2,3,4-Tetrahydro-isoquinoline-3-carboxylic acid (1-(4-chloro-benzyl)-2-{4-[1-(2-fluoro-phenyl)-2-methanesulfonylamino-ethyl]-piperazin-1-yl}-2-oxo-ethyl)-amide,

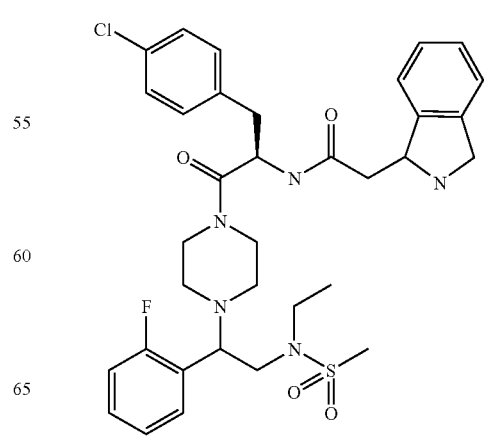

"A" isomer#2, "C" isomer#2

N-(1-(4-Chloro-benzyl)-2-{4-[2-(ethyl-methanesulfonyl-amino)-1-(2-fluoro-phenyl)-ethyl]-piperazin-1-yl}-2-oxo-ethyl)-2-(2,3-dihydro-1H-isoindol-1-yl)-acetamide,

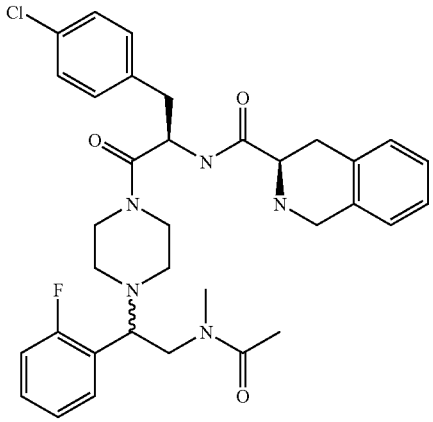

1,2,3,4-Tetrahydro-isoquinoline-3-carboxylic acid [2-{4-[2-(acetyl-methyl-amino)-1-(2-fluoro-phenyl)-ethyl]-piperazin-1-yl}-1-(4-chloro-benzyl)-2-oxo-ethyl]-amide,

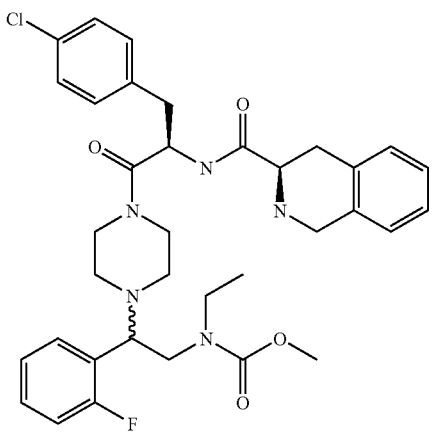

[2-(4-{3-(4-Chloro-phenyl)-2-[(1,2,3,4-tetrahydro-isoquinoline-3-carbonyl)-amino]propionyl}-piperazin-1-yl)-2-(2-fluoro-phenyl)-ethyl]-ethyl-carbamic acid methyl ester,

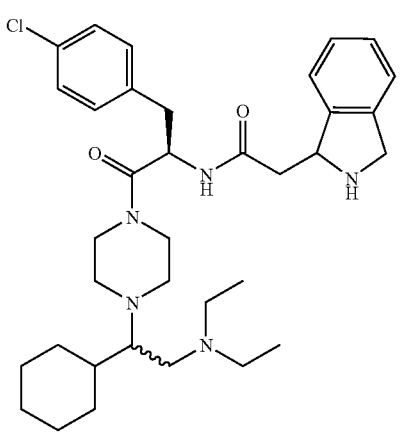

N-{1-(4-chloro-benzyl)-2-[4-(1-cyclohexyl-2-diethy-lamino-ethyl)-piperazin-1-yl]-2-oxo-ethyl}-2-(2,3-dihydro-1H-isoindol-1-yl)-acetamide,

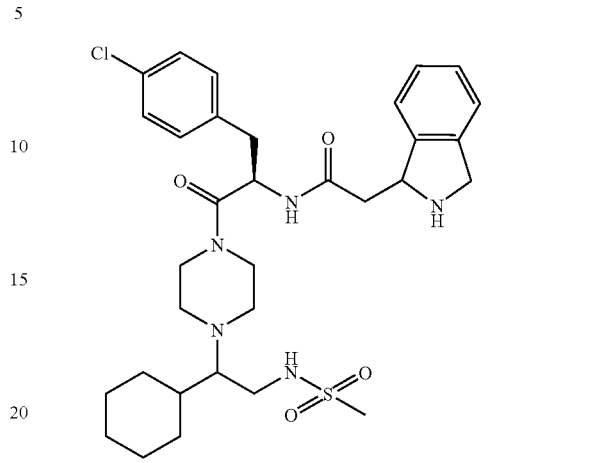

"C" isomer#2

N-{1-(4-chloro-benzyl)-2-[4-(1-cyclohexyl-2-methane-sulfonylamino-ethyl)-piperazin-1-yl]-2-oxo-ethyl}-2-(2,3-dihydro-1H-isoindol-1-yl)-acetamide, and

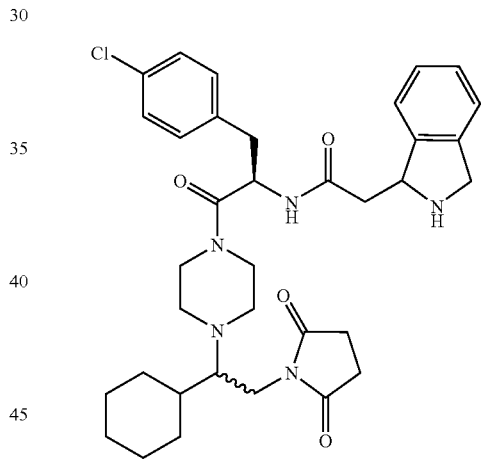

"C" isomer#2

N-(1-(4-chloro-benzyl)2-{4-[1-cyclohexyl-2-(2,5-dioxo-pyrrolidin-yl)-ethyl]-piperazin-1-yl}-2-oxo-ethyl]-2-(2,3-dihydro-1H-isoindol-1-yl)-acetamide, and pharmaceutically acceptable salt, stereoisomer and solvate thereof.

Preparation of the Compounds of the Invention

The preparation of the compounds of the present invention may be carried out via sequential or convergent synthetic routes. The skilled artisan will recognize that the three domains of a compound of formula I or II are connected via amide bonds. The skilled artisan can, therefore, readily envision numerous routes and methods of connecting the three domains via standard peptide coupling reaction conditions.

The phrase "standard peptide coupling reaction conditions" means coupling a carboxylic acid with an amine using a activating agent such as EDC, DCC, and HATU, in an inert solvent such as DCM, in the presence of a catalyst such as HOBT. The uses of protective groups for amine and carboxylic acids to facilitate the desired reaction and minimize undesired reactions are well documented. Conditions required to remove protecting groups which may be present can be found in Greene, et al., *Protective Groups in Organic Synthesis*, John Wiley & Sons, Inc., New York, N.Y. 1991. CBZ and BOC protecting groups are used extensively in the synthesis, and their removal conditions are known to those skilled in the art. For example, removal of CBZ groups can he achieved by catalytic hydrogenation with hydrogen in the presence of a noble metal or its oxide such as palladium on activated carbon in a protic solvent such as ethanol. In cases where catalytic hydrogenation is contraindicated by the presence of other potentially reactive functionality, removal of CBZ groups can also be achieved by treatment with a solution of hydrogen bromide in acetic acid. Removal of BOC protecting groups is carried out in a solvent such as DCM, methanol, or ethyl acetate, with a strong acid, such as TFA, HCl, or HCl gas.

However prepared, the compound of formula I or II, when existing as a diastereomeric mixture, may be separated into diastereomeric pairs, for example, by fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent. Alternatively, any enantiomer of a compound of the formula I may be obtained by stereospecific synthesis using optically pure starting materials or reagents of known configuration. Additionally, any enantiomer of a compound may be separated by chiral chromatography.

The A domains of the present invention, in general, may be prepared from commercially available starting materials via known chemical transformations. For example, the synthesis of certain "A" domains of the present invention is illustrated by Schemes 1–2 below.

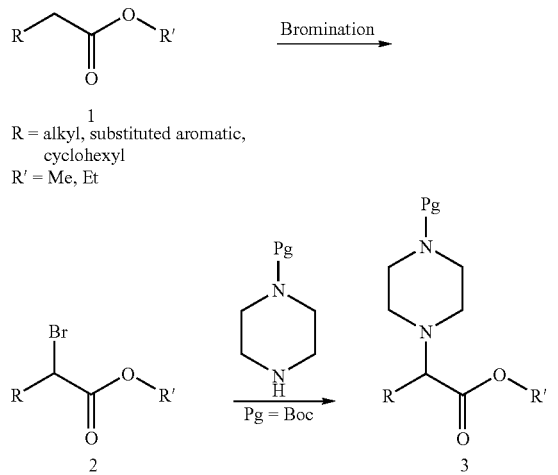

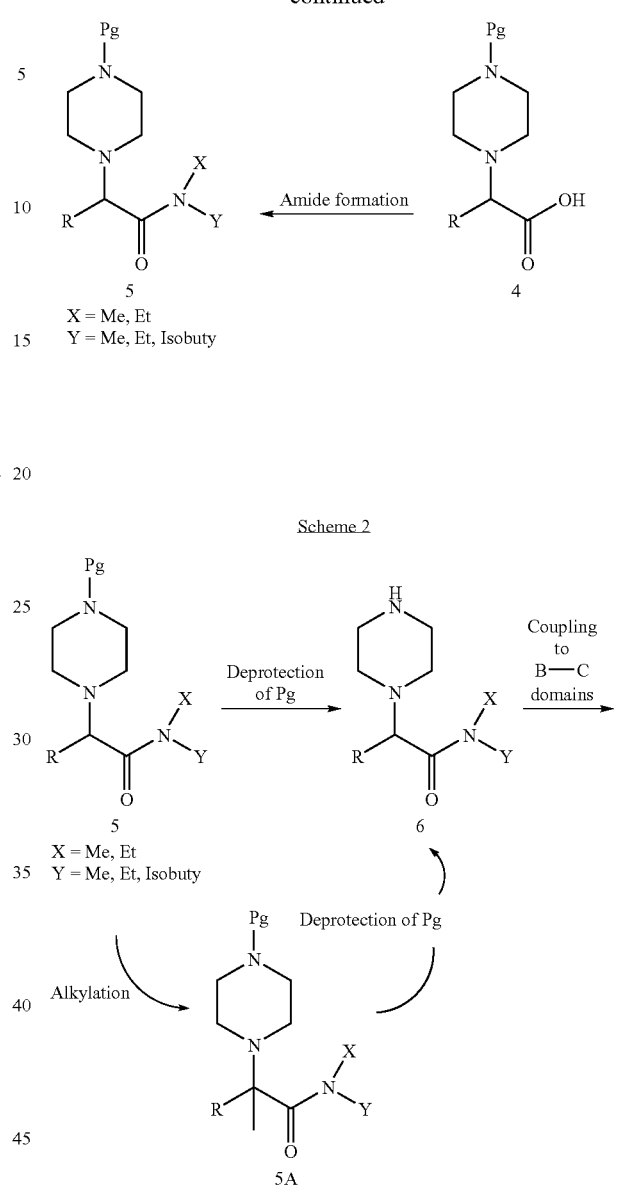

As shown in Scheme 1 and 2, synthesis of the internal amide "A" domains may begin with the appropriate esters of compound 1. Compound 1 may be brominated with N-bromosuccinimide or treated with LDA, followed by quenching with bromine, to yield α-bromo esters of compound 2. Compound 3 examples were prepared by reacting compound 2 with N-Boc piperazine and potassium carbonate. Saponification of the ester, with bases such as NaOH, in EtOH, yielded the acids of compound 4. Dialkyl amides of compound 5, were prepared from compound 4, the appropriate amine and coupling agents such as diethyl cyanophosphonate or EDC. The amides could then be deprotected with TFA to yield compound 6, or alkylated a to the amide (compound 5A), followed by deprotection. The piperazine amines of compound 6 were then coupled to the appropriate BC domains using standard coupling reagents such EDC or HATU.

Specifically, the A domain of certain compounds of the invention may be prepared as shown in Scheme 3 below.

Scheme 3

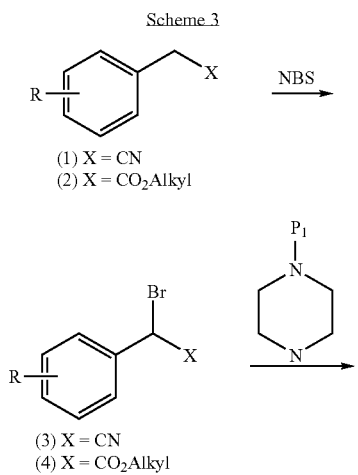

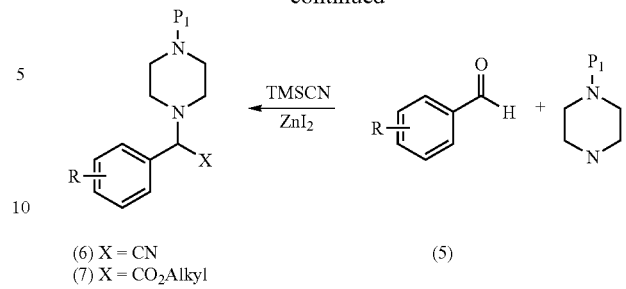

To the appropriately substituted benzyl nitrile or ester, (1) or (2) in Scheme 3, was added N-bromosuccinimide to form the benzyl bromide or other halide derivative, 3 or 4. The halides are then subjected to displacement reactions with N-Boc-piperazine to form compounds 6 or 7 respectively. Alternatively, compound 6 or 7 could be formed from a Strecker synthesis using compound 5 and the appropriately protected piperazine derivative.

Certain compounds of the invention may also be prepared following a scheme such as Scheme 4 below:

Scheme 4

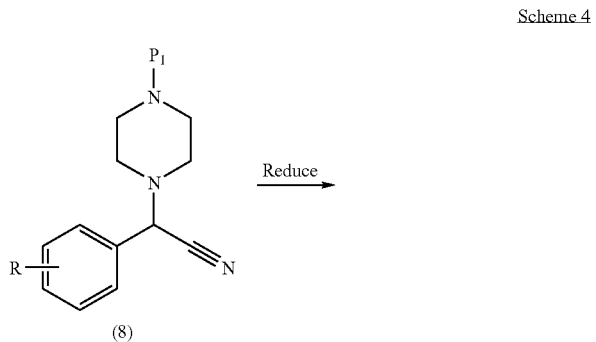

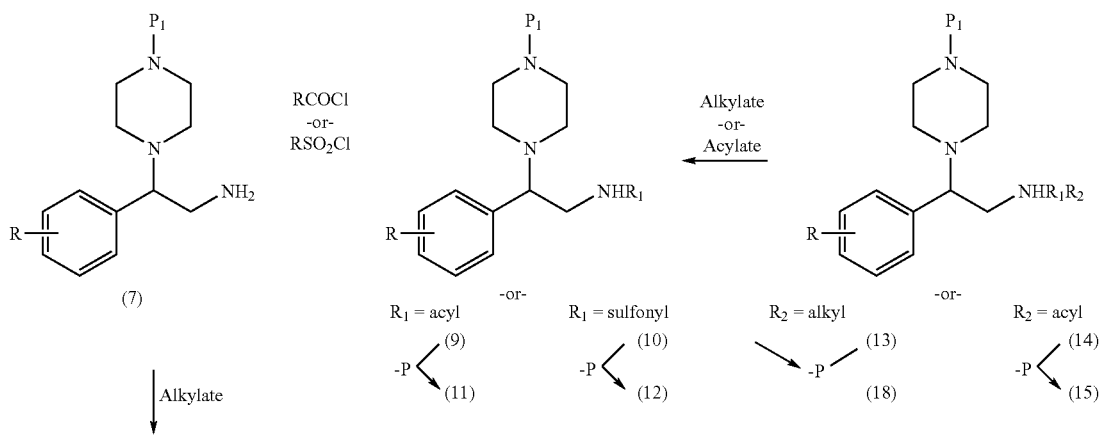

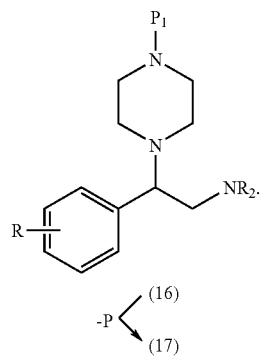

The nitrile of 6, scheme 4, may be reduced with LAH or other suitable reducing agent to form the primary amine (7). This amine could then be bis-alkylated, followed by protecting group removal, to form (16) or (17). The primary amine (7) may also be acylated or sulfonylated to form (9) or (10), respectively. The sulfonylated amine (10) could be alkylated to form (13), and the acylated compound (9) could be reduced, followed by sulfonylation, to form (14). Compounds of formula 9, 10, 13, and 14 may be deprotected to afford compounds of formula 11, 12, 13, and 15 respectively.

Unless otherwise indicated, reagents and procedures for effecting the reactions described herein are known to one of skill in the art and may be found in general reference texts such as *Advanced Organic Chemistry* by J. March, 5$^{th}$ edition, Wiley Interscience Publishers, New York, N.Y., and references therein.

Scheme 5 shows a method for resolving enantiomers formed by the A-domain pieces of compounds of formula I Scheme 5

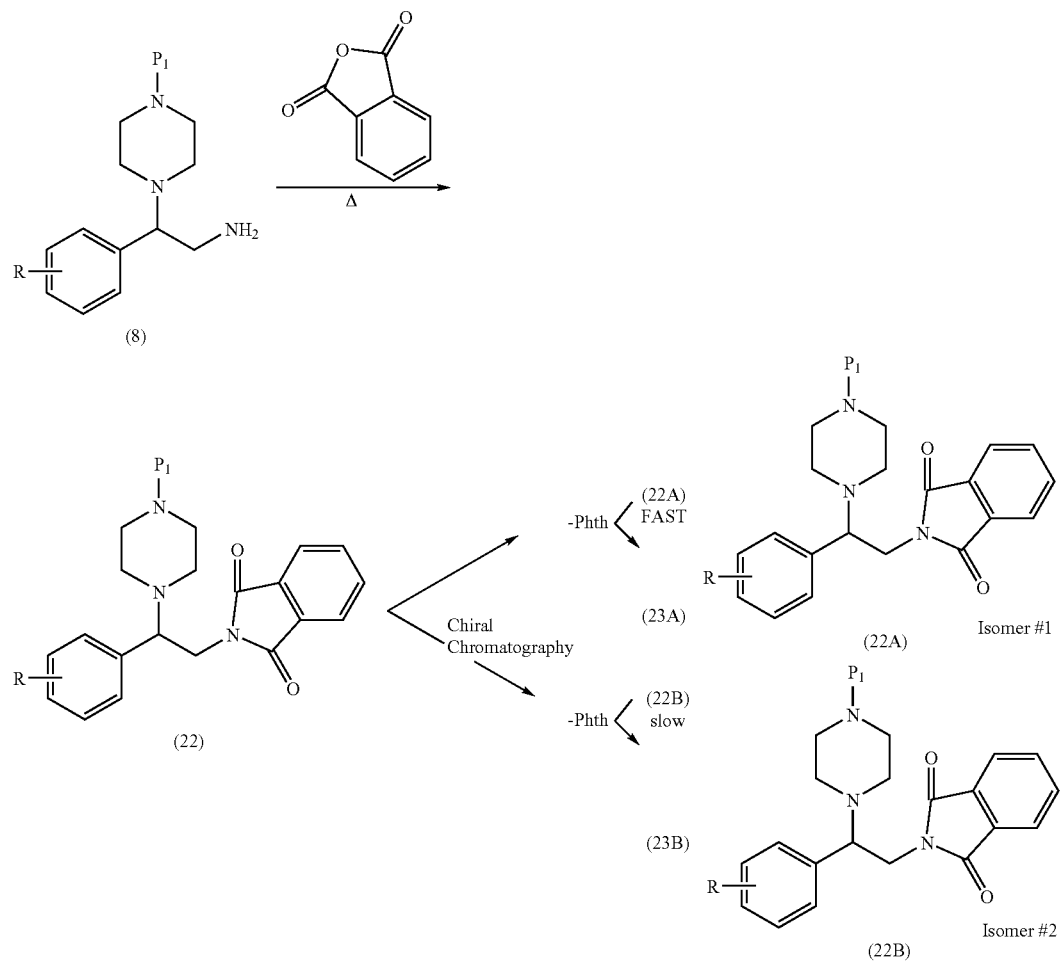

Chiral resolution of the appropriately substituted phenyl glycine derivative, i.e. compound (8) scheme 5, may be accomplished by formation of the phthalimide (22) followed by chiral chormatography. The faster eluting isomers are labelled isomer 1 and the next eluting isomer 2. Methods for preparing phthalimide derivatives of primary amine via phthalic anhydride are known to one of skill in the art. Similarly, protocols for chiral chromatography and other resolution methods are known to one of skill in the art.

An alternate protocol for preparing the non-glycine derivative A-domain is shown in scheme 6 below:

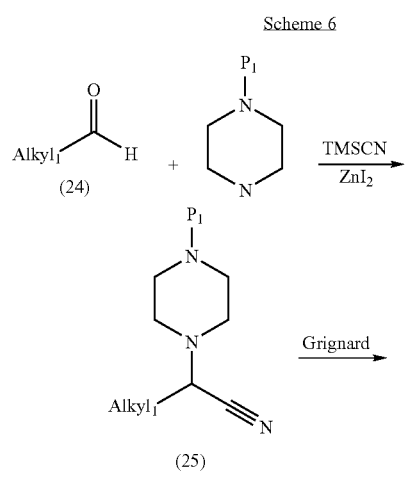

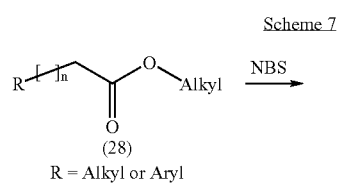
R = Alkyl or Aryl

For example, the diakyl piperazine derivatives, (26) or (27) scheme 6, are prepared from a Grignard addition to the nitrile (25). The nitrile (25), in turn, may be generated from a Strecker reaction with the appropriate alkyl aldehyde i.e. compound (24) and N-Boc piperazine.

An alternative protocol for preparing the A-domain is shown in scheme 7 below:

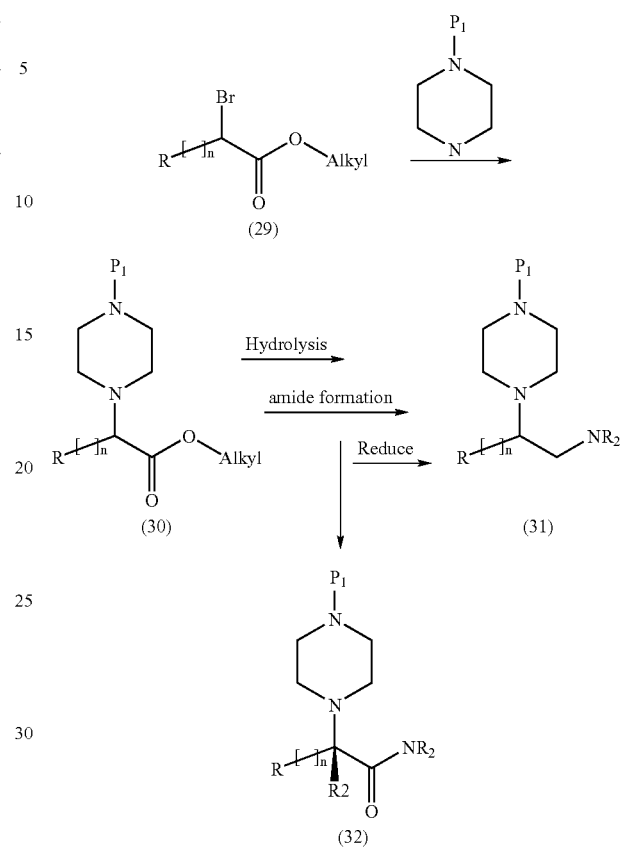

As shown in Scheme 7, an appropriately substituted ester i.e. compound (28) may be brominated using an N-bromosuccinimide (NBS) protocol to afford compound (29). The bromide of (29) is displaced with Boc-piperazine to yield the "A" domain ester (30). The ester (30) is then hydrolyzed to give the carboxylic acid, which is subsequently treated with the appropriate amine using standard amide forming procedures to form the dialkyl amide (32). The amide (32) may be reduced to yield the dialkyl amine (31). The bromination, piperazine displacement and alkylation protocols are known to one of skill in the art.

Compounds containing saturation in the A-domain can be prepared as follows as shown in the general Scheme 8 below:

Scheme 8

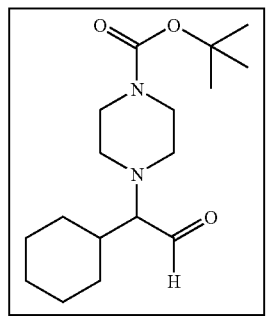

Preparation 2

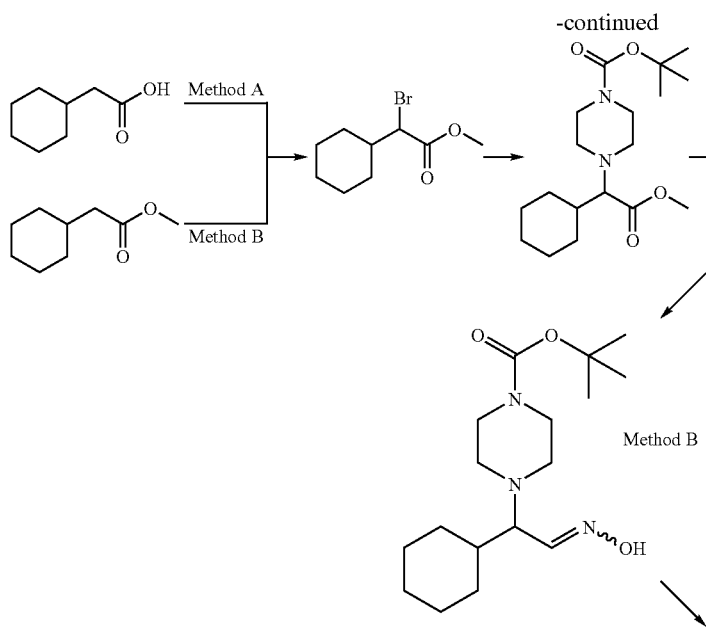
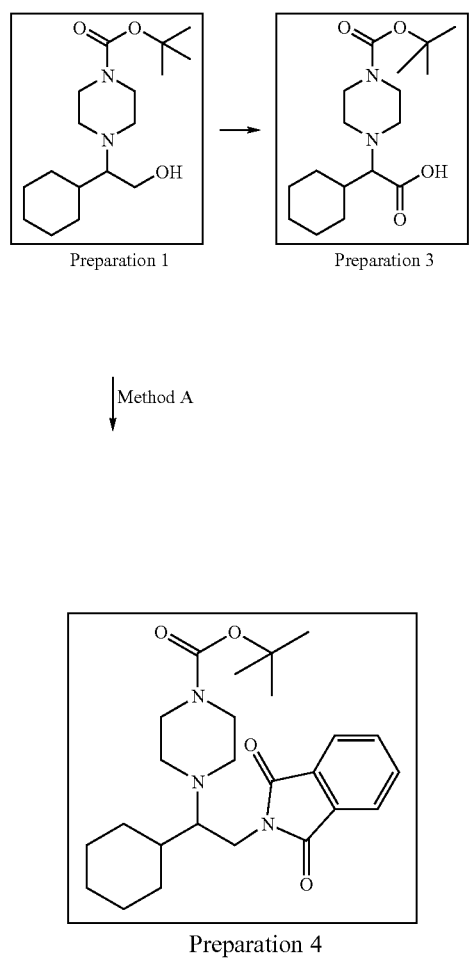

Preparation 1 Preparation 3

Method B Method A

Preparation 4

Synthesis begins with bromination of the commercially available cyclohexyl acetic acid, which provides the corresponding a-bromo derivative. This material can be reacted with a mono-protected piperazine to afford an α-piperazino ester. The ester moiety in this molecule can be reduced to the primary alcohol and then coupled with phthalimide under standard reaction conditions known to one of skill in the art. Alternatively, the phthalimido compound can be fashioned from the α-piperazino ester first by reduction to the aldehyde, followed by oxime formation, reduction to the amine, and condensation with phthalic anhydride. This intermediate is easily resolved into each antipode with chiral chromatography. Liberation of the amine by reducing the phthalimido intermide with excess hydrazine, followed by further functionalization provides acyl, sulfonyl, alkyl-acyl, alkyl-sulfonyl, and imide derivatives. These materials in turn are converted to the desired final products by coupling to the B and C fragments with standard peptide coupling methods. The reaction protocols described herein are known to one of skill in the art, are found in standard organic chemistry reference texts (i.e. J. March, supra), and are described in the experimental section.

Compounds that contain homologues of aryl glycine can be prepared in a similar fashion by starting with homologues of phenylacetic acid. Bromination affords the α-bromo material (homologue of phenyl acetic acid), which can be reacted with piperazine derivatives giving the α-piperizino acid derivatives. These materials can be converted to the desired amine substituted materials with protocols similar to the ones described for the saturated analogs described above. Details of the above procedures are found in the experimental section and also in standard reference texts.

"A" domain pieces wherein "y" is 1, or 2 are prepared utilizing the corresponding mono-Boc-homopiperazine analog i.e. diazepine when y is 2. This results in the corresponding "A" domain piece when reacted with an α-bromo material. The A-domain piece is processed further to obtain compounds of formula I or II-as described for the piperazine "A" domain compounds herein.

The "B" domain piece as used herein may be purchased, or prepared from readily available starting materials. A preferred "B" domain piece is 4-chloro-D-Phe available commercially.

The present invention also provides novel processes for preparing certain intermediates and/or compounds of the invention. For example a convergent synthesis of a key intermediate isoindoline (5) (see Scheme 9 below) via a Heck coupling, followed by a reductive amination, a ring cyclization and a resolution has been developed. Also, alternate asymmetric approaches including asymmetric Michael addition and asymmetric hydrogenation have also been developed to prepare compounds of the invention and/or intermediates thereof.

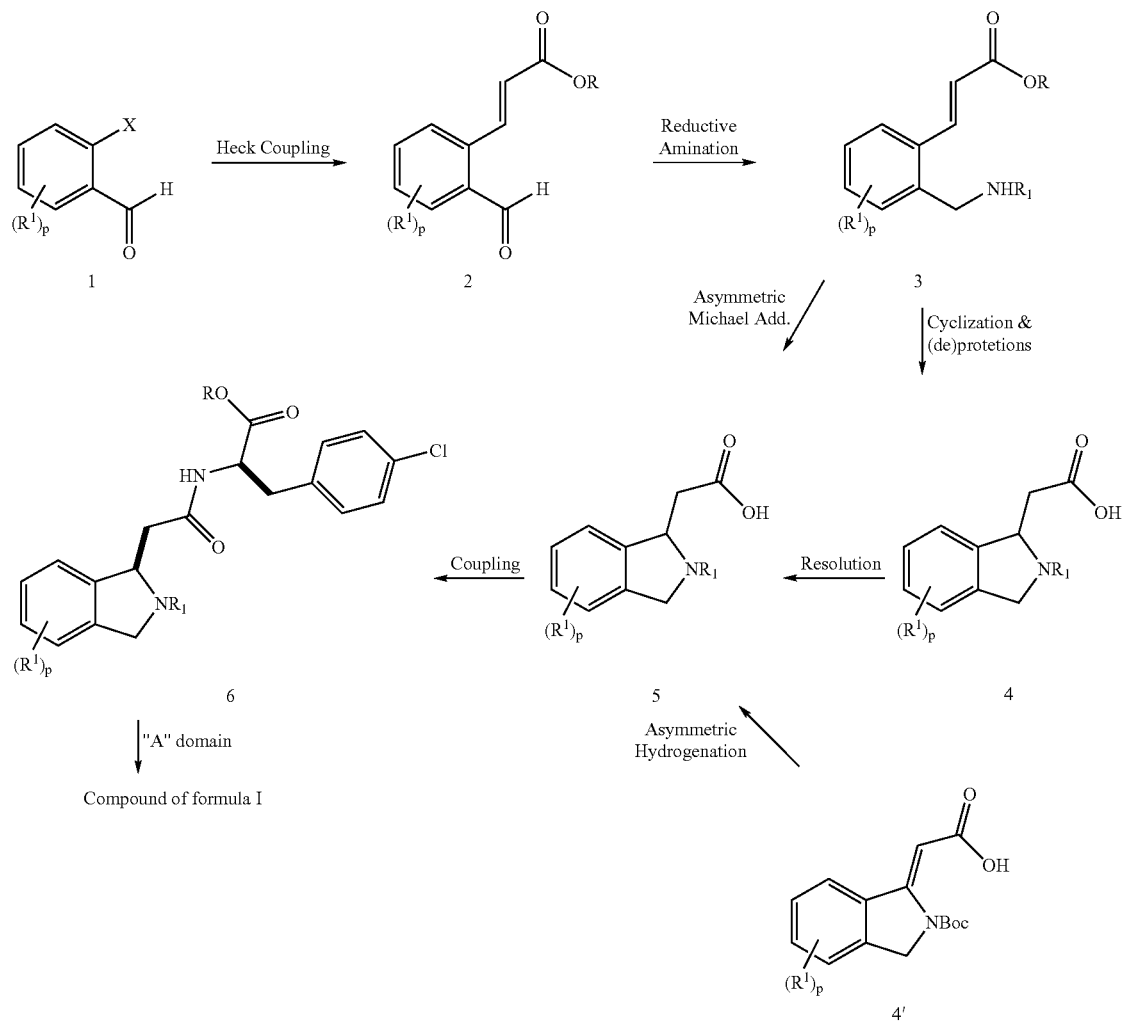

Scheme 9

As shown in scheme 9, the isoindoline compounds of the present invention may be prepared from 2-halobenzaldehyde 1 or substituted analog thereof (scheme 9) Preferred starting material is 2-bromobenzaldehyde or substituted analog thereof. Pd-mediated Heck coupling of 2-bromobenzaldehydes 1 with for example, methyl acrylate, provided α,β-unsaturated methyl esters 2, which undergoes reductive amination to give amines (or carbamates where $R_1$ is for example, Boc) 3. Various Heck coupling reagents and conditions were found suitable to effect the coupling reaction. Useful catalyst and ligands include $Pd(OAc)_2/PPh_3$, $Pd(OAc)PPh_3/BU_4NBr$, $Pd(PPH_3)_2Cl_2/CUI$, $Pd(OAC)_2/P(O\text{-Tol})_3$. Suitable solvent or solvent systems for the Heck coupling reaction include DMF, toluene and ethyl acetate. Most preferred base is triethylamine.

Reductive amination of the aldehyde functionality of 2 to amines is accomplished in good yields by reaction with benzylamine or α-methylbenzylamine in acidic conditions, followed by in situ reduction of the incipient imines with $NaCNBH_3$ at about pH 5. Other reducing agents including $Na(OAc)_3BH$ and $NaBH_4/H$ may also be used to effect reduction of the incipient imines. Interestingly, the resulting amines immediately cyclized to the isoindoline compounds under the same acidic conditions conditions for the reduction. Direct preparation of compound 4 may also be effected by use of $BocNH_2$ instead of benzylamine in the reductive amination step. Screening of various reducing agents demonstrated that the combination of $Et_3SiH$ and TFA in $CH_3CN$ represents the preferred method for effecting reductive amination using $BocNH_2$.

The N-Boc isoindolinecarboxylic acid 5 may also be prepared from 3 as the carbamate, by an intra-molecular Michael addition and ester hydrolysis. The resolution of the isoindolinecarboxylic acids 4 by crystallization afforded enantio-pure compounds 5.

Two alternate asymmetric approaches have also been developed for the synthesis of isoindolinecarboxylic acid 5 i.e. asymmetric Michael additions and asymmetric hydrogenation. In the asymmetric Michael addition approach, α-methylbenzyl amine is used as a chiral auxiliary to induce the enantio-selectivity. In the asymmetric hydrogenation approach, compound 4' could be converted to 5 stereoselectively in the presence of chiral ligands.

Finally the coupling of the isoindolines 5 with the "B" domain piece, i.e. D-Cl-Phe to afford compound 6 ("BC" piece) is accomplished by standard amino acid coupling reactions such as, for example, by the use of EDC or EDCI or other activating agents in the presence of suitable is dimethylaminopyridine (DMAP). The product (6) is then coupled with an "A" domain piece such as for example, 4-[2-Amino-1-(2-fluoro-phenyl)-ethyl]-piperazine-1-carboxylic acid tert-butyl ester (compound 207, table V), as discussed herein to afford the target MC$_4$R agonist compound of formula I by coupling reactions known to one of skill in the art.

Preferably, the isoindole or other "C" domain piece is coupled to an "AB" coupled domain piece to form the compound of formula I.

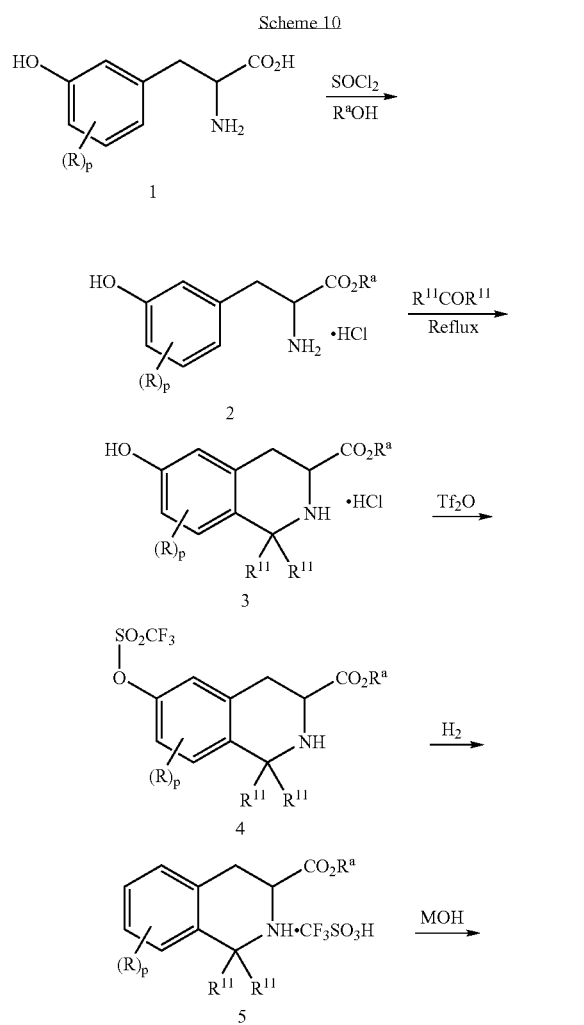

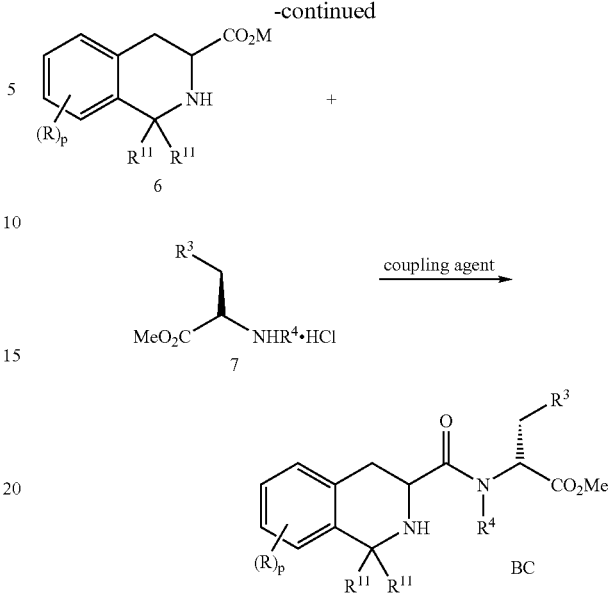

As shown in Scheme 10, m-tyrosine ester or analogs, including substituted analogs thereof, may be esterified by forming the acid halide followed by nucleophilic displacement of halide by the alkoxy group from an alcohol, i.e. methanol or ethanol. Where thionyl chloride or other halide source is used the product may be isolated as the acid addition salt (2). The resulting ester (2) is subjected to a Pictet-Spengler reaction by heating with a suitable ketone or aldehyde in refluxing conditions. For example, an unsubstituted isoquinoline backbone (3) may be formed by employing formaldehyde in the pictet-Spengler reaction. On the other hand, a gem-dimethyl substituted isoquinoline wherein R$^{11}$ is methyl, may be formed by using acetone as the ketone source and solvent. Other less reactive substituents may be substituted as the R11 group for the practice of the present invention. The product isoquinoline (3) may be isolated preferably as the acid addition salt. Where m-tyrosine is used as the starting material, the free hydroxyl group is removed first by protection/activation with a good leaving group such as, for example, reaction with triflic anhydride (trifluoromethane sulfonic anhydride) or methanesulfonic acid to form the triflate or mesylate in the presence of a base. The triflate is a preferred group used to set up the compound (3) for deoxygenation because of the extra electron withdrawing effect of the trifluoromethane substituent. The deoxygenation reaction is effected by hydrogenation at pressures of about 50psi. The product (4) may be isolated as the acid addition salt. The product (4) is hydrolyzed under basic conditions to afford the acid salt. Suitable bases for the above hydrolysis include aqueous sodium hydroxide, potassium hydroxide and sodium lithium hydroxide. The reaction is preferably performed in a mixture of aqueous and organic solvents. An exotherm during addition of base may be regulated (i.e. less than about 35° C.) to avoid overheating or "runaway reactions." The reaction product may be isolated by aqueous work up. Alternatively, the entire mixture may be concentrated and washed with organic solvents to afford the desired product (6) after crystallization.

The product (6) is then reacted with a "B" domain substrate such as, for example, 4-chloro-D-phenylalanine as described previously and in the experimental section. The resulting "BC" combination product is then reacted with an "A" domain piece such as, for example, 4-[2-Amino-1-(2fluoro-phenyl)-ethyl]-piperazine-1-carboxylic acid tert-butyl ester (compound 207, table V) to form the respective compound of formula I. Alternatively, the product (6) may be reacted with an "AB" domain combination product to afford a compound of formula I.

One of skill is aware that certain protections and deprotections of intermediates in Scheme 10, to form the carbamate, substituted amine or free amine at the isoquinolinyl nitrogen are possible and contemplated as within the scope of this invention. Unless otherwise specified, reagents and procedures for effecting the reactions described herein are known to one of skill in the art and may be found in general reference texts such as *Advanced Organic Chemistry* by J. March, 5$^{th}$ edition, Wiley Interscience Publishers, New York, N.Y., and references therein.

In an alternate procedure, the isoquinoline product i.e. compound (3) or (5) including their N-protected analogs may be resolved by reaction with a resolving agent .such as for example, L-tartaric acid, dehydroabietylamine or other resolving agents known to one of skill in the art.

Alternatively, asymmetric analogs of product (6) may be prepared by using asymmetric starting materials. For example, L-DOPA may be used in place of m-tyrosine ester in reactions essentially similar to those described and illustrated in Scheme 10, and in the examples, to afford the asymmetric analog of compound (6).

Tetrahydroisoquinoline acetic acid derivatives may be prepared and utilized as shown in Scheme 10a below:

of formula 10b. The compound of formula 10b may be protected as the compound 10c with a suitable protecting group (Pg) and then subjected to hydrogenation conditions including for example asymmetric hydrogenation to form a compound of formula 10d which may be chiral (depending on hydrogenation conditions, i.e. asymmetric versus non-assymetric hydrogenation). The compound of formula 10d or stereoisomer thereof, is reacted with a B-domain piece such as, for example, 4-chloro-D-phe to afford a BC piece (10e). The compound of formula 10e is then reacted with an A-domain piece to afford a compound of formula I. The details of the specific reaction steps are similar to or analogous to reactions taught herein, and in the experimental section. Furthermore, one of skill in the art is aware of that such intermediate reactions as hydrolysis and deprotection may be necessary to achieve optimum yields in certain steps of the scheme as shown. One of skill in the art is also aware of further common manipulations such as N-alkylation, or N-acylation, and alkylations on the benzene ring to afford other compounds of formula I.

Formulation

The compound of formula I or II is preferably formulated in a unit dosage form prior to administration. Therefore, yet another embodiment of the present invention is a pharmaceutical composition comprising a compound of formula I or II and one or more pharmaceutically acceptable carriers, diluents or excipients.

The present pharmaceutical compositions are prepared by known procedures using well-known and readily available ingredients. In making the formulations of the present invention, the active ingredient (formula I or II compound) will usually be mixed with a carrier, or diluted by a carrier, or

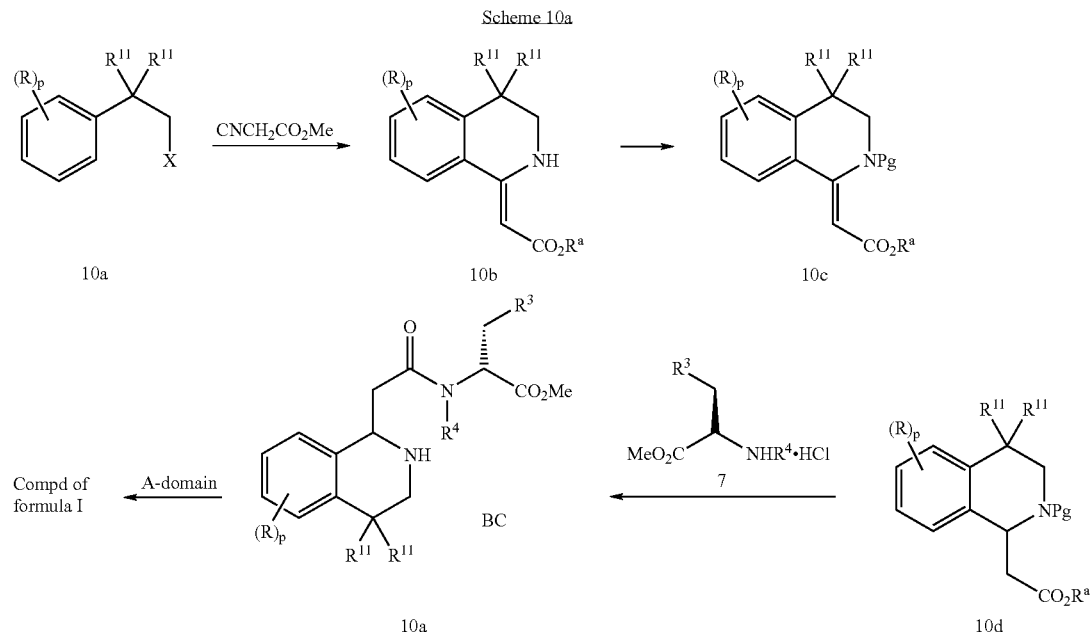

Scheme 10a

As shown in Scheme 10a, a compound of formula 10a wherein X is halogen, preferably bromo or chloro, and R and R$^{11}$ are as defined previously, and which is obtained commercially or prepared from commercial starting materials is reacted with cyanomethylethylacetate to afford a compound enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

Dose

The specific dose administered is determined by the particular circumstances surrounding each situation. These circumstances include, the route of administration, the prior medical history of the recipient, the pathological condition or symptom being treated, the severity of the condition/symptom being treated, and the age and sex of the recipient. However, it will be understood that the appropriate caregiver in light of the particular circumstances of the patient or recipient will determine the therapeutic dosage administered.

Generally, an effective minimum daily dose of a compound of formula I or II is about 1, 5, 10, 15, or 20 mg. Typically, an effective maximum dose is about 500, 100, 60, 50, or 40 mg. The exact dose may be determined, in accordance with the standard practice in the medical or veterinary arts of "dose titrating" the recipient; that is, initially administering a low dose of the compound, and gradually increasing the does until the desired therapeutic effect is observed.

Route of Administration

The compounds may be administered by a variety of routes including the oral, rectal, transdermal, subcutaneous, topical, intravenous, intramuscular or intranasal routes.

Combination Therapy

Compounds of Formula I or II may be used in combination with other drugs that are used in the treatment of the diseases or conditions for which compounds of formula I or II are useful. Such other drugs may be administered, by a route and in an amount commonly used therefor, contemporaneously or sequentially with a compound of formula I or II. When a compound of formula I or II is used contemporaneously with one or more other drugs, a pharmaceutical composition containing such other drugs in addition to the compound of formula I or II is preferred. Accordingly, the pharmaceutical compositions of the present invention include those that also contain one or more other active ingredients, in addition to a compound of formula I. Examples of other active ingredients that may be combined with a compound of formula I or II, either administered separately or in the same pharmaceutical compositions, include, but are not limited to:

(a) insulin sensitizers including (i) PPARγ agonists such as the glitazones (e.g. troglitazone, pioglitazone, englitazone, MCC-555, BRL49653 and the like), and compounds disclosed in WO97/27857, 97/28115, 97/28137 and 97/27847; (ii) biguanides such as metformin and phenformin;

(b) insulin or insulin mimetics;
(c) sulfonylureas such as tolbutamide and glipizide;
(d) alpha glucosidase inhibitors (such as acarbose),
(e) cholesterol lowering agents such as (i) HMG-CoA reductase inhibitors (lovastatin, simvastatin and pravastatin, fluvastatin, atorvastatin, and other statins), (ii) sequestrants (cholestyramine, colestipol and a dialkylaminoalkyl derivatives of a cross-linked dextran), (iii) nicotinyl alcohol nicotinic acid or a salt thereof, (iv) proliferator-activater receptor alpha agonists such as fenofibric acid derivatives (gemfibrozil, clofibrat, fenofibrate and benzafibrate), (v) inhibitors of cholesterol absorption for example beta-sitosterol and (acyl CoA:cholesterol acyltransferase) inhibitors for example melinamide, (vi) probucol, (vii) vitamin E, and (viii) thyromimetics;
(f) PPARδ agonists such as those disclosed in WO97/28149;
(g) antiobesity compounds such as fenfluramine, dexfenfluramine, phentermine, sibutramine, orlistat, and other beta-3 adrenergic receptor agonists such as those described in U.S. patent application Ser. No.'s 60/217,965, 60/241,614 and 60/247,304;
(h) feeding behavior modifying agents such as neuropeptide Y antagonists (e.g. neuropeptide Y5) such as those disclosed in WO 97/19682, WO 97/20820, WO 97/20821, WO 97/20822 and WO 97/20823;
(i) PPAR alpha agonists such as described in WO 97/36579 by Glaxo;
(j) PPARγ antagonists as described in WO97/10813;
(k) serotonin reuptake inhibitors such as fluoxetine and sertraline;
(l) growth hormone secretagogues such as MK-0677; and
(m) agents useful in the treatment of male and/or female sexual dysfunction such as phosphodiester V inhibitors such as sildenafil and ICI-351, and alpha-2 adrenergic receptor antagonists, such as phentolamine mesylate; and dopamine-receptor agonists, such as apomorphine.

Demonstration of Function

A. Binding Assay.

The radioligand binding assay is used to identify competitive inhibitors of $^{125}$I-NDP-alpha-MSH binding to cloned human MCRs using membranes from stably transfected human embryonic kidney (HEK) 293 cells.

HEK 293 cells transfected with human or rat melanocortinin receptors are grown either as adherent monolayers or suspension culture. Monolayer cells are grown in roller bottle cultures at 37° C. and 5% $CO_2$/air atmosphere in a 3:1 mixture of Dulbecco's modified Eagle medium (DMEM) and Ham's F12 containing 25 mM L-glucose, 100 units/ml penicillin G, 100 microgram/ml streptomyocin, 250 nanogram/ml amphoterin B, 300 microgram/ml genticin and supplemented with 5% fetal bovine serum. Monolayer cells are adapted to suspension culture (Berg et al., Biotechniques Vol. 14, No.6, 1993) and are grown in spinner or shaker flasks (37° C. and 7.5% $CO_2$/air overlay) in a modified DME/F12 medium containing 0.1 mM $CaCl_2$, 2% equine serum and 100 microgram/ml sodium heparin (to prevent cell-cell aggregation). Cells are harvested by centrifugation, washed in PBS, and pellets are stored frozen at −80° C. until membrane preparations.

The cell pellets are resuspended in 10 volumes of membrane preparation buffer (i.e., 1 g pellet to 10 ml buffer) having the following composition: 50 mM Tris pH 7.5 @ 4° C., 250 mM sucrose, 1 mM $MgCl_2$, Complete® EDTA-free protease inhibitor tablet (Boehringer Mannheim), and 24 micrograms/ml DNase I (Sigma, St. Louis, Mo.). The cells are homogenized with a motor-driven dounce using 20 strokes, and the homogenate is centrifuged at 38,000×g at 4° C. for 40 minutes. The pellets are resuspended in membrane preparation buffer at a concentration of 2.5–7.5 mg/ml and 1 milliliter aliquots of membrane homogenates are quickly frozen in liquid nitrogen and then stored at −80° C.

Solutions of a compound of formula I (300 picomolar to 30 micromolar) or unlabelled NDP-alpha-MSH (1 picomolar to 100 nanomolar) are added to 150 microliters of membrane binding buffer to yield final concentrations (listed in parantheses). The membrane binding buffer has the following composition: 25 mM HEPES pH 7.5; 10 mM $CaCl_2$; 0.3% BSA). One hundred fifty microliters of membrane binding buffer containing 0.5–5.0 microgram membrane protein is added, followed by 50 nanomolar $^{125}$I-NDP-alpha-MSH to final concentration of 100 picomolar. Additionally, fifty microliters of SPA beads (5 mg/ml) are added and the resulting mixture is agitated briefly and incubated for 10 hours at room temperature. The radioactivity is quantified in a Wallac Trilux Microplate Scintillation counter. $IC_{50}$ values obtained in competition assays are converted to affinity constants ($K_i$ values) using the Cheng-Prusoff equation: $K_i = IC_{50}/(1+D/K_d)$.

B. Functional assays.

Functional cell based assays are developed to discriminate agonists and antagonists.

Agonist Assay: HEK 293 cells stably expressing a human melanocortin receptor (see e.g., Yang, et al., *Mol-Endocrinol.*, 11(3): 274–80, 1997) are dissociated from tissue culture flasks using a trypsin/EDTA solution(0.25%; Life Technologies, Rockville, MD). Cells are collected by centrifugation and resuspended in DMEM (Life Technologies, Rockville, Md.) supplemented with 1% L-glutamine and 0.5% fetal bovine serum. Cells are counted and diluted to $4.5 \times 10^5$/ml.

A compound of formula I is diluted in dimethylsulfoxide (DMSO) ($3 \times 10^{-5}$ to $3 \times 10^{-10}$ M final concentrations) and 0.05 volume of compound solution is added to 0.95 volumes of cell suspension; the final DMSO concentration is 0.5%. After incubation at 37° C./5% $CO_2$ for 5 hours, cells are lysed by addition of luciferin solution (50 mM Tris, 1 mM $MgCl_2$, 0.2% Triton-X100, 5 mM DTT, 500 micromolar Coenzyme A, 150 micromolar ATP, and 440 micromolar luciferin) to quantify the activity of the reporter gene luciferase, an indirect measurement of intracellular cAMP production.

Luciferase activity is measured from the cell lysate using a Wallac Victor 2 luminometer. The amount of lumen production which results from a compound of formula I is compared to that amount of lumens produced in response to NDP- alpha-MSH, defined as a 100% agonist, to obtain the relative efficacy of a compound. The $EC_{50}$ is defined as the compound concentration that results in half maximal stimulation, when compared to its own maximal level of stimulation.

Melanocortin Receptor Whole Cell cAMP Accumulation Assay

Compound Preparation:

In the agonist assay, compounds are prepared as 10 mM and NDP-aMSH (control) as 33.3 µM stock solutions in 100% DMSO. These are serially diluted in 100% DMSO. The compound plate is further diluted 1:200 in compound dilution buffer (HBSS-092, 1 mM Ascorbic Acid, 1 mM IBMX, 0.6% DMSO, 0.1% BSA). The final concentration range being 10 µM–100 pM for compound and 33.33 nM–0.3 pM for control in 0.5% DMSO. Transfer 20 µl from this plate into four PET 96-well plates (all assays are performed in duplicate for each receptor).

Cell Culture and Cell Stimulation:

HEK 2.93 cells stably transfected with the MC3R and MC4R were grown in DMEM containing 10% FBS and 1% Antibiotic/Antimycotic Solution. On the day of the assay the cells were dislodged with enzyme free cell dissociation solution and resuspended in cell buffer (HBSS-092, 0.1% BSA, 10 mM HEPES) at 1×e6 cells/ml. Add 40 µl of cells/well to the PET 96-well plates containing 20 ul diluted compound and control. Incubate @ 37° C. in a waterbath for 20 minutes. Stop the assay by adding 50 µl Quench Buffer (50 mM Na Acetate, 0.25% Triton X-100).

Radioligand Binding Assays:

Radioligand binding assays were run in SPA buffer (50 mM Sodium Acetate, 0.1% BSA). The beads, antibody and radioligand were diluted in SPA buffer to provide sufficient volume for each 96-well plate. To each quenched assay well was added 100 ul cocktail containing 33.33 ul of beads, 33.33 µl antibody and 33.33 µl $^{125}$I-cAMP. This was based on a final concentration of 6.3 mg/ml beads, 0.65% anti-goat antibody and 61 pM of $^{125}$I-cAMP (containing 25000–30000 CPM) in a final assay volume of 210 µl. The plates were counted in a Wallac MicroBeta counter after a 12-hour incubation.

The data was converted to pmoles cAMP using a standard curve assayed under the same conditions. The data was analyzed using Activity Base software to generate agonist potencies ($EC_{50}$) and percent relative efficacy data to NDP-aMSH.

C. In Vivo Food Intake Models.

1) overnight food intake. Sprague Dawley rats are injected intracerebroventricularly with a test compound in 400 nL of 50% propylene glyco/artificial cerebrospinal fluid one hour prior to onset of dark cycle (12 hours). Food intake is determined using a computerized system in which each rat's food is placed on a computer monitored balance. Cumulative food intake for 16 hours post compound administration is measured.

2) Food intake in diet induced obese mice. Male C57/B16J mice maintained on a high fat diet (60% fat calories) for 6.5 months from 4 weeks of age are dosed intraperitoneally with a compound of formula I or II. Food intake and body weight are measured over an eight day period. Biochemical parameters relating to obesity, including leptin, insulin, triglyceride, free fatty acid, cholesterol and serum glucose levels are determined.

D. Rat Ex Copula Assay

Sexually mature male Caesarian Derived Sprague Dawley (CD) rats (over 60 days old) are used with the suspensory ligament surgically removed to prevent retraction of the penis back into the penile sheath during the ex copula evaluations. Animals receive food and water ad lib and are kept on a normal light/dark cycle. Studies are conducted during the light cycle.

1) Conditioning to Supine Restraint for Ex Copula Reflex Tests. This conditioning takes about 4 days. Day 1, the animals are placed in a darkened restrainer and left for 15–30 minutes. Day 2, the animals are restrained in a supine position in the restrainer for 15–30 minutes. Day 3, the animals are restrained in the supine position with the penile sheath retracted for 15–30 minutes. Day 4, the animals are restrained in the supine position with the penile sheath retracted until penile responses are observed. Some animals require additional days of conditioning before they are completely acclimated to the procedures; non-responders are removed from further evaluation. After any handling or evaluation, animals are given a treat to ensure positive reinforcement.

2) Ex Copula Reflex Tests. Rats are gently restrained in a supine position with their anterior torso placed inside a cylinder of adequate size to allow for normal head and paw grooming. For a 400–500 gram rat, the diameter of the cylinder is approximately 8 cm. The lower torso and hind limbs are restrained with a non-adhesive material (vetrap). An additional piece of vetrap with a hole in it, through which the glans penis will be passed, is fastened over the animal to maintain the preputial sheath in a retracted position. Penile responses will be observed, typically termed ex copulu genital reflex tests. Typically, a series of penile erections will occur spontaneously within a few minutes after sheath retraction. The types of normal reflexogenic erectile responses include elongation, engorgement, cup and flip. An elongation is classified as an extension of the penile body. Engorgement is a dilation of the glans penis. A cup is defined as an intense erection where the distal margin of the glans penis momentarily flares open to form a cup. A flip is a dorsiflexion of the penile body.

Baseline and/or vehicle evaluations are conducted to determine how and if an animal will respond. Some animals have a long duration until the first response while others are non-responders altogether. During this baseline evaluation, latency to first response time, number and type of responses are recorded. The testing time frame is 15 minutes after the first response.

After a minimum of 1 day between evaluations, these same animals are administered a compound of formula I at 20 mg/kg and evaluated for penile reflexes. All evaluations are videotaped and scored later. Data are collected and analyzed using paired 2 tailed t-tests to compared baseline and/or vehicle evaluations to drug treated evaluations for individual animals. Groups of a minimum of 4 animals are utilized to reduce variability.

Positive reference controls are included in each study to assure the validity of the study. Animals can be dosed by a number of routes of administration depending on the nature of the study to be performed. The routes of administration includes intravenous (IV), intraperitoneal (IP), subcutaneous (SC) and intracerebral ventricular (ICV).

E. Models of Female Sexual Dysfunction

Rodent assays relevant to female sexual receptivity include the behavioral model of lordosis and direct observations of copulatory activity. There is also a urethrogenital reflex model in anesthetized spinally transected rats for measuring orgasm in both male and female rats. These and other established animal models of female sexual dysfunction are described in McKenna, et al., *Am. J. Physiol.*, (Regulatory Integrative Comp. Physiol 30):R1276–R1285, 1991; McKenna, et al., *Pharm. Bioch. Behav.*, 40:151–156, 1991; and Takahashi, et al., *Brain Res.*, 359:194–207, 1985.

Results

Sample assay results showing the $MC_4$ agonist potency ($EC_{50}$), MC4 binding and relative efficacy of compounds of the present invention is provided in the results table below:

| Compd# or Example# | MC4 Binding Ki (nM) | MC4 $EC_{50}$ (nM) | Relative Eff. |
|---|---|---|---|
| Example N38 | 10.0 | 69.3 | 115.6 |
| Example N71 | 11.3 | 8.4 | 102.6 |
| Compd 814 | 18.1 | 127.0 | 108.6 |
| Compd 3251 | 5.8 | 76.7 | 67.0 |

Experimental Section

The following abbreviations have been used in this application for brevity:

| | |
|---|---|
| BINAP | 2,2'-Bis(diphenylphosphino)-1,1'-binaphthyl |
| Boc | t-butoxycarbonyl |
| CBZ | benzyloxycarbonyl |
| DCM | ($MeCl_2$) dichloromethane |
| DEAD | diethyl azodicarboxylate |
| DIPEA | diisopropylethylamine (also DIEA) |
| DMAP | 4-dimethylamino pyridine |
| DMF | N,N-dimethylformamide |
| DMSO | dimethylsulfoxide |
| aq. | aqueous |
| eq. | equivalent(s) |
| EDC | 1-(3-dimethylaminopropyl)-3-ethylcarbodiimide HCl |
| ESI-MS | electron spray ion-mass spectroscopy |
| Et | ethyl |
| EtOAc | ethyl acetate |
| HATU | O-(7-azabenzotriazol-1-yl)-N,N,N',N' tetramethyluronium hexafluorophosphate |
| HOAT: | 1-hydroxy-7-azabenzotriazole |
| HOBT | 1-hydroxybenzotriazole hydrate |
| HPLC | high performance liquid chromatography |
| HRMS | high resolution mass |
| MS | mass spectroscopy |
| | LRMS low resolution mass |
| Me | methyl |
| Ms | methylsulfonyl |
| $Pd_2(dba)_3$ | tris(dibenzylideneacetone)-dipalladium(0) |
| Ph | phenyl |
| Phe | phenylalanine |
| Pr | propyl |
| TBS | tertbutyldimethylsilyl |
| TFA | trifluoroacetic acid |
| TEA | triethylamine |
| THF | tetrahydrofuran |
| Tic | 1,2,3,4-tetrahydroisoquinoline-3-carboxylic acid |
| TLC | thin-layer chromatography |
| h | hour |
| rt | room temperature (also RT or r.t.) |

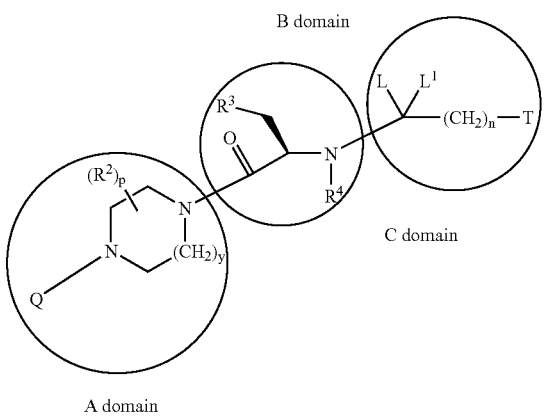

A domain / B domain / C domain

The following experimentals describe the synthesis of mc4 agononists of the above motif where an "a" domain is linked by an amide bond to a "b" domain which is connected by an amide or amine linkage to a "c" domain.

Compounds 1–19 (listed in Table I. below) were prepared substantially analogous to the following procedures from the respective commercially available materials.

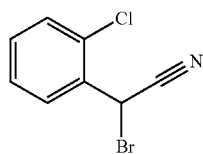

Procedure A

Preparation of Bromo-(2-chloro-phenyl)-acetonitrile (1).

To a solution of 2-chlorobenzylcyanide (1.0 g, 6.60 mmol) in CCl$_4$ (25 mL) was added N-bromosuccinamide (1.29 g, 7.26 mmol) and 2,2'-azobis-(2-methylpropionitrile) (0.05 g, 0.33 mmol). The reaction mixture was allowed to reflux for 48 h. The reaction mixture was then diluted with EtOAc (50 mL) and washed with 0.1 M NaOH (50 mL). The organic phase was concentrated to dryness yielding 1.0 g (66%) product.

MS (ES) N/A (M+1)

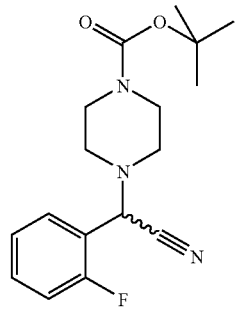

Procedure C

Preparation of 4-[Cyano-(2-fluoro-phenyl)-methyl] piperazine-1-carboxylic acid tert-butyl ester (7)

To 2-fluorobenzaldehyde (10.0 g, 80.57 mmol) in ether (10 mL) was added TMSCN (9.97 g, 100.72 mmol) followed by a catalytic amount of ZnI$_2$ and the solution was stirred while cooling with an ice bath as necessary until the catalyst dissolved and re-precipitated out. Boc-piperazine (14.9 g, 80.57 mmol) in MeOH (60 mL) was then added and the solution was allowed to stir at reflux for 4 h and then at room temperature for 18 h. The reaction mixture was then cooled to 0° C. and the product was collected by filtration. Concentration of the mother liquor and recrystallization from methanol provided 20.0 g (78%) product.

MS N/A [M+1]

TABLE I

| Cmpd. # | Structure | Prepared Analagous to Procedure | MS (ES) [M + 1] | Additional Information |
|---|---|---|---|---|
| 1 | 2-Cl-C$_6$H$_4$-CH(Br)-CN | A | N/A | |
| 2 | 3-Cl-C$_6$H$_4$-CH(Br)-CN | A | N/A | |

TABLE I-continued
| Cmpd. # | Structure | Prepared Analagous to Procedure | MS (ES) [M + 1] | Additional Information |
|---|---|---|---|---|
| 3 | 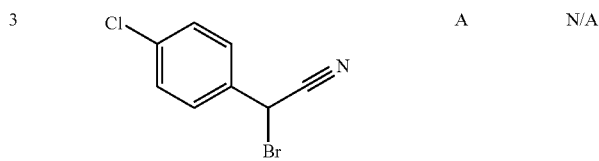 | A | N/A | |
| 4 | 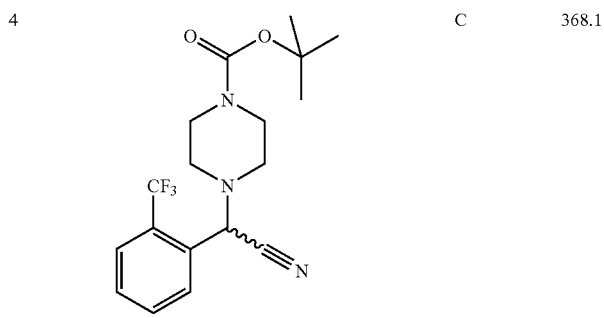 | C | 368.1 | |
| 5 | 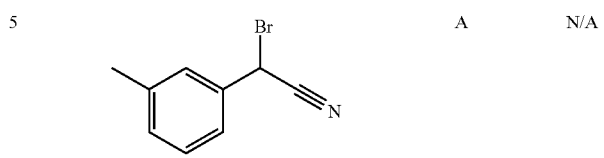 | A | N/A | |
| 6 | 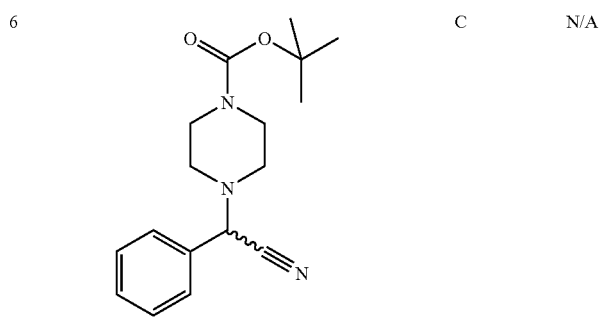 | C | N/A | |
| 7 | 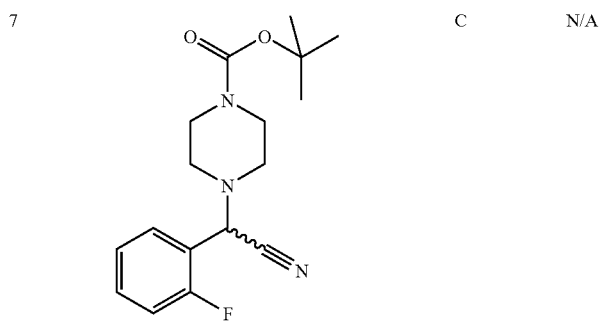 | C | N/A | |

TABLE I-continued

| Cmpd. # | Structure | Prepared Analagous to Procedure | MS (ES) [M + 1] | Additional Information |
|---|---|---|---|---|
| 8 | 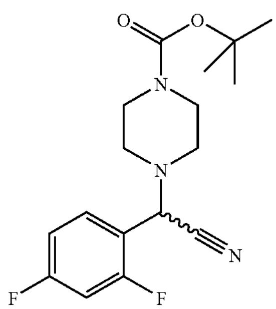 | C | N/A | |
| 9 | 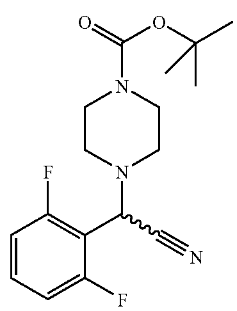 | C | N/A | |
| 10 | 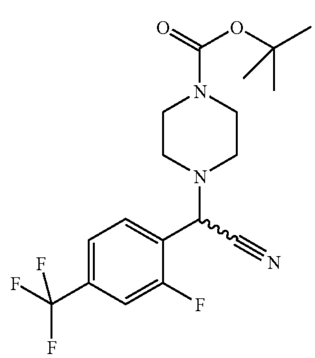 | C | N/A | |
| 11 | 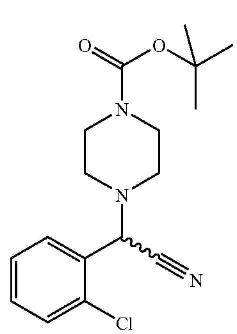 | C | N/A | |
| 12 | 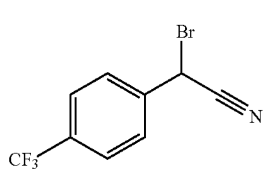 | A | N/A | |

TABLE I-continued
| Cmpd. # | Structure | Prepared Analagous to Procedure | MS (ES) [M + 1] | Additional Information |
|---|---|---|---|---|
| 13 | 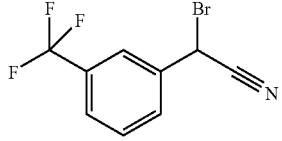 | A | N/A | |
| 14 | 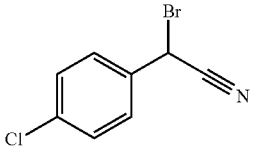 | A | N/A | |
| 15 | 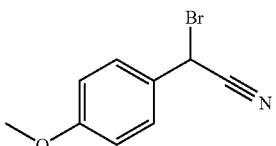 | A | N/A | |
| 16 | 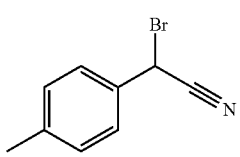 | A | N/A | |
| 17 | 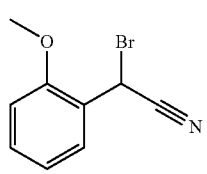 | A | N/A | |
| 18 | 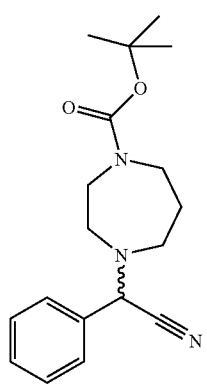 | C | 320.1 | |
| 19 | 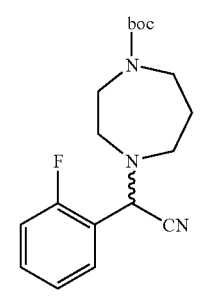 | C | 334.1 | |

Compounds 101–110 (listed in Table III. below) were prepared utilizing substantially analogous procedures from the respective bromobenzylnitriles.

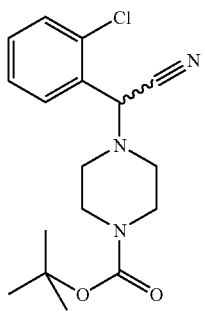

Procedure B

Preparation of 4-[(2-Chloro-phenyl)-cyano-methyl]-piperazine-1-carboxylic acid tert-butyl ester (101)

To a solution of bromo-(2-chloro-phenyl)-acetonitrile (1) (1.5 g, 6.45 mmol) in MeCN (25 mL) was added K$_2$CO$_3$ (1.78 g, 12.91 mmol), piperazine-1-carboxylic acid tert-butyl ester (1.32 g, 7.10 mmol) and tetrabutylammonium iodide (0.02 g, 0.06 mmol). The reaction mixture was allowed to reflux for 24 h. The reaction mixture was then diluted with EtOAc (100 mL) and washed with brine (100 mL). The organic phase was concentrated to dryness. The crude material was purified by chromatography (silica gel 60 mesh, eluting with a gradient of 5% EtOAc in hexanes to 1:1 hexanes/EtOAc) yielding 1.4 g (65%) of pure product.

MS (ES) 336.1 (M+1)

TABLE II

| Cmpd. # | Structure | Analagous To Procedure | MS (ES) [M + 1] |
|---|---|---|---|
| 101 | | B | 336.1 |
| 102 | 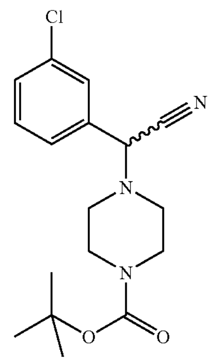 | B | 336.1 |
| 103 | 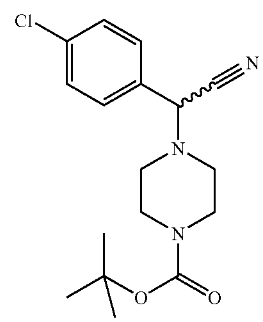 | B | 336.1 |
| 104 | 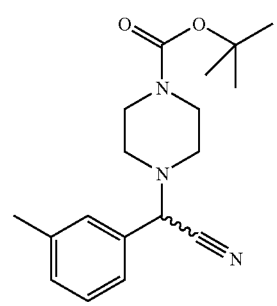 | B | N/A |
| 105 | 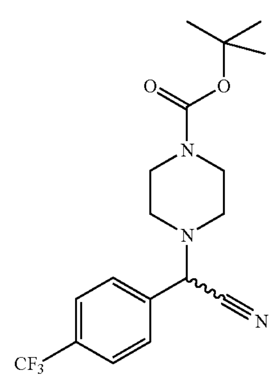 | B | 368.1 |

TABLE II-continued

| Cmpd. # | Structure | Analagous To Procedure | MS (ES) [M + 1] |
|---|---|---|---|
| 106 | 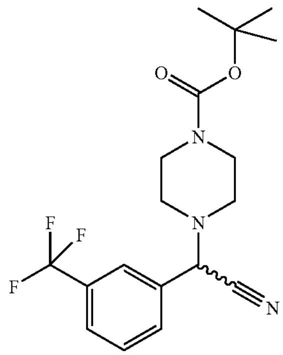 | B | 368.1 |
| 107 | 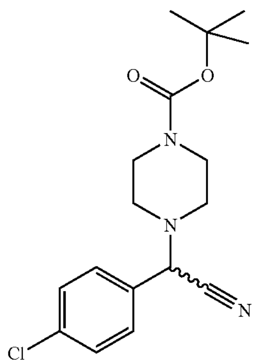 | B | 336.1 |
| 108 | 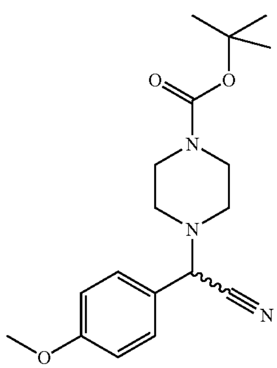 | B | 334.1 |
| 109 | 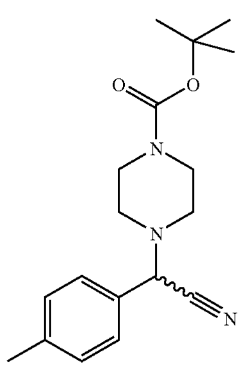 | B | N/A |
| 110 | 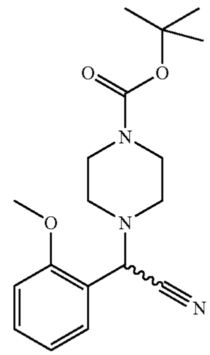 | B | 334.1 |

Compounds 201–223 (listed in Table V. below) were prepared utilizing substantially analogous procedures for reduction of the respective nitriles, amides or phthalimide-protected amines.

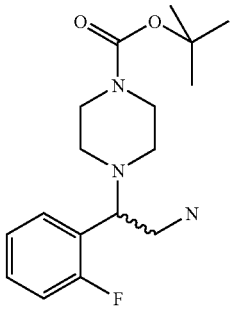

Procedure D

Preparation of 4-[2-Amino-1-(2-fluoro-phenyl)-ethyl]-piperazine-1-carboxylic acid tert-butyl ester (207)

1M LAH in THF (250 mL, 250 mmol) was cooled to −40° C. and 4-[Cyano-(2-fluoro-phenyl)-methyl]-piperazine-1-carboxylic acid tert-butyl ester (7) (20 g, 62.66 mmol) in THF (100 mL) was added slowly via addition funnel. The reaction mixture was allowed to stir for 2 h at −40° C. and then allowed to warm to 0° C. Reaction progress was monitored by H¹ NMR. The reaction mixture was then cooled to −40° C. again and H₂O (9.5 mL) was added. The reaction mixture was then diluted with THF (1 L) followed by the addition of 15% NaOH (9.5 mL) and H₂O (28.5 mL). The solution was then allowed to warm to room temperature. The aluminum salts were removed by filtration and the filtrate was concentrated to dryness. The resulting residue was taken up in EtOAc (500 mL) and H₂O (500 mL) and the aqueous layer was made acidic (pH=4) by cautious addition of a 25% aqueous solution of KHSO₄. The aqueous phase was then made basic (pH=10) with 5N NaOH and the product was extracted into EtOAc (500 ml) and concentrated to dryness. The starting material (nitrile) can be recovered by concentration of the original organic phase and purified by recrystallization from MeOH. The yield was 9.2 g (46%) pure product.

MS (ES) 324.2 [M+1]

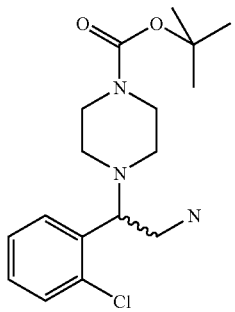

Procedure E

Preparation of 4-[2-Amino-1-(2-chloro-phenyl)-ethyl]-piperazine-1-carboxylic acid tert-butyl ester (201)

To NaBH$_4$ (0.79 g, 20.84 mmol) in THF (20 mL) at 0° C. was added TFA (2.38 g, 20.84 mmol) dropwise. To this cooled mixture was added 4-[(2-Chloro-phenyl)-cyano-methyl)-piperazine-1-carboxylic acid tert-butyl ester (101) (1.40 g, 4.17 mmol) in THF (10 mL) dropwise. The reaction mixture was allowed to stir at room temperature for 18 h. The reaction was quenched with H$_2$O (50 mL) and diluted with EtOAc (100 mL). The organic phase was washed with H$_2$O (100 mL) and brine (100 mL). The crude material was purified by chromatography (silica gel 60 mesh, eluting with 10% TEA/10% MeOH in EtOAc) yielding 0.49 g (34%) pure product.

MS (ES) N/A [M+1]

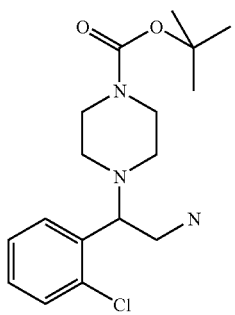

Procedure G

Preparation of 4-[2-Amino-1-(2-chloro-phenyl)-ethyl]piperazine-1-carboxylic acid tert-butyl ester (213)

To 4-[1-(2-Chloro-phenyl)-2-(1,3-dioxo-1,3-dihydro-isoindol-2-yl)-ethyl]-piperazine-1-carboxylic acid tert-butyl ester (302) (1.0 g, 2.15 mmol) in EtOH (5 mL) was added hydrazine (0.67 mL, 21.5 mmol) and the solution was heated at 60° C. for 1 h. The reaction mixture is then taken up in EtOAc (50 mL) and washed with 1N NaOH (50 mL). The organic phase was concentrated to dryness yielding 0.73 g (100%) pure product.

MS (ES) 340.2 [M+1]

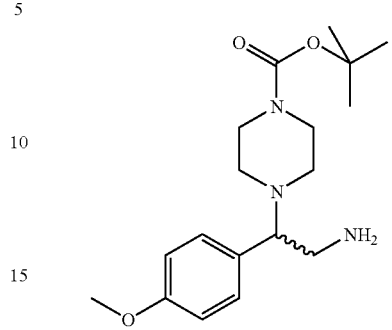

Procedure BB

Preparation of 4-[2-Amino-1-(4-methoxy-phenyl)-ethyl]-piperazine-1-carboxylic acid tert-butyl ester (218)

To a solution of 4-[2-Amino-1-(4-methoxy-phenyl)-ethyl]-piperazine-1-carboxylic acid tert-butyl ester (108) (1.01 g, 3.01 mmol) in 2M ammonia in methanol (100 mL) was added Raney nickel (0.50 g). The solution was allowed to stir at 40° C. under a hydrogen atmosphere (60 psi) for 18 h. The reaction mixture was then filtered through Celite. The filtrate was concentrated to dryness. The crude material was purified by chromatography (silica gel 60 mesh, eluting with a gradient of % TEA/5% MeOH in EtOAc) yielding 0.38 g (38%) pure product.

MS (ES) 336.2 (M+1)

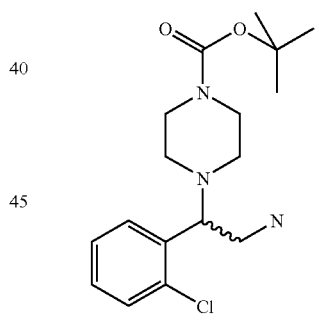

Procedure J

Preparation of 4-[2-Amino-1-(2-chloro-phenyl)-ethyl]-piperazine-1-carboxylic acid tert-butyl ester (212)

To 4-[Carbamoyl-(2-chloro-phenyl)-methyl]-piperazine-1-carboxylic acid tert-butyl ester 462(0.45 g, 1.27 mmol) in THF (10 mL) at 0° C. was added 1.0M BH$_3$ in THF (5.1 mL). The reaction was allowed to stir at reflux for 18 h. MeOH (5.0 mL) was added to the reaction mixture and mixture was then concentrated to dryness. The resulting residue was taken up in MeOH (10 mL) and allowed to reflux for 1 h. The reaction mixture was concentrated to dryness and the resulting residue was taken up in EtOAc (30 mL) and washed with sat. NaHCO$_3$ (30 mL) and brine (30 mL). The organic phase was concentrated to dryness yielding 0.18 g (43%) product.

MS (ES) 340.1[M+1]

TABLE V

| Cmpd. # | TABLE V, Structure | Prepared Analagous to Procedure | MS (ES) [M + 1] | Add'nal Info |
|---------|---------------------|-------------------------------|-----------------|--------------|
| 201 | | E | 340.1 | |
| 202 | | E | 340.1 | |
| 203 | | E | 340.1 | |
| 204 | | E | 374.2 | |

TABLE V-continued

| Cmpd. # | TABLE V, Structure | Prepared Analagous to Procedure | MS (ES) [M + 1] | Add'nal Info |
|---|---|---|---|---|
| 205 | | BB | 320.3 | |
| 206 | | E | N/A | |
| 207 | | D | 324.2 | |
| 208 | | G | 324.2 | "A" isomer #2 |

TABLE V-continued

| Cmpd. # | TABLE V, Structure | Prepared Analagous to Procedure | MS (ES) [M + 1] | Add'nal Info |
|---|---|---|---|---|
| 209 | | D | 342.2 | |
| 210 | | D | 342.2 | |
| 211 | | D | 392.3 | |
| 212 | | D | 340.1 | |

TABLE V-continued

| Cmpd. # | TABLE V, Structure | Prepared Analagous to Procedure | MS (ES) [M + 1] | Add'nal Info |
|---|---|---|---|---|
| 213 | | G | 340.0 | "A" isomer #2 |
| 214 | | G | 374.1 | "A" isomer #2 |
| 215 | | E | 374.1 | |
| 216 | | E | 374.1 | |

TABLE V-continued

| Cmpd. # | TABLE V, Structure | Prepared Analagous to Procedure | MS (ES) [M + 1] | Add'nal Info |
|---|---|---|---|---|
| 217 | | E | 340.1 | |
| 218 | | BB | 336.2 | |
| 219 | | E | 320.2 | |
| 220 | | BB | 336.2 | |

TABLE V-continued

| Cmpd. # | TABLE V, Structure | Prepared Analagous to Procedure | MS (ES) [M + 1] | Add'nal Info |
|---|---|---|---|---|
| 221 | | G | 340.0 | "A" isomer #1 |
| 222 | | G | 275.1 | |
| 223 | | G | 338.1 | |

Compounds 301–303 (listed in Table VI. below) were prepared substantially analogous to the following procedure F.

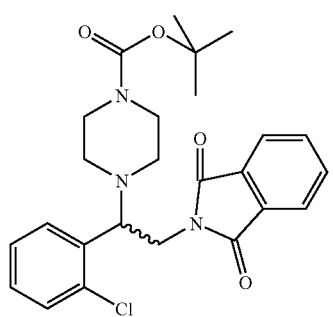

Procedure F

Preparation and resolution of 4-[1-(2-Chloro-phenyl)-2-(1,3-dioxo-1,3-dihydro-isoindol-2-yl)-ethyl]-piperazine-1-carboxylic acid tert-butyl ester (302)

To 4-2[-amino-1-(2-chloro-phenyl)-ethyl]-1-Boc-piperazine (201) (4.34g, 12.7 mmol) was added phthalic anhydride (1.89 g, 12.7 mmol). The mixture was heated at 130° C. for 1 h and then allowed to cool to room temperature. The resulting solid was recrystallized from MeOH. The enantiomers of the phthalimide-protected product were separated by chiral chromatography, using a Chiralcel OD (4.6×250 mm) column, eluting with 5% 3A alcohol in heptane at 1 mL/min. The first eluting isomer was labeled isomer #1 and the second eluting isomer #2. 5.6 g (95%) of the mixture was isolated and separated.

MS (ES) 470.3 [M+1].

TABLE VI
| Cmpd. # | TABLE VI, Structure | Prepared Analagous to Procedure | MS (ES) [M + 1] |
|---|---|---|---|
| 301 | 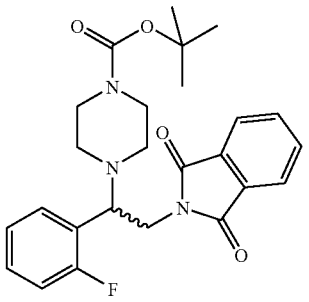 | F | 454.2 |
| 302 | 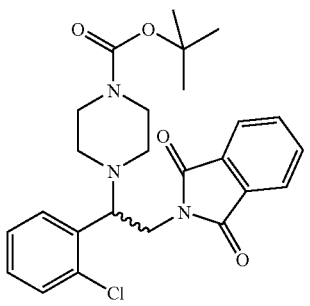 | F | 470.3 |
| 303 | 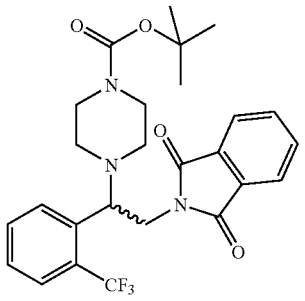 | F | 504.3 |

Compounds 351–352 (listed in Table VII. below) were prepared substantially analogous to the following procedure GG.

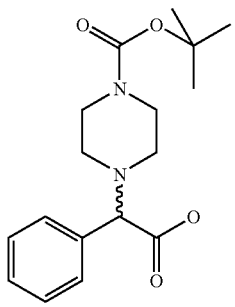

Procedure GG

Preparation of 4-(Carboxy-phenyl-methyl)-piperazine-1-carboxylic acid tert-butyl ester (351)

To 4-(Methoxycarbonyl-phenyl-methyl)-piperazine-1-carboxylic acid tert-butyl ester (151) (30.4 g, 87.25 mmol) in EtOH (200 mL) was added of 1N NaOH (192 mL) and the reaction mixture was allowed to stir at room temperature for 18 h. The reaction mixture is then concentrated to dryness. The resulting residue is taken up in $H_2O$ and acidified slowly at 0° C. with 10% $NaSO_4$ (pH=5–6). The desired product was then extracted into EtOAc. The organic phase was then concentrated to dryness yielding 24.3 g (86%) product.

MS (ES) 319.4 [M−1]

TABLE VII

| Cmpd. # | TABLE VII, Structure | Prepared Analagous to Procedure | MS (ES) [M + 1] | Add'nal Info |
|---|---|---|---|---|
| 351 | | GG | | N/A |
| 352 | | GG | | N/A |

Compounds 361 (listed in Table VIII. below) were prepared substantially analogous to the following procedure HH.

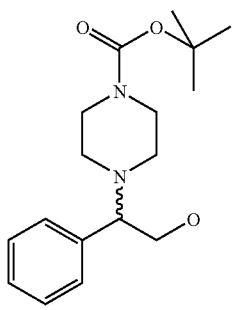

Procedure HH

Preparation of 4-(2-Hydroxy-1-phenyl-ethyl)-piperazine-1carboxylic acid tert-butyl ester (361)

To 4-(Carboxy-phenyl-methyl)-piperazine-1-carboxylic acid tert-butyl ester (351) (10.7 g, 33.43 mmol) in THF (120 mL) at 0° C. was slowly added $BH_3$—$SMe_2$ (6.69 mL, 66.86 mmol). The reaction mixture was allowed to warm to room temperature and then stirred at room temperature for 96 h. The reaction mixture was then quenched with sat. $NaHCO_3$ (120 mL) at 0° C. and diluted with $Et_2O$. The organic phase was dried with $MgSO_4$ and then concentrated to dryness. The crude material was purified by chromatography (silica gel 60 mesh, eluting with 50% EtOAc/50% hexanes); yielding 3.78 g (86%) pure product.

MS (ES) 307.3 [M+1]

Compounds 371 (listed in Table IX. below) were prepared substantially analogous to the following procedure II.

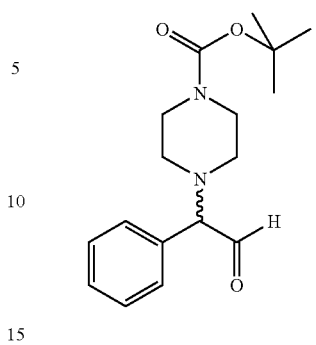

Procedure II

Preparation of 4-(2-Oxo-1-phenyl-ethyl)-piperazine-1-carboxylic acid tert-butyl ester (371)

To DMSO (2.19 mL) in $MeCl_2$ (40 mL) at −78° C. was added $(COCl)_2$ (1.29 mL, xmmol) dropwise. The reaction mixture was allowed to stir at −78° C. for 15 minutes and then 4-(2-Hydroxy-1-phenyl-ethyl)piperazine-1-carboxylic acid tert-butyl ester (364) (3.78 g, 12.34 mmol) in $MeCl_2$ (8 mL) was added. The reaction mixture was allowed to stir at −78° C. for 1 h and then TEA (8.6 mL) amine added. The reaction mixture was allowed to stir at −78° C. for another 3 h and then allowed to warm to room temperature and stirred for 18 h. The reaction mixture is then quenched with sat. $NH_4Cl$ (55 mL). The desired product is extracted into EtOAc (100 mL). The organic phase is dried over $MgSO_4$ and concentrated to dryness. The crude material was purified by chromatography (silica gel 60 mesh, eluting with 30% EtOAc in hexanes) yielding 2.37 g (63%) pure product.

MS (ES) 303.4 [M−1]

TABLE VIII

| Cmpd. # | TABLE VIII, Structure | Prepared Analagous to Procedure | MS (ES) [M + 1] |
|---|---|---|---|
| 361 | | HH | 307.3 |

TABLE IX

| Cmpd. # | TABLE VIII, Structure | Prepared Analagous to Procedure | MS (ES) [M + 1] |
|---|---|---|---|
| 371 | ![structure] | II | |

Compounds 401–463 (listed in Table X. below) were prepared substantially analogous to the following procedures for alkylation, sulfonylation, acylation, etc. of the respective 1° amines or acids.

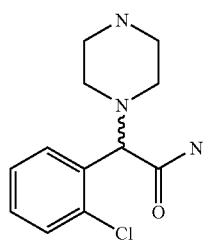

Procedure H

Preparation of 2-(2-Chloro-phenyl)-2-piperazin-1-yl-acetamide (461)

4-[(2-Chloro-phenyl)-cyano-methyl]-piperazine-1-carboxylic acid tert-butyl ester (11) (1.0 g, 2.98 mmol) was dissolved in $H_2SO_4$ (5.0 mL) and allowed to stir at room temperature for 18 h. The reaction mixture was cautiously poured over ice (50 mL) and made basic with 5N NaOH (50 mL). The desired product was extracted into EtOAc (100 mL) The organic phase was concentrated to dryness yielding 0.64 g (85%) product.
MS (ES) 254.1 [M+1]

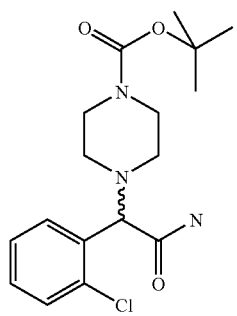

Procedure I

Preparation of 4-[Carbamoyl-(2-chloro-phenyl)-methyl]-piperazine-1-carboxylic acid tert-butyl ester (462)

To 2-(2-Chloro-phenyl)-2-piperazin-1-yl-acetamide (461) (0.64 g, 2.52 mmol) in a 1:1 mixture of $THF/H_2O$ (5.0 mL) was added $K_2CO_3$ (0.77 g, 5.55 mmol). The mixture was allowed stir for 15 min at room temperature. Boc-anhydride (0.60 g, 2.72 mmol) was then added and the reaction was allowed to stir at room temperature for 18 h. The reaction mixture was then diluted with EtOAc (50 mL) and washed with sat. $NaHCO_3$ (50 mL) and brine (50 mL). The crude material was purified by chromatography (silica gel 60 mesh, eluting with 5% MeOH in $CHCl_3$) yielding 0.50 g (56%) pure product.

MS (ES) 354.2 [M+1]

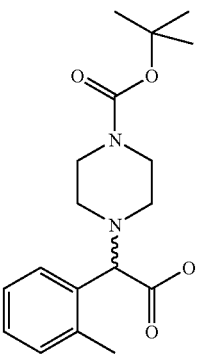

Procedure K

Preparation of 4-(Carboxy-o-tolyl-methyl)-piperazine-1-carboxylic acid tert-butyl ester (456)

To 4-(Ethoxycarbonyl-o-tolyl-methyl)-piperazine-1-carboxylic acid tert-butyl ester (152) (0.83 g, 2.27 mmol) in EtOH (10 mL) was added NaOH (0.46 g, 11.38 mmol) and the mixture stirred at room temperature for 18 h. The reaction mixture was then concentrated to dryness. The resulting residue was taken up in H$_2$O (100 mL) and acidified (pH=4–6) with 25% KHSO$_4$, and the desired acid was extracted into EtOAc (100 mL). The organic phase was washed with H$_2$O (100 mL) and brine (100 mL) and concentrated to dryness yielding 0.66 g (86%) pure product.

MS (ES) 279.1 [M+1]

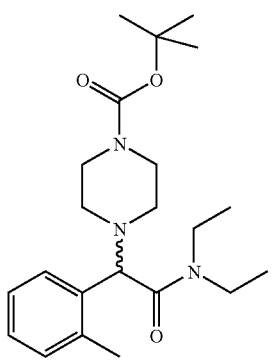

Procedure L

Preparation of 4-(Diethylcarbamoyl-o-tolyl-methyl)-piperazine-1-carboxylic acid tert-butyl ester (457)

To 4-(Carboxy-o-tolyl-methyl)-piperazine-1-carboxylic acid tert-butyl ester (352) (0.654 g, 1.95 mmol) in DMF (5 mL) was added diethyl cyanophosphonate (0.29 mL, 1.95 mmol), diethylamine (0.24 mL, 2.35 mmol) and TEA (0.32 mL, 2.35 mmol). The mixture was stirred at room temperature for 12 h and then diluted with EtOAc (50 mL). The reaction mixture was washed with sat. NaHCO$_3$ (50 mL), H$_2$O (50 mL) and brine (50 mL). The organic phase was concentrated to dryness. The crude material was purified by chromatography (silica gel 60 mesh, eluting with 50% hexanes/50% EtOAc) yielding 0.60 g (79%) pure product.

MS (ES) 390.3 [M+1]

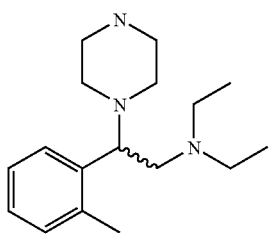

Procedure M

Preparation of Diethyl-(2-piperazin-1-yl-2-o-tolyl-ethyl)-amine (459)

To LAH (0.08 g, 2.23 mmol) in THF (10 mL) was added N,N-Diethyl-2-piperazin-1-yl-2-o-tolyl-acetamide (548) (0.22 g, 0.74 mmol) in THF (10 mL). The reaction mixture was allowed to stir at reflux for 8 h. Reaction was allowed to cool to room temperature and was then quenched by the addition of H$_2$O (0.08 mL), 15% NaOH (0.25 mL) and H$_2$O (0.08 mL) again. The resulting aluminum salts were allowed to stir at room temperature for 1 h and then removed by filtration. The filtrate was concentrated to dryness yielding 0.20 g (98%) product.

MS (ES) 190.1 [M+1]

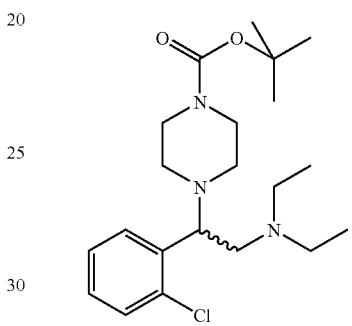

Procedure N

Preparation of 4-[1-(2-Chloro-phenyl)-2-diethylamino-ethyl]-piperazine-1-carboxylic acid tert-butyl ester (449)

To 4[-2-Amino-1-(2-chloro-phenyl)-ethyl]-piperazine-1-carboxylic acid tert-butyl ester (201) (2.15 g, 6.34 mmol) in DMF (15 mL) was added K$_2$CO$_3$ (4.38 g , 31.71 mmol) and ethyl bromide (2.07 g, 19.03 mmol). The reaction mixture was allowed to stir at room temperature for 18 h. The reaction mixture was diluted with EtOAc (100 mL) and washed with H$_2$O (100 mL) The organic phase was concentrated to dryness. The crude material was purified by chromatography (silica gel 60 mesh, eluting with 5% MeOH in CHC$_{13}$) yielding 1.55 g (62%) pure product.

MS (ES) 396.2 [M+1]

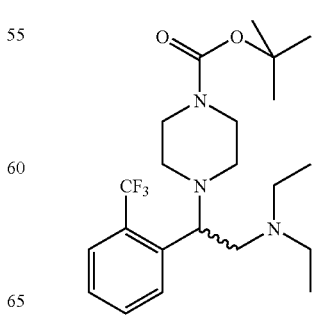

Procedure O

Preparation of 4-[2-Diethylamino-1-(2-trifluoromethyl-phenyl)-ethyl]-piperazine-1-carboxylic acid tert-butyl ester (404)

To a solution of a 4-[2-Amino-1-(2-trifluoromethyl-phenyl)-ethyl]-piperazine-1-carboxylic acid tert-butyl ester (204) (0.75 g, 2.01 mmol) in EtOH (50 mL) was added acetaldehyde (3.37 mL, 60.3 mmol) via RT distillation (warming flask with hand). Halfway through the addition of the acetaldehyde, sodium cyanoborohydride (0.631 g, 10.05 mmol) was added. The reaction was allowed to stir at room temperature for 18 h. The reaction mixture was concentrated to dryness. The resulting residue was taken up in EtOAc (50 mL) and washed with sat. NaHCO$_3$ (50 ml) and brine (50 mL). The organic phase was concentrated to dryness yielding 0.860 g (99%) product.

MS (ES) 430.2 [M+1]

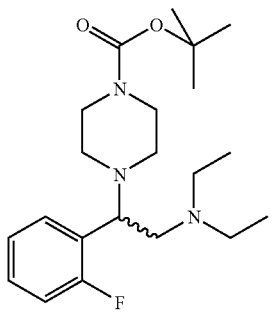

Procedure P

Preparation of 4-[2-Diethylamino-1-(2-fluoro-phenyl)-ethyl]-piperazine-1-carboxylic acid tert-butyl ester (407)

To 4-[2-Amino-1-(2-fluoro-phenyl)-ethyl]-piperazine-1-carboxylic acid tert-butyl ester (207) (0.10 g, 0.309 mmol) in DMSO (8.0 mL) was added K$_2$CO$_3$ (0.02 g, 0.111 mmol) and ethyl bromide (0.07 g, 0.618 mmol). The reaction was allowed to stir at room temperature for 18 h. A catalytic amount of BU$_4$N$^+$I$^-$ was added and the reaction was allowed to stir another 4 h. The reaction mixture was diluted with CHCl$_3$ (30 mL) and washed with H$_2$O (30 mL) and brine (30 mL). The organic phase was concentrated to dryness. The crude material was purified by chromatography (silica gel 60 mesh, eluting with a gradient of 100% EtOAc to 5% MeOH/5% TEA in EtOAc) yielding 0.06 g (50%) pure product.

MS (ES) 380.3 [M+1]

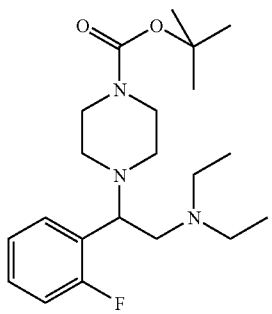

Procedure Q

Preparation of 4-[2-Diethylamino-1-(2-fluoro-phenyl)-ethyl]-piperazine-1-carboxylic acid tert-butyl ester (413)

To 4-[2-Amino-1-(2-fluoro-phenyl)-ethyl]-piperazine-1-carboxylic acid tert-butyl ester (208) (0.10 g, 0.309 mmol) in acetic acid (3.0 mL) at 0° C. was added NaBH$_4$ cautiously. The reaction was allowed to stir at room temperature for 2 h. The reaction mixture was allowed to stir at reflux for 18 h. The reaction mixture was cooled to room temperature and chilled 35% NaOH (30 mL) was added. The desired product was extracted with MeCl$_2$ (30 mL) and washed with H$_2$O (30 mL). The organic phase was concentrated to dryness yielding 0.11 g (94%) product.

MS (ES) 380.3 [M+1]

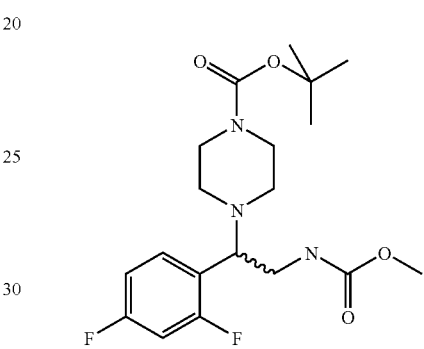

Procedure R

Preparation of 4-[1-(2,4-Difluoro-phenyl)-2-methoxycarbonylamino-ethyl]-piperazine-1-carboxylic acid tert-butyl ester (420)

To 4-[2-Amino-1-(2,4-difluoro-phenyl)-ethyl]-piperazine-1-carboxylic acid tert-butyl ester (209) (0.38 g, 1.13 mmol) in a 1:1 mixture of THF/H$_2$O (30 mL) was added NaOH (0.05 g, 1.24 mmol) and methyl chloroformate (0.11 g, 1.13 mmol ). The reaction was allowed to stir at room temperature for 2 h. The reaction mixture was then diluted with EtOAc (200 mL) and washed with H$_2$O (100 mL) and brine (100 mL). The organic phase was concentrated to dryness. The crude material was purified by chromatography (silica gel 60 mesh, eluting with 50% hexanes/50% EtOAc) yielding 0.23 g (50%) pure product.

MS (ES) 400.2 [M+1]

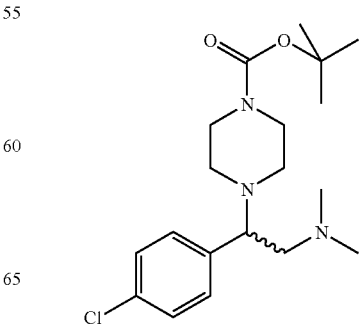

Procedure S

Preparation of 4-[1-(4-Chloro-phenyl)-2-dimethylamino-ethyl]-piperazine-1-carboxylic acid tert-butyl ester (403)

To 4-[2-Amino-1-(4-chloro-phenyl)-ethyl]-piperazine-1-carboxylic acid tert-butyl ester (203) (0.18 g, 0.529 mmol) in MeCN (3.0 mL) at 0° C. was added formaldehyde(0.64 g, 21.18 mmol) and NaCNBH$_3$ (0.17 g, 2.65 mmol). The reaction was allowed to warm to room temperature over 1 h. The reaction mixture was concnetrated to dryness. The resulting residue was taken up in EtOAc (50 mL) and washed with sat. NaHCO$_3$ (50 mL) and H$_2$O (50 mL). The desired product was then extracted into 1N HCl (50 mL) and washed with EtOAc. This aqueous phase was made alkaline with 5N NaOH (25 mL) and the desired product was extracted into EtOAc (100 mL). The organic phase was concentrated to dryness yielding 0.10 g (53%) product.
MS (ES) 368.1 [M+1]

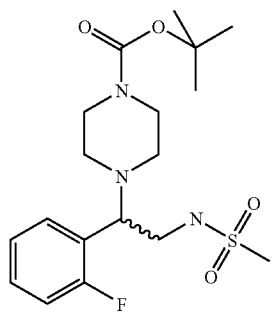

Procedure T

Preparation of 4-[1-(2-Fluoro-phenyl)-2-methanesulfonylamino-ethyl]-piperazine-1-carboxylic acid tert-butyl ester (408)

To a solution of 4-[2-Amino-1-(2fluoro-phenyl)-ethyl]-piperazine-1-carboxylic acid tert-butyl ester (207) (0.71 g, 2.19 mmol) in THF (5 mL) at 0° C. was added diisopropylethylamine (0.42 mL, 2.42 mmol). The solution was allowed to stir for 10 min. Methansulfonyl chloride (0.17 mL, 2.19 mmol) was then added and the solution was allowed to stir at room temperature for 18 h. The reaction mixture was diluted with EtOAc (50 mL) and washed with brine (50 mL) and H$_2$O (50 mL). The organic phase was concentrated to dryness yielding 0.86 g (98%) product.
MS (ES) 402.2 [M+1]

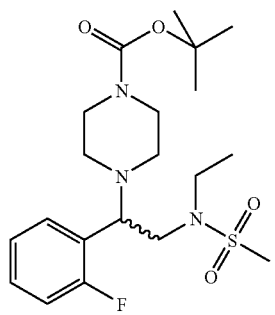

Procedure U

Preparation of 4-[2-(Ethyl-methanesulfonyl-amino)-1-(2-fluoro-phenyl)-ethyl]-piperazine-1-carboxylic acid tert-butyl ester (409)

To 4-[1-(2-Fluoro-phenyl)-2-methanesulfonylamino-ethyl]-piperazine-1-carboxylic acid tert-butyl ester (408) (1.43 g, 3.56 mmol) in THF (30 mL) was added NaH (60% in oil) (0.16 g, 3.92 mmol) and the solution was allowed to stir for 1 h at room temperature. Iodoethane (0.31 mL, 3.92 mmol) was then added and the reaction was allowed to stir for 18 h. The reaction mixture was diluted with EtOAc (100 mL) and washed with H$_2$O (100 mL). The organic phase was concentrated to dryness. The crude material was purified by chromatography (silica gel 60 mesh, eluting with 10% MeOH in CHCl$_3$) yielding 0.54 g (36%) pure product.
MS (ES) 430.2 [M+1]

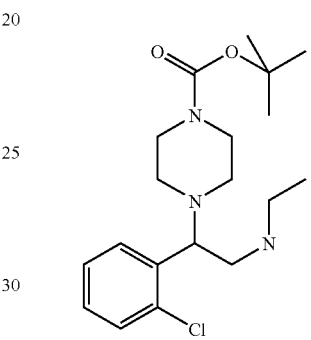

Procedure V

Preparation of 4-1-(2-Chloro-phenyl)-2-ethylaminoethyl]-piperazine-1-carboxylic acid tert-butyl ester (418)

To 4-[2-Amino-1-(2-chloro-phenyl)-ethyl]-piperazine-1-carboxylic acid tert-butyl ester (201) (0.64 g, 1.68 mmol) in THF (5.0 mL) was added 1M borane-THF complex in THF (15.02 mL, 5.03 mmol). The reaction was allowed to stir at 60° C. for 1 h and then allowed to cool to room temperature. MeOH (6.0 mL) and diisopropylethylamine (3.0 mL) were then added followed by I$_2$ (0.84 g, 3.35 mmol) in THF (10 mL). The mixture was allowed to stir at room temperature for 30 min. The mixture was then diluted with EtOAc (50 mL) and washed with 1N sodium thiosulfate (50 mL) and H$_2$O (50 mL). The organic phase was concentrated to dryness yielding 0.53 g (86%) pure product.
MS (ES) 368.2 [M+1]

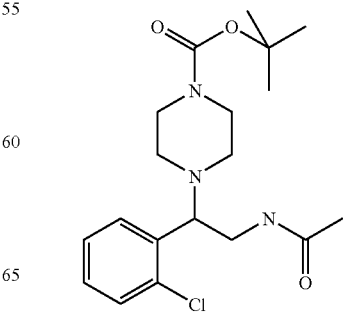

Procedure W

Preparation of 4-[2-Acetylamino-1-(2-chloro-phenyl)-ethyl]-piperazine-1-carboxylic acid tert-butyl ester (416)

To 4-[2-Amino-1-(2-chloro-phenyl)-ethyl]-piperazine-1-carboxylic acid tert-butyl ester (201) (0.75 g, 2.21 mmol) in pyridine (5 mL) was added Ac$_2$O (5 mL). The reaction was allowed to stir at 60° C. for 1 h and then allowed to cool to room temperature. The reaction mixture was diluted with EtOAc (100 mL) and washed with sat. NaHCO$_3$ (100 mL)), H$_2$O (100 mL) and brine (100 mL). The organic phase was concentrated to dryness yielding 0.85 g (99%) product.

MS (ES) 388.2 [M+1]

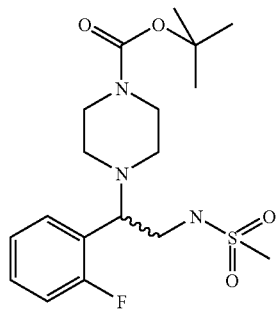

Procedure CC

Preparation of 4-[1-(2-Fluoro-phenyl)-2-methanesulfonylamino-ethyl]-piperazine-1-carboxylic acid tert-butyl ester (408)

To 4-[2-Amino-1-(2-fluoro-phenyl)-ethyl]-piperazine-1-carboxylic acid tert-butyl ester (207) (1.45 g, 4.48 mmol) in MeCl$_2$ (10 mL) was added methanesulfonyl chloride (0.51 g, 4.48 mmol) and pyridine. The reaction was allowed to stir at room temperature for 18 h. The reaction mixture was then diluted with EtOAc (50 mL) and washed with H$_2$O (50 mL) and brine (50 mL). The organic phase was concentrated to dryness yielding 1.43 g (80%) product.

MS (ES) 402.2 [M+1]

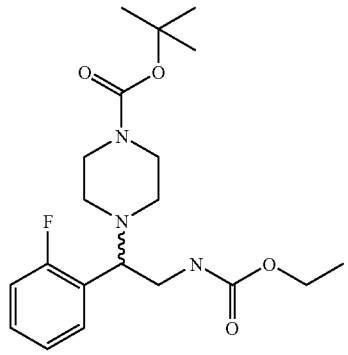

Procedure DD

Preparation of 4-[2-Ethoxycarbonylamino-1-(2-fluoro-phenyl)-ethyl]-piperazine-1-carboxylic acid tert-butyl ester (424)

To 4-[2-Amino-1-(2-fluoro-phenyl)-ethyl]-piperazine-1-carboxylic acid tert-butyl ester (207) (1.0 g, 3.09 mmol) was added ethyl chloroformate (15 mL) and the reaction mixture is allowed to reflux for 18 h. The reaction mixture is then concentrated to dryness yielding 1.05 g (97%) product.

MS (ES) 352.2 [M+1]

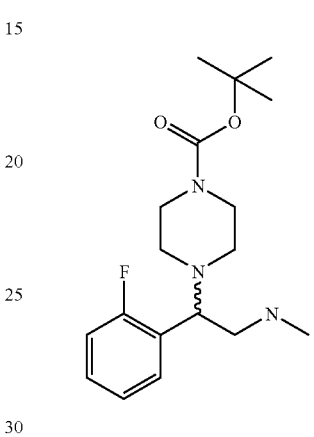

Procedure EE

Preparation of 4-[1-(2-Fluoro-phenyl)-2-methylamino-ethyl]-piperazine-1-carboxylic acid tert-butyl ester (425)

To Ethoxycarbonylamino-1-(2-fluoro-phenyl)-ethyl]-piperazine-1-carboxylic acid tert-butyl ester (207) (1.05 g, 3 mmol) in THF (10 mL) at −78° C. was added 1M borane in THF (4.5 mL). The reaction is stirred at −78° C. for 1 h and then was allowed to warm to room temperature (2 h). 5N aqueous sodium hydroxide was then added and the reaction was allowed to stir for 2 h. The reaction mixture was then diluted with EtOAc and the layers are separated. The organic phase was dried with sodium sulfate and concentrated to dryness yielding 0.95 g (94%) product.

MS (ES) X [M+1]

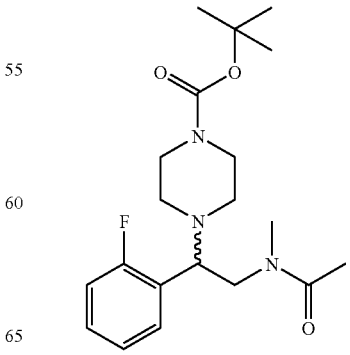

Procedure FF

Preparation of 4-[2-(Acetyl-methyl-amino)-1-(2-fluoro-phenyl)-ethyl]-piperazine-1-carboxylic acid tert-butyl ester (426)

To 4-[1-(2-Fluoro-phenyl)-2-methylamino-ethyl]-piperazine-1-carboxylic acid tert-butyl ester (425) (0.95 g, 2.81 mmol) in MeCl$_2$(10 mL) was added TEA (0.43 mL, 3.10 mmol). The solution was cooled to 0° C. and allowed to stir for 15 min. Acetyl chloride (0.20 mL, 2.81 mmol) was then added. The reaction was allowed to stir at 0° C. for 35 min and then at room temperature for 132 h. Additional triethylamine (0.39 mL, 2.81 mmol), and acetyl chloride (0.2 mL, 2.81 mmol) were added. The reaction mixture was then diluted with 10% aq. sodium bisulfate (20 mL). The organic layer was separated and the aqueous portion was extracted with dichloromethane (3×). The organics are combined, dried with sodium sulfate and concentrated to dryness. The crude material was purified by chromatography (silica gel 60 mesh, eluting with 2% (2M NH$_3$ in MeOH) in MeCl$_2$) yielding 0.17 g (16%) pure product.

MS (ES) 380.3 [M+1]

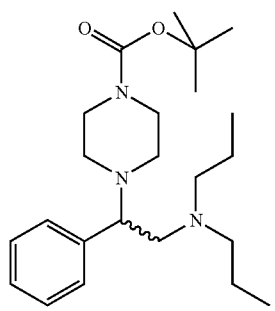

Procedure JJ

Preparation of 4-(2-Dipropylamino-1-phenyl-ethyl)-piperazine-1-carboxylic acid tert-butyl ester (427)

To 4-(2-Oxo-1-phenyl-ethyl)-piperazine-1-carboxylic acid tert-butyl ester (206) (0.47 g, 1.56 mmol) in dichloroethane (5 mL) was added diisopropylamine (0.21 mL, 1.56 mmol) and sodium triacetoxyborohydride (0.45 g, 2.15 mmol). The reaction was allowed to stir at room temperature for 18 h. The reaction mixture was then quenched with 5N NaOH (5.6 mL) and diluted with EtOAc. The organic phase was dried with MgSO$_4$ and concentrated to dryness. The crude material was purified by chromatography (silica gel 60 mesh, eluting with 100% EtoAc) yielding 0.30 g (49%) pure product.

MS (ES) 390.4 [M+1]

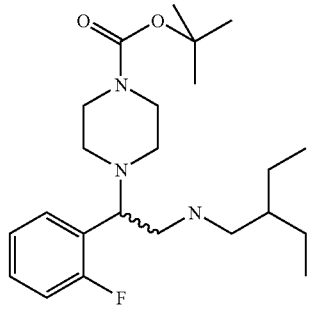

Procedure KK

Preparation of 4-[2-(2-Ethyl-butylamino)-1-(2-fluoro-phenyl)-ethyl]-piperazine-1-carboxylic acid tert-butyl ester (438)

To 4-[2-Amino-1-(2-fluoro-phenyl)-ethyl]-piperazine-1-carboxylic acid tert-butyl ester (207) (0.18 g, 0.56 mmol) in DMF (3 mL) was added 1-bromo-2-ethyl-butane (0.083 mL, 0.59 mmol) and potassium carbonate (0.093 g, 0.68 mmol). The reaction was allowed to stir at room temperature for 18 h. The reaction mixture was then diluted with EtOAc (30 mL) and H$_2$O (30 mL). The organic phase was dried with sodium sulfate and concentrated to dryness. The crude material was purified by chromatography (silica gel 60 mesh, eluting with 3% (2M NH$_3$ in MeOH) in MeCl$_2$) yielding 0.13 g (59%) pure product.

MS (ES) 408.4 [M+1]

TABLE X

| Cmpd. # | TABLE X, Structure | Prepared Analagous to Procedure | MS (ES) [M + 1] | Add'nal Info |
|---|---|---|---|---|
| 401 | ![structure] | S | 368.1 | |

TABLE X-continued
| Cmpd. # | TABLE X, Structure | Prepared Analagous to Procedure | MS (ES) [M + 1] | Add'nal Info |
|---|---|---|---|---|
| 402 | 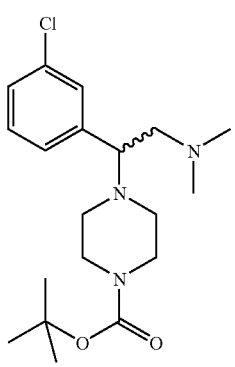 | S | 368.1 | |
| 403 | 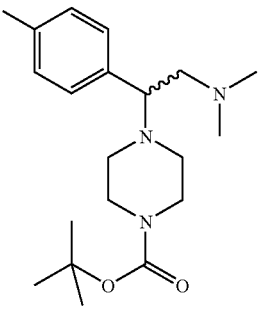 | S | 368.1 | |
| 404 | 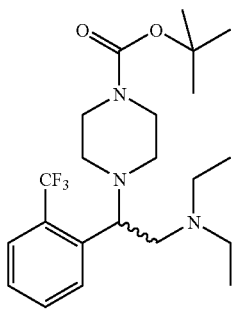 | O | 430.2 | |
| 405 | 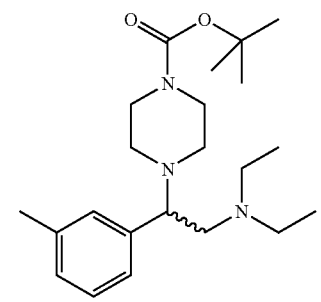 | O | 376.3 | |

TABLE X-continued

| Cmpd. # | TABLE X, Structure | Prepared Analagous to Procedure | MS (ES) [M + 1] | Add'nal Info |
|---|---|---|---|---|
| 406 | | O | N/A | |
| 407 | | N | 380.3 | |
| 408 | | T | 402.2 | |
| 409 | | U | 430.2 | |

TABLE X-continued
| Cmpd. # | TABLE X, Structure | Prepared Analagous to Procedure | MS (ES) [M + 1] | Add'nal Info |
|---|---|---|---|---|
| 410 | 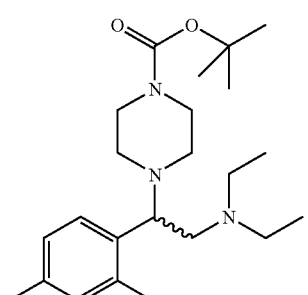 | N | 398.2 | |
| 411 | 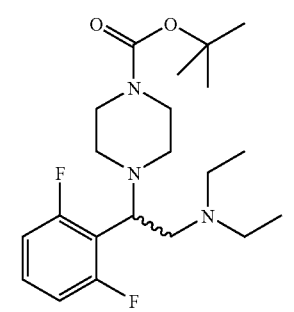 | N | 398.2 | |
| 412 | 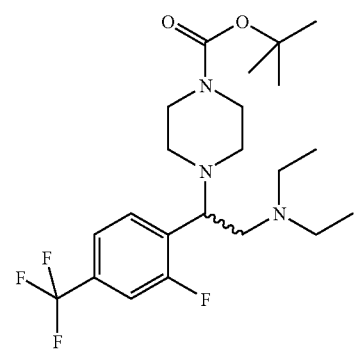 | N | 448.4 | |
| 413 | 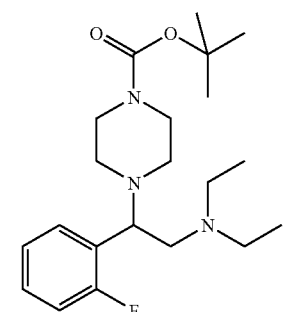 | N | 380.3 | |

TABLE X-continued

| Cmpd. # | TABLE X, Structure | Prepared Analagous to Procedure | MS (ES) [M + 1] | Add'nal Info |
|---|---|---|---|---|
| 414 | | N | 396.3 | |
| 415 | | FF | 366.2 | |
| 416 | | W | 388.2 | |
| 417 | | V | 352.3 | |

TABLE X-continued

| Cmpd. # | TABLE X, Structure | Prepared Analagous to Procedure | MS (ES) [M + 1] | Add'nal Info |
|---|---|---|---|---|
| 418 | | V | 368.2 | |
| 419 | | T | 446.2 | |
| 420 | | R | 400.2 | |
| 421 | | R | 382.1 | |

TABLE X-continued

| Cmpd. # | TABLE X, Structure | Prepared Analagous to Procedure | MS (ES) [M + 1] | Add'nal Info |
|---|---|---|---|---|
| 422 | | R* | 396.2 | w/ EtCl-Formate |
| 423 | | R* | 410.2 | w/ iPrCl-Formate |
| 424 | | DD | 352.2 | |
| 425 | | EE | N/A | |

TABLE X-continued

| Cmpd. # | TABLE X, Structure | Prepared Analagous to Procedure | MS (ES) [M + 1] | Add'nal Info |
|---|---|---|---|---|
| 426 | | FF | 380.3 | |
| 427 | | JJ | 390.4 | |
| 428 | | JJ* | 390.4 | w/ iPrAmine |
| 429 | | JJ* | 374.3 | w/ Pip |

TABLE X-continued

| Cmpd. # | TABLE X, Structure | Prepared Analagous to Procedure | MS (ES) [M + 1] | Add'nal Info |
|---|---|---|---|---|
| 430 | | JJ* | 376.3 | w/ Morph |
| 431 | | JJ* | 360.4 | w/ pyrr |
| 432 | | FF | 394.2 | |
| 433 | | FF | 408.2 | |

TABLE X-continued

| Cmpd. # | TABLE X, Structure | Prepared Analagous to Procedure | MS (ES) [M + 1] | Add'nal Info |
|---|---|---|---|---|
| 434 | | FF | 422.2 | |
| 435 | | DD | 410.3 | |
| 436 | | DD | 424.3 | |
| 437 | | DD | 438.4 | |
| 438 | | KK | 408.4 | |

TABLE X-continued

| Cmpd. # | TABLE X, Structure | Prepared Analagous to Procedure | MS (ES) [M + 1] | Add'nal Info |
|---|---|---|---|---|
| 439 | | KK | 420.4 | |
| 440 | | FF | 450.4 | |
| 441 | | FF | 462.4 | |
| 442 | | N | 430.2 | "A" isomer #2 |

TABLE X-continued

| Cmpd. # | TABLE X, Structure | Prepared Analagous to Procedure | MS (ES) [M + 1] | Add'nal Info |
|---|---|---|---|---|
| 443 | | T | 402.2 | "A" isomer #2 |
| 444 | | O | 429.2 | |
| 445 | | O | 429.2 | |
| 446 | | O | 396.3 | |

TABLE X-continued

| Cmpd. # | TABLE X, Structure | Prepared Analagous to Procedure | MS (ES) [M + 1] | Add'nal Info |
|---|---|---|---|---|
| 447 | | O | 392.3 | |
| 448 | | O | 376.3 | |
| 449 | | O | 396.3 | |
| 450 | | O | 392.3 | |

TABLE X-continued

| Cmpd. # | TABLE X, Structure | Prepared Analagous to Procedure | MS (ES) [M + 1] | Add'nal Info |
|---|---|---|---|---|
| 451 | | T | 418.2 | |
| 452 | | W | 366.2 | "A" isomer #2 |
| 453 | | V | 352.3 | "A" isomer #2 |
| 454 | | T | 430.3 | "A" isomer #2 |

TABLE X-continued
| Cmpd. # | TABLE X, Structure | Prepared Analagous to Procedure | MS (ES) [M + 1] | Add'nal Info |
|---|---|---|---|---|
| 455 | 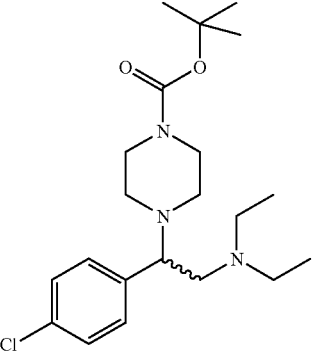 | N | 396.3 | "A" isomer #1 |
| 456 | 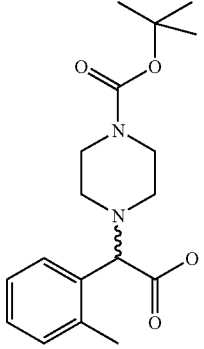 | K | 279.1 | |
| 457 | 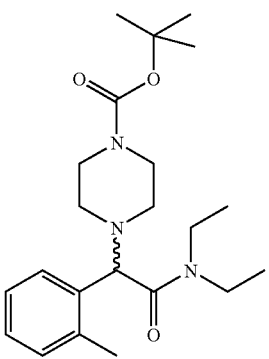 | L | 390.3 | |

TABLE X-continued

| Cmpd. # | TABLE X, Structure | Prepared Analagous to Procedure | MS (ES) [M + 1] | Add'nal Info |
|---|---|---|---|---|
| 458 | | X | 290.3 | |
| 459 | | M | N/A | |
| 460 | | N | 375.1 | |
| 461 | | H | 254.1 | |
| 462 | | I | 354.2 | |

TABLE X-continued

| Cmpd. # | TABLE X, Structure | Prepared Analagous to Procedure | MS (ES) [M + 1] | Add'nal Info |
|---|---|---|---|---|
| 463 | (structure: boc-protected diazepane linked via CH to 2-fluorophenyl and CH2-N(Et)2) | N | 394.1 | |

Compounds 491–492 (listed in Table XI. below) were prepared substantially analogous to the following procedure for the chiral synthesis of the "A" piece from the appropriate commercially available materials.

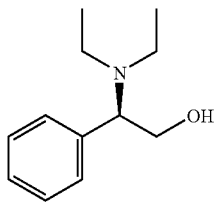

Procedure LL

Preparation of 2-Diethylamino-1-phenyl-ethanol (491)

To (R)-phenylglycinol (0.50 g, 3.60 mmol) in THF (15 mL) was added $Na_2CO_3$ (1.14 g, 10.80 mmol), tetrabutylammonium iodide (0.66 g, 1.80 mmol) and ethyl iodide (0.60 g, 7.3 mmol). The reaction was allowed to reflux for 24 h. The reaction mixture was allowed to cool to room temperature and the precipitate was removed by filtration. The filtrate was concentrated to dryness. The resulting residue was taken up in EtOAc (50 mL) and washed with $H_2O$ (50 mL). The organic phase was dried with $Na_2SO_4$ and concentrated to dryness. The crude material was purified by chromatography (silica gel 60 mesh, eluting with 5% TEA/ 5% MeOH in EtOAc) yielding 0.67 g (96%) pure product. MS (ES) 194.2 [M+1]

TABLE XI

| Cmpd. # | TABLE XI, Structure | Prepared Analagous to Procedure | MS (ES) [M + 1] | Add'nal Info |
|---|---|---|---|---|
| 491 | (structure: (R)-2-phenyl-substituted ethanol with OH) | LL | 194.2 | |
| 492 | (structure: (S)-2-phenyl-substituted ethanol with OH) | LL | 194.2 | |

Compounds 501–549 (listed in Table XII. below) were prepared substantially analogous to the following procedures for Boc-deprotection of the appropriate "A" pieces or chiral synthesis.

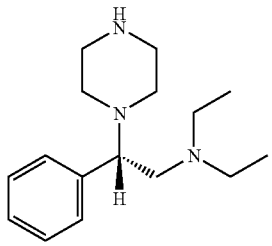

Procedure MM

Preparation of Diethyl-(2-phenyl-2-piperazin-1-yl-ethyl)-amine (545)

To 2-Diethylamino-1-phenyl-ethanol (491) (0.68 g, 3.50 mmol) in Et$_2$O (10 mL) was added TEA (1.40 mL, 10.50 mmol). The reaction mixture was cooled to 0° C. and methanesulfonyl chloride (0.40 mL, 4.90 mmol) was added dropwise. The reaction mixture was allowed to stir at room temperature for 30 min. N-Boc-piperazine (1.30 g, 7.20 mmol) was then added and the reaction was stirred at room temperature for 18 h. The reaction mixture was diluted with EtOAc (10 mL) and washed with H$_2$O (5 mL). The organic phase was dried with Na$_2$SO$_4$ and concentrated to dryness. The residue was purified by medium pressure chromatography (eluting with 5% TEA/5% MeOH in EtOAc) to afford the N-Boc protected product in >98% EE (determined by chiral HPLC Chiralpak AD, Hexane-TFA 0.05%, 1 mL/min, t=9.748). A solution of the N-Boc derivative (0.68 g, 1.88 mmol) in 1N HCl/EtOAc (25 mL) was stirred at room temperature for 18 h. The reaction mixture was concentrated to dryness and the resulting residue was washed with Et$_2$O (100 mL) yielding 0.48 g (52%) product.

MS (ES) 262.2 [M+1]

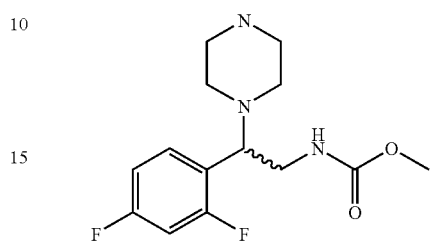

Procedure X

Preparation of [2-(2,4-Difluoro-phenyl)-2-piperazin-1-yl-ethyl]-carbamic acid methyl ester (516)

To 4-[1-(2,4-Difluoro-phenyl)-2-methoxycarbonylamino-ethyl]-piperazine-1-carboxylic acid tert-butyl ester (420) (0.225 g, 0.564 mmol) in MeCl$_2$ (2.0 mL) was added TFA (2.0 mL). The reaction was allowed to stir at room temperature for 1 h. The reaction mixture was concentrated to dryness. The resulting residue was taken up in 1N HCl (30 mL) and washed with EtOAc (30 mL). The aqueous layer was made alkaline with 5N NaOH (10 mL) and the desired product was extracted into EtOAc. The organic phase was concentrated to dryness yielding 0.14 g (83%) pure product.

MS (ES) 300.2 [M+1]

TABLE XII

| Cmpd. # | TABLE XII, Structure | Prepared Analagous to Procedure | MS (ES) [M + 1] | Add'nal Info |
|---|---|---|---|---|
| 501 | (2-Cl phenyl structure) | X | 268.1 | |
| 502 | (3-Cl phenyl structure) | X | 268.1 | |

TABLE XII-continued

| Cmpd. # | TABLE XII, Structure | Prepared Analagous to Procedure | MS (ES) [M + 1] | Add'nal Info |
|---|---|---|---|---|
| 503 | | X | 268.1 | |
| 504 | | X | 330.2 | |
| 505 | | X | 276.3 | |
| 506 | | X | N/A | |
| 507 | | X | 287.1 | |
| 508 | | X | 302.2 | |

TABLE XII-continued

| Cmpd. # | TABLE XII, Structure | Prepared Analagous to Procedure | MS (ES) [M + 1] | Add'nal Info |
|---|---|---|---|---|
| 509 | | X | 330.2 | |
| 510 | | X | 298.2 | |
| 511 | | X | 298.2 | |
| 512 | | X | 348.2 | |
| 513 | | X | 287.1 | "A" isomer#2 |
| 514 | | X | 296.3 | "A" isomer#2 |

TABLE XII-continued
| Cmpd. # | TABLE XII, Structure | Prepared Analagous to Procedure | MS (ES) [M + 1] | Add'nal Info |
|---|---|---|---|---|
| 515 | 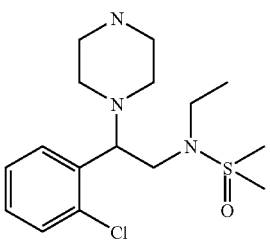 | X | 346.1 | "A" isomer#2 |
| 516 | 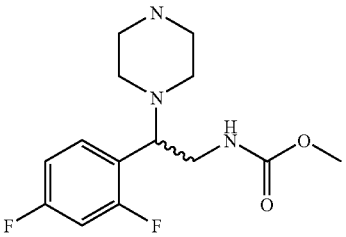 | X | 300.2 | |
| 517 | 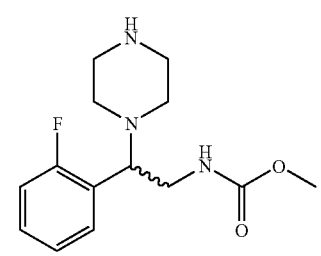 | X | 282.1 | |
| 518 | 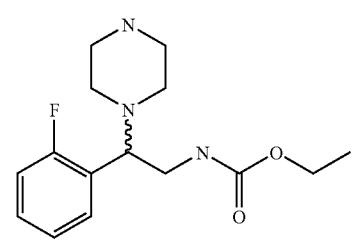 | X | 296.1 | |
| 519 | 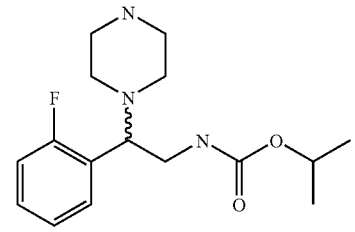 | X | 310.1 | |
| 520 | 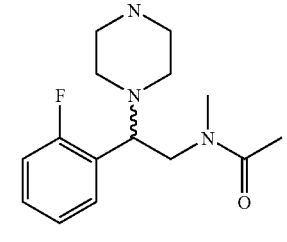 | X | 280.1 | |

TABLE XII-continued
| Cmpd. # | TABLE XII, Structure | Prepared Analagous to Procedure | MS (ES) [M + 1] | Add'nal Info |
|---|---|---|---|---|
| 521 | 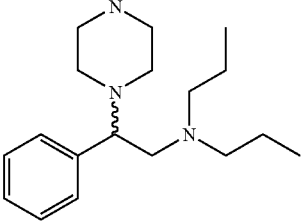 | X | 290.3 | |
| 522 | 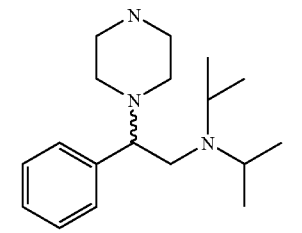 | X | 290.3 | |
| 523 | 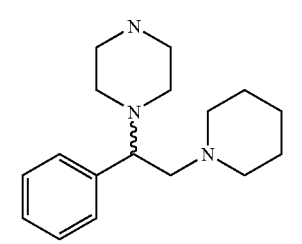 | X | 274.2 | |
| 524 | 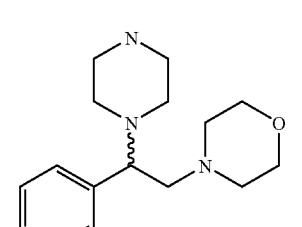 | X | 276.2 | |
| 525 | 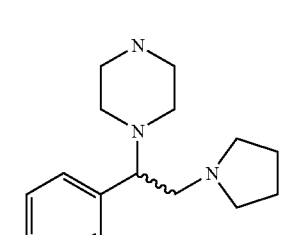 | X | 260.2 | |
| 526 | 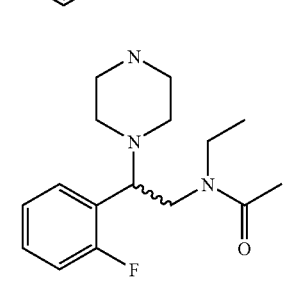 | X | 294.2 | |

TABLE XII-continued

| Cmpd. # | TABLE XII, Structure | Prepared Analagous to Procedure | MS (ES) [M + 1] | Add'nal Info |
|---|---|---|---|---|
| 527 | | X | 308.2 | |
| 528 | | X | 322.2 | |
| 529 | | X | 310.3 | |
| 530 | | X | 324.3 | |
| 531 | | X | 328.3 | |
| 532 | | X | 350.4 | |

TABLE XII-continued

| Cmpd. # | TABLE XII, Structure | Prepared Analagous to Procedure | MS (ES) [M + 1] | Add'nal Info |
|---|---|---|---|---|
| 533 | | X | 362.4 | |
| 534 | | X | 330.1 | "A" isomer#2 |
| 535 | | X | 302.2 | "A" isomer#2 |
| 536 | | X | 330.1 | |
| 537 | | X | 330.1 | |

TABLE XII-continued
| Cmpd. # | TABLE XII, Structure | Prepared Analagous to Procedure | MS (ES) [M + 1] | Add'nal Info |
|---|---|---|---|---|
| 538 | 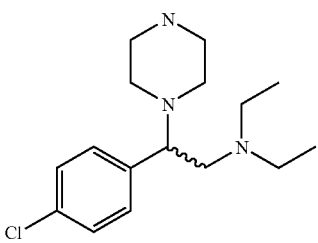 | X | 296.3 | |
| 539 | 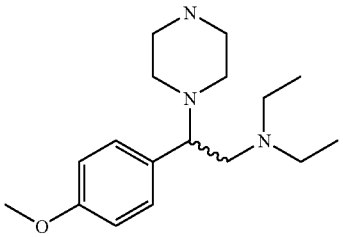 | X | 292.3 | |
| 540 | 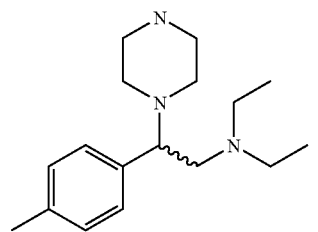 | X | 276.3 | |
| 541 | 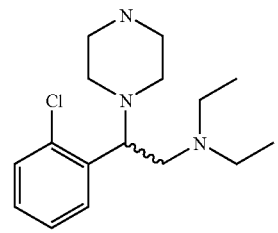 | X | 296.3 | |
| 542 | 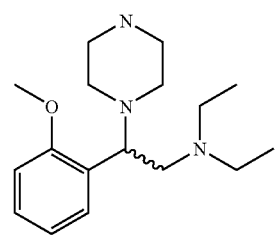 | X | 292.3 | |

TABLE XII-continued
| Cmpd. # | TABLE XII, Structure | Prepared Analagous to Procedure | MS (ES) [M + 1] | Add'nal Info |
|---|---|---|---|---|
| 543 | 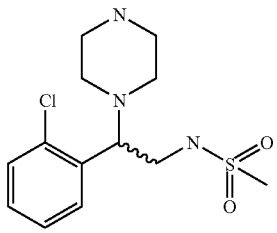 | X | 318.1 | |
| 544 | 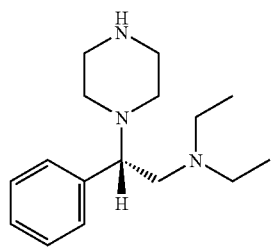 | MM | 262.2 | |
| 545 | 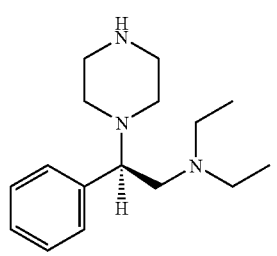 | MM | 262.2 | |
| 546 | 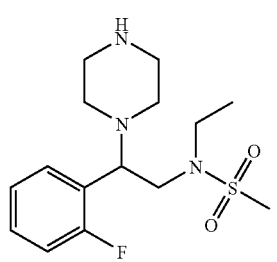 | X | 330.2 | "A" isomer190 1 |
| 547 | 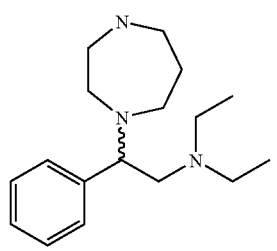 | X | 275.1 | |

TABLE XII-continued

| Cmpd. # | TABLE XII, Structure | Prepared Analagous to Procedure | MS (ES) [M + 1] | Add'nal Info |
|---|---|---|---|---|
| 548 | | X | 290.2 | |
| 549 | | X | 294.1 | |

Compounds 601–622 (listed in Table XIII. below) were prepared substantially analogous to the following procedures for amide coupling of the respective de-protected "A" pieces to the Boc-protected "B" piece (i.e 4-Cl-D-Phe).

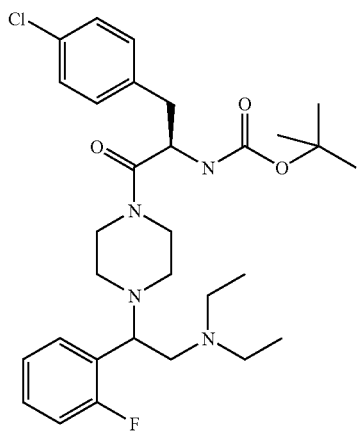

Procedure Y

Preparation of (1-(4-Chloro-benzyl)-2-{4-[2-diethylamino-1-(2-fluoro-phenyl)-ethyl]-piperazin-1-yl}-2-oxo-ethyl)-carbamic acid tert-butyl ester (608)

To Diethyl-[2-(2-fluoro-phenyl)-2-piperazin-1-yl-ethyl]-amine (513) (0.206 g, 0.738 mmol) was added Boc-4-chloro-D-Phe (0.221 g, 0.738 mmol), 1-[3-(Dimethylamino) propyl]-3-ethylcarbodiimide hydrochloride (0.141 g, 0.738 mmol), 1-Hydroxybenzotriazole hydrate (0.099 g, 0.738 mmol), DCM (5.0 mL) and 4-methylmorpholine (0.243 mL, 2.215 mmol). The reaction was allowed to stir at room temperature for 4 h. The reaction mixture was concentrated to dryness. The resulting residue was taken up in EtOAc (30 mL) and washed with sat. NaHCO₃ and brine. The crude material was purified by chromatography (silica gel 60 mesh, eluting with 5% MeOH/5% TEA in EtOAc) yielding 0.41 g (99%) pure product.

MS 561.2 [M+1]

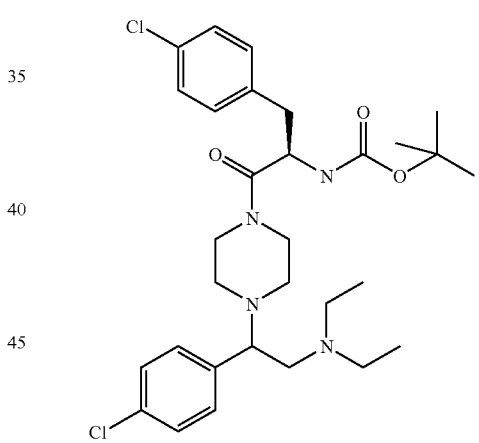

Procedure NN

Preparation of (1-(4-Chloro-benzyl)-2-{4-[1-(4-chloro-phenyl)-2-diethylamino-ethyl]-piperazin-1-yl}-2-oxo-ethyl)-carbamic acid tert-butyl ester (621)

From [2-(4-Chloro-phenyl)-2-piperazin-1-yl-ethyl]-diethyl-amine (538) 621 was synthesized substantially analogous to Procedure Y and the diastereomers were separated by chiral chromatography on a Chiralpak AD(4.6×250 mm)column, eluting with 5% 3A alcohol, 95% heptane with 0.2% DMEA at 1 mL/min. The second eluting isomer was labeled isomer 2.

MS (ES) 627.1 [M+1]

TABLE XIII
| Cmpd. # | TABLE XIII, Structure | Prepared Analagous to Procedure | MS (ES) [M + 1] | Add'nal Info |
|---|---|---|---|---|
| 601 | 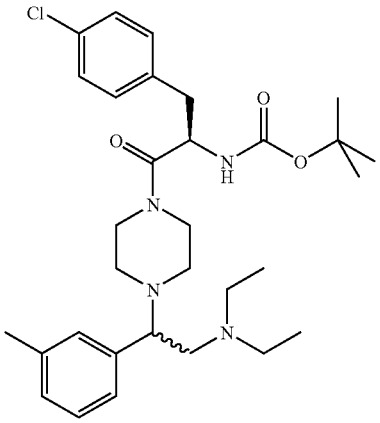 | Y | 557.4 | |
| 602 | 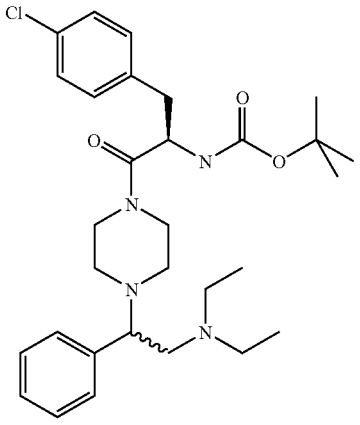 | Y | N/A | |
| 603 | 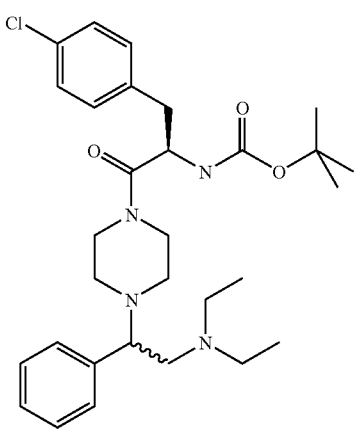 | Y | 611.2 | |

TABLE XIII-continued
| Cmpd. # | TABLE XIII, Structure | Prepared Analagous to Procedure | MS (ES) [M + 1] | Add'nal Info |
|---|---|---|---|---|
| 604 | 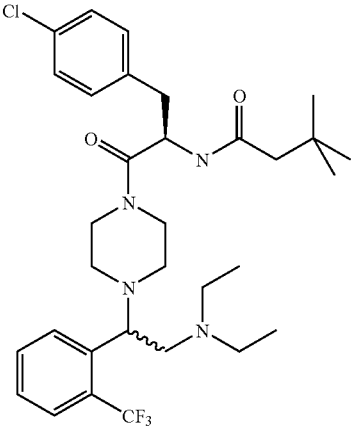 | Y | 611.2 | |
| 605 | 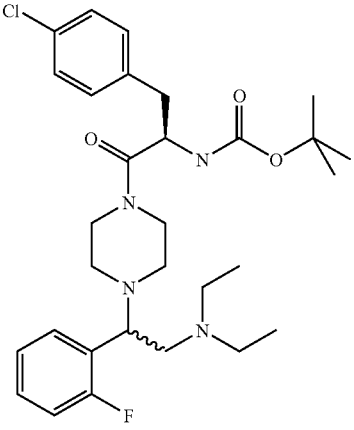 | Y | 561.3 | |
| 606 | 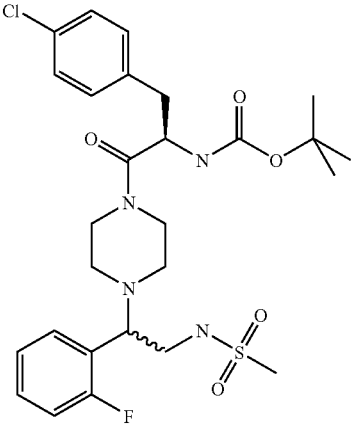 | Y | 583.3 | |

TABLE XIII-continued
| Cmpd. # | TABLE XIII, Structure | Prepared Analagous to Procedure | MS (ES) [M + 1] | Add'nal Info |
|---|---|---|---|---|
| 607 | 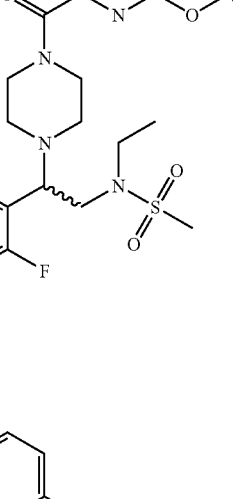 | Y | 611.4 | |
| 608 | 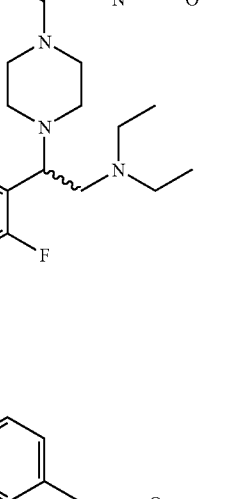 | Y | 561.3 | "A" isomer#2 |
| 609 | 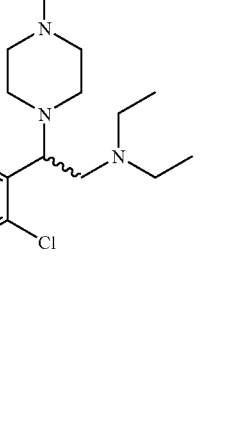 | Y | 577.2 | "A" isomer#2 |

TABLE XIII-continued
| Cmpd. # | TABLE XIII, Structure | Prepared Analagous to Procedure | MS (ES) [M + 1] | Add'nal Info |
|---|---|---|---|---|
| 610 | 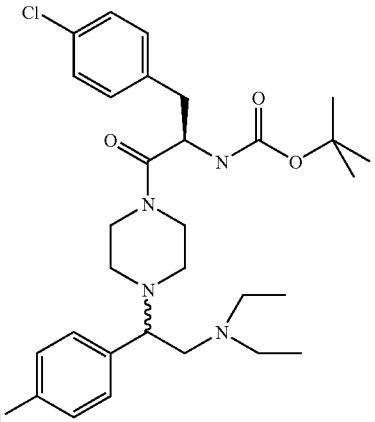 | Y | 577.2 | |
| 611 | 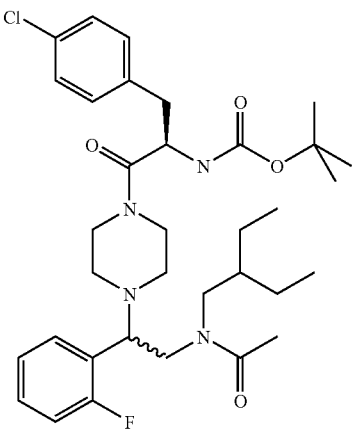 | Y | N/A | |
| 612 | 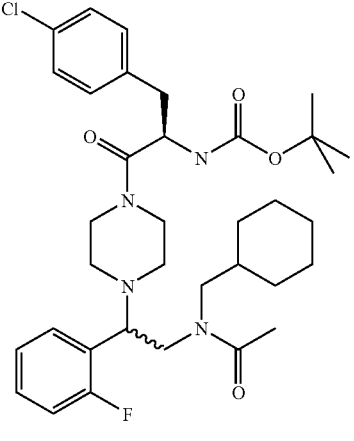 | Y | N/A | |

TABLE XIII-continued
| Cmpd. # | TABLE XIII, Structure | Prepared Analagous to Procedure | MS (ES) [M + 1] | Add'nal Info |
|---|---|---|---|---|
| 613 | 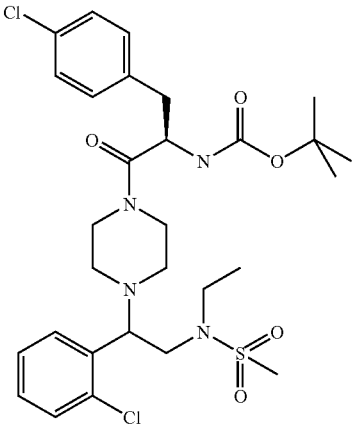 | Y | 627.1 | "A" isomer#2 |
| 614 | 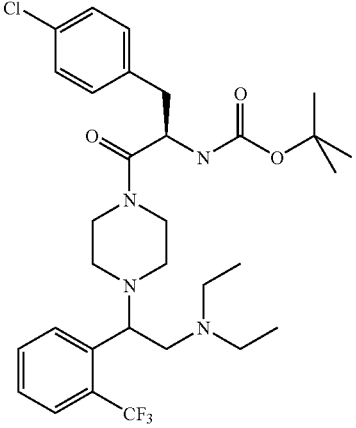 | Y | 611.1 | "A" isomer#2 |
| 615 | 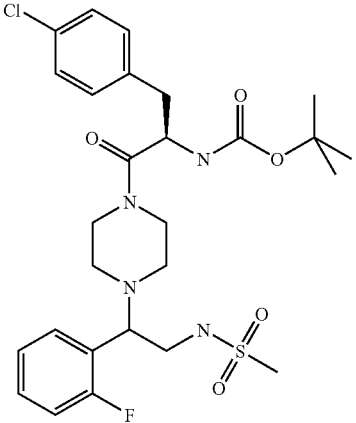 | Y | 583.1 | "A" isomer#2 |

TABLE XIII-continued
| Cmpd. # | TABLE XIII, Structure | Prepared Analagous to Procedure | MS (ES) [M + 1] | Add'nal Info |
|---|---|---|---|---|
| 616 | 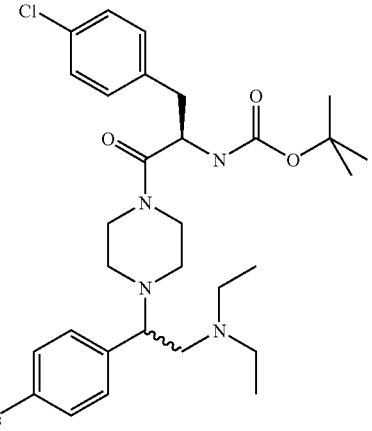 | Y | 611.1 | |
| 617 | 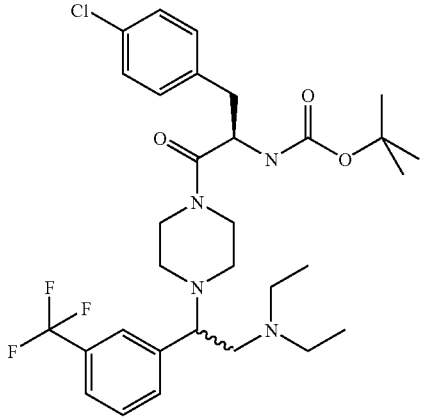 | Y | 611.1 | |
| 618 | 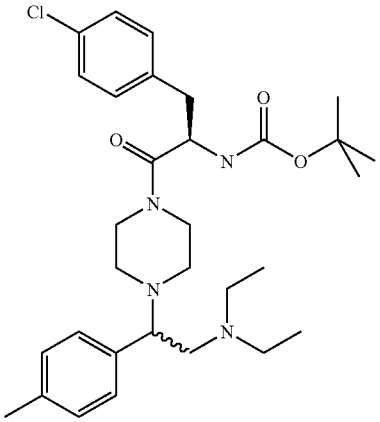 | Y | 557.3 | |

TABLE XIII-continued
| Cmpd. # | TABLE XIII, Structure | Prepared Analagous to Procedure | MS (ES) [M + 1] | Add'nal Info |
|---|---|---|---|---|
| 619 | 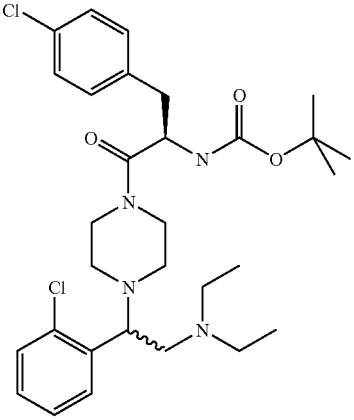 | Y | 627.1 | |
| 620 | 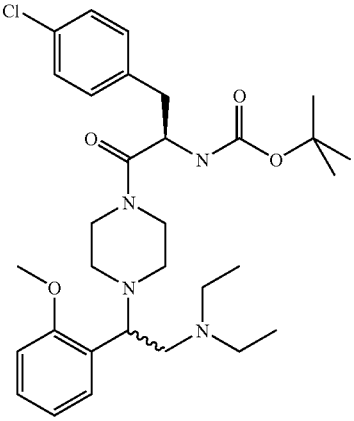 | Y | 573.4 | |
| 621 | 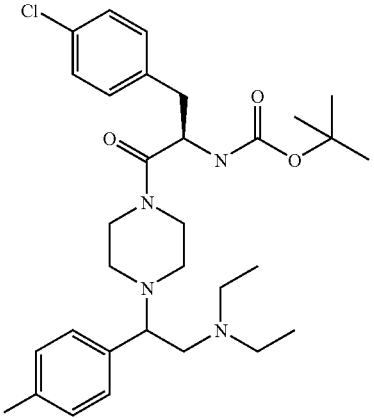 | NN | 627.1 | "A–B" isomer#2 |

TABLE XIII-continued

| Cmpd. # | TABLE XIII, Structure | Prepared Analagous to Procedure | MS (ES) [M + 1] | Add'nal Info |
|---|---|---|---|---|
| 622 | 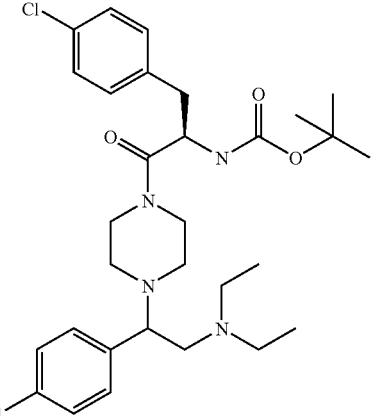 | NN | 627.1 | "A–B" isomer#1 |

Compounds 701–721 (listed in Table XIV. below) were prepared substantially analogous to Procedure X described above for Boc-deprotection of the respective Boc-protected coupled "A-B" pieces.

TABLE XIV

| Cmpd. # | TABLE XIV Structure | Prepared Analagous to Procedure | MS (ES) [M + 1] | Add'nal Info |
|---|---|---|---|---|
| 701 | 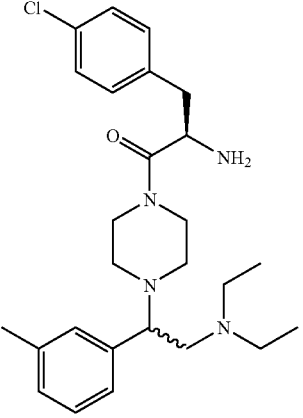 | X | 457.4 | |

TABLE XIV-continued

| Cmpd. # | TABLE XIV Structure | Prepared Analagous to Procedure | MS (ES) [M + 1] | Add'nal Info |
|---|---|---|---|---|
| 702 | | X | N/A | |
| 703 | | X | 511.3 | |

TABLE XIV-continued

| Cmpd. # | TABLE XIV Structure | Prepared Analagous to Procedure | MS (ES) [M + 1] | Add'nal Info |
|---|---|---|---|---|
| 704 | | X | 461.3 | |
| 705 | | X | 583.3 | |

TABLE XIV-continued
| Cmpd. # | TABLE XIV Structure | Prepared Analagous to Procedure | MS (ES) [M + 1] | Add'nal Info |
|---|---|---|---|---|
| 706 | 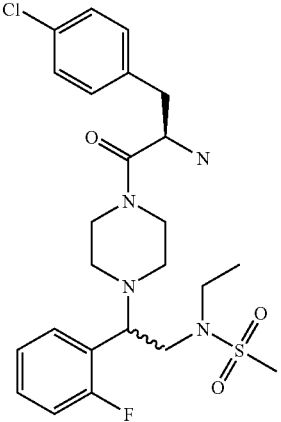 | X | 511.3 | |
| 707 | 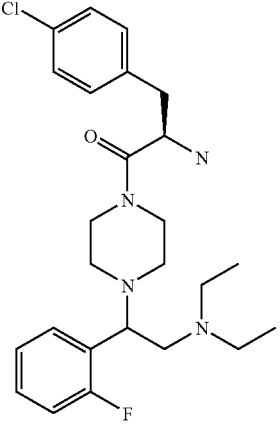 | X | 461.3 | "A" isomer#2 |

TABLE XIV-continued

| Cmpd. # | TABLE XIV Structure | Prepared Analagous to Procedure | MS (ES) [M + 1] | Add'nal Info |
|---|---|---|---|---|
| 708 | | X | 477.2 | "A" isomer#2 |
| 709 | | X | 477.2 | |

TABLE XIV-continued
| Cmpd. # | TABLE XIV Structure | Prepared Analagous to Procedure | MS (ES) [M + 1] | Add'nal Info |
|---|---|---|---|---|
| 710 | 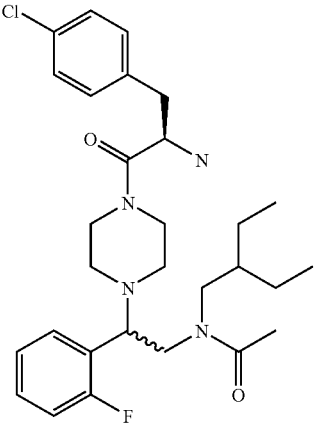 | X | N/A | |
| 711 | 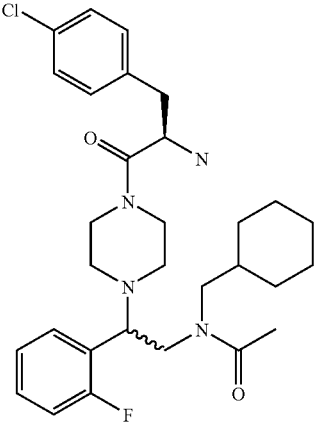 | X | N/A | |

TABLE XIV-continued

| Cmpd. # | TABLE XIV Structure | Prepared Analagous to Procedure | MS (ES) [M + 1] | Add'nal Info |
|---|---|---|---|---|
| 712 | | X | 527.1 | "A" isomer#2 |
| 713 | | X | 511.1 | "A" isomer#2 |

TABLE XIV-continued

| Cmpd. # | TABLE XIV Structure | Prepared Analagous to Procedure | MS (ES) [M + 1] | Add'nal Info |
|---|---|---|---|---|
| 714 | | X | 483.1 | "A" isomer#2 |
| 715 | | X | 511.1 | |

TABLE XIV-continued
| Cmpd. # | TABLE XIV Structure | Prepared Analagous to Procedure | MS (ES) [M + 1] | Add'nal Info |
|---|---|---|---|---|
| 716 | 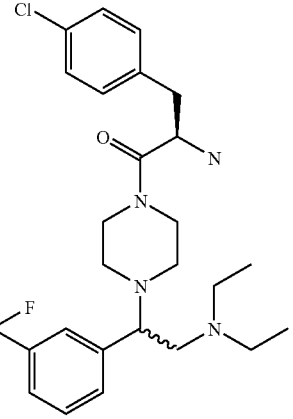 | X | 511.1 | |
| 717 | 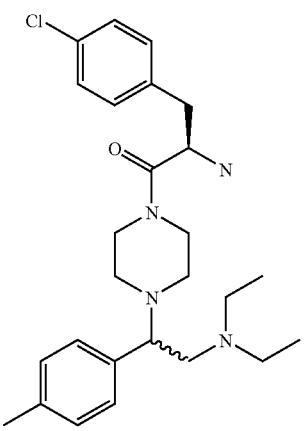 | X | 457.3 | |

TABLE XIV-continued

| Cmpd. # | TABLE XIV Structure | Prepared Analogous to Procedure | MS (ES) [M + 1] | Add'nal Info |
|---|---|---|---|---|
| 718 | | X | 527.1 | |
| 719 | | X | 473.3 | |

TABLE XIV-continued

| Cmpd. # | TABLE XIV Structure | Prepared Analagous to Procedure | MS (ES) [M + 1] | Add'nal Info |
|---|---|---|---|---|
| 720 | | X | 527.1 | "A" isomer#2 |
| 721 | | X | 527.1 | "A" isomer#1 |

Compounds 801–849 (listed in Table XV. below) were prepared substantially analogous to Procedure Y described above for amide coupling of the respective de-protected "A-B" piece to the respective "C" piece (the synthesis of each non-commercially available "C" piece is described in the section entitled "Preparation of Novel "C" and "B-C" Pieces" and other sections herein).

TABLE XV

| Cmpd. # | TABLE XV, Structure | Prepared Analogous to Procedure | MS (ES) [M+ 1] | Add'nal Info | "C"Prep Described in . . . |
|---|---|---|---|---|---|
| 801 | | Y | 716.4 | | Preparation C2 |
| 802 | | Y | 716.5 | | Preparation C3 |

| Cmpd. # | TABLE XV, Structure | Prepared Analogous to Procedure | MS (ES) [M+ 1] | Add'nal Info | "C"Prep Described in . . . |
|---|---|---|---|---|---|
| 803 | 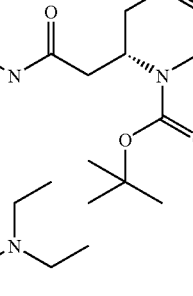 | Y | 716.3 | | "C" carboxylic acid is comm. Available |
| 804 | 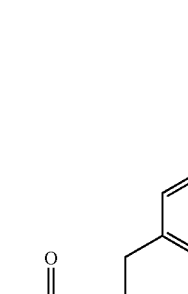 | Y | 716.3 | | "C" carboxylic acid is comm. Available |
| 805 | 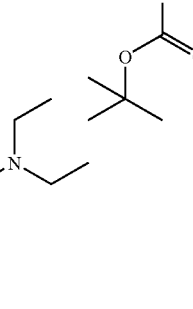 | Y | 770.5 | | Preparation C2 |

TABLE XV-continued
| Cmpd. # | TABLE XV, Structure | Prepared Analogous to Procedure | MS (ES) [M+ 1] | Add'nal Info | "C"Prep Described in . . . |
|---|---|---|---|---|---|
| 806 | 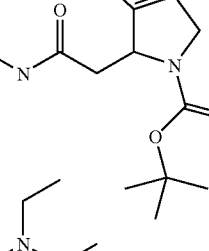 | Y | 770.5 | | Preparation C2 cis isomer 1 |
| 807 |  | Y | 770.5 | | Preparation C2 cis isomer 2 |
| 808 | 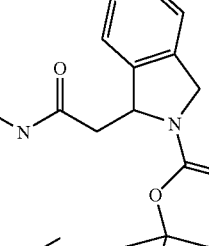 | Y | 720.4 | | Preparation C2 isomer 2 |

TABLE XV-continued

| Cmpd. # | TABLE XV, Structure | Prepared Analogous to Procedure | MS (ES) [M+ 1] | Add'nal Info | "C"Prep Described in . . . |
|---|---|---|---|---|---|
| 809 | | Y | 742.4 | | Preparation C2 isomer 2 |
| 810 | | Y | 770.4 | | Preparation C2 |
| 811 | | Y | 720.4 | "A" isomer#2 | Preparation C2 isomer 2 |

TABLE XV-continued
| Cmpd. # | TABLE XV, Structure | Prepared Analogous to Procedure | MS (ES) [M+ 1] | Add'nal Info | "C"Prep Described in . . . |
|---|---|---|---|---|---|
| 812 | 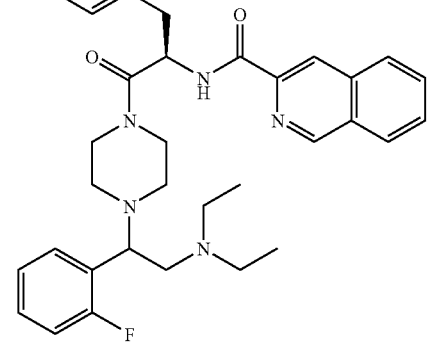 | Y, AA | 616.2 | "A" isomer#2 | "C" carboxylic acid is comm. Available |
| 813 | 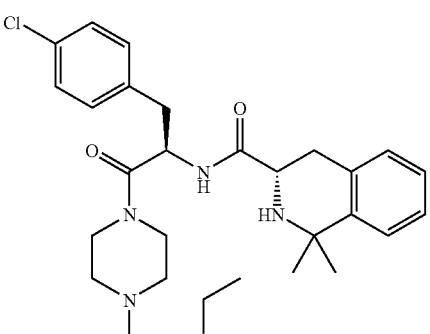 | Y, AA | 648.6 | "A" isomer#3 | |
| 814 | 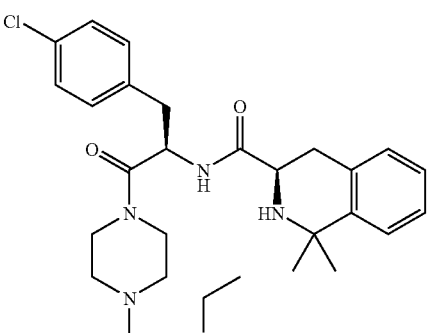 | Y, AA | 648.6 | "A" isomer#4 | |

TABLE XV-continued
| Cmpd. # | TABLE XV, Structure | Prepared Analogous to Procedure | MS (ES) [M+ 1] | Add'nal Info | "C"Prep Described in . . . |
|---|---|---|---|---|---|
| 815 | 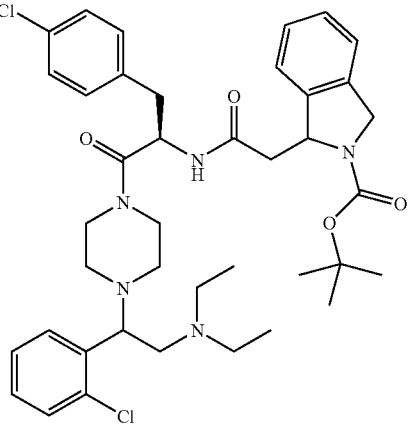 | Y | 736.6 | "A" isomer#2 | Preparation C2 isomer 2 |
| 816 | 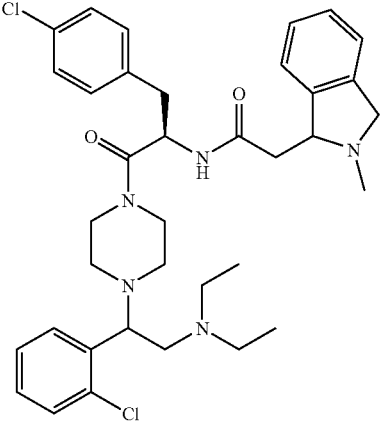 | Y | 650.3 | "A" isomer#2 | Preparation C5 isomer 2 |
| 817 | 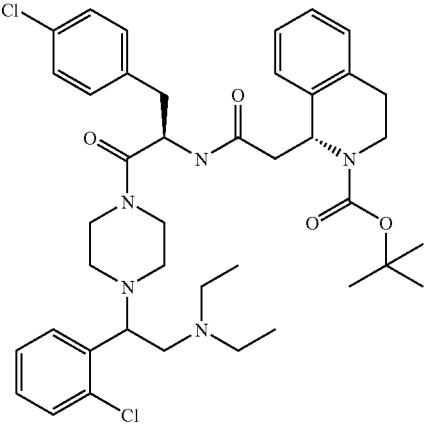 | Y | 750.3 | "A" isomer#2 | Preparation C3 |

TABLE XV-continued

| Cmpd. # | TABLE XV, Structure | Prepared Analogous to Procedure | MS (ES) [M+ 1] | Add'nal Info | "C"Prep Described in . . . |
|---|---|---|---|---|---|
| 818 | | Y | 750.3 | "A" isomer#2 | Preparation C3 |
| 819 | | Y | 734.3 | "A" isomer#2, "C" isomer#2 | Preparation C3 |
| 820 | | Y | 634.3 | "A" isomer#2 | Preparation C6 isomer 2 |

TABLE XV-continued

| Cmpd. # | TABLE XV, Structure | Prepared Analogous to Procedure | MS (ES) [M+ 1] | Add'nal Info | "C"Prep Described in . . . |
|---|---|---|---|---|---|
| 821 | | Y | 734.4 | "A" isomer#2, "C" isomer#1 | Preparation C3 |
| 822 | | Y | 720.3 | | Preparation C9 |
| 823 | | Y | 720.3 | | Preparation C15 |

TABLE XV-continued
| Cmpd. # | TABLE XV, Structure | Prepared Analogous to Procedure | MS (ES) [M+ 1] | Add'nal Info | "C"Prep Described in . . . |
|---|---|---|---|---|---|
| 824 | 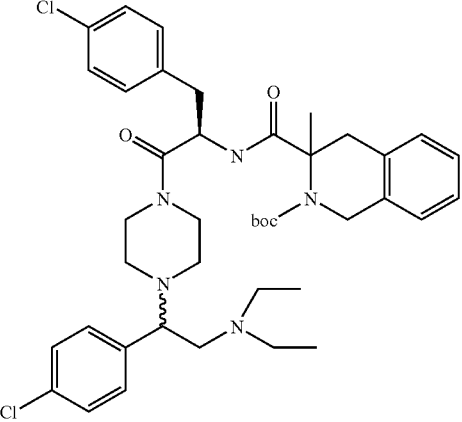 | Y | 750.6 | "C" isomer#1 | Preparation C9 |
| 825 | 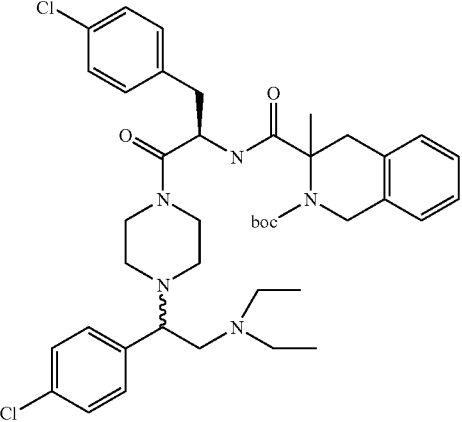 | Y | 750.6 | "C" isomer#2 | Preparation C10 |
| 826 | 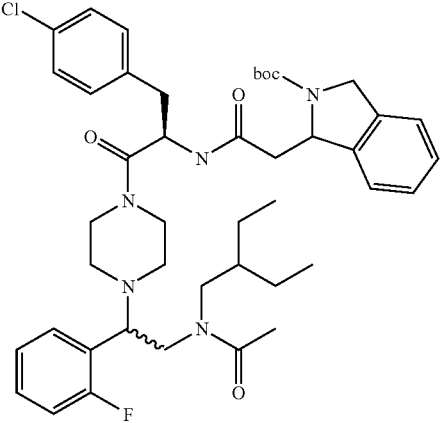 | Y | 790.5 | | Preparation C2 isomer 2 |

TABLE XV-continued

| Cmpd. # | TABLE XV, Structure | Prepared Analogous to Procedure | MS (ES) [M+ 1] | Add'nal Info | "C"Prep Described in . . . |
|---|---|---|---|---|---|
| 827 | | Y | 802.4 | | Preparation C2 isomer 2 |
| 828 | | Y | 786.1 | "A" isomer#2 | Preparation C2 isomer 2 |
| 829 | | Y | 800.1 | "A" isomer#2 | Preparation C3 isomer 2 |

TABLE XV-continued
| Cmpd. # | TABLE XV, Structure | Prepared Analogous to Procedure | MS (ES) [M+ 1] | Add'nal Info | "C"Prep Described in . . . |
|---|---|---|---|---|---|
| 830 | 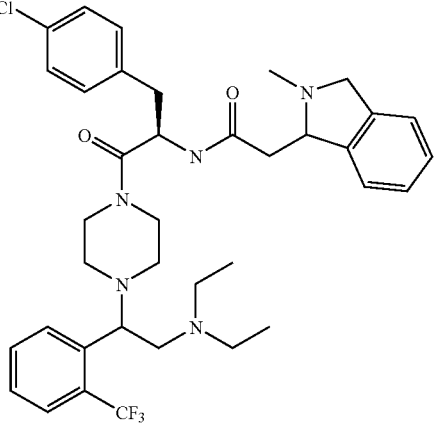 | Y | 684.1 | "A" isomer#2 | Preparation C6 isomer 2 |
| 831 | 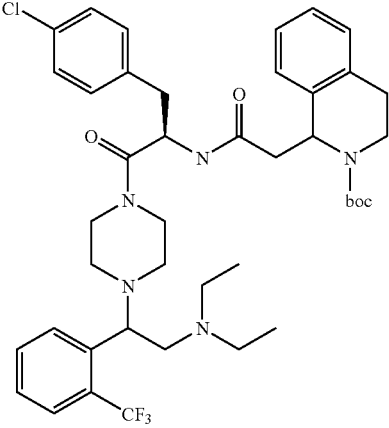 | Y | 784.1 | "A" isomer#2 | Preparation C3 isomer 2 |
| 832 | 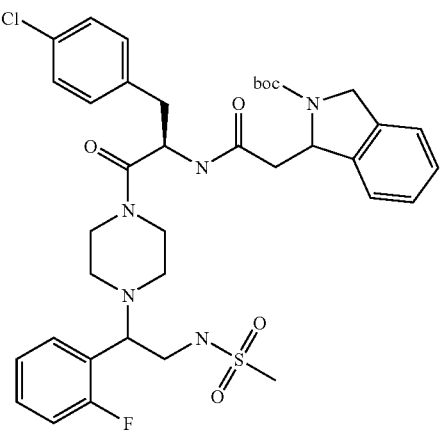 | Y | 742.1 | "A" isomer#2 | Preparation C2 isomer 2 |

TABLE XV-continued
| Cmpd. # | TABLE XV, Structure | Prepared Analogous to Procedure | MS (ES) [M+ 1] | Add'nal Info | "C"Prep Described in . . . |
|---|---|---|---|---|---|
| 833 | 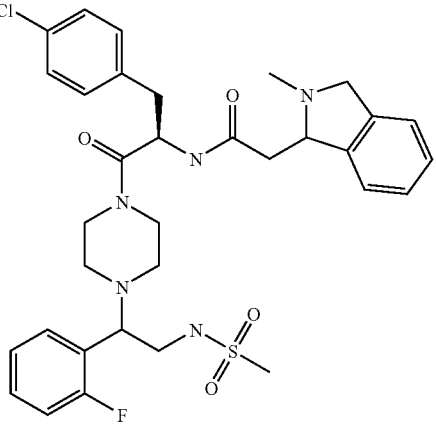 | Y | 656.1 | "A" isomer#2 | Preparation C6 isomer |
| 834 | 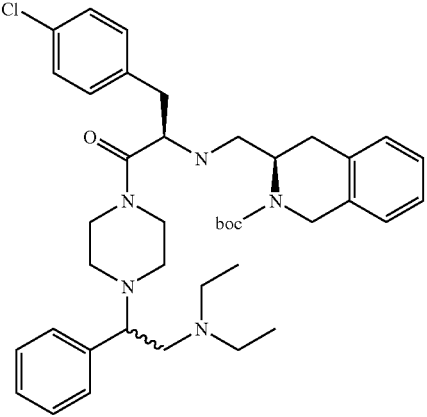 | see Preparation BC3-C | 688.1 | | Preparation BC3 |
| 835 | 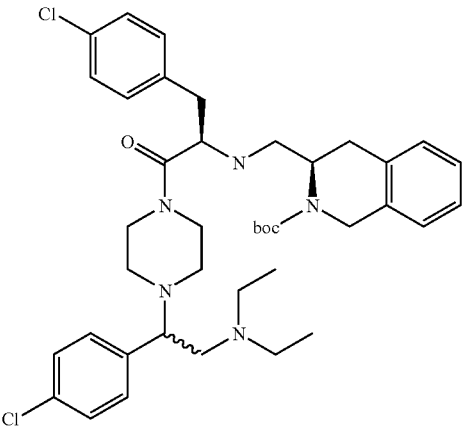 | see Preparation BC3-C | 722.1 | | Preparation BC3 |

TABLE XV-continued
| Cmpd. # | TABLE XV, Structure | Prepared Analogous to Procedure | MS (ES) [M+ 1] | Add'nal Info | "C"Prep Described in . . . |
|---|---|---|---|---|---|
| 836 | 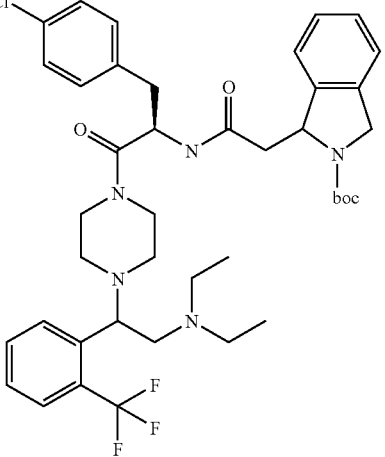 | Y | 770.3 | "A" isomer#2 | Preparation C2 isomer 2 |
| 837 | 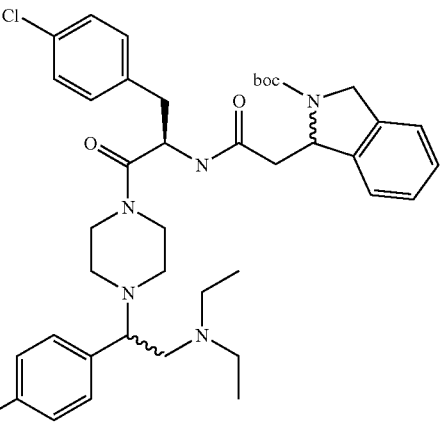 | Y | 736.3 | | Preparation C2 |
| 838 | 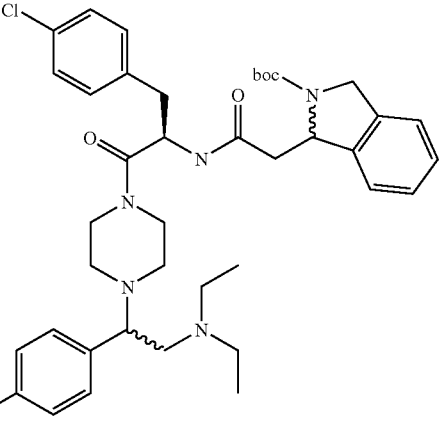 | Y | 770.3 | | Preparation C2 |

TABLE XV-continued

| Cmpd. # | TABLE XV, Structure | Prepared Analogous to Procedure | MS (ES) [M+ 1] | Add'nal Info | "C"Prep Described in . . . |
|---|---|---|---|---|---|
| 839 | | Y | 770.3 | | Preparation C2 |
| 840 | | Y, AA | 632.2 | | "C" carboxylic acid is comm. Available |
| 841 | | Y | 716.4 | | Preparation C2 |

TABLE XV-continued
| Cmpd. # | TABLE XV, Structure | Prepared Analogous to Procedure | MS (ES) [M+ 1] | Add'nal Info | "C"Prep Described in ... |
|---|---|---|---|---|---|
| 842 | 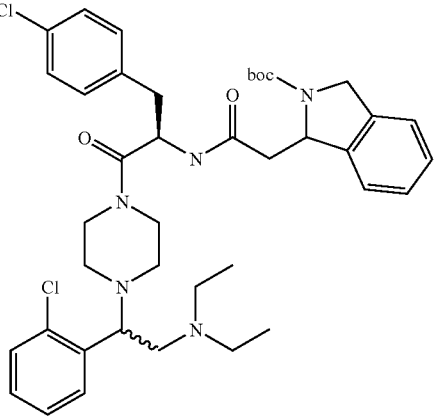 | Y | 736.3 | | Preparation C2 isomer 1 |
| 843 | 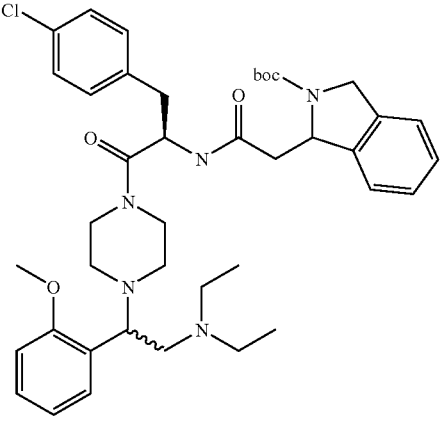 | Y | 732.2 | | Preparation C2 isomer 2 |
| 844 | 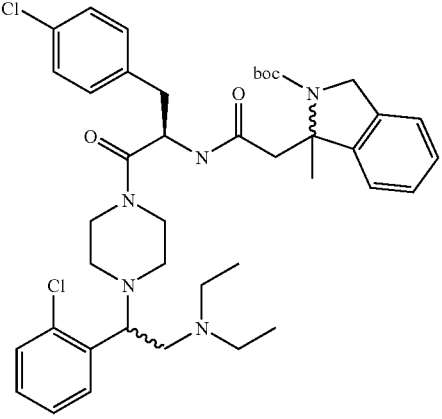 | Y | 750.5 | | Preparation C14 |

TABLE XV-continued
| Cmpd. # | TABLE XV, Structure | Prepared Analogous to Procedure | MS (ES) [M+ 1] | Add'nal Info | "C"Prep Described in . . . |
|---|---|---|---|---|---|
| 845 | 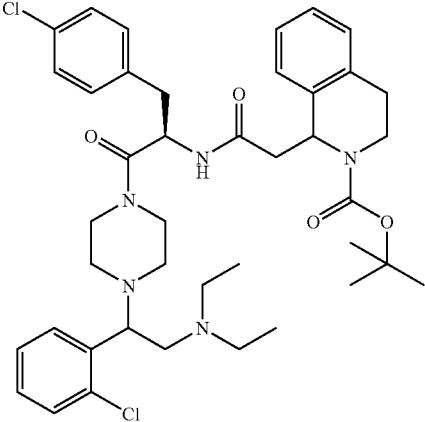 | Y | 750.4 | "A" isomer#2, "C" isomer#2 | Preparation C3 |
| 846 | 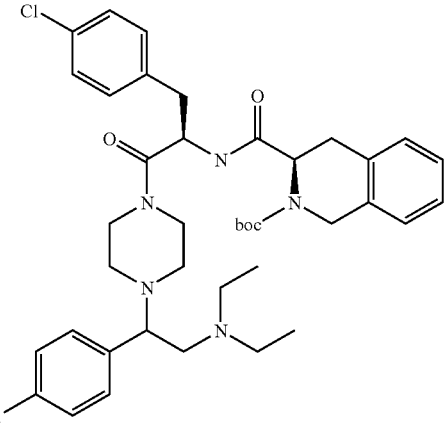 | Y | 736.4 | "A" isomer#1 | "C"carboxylic acid is comm. Available |
| 847 | 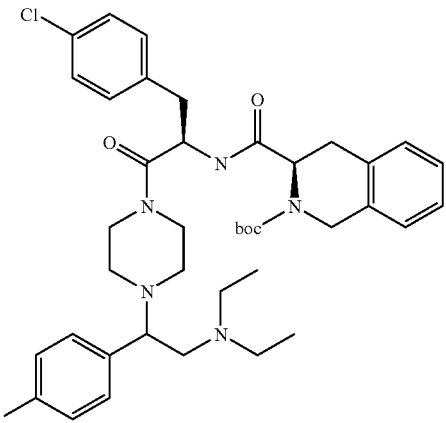 | Y | 736.4 | "A" isomer#2 | "C" carboxylic acid is comm. Available |

TABLE XV-continued
| Cmpd. # | TABLE XV, Structure | Prepared Analogous to Procedure | MS (ES) [M+ 1] | Add'nal Info | "C"Prep Described in . . . |
|---|---|---|---|---|---|
| 848 | 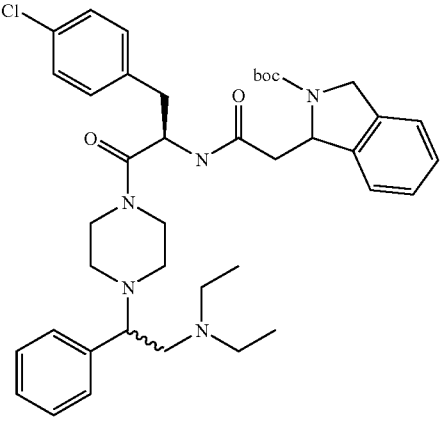 | Y | | | Preparation C2 isomer 2 |
| 849 | 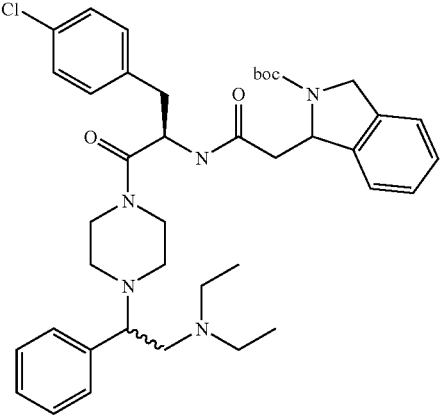 | Y | | | Preparation C2 isomer 1 |

325

Compounds 901–902 (listed in Table XVI. below) were prepared substantially analogous to the following procedure for amide coupling of the respective de-protected "A" pieces to the respective pre-coupled "B-C" piece (the synthesis of each non-commercially available "B-C" piece is described in the section entitled "Preparation of Novel "C" and "B-C" Pieces" and other section herein).

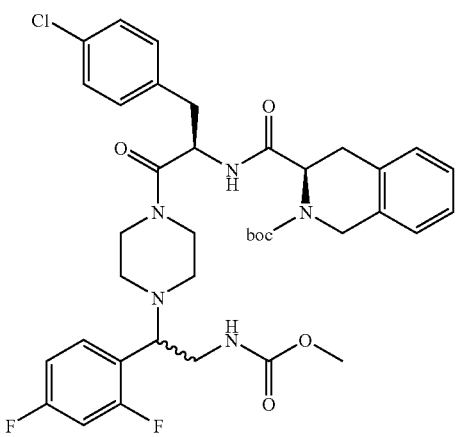

326

Procedure Z

Preparation of 3-(1-(4-Chloro-benzyl)-2-{4-[1-(2,4-difluoro-phenyl)-2-methoxycarbonylamino-ethyl]-piperazin-1-yl}-2-oxo-ethylcarbamoyl)-3,4-dihydro-1H-isoquinoline-2-carboxylic acid tert-butyl ester (917)

To [2-(2,4-Difluoro-phenyl)-2-piperazin-1-yl-ethyl]-carbamic acid methyl ester (516) (0.14 g, 0.47 mmol), 3-[1-Carboxy-2-(4-chloro-phenyl)-ethylcarbamoyl]-3,4-dihydro-1H-isoquinoline-2-carboxylic acid tert-butyl ester (0.22 g, 0.47 mmol) and O-(7-Azabenzotriazol-1-yl)-N,N,N',N'-tetramethyluronium hexafluorophosphate (0.178 g, 0.47 mmol) was added MeCl$_2$ (1.0 mL) and DMF (0.2 mL) followed by DIPEA (0.82 mL, 4.7 mmol). The reaction was allowed to stir at room temperature for 4 h. The reaction mixture was then concentrated to dryness. The resulting residue was taken up in EtOAc (30 mL) and washed with sat. NaHCO$_3$ (30 mL) and brine (30 mL). The organic phase was concentrated to dryness. The crude material was purified by chromatography (silica gel 60 mesh, eluting with a gradient of 100% EtOAc to 5% TEA/5% MeOH in EtOAc) yielding 0.34 g (98%) pure product.

MS (ES) 740.2 [M+1]

TABLE XVI

| Compound # | Structure | Prepared analogous to Procedure | MS ES (M + 1) | Additional info |
|---|---|---|---|---|
| 951 | 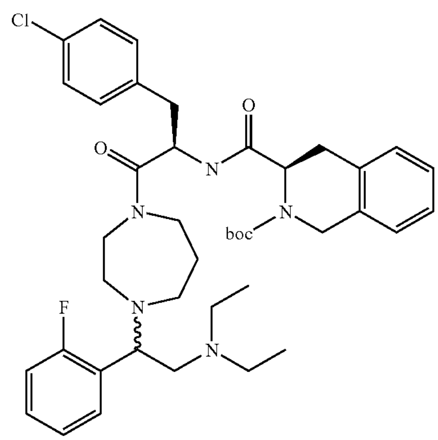 | Z | 734.7 | |

TABLE XVI-continued

| Compound # | Structure | Prepared analogous to Procedure | MS ES (M + 1) | Additional info |
|---|---|---|---|---|
| 952 | 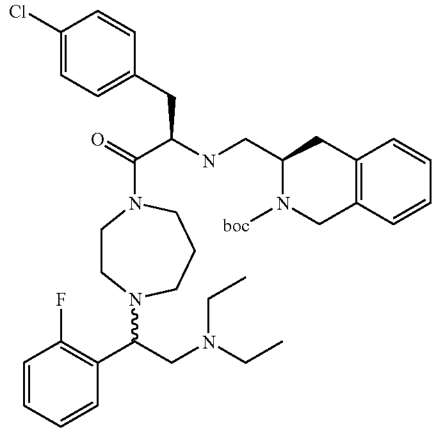 | Z | 720.7 | |

The TFA or HCl salts of compounds 1001–1105 (listed in Table XVII below) were prepared substantially analogous to the following procedure for deprotection and purification of their respective Boc-protected "A-B-C" precursor. HPLC purification as described may allow for resolution of a racemic compound.

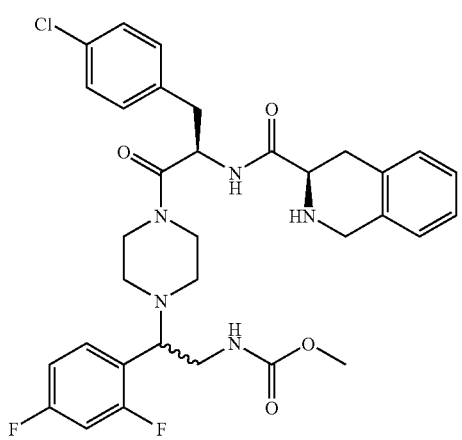

Procedure AA

Preparation of 5[2-(4-{3-(4-Chloro-phenyl)-2-[(1,2,3,4-tetrahydro-isoquinoline-3-carbonyl)-amino]-propionyl}-piperazin-1-yl)-2-(2,4-difluoro-phenyl)-ethyl]-carbamic acid methyl ester (1035)

To 3-(1-(4-Chloro-benzyl)-2-{4-[1-(2,4-difluoro-phenyl)-2-methoxycarbonylamino-ethyl]-piperazin-1-yl}-2-oxo-ethylcarbamoyl)-3,4-dihydro-1H-isoquinoline-2-carboxylic acid tert-butyl ester (917) (0.340 g, 0.461 mmol) in MeCl$_2$ (1.0 mL) was added TFA (1.0 mL) and the reaction was allowed to stir at room temperature for 1 h. The reaction mixture was then concentrated to dryness. The product was isolated as the TFA salt by trituration with Et$_2$O and filtration. The compound was further purified by HPLC (Waters Symmetry column—Part # WAT066245, flow rate: 20 mL/min, gradient: 10% MeCN in H$_2$O (with TFA modifier) to 40% MeCN in H$_2$O). 0.320 g (80%) pure TFA salt of the desired product was isolated.

MS (ES) 640.2 [M+1]. The TFA salt can be converted to the HCl salt by using an HCl modifier/buffer during the HPLC run, or by dissolving the TFA salt in 1N HCl and lyophilizing overnight or as appropriate.

TABLE XVII

| Cmpd. # | Structure | Prepared Analogous to Procedure | MS ES [M + 1] | Additional Info. |
| --- | --- | --- | --- | --- |
| 1001 | 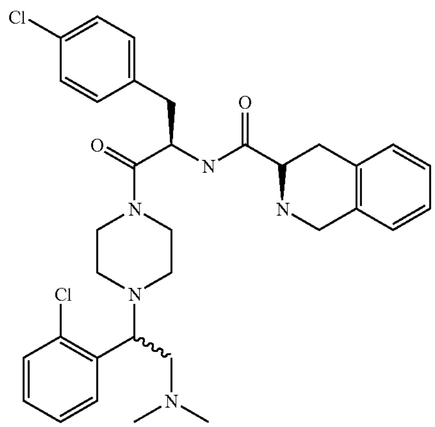 | AA | 608.1 | |
| 1002 | 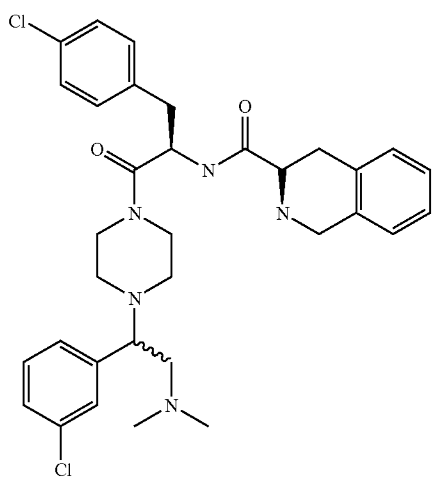 | AA | 608.1 | |
| 1003 | 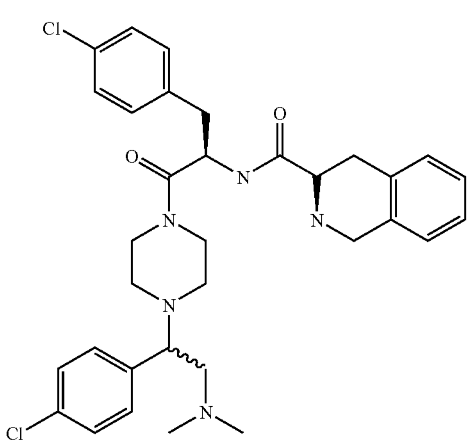 | AA | 608.1 | |

TABLE XVII-continued

| Cmpd. # | Structure | Prepared Analogous to Procedure | MS ES [M + 1] | Additional Info. |
|---|---|---|---|---|
| 1004 | 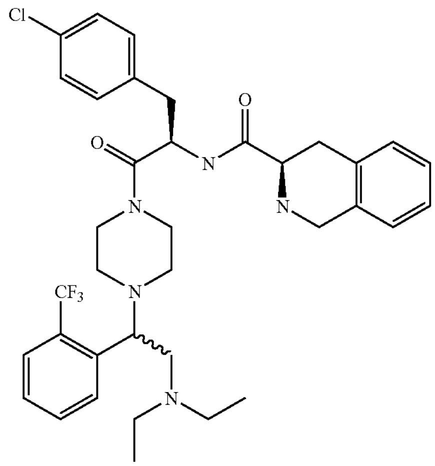 | AA | 660.3 | |
| 1005 | 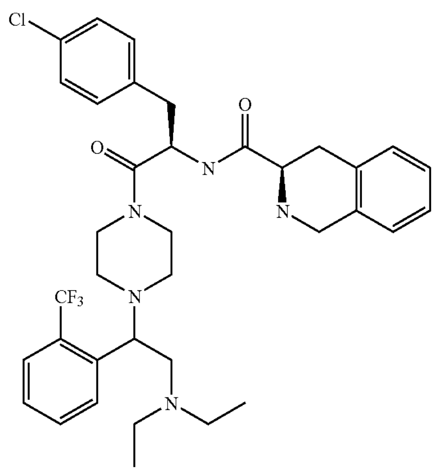 | AA | 660.3 | isomer #1 (of 2 - HPLC) |
| 1006 | 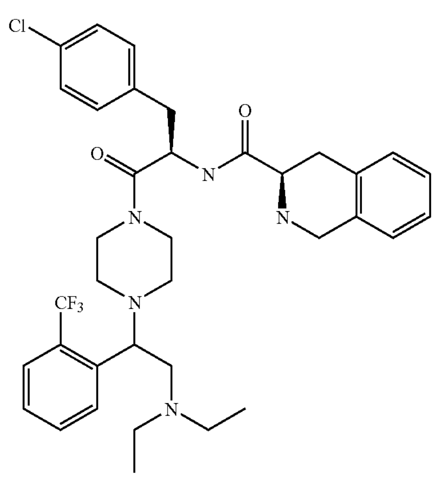 | AA | 660.3 | isomer #2 (of 2 - HPLC) |

TABLE XVII-continued
| Cmpd. # | Structure | Prepared Analogous to Procedure | MS ES [M + 1] | Additional Info. |
|---|---|---|---|---|
| 1007 | 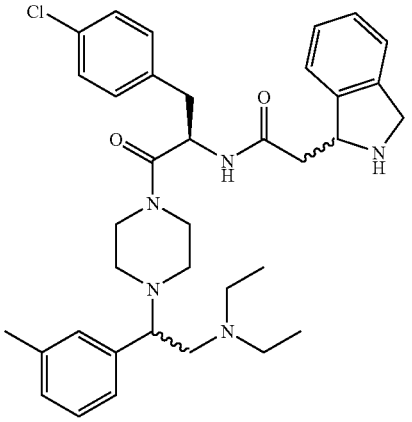 | AA | 616.4 | |
| 1008 | 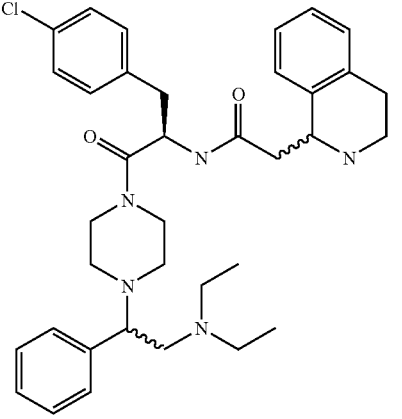 | AA | 616.4 | |
| 1009 | 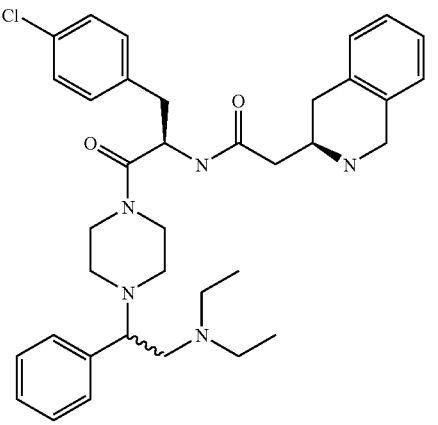 | AA | 616.4 | |

TABLE XVII-continued
| Cmpd. # | Structure | Prepared Analogous to Procedure | MS ES [M + 1] | Additional Info. |
|---|---|---|---|---|
| 1010 | 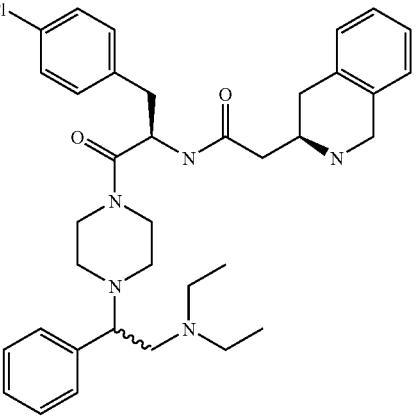 | AA | 616.4 | |
| 1011 | 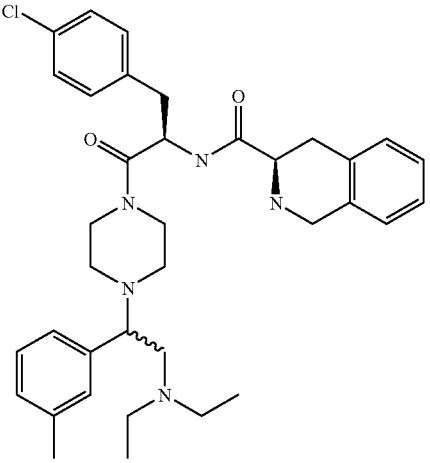 | AA | 616.4 | |
| 1012 | 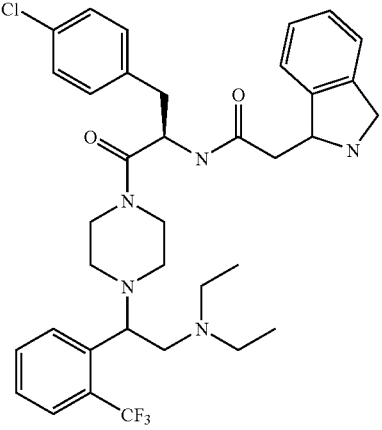 | AA | 670.2 | isomer #2 - UNK (of 4 - HPLC) |

TABLE XVII-continued
| Cmpd. # | Structure | Prepared Analogous to Procedure | MS ES [M + 1] | Additional Info. |
|---|---|---|---|---|
| 1013 | 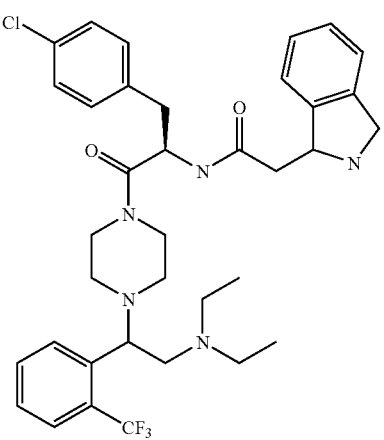 | AA | 670.2 | isomer #4 - UNK (of 4 - HPLC) |
| 1014 | 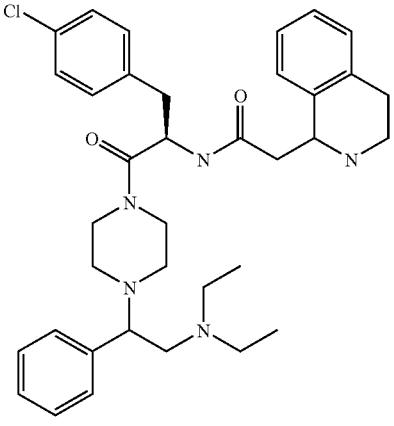 | AA | 616.4 | isomer #1 (of 4 - HPLC) |
| 1015 | 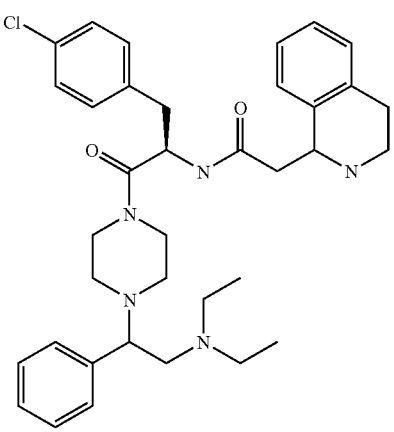 | AA | 616.4 | isomer #2 (of 4 - HPLC) |

TABLE XVII-continued
| Cmpd. # | Structure | Prepared Analogous to Procedure | MS ES [M + 1] | Additional Info. |
|---|---|---|---|---|
| 1016 | 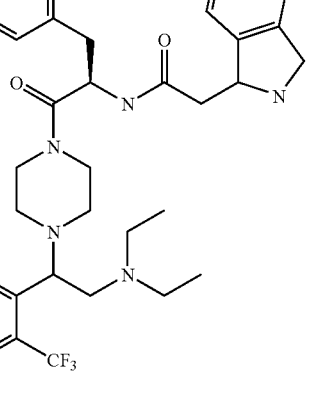 | AA | 670.2 | isomer #1 (of 2 - HPLC) C domain isomer #2 |
| 1017 | 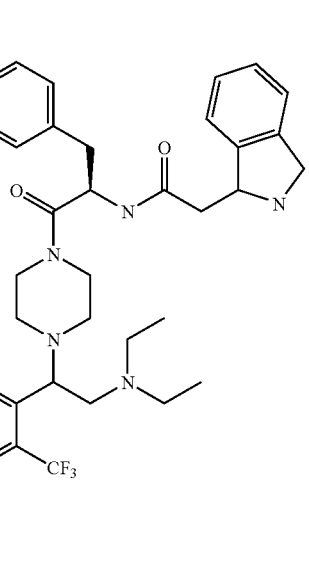 | AA | 670.2 | isomer #2 (of 2 - HPLC) C domain isomer #1 |
| 1018 | 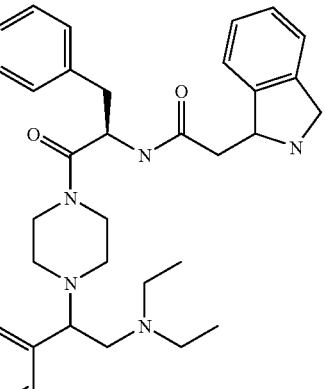 | AA | 670.2 | isomer #1 (of 2 - HPLC) C domain isomer #2 |

TABLE XVII-continued
| Cmpd. # | Structure | Prepared Analogous to Procedure | MS ES [M + 1] | Additional Info. |
|---|---|---|---|---|
| 1019 | 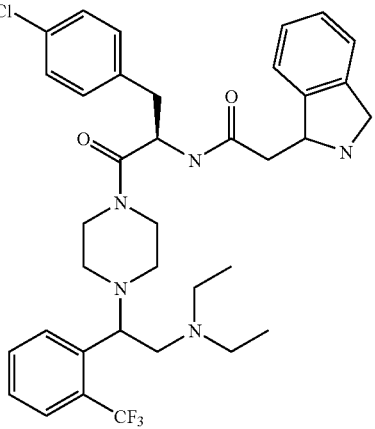 | AA | 670.2 | isomer #2 (of 2 - HPLC) C domain isomer #2 |
| 1020 | 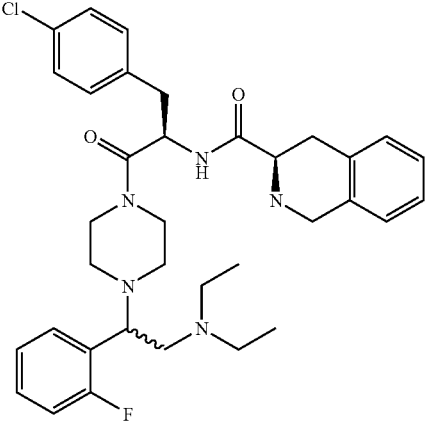 | AA | 620.3 | |
| 1021 | 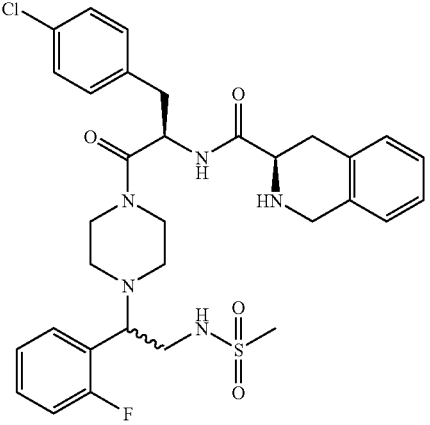 | AA | 640.4 | |

TABLE XVII-continued

| Cmpd. # | Structure | Prepared Analogous to Procedure | MS ES [M + 1] | Additional Info. |
|---|---|---|---|---|
| 1022 | 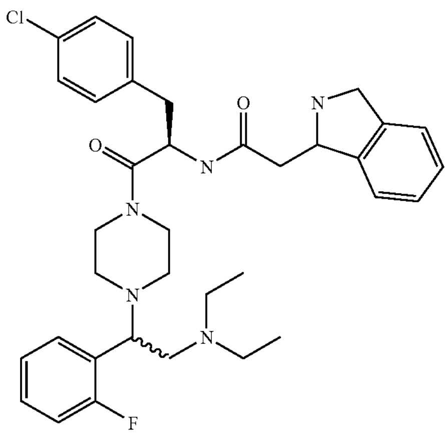 | AA | 620.4 | C domain isomer #2 |
| 1023 | 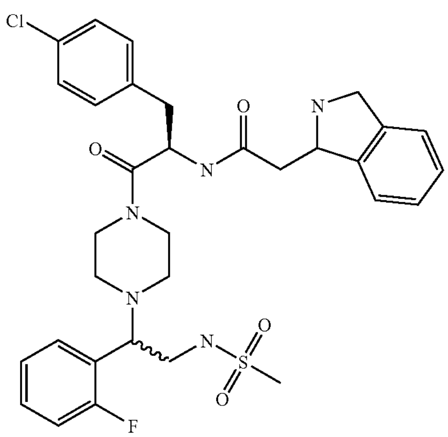 | AA | 642.4 | C domain isomer #2 |
| 1024 | 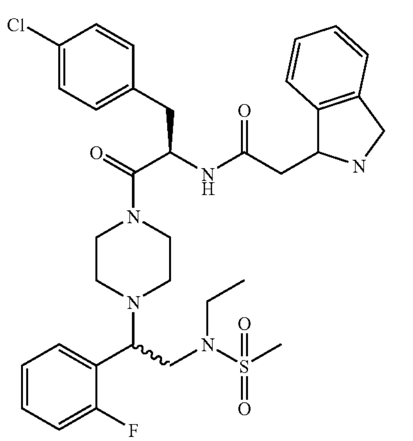 | AA | 670.3 | |

TABLE XVII-continued
| Cmpd. # | Structure | Prepared Analogous to Procedure | MS ES [M + 1] | Additional Info. |
|---|---|---|---|---|
| 1025 | 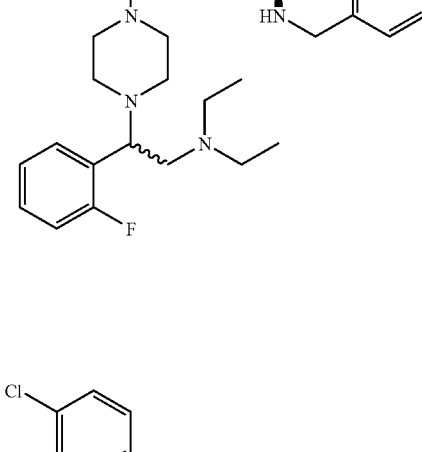 | AA | 606.4 | |
| 1026 | 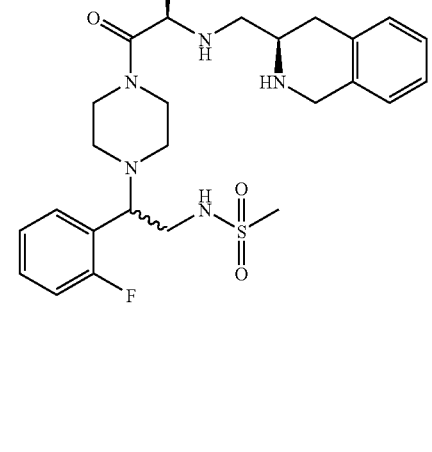 | AA | 628.1 | |
| 1027 | 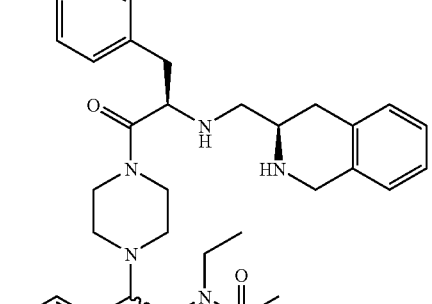 | AA | 656.4 | |

TABLE XVII-continued
| Cmpd. # | Structure | Prepared Analogous to Procedure | MS ES [M + 1] | Additional Info. |
|---|---|---|---|---|
| 1028 | 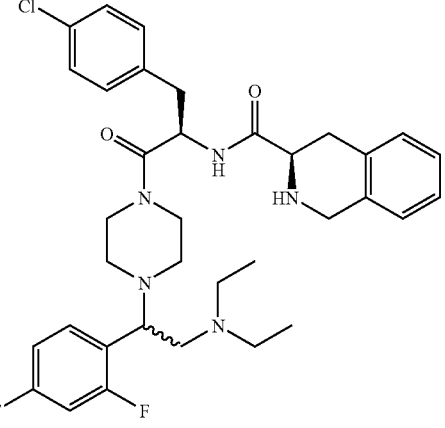 | AA | 638.2 | |
| 1029 | 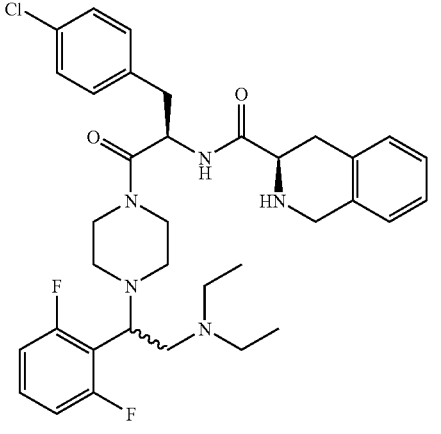 | AA | 638.2 | |
| 1030 | 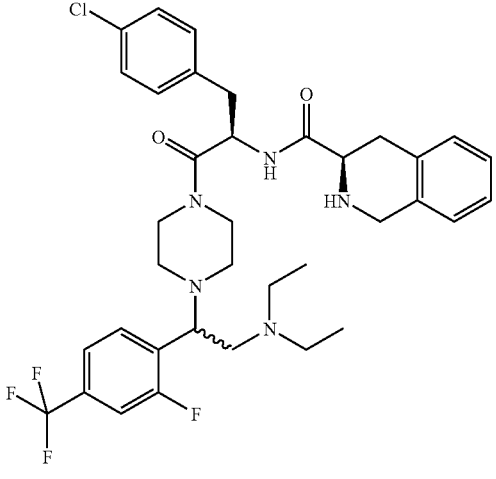 | AA | 688.2 | |

TABLE XVII-continued

| Cmpd. # | Structure | Prepared Analogous to Procedure | MS ES [M + 1] | Additional Info. |
|---|---|---|---|---|
| 1031 | 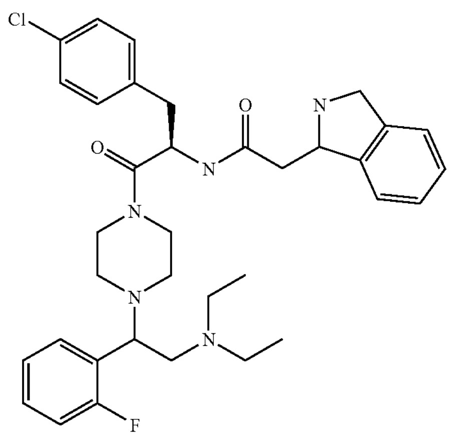 | AA | 620.3 | "A" isomer #2 C domain isomer #2 |
| 1032 | 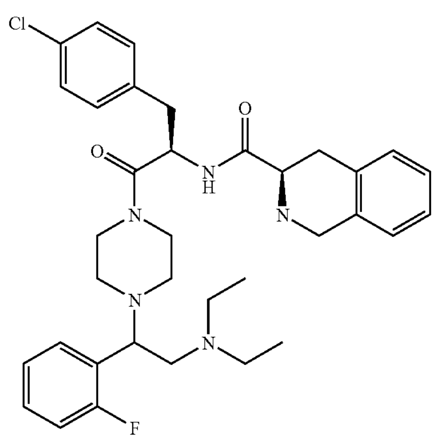 | AA | 620.4 | "A" isomer #2 |
| 1033 | 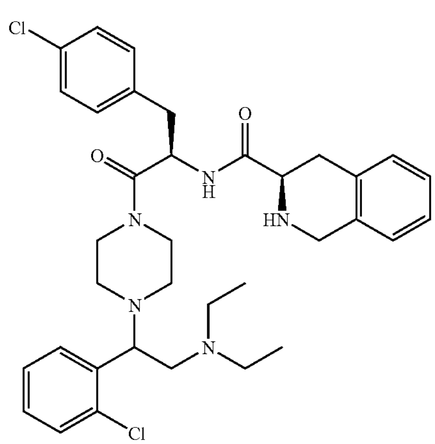 | AA | 636.3 | "A" isomer #2 |

TABLE XVII-continued
| Cmpd. # | Structure | Prepared Analogous to Procedure | MS ES [M + 1] | Additional Info. |
|---|---|---|---|---|
| 1034 | 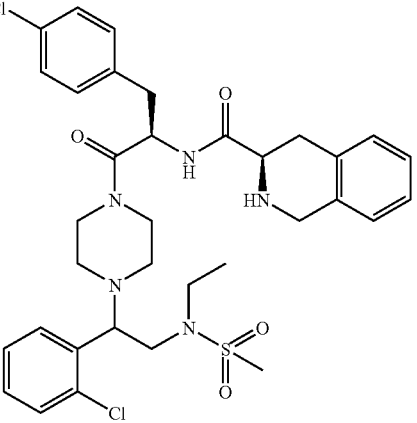 | AA | 686.2 | "A" isomer #2 |
| 1035 | 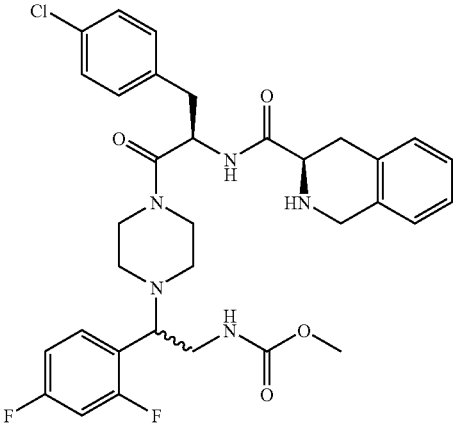 | AA | 640.2 | |
| 1036 | 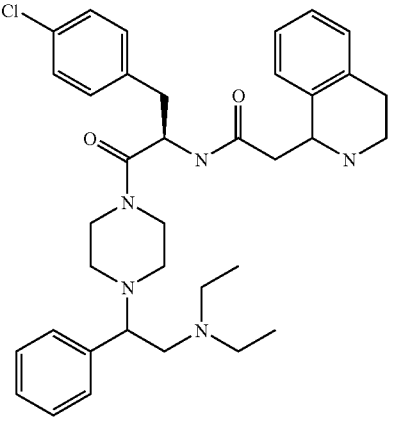 | AA | 616.4 | isomer #3 (of 4 - HPLC) |

TABLE XVII-continued

| Cmpd. # | Structure | Prepared Analogous to Procedure | MS ES [M + 1] | Additional Info. |
|---|---|---|---|---|
| 1037 | 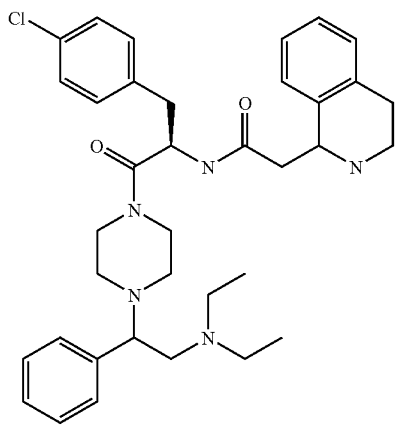 | AA | 616.4 | isomer #4 (of 4 - HPLC) |
| 1038 | 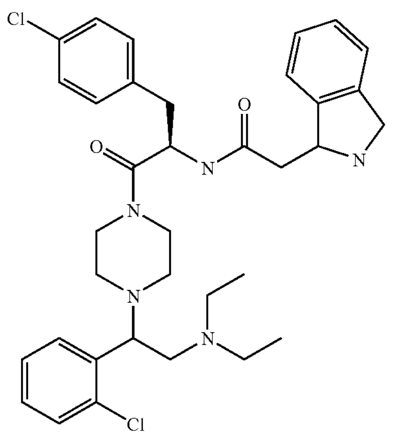 | AA | 636.2 | "A" isomer #2 C domain isomer #2 |
| 1039 | 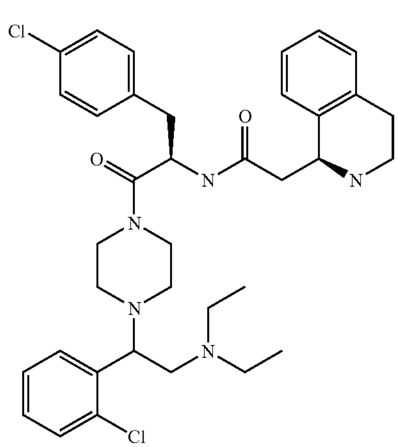 | AA | 650.3 | "A" isomer #2 |

TABLE XVII-continued
| Cmpd. # | Structure | Prepared Analogous to Procedure | MS ES [M + 1] | Additional Info. |
|---|---|---|---|---|
| 1040 | 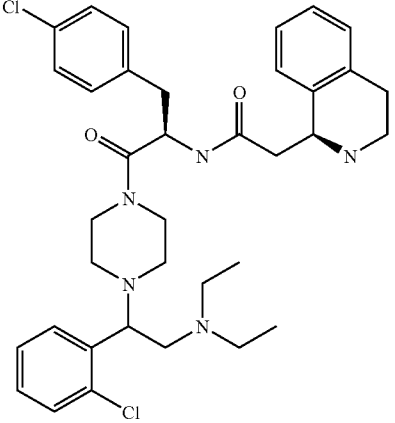 | AA | 650.3 | "A" isomer #2 |
| 1041 | 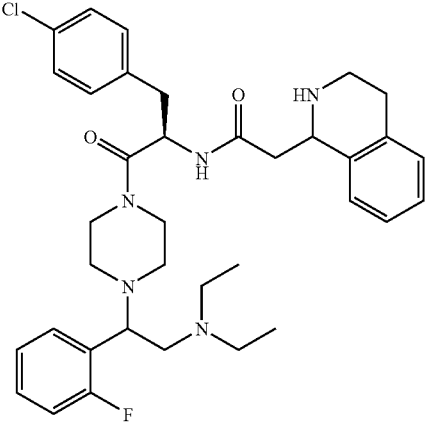 | AA | 635.1 | "A" isomer #2, "C" isomer #1 |
| 1042 | 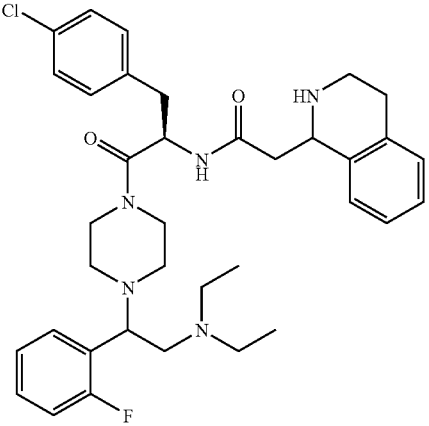 | AA | 634.1 | "A" isomer #2, "C" isomer #1 |

TABLE XVII-continued
| Cmpd. # | Structure | Prepared Analogous to Procedure | MS ES [M + 1] | Additional Info. |
|---|---|---|---|---|
| 1043 | 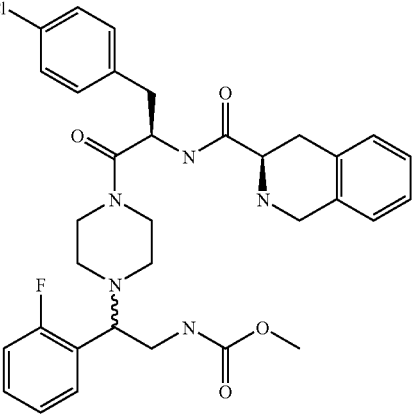 | AA | 622.1 | |
| 1044 | 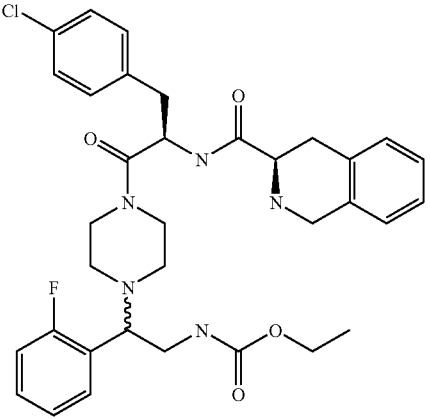 | AA | 636.2 | |
| 1045 | 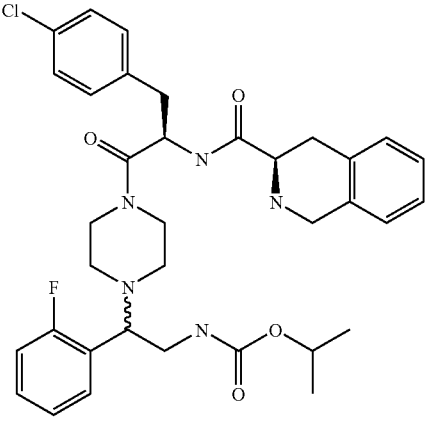 | AA | 650.2 | |

TABLE XVII-continued

| Cmpd. # | Structure | Prepared Analogous to Procedure | MS ES [M + 1] | Additional Info. |
|---|---|---|---|---|
| 1046 | 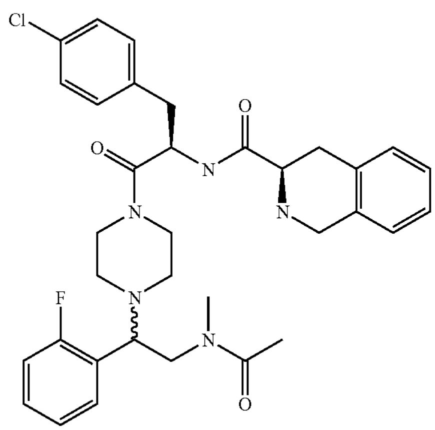 | AA | 620.2 | |
| 1047 | 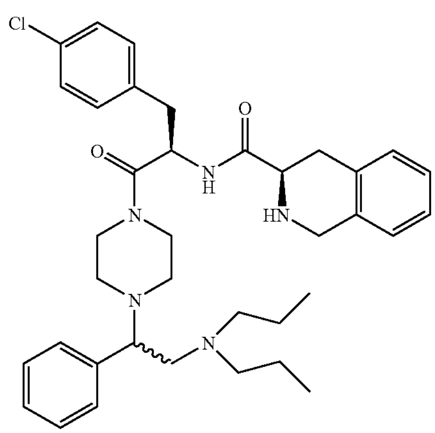 | AA | 630.3 | |
| 1048 | 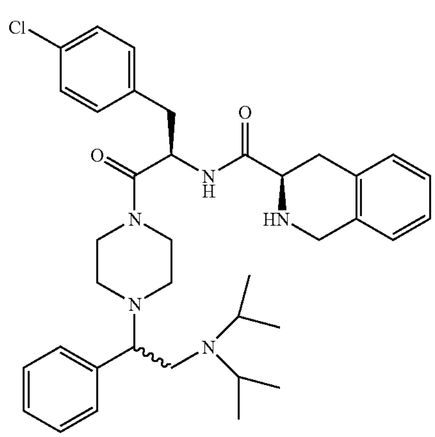 | AA | 630.3 | |

TABLE XVII-continued
| Cmpd. # | Structure | Prepared Analogous to Procedure | MS ES [M + 1] | Additional Info. |
|---|---|---|---|---|
| 1049 | 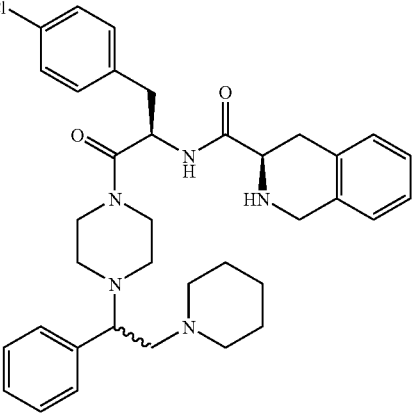 | AA | 614.2 | |
| 1050 | 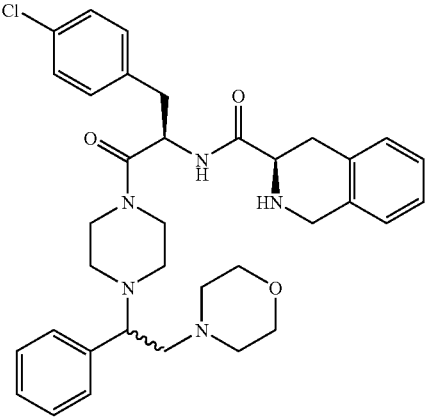 | AA | 616.2 | |
| 1051 | 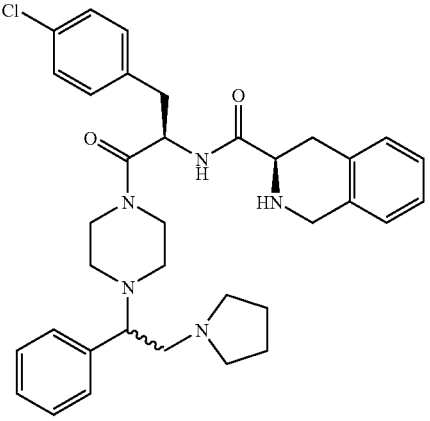 | AA | 600.2 | |

TABLE XVII-continued

| Cmpd. # | Structure | Prepared Analogous to Procedure | MS ES [M + 1] | Additional Info. |
|---|---|---|---|---|
| 1052 | 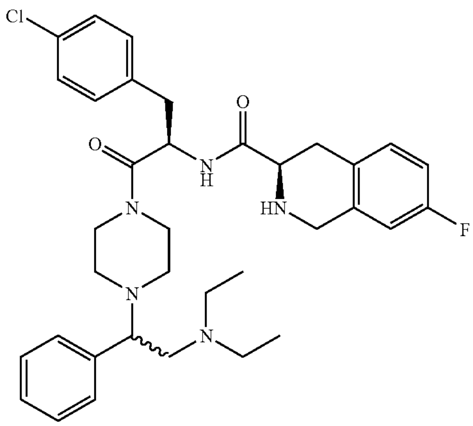 | AA | 620.3 | |
| 1053 | 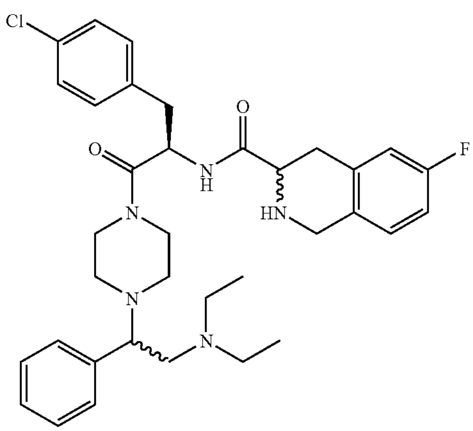 | AA | 620.3 | |
| 1054 | 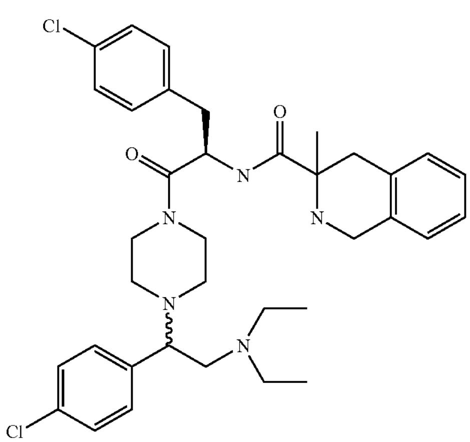 | AA | 650.3 | "C" isomer #1 |

TABLE XVII-continued
| Cmpd. # | Structure | Prepared Analogous to Procedure | MS ES [M + 1] | Additional Info. |
|---|---|---|---|---|
| 1055 | 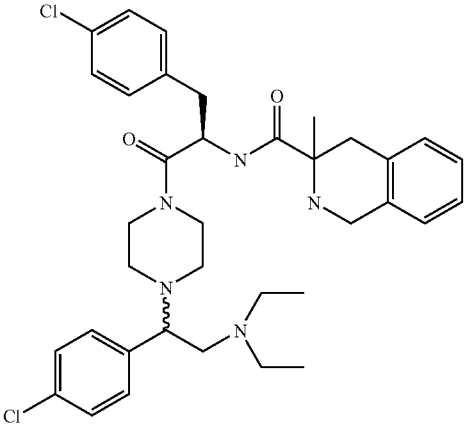 | AA | 651.3 | "C" isomer #2 |
| 1056 | 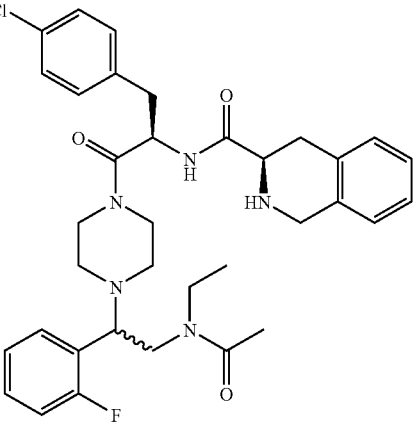 | AA | 634.2 | |
| 1057 | 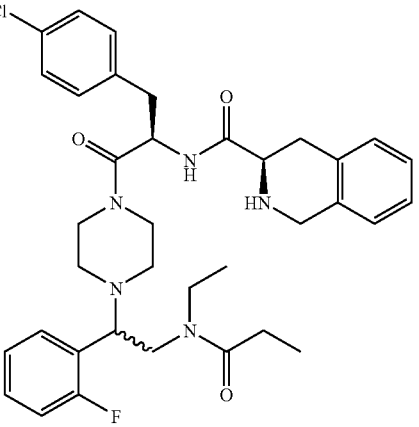 | AA | 648.2 | |

TABLE XVII-continued
| Cmpd. # | Structure | Prepared Analogous to Procedure | MS ES [M + 1] | Additional Info. |
|---|---|---|---|---|
| 1058 | 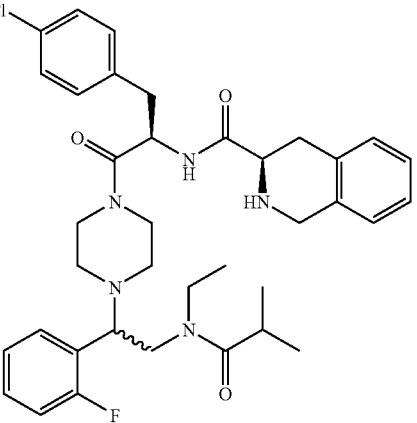 | AA | 662.2 | |
| 1059 | 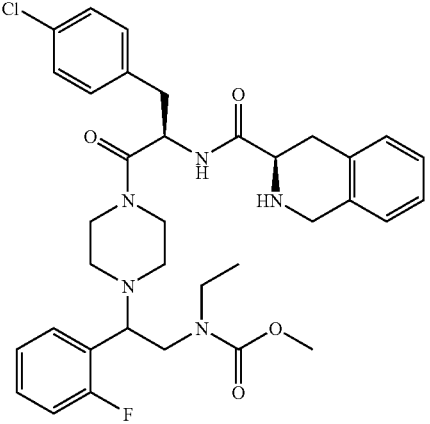 | AA | 650.3 | |
| 1060 | 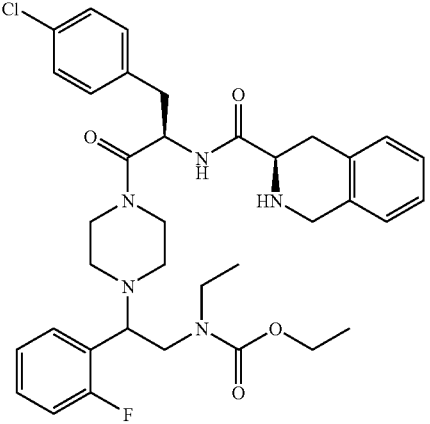 | AA | 664.4 | |

| Cmpd. # | Structure | Prepared Analogous to Procedure | MS ES [M + 1] | Additional Info. |
|---|---|---|---|---|
| 1061 | 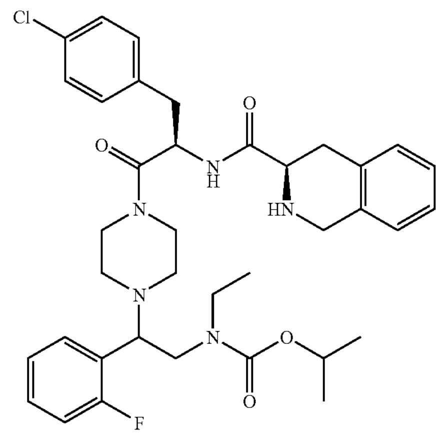 | AA | 678.4 | |
| 1062 | 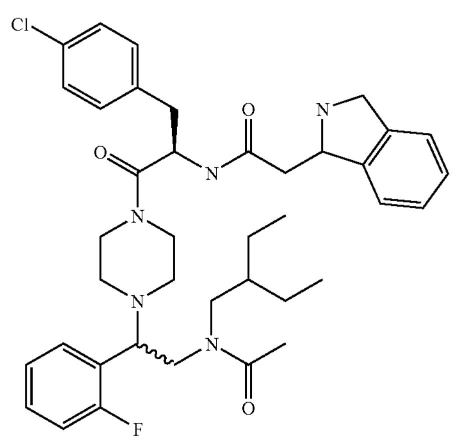 | AA | 690.5 | C domain isomer #2 |
| 1063 | 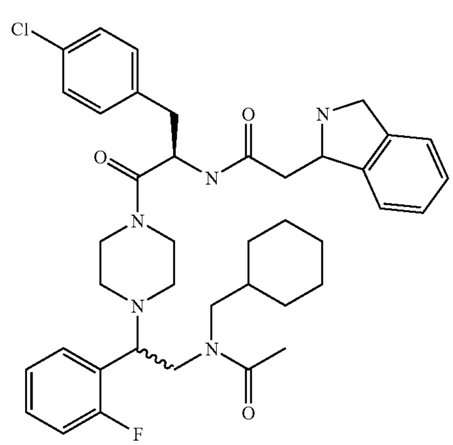 | AA | 702.3 | C domain isomer #2 |

TABLE XVII-continued

| Cmpd. # | Structure | Prepared Analogous to Procedure | MS ES [M + 1] | Additional Info. |
|---|---|---|---|---|
| 1064 | 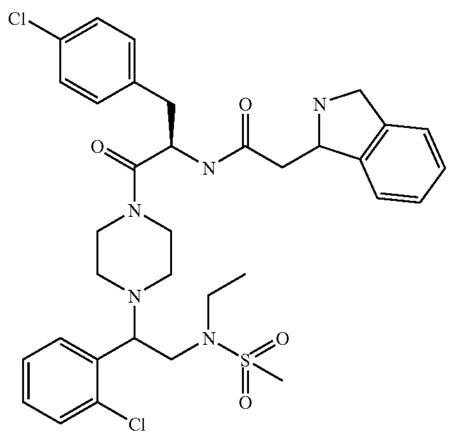 | AA | 686.1 | "A" isomer #2 C domain isomer #2 |
| 1065 | 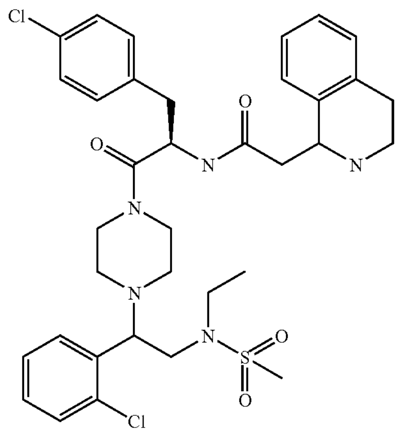 | AA | 700.1 | "A" isomer #2 |
| 1066 | 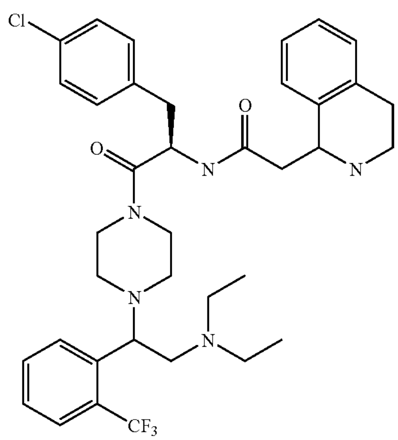 | AA | 684.1 | "A" isomer #2 |

TABLE XVII-continued
| Cmpd. # | Structure | Prepared Analogous to Procedure | MS ES [M + 1] | Additional Info. |
|---|---|---|---|---|
| 1067 | 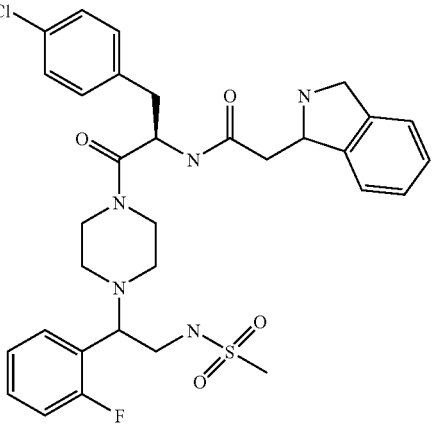 | AA | 642.1 | "A" isomer #2 C domain isomer #2 |
| 1068 | 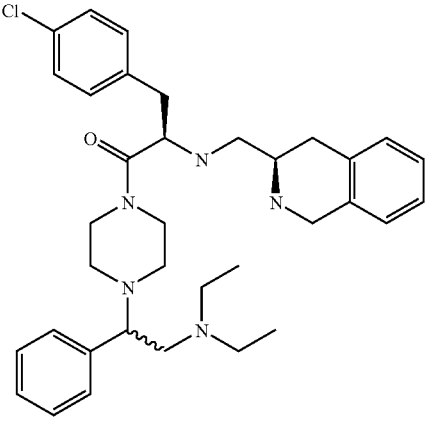 | AA | 588.1 | |
| 1069 | 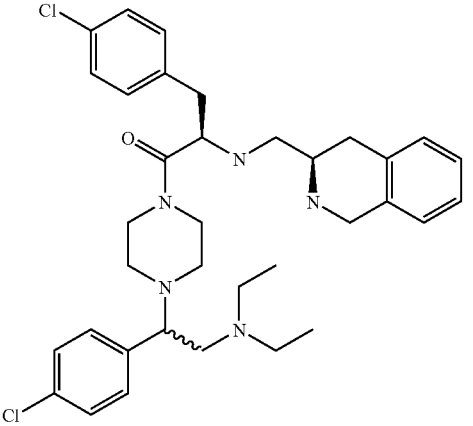 | AA | 622.1 | |

TABLE XVII-continued

| Cmpd. # | Structure | Prepared Analogous to Procedure | MS ES [M + 1] | Additional Info. |
|---|---|---|---|---|
| 1070 | 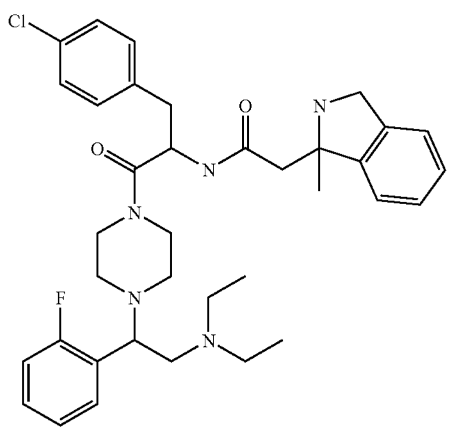 | AA | 634.3 | "A" isomer #2, "C" isomer #1 |
| 1071 | 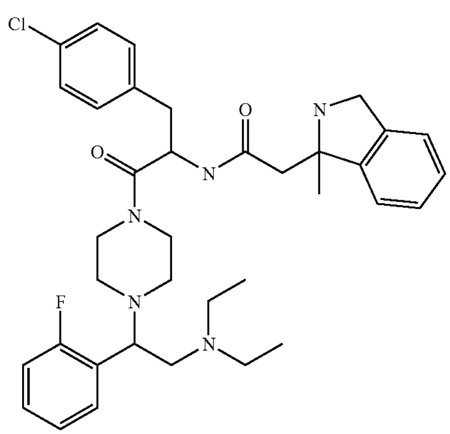 | AA | 634.3 | "A" isomer #2, "C" isomer #2 |
| 1072 | 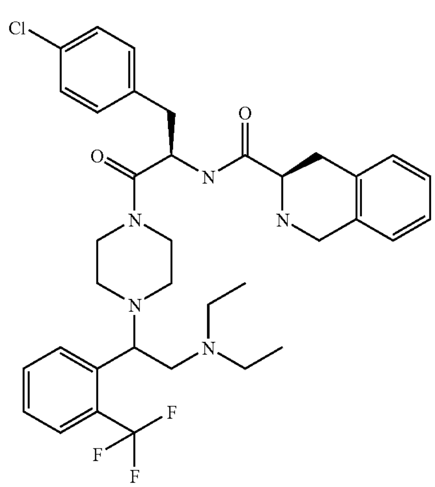 | AA | 670.3 | "A" isomer #2 |

TABLE XVII-continued
| Cmpd. # | Structure | Prepared Analogous to Procedure | MS ES [M + 1] | Additional Info. |
|---|---|---|---|---|
| 1073 | 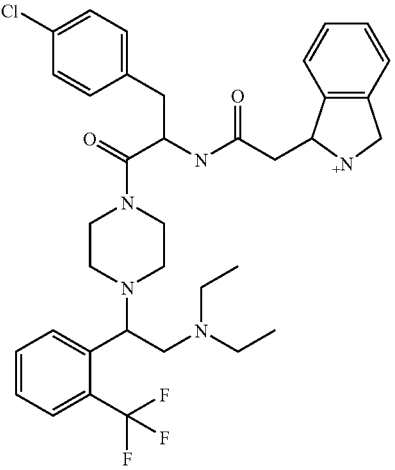 | AA | 670.3 | "A" isomer #2 |
| 1074 | 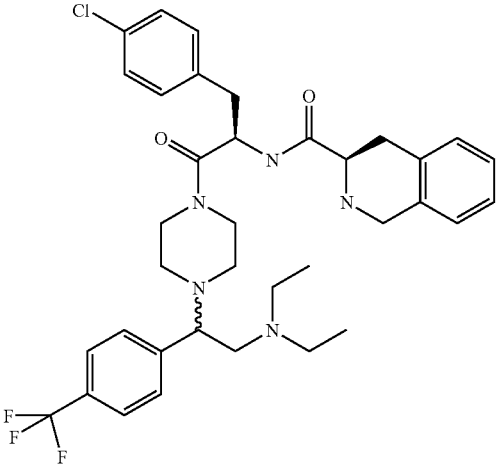 | AA | 670.2 | |
| 1075 | 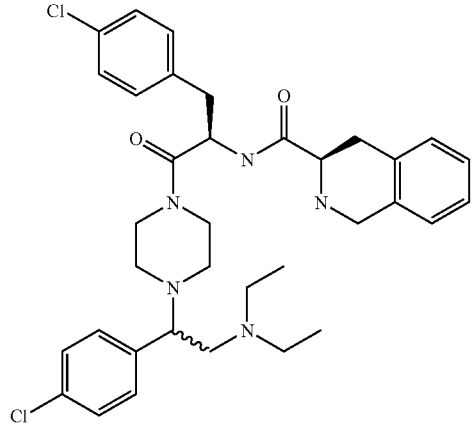 | AA | 636.1 | |

TABLE XVII-continued

| Cmpd. # | Structure | Prepared Analogous to Procedure | MS ES [M + 1] | Additional Info. |
|---|---|---|---|---|
| 1076 | 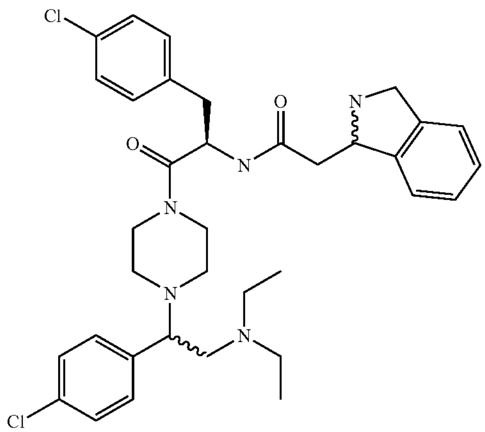 | AA | 636.0 | |
| 1077 | 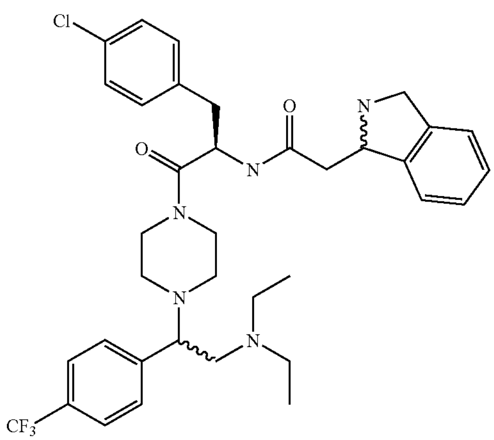 | AA | 670.2 | |
| 1078 | 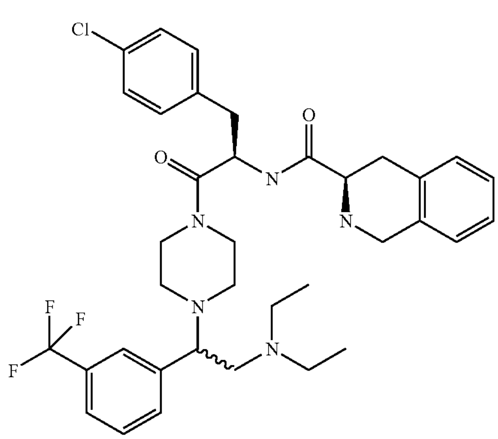 | AA | 670.2 | |

TABLE XVII-continued
| Cmpd. # | Structure | Prepared Analogous to Procedure | MS ES [M + 1] | Additional Info. |
|---|---|---|---|---|
| 1079 | 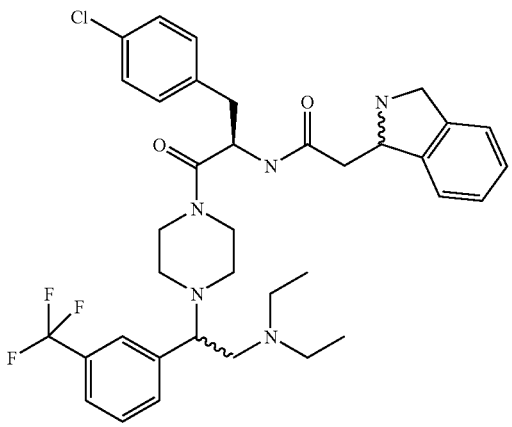 | AA | 670.2 | |
| 1080 | 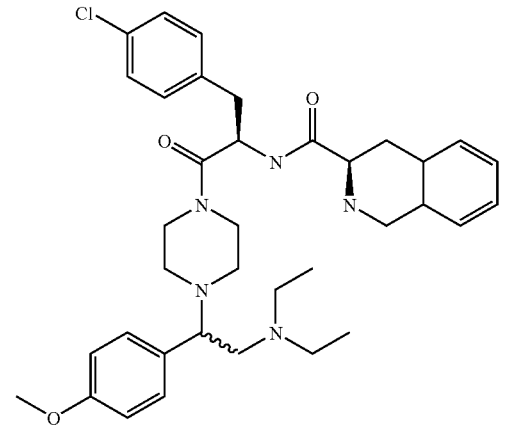 | AA | 632.4 | |
| 1081 | 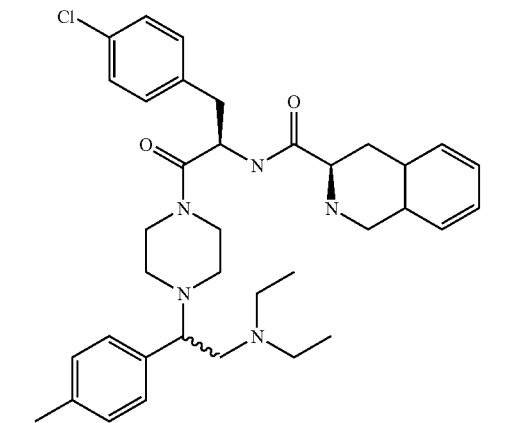 | AA | 616.4 | |

TABLE XVII-continued
| Cmpd. # | Structure | Prepared Analogous to Procedure | MS ES [M + 1] | Additional Info. |
|---|---|---|---|---|
| 1082 | 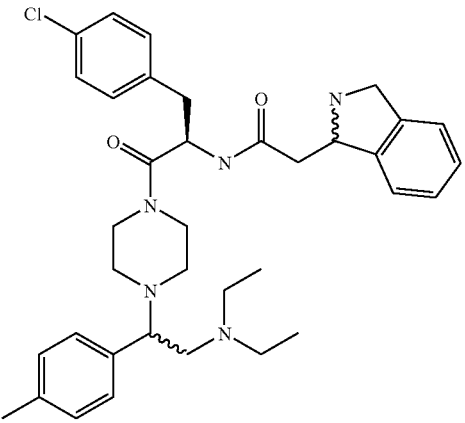 | AA | 616.4 | |
| 1083 | 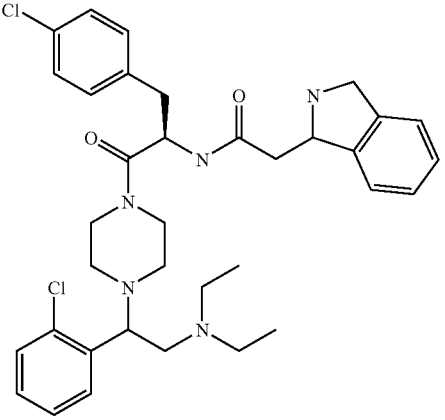 | AA | 636.0 | "A" isomer #1 C domain isomer #1 |
| 1084 | 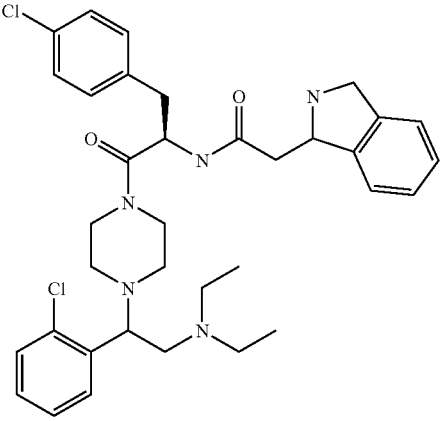 | AA | 636.0 | "A" isomer #2 C domain isomer #1 |

TABLE XVII-continued
| Cmpd. # | Structure | Prepared Analogous to Procedure | MS ES [M + 1] | Additional Info. |
|---|---|---|---|---|
| 1085 | 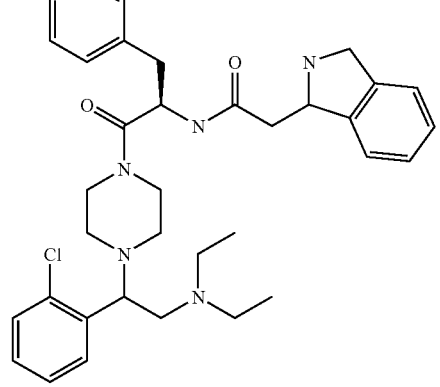 | AA | 636.0 | "A" isomer #1 |
| 1086 | 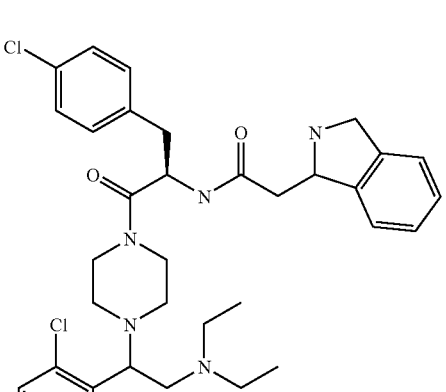 | AA | 636.0 | "A" isomer #2 C domain isomer #2 |
| 1087 | 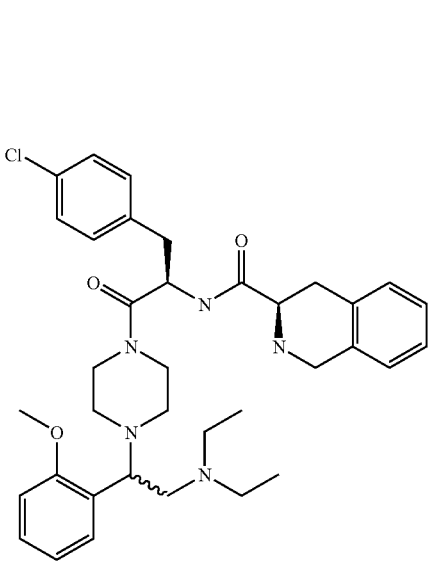 | AA | 632.3 | |

TABLE XVII-continued
| Cmpd. # | Structure | Prepared Analogous to Procedure | MS ES [M + 1] | Additional Info. |
|---|---|---|---|---|
| 1088 | 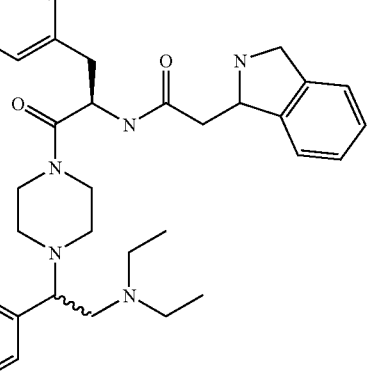 | AA | 632.3 | C domain isomer #2 |
| 1089 | 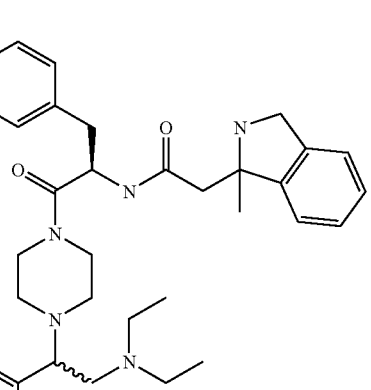 | AA | 650.3 | "C" isomer #1 |
| 1090 | 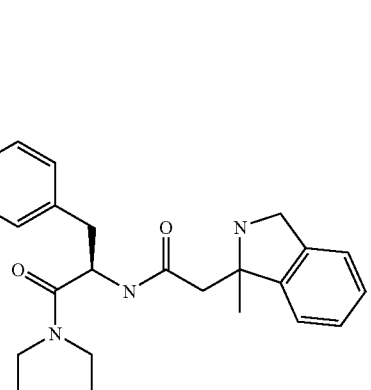 | AA | 650.3 | "C" isomer #2 |

TABLE XVII-continued

| Cmpd. # | Structure | Prepared Analogous to Procedure | MS ES [M + 1] | Additional Info. |
|---------|-----------|---------------------------------|---------------|------------------|
| 1091 | 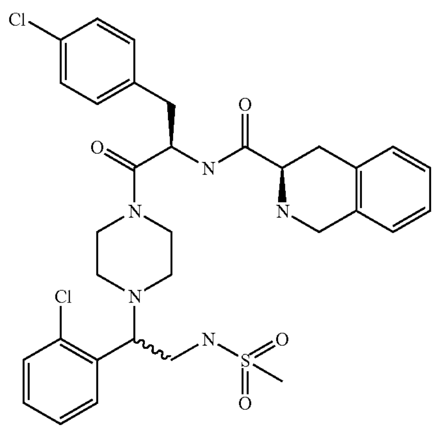 | AA | 658.2 | |
| 1092 | 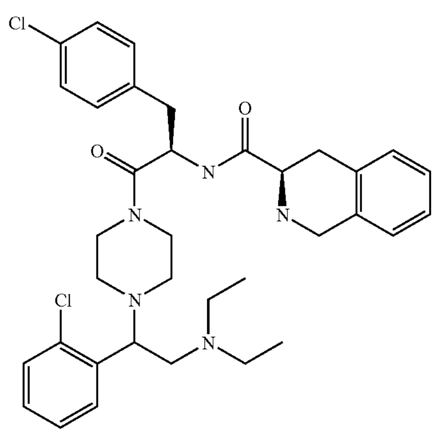 | AA | 620.3 | |
| 1093 | 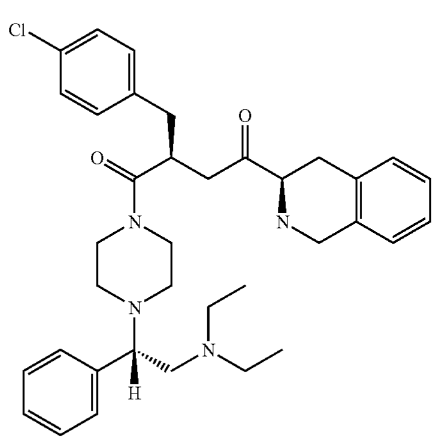 | AA | 602.3 | |

TABLE XVII-continued

| Cmpd. # | Structure | Prepared Analogous to Procedure | MS ES [M + 1] | Additional Info. |
|---|---|---|---|---|
| 1094 | 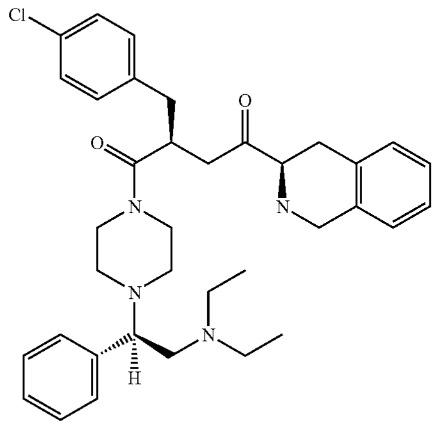 | AA | 602.3 | |
| 1095 | 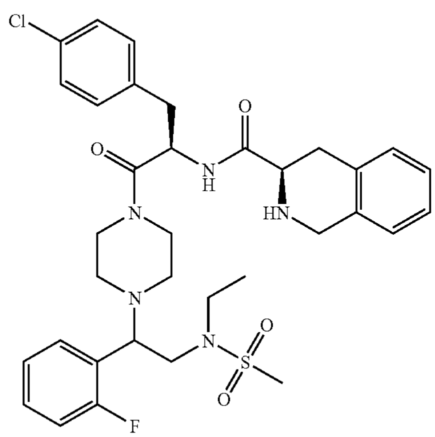 | AA | 670.3 | "A" isomer #2 |
| 1096 | 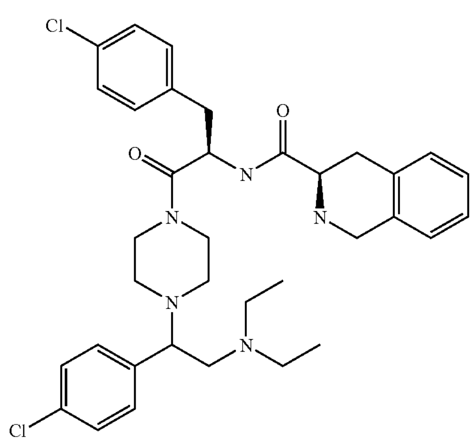 | AA | 636.3 | "A" isomer #1 |

TABLE XVII-continued
| Cmpd. # | Structure | Prepared Analogous to Procedure | MS ES [M + 1] | Additional Info. |
|---|---|---|---|---|
| 1097 | 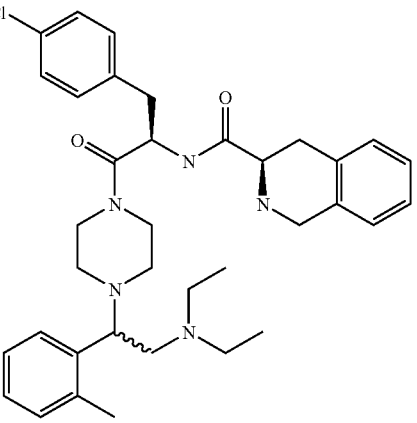 | AA | 616.4 | |
| 1098 | 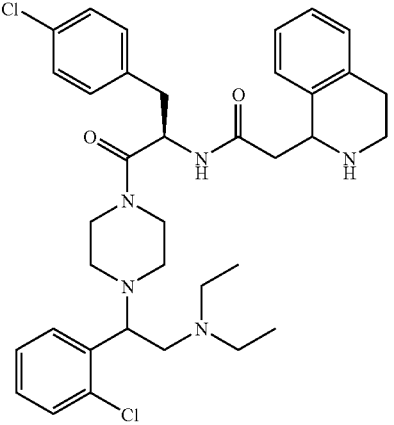 | AA | 650.3 | "A" isomer #2, "C" isomer #2 |
| 1099 | 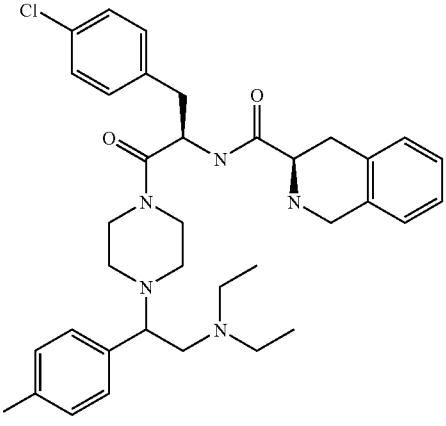 | AA | 636.3 | "A–B" isomer #1 |

TABLE XVII-continued
| Cmpd. # | Structure | Prepared Analogous to Procedure | MS ES [M + 1] | Additional Info. |
|---|---|---|---|---|
| 1100 | 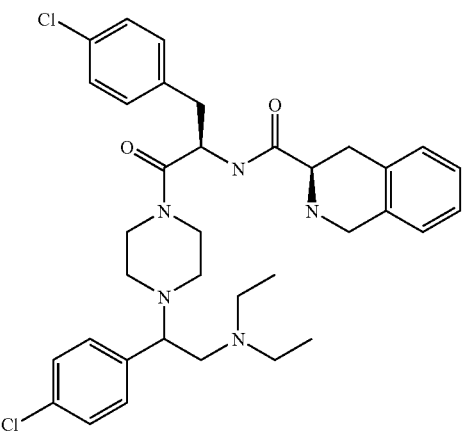 | AA | 636.3 | "A–B" isomer #2 |
| 1101 | 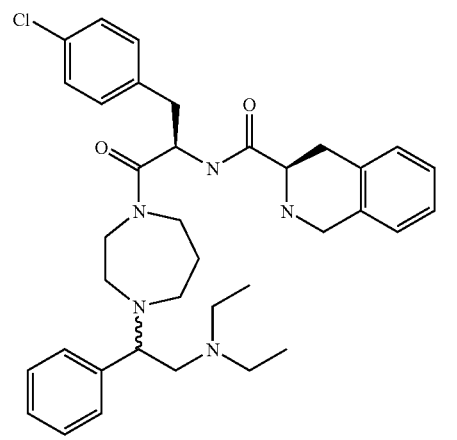 | AA | 616.3 | |
| 1102 | 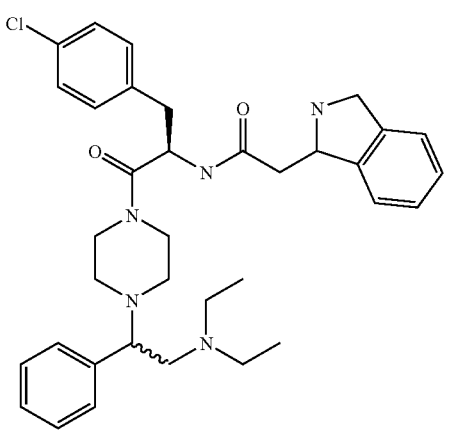 | AA | 602.0 | C domain isomer #2 |

TABLE XVII-continued

| Cmpd. # | Structure | Prepared Analogous to Procedure | MS ES [M + 1] | Additional Info. |
|---|---|---|---|---|
| 1103 | 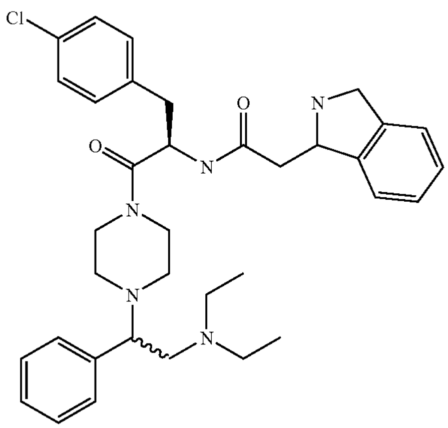 | AA | 602.0 | C domain isomer #1 |
| 1104 | 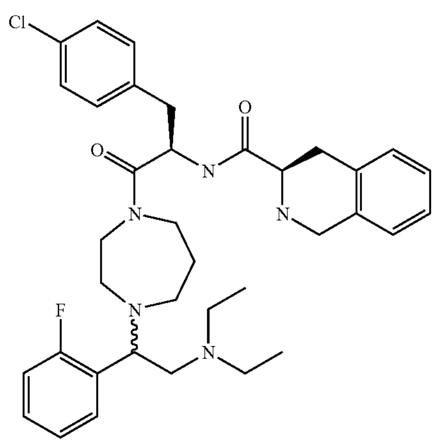 | AA | 634.4 | |
| 1105 | 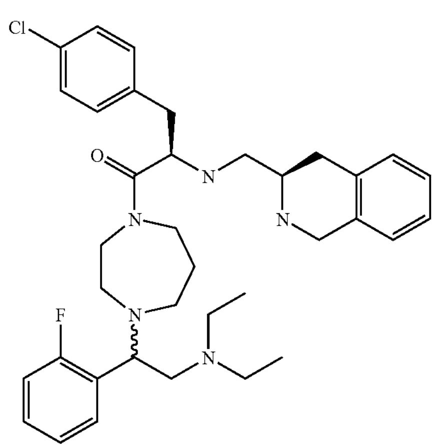 | AA | 620.5 | |

Preparation of Novel C-Domain Pieces

Heck Coupling

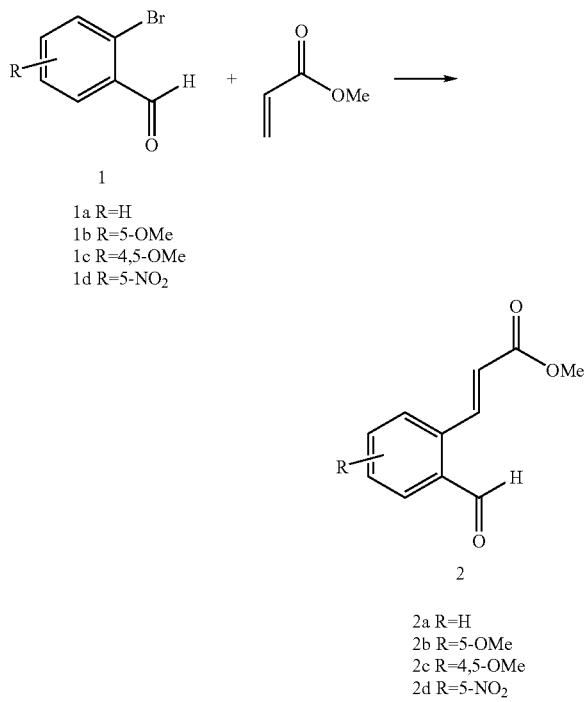

1a R=H
1b R=5-OMe
1c R=4,5-OMe
1d R=5-NO$_2$

2a R=H
2b R=5-OMe
2c R=4,5-OMe
2d R=5-NO$_2$

Preparation PP1

Synthesis of Compound (2a) by a Heck Coupling of 2-bromobenzaldehyde (1a) with methyl acrylate (Pd(OAc)$_2$/PPh$_3$ as the catalyst):

A mixture of 2-bromobenzaldehye (1a) (24.5 g, 132 mmol), methyl acrylate (17.9 mL, 199 mmol), Pd(OAc)$_2$ (590 mg, 2.65 mmol, 2 mol %), PPh$_3$ (1.39 g, 5.30 mmol, 4 mol %) and Et$_3$N (46 mL, 331 mmol) was stirred at 80° C. for 15 h. Large amount of yellow solid was formed after the reaction was done. The mixture was cooled to rt, concentrated, and mixed with H$_2$O (200 mL). The organic solid was collected by filtration, and then applied to a plug of silica gel (25 g) (EtOAc/hexane 1:1) to give a dark yellow solid. The solid was purified by crystallization (100 mL EtOAc bottom layer, 120 mL hexane top layer) to provide 17.57 g (70%) (100% pure by NMR) of the first crop and 5.23 g (21%) (95% by NMR) of the second crop of 2a.

Preparation PP2

Synthesis of Compound (2a) by a Heck Coupling of 2-bromobenzaldehyde (1a) with Methyl Acrylate (R═H) (Pd(OAc)$_2$/P(O-Tolyl)$_3$ as the catalyst):

The compound 1a (9.998 g, 54.04 mmol) was dissolved in toluene (20 mL) at r.t. Methylacrylate (5.996 g, 69.65 mmol, 1.29 eq.), NEt$_3$ (15 mL), Pd(OAc)$_2$ and P(O-Tolyl)$_3$ were successively added and the mixture was stirred under reflux. After 2 hours, the reaction mixture was allowed to cool to RT. Then the precipitated yellow catalyst was removed by filtration. The catalyst was rinsed with toluene (2×10 mL) and the filtrates were concentrated to dryness under reduced pressure. The residual oil was dried under vacuum over the weekend to give a crude solid (11.449 g). The solid was taken-up with isopropanol (25 mL) and stirred overnight at RT. Then, the precipitate was filtered and rinsed with isopropanol (5 mL). The wet cake (8.240 g) was dried overnight at RT affording the highly pure 2-carboxaldehyde-methyl-cinnamate with 74% yield (7.627 g, 40.1 mmol).

Preparation PP3

Heck Coupling of 1b and methyl acrylate to form 2b (R=5-OMe):

A mixture of 2-bromo-5-methoxybenzaldehyde (1b) (4.5 g, 20.9 mmol, Aldrich), methyl acrylate (2.7 g, 1.5 eq, 2.83 mL), Et$_3$N (7.4 g, 3.5 eq, 10.2 mL), Pd(OAc)$_2$ (93 mg, 0.02 eq), and P(O-Tol)$_3$ was stirred and heated to 80° C. over 2–3 days. The reaction mixture was cooled to r.t., partitioned between EtOAc (50 mL) and brine (50 mL). The aqueous was extracted with EtOAc (2×50 mL). The combined organic was washed with brine (1×50 mL), dried over MgSO$_4$, filtered, concentrated to yield a yellow brown oil (5.01 g, 109%). This crude oil was purified in a hot solvent Hex/EtOAc (80 mL/ 15 mL) to yield 2b as a pale yellow solid (3.5 g, 76%).

Preparation PP4

Heck Coupling of 1c and Methyl Acrylate to Form 2c (R=4,5-OMe):

To a solution of 1c (906 mg, 3.70 mmol) in toluene (2 mL) was added Pd(OAc)$_2$ (17 mg, 0.074 mmol, 2 mol %), P(O-Tolyl)$_3$ (45 mg, 0.148 mmol, 4 mol %), methyl acrylate (0.5 mL, 5.55 mmol) and Et$_3$N (1.5 mL, 11.1 mmol). The mixture was stirred at 80 C° for 21 h, cooled to rt, and mixed with H$_2$O (40 mL). The organic compounds were extracted with EtOAc (50 mL), washed with brine (40 mL), dried (Na$_2$SO$_4$), and concentrated. The residue was purified by flash chromatography to provide 466 mg (47%) of recovered 1c followed by 450 mg (49%) of 2c (4,5-Ome).

Preparation PP5

Heck Coupling of 1d and Methyl Acrylate to Form 2d (R=5-NO$_2$):

The procedure is same as that of 2c, yielding 82% of 2d after purification.

Preparation PP6

Reductive Amination

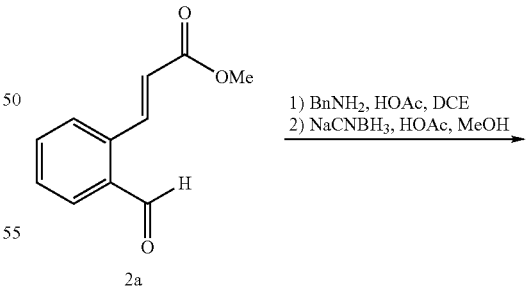

2a

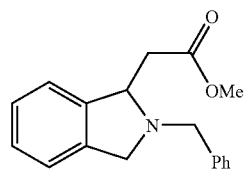

10a

Reductive amination of (2a) with benzyl amine to form isoindoline (10a). To a solution of 2a (11.27 g, 59.2 mmol) in ClCH$_2$CH$_2$Cl (60 mL) was added BnNH$_2$ (6.47 mL, 59.2 mmol), followed by HOAc (5.1 mL, 89 mmol). The mixture was stirred at rt for 1 h. NaCNBH$_3$ (5.58 g, 88.8 mmol) and MeOH (30 mL) were then added to the above solution. The resulting mixture was stirred at rt for another 2 h and quenched with sat. NaHCO$_3$ solution (150 mL). The mixture was extracted with EtOAc (2×100 mL) and the combined organic layers were washed with brine (150 mL), dried (Na$_2$SO$_4$), and concentrated to provide 15.3 g of crude product of 10a which was carried out for the next hydrogenolysis reaction.

Preparation PP7

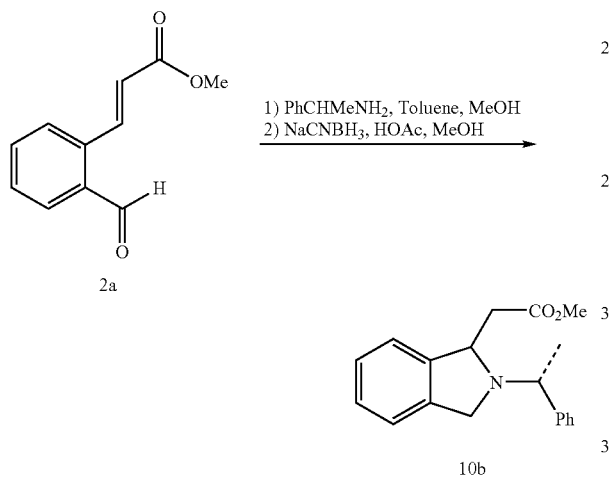

2a

1) PhCHMeNH$_2$, Toluene, MeOH
2) NaCNBH$_3$, HOAc, MeOH

10b

One-pot process from 2-carboxaldehyde-methyl-cinnamate to target cyclized isoindoline product using NaBH$_3$CN. 2-carboxaldehyde-methyl-cinnamate 2a (3.254 g, 17.1 mmol) was dissolved in a 1:1 MeOH: PhCH$_3$ mixture (20 mL) at RT. R-(+)-phenethylamine (2.073 g, 17.1 mmol) was added and the solution was heated under reflux for 2 hours. HPLC in process control indicated that the imine formation was completed. Then, AcOH (2.055 g, 34.2 mmol) and NaBH$_3$CN (2.15 g, 34.2 mmol) were successively added at RT, the reaction mixture being cooled with a water-bath. The reaction mixture was post-agitated overnight. Water (10 mL), MeOH (20 mL) and 37% HCl (2.8 mL) were successively added and the organic layer was extracted. The aqueous layer was washed with PhCH$_3$ (10 mL). Then, the aqueous layer was made basic with 5N NaOH (20 mL) and MeOH was concentrated to partly remove MeOH. Extraction with EtOAc (2×25 mL) was performed. The combined organic layers were dried over MgSO4, filtered and rinsed with EtOAc (10 mL). The filtrates were concentrated under reduced pressure and the residual oil was dried under vacuum overnight at RT to afford the target cyclized isoindoline product 10b with 92% yield (4.642 g, 15.7 mmol). HPLC % area indicated that the 2 diastereomers were produced in a 55:45 ratio. $^1$H NMR confirmed this result by integration of the methyl group of the phenethyl substituent.

Note: The Heck or Heck-type coupling was performed in toluene with a slight excess of methylacrylate which was removed by distillation before the MeOH and the R-(+)-phenethylamine addition.

Preparation PP8

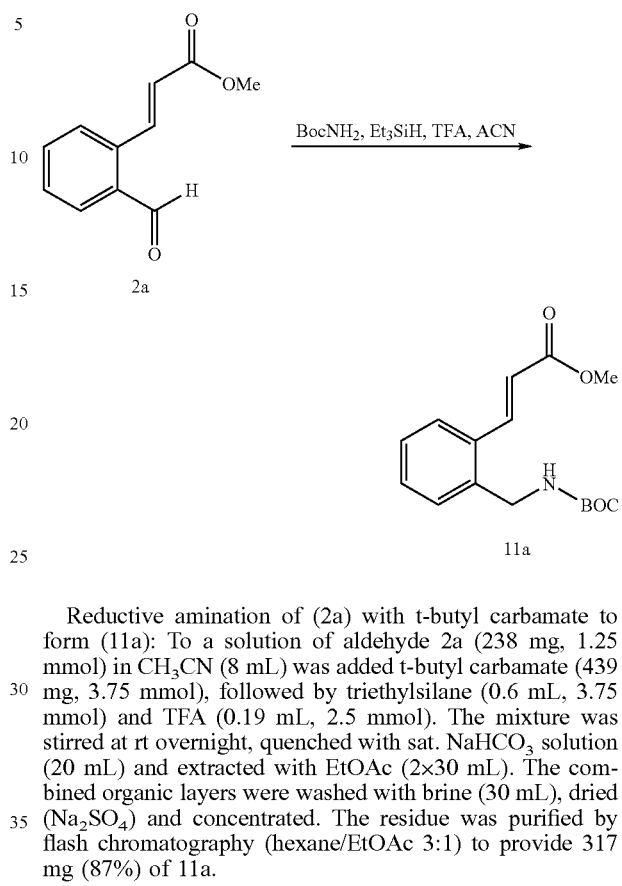

Reductive amination of (2a) with t-butyl carbamate to form (11a): To a solution of aldehyde 2a (238 mg, 1.25 mmol) in CH$_3$CN (8 mL) was added t-butyl carbamate (439 mg, 3.75 mmol), followed by triethylsilane (0.6 mL, 3.75 mmol) and TFA (0.19 mL, 2.5 mmol). The mixture was stirred at rt overnight, quenched with sat. NaHCO$_3$ solution (20 mL) and extracted with EtOAc (2×30 mL). The combined organic layers were washed with brine (30 mL), dried (Na$_2$SO$_4$) and concentrated. The residue was purified by flash chromatography (hexane/EtOAc 3:1) to provide 317 mg (87%) of 11a.

Preparation PP9

Reductive amination of 2b with t-butyl carbamate to form 11b: A mixture of aldehyde 2b (600 mg, 2.72 mmol) Et$_3$SiH (955 mg, 3 eq, 1.31 mL), TFA (620 mg, 2 eq, 420 uL), t-butyl carbamate (980 mg, 3 eq) in acetonitrile (15 mL) was stirred at room temperature over 2 days. Removed the solvent on a Rotary evaporator and purified the crude residue on a flash column (100 g SiO₂, 7:1→6:1 Hex/EtOAc). Collected 307 mg good desired product 11b (35%); 195 mg product contaminated with aldehyde SM (22%).

Preparation PP10

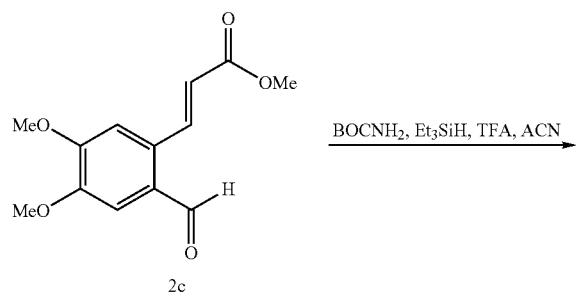

2c

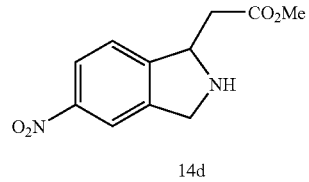

11c

Reductive amination of (2c) with t-butyl carbamate to form (11c): To a solution of aldehyde 2c (411 mg, 1.64 mmol) in CH₃CN (10 mL) was added t-butyl carbamate (580 mg, 4.93 mmol), followed by triethylsilane (0.8 mL, 4.93 mmol) and TFA (0.25 mL, 3.28 mmol). The mixture was stirred at rt overnight, quenched with sat. NaHCO₃ solution (30 mL) and extracted with EtOAc (2×30 mL). The combined organic layers were washed with brine (30 mL), dried (Na₂SO₄) and concentrated. The residue was purified by flash chromatography (hexane/EtOAc 3:1, hexane/EtOAc 1:1) to provide 535 mg (93%) of 11c.

Preparation PP11

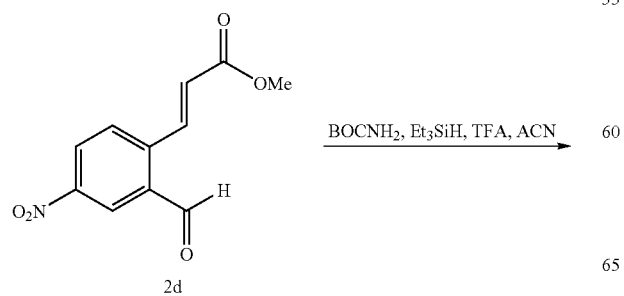

2d

-continued

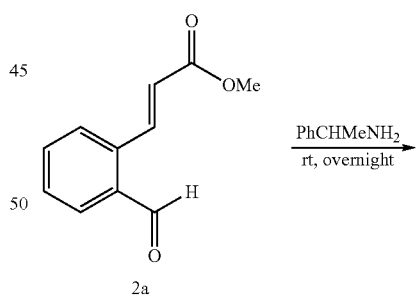

14d

To a solution of 2d (1.02 g, 4.34 mg) in CH₂Cl₂/CH₃CN (1:1 24 mL) was added BocNH₂ (1.5 g, 13.02 mmol), Et₃SiH (2.1 mL, 13.02 mmol), and TFA (0.67 mL, 8.67 mmol). The mixture was stirred at rt for 7 h. A precipitate was formed during the reaction. The reaction mixture was quenched with sat. NaHCO₃ solution (30 mL), and diluted with CH₂Cl₂ (40 mL). The organic layer was washed with brine (30 mL), dried (Na₂SO₄), and concentrated. The residue was purified by flash chromatography (hexane/EtOAc 3:1, then CH₂Cl₂/EtOAc 10:1) to provide 2.08 g yellow solid which still containing BocNH₂. The product is not the desired Boc-carbamate 14c. LC-MS result showed that the product is the Schiff base intermediate.

To the above product (420 mg) in CH₂Cl₂ (10 mL) was added Et₃SiH (1 mL) and TFA (6.4 mL). The mixture was stirred at rt for 1 h and small amount of sample was taken for NMR. NMR analysis demonstrated that the starting material was consumed and the product was 14c. TFA (0.7 mL) was then added to the above mixture and the resultant solution was stirred at rt for another 5 h and concentrated. The residue was dissolved in EtOAc (20 mL) and washed with H₂O (10 mL). The aqueous layer was basified with sat. NaHCO₃ (30 mL) and the organic compounds were extracted with CH₂Cl₂ (2×25 mL). The combined organic layers were washed with brine (20 mL), dried (Na₂SO₄) and concentrated to provide 218 mg of the cyclized compound 14c.

Preparation PP12

2a

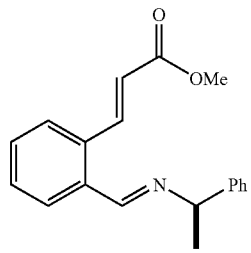

9

Condensation of 2a with α-Methylbenzylamine to Form Imine 9. 2-carboxaldehyde-methyl-cinnamate 2a (0.897 g, 4.72 mmol) was dissolved in MeOH (10 mL) at RT. R-(+)-phenethylamine (0.577 g, 4.76 mmol) was added and the solution was heated under reflux for 2 hours. HPLC in process control indicated that the imine formation was completed. The solvent was stripped on a rotary evaporator and the resulting oil was dried at RT under vacuum overnight. The Schiff base 9 was obtained almost quantitatively (1.412 g, 4.81 mmol).

Preparation PP13

Michael Addition:

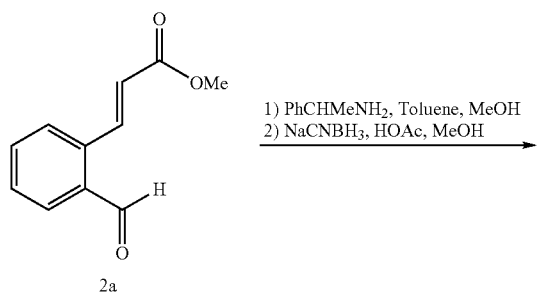

1) PhCHMeNH₂, Toluene, MeOH
2) NaCNBH₃, HOAc, MeOH 10b
(1.2:1)

The compound of α-Methyl benzylamine was applied as the auxiliary. As shown above, the one-pot reaction of aldehyde 2a and α-Methyl benzylamine gave 90% of 10b with a ratio of 1.2:1.

Step-wise reduction, amination, and cyclization: Condensation of aldehyde 2a with α-methylbenzylamine in acetonitrile, methanol, methanol/toluene (1:1) or toluene afforded imine 9 in excellent yield. Reduction of the imine was initially carried out at RT with NaCNBH₃/HOAc. As a result, a poor ee ratio (1.2:1) was obtained, similarly to the previous described one-pot procedure. But when the reaction was carried out with NaBH₄/TFA at RT, the ratio was elevated to 2:1. By lowering the reaction temperature to −78° C., the ratio was increased to 5 to 6:1.

Preparation PP14

Cyclization of t-Butyl carbamate (11a):

The N-Boc isoindoline methyl ester 12 was originally synthesized from 11a via deprotection of Boc with TFA, followed by basic workup, and protection with a Boc group. This procedure has been greatly improved by a one-step procedure.

Preparation PP15

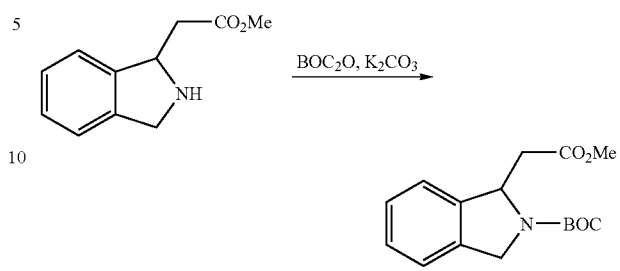

In a 3 L 3-neck round bottom flask equipped with a nitrogen inlet, thermocouple and mechanical stirrer, a solution of 160 g (1.15 moles) of K₂CO₃ in 180 mL of water was stirred at rt. Solid BOC anhydride 120 g (0.55 moles) was added in one portion forming a semi-solution. To the reaction mixture, a solution of the crude amino ester starting material, 87 g (0.46 moles) in 120 mL of THF was added slowly at such a rate to keep the internal temperature below 35° C. A mild effervescence was observed. The reaction mixture was stirred for 18 hours at rt. Analysis of a reaction aliquot via NMR (DMSO₆) indicates the desired product. The reaction was diluted with brine and the product extracted with EtOAc. The organic layer was dried over Na₂SO₄, filtered, and concentrated to yield a dark oil, 150.1 g, >100% yield. The crude material was taken on to the next step.

Preparation PP16

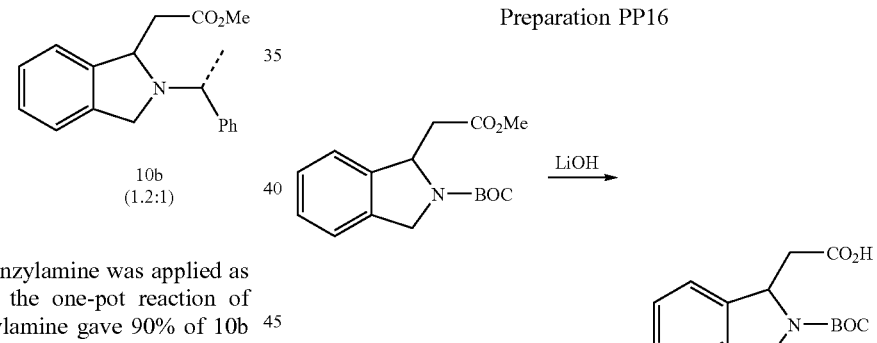

In a 3-L 3-neck round bottom flask equipped with a mechanical stirrer, thermocouple, and reflux condenser, a solution of 150 g (approx. 0.46 moles) of crude N-BOC ester starting material in 750 mL of methanol was stirred at rt. To the solution, 750 mL of water was added and the cloudy mixture was stirred vigorously. Solid LiOH 25 g (1.03 moles) was added in small portions at such a rate to maintain the internal temperature below 45° C. Upon completion of addition, the reaction was stirred overnight at rt becoming a dark green color. After 18 hours the reaction was concentrated to yield a thick semisolid. The crude product was dissolved in EtOAc and washed with 1 N HCl quickly, followed by two brine washes. The organic layer was dried with Na₂SO₄, filtered and concentrated to yield 81 g of a dark green solid. The aqueous layers were combined and back extracted with methylene chloride, dried over Na₂SO₄, filtered, and concentrated to yield 6 g of a dark green solid. Both solids were combined to yield 87 g of desired product confirmed via NMR (DMSO₆).

Preparation PP17

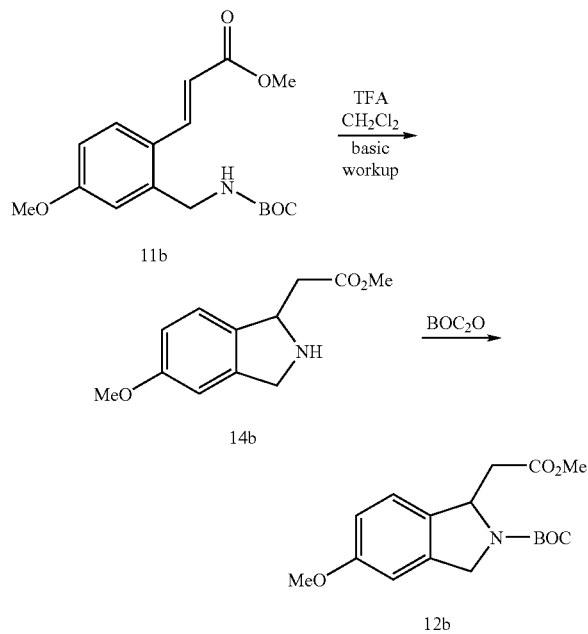

Synthesis of 14b:
Dissolved the N-boc compound 11b (200 mg, 0.62 mmol) in CH$_2$Cl$_2$ (1.0 mL). Cooled the clear light yellow solution to 0° C. Added slowly TFA (~710 mg, 10 eq, ~500 □L) via a syringe. Removed the cooling bath and stirred the clear light brown solution at RT overnight. TLC (3:1 Hex/EtOAc, UV) confirmed a complete reaction. Removed the TFA on a rotavapor. Added EtOAc and concentrated again (twice). The crude residue was partitioned between EtOAc (10–15 mL) and a sat. NaHCO$_3$ (10–15 mL). The aqueous was extracted with EtOAc (2×10 mL). The combined organic was dried over MgSO$_4$, filtered, and concentrated to yield a light brown wet solid (212 mg, 138 %). NMR (CD$_3$OD) confirmed the desired isoindoline 14b. This crude isoindoline was used in the next protection step without purification.

Preparation PP18

Synthesis of 12b:
To a mixture of the isoindoline 14b (190 mg, 0.859 mmol), K$_2$CO$_3$ (189 mg, 1.5 eq) in a solvent 1:1 THF/H$_2$O (1.0 mL) at RT was added BOC$_2$O (210 mg, 1.1 eq). The reaction mixture was stirred at RT overnight. TLC (3:1 Hex/EtOAc, UV) confirmed a complete reaction. Diluted the mixture with EtOAc (15 mL), and washed with H$_2$O (1×20 mL). The aqueous was extracted with EtOAc (1×20 mL). The combined organic was washed with brine (1×20 mL), dried over MgSO$_4$, filtered, concentrated to yield a clear brown oil (340 mg, 123%). This crude oil was purified on a prep TLC plate (2×1,000 micron, solvent 2:1.5:0.5 CHCl$_3$/Hex/EtOAc) to yield 12b a clear yellow oil (190 mg, 69%). $^1$H and $^{13}$C NMR (CDCl$_3$) were obtained.

Procedure PP19

Synthesis of 12d (5-NO$_2$) by Boc-protection.
The compound was prepared by following the same procedure as described for 12b.

Preparation PP20

The imine 9 (1.412 g, 4.81 mmol) was dissolved in anhydrous THF (10 mL) at RT and TFA (5 mL) was added. The black solution was then cooled to −78° C. (dry ice bath) and NaBH$_4$ (0.893 g, 23.6 mmol, 5 eq) was added in 2 portions over 5 minutes. Then, the reaction mixture was post-agitated at −78° C. for 3 hours and allowed to gently warm at RT overnight. Water (20 mL), cyclohexane (10 mL) and EtOH (20 mL) were successively added and the organic layer was extracted and discarded. The aqueous layer was made basic with 5N NaOH (20 mL) and extrated two times with a 2:1 EtOAC/PhCH$_3$ mixture (30 mL). The combined organic layers were dried over MgSO4, filtered and rinsed with EtOAc (10 mL). The filtrates were concentrated under reduced pressure and the residual oil was dried under vacuum overnight at RT to afford the target cyclized isoindoline product 10b (1.273 g, 4.31 mmol) with 91.4% yield. HPLC % area indicated that the 2 diastereomers were produced in a 84:16 ratio (de 68%). $^1$H NMR confirmed this result by integration of the methyl group of the phenethyl substituent.

Preparation PP20

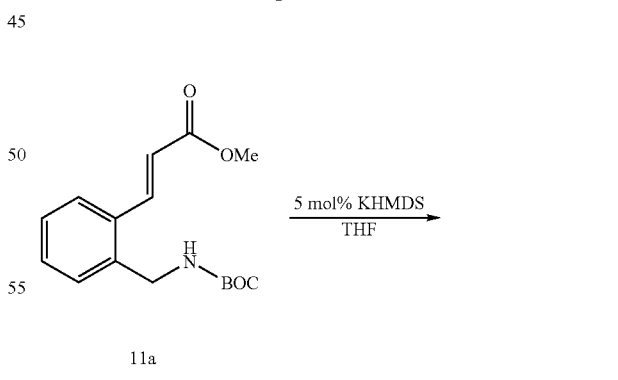

N-Boc methyl ester 11a (36.3 g, 0.125 mol) was dissolved in THF (250 mL), and the solution was cooled to about 0° C. A solution of potassium bis(trimethylsilyl) amide (1.24 g, 0.05 mol. Eq.) was added slowly via a syringe under nitrogen atmosphere. The temperature was raised about 8 degrees during the addition. The cooling bath was removed and the solution was stirred at r.t. for 30–45 min. The clear brown solution was poured into a separation funnel containing about 100 mL of a saturated NH$_4$Cl. The layers were separated. The aqueous layer was extracted with EtOAc (2×50 mL). The combined organic was washed with brine (1×100 mL), dried over Na$_2$SO$_4$, filtered, concentrated on a Rotary evaporator to a clear yellow oil (37.3 g). This crude oil was purified on a flash column (600 g SiO$_2$), with a gradient solvent 6:1 Hex/EtOAc (2.1 L), 5:1 Hex/EtOAc (1.2 L), 4:1 Hex/EtOAc (1.5 L) to yield 12a as a clean yellow oil (34.5 g, 95%).

Preparation PP21

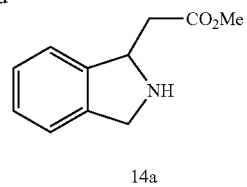

14a

Hydrogenolysis of 10a (R=Bn) to Form (14a): To a solution of crude 10a (15.3 g, 54.4 wool) in MeOH (100 mL) was added Pd(OH)$_2$/C (Pearlman s catalyst, 1.02 g, 6 mol %) in a par-shaker bottle. The suspension was shaken under 30 psi H$_2$ pressure overnight in the par-shaker, and filtered through a plug of celite. The filtrate was concentrated to provide 10.1 g of crude 14a as brown oil. (The procedure is same for the methyl benzylamine isoindoline substrate 10b)

Preparation PP23

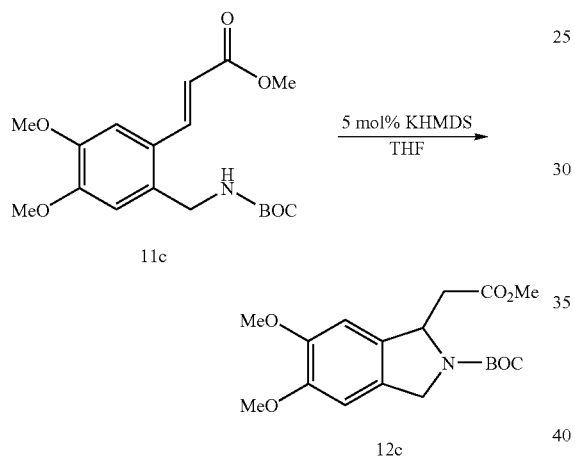

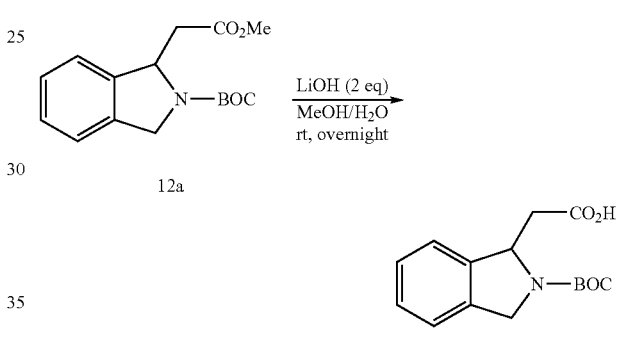

To a solution of 11c (535 mg, 1.52 mmol) in THF (10 mL) was added KHMDS (0.5 M in toluene, 0.1 mL, 0.05 mmol, 2 mol %). The mixture was stirred at r.t. for 20 min, quenched with sat. NH$_4$Cl solution (20 mL), and diluted with EtOAc (20 mL). The organic layer was separated, washed with brine (20 mL), dried (Na$_2$SO$_4$) and concentrated. The residue was filtered through a plug of silica gel (EtOAc/CH$_2$Cl$_2$ 1:10) to give 530 mg (99%) of 12c as an off white soild.

Preparation PP22

Deprotections:

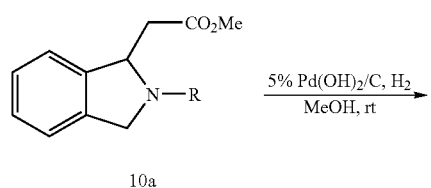

10a

In a typical reaction a mixture of the isoindoline ester 12a (92 mg, a.316 mmol) in 1:1 MeOH/H$_2$O (2 ml) was treated with LiOH (15 mg, 2 eq) at RT overnight. Diluted the mixture with CH$_2$Cl$_2$ (5 ml) and water (5 ml). Adjusted the pH of the reaction mixture to 1–3 with a 10% NaHSO$_4$ solution. Separated the layers. The aqueous was extracted with CH$_2$Cl$_2$ (1×10 ml). The combined organic was dried over Na$_2$SO$_4$, filtered, concentrated to yield 16a as a pale yellow foam (76 mg, 87%). NMR (CDCl$_3$) showed a clean desired acid product.

It is noted that he reaction time must be more than 6 hours. The crude foam can be purified by slurry in warm hexane and then filter to yield a tan solid. Hydrolysis using KOH (2–5 eq) in 1:1 MeOH/H$_2$O overnight would give the same result.

Preparation PP24

Resolution:

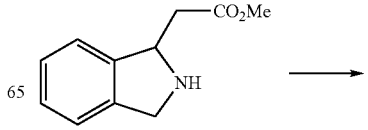

-continued

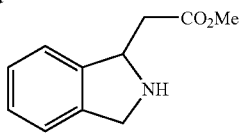

Purification of Partially Resolved Isoindolinecaboxylic acid methyl ester: A solution of the crude material (97.62 g) isoindoline-caboxylic acid methyl ester in $CH_2Cl_2$ (350 mL) was extracted with 1M HCl (400 mL, 200 mL). The combined aqueous portions were washed with $CH_2Cl_2$ (4×250 mL) and then made basic with $K_2CO_3$ solution (85 g in 150 mL of water). The mixture was extracted with $CH_2Cl_2$ (6×100 mL) and the combined organic extracts were dried ($Na_2SO_4$) and concentrated to give partially resolved Isoindolinecaboxylic acid methyl ester as an oil (33.2 g). 60% ee by chiral CE.

Preparation PP25

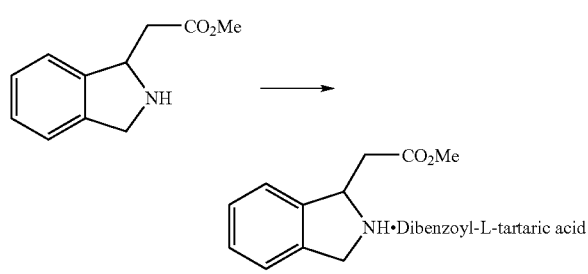

Resolution of Partially Resolved Isoindolinecaboxylic acid methyl ester: A solution of partially resolved isoindoline-caboxylic acid methyl ester (33.24 g, 0.174 mol) in EtOH (130 mL) was treated slowly with a solution of dibenzoyl-L-tartaric acid (56.06 g, 0.156 mol) in EtOH (200 mL). The solution was seeded with seeded with product and stirred at RT for 4 hours. Pure product was collected by filtration, washed with EtOH (30 mL) and dried to off-white crystals (60.49 g). 96.5% ee by chiral CE.

Preparation PP26

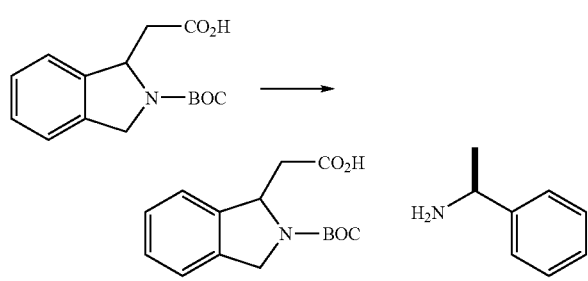

Resolution of N-BOC Isoindolinecaboxylic acid: A solution/slurry of racemic N-BOC Isoindolinecaboxylic acid (114.5 g, 0.413 mol) in EtOAc (1000 mL) was treated slowly with triethylamine (28.8 mL, 0.206 mol), followed by (S)-(−)-□-methylbenzylamine. The solution was seeded with product and stirred at RT overnight. The product was collected by filtration, washed with EtOAc (200 mL) and dried to a white powder (62.98 g). 97.6% ee by chiral CE.

Asymmetric Hydrogenation Routes

Part I: Synthesis of the Z-isomer (Precursor of Asymmetric Hydrogenation)

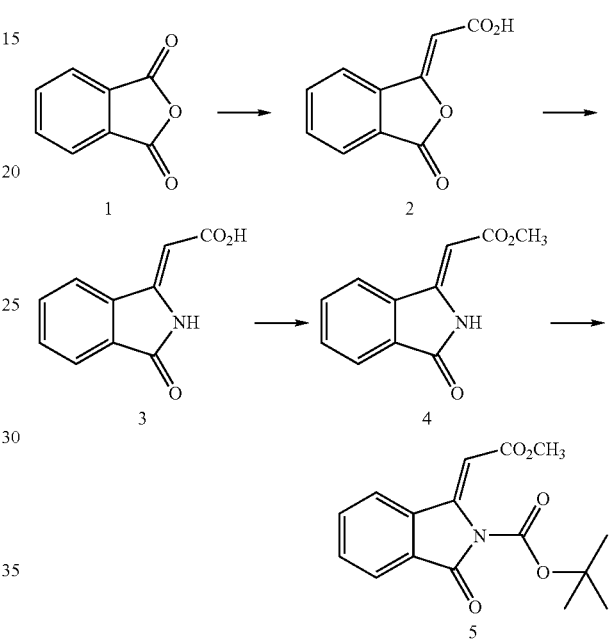

Preparation PP27

Z-isomer 5 was synthesized as outlined in Scheme P1. Compound 5 was shown to be a single isomer by HPLC and H-1 nmr. The double bond stereochemistry was derived from comparative NOE data using the purported E-isomer (Scheme P1). The best chiral induction was achieved using compound 8/Ferrotane/MeOH-THF. With regard to the conversion of 9 to 10, which would constitute a formal asymmetric synthesis of isoindolene 10, this has been achieved using Super hydride-$BF_3.OEt_2$. However, the product was a mixture of 10 and the corresponding de-BOC (deprotected) compound.

Preparation PP28

Compound 2 (scheme P1)

Phthalic anhydride (751.5 g, 5.014 mole), potassium acetate (498 g, 5.014 mole) and acetic anhydride (1 L) were stirred together under nitrogen. The mixture was slowly warmed to 145–150° C. and stirred for 10 minutes, then at 140° C. for 20 minutes. The mixture was allowed to slowly cool to 80° C. over 1 hour. Three volumes of water were added causing precipitation of a solid. After filtration, the filtered solid was washed with warm water and pulled as dry as possible for 30 minutes. The solid was then washed with ethanol and acetone respectively. If required further purification could be achieved by slurrying the solid in acetone, at room temperature, for 15 minutes, then filtration. Drying in vacuo at 50° C. for 20 hours gave compound 2 as an off-white solid, 470 g (48%) with an NMR purity of approx. 90%.

Preparation PP29

Compound 3 (Scheme P1)

Compound 2 (470 g, 2.47 mole) was added to stirred aqueous ammonia (470 ml conc. $NH_3$ in 4.7 L water). The resultant mixture was stirred at room temperature for 1 hour then filtered. The filtered solid was washed with water. The combined aqueous filtrate and washings were carefully acidified with 6M aq. HCl (2.35 L). The precipitate was removed by filtration and dried in vacuo at 50° C. to give compound 3 as a yellow solid, 259 g (52%).

Preparation PP30

Compound 4 (Scheme P1)

Compound 3 (511 g, 2.7 mole) was slurried in toluene (10 vol). Thionyl chloride (385 g, 3.24 mole) was added over 10 minutes to the stirred mixture, which was then heated to reflux for 1.5 hours. H-1 NMR analysis indicated approx. 80% conversion to acid chloride). DMF (3.7 ml) was added and the mixture refluxed an additional 3 hours. The resultant mixture was allowed to cool to 35° C. and methanol (1.27 L) added at such a rate that the reaction temperature was maintained at 30–35° C. The reaction mixture was kept at this temperature a further 15 minutes then concentrated in vacuo to give compound 4 as a brown solid, 536 g (quantitative).

Preparation PP31

Compound 5 (Scheme P1)

Compound 4 (750 g, 3.65 mole) was dissolved in acetonitrile (15 L). The stirred mixture was cooled to 0–5° C. and DMAP (624 g, 5.11 mole) added in one portion. After 10 minutes BOC anhydride (1115 g, 5.11 mole) was added in one portion: there was a slight exotherm accompanied by gas evolution. The mixture was stirred at room temperature for 5 hours, and then concentrated in vacuo. The residue was dissolved in EtOAc and washed with 10% aqueous citric acid, satd. aq. $Na_2CO_3$ and water respectively. After drying, concentration of the organics gave a thick syrup. This material was run through a plug of silica gel (1.5 kg) eluting with 1:1 EtOAc-hexane. Compound 5 was isolated as a dark solid, 619 g (55%). Careful chromatography on silica gel eluting with 20% EtOAc-hexane gave 5 as a fluffy white solid.

Scheme P2

Part II: Synthesis of the E-isomer (Precursor of Asymmetric Hydrogenation)

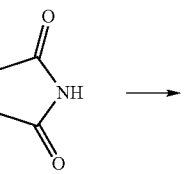

6

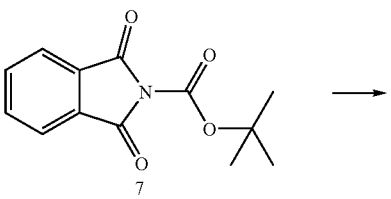

7

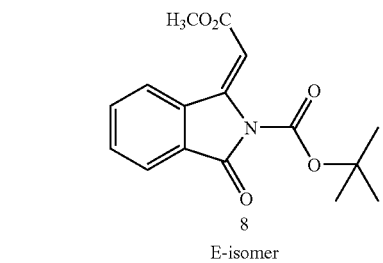

8
E-isomer

Preparation PP32

The E-isomer of Compound 8 (Scheme P2) was prepared as shown in Scheme P2.

Preparation PP33

Compound 7 (Scheme P2)

The compound 7 was prepared according to the procedure of Einhorn et al, *Synth. Commun.* 2001, 31(5), 741–748.

Preparation PP34

Compound 8 (Scheme P2)

Compound 7 (15.00 g, 60.7 mmole) and methyl(triphenyl phosphoranylidene) acetate (41.40 g, 121.3 mmole) were slurred in toluene (150 ml). The mixture was stirred at reflux and monitored for reaction of 7 by GC. After 1.5 hours the reaction appears complete by GC. After cooling to room temperature, the mixture was filtered. The solid on the filter was washed with toluene until colorless. The combined filtrate/washings were concentrated in vacuo to leave a tan solid. This material was coated on silica gel and chromatographed on silica gel (1 kg) eluting with 10% EtOAc-hexane. Compound 8 was isolated as a white or pale yellow powder, 5.52 g (30%).

Scheme P3

Asymmetric hydrogenation:

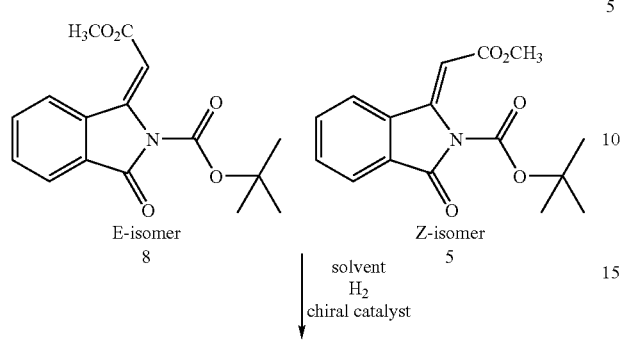

E-isomer
8

Z-isomer
5 solvent
H$_2$
chiral catalyst

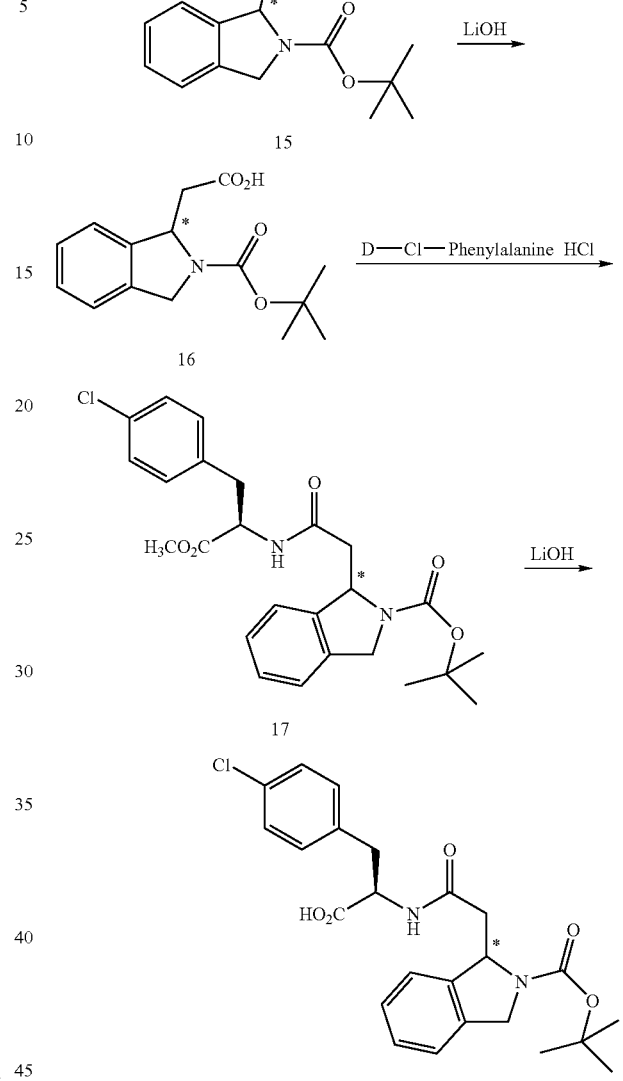

Preparation PP35

Screening of chiral hydrogenation conditions indicated that the best chiral induction was achieved using compound 8/Ferrotane/MeOH-THF. With regard to the conversion of 9 to 10, which would constitute a formal asymmetric synthesis of isoindolene 10, this has been achieved using Super hydride-BF$_3$.OEt$_2$. However, the product was a mixture of 10 and the corresponding de-BOC (deprotected) compound.

Scheme P4

Coupling of chiral isoindoline with D-4-chloro-Phenylalanine using tartrate salt:

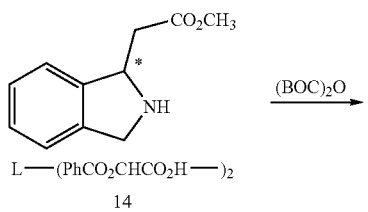

L—(PhCO$_2$CHCO$_2$H—)$_2$
14

Preparation PP36

Compound 15 (Scheme P4)

Tartrate salt 14 (58.00 g, 100.27 mmole) was slurried in water (580 ml). Solid NaHCO$_3$ (25.27 g, 300.8 mmole) was carefully added. BOC anhydride (22.98 g, 105.28 mmole) was added in one portion and the progress of the reaction monitored by reverse phase HPLC. After 1 hour additional BOC anhydride (2.18 g, 10.00 mmole) was added. The reaction was complete (by HPLC) after 3 hours. The mixture was extracted with EtOAc (2×250 ml). The combined organic extracts were washed with water (250 ml) and dried (MgSO$_4$). Filtration and concentration in vacuo gave 15 as a clear light brown oil (31.33 g) contaminated with a small amount of t-BiOH and BOC anhydride. This material was used directly in the next reaction.

Preparation PP37

Compound 16 (Scheme P4)

Ester 15 (29.21 g, 100.26 mmole) was dissolved in 3:1 THF-water (100 ml). LiOH (6.00 g, 250.65 mmole) was added in 1 portion to the stirred solution. After 17 hours, the mixture was stripped to dryness and the residue dissolved in water (500 ml). EtOAc (250 ml) was added and solid NaHSO$_4$ added to the stirred mixture until the pH=3. The organic layer was separated and the aqueous layer extracted with EtOAc (250 ml). The combined EtOAc layers were dried (MgSO$_4$) Filtration and concentration in vacuo gave acid 16 as a light tan solid, 27.10 g (97%).

Scheme P5

Rrom alpha-methyl benzylamine salt:

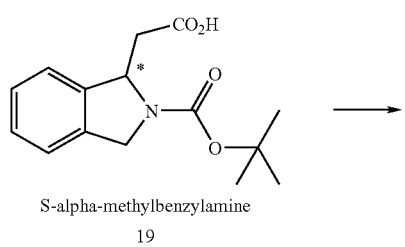

S-alpha-methylbenzylamine
19

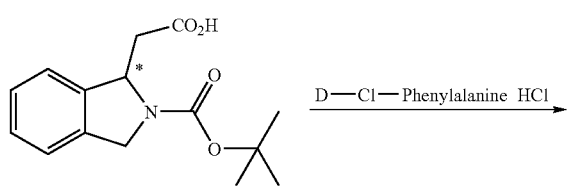

method A: -isolated acid
method B: -non-isolated acid
16

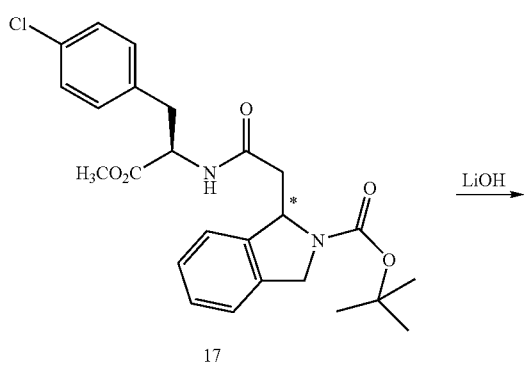

17

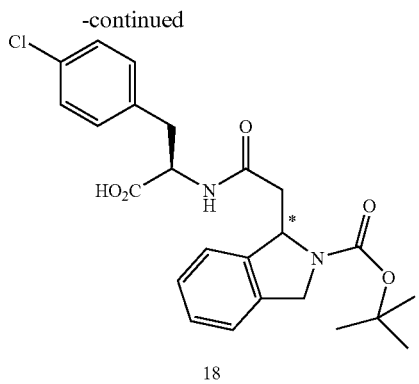

18

The chemistry used is shown in Scheme P5. Two protocols were used: method A used isolated 16, method B used a solution of 16 derived from resolved salt 19.

Preparation PP38

Compound 17 (Scheme P5, method A)

Acid 16 (24.18 g, 87.2 mmole) and D-chloro-phenylalanine hydrochloride (21.81 g, 87.2 mmole) were dissolved in CH$_2$Cl$_2$ (100 ml) and DMF (25 ml). The mixture was stirred at ambient temperature. HOBT (13.55 g, 100.3 mmole) and Hunig's base (45.6 ml, 33.81 g, 261.6 mmole) were added. HATU (38.13 g, 100.3mmole) was added in 1 portion (there was a rapid exotherm to 50° C.). The mixture was stirred for 90 minutes then diluted with EtOAc (750 ml). The resulting mixture was washed with water, 5% KHSO$_4$, brine and satd. NaHCO$_3$ respectively, then dried. Filtration and concentration in vacuo gave crude 17 as a brown foam. The product was purified by chromatography on silica gel (1 kg) eluting with 1:1 EtOAc-hexane. Ester 17 was isolated as a tan powder, 38.85 g (94%).

Preparation PP39

Compound 17 (Scheme P5, method B)

Resolved salt 19 (96.27 g, 232.5 mmole) was partitioned between water (500 ml) and CH$_2$Cl$_2$ (250 ml) Solid KHSO4 was added portion wise until pH=2.5. Separate the organic layer and extract the aqueous layer with CH$_2$Cl$_2$ (150 ml). The combined organic layers were dried (MgSO$_4$) then filtered. To this solution was added 4-chloro-D-phenylalanine (58.16 g, 232.5 mmole), HOBT (34.57 g, 255.8 mmole), Hunig's base (93.2 ml, 69.13 g, 534.9 mmole) and finally HATU (97.26 g, 255.8 mmole). The resultant mixture was stirred at room temperature for 18.5 hours, and then poured onto a plug of silica gel (1 kg). This was washed with 1:1 EtOAc-hexane until no more product elutes. Ester 17 was isolated as a pink foam, 101.79 g (93%): contains about 1% unreacted 16.

Preparation PP40

Compound 18 (Scheme P5)

Ester 17 (38.64 g, 81.7 mmole) was dissolved in 3:1 THF-water (200 ml). LiOH (2.15 g, 89.9 mmole) was added to the mixture, which was stirred at room temperature for 2 hours. The solvent was then removed in vacuo and the residual solid taken up in water (600 ml). This was extracted with MTBE (250 ml). The aqueous layer was separated and stirred with EtOAc (250 ml), and solid KHSO$_4$ was added portion wise until pH=3. The layers were separated and the aqueous extracted with EtOAc (250 ml). The combined organic layers were dried over MgSO$_4$. Filtration and concentration in vacuo gave acid 18 as a light pink foam, 38.41 g (35.71 g corrected for residual solvent, 95%).

Preparation PP41

Step 1: Esterification

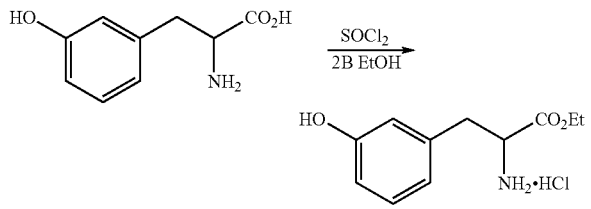

In a 22 L 4-neck round bottom flask equipped with a reflux condenser, thermocouple and nitrogen inlet, a slurry of 1000 g (5.4 moles) of m-tyrosine in 10 L of 2B-3 EtOH was cooled to 5° C. To the slurry, 350 mL (12.4 moles) of thionyl chloride were added dropwise via an addition funnel at such a rate to maintain the reaction temperature below 20° C. Upon completion of addition, the reaction was heated to reflux temperature and stirred for 18 hrs. The reaction was concentrated to one-third the volume and 8 L of MTBE were charged. The resulting thick slurry was stirred for 14 hrs in a rotary evaporator at rt. The resulting solid was isolated on a filter pad and dried at 40° C. for 48 hrs yielding 1288 g (95%). NMR (DMSOd$_6$) indicated desired material.

Preparation PP42

Step 2: Pictet-Spengler

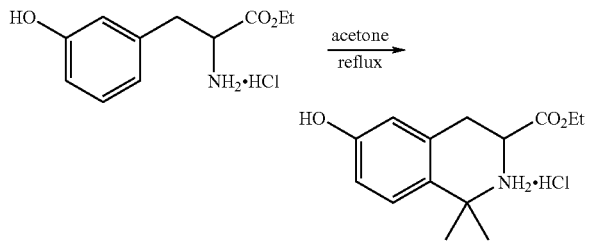

In a 22 L 4 neck round bottom flask equipped with a mechanical stirrer, thermocouple, and reflux condenser placed on top of a Soxhlet extractor charged with 4° A sieves, a semi-solution of m-tyrosine ethyl ester hydrochloride 1288 g (5.26 moles) in 13 L of acetone was heated to reflux temperature. The condensate was filtered through the sieves to remove water. The reaction was stirred vigorously at reflux for 48 hrs. An NMR sample in DMSOd$_6$ indicated the absence of starting material. The reaction was cooled to rt and concentrated to yield an off-white solid, 1411 g (94%).

Preparation PP43

Step 3: Triflation

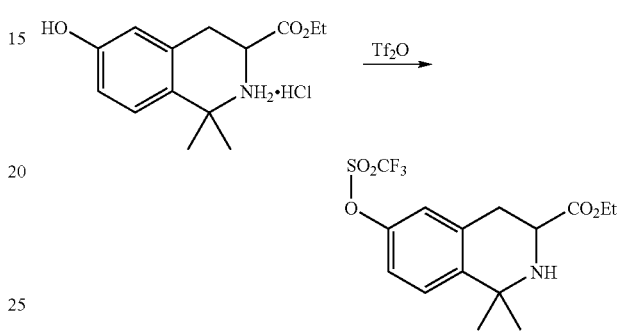

In a 22 L 4 neck round bottom flask equipped with a reflux condenser, mechanical stirrer, nitrogen inlet, and a thermocouple, 1240 g (4.35 moles) of the starting material salt in 12.4 L of methylene chloride was cooled to 4° C. To the mixture, 1452 mL (10.4 moles) of triethylamine were added and stirred into solution. Triflic anhydride, 1472 mL (5.22 moles) was added dropwise to the reaction at such a rate to maintain the internal temperature below 10° C. The ice bath was removed and the reaction warmed to rt. and stirred for 18 hrs. The reaction was concentrated to a oil then dissolved in 4 L of EtOAc and concentrated again to an oil in an effort to remove excess triflic anhydride The crude residue was dissolved in 4 L of EtOAc and washed with water and saturated sodium bicarbonate solution. The organic layer was isolated and dried with sodium sulfate, filtered and concentrated to yield 1720 g (>100%) of a crude dark oil which was used without further purification.

Preparation PP44

Step 4: Deoxygenation

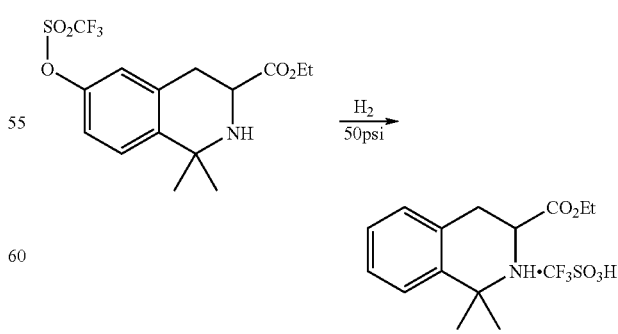

A solution of 1720 g (4.35 moles) of crude starting material in 14 L of acetone was charged to a 10 gallon stainless steel autoclave. To the solution, a slurry of 5% Pd/C in 1.2 L of toluene was added. The reaction mixture was evacuated and purged with $H_2$ gas at 50 psi two times. The reaction was stirred overnight at 50° C. with $H_2$ at 50 psi. A sample aliquot indicated no reaction had occurred. The mixture was filtered and concentrated to a thick oil and resubjected to reaction conditions. After 18 hrs, NMR of a sample aliquot indicated absence of starting material. The reaction mixture was filtered and the filtrate concentrated to yield 1581 g of an off-white solid (95%).

Preparation PP45

Step 5: Hydrolysis/Salt Formation

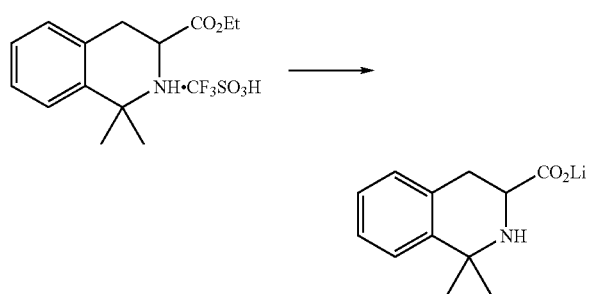

To a 2 L 3 neck round bottom flask equipped with a mechanical stirrer, thermocouple, and nitrogen inlet, a mixture of 700 g (1.83 moles) of the triflate salt starting material was charged. A solution of 427 g (1.83 moles) of the starting material free base in 13.3 L of THF was added followed by 700 mL of water. The semi-solution was stirred vigorously at rt. To the reaction flask, 43.7 g (1.83 moles) of solid LiOH were added in small portions at such a rate to maintain the internal temperature below 35° C. The reaction was stirred for 18 hrs at rt and concentrated to yield a thick oil. THF (4 L) was added and the semi-solution was concentrated. This was repeated with toluene and the semi-solid was placed under house vacuum on the roto vap with stirring for 18 hrs to yield 650 g of a crude solid. The solid was reslurried in EtOAc, filtered, isolated and dried to yield 525 g (68%) of the lithium salt as an off-white solid.

Preparation PP46

Step 6: Coupling

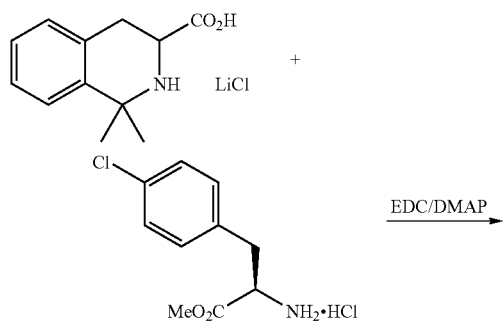

-continued

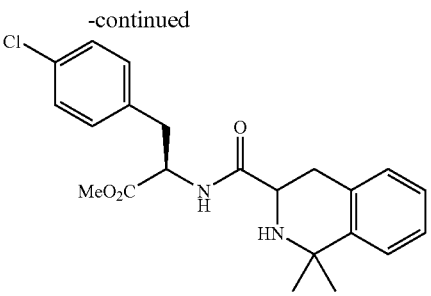

To a 12 L 4 neck flask equipped with a mechanical stirrer, water-cooled reflux condenser, thermocouple, and nitrogen inlet, a mixture of 400 g (1.62 mole) of the starting material free acid, 2 L of DMF, and 2 L of methylene chloride was stirred vigorously. Solid d-chloro-phenylalanine 446 g (1.78 moles) was added to the semi-solution followed by 20 g (0.162 moles) of DMAP. The resulting mixture was stirred for 15 minutes then solid EDCl (1-(3-dimethylaminopropyl)-3-ethylcarbodiimide hydrochloride) 390 g (2.03 moles) was added. The reaction mixture was heated to 80° C. and stirred for 18 hours. Thin layer chromatography (1:1 EtOAc: Hex) indicated very little starting material present. The reaction was cooled to rt and concentrated to yield a thick oil. The crude oil was dissolved in EtOAc and washed with water, and brine. The solution was dried with sodium sulfate, filtered and concentrated to yield a thick oil, 426 g. The crude oil was chromatographed in several lots using a Waters Prep 500 chromatography apparatus. The eluent consisted of a gradient system, 5%–80% EtOAc in heptane at a flow rate of 240 ml/min over 38 minutes. The two diasteromers were separated and isolated to yield 119.04 g for the top spot and 111.3 g for the bottom spot. Conformation of both desired diastereomers was achieved via NMR ($DMSO_6$).

Preparation PP47

Resolution of tetrahydroisoquinolinecarboxylic acid ethyl ester to prepare 1-tartaric acid salt:

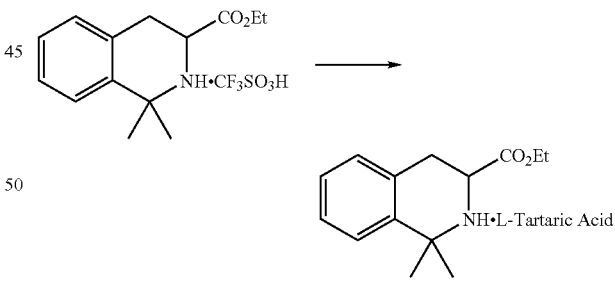

Preparation of free-base: A racemic mixture of tetrahydroisoquinolinecarboxylic acid (7.43 g) in EtOAc (60 mL) was treated with saturated $NaHCO_3$ solution (60 mL) and saturated $Na_2CO_3$ solution (10 mL). The mixture was agitated and the layers were separarted. The organic phase was dried ($Na_2SO_4$) and concentrated to give the corresponding free-base as an oil (4.85 g)

Resolution: A mixture of the above free base (467 mg, 2.0 mmol), and L-tartaric acid (300 mg, 2.0 mmol) in acetone (4 mL) was stirred at RT overnight. The title L-tartaric acid salt was collected by filtration, washed with acetone (about 2 mL) and dried to a white powder (367 mg). 100% ee by chiral CE.

Preparation PP48

Resolution of N-BOC tetrahydroisoquinolinecarboxylic acid

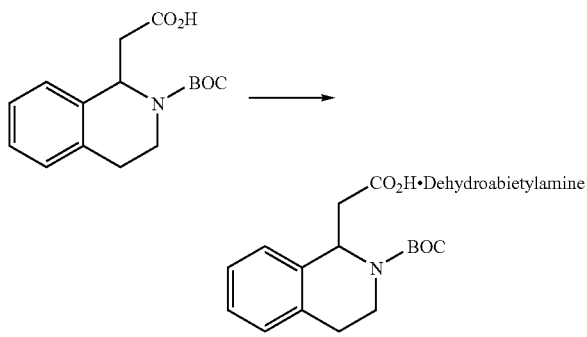

2-{2-[(tert-butyl)oxycarbonyl]-1,2,3,4-tetrahydroisoquinolyl}acetic acid dehydroabietylamine salt: Racemic 2-{2-[(tert-butyl)oxycarbonyl]-1,2,3,4-tetrahydroisoquinolyl}acetic acid (30.15 g, 103.5 mmol) was dissolved in i-PA (300 mL). Dehydroabietylamine (22.11 g, 52.7 mmol of a 68 weight % mixture) was added to the solution, which was then agitated on a multi-arm shaker for 63 h. The resultant thick paste was filtered and rinsed with i-PA (50 mL, 25 mL). Dried in a 50° C. vacuum oven to obtain a white solid (27.73 g, 52% ee by chiral CE analysis). The product was reslurried in i-PA (266 mL) and agitated on a multi-arm shaker for 23.5 h. Filtered the thick slurry and rinsed with cold i-PA (50 mL, 30 mL). Dried the cake in a 50° C. vacuum oven and obtained the product as a white solid (23.63 g, 40% yield, 94% ee by chiral CE analysis).

Scheme P6

Asymmetric Hydrogenation:

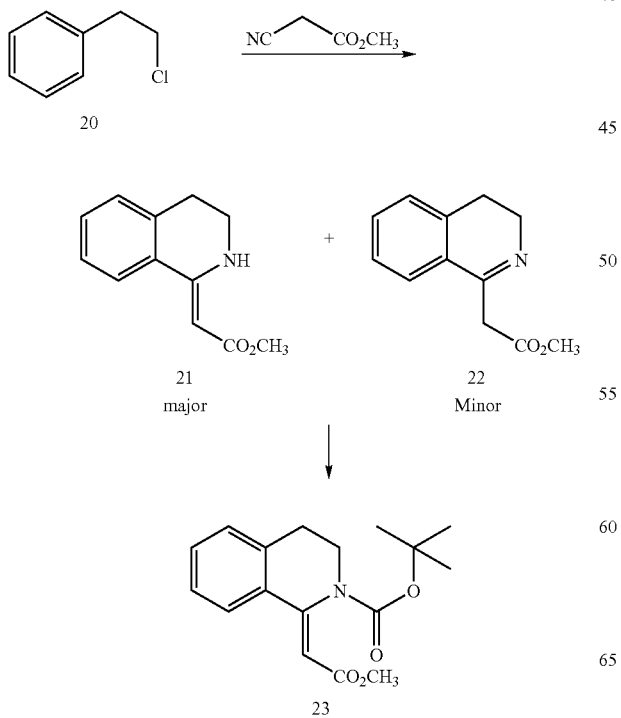

Preparation PP49

Enamine 21 (Scheme P6) was prepared as a substrate for asymmetric hydrogenation screening studies. It is formed as an approx. 10:1 mixture with imine 22. The enamine (21) may be NH-protected i.e. by a Boc protecting group. The resulting compound 23 may be subjected to asymmetric hydrogenation to afford the acetic acid or methylacetate substituted isoquinoline, which may be processed into a compound of formula I as demonstrated previously.

Preparation PP50

Compound 21 (Scheme P6)

Prepared as published W Sobotka et al, *J. Org. Chem.*, 1965, 30, 3667

Scheme P7

Synthesis of Gem-dimethyl TIC:

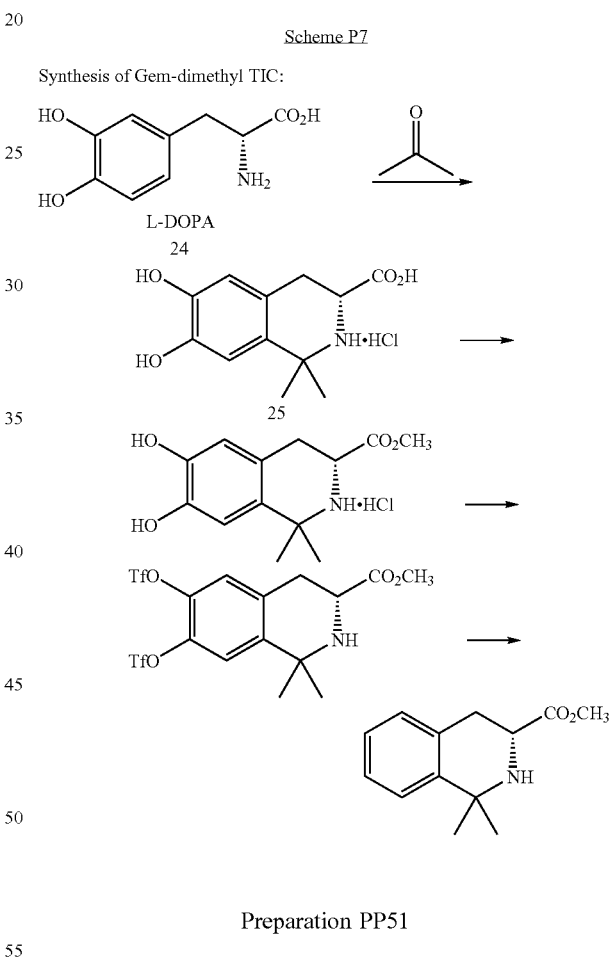

Preparation PP51

The chiral synthesis of gem-dimethyl TIC using L-Dopa as the starting material instead of tyrosine was successfully demonstrated up to the Pictet-Spengler reaction with L-DOPA and acetone. The product is a mixture of starting material 24 and product 25 (major component). The product was isolated by using common isolation procedures. An alternative isolation method is to react the mixture (24 and 25) with BOC anhydride wherein the less hindered N—H in 24 leads to preferential BOC protection of 24, allowing for ready separation of 25. Chemistry for the rest of the sequence i.e. deoxygenation reaction, has been demonstrated herein.

Preparation of Novel "B-C" Domain Pieces

Preparation BC1

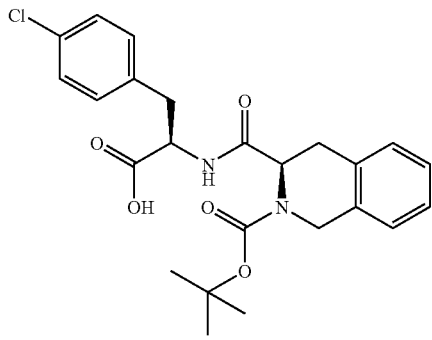

3-[2-(4-Chloro-phenyl)-1-methoxycarbonyl-ethyl-carbamoyl]-3,4-dihydro-1H-isoquinoline-2-carboxylic acid tert-butyl ester A. To a 0° C. solution of 4-Chloro-D-Phe methyl ester (23.8 g, 111.0 mmol), Boc protected D-Tic (30.8 g, 111.0 mmol) and 4-DMAP (75 mg, 0.61 mmol) in 200 mL of DCM was added EDC (30.8 g, 111.0 mmol) and the mixture stirred for 20 minutes. The ice bath was removed and the mixture stirred at room temperature for 4 h. After washing with water (4×200 mL), the combined aqueous portions were back extracted with DCM (2×200 mL). The combined organic portions were washed with brine, dried (MgSO$_4$), and concentrated to dryness. The desired product was purified by flash chromatography (SiO$_2$, eluting with 35% EtOAc in Hexanes) affording 43.0 g (83%) of the ester. EIS MS 473 [M+1].

B. To the above formed ester (43.0 g, 91.0 mmol), in MeOH (170 mL) at 0° C., was added 1N NaOH (227.0 mL, 227.0 mmol), dropwise. After 20 minutes the ice bath was removed and the mixture stirred at room temperature for 3 h. The mixture was concentrated to dryness, and the resulting residue suspended in 200 mL of water. The aqueous layer was made acidic (pH 1) with 5 N hydrochloric acid and extracted with EtOAc (4×200 mL). The combined organics were dried (MgSO$_4$), filtered, and concentrated to dryness, affording 39.0 g (93%) of the title compound. EIS-MS 459 [M+1].

Preparation C1

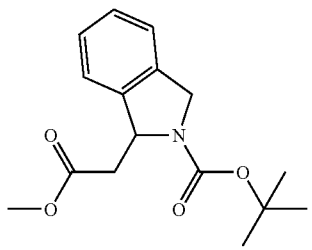

1-Methoxycarbonylmethyl-1,3-dihydro-isoindole-2-carboxylic acid tert-butyl ester A. (2-Bromo-benzyl)-carbamic acid tert-butyl ester To 2-bromobenzylamine hydrochloride (125.0 g, 561.8 mmol), in THF/water (1:1, 300 mL), was added potassium carbonate (170.7 g, 1236.0 mmol) and di-tert-butyl dicarbonate (134.9 g, 618.0 mmol), in four portions over 20 minutes. The mixture was stirred at room temperature for 16 h and diluted with 300 mL of EtOAc and 300 mL of water. The organic portion was separated and the aqueous portion was extracted with EtOAc (3×200mL). The combined EtOAc portions were washed with 250 mL of 10% aqueous sodium bisulfate, dried (MgSO4), and concentrated to dryness to afford 161.0 g of the title compound.

B. 3-[2-(tert-Butoxycarbonylamino-methyl)-phenyl]-acrylic acid methyl ester

To the product from part A (161.0 g, 561.8 mmol), in DMF (800 mL), was added methyl acrylate (58.0 g, 674.2 mmol), TEA (170.5 g, 1685.4 mmol), and dichlorobis(triphenylphosphine)palladium(II) (7.9 g, 11.2 mmol) and the mixture was heated at 80° C. for 32 h. The mixture was cooled, diluted with 1000 mL of EtOAc and washed with 10% aqueous sodium bisulfate. The aqueous portion was extracted three times with EtOAc and the combined organics were dried(Na$_2$SO$_4$) and concentrated to dryness. The residue was dissolved in a small amount of DCM and filtered through 7 in. of silica gel in a 2 L sintered glass funnel eluting with 25% EtOAc/hexanes. The eluent was concentrated to dryness and recrystallized from EtOAc/hexanes to afford 116.9 g (71%) of the title compound.

C. To a 0° C. solution of the material from Part B (116.9 g, 401.2 mmol) in 800 mL of DCM was added 200 mL of TFA dropwise over 15 min. After removing the cooling bath, the mixture was stirred for 2.5 h and concentrated to dryness. The residue was dissolved in 500 mL of DCM and saturated aqueous sodium bicarbonate was slowly added until the mixture was slightly basic. The organic portion was separated and the aqueous portion was extracted two times with DCM. The combined organic portions were dried (Na$_2$SO$_4$) and concentrated to dryness. The residue was dissolved in 800 mL of DCM and to the mixture was added DIPEA (57.,0 g, 441.4 mmol) and di-tert-butyl dicarbonate (96.3 g, 441.4 mmol) in five portions over 45 minutes and the mixture stirred at room temperature for 16 h. The mixture was washed with 10% aqueous sodium bisulfate, the organic portion was separated and the aqueous portion extracted two times with DCM. The combined organic extracts were dried (Na$_2$SO$_4$) and concentrated. The residue was dissolved in a small amount of DCM and filtered through 7 in. of silica gel in a 2 L sintered glass funnel eluting with 25% EtOAc/hexanes. The eluent was concentrated to dryness and the enantiomers separated by chiral chromatography (Chiralcel OD). The first eluting isomer was labeled isomer #1 and the second eluting isomer #2; affording 52.6 g (45%) of the title compound (isomer 2).

EIS-MS 292 [M+1].

Preparation C2

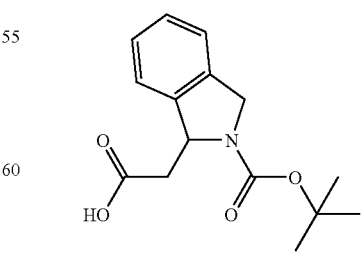

1-Carboxymethyl-1,3-dihydro-isoindole-2-carboxylic acid tert-butyl ester

To the product from Preparation C1 (52.6 g, 180.5 mmol), in MeOH (500 mL), was added 1 N NaOH (199 mL, 199.0 mmol). The mixture was stirred at room temperature for 48 h and then concentrated to dryness. The resulting residue was dissolved in water (300 ml,) and extracted with diethyl ether (2×). The aqueous portion was acidified to pH 2 with 10% aqueous sodium bisulfate and extracted with EtOAc. The combined organic extracts were dried (MgSO₄) and concentrated to dryness. Yield: 49.8 g, 99%. EIS-MS 276 [M−1].

Preparation BC2

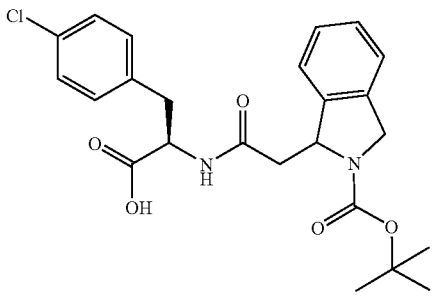

1-{[1-Carboxy-2-(4-chloro-phenyl)-ethylcarbamoyl]-methyl}-1,3-dihydro-isoindole-2-carboxylic acid tert-butyl ester A. To a suspension of 4-Cl-D-Phe methyl ester hydrochloride (40.4 g, 161.5 mmol), in DCM (250 mL), was added saturated aqueous sodium bicarbonate (250 mL) and the mixture stirred at room temperature for 1 h. The organic portion was separated and the aqueous portion was extracted with DCM (2×). The combined organic portions were dried (Na₂SO₄) and concentrated to dryness To the free amine, in DCM (400 mL) at 0° C., was added example C₂ (isomer 2, 44.8 g, 161.5 mmol), EDC (31.0 g, 161.5 mmol) and 4-DMAP (2.0 g, 16.1 mmol). The reaction mixture was stirred at 0° C. for 30 minutes whereupon the cooling bath was removed and the reaction mixture was stirred for another 5 h at room temperature. The mixture was then washed with saturated aqueous sodium bicarbonate (200 mL), 10% aqueous sodium bisulfate (200 mL), dried (Na₂SO₄), and the organic phase was concentrated to dryness to afford 76.4 g (100%) of the ester. EIS-MS 471 [M−1].

B. To the ester from Part A (76.4 g, 161.5 mmol), in MeOH (760 mL), was added 1 N NaOH (242.0 mL, 242.0 mmol) and the mixture heated at 50° C. for 4 h. then stirred for another 16 h at room temperature. After concentrating to dryness, the resulting residue was taken up in 500 mL of water and washed with diethyl ether (2×). The aqueous portion was acidified to pH 2 with 10% aqueous sodium bisulfate and extracted with EtOAc (4×200 mL). The combined organic extracts were dried (MgSO₄) and concentrated to dryness. The resulting solid was suspended in hexanes, filtered, and dried to afford 67.7 g (91%) of the title compound.

EIS-MS 457 [M−1].

Preparation C3

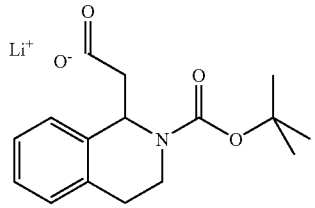

1-Carboxymethyl-3,4-dihydro-1H-isoquinoline-2-carboxylic acid tert-butyl ester, lithium salt A. (1,2,3,4-Tetrahydro-isoquinolin-1-yl)-acetic acid methyl ester To Boc-tetrahydoisoquinoline-1-acetic acid (100.4 g, 520.0 mmol), in MeOH (200 mL), was added 400 mL of 2.3 M HCl in methanol. The mixture was stirred overnight and then concentrated to dryness. The resulting residue was dissolved in EtOAc, washed with saturated sodium bicarbonate, brine, dried (Na₂SO₄), and concentrated to dryness; affording 109.5 g (100%) of the ester.
EIS-MS 206 [M+1].

B. 1-Methoxycarbonylmethyl-3,4-dihydro-1H-isoquinoline-2-carboxylic acid tert-butyl ester To a 0° C. solution of material from part A (50.5 g, 240.0 mmol), in THF (250 mL), was added di-tert-butyl dicarbonate (59.3 g, 270.0 mmol), in THF (50 mL), dropwise. After stirring 45 minutes, the mixture was concentrated to dryness. The resulting residue was dissolved in EtOAc, washed with saturated sodium bicarbonate, brine, dried (Na₂SO₄), and concentrated to dryness. Chiral chromatography (Chiracel OD) of the residue afforded both enantiomers, with the first eluting isomer labeled isomer 1 and the second isomer 2.
EIS-MS 306 [M+1].

C. To a solution of material from part B (10.2 g, 33.4 mmol), in dioxane (220 mL), was added a solution of lithium hydroxide monohydrate (1.67 g, 39.8 mmol), in water (110 mL), portionwise so as to maintain a temperature below 30° C. The mixture was stirred for 16 h and then concentrated to dryness; affording 11.2 g of the lithium salt.
EIS-MS 292 [M+1].

Preparation BC3

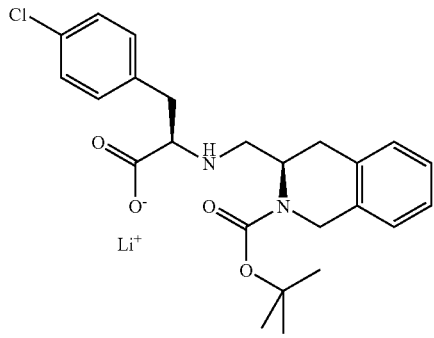

Lithium 2-[(2-tert-butoxycarbonyl-1,2,3,4-tetrahydro-isoquinolin-3-ylmethyl)-amino]-3-(4-chlorophenyl)-propionate A. 3-(Methoxy-methyl-carbamoyl)-3,4-dihydro-1H isoquinoline-2-carboxylic acid tert-butyl ester To Boc-D-1,2,3,4-tetrahydroisoquinoline carboxylic acid (14.9 g, 53.7 mmol), in THF (500 mL), was added N,O-dimethylhydroxylamine hydrochloride (5.24 g, 53.7 mmol), EDC (11.3 g, 59.1 mmol), HOBT (7.98 g, 59.1 mmol) and DIPEA (9.83 ml, 56.4 mmol) The mixture was stirred for 16 h, at room temperature and under nitrogen and then concentrated to dryness. The resulting residue was taken up in EtOAc, washed with 1M HCl, saturated sodium bicarbonate, brine, and dried (Na$_2$SO$_4$). After concentrating to dryness, the resulting residue was purified by flash chromatography (SiO$_2$, eluting with 1:1 EtOAc/hexane) to give 12.3 g (71%) of the ester. EIS-MS 321 [M+1].

B. 3-Formyl-3,4-dihydro-1H-isoquinoline-2-carboxylic acid tert-butyl ester

To a 0° C. solution of material from part A (1.28 g, 4.00 mmol) in THF (30 mL), was slowly added 1.0 M LAH (in THF, 5.1 ml, 5.1 mmol). The reaction mixture was stirred at 0° C. for another 15 minutes. To the mixture was slowly added 20 mL of 5% aqueous potassium hydrogensulfate and the mixture extracted with Et$_2$O (2×). The combined organic portions were washed with 1M hydrochloric acid, saturated sodium bicarbonate, brine, dried (Na$_2$SO$_4$), and concentrated to dryness; affording 0.78 g (75%) of the title compound.

EIS-MS 262 [M+1].

C. 3-{[2-(4-Chloro-phenyl)-1-methoxycarbonyl-ethylamino]methyl}-3,4-dihydro-1H-isoquinoline-2-carboxylic acid tert-butyl ester To a 0° C. solution of 4-Cl-D-Phe methyl ester (6.27 g, 25.1 mmol) and sodium acetate (8.23 g, 1100.0mmol), in 850 ml dry MeOH, was added material from part B (9.8 g, 37.6 mmol), in 50 ml MeOH. The mixture was stirred for 15 minutes and then sodium cyanoborohydride (2.37 g, 37.6 mmol) added. The cooling bath was removed and the reaction stirred for 16 h at room temperature. The mixture was concentrated to dryness and the resulting residue taken up in water and 1ml of 1M HCl. The mixture was extracted with EtOAc and the organics washed with saturated sodium bicarbonate, brine, dried (Na$_2$SO$_4$), and concentrated to dryness. The resulting residue was purified by flash chromatography (SiO$_2$, eluting with 2:1 hexane/EtOAc) affording 8.62 g (75%) of the title compound. EIS-MS 459 [M+1].

D. To a 12° C. solution of material from part C (1.11 g, 2.42 mmol), in dioxane (15 ml), was added a solution of lithium hydroxide (0.10 g, 2.42 mmol), in water (7.5 mL). The mixture was stirred for 16 h and then concentrated to dryness; affording 1.08 g (100%) of the title compound.

EIS-MS 445 [M+1].

Preparation C4

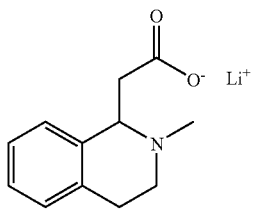

A. (1,2,3,4-Tetrahydro-isoquinolin-1-yl)-acetic acid methyl ester

To the product from Preparation C3, part B (9.98 g, 32.7 mmol) was added 500 mL of cold 4M HCl in dioxane. After one hour, the mixture was concentrated to dryness. The resulting residue was dissolved in EtOAc, the organics washed with saturated sodium bicarbonate, brine, dried (Na$_2$SO$_4$), and concentrated to dryness; affording 6.9 g (100%) of the amine. EIS-MS 206 [M+1].

(2-Methyl-1,2,3,4-tetrahydro-isoquinolin-1-yl)-acetic acid methyl ester

B. To the product from part A (6.71 g, 32.0 mmol), in dichloroethane (175 mL), was added 37% aqueous formaldehyde (22.6 mL, 300 mmol). After 10 minutes, sodium triacetoxyborohydride (31.2 g, 147.0 mmol) was added in 2–3 g portions, with cooling maintain so as to maintain ambient temperature. Upon completion of addition, the mixture was stirred for 16 h at room temperature. DCM and water was then added and the mixture adjusted to pH 9–10 with 5N NaOH. The organic layer was separated, washed with brine, dried (Na$_2$SO$_4$), and concentrated to dryness. The resulting residue was purified by flash chromatography (SiO$_2$, eluting with DCM/2N ammonia in methanol, 95:5); affording 6.9 g (96%) of the title compound. EIS-MS 220 [M+1].

C. To part B (4.45 g, 18.9 mmol), in dioxane (120 mL), was added lithium hydroxide monohydrate (1.02 g, 22.7 mmol), in water (65 mL) portion-wise; thereby keeping the temperature below 30° C. After 16 h the mixture was concentrated to dryness; affording 8.12 g of the title compound. EIS-MS 206 [M+1].

Preparation C5

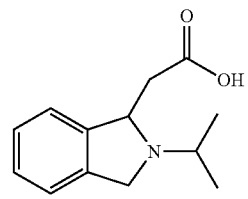

A. (2,3-dihydro-1H-isoindol-1-yl)-acetic acid methyl ester

To the product from Preparation C1 (11.75 g., 40.41 mmol), in DCM (50 mL), was added TFA (50 mL) dropwise. After 2 hr, the solution was concentrated to dryness and the resulting residue partioned with saturated aqueous sodium bicarbonate (200 mL) and EtOAc (300 mL). The organic portion was separated and the aqueous layer was extracted with DCM (4×500 mL). The combined DCM extracts were combined, dried (Na$_2$SO$_4$), and concentrated to dryness to afford 3.97 g (51%) of the title compound.

B. (2-Isopropyl-2,3-dihydro-1H-isoindol-1-yl)-acetic acid methyl ester

To the product from part A (0.50 g, 2.61 mmol), in dichloroethane (46 mL), was added acetone (1.76 mL, 24.01 mmol) and sodium triacetoxyborohydride (2.48 g., 11.74 mmol). After 6 h, the mixture was diluted with 1.0N NaOH (100 mL), the organic portion was separated and the aqueous layer extracted with DCM (3×100 mL). The combined DCM extracts were combined, dried (MgSO$_4$), and concentrated to dryness to afford 0.60 g (99%) of the title compound. EIS-MS 235 [M+1].

C. To the product from part B (0.53 g., 2.30 mmol), in MeOH (5.1 mL), was added 1.0N NaOH (2.53 mL, 2.53 mmol). After two days, the solution was concentrated to dryness. The resulting residue was diluted with 1.0N HCl and water then loaded onto a strong cation exchange resin. The resin was washed with water, THF/water (1:1), water, and the product eluted from the resin with pyridine/water (1:9). The eluent was concentrated to dryness to afford 0.43 g (85%) of the title compound. EIS-MS 220 [M+1].

Preparation C6

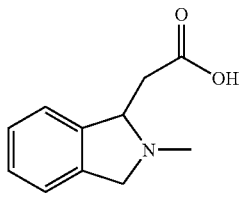

(2-Methyl-2,3-dihydro-1H-isoindol-1-yl)-acetic acid
A. (2-Methyl-2,3-dihydro-1H-isoindol-1-yl)-acetic acid methyl ester To the Boc carbamate removed, as described in Step A of Preparation C5, product from Preparation C1 (0.50 g, 2.61 mmol), in dichloroethane (46 mL), was added 37% aqueous formaldehyde solution (1.80 mL, 24.01 mmol) and sodium triacetoxyborohydride (2.48 g., 11.74 mmol). After 3 days, the mixture was diluted with 1.0N NaOH (100 mL). The organic portion was separated and the aqueous layer extracted with DCM (3×100 mL). The combined DCM extacts were dried (Na$_2$SO$_4$) and concentrated to dryness. The resulting residue was purified by flash chromatography (SiO$_2$, eluting with 100% EtOAc); affording 0.43 g (79%) of the alkylated isoindole. EIS-MS 206 [M+1].

B. To the product from part A (0.34 g., 1.66 mmol), in MeOH (3.7 mL), was added 1.0N NaOH (1.82 mL, 1.82 mmol). After 2 days, the solution was concentrated to dryness. The resulting residue was diluted with 1.0N HC$_1$ and water then loaded onto a strong cation exchange resin. The resin was washed with water, THF/water (1:1), water, and the product eluted from the resin with pyridine/water (1:9). The eluent was concentrated to dryness to afford 0.31 g (98%) of the title compound. EIS-MS 192 [M+1].

Preparation C7

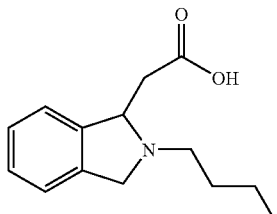

(2-Butyl-2,3-dihydro-1H-isoindol-1-yl)-acetic acid
A. (2-Butyl-2,3-dihydro-1H-isoindol-1-yl)-acetic acid methyl ester To the Boc carbamate removed, as described in Step A of Preparation C5, product from Preparation C1 (0.50 g, 2.61 mmol), in dichloroethane (46 mL), was added butyraldehyde (2.16 mL, 24.01 mmol) and sodium triacetoxyborohydride (2.48 g., 11.74 mmol). After 3 days, the mixture was diluted with 1.0N NaOH (100 mL). The organic portion was separated and the aqueous layer extracted with DCM (3×75 mL). The combined DCM layers were dried (Na$_2$SO$_4$) and concentrated to dryness. The resulting residue was purified by flash chromatography (SiO$_2$, eluting with 1:3, EtOAc/hexanes); affording 0.51g (77%) of the alkylated isoindole. EIS-MS 249 [M+1].

B. To the product from part A (0.47 g., 1.89 mmol) in MeOH (4.2 mL) was added 1.0N NaOH (2.08 mL, 2.08 mmol). After 2 days, the solution was concentrated to dryness. The residue was diluted with 1.0N HCl and water then loaded onto a strong cation exchange resin. The resin was washed with water, THF/water (1:1), water, and the product eluted from the resin with pyridine/water (1:9). The eluent was concentrated to dryness to afford 0.28 g (64%) of the title compound. EIS-MS 234 [M+1].

Preparation C8

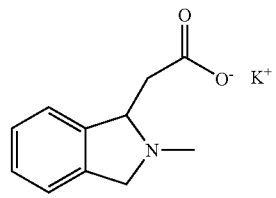

Potassium (2-methyl-2,3-dihydro-1H-isoindol-1-yl)-acetate

To Preparation C6, part A (2.65 gm, 12.9 mmol), in THF (27 mL) was added potassium trimethylsilanolate (1.66 gm, 12.9 mmol) and the reaction stirred for two days. After concentrating to dryness the resulting thick solid was triturated with diethyl ether, filtered, washed with diethyl ether, and dried at room temperature to afford 2.73 g (92%) of the title compound. EIS-MS 192 [M+1].

Preparation C9

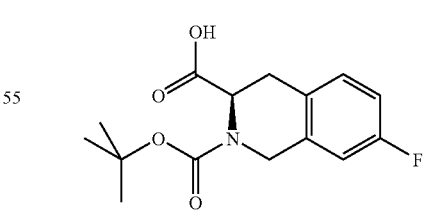

7-Fluoro-3,4-dihydro-1H-isoquinoline-2,3-dicarboxylic acid 2-tert-butyl ester

A. 2-Amino-3-(4-fluoro-phenyl)-propionic acid

To N-Boc-4-Fluoro-D-Phe (2.37 g, 8.366 mmol), in MeOH, 3 mL of concentrated sulfuric acid was added. The reaction mixtured was heated to reflux overnight then concentrated to dryness to afford the title compound. EIS-MS 198 [M+1].

B. 2-Ethoxycarbonylamino-3-(4-fluoro-phenyl)-propionic acid

To a 0° C. mixture of material from part A (1.65 g, 8.37 mmol) and pyridine (1.35 mL, 17.4 mmol), in DCM, was slowly added ethyl chloroformate (0.85 mL, 8.87 mmol). After 30 minutes the mixture was partitioned between water and EtOAc. The aqueous layer was extracted with EtOAc (2×). The combined organic extracts were dried (MgSO$_4$) and concentrated to dryness to afford 2.17 g (96%) of the title compound. EIS-MS 270 [M+1].

C. 7-Fluoro-3,4-dihydro-1H-isoquinoline-2,3-dicarboxylic acid 2-ethyl ester

A mixture of material from part B (2.17 g, 8.06 mmol), paraformaldehyde (0.254 g, 8.46 mmol), and 10 mL of 3:1 glacial acetic acid/concentrated sulfuric acid was stirred at room temperature for 48 h. The mixture was then partitioned between water and EtOAc. The organic portion was separated and the aqueous layer extracted with EtOAc(3×). The combined EtOAc extracts were dried (MgSO$_4$), and concentrated to dryness. Flash chromatography of the resulting residue (SiO$_2$, eluting with 25% EtOAc/Hexane); affording 1.31 g (58%) of the title compound. EIS-MS 282 [M+1].

D. 7-Fluoro-1,2,3,4-tetrahydro-isoquinoline-3-carboxylic acid

The product from Part C (1.31 g, 4.656 mmol), in 20 mL of 5N HCl, was heated at reflux for 24 h. The solution was then concentrated to dryness. The resulting white solid was washed with Et$_2$O to afford 0.87 g (81%) of the title compound. EIS-MS 196 [M+1].

E. To the product from part D (0.87 g, 3.75 mmol), in 20 ml of 1:1 dioxane/water, was added Di-t-butyl-dicarbonate (0.90 g, 4.13 mmol) and TEA (2.36 mL, 16.90 mmol). The mixture was stirred at room temperature for 16 h and then diluted with EtOAc. The organic portion was separated and the aqueous layer extracted with EtOAc (3×). The combined organic portions were dried (MgSO$_4$) and concentrated to dryness to give 0.64 g (58%) of the title compound. EIS-MS 294 [M+1].

Preparation C10

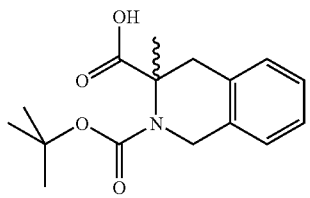

3-Methyl-3,4-dihydro-1H-isoquinoline-2,3-dicarboxylic acid 2-tert-butyl ester

The compound of Preparation C10 was prepared from α-methyl-D,L-Phe by following the substantially similar procedure described in Preparation C9; yielding 1.7 g, of the title compound. EIS-MS 292 [M+1].

Preparation C11

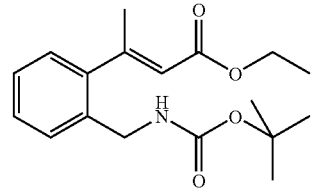

3-[2-(tert-Butoxycarbonylamino-methyl)-phenyl]-but-2-enoic acid ethyl ester

N-Boc-2-bromobenzylamine (7.15 g, 25 mmol) was dissolved into tributylamine (12 mL) and degassed under vacuum. Palladium acetate (224 mg, 1 mmol) and tri-o-tolylphosphine (608 mg, 2 mmol) was then added and the mixture degassed under vacuum. Trans-ethylcrotonate (6.25 mL, 50 mmol) was then added and the mixture was degassed with nitrogen. The tube was sealed and the mixture was heated to 110° C. for 48 h. The solution was cooled to room temperature, diluted with diethyl ether (200 mL) and filtered through celite. The solution was washed with 1N HCl (2×50 mL) and brine (50 mL) dried over magnesium sulfate and concentrated to dryness. Flash chromatography (9:1 hexanes/ethyl acetate) gave the title compound as a yellow oil (1.6 g, 20%). $^1$H NMR 7.22–7.37 (m, 3H), 7.08 (dd, J=7.4, 1.6 Hz, 1H), 5.75 (d, J=1.3 Hz, 1H), 4.29–4.31 (m, 2H), 4.20 (q, J=7.1 Hz, 2H), 2.45 (d, J=1.3 Hz, 3H), 1.44 (s, 9H), 1.30 (t, J=7.1 Hz, 3H).

Preparation C12

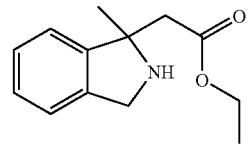

(1-Methyl-2,3-dihydro-1H-isoindol-1-yl)-acetic acid ethyl ester

To Preparation C11 (1.6 g, 5 mmol), in CH$_2$Cl$_2$, was added TFA (10 mL). The mixture was stirred for 1 h at room temperature and concentrated to a yellow oil. TEA (5 mL) was added and the solution was stirred for 15 minutes and concentrated to dryness. Purification by flash chromatography (SiO2, eluting with 5% 2N NH$_3$ in MeOH/EtOAc) gave the title compound as a clear oil (1.0 g, 92%).

Preparation C13

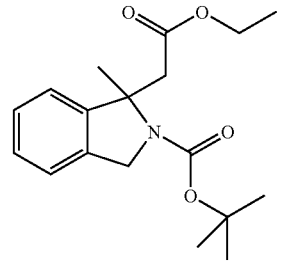

1-Ethoxycarbonylmethyl-1-methyl-1,3-dihydro-isoindole-2-carboxylic acid tert-butyl ester (1-Methyl-2,3-dihydro-1H-isoindol-1-yl)-acetic acid ethyl ester (1.0 g, 4.6 mmol) and di-tert-butyl dicarbonate (1.1 g, 5.06 mmol) were dissolved into DCM (10 mL) under nitrogen atmosphere. The solution was cooled to 0° C. followed by dropwise addition of TEA (0.71 mL, 5.06 mmol). The solution was warmed to room temperature and stirred 72 h. DCM (50 mL) was added and the solution washed with saturated sodium bicarbonate (5 mL), H₂O (5 mL) and brine (5 mL). The organic phase was dried over magnesium sulfate and concentrated to a clear oil. Purification by flash chromatography (SiO₂) gave the title compound as a clear oil (1.18 g, 81%). 1H NMR (CDCl3) δ 7.10–7.30 (m, 4H), 4.65–4.70 (m, 2H), 3.84–3.92 (m, 2H), 3.42–3.48 (m, 0.5H), 2.65–2.80 (m, 1.5H), 1.75 (s, 1.6H), 1.68 (s, 1.4H), 1.55 (s, 5H), 1.48 (s, 4H).

Preparation C14

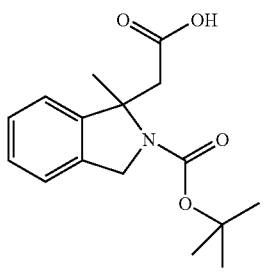

1-Carboxymethyl-1-methyl-1,3-dihydro-isoindole-2-carboxylic acid tert-butyl ester Compound of Preparation C13 (1.14 g, 3.56 mmol) was dissolved into ethanol (10 mL) and H₂O (2 mL) and cooled to 0° C. Lithium hydroxide (470 mg, 11.1 mmol) was added and the mixture was stirred at room temperature for 24 h. Lithium hydroxide (340 mg, 8 mmol) was added and the solution was stirred for about 24 h. A 1 N solution of NaOH (5 mL) was added and the solution was washed with hexanes (10 mL). The aqueous solution was acidified with 1N HCl to pH 1. The solution was extracted with EtOAc (3×20 mL), dried over magnesium sulfate and concentrated to a white solid. The residue was recrystallized from hexanes to give the title compound (850 mg, 82%). ¹H NMR (CDCl₃) δ 7.10–7.30 (m, 4H), 4.60 (s, 2H), 3.65–3.80 (m, 0.6H), 3.30–3.40 (m, 0.4H), 2.70–2.80 (m, 1H), 1.65–75 (m, 3H), 1.45–1.60 (m, 9H).

Preparation of C15

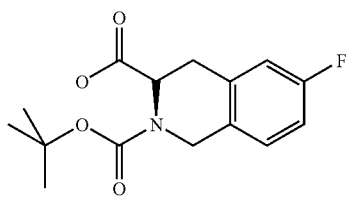

6-Fluoro-3,4-dihydro-1H-isoquinoline-2,3-dicarboxylic acid 2-tert-butyl ester

Compound C15 was prepared N-Boc-3-Fluoro-D-Phe by following the same procedure as described in the Preparation of C9.
EIS-MS 294 [M+1].

Preparation BC4

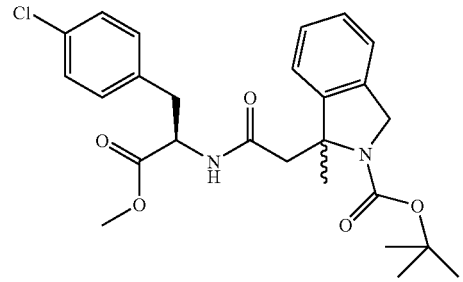

To 4-Chloro-D-Phenylalanine methyl ester hydrochloride (0.432 g, 1.73 mmol) was added Compound of preparation C13 (0.504 g, 1.73 mmol), EDC (0.330 g, 1.73 mmol) and HOBT (0.233 g, 1.73 mmol). This was followed by addition of dichloromethane (5 mL) and DIPEA (0.452 mL). The solution was stirred for 3 h then diluted with EtOAc (50 mL). The organics were washed with saturated NaHCO₃ (50 mL), water (50 mL), and concentrated to dryness. The crude product was purified by flash chromatography (SiO₂, eluting with Hexane/EtOAc, 80:20) yielding 0.724 g, 86% of the title compound as a white solid. EIS-MS 487.2 [M+1].

Preparation BC5

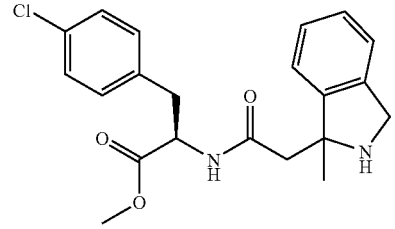

3-(4-Chloro-phenyl)-2-[2-(1-methyl-2,3-dihydro-1H-isoindol-1-yl)-acetylamino]-propionic acid methyl ester.

To compound of Preparation BC4 in DCM (3 mL), was added TFA (3 mL) and the mixture was allowed to stand for 2 h. After concentrating to dryness, the diastereomers were separated by reverse phase HPLC [Waters Symmetry C18 column, eluting with H₂O (0.05% HCl)/CH₃CN, 90:10 to 60:40, following a straight line gradient]. The first eluting isomer was labeled isomer 1 and the second isomer 2. EIS-MS 387.1 [M+1] for both isomers.

Preparation BC6

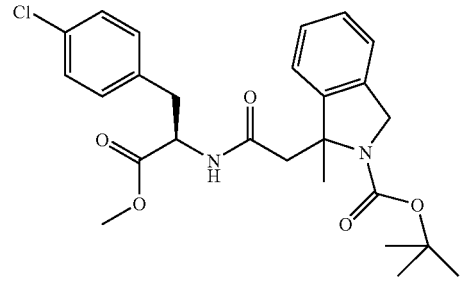

1-{[2-(4-Chloro-phenyl)-1-methoxycarbonyl-ethyl-carbamoyl]methyl}-1-methyl-1,3-dihydro-isoindole-2-carboxylic acid tert-butyl ester, isomer 1

To the compound of Preparation BC5 (isomer 1, 0.321 g, 0.831 mmol), in THF/H2O 1:1, 4 mL) was added K₂CO₃ (0.253 g, 1.83 mmol) and BOC₂O. The mixture stirred for 12 h and then the crude mixture was diluted with EtOAc (25 mL), the organics washed with H₂O and concentrated to dryness; yielding the title compound (0.33 g, 81%). EIS-MS 487.1 [M+1].

Preparation BC7

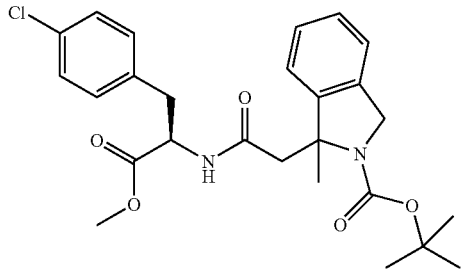

1-{[2-(4-Chloro-phenyl)-1-methoxycarbonyl-ethyl-carbamoyl]-methyl}-1-methyl-1,3-dihydro-isoindole-2-carboxylic acid tert-butyl ester, isomer 2

The compound of Preparation BC7 was prepared from the compound of Preparation BC5 (isomer 2) by following the substantially similar procedure described in Preparation BC6.

Preparation BC8

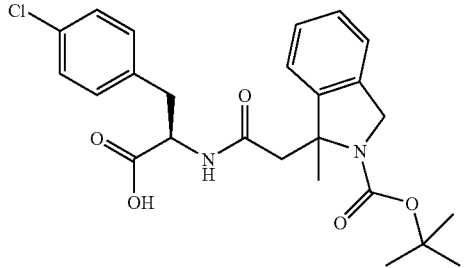

1-{[1-Carboxy-2-(4-chloro-phenyl)-ethylcarbamoyl]-methyl}-1-methyl-1,3-dihydro-isoindole-2-carboxylic acid tert-butyl ester, isomer 1

To the product from Preparation BC6 (isomer 1, 0.330 g, 0.679 mmol) in H₂O/THF 1:1 (10 mL) was added LiOH (0.050 g, 2.01 mmol). The mixture was stirred for 5 h, then diluted with H₂O (50 mL) and acidified to pH 4 with 25% KHSO₄. The aqueous mixture was extracted with EtOAc (100 mL) and concentrated to dryness; yielding the title compound (0.335 g). EIS-MS 473.2 [M+1].

Preparation BC9

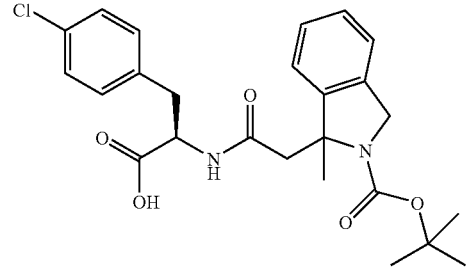

1-{[1-Carboxy-2-(4-chloro-phenyl)-ethylcarbamoyl]-methyl}-1-methyl-1,3-dihydro-isoindole-2-carboxy acid tert-butyl ester, isomer 2

Preparation BC9 was prepared from the compound of Preparation BC7 (isomer 2) by following the substantially similar procedure described in Preparation BC8; yielding 0.26 g, 95% of the title-compound.
EIS-MS 473.3 [M+1].

Preparation BC10

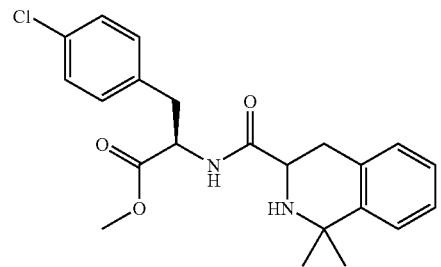

3-(4-Chloro-phenyl)-2-[(1,1-dimethyl-1,2,3,4-tetrahydro-isoquinoline-3-carbonyl)-amino]-propionic acid methyl ester To a solution of 1,1-dimethyl TIC (240 mg, 1.17 mmol), 4-Cl-D-Phe methyl ester (322 mg, 1.28 mmol), HOBT (197 mg, 1.46 mmol), and DIPEA (0.81 mL, 44.68 mmol, 4.0 eq) in CH₂Cl₂/DMF (1:1) was added EDC (280 mg, 1.46 mmol). The resulting mixture was stirred at room temperature overnight. The reaction mixture was then diluted with EtOAc(100 mL), washed with saturated aqueous NaHCO₃, brine, dried (Na₂SO₄) and concentrated to dryness. Purification and separation of diastereomers by flash chromatography (35 g SiO₂, linear gradient, 40 mL/min 10–50% EtOAc/hexane for 25 minutes and 50% EtOAc/hexane for 7 minutes) afforded title compound.

Preparation BC11

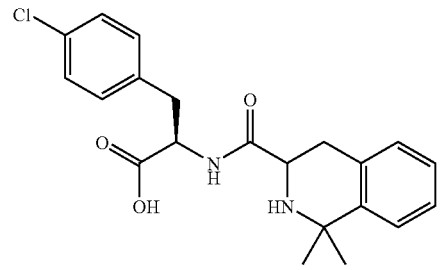

3-(4-Chloro-phenyl)-2-[(1,1-dimethyl-1,2,3,4-tetrahydro-isoquinoline-3-carbonyl)-amino]-propionic acid To Preparation BC10 (5.95 g, 14.88 mmol), in a 1:1 mixture of THF/H2O (50 mL), was added lithium hydroxide hydrate (0.75 g, 17.87 mmol). The reaction was stirred at room temperature for 18 h. The mixture was then concentrated to dryness. The resulting residue was dissolved in water (50 mL), made acidic with 1N HCl (25 mL) and washed with Et₂O (100 mL) The aqueous layer was evaporated to dryness, yielding 6.18 g (98%) of the title compound. EIS-MS 387

Preparation BC12

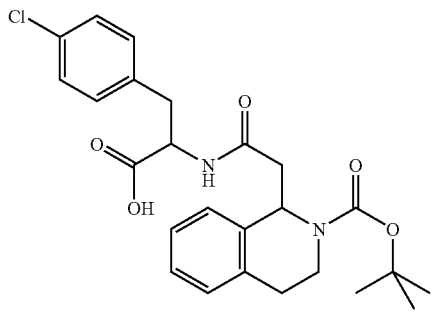

1-{[1-Carboxy-2-(4-chloro-phenyl)-ethylcarbamoyl]-methyl}-3,4-dihydro-1H-isoquinoline-2-carboxylic acid tert-butyl ester, isomer 1

A. To a solution of D-4-chlorophenylalanine methyl ester hydrochloride (883 mg, 3.53 mmol), Preparation C3 (isomer 1) (1.0 g, 3.36 mmol), HOBT (568 mg, 4.2 mmol), and DIPEA (2.92 mL, 16.8 mmol) in CH₂Cl₂ (35 mL) was added EDC (805 mg, 4.2 mmol). The resulting mixture was stirred at room temperature for 48 h. The reaction mixture was poured into a mixture CH₂Cl₂-water (1:1) and the organic phase washed with water (2×), dried (Na₂SO₄), filtered, and concentrated to dryness. Final purification by flash chromatography EtOAc-hexane (3:7) afforded 1.38 g of desired compound as a white solid. MS m/z 485.2 (M⁺-1)

B. To a solution of the above-formed ester (1.38 g, 2.83 mmol) in THF (15 ML), a 1M aqueous solution of LiOH.H₂O (14.15 mL, 14.15 mmol) was added and mixture stirred at room temperature for 1 h. Reaction was cooled to 0° C. and pH was adjusted to ≈1 upon addition of 1M HCl. Aqueous layer was extracted with EtOAc, dried (Na₂SO₄), and evaporated to afford 1.32 g of the title compound as a white solid. MS m/z 471.2 (M⁺-1)

Preparation BC13

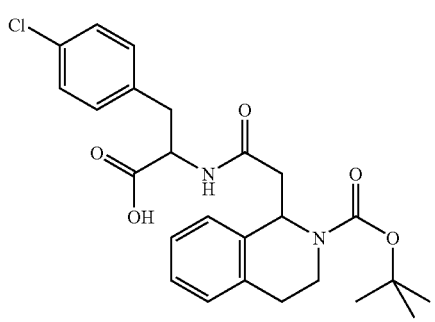

1-{[1-Carboxy-2-(4-chloro-phenyl)-ethylcarbamoyl]-methyl}-3,4-dihydro-1H-isoquinoline-2-carboxylic acid tert-butyl ester, isomer 2

The compound of Preparation BC13 was prepared from Preparation C3 (isomer 2) by following a procedure substantially similar to that described in Preparation BC12.

MS m/z 471.2 (M⁺-1)

Preparation BC14

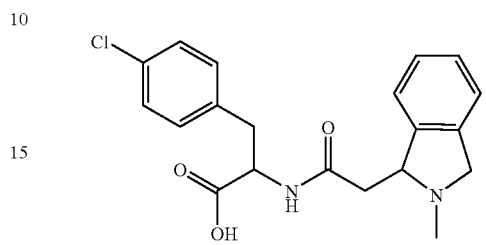

3-(4-Chloro-phenyl)-2-[2-(2-methyl-2,3-dihydro-1H-isoindol-1-yl)-acetylamino]-propionic acid A. To a solution of D-4-chlorophenylalanine methyl ester hydrochloride (1.37 g, 5.49 mmol), Preparation C6 (1.2 g, 5.23 mmol), HOBT (883 mg, 6.54 mmol), and DIPEA (4.55 mL, 26.2 mmol) in CH₂Cl₂ (35 mL) was added EDC (1.25 g, 6.54 mmol). The resulting mixture was stirred at room temperature for 48 h. The reaction mixture was poured into a mixture CH₂Cl₂-water (1:1) and the organic phase washed with water (2×), dried (Na₂SO₄), filtered, and concentrated to dryness. Final purification by flash chromatography (EtOAc, then EtOAc/MeOH/AcOH 95:5:5) afforded 1.71 g of desired compound as a solid. MS m/z 387.1 (M⁺+1)

B. To a solution of the above-formed ester. (1.71 g, 4.4 mmol) in THF (40 mL), a 1M aqueous solution of LiOH.H₂O (22.1 mL, 22.1 mmol) was added and mixture stirred at room temperature for 1 h. Reaction was cooled to 0° C. and pH was adjusted to &1 upon addition of 1M HCl. Aqueous layer was extracted with EtOAc, dried (Na₂SO₄), and evaporated to afford 1.6 g of the title compound as a solid. MS m/z 373.2 (M⁺+1)

Preparation of Compound 3000

Procedure AAA

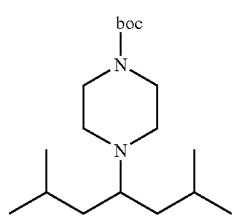

Compound 3000

To a solution of Compound 3025 (4.00 g, 14.23 mmol) in THF (100 mL) was added iso-butyl magnesium bromide 2

M in Et2O (21.34 mL, 42.69 mmol) and stirred for 12 h. The mixture was then poured into water (200 mL) and extracted with EtoAc (200, mL). The organics were separated and concentrated to dryness. The title compound was collected cleanly with out purification. Yield: 3.71 g, 84%, ES MS (M+1) 313.3

Preparation of Compound 3001

Procedure BBB

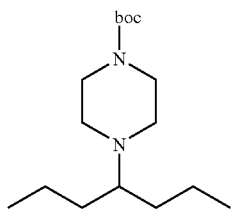

Compound 3001

To a solution of 4-heptanal (5.00 g, 43.86 mmol) and Boc-piperazine (8.16 g, 43.86 mmol) in MeOH (35 mL) was added acetic acid (2.63 g, 43.86 mmol) followed by NaCNBH3 (2.76 g, 43.86 mmol). The mixture was stirred for 12 h and concentrated to a thick oil. The crude martial was diluted with water (300 mL) and extracted with EtoAc (200 mL). The organics were separated and concentrated to dryness. The crude product was purified by column chromatography (silica gel 60 mesh) eluting with Hexane/EtoAc (80/20). Yield 5.1 g, 41%, ES MS (m+l) 285.3

Procedures for preparing certain A-domain pieces are described beloew.

Preparation of Compound 3002

Procedure CCC

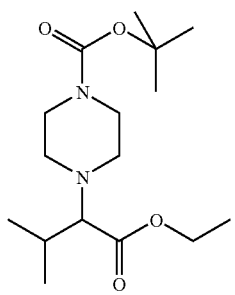

Compound 3002

To α-bromo ethyl valerate (22.66 g, 108.37 mmol), was added N-Boc-Piperazine (20.15 g, 108.37), Et$_3$N (15.2 mL, 108.37 mmol), THF (100 mL), and the mixture heated at reflux for 16 h. After cooling to room temperature, the mixture was diluted with EtOAc (5 fold) and the organics washed with saturated NaHCO$_3$, H$_2$O, and concentrated to dryness. The crude material was taken up in TFA (25 mL), stirred for 30 minutes and then concentrated to dryness. The resulting residue was taken up in H$_2$O, washed with EtOAc, and then the aqueous layer made basic with 5N NaOH and the desired amine extracted into EtOAc. The organics were concentrated to dryness and the resulting residue taken up in THF/H$_2$O (1:1, 50 mL) and Boc$_2$O (7.25 g, 33.2 mmol), and K$_2$CO$_3$ (4.59 g, 33.2 mmol) added and the mixture stirred for 2 h. After diluting with EtOAc (10 fold), the organics were washed with H$_2$O and concentrated to dryness. The desired product was purified by flash chromatography (SiO$_2$, eluting with 10%EtOAc in Hexanes). Yield: 25.4 g, 75%. Ion spray MS: 315.3 [M+H].

Preparation of Compound 3003

Procedure DDD

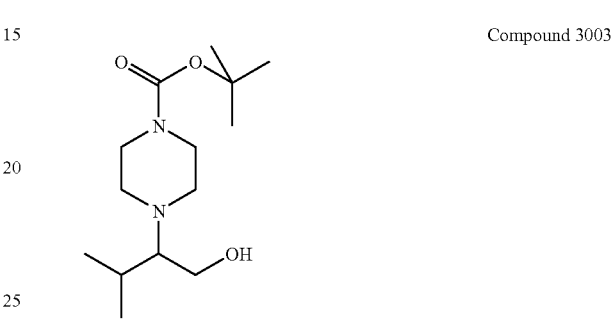

Compound 3003

To compound 3002 (2.26 g, 7.18 mmol), in THF (25 mL), at 0° C., was added LAH (0.571 g, 15.0 mmol) portionwise. Upon completion of addition the mixture was stirred for 1 h and then quenched, sequentially with 0.57 mL H$_2$O, 0.57 mL 15% NaOH, and 1.7 mL H$_2$O. The resulting aluminum salts were stirred at room temperature for 1 h and then removed by filtration. The filtrate was concentrated to dryness.

Yield: 1.65 g, 85%. Ion spray MS: 273.1 [M+H].

Preparation of Compound 3004

Procedure EEE

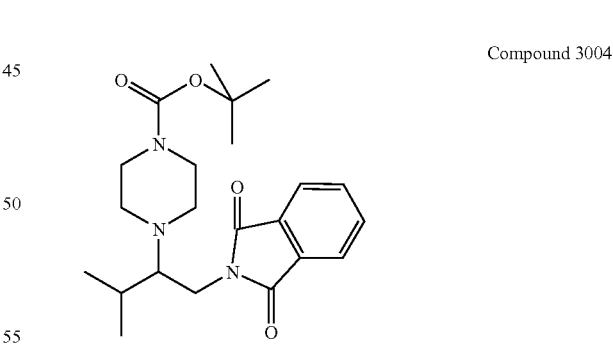

Compound 3004

To compound 3003 (1.63 g, 5.98 mmol), in THF (10 mL), at 0° C., was added PPh$_3$ (1.72 g, 6.58 mmol), phthalimide (1.15 g, 6.58 mmol), and the mixture stirred for 10 minutes and then diethyl azodicarboxylate (1.04 mL, 6.58 mmol) added. Stirring was continued for 1 h and then the mixture was diluted 10 fold with EtOAc and the organics washed with H$_2$O, brine, and concentrated to dryness. The desired product was purified by flash chromatography (SiO$_2$, eluting with 20% EtOAc in Hexanes). Yield: 2.16 g, 90%. Ion spray MS: 402.2 [M+H].

Preparation of Compound 3005

Procedure FFF

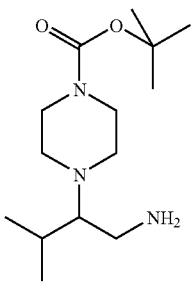

Compound 3005

To compound 3004 (2.15 g, 5.35 mmol), in EtOH (20 mL), was added hydrazine (1.7 mL, 53.5 mmol) and the mixture heated at 60° C. for 30 minutes. After cooling to room temperature, the suspension was concentrated to dryness and the resulting residue partitioned between EtOAc and 1N NaOH. The organics were concentrated to dryness.
Yield: 1.36 g, 94W. Ion spray MS: 272.2 [M+H].

Preparation of Compound 3006

Procedure GGG

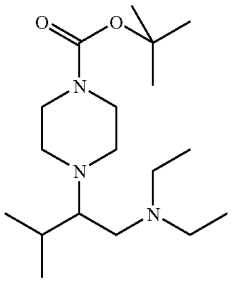

Compound 3006

To compound 3005, in DMF (15 mL), was added $K_2CO_3$ (3.43 g, 24.85 mmol), and bromoethane (0.93 mL, 12.43 mmol). The mixture was stirred at room temperature for 48 h and then diluted 10 fold with EtOAc. The organics were washed with $H_2O$ and concentrated to dryness. The desired product was purified by flash chromatography ($SiO_2$, eluting with 90:5:5, EtOAc-$Et_3$N-MeOH). Yield: 1.23 g, 76%. Ion spray MS: 328.2 [M+H].

Preparation of Compound 3007

Procedure HHH

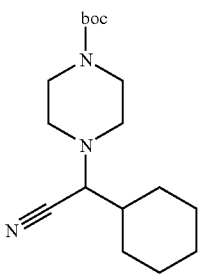

Compound 3007

To a solution of KCN (1.61 g, 24.8 mmol) in $H_2O$ (15 mL) N-Boc-piperazine (4.6 g, 24.6 mmol) was added and the mixture cooled to 0° C. Then 1M aqueous HCl (23.9 mL, 23.9 mmol) was added followed by cyclohexanecarboxaldehyde (2.0 mL, 16.5 mmol) and the mixture stirred for 20 h. It was poured over $Et_2O$ and the aqueous phase extracted with $Et_2O$, dried ($MgSO_4$), and evaporated. The crude was purified by flash chromatography (hexane-EtOAc 4:1→3:1) to afford 4.2 g of 3007.

Preparation of Compound 3200

Procedure III

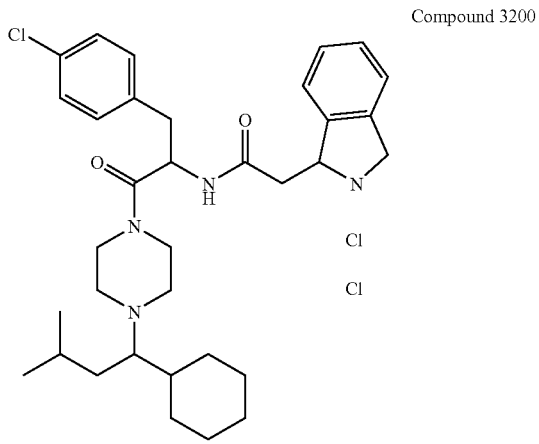

Compound 3200

N-{1-(4-Chloro-benzyl)-2-[4-(1-cyclohexyl-3-methyl-butyl)-piperazin-1-yl]-2-oxo-ethyl}-2-(2,3-dihydro-1H-isoindol-1-yl)-acetamide dihydrochloride salt. A solution of 3102 as the dihydrochloride salt (332 mg, 1.21 mmol), BC2 (638 mg, 1.39 mmol), 1-hydroxy-7-azabenzotriazole (206 mg, 1.51 mmol), O-(7-azabenzotriazol-1-yl)-N,N,N',N'-tetramethyluronium hexafluorophosphate (574 mg, 1.51 mmol), and diisopropylethylamine (2.1 mL, 12.1 mmol) in $CH_2Cl_2$ (10 mL) and DMF (2.5 mL) was stirred at 23° C. for 16 h, diluted with $CH_2Cl_2$ and washed with brine, dried ($Na_2SO_4$), and evaporated. Purification by flash chromatography (hexane-EtOAc 4:1) gave rise to the coupled product. The Boc group was removed by stirring at room temperature in methylene chloride/TFA (1:1, 20 mL) for 2 hours. The solvent was evaporated and the residue purified by a SCX cartridge (MeOH→2M $NH_3$ in MeOH). The resulting oil was dissolved in 0.1 M HCl in EtOAc and stirred for 10 min. Final evaporation of the solvent afford the desired product 3200. MS m/z 580 ($M^+$+1).

The following compounds were prepared from a monoprotected piperazine and the appropriate ketone or aldehyde using procedures substantially similar to procedures C or HHH were appropriate.

TABLE XXX

| Cmpd. # | Structure | Analogous to procedure | MS ES (m + 1) |
|---|---|---|---|
| 3025 | 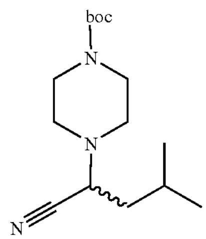 | C | 282.2 |
| 3026 | 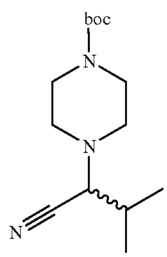 | C | 268.2 |

TABLE XXX-continued

| Cmpd. # | Structure | Analogous to procedure | MS ES (m + 1) |
|---|---|---|---|
| 3007 | 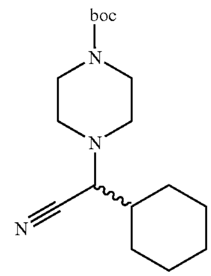 | HHH | |
| 3028 | 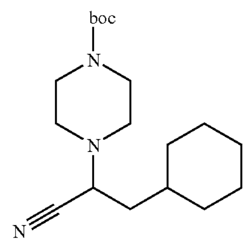 | C | |

The following compounds were prepared from the appropriate precursor (see table) and procedures substantially similar to AAA, BBB or GGG were applicable.

TABLE XXXI

| Cmpd. # | Structure | Analogous to procedure | MS ES (m + 1) | Originating from |
|---|---|---|---|---|
| 3050 | 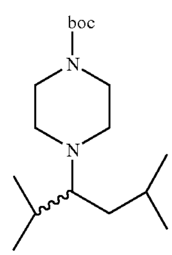 | AAA | 299 | 3026 |
| 3051 | 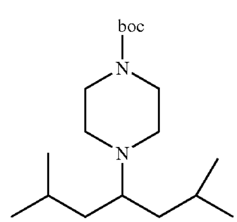 | AAA | 313.3 | 3025 |

TABLE XXXI-continued

| Cmpd. # | Structure | Analogous to procedure | MS ES (m + 1) | Originating from |
|---|---|---|---|---|
| 3052 | boc-piperazine-CH(cyclohexyl)CH2CH(CH3)2 | AAA | 339 | 3007 |
| 3053 | boc-piperazine-CH(CH2-cyclohexyl)2 | AAA | 393 | 3028 |
| 3001 | boc-piperazine-CH(CH2CH2CH3)2 | BBB | 285.3 | |
| 3006 | boc-piperazine-C(iPr)(CH2N(Et)2) | GGG | 328.2 | 3005 |

Compounds 3100 to 3106 were prepared from the substituted Boc-protected piperazines by procedures substantially similar to X.

TABLE XXXII

| Cmpd. # | Structure | Analogous to procedure | ES MS (m + 1) | Originating from compound |
|---|---|---|---|---|
| 3100 | H-piperazine-CH(iPr)CH2CH(CH3)2 | X | 199.2 | 3050 |

TABLE XXXII-continued

| Cmpd. # | Structure | Analogous to procedure | ES MS (m + 1) | Originating from compound |
|---|---|---|---|---|
| 3101 | 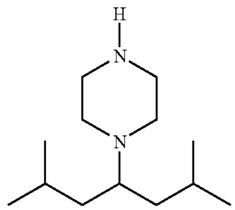 | X | 213.3 | 3051 |
| 3102 | 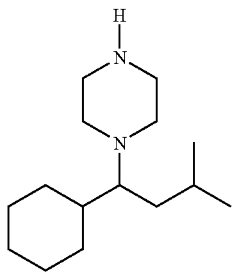 | X | 239 | 3052 |
| 3103 | 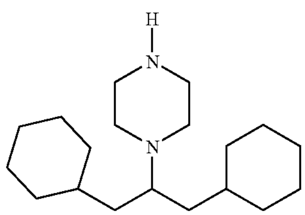 | X | 293 | 3053 |
| 3105 | 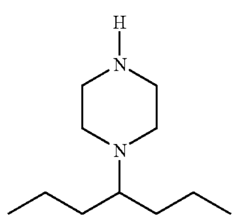 | X | 185.2 | 3001 |
| 3106 | 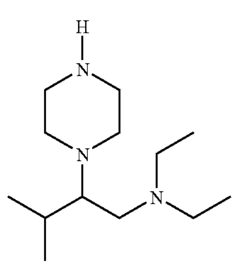 | X | 228.1 | 3006 |

Compounds 3000, 3001, 3105 and 3006 were prepared from the appropriate substituted piperazines using procedures substantially similar to Z.
TABLE XXXIII
| Cmpd. # | Structure | Analogous to procedure | ES MS (m + 1) | Originating from | B-C Domain used |
|---|---|---|---|---|---|
| 3150 | 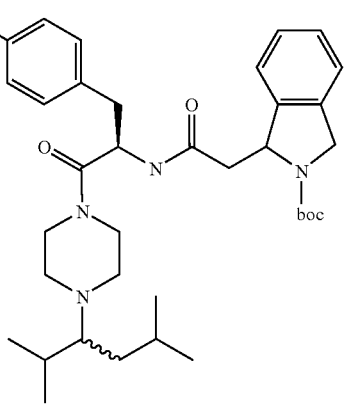 | Z | 639.4 | 3100 | BC2 |
| 3151 | 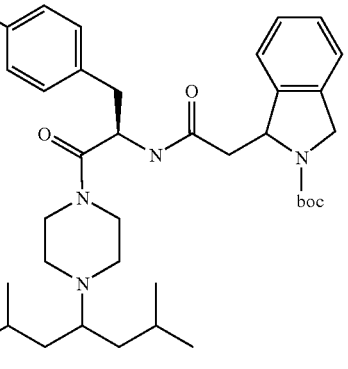 | Z | 653.4 | 3101 | BC2 |
| 3152 | 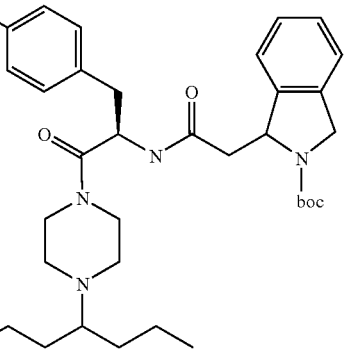 | Z | 625.3 | 3105 | BC2 |

TABLE XXXIII-continued

| Cmpd. # | Structure | Analogous to procedure | ES MS (m + 1) | Originating from | B-C Domain used |
|---|---|---|---|---|---|
| 3153 | 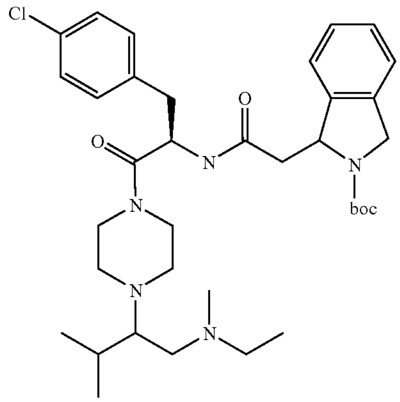 | Z | 668.3 | 3006 | BC2 |

Compounds 3000 and 3202 were prepared from the appropriately substituted piperazines using procedures substantially similar to procedure III.

Compounds 3250 to 3253 were prepared from the Boc-protected precursor by procedures substantially similar to procedure AA.

TABLE XXXIV

| Cmpd. # | Structure | Analogous to procedure | ES MS (m + 1) | Originating from | B-C Domain used |
|---|---|---|---|---|---|
| 3200 | 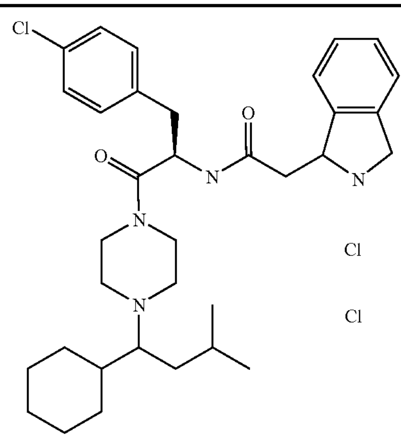 | III | 580 | 3102 | BC2 |
| 3202 | 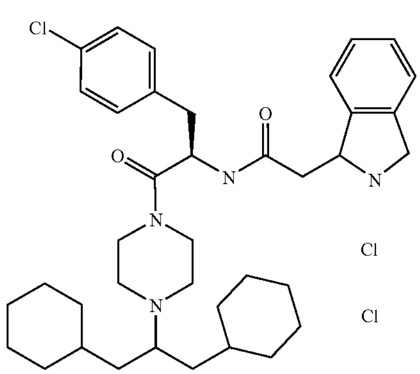 | III | 633 | 3103 | BC2 |

TABLE XXXV
| Cmpd. # | Structure | Analogous to procedure | ES MS (m + 1) | Originating from |
|---|---|---|---|---|
| 3250 | 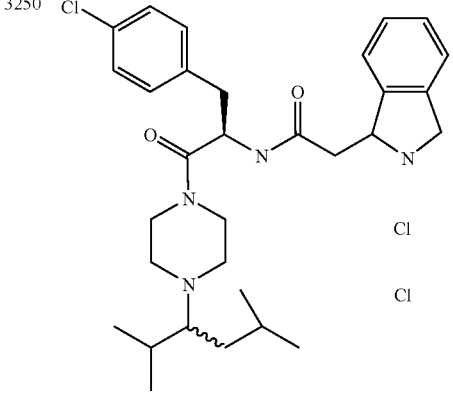 Cl Cl | AA | 539.3 | 3150 |
| 3251 | 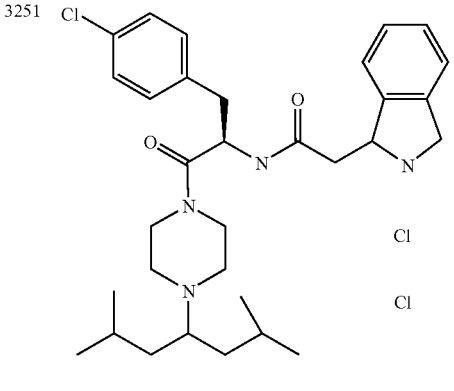 Cl Cl | AA | 553.2 | 3151 |
| 3252 | 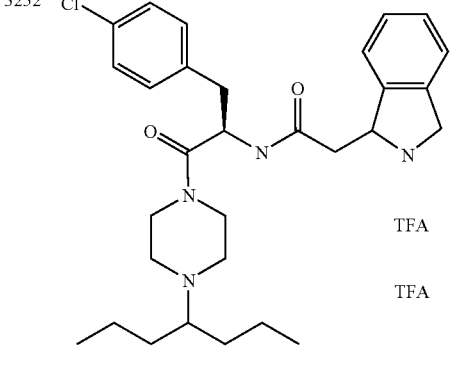 TFA TFA | AA | 525.3 | 3152 |

TABLE XXXV-continued

| Cmpd. # | Structure | Analogous to procedure | ES MS (m + 1) | Originating from |
|---|---|---|---|---|
| 3253 | [structure shown] TFA TFA TFA | AA | 568.3 | 3153 |

Preparation G1

[structure: methyl 2-bromo-2-(2-fluorophenyl)acetate]

To 2-fluorophenylacetic ester (5.3 g, 31.5 mmol), in CCl$_4$ (30 mL), was added N-bromosuccinimide (6.17 g, 34.6 mmol) and a catalytic amount of 2,2'-azobisisobutyronitrile. The mixture was heated at reflux for 12 h and then allowed to cool to room temperature. The resulting precipitate was removed by filtration and the filtrate concentrated to dryness. The desired product was purified by flash chromatography (SiO$_2$, eluting with 10% EtOAc in Hexanes).

Yield: 7.52 g, 97%. EIS-MS 248.1 [M+1].

Preparation G2

[structure shown]

To compound of preparation G1 (7.52 g, 30.4 mmol), in DCM (60 mL), was added TEA (8.5 mL, 60.8 mmol) and N-Boc piperazine (5.67 g, 30.4 mmol) and the mixture stirred at room temperature for 12 h. After concentrating to dryness, the resulting residue was taken up in EtOAc (100 mL), the organics washed with H$_2$O, brine, and concentrated to dryness. The resulting residue was purified by flash chromatography (SiO2, eluting with 10% EtOAc in Hexanes).

Yield: 10.2 g, 95%. EIS-MS 353.2 [M+1].

Preparation G3

[structure shown]

To compound of preparation G2 (1.57 g. 4.45 mmol), in EtOH (20 mL) and H$_2$O (2 mL), was added NaOH (4.45 g, 113.3 mmol). The mixture was stirred at room temperature for 6 h and the concentrated to dryness. The resulting acid salt was taken up in H$_2$O, washed with Et$_2$O, and the aqueous layer made slightly acidic (pH 4–5) by the cautious addition of 5N HCl. The desired acid was extracted into EtOAc and the organics washed with-brine and concentrated to dryness. Yield: 1.2 g, 80%. EIS-MS 339.2 [M+1].

Preparation G4

[structure shown]

To compound of preparation G3 (1.11 g, 3.28 mmol), in DMF (10 mL), was added diethylcyanophosphonate (0.55 mL, 3.6 mmol), diethylamine (0.40 mL, 3.94 mmol), and TEA (0.55 mL, 3.94 mmol). The mixture was stirred at room temperature for 3 h and the diluted with EtOAc (100 mL). The organics were washed with saturated $NaHCO_3$, $H_2O$, brine, and concentrated to dryness. Yield: 1.25 g, 97%.

EIS-MS 394.3 [M+1].

Preparation G5

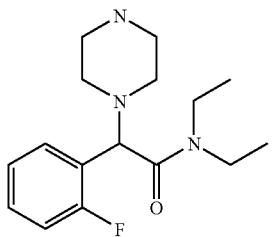

To compound of preparation G4 (0.698 g, 1.77 mmol), in $CH_2Cl_2$ (5 mL), was added TFA (5 mL) and the mixture stirred at room temperature for 45 minutes. After concentrating to dryness, the resulting residue was taken up with 1N NaOH and the desired "free" amine extracted into EtOAc (50 mL). The organic extracts were concentrated to dryness. Yield: 508 mg, 98%. EIS-MS 294.2 [M+1].

Preparation G6

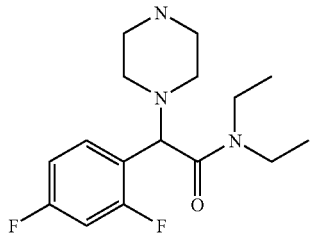

The compound of preparation G6 was prepared from 2,4-difluorophenyl acetic ester by following substantially similar procedures described in preparations 1–5. EIS-MS 312.2 [M+1].

EXAMPLE G1

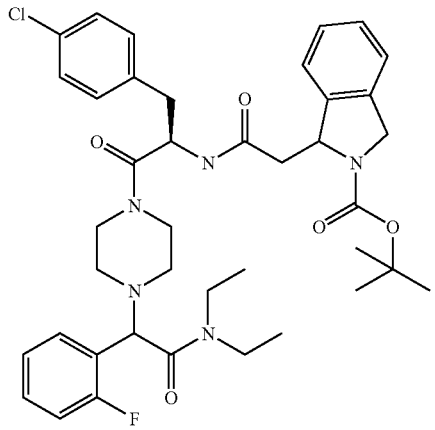

To compound of preparation G5 (0.344 g, 1.17 mmol) in DCM (10 mL), was added was added compound of preparation BC2 (isomer 2, 0.538 g, 1.17 mmol), DIPEA (1 mL, 5.87 mmol), and HATU (0.446 g, 1.17 mmol). The mixture was stirred at room temperature overnight and then concentrated to dryness., The resulting residue was taken up in EtOAc (50 mL), the organics washed with saturated $NaHCO_3$, $H_2O$, brine, and concentrated to dryness. The desired product was purified by flash chromatography ($SiO_2$, eluting with EtOAc). Yield: 0.654 g, 74%. EIS-MS 734.1 [M+1].

EXAMPLE G2

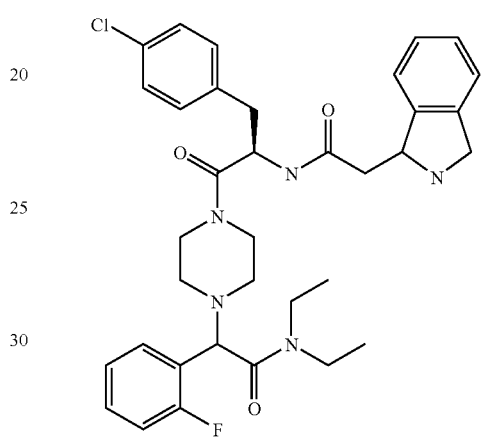

To compound of Example G1 (0.654 g, 0.891 mmol), in DCM (10 mL), was added TFA (5 mL) and the mixture stirred at room temperature for 45 minutes. After concentrating to dryness, the resulting residue was triturated with $Et_2O$, the resulting solid collected by filtration and dried.

Yield: 0.540 g, 85%. EIS-MS 634.3 [M+1].

EXAMPLE G3

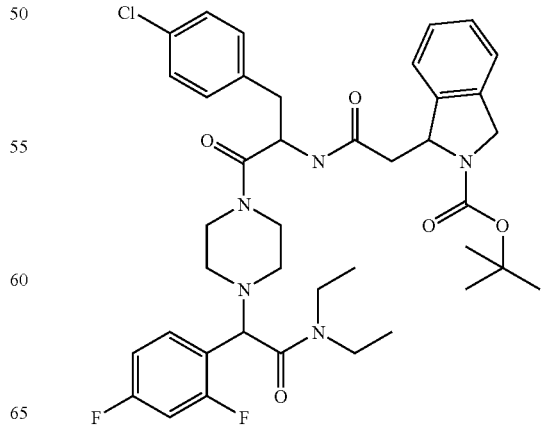

To compound of preparation G6 (0.298 g, 0.958 mmol) in DCM (10 mL), was added was added compound of preparation BC2 (isomer 2, 0.439 g, 0.958 mmol), DIPEA (0.83 mL, 4.79 mmol), and HATU (0.364 g, 0.958 mmol). The mixture was stirred at room temperature overnight and then concentrated to dryness. The resulting residue was taken up in EtOAc (50 mL), the organics washed with saturated NaHCO₃, H₂O, brine, and concentrated to dryness. The desired product was purified by flash chromatography (SiO₂, eluting with EtOAc). Yield: 0.637 g, 89%. EIS-MS 752.2 [M+1].

EXAMPLE G4

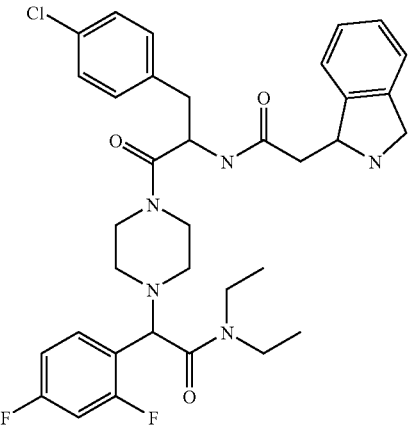

To compound of Example G3 (0.635 g, 0.845 mmol), in DCM (10 mL), was added TFA (5 ml) and the mixture stirred at room temperature for 45 minutes. After concentrating to dryness, the resulting residue was triturated with Et₂O, the resulting solid collected by filtration and dried.
Yield: 669 mg, 90%. MS (ES) 652.2 [M+1].

EXAMPLE G5

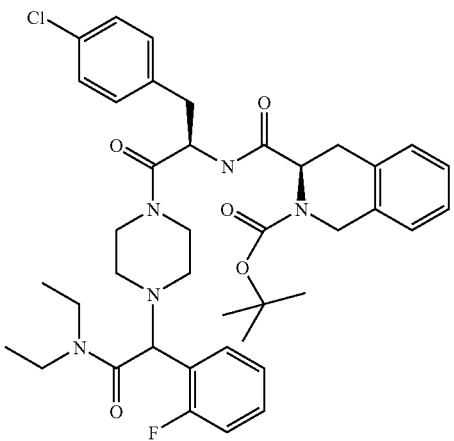

To compound of preparation G5 (0.047 g, 0.16 mmol), in DCM (4 mL) and DMF (1 mL), was added preparation BC1 (0.08 g, 0.176 mmol), DIPEA (0.14 mL, 0.80 mmol), and HATU (0.061 g, 0.16 mmol). The mixture was stirred at room temperature overnight and then concentrated to dryness. The resulting residue was taken up in EtOAc (50 mL), the organics washed with saturated NaHCO₃, H₂O, brine, and concentrated to dryness. The desired product was purified by flash chromatography (SiO₂, eluting with 20% EtOAc in Hexanes). Yield: 0.100 g, 85%. MS (ES) NA [M+1].

EXAMPLE G6

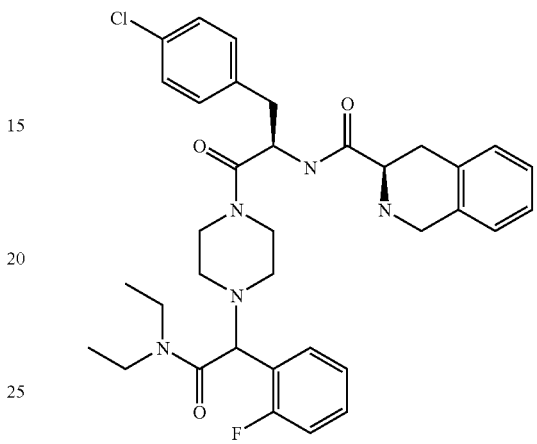

To the compound of Example 5 (0.10 g, 0.136 mmol), in DCM (10 mL), was added TFA (5 mL) and the mixture stirred at room temperature for 30 minutes. After concentrating to dryness, the resulting residue was triturated with Et₂O, the resulting solid collected by filtration and dried.
Yield: 65 mg, 55%. EIS-MS NA [M+1].

Preparation G7

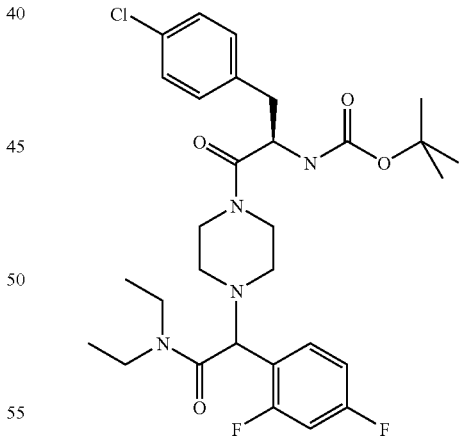

To compound of preparation G6 (0.30 g, 1.09 mmol) was added N-Boc-4-Cl-D-Phe (0.325 g, 1.09 mmol), EDC (0.209 g, 1.09 mmol), HOBT (0.171 g, 1.09 mmol), and DCM (10 mL). The mixture was stirred at room temperature for 1 h and then diluted with EtOAc (50 mL). The organics were washed with saturated NaHCO₃, H₂O, brine, and concentrated to dryness. The resulting residue was purified by flash chromatography (SiO2, eluting with 25% EtOAc in Hexanes).
Yield: 308 mg, 48%. EIS-MS 593.2 [M+1].

Preparation G8

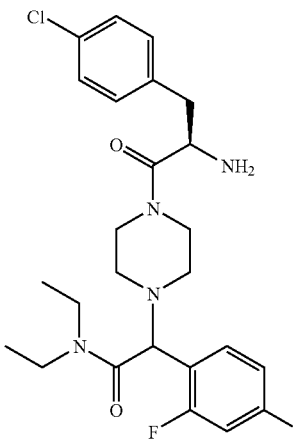

To compound of preparation G7 (0.698 g, 1.77 mmol), in DCM (5 mL), was added TFA (5 mL) and the mixture stirred at room temperature for 45 minutes. After concentrating to dryness, the resulting residue was taken up with 1N NaOH and the desired "free" amine extracted into EtOAc (50 mL). The organic extracts were concentrated to dryness. Yield: 508 mg, 98%. EIS-MS 294.2 [M+1].

EXAMPLE G7

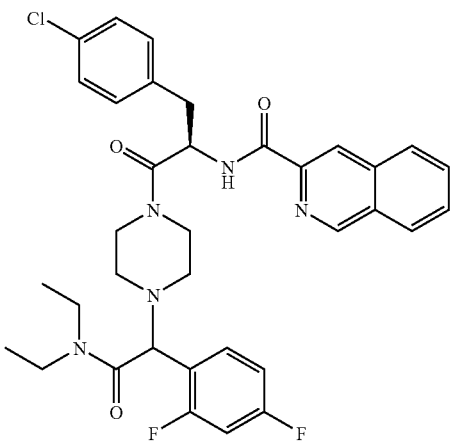

To compound of Preparation G8 (0.196 g, 0.398 mmol) was added isoquinoline 3-carboxylic acid (0.076 g, 0.398 mmol), EDC (0.077 g, 0.398 mmol), HOBT (0.062 g, 0.398 mmol), and DCM (10 mL). The mixture was stirred at room temperature for 1 h and then diluted with EtOAc (50 mL). The organics were washed with saturated NaHCO$_3$, H$_2$O, brine, and concentrated to dryness. The resulting residue was purified by flash chromatography (SiO2, eluting with 5% MeOH in EtOAc). Yield: 253 mg, 98%.

EIS-MS 648.3 [M+1].

Preparation G9

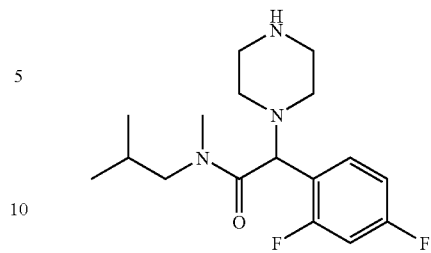

The compound of Preparation G9 was prepared from 2,4-difluorophenyl acetic ester following substantially similar procedures described in preparation G1–G5. EIS-MS 326.2 [M+1].

EXAMPLE G8

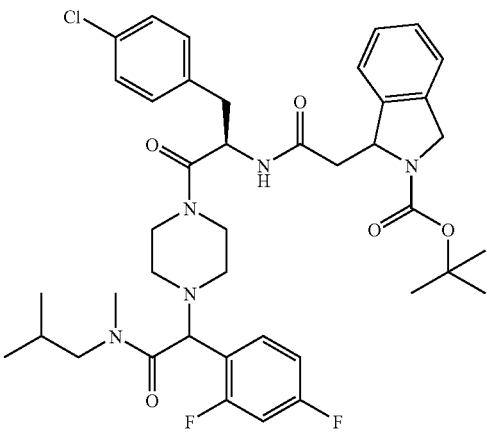

To the compound of Preparation G9 (0.252 g, 0.775 mmol), in DCM (4 mL)/DMF (1 mL), was added was added compound of Preparation BC2 (isomer 2, 0.355 g, 0.775 mmol), DIPEA (1.35 mL, 7.75 mmol), and HATU (0.295 g, 0.775 mmol). The mixture was stirred at room temperature overnight and then concentrated to dryness. The resulting residue was taken up in EtOAc (50 mL), the organics washed with saturated NaHCO$_3$, H$_2$O, brine, and concentrated to dryness. The desired product was purified by flash chromatography (SiO$_2$, eluting with 100% EtOAc to 90:5:5, EtOAc-Et$_3$-N-MeOH).

Yield: 0.438 g, 74%. EIS-MS 766.3 [M+1].

EXAMPLE G9

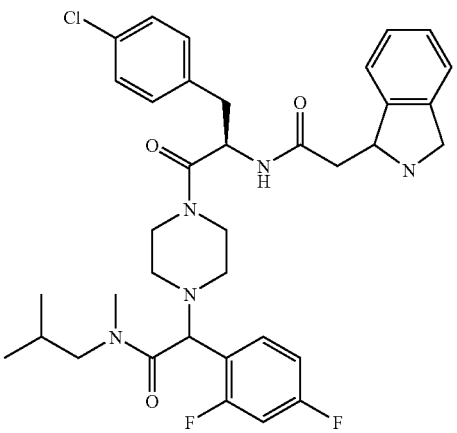

To the compound of Example G8 (0.438 g, 0.572 mmol), in DCM (10 mL), was added TFA (5 mL) and the mixture stirred at room temperature for 45 minutes. After concentrating to dryness, the resulting residue was triturated with Et₂O, the resulting solid collected by filtration and dried. Yield: 388 mg, 96%. EIS-MS 666.3 [M+1].

Preparation G10

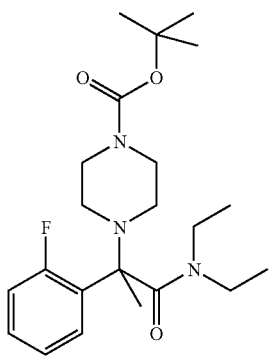

To the compound of Preparation G4 (0.407 g, 1.03 mmol), in THF (15 mL) at −78° C. was added lithium diisopropylamide (2 M, 1.3 mL, 2.58 mmol) such that the temperature was <−70° C. Upon completion of addition, the mixture was stirred for 1 h at −78° C. and then iodomethane (0.13 mL, 2.06 mmol, which was passed through a short column of basic alumina) was added. The mixture was allowed to warm to room temperature over a period of 30 minutes, and then diluted with EtOAc (100 mL). The organics were washed with saturated NaHCO₃, H₂O, brine, and concentrated to dryness. The resulting residue was purified by flash chromatography (SiO₂, eluting with 30% EtOAc in Hexanes).

Yield: 220 mg, 52%. EIS-MS 408.3 [M+1].

Preparation G11

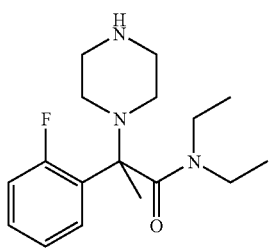

To the compound of Preparation G10 (0.220 g, 0.539 mmol), in DCM (10 mL), was added TFA (5 mL) and the mixture stirred at room temperature for 45 minutes. After concentrating to dryness, the resulting residue was taken up with 1N NaOH and the desired "free" amine extracted into EtOAc (50 mL). The organic extracts were concentrated to dryness. Yield: 137 mg, 83%. EIS-MS 308.2 [M+1].

EXAMPLE G10

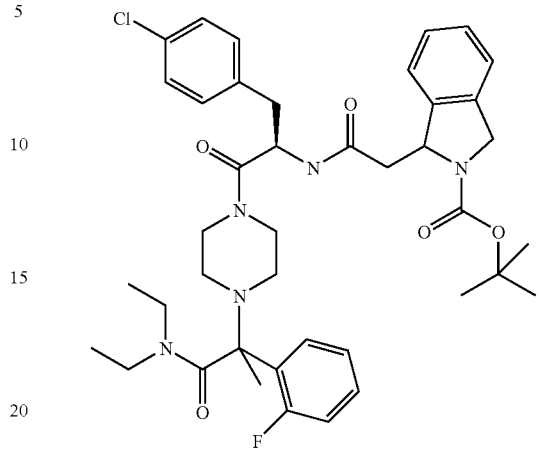

To the compound of Preparation G11 (0.136 g, 0.442 mmol), in DCM (10 mL), was added preparation BC2 (isomer 2, 0.203 g, 0.442 mmol), DIPEA (0.38 mL, 2.21 mmol), and HATU (0.168 g, 0.442 mmol). The mixture was stirred at room temperature overnight and then concentrated to dryness. The resulting residue was taken up in EtOAc (50 mL), the organics washed with saturated NaHCO₃, H₂O, brine, and concentrated to dryness. The desired product was purified by flash chromatography (SiO₂, eluting with 100% EtOAc). Yield: 0.310 g, 94%. EIS-MS 748.3 [M+1].

EXAMPLE G11

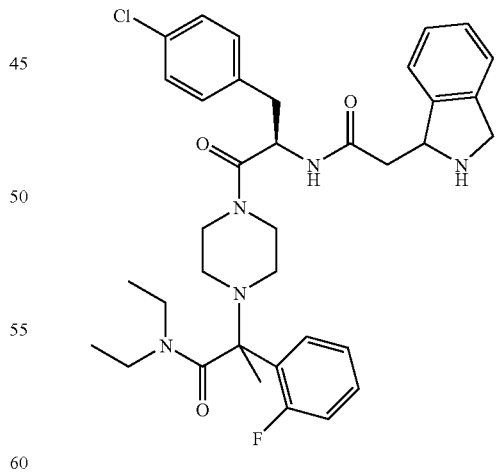

To the compound of Example G10 (0.308 g, 0.411 mmol), in DCM (10 mL), was added TFA (5 mL) and the mixture stirred at room temperature for 45 minutes. After concentrating to dryness, the resulting residue was triturated with Et₂O, the resulting solid collected by filtration and dried. Yield: 324 mg, 90%. EIS-MS 648.3 [M+1].

Preparation G12

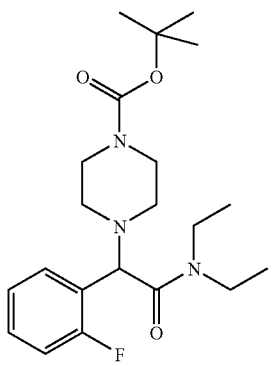

The enantiomers of Preparation G4 (5.25 g) were separated by chiral chromatography, using a Chiralpak AD(4.6× 250 mm) column, eluting with 7% IPA, 93% heptane containing 0.2% DMEA at 1 mL/min. The first eluting isomer was labeled isomer #1 (2.49 g) and the second eluting isomer #2 (2.34 g).

Preparation G13

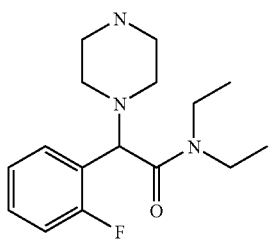

To isomer 1 of the compound of preparation G12 (2.49 g, 6.33 mmol), in DCM (20 mL), was added TFA (10 mL) and the mixture stirred at room temperature for 45 minutes. After concentrating to dryness, the resulting residue was taken up with 1N NaOH and the desired "free" amine extracted into EtOAc (50 mL). The organic extracts were concentrated to dryness. Yield: 1.55 g, 83%. EIS-MS 294.2 [M+1].

Preparation G14

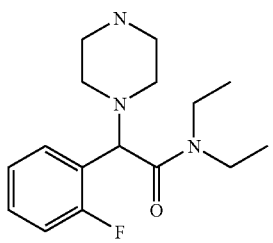

To isomer 2 of the compound of preparation G12 (2.34 g, 5.95 mmol), in DCM (20 mL), was added TFA (10 mL) and the mixture stirred at room temperature for 45 minutes. After concentrating to dryness, the resulting residue was taken up with 1N NaOH and the desired "free" amine extracted into EtOAc (50 mL). The organic extracts were concentrated to dryness. Yield: 1.66 g, 95%. EIS-MS 294.2 [M+1].

EXAMPLES G12–G13

The compounds of examples G12–G13 were prepared from the appropriate A domain and the compound of Preparation BC2 (isomer 2) by following procedures substantially similar to those described in Examples G10–G11.

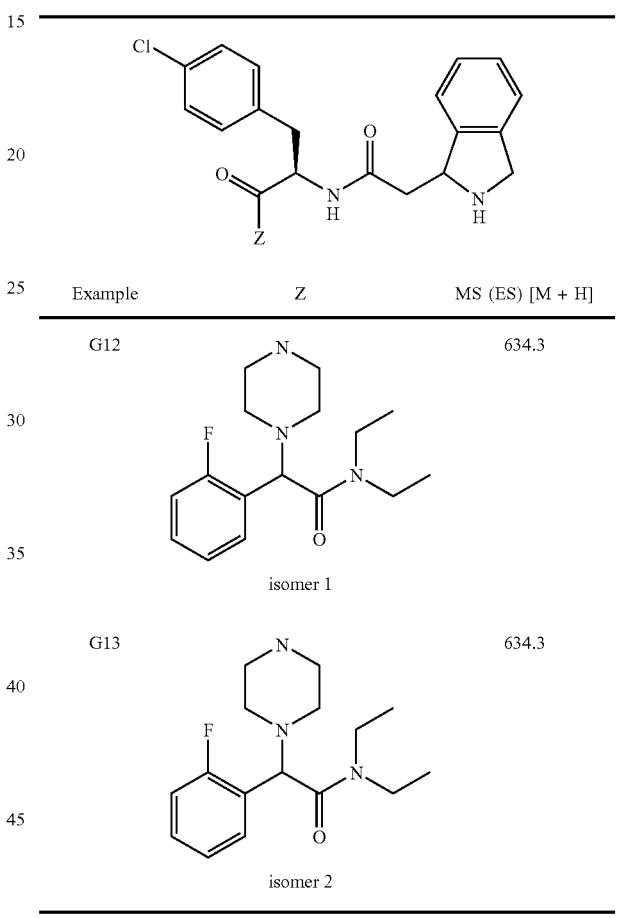

| Example | Z | MS (ES) [M + H] |
|---------|---|-----------------|
| G12 | isomer 1 | 634.3 |
| G13 | isomer 2 | 634.3 |

Preparation G15

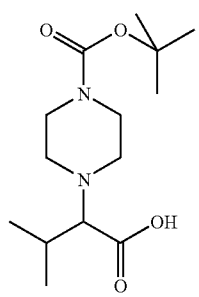

To the ester, whose preparation is described in Preparation G2, (4.68 g, 14.88 mmol), was added EtOH (25 mL), H₂O (5 mL), and NaOH (2.97 g, 74.4 mmol). The mixture was stirred at room temperature overnight and then an additional 20 equivalents of NaOH was added. The mixture was allowed to stir for 24 h more then concentrated to dryness. The resulting residue was taken up in H₂O, washed with EtOAc, and the aqueous layer made slightly acidic with 5N HCl (pH 5–6). The desired acid was extracted into EtOAc. The organics were washed with brine and concentrated to dryness. Yield: 1.6 g, 38%.

EIS-MS 287.2 [M+1].

Preparation G16

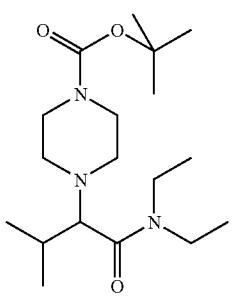

To the compound of Preparation G15 (1.59 g, 5.55 mmol), in DMF (10 mL), was added diethylcyanophosphonate (0.84 mL, 5.55 mmol), diethylamine (0.69 mL, 6.66 mmol), and TEA (0.93 mL, 6.66 mmol) and the mixture stirred at room temperature for 12 h. After diluting with EtOAc (10 fold), the organics were washed with 1N NaOH, H₂O, brine, and concentrated to dryness. The desired product was purified by flash chromatography (SiO₂, eluting with 30% EtOAc in Hexanes). Yield: 1.51 g, 80%. EIS-MS 342.3 [M+1].

Preparation G17

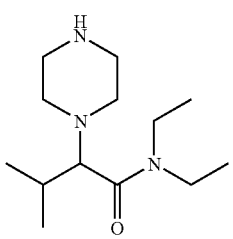

To the compound of Preparation G16 (0.55 g, 1.61 mmol), in DCM (10 mL), was added TFA (5 mL) and the mixture stirred at room temperature for 45 minutes. After concentrating to dryness, the resulting residue was taken up in 1N NaOH, the desired amine extracted into EtOAc, the organics washed with H₂O, brine, and concentrated to dryness. Yield: quantitative. EIS-MS 242.2 [M+1].

EXAMPLE G14

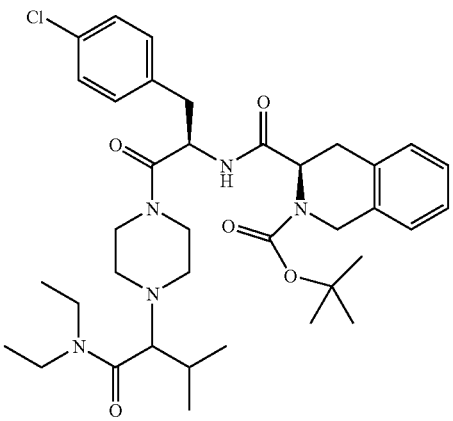

The above titled compound was prepared from the compound of Preparation G17 (0.281 g, 1.16 mmol) and the compound of Preparation BC1 by following a procedure substantially similar to that described in Example G5. Yield: 670 mg, 85%. EIS-MS 683.4 [M+1].

EXAMPLE G15

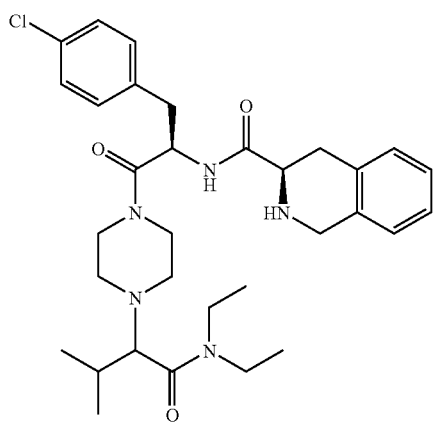

To the compound of Example G14 (0.665 g, 0.97 mmol), in DCM (10 mL), was added TFA (5 mL) and the mixture stirred at room temperature for 45 minutes. After concentrating to dryness, the resulting residue was purified by reverse phase HPLC (Waters Symmetry C18 column, eluting with 0.05% HCL in H₂O/CH₃CN, 90:10 to 60:40, following a straight line gradient). Yield: 540 mg, 85%. EIS-MS 582.3 [M+1].

Preparation G18

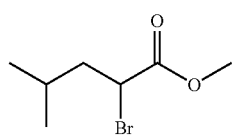

To a solution of LiHMDS (1.0M in THF, 24 mL, 24 mmol), in THF (30mL) at −78° C. was added methyl-4-methylvalerate (2.5 g, 19.2 mmol), in THF (10 mL). The mixture was stirred for 30 minutes at −78° C. and then transferred, via a cannula needle, to a solution of bromine (1.18 mL, 23.04 mmol), in THF (20mL) at −78° C., and the resulting mixture allowed to warm to room temperature (30 minutes). After quenching with pH 7 buffer (20 mL), the organics were washed with saturated sodium metabisulfite solution and concentrated to dryness. The crude material was taken on without any additional purification.

Preparation G19

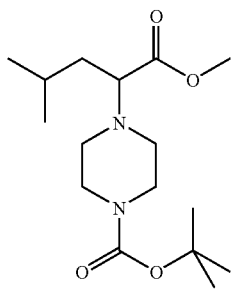

To the compound of Preparation G18 (19.2 mmol) was added N-Boc-piperazine (3.57 g, 19.2 mmol), $K_2CO_3$ (5.3 g, 38.4 mmol), and $CH_3CN$ (20 mL) and the mixture heated at reflux for 4 h. After cooling to room temperature, the mixture was diluted 10 fold with EtOAc, the organics washed with $H_2O$ and concentrated to dryness. The resulting residue was purified by flash chromatography ($SiO_2$, eluting with 15% EtOAc in Hexanes). Yield: 1.41 g, 23%. EIS-MS 315.2 [M+1].

Preparation G20

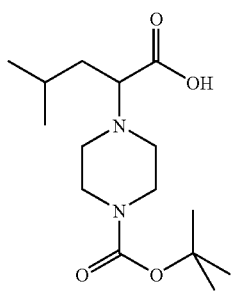

To the compound of Preparation G19 (1.41 g, 4.49 mmol), in $EtOH/H_2O$ (10:1, 11 mL), was added NaOH (1.79 g, 44.9 mmol) and the mixture stirred at room temperature for 2 h. After concentrating to dryness, the resulting residue taken up in $H_2O$, washed with $Et_2O$, and then the aqueous layer made slightly acidic (pH 4–6) with 5N HCl. The desired acid was extracted into EtOAc and the organics concentrated to dryness. Yield: 1.05 g, 78%. EIS-MS 301.2 [M+1].

Preparation G21

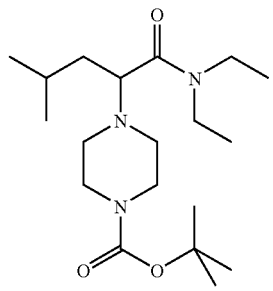

To the compound of Preparation G20 (1.03 g, 3.42 mmol), in DMF (10 mL), was added diethylcyanophosphonate (0.57 mL, 3.77 mmol), diethylamine (0.42 mL, 4.11 mmol), and TEA (0.57 mL, 4.11 mmol) and the mixture stirred at room temperature for 24 h. After diluting with EtOAc (10 fold), the organics were washed with 1N NaOH, $H_2O$, brine, and concentrated to dryness. The desired product was purified by flash chromatography ($SiO_2$, eluting with 1:1 EtOAc/Hexanes). Yield: 0.9 g, 74%. EIS-MS 356.3 [M+1].

Preparation G22

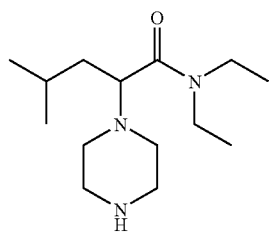

To the compound of Preparation G21 (0.9 g, 2.53 mmol), in DCM (10 mL), was added TFA (5 mL) and the mixture stirred at room temperature for 45 minutes. After concentrating to dryness, the resulting residue was taken up in 1N NaOH, the desired amine extracted into EtOAc, the organics washed with $H_2O$, brine, and concentrated to dryness. Yield: 485 mg, 75%. ESI-MS 256.2 [M+1].

EXAMPLE G16

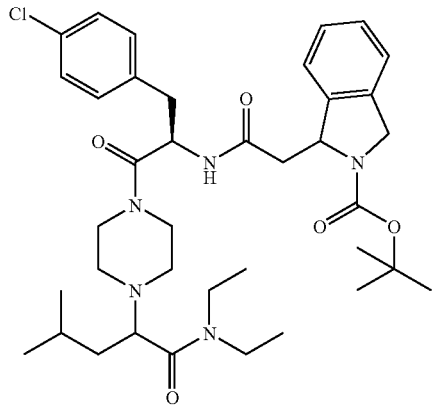

The compound of Example G16 was prepared from the compound of Preparation G22 (0.193 g, 0.755 mmol) and preparation BC2 (isomer 2, 0.346 g, 0.755 mmol), by following a procedure substantially similar to that described in Preparation G14. Yield: 420 mg, 80%. EIS-MS 696.3 [M+1].

EXAMPLE G17

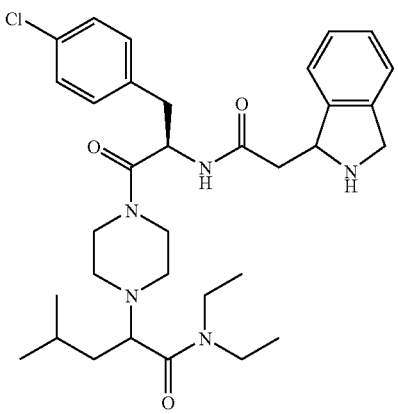

To the compound of Example G16 (0.420 g, 0.603 mmol), in DCM (10 mL), was added TFA (5 mL) and the mixture stirred at room temperature for 45 minutes. After concentrating to dryness the resulting residue was purified by reverse phase HPLC (Waters Symmetry C18 column, eluting with 0.05% HCL in $H_2O$/$CH_3CN$, 90:10 to 60:40 following a straight-line gradient). Yield: 362 mg, 90%. EIS-MS 596.3 [M+1].

Preparation G23

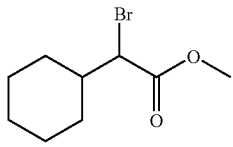

A mixture of cyclohexylacetic acid (25.0 g, 175.8 mmol) and $SOCl_2$ (51.3 mL, 703.2 mmol), in $CCl_4$ (25 mL), was heated at 65° C. for 30 minutes. Then, a suspension of NBS (37.5 g, 211.0 mmol) in $CCl_4$ (100 mL) was added, followed by addition of HBr (48%) (15 drops). The reaction was heated at 85° C. for 2 h and then cooled down to room temperature. The mixture was poured carefully onto cold MeOH (400 mL) and stirred for 15 minutes. Volatiles were evaporated under reduced pressure and the residue was taken into EtOAc. The resulting solution was washed with $H_2O$ and brine, dried ($Na_2SO_4$) and concentrated to dryness. The resulting residue was purified by flash chromatography ($SiO_2$, eluting with hexane-EtOAc, 30:1) to give the α-bromoester (95%) as a pale yellow oil. EIS-MS 235.1 [M$^+$+1].

Preparation G24

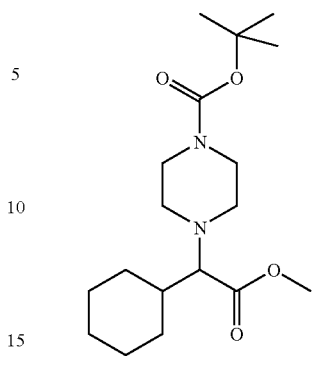

To the compound of Preparation G23 (25.0 g, 106.3 mmol), in anhydrous $CH_3CN$ (500 mL), was added $K_2CO_3$ (29.3 g, 212.0 mmol), N-Boc-piperazine (20.8 g, 111.6 mmol), and a catalytic amount of $nBu_4NI$ (7.85 g, 21.3 mmol). The mixture was heated under reflux for 48 h and then cooled to room temperature. The reaction was diluted with EtOAc, washed with $H_2O$, brine, dried ($Na_2SO_4$), and concentrated to dryness. The resulting residue was purified by flash chromatography ($SiO_2$, eluting with hexane-EtOAc, 9:1) to afford the title compound (34%) as a white solid. EIS-MS 341.2 [M$^+$+1].

Preparation G25

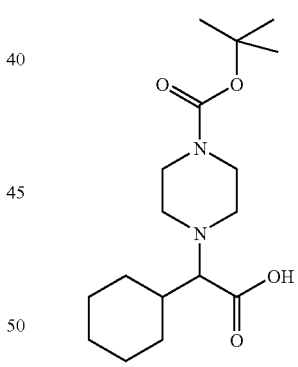

To the compound of Preparation G24 (1.0 g, 3.21 mmol), in acetone (22 mL) at 0° C., Jones reagent (5.6 mL) was added. The reaction mixture was allowed to react at 0° C. for 1 h and then 2.5 h at room temperature. Then, $H_2O$ (20 mL) and isopropanol (20 mL) were added, and the pH adjusted to 6–7 with the addition of 1N KOH. The aqueous solution was extracted with EtOAc (4×) and the combined organic layers dried ($MgSO_4$) and concentrated to dryness; affording the title compound (70%) as a solid. EIS-MS 326.7 [M++1].

Preparation G26

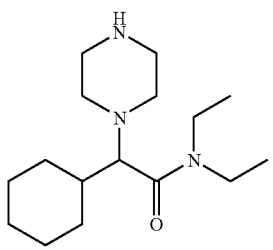

To the compound of Preparation G25 (300 mg, 0.92 mmol), in DCM (4.8 mL) and DMF (1 mL) at roomtemperature, diisopropylethyl amine (0.8 mL, 4.6 mmol), diethylamine (0.114 mL, 1.10 mmol) and HOBT (155 mg, 1.15 mmol) were added and the mixture stirred for 5 minutes. Then, EDC (220 mg, 1.15 mmol) was added and the reaction stirred overnight at room temperature. Then, $H_2O$ (10 mL) was added and mixture diluted with DCM (10 mL). The layers were separated and the aqueous phase was extracted with DCM. The combined organic layers were dried ($MgSO_4$) and concentrated to dryness. The resulting residue was purified by flash chromatography ($SiO_2$, eluting with hexane/EtOAc, 7:3) to afford the N-Boc protected amide as an oil. A solution of the N-Boc derivative (203 mg, 0.53 mmol) in 1N HCl/EtOAc (20 mL) was stirred at room temperature overnight. After concentrating to dryness, the resulting solid was washed twice with $Et_2O$ to afford the title compound (58%) as a white solid. EIS-MS 281.9 [$M^+$+1].

Preparation G27

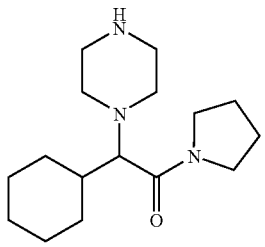

Following the general procedure described in Preparation G26, and using pyrrolidine and the compound of Preparation G25 as starting materials, the title compound was prepared (40%). EIS-MS 279.8 [M++1].

EXAMPLES G18–G19

The compounds of Examples G18–G19 were prepared from the appropriate A domain and the compound of Preparation BC2 by following substantially similar procedures described in Examples G3–G4.

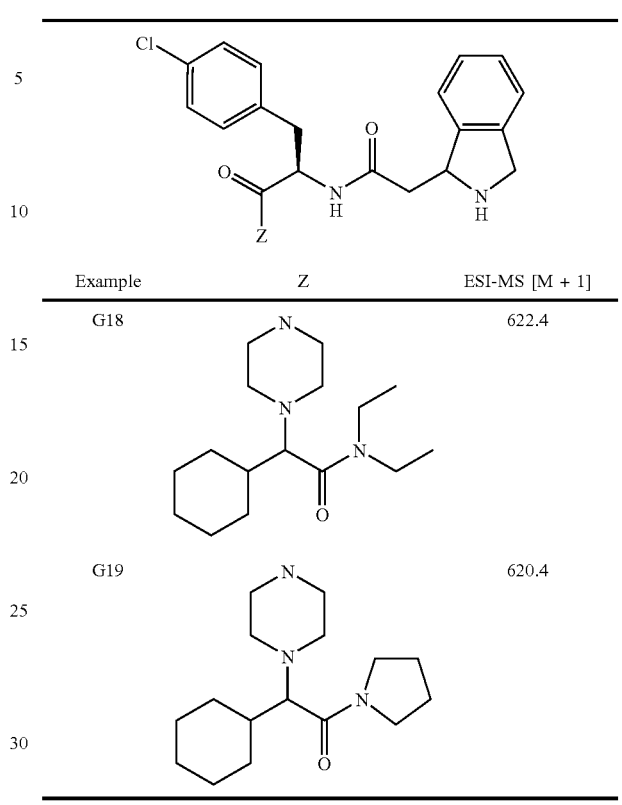

Preparation G27.5

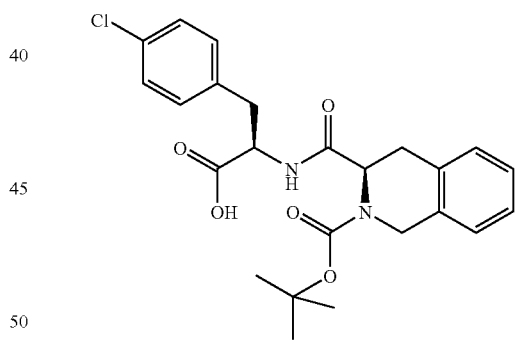

3-[2-(4-Chloro-phenyl)-1-methoxycarbonyl-ethyl-carbamoyl]-3,4-dihydro-1H-isoquinoline-2-carboxylic acid tert-butyl ester A. To a 0° C. solution of 4-Cl-D-Phe methyl ester (23.8 g, 111.0 mmol), Boc-D-Tic (30.8 g, 111.0 mmol) and 4-DMAP (75 mg, 0.61 mmol) in 200 mL of DCM was added EDC (30.8 g, 111.0 mmol) and the mixture stirred for 20 minutes. The ice bath was removed and the mixture stirred at room temperature for 4 h. After washing with water (4×200 mL), the combined aqueous portions were back extracted with DCM (2×200 mL). The combined organic portions were washed with brine, dried ($MgSO_4$), and concentrated to dryness. The desired product was purified by flash chromatography (SiO$_2$, eluting with 35% EtOAc in Hexanes) affording 43.0 g (83%) of the ester. EIS MS 473 [M+1].

B. To the above formed ester (43.0 g, 91.0 mmol), in MeOH (170 mL) at 0° C., was added 1N NaOH (227.0 mL, 227.0 mmol), dropwise. After 20 minutes the ice bath was removed and the mixture stirred at room temperature for 3 h. The mixture was concentrated to dryness, and the resulting residue suspended in 200 mL of water. The aqueous layer was made acidic (pH 1) with 5 N hydrochloric acid and extracted with EtOAc (4×200 mL). The combined organics were dried (MgSO$_4$), filtered, and concentrated to dryness; affording 39.0 g (93%) of the title compound. EIS-MS 459 [M+1].

Preparation G28

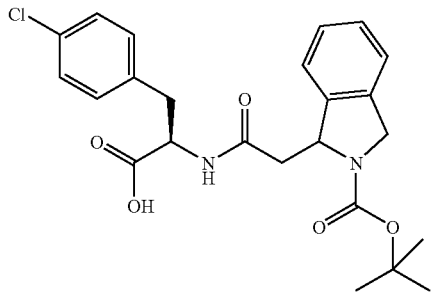

1-{[1-Carboxy-2-(4-chloro-phenyl)-ethylcarbamoyl]-methyl}-1,3-dihydro-isoindole-2-carboxylic acid tert-butyl ester A. To a suspension of 4-Cl-D-Phe methyl ester hydrochloride (40.4 g, 161.5 mmol), in DCM (250 mL), was added saturated aqueous sodium bicarbonate (250 mL) and the mixture stirred at room temperature for 1 h. The organic portion was separated and the aqueous portion was extracted with DCM (2×). The combined organic portions were dried (Na$_2$SO$_4$) and concentrated to dryness. To the free amine, in DCM (400 mL) at 0° C., was added example 82 (isomer 2, 44.8 g, 161.5 mmol), EDC (31.0 g, 161.5 mmol) and 4-DMAP (2.0 g, 16.1 mmol). The reaction mixture was stirred at 0° C. for 30 minutes whereupon the cooling bath was removed and the reaction mixture was stirred for another 5 h at room temperature. The mixture was then washed with saturated aqueous sodium bicarbonate (200 mL), 10% aqueous sodium bisulfate (200 mL), dried (Na$_2$SO$_4$), and concentrated to dryness to afford 76.4 g (100%) of the ester. EIS-MS 471 [M−1].

B. To the ester from Part A (76.4 g, 161.5 mmol), in MeOH (760 mL), was added 1 N NaOH (242.0 mL, 242.0 mmol) and the mixture heated at 50° C. for 4 h. then stirred for another 16 h at room temperature. After concentrating to dryness, the resulting residue was taken up in 500 mL of water and washed with diethyl ether (2×). The aqueous portion was acidified to pH 2 with 10% aqueous sodium bisulfate and extracted with EtOAc (4×200 mL). The combined organic extracts were dried (MgSO$_4$) and concentrated to dryness. The resulting solid was suspended in hexanes, filtered, and dried to afford 67.7 g (91%) of the title compound.

EIS-MS 457 [M−1].

Preparation of Sulfonated Derivatives and More

Preparation SM 1

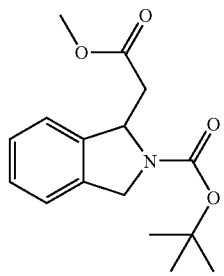

1-Methoxycarbonylmethyl-1,3-dihydro-isoindole-2-carboxylic acid tert-butyl ester A. (2-Bromo-benzyl)-carbamic acid tert-butyl ester: To a mixture of 125.0 g (561.8 mmol) of 2-bromobenzylamine hydrochloride and 170.7 g (1236.0 mmol) of potassium carbonate in 300 mL of 50% tetrahydrofuran/water was added 134.9 g (618.0 mmol) of di-tert-butyl dicarbonate in four portions over 20 min. The mixture was stirred at room temperature for 16 hr. and diluted with 300 mL of ethyl acetate and 300 mL of water. The organic portion was separated and the aqueous portion was extracted three times with 200 mL each of ethyl acetate. The combined ethyl acetate portions were washed once with 250 mL of 10% aqueous sodium bisulfate. The organic portion was dried (MgSO4), filtered and concentrated in vacuo to afford 161.0 g of the title compound.

B. 3-[2-(tert-Butoxycarbonylamino-methyl)-phenyl]-acrylic acid methyl ester: To a solution of 161.0 g (561.8 mmol) of material from Part A, 58.0 g (674.2 mmol) of methyl acrylate and 170.5 g (1685.4 mmol) of triethylamine in 800 mL of N,N-dimethylformamide was added 7.9 g (11.2 mmol) of dichlorobis(triphenylphosphine)palladium(II) and the mixture was heated at 80° C. for 32 hr. The mixture was cooled, diluted with 1000 mL of ethyl acetate and washed with 10% aqueous sodium bisulfate. The aqueous portion was extracted three times with ethyl acetate and the combined organics were dried (Na$_2$SO$_4$), filtered and concentrated in vacuo. The residue was dissolved in a small amount of dichloromethane and filtered through 7 in. of silica gel in a 2 L sintered glass funnel eluting with 25% ethyl acetate/hexanes. The eluant was concentrated in vacuo and recrystallized from ethyl acetate/hexanes to afford 116.9 g (71%) of the title compound.

C. To a 0° C. solution of 116.9 g (401.2 mmol) of material from Part B in 800 mL of dichloromethane was added 200 mL of trifluoroacetic acid dropwise over 15 min. After removing the cooling bath, the mixture was stirred for 2.5 hr. and concentrated in vacuo. The residue was dissolved in 500 mL of dichlorormethane and saturated aqueous sodium bicarbonate was slowly added until the mixture was slightly basic. The organic portion was separated and the aqueous portion was extracted two times with dichloromethane. The combined organic portions were dried (Na$_2$SO$_4$), filtered and concentrated in vacuo. The residue was dissolved in 800 mL of dichloromethane and 57.0 g (441.4 mmol) of N,N-diisopropylethylamine was added. To the mixture was added 96.3 g (441.4 mmol) of di-tert-butyl dicarbonate in five portions over 45 min. and the mixture was stirred at room temperature for 16 hr. The mixture was washed with 10% aqueous sodium bisulfate. The organic portion was separated and the aqueous portion was extracted two times with dichloromethane. The combined organics were dried (Na₂SO₄), filtered and concentrated in vacuo. The residue was dissolved in a small amount of dichloromethane and filtered through 7 in. of silica gel in a 2 L sintered glass funnel eluting with 25% ethyl acetate/hexanes. The eluant was concentrated in vacuo and chiral chromatography of the residue (Chiralcel OD) afforded 52.6 g (45%) of the title compound.

Mass Spectrum: M+1=292.

Preparation SM2

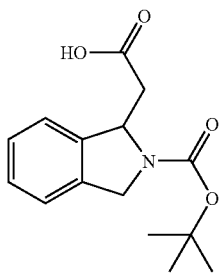

1-Carboxymethyl-1,3-dihydro
isoindole-2-carboxylic acid tert-butyl ester

To a solution of 52.6 g (180.5 mmol) of material from Prepration SM1 in 500 mL of methyl alcohol was added 199.0 mL (199.0 mmol) of 1 N sodium hydroxide. The mixture was stirred at room temperature for 48 hr. and concentrated in vacuo. The residue was dissolved in 300 mL of water and extracted two times with diethyl ether. The aqueous portion was acidified to pH 2 with 10% aqueous sodium bisulfate and extracted four times with ethyl acetate. The combined ethyl acetate portions were dried (MgSO₄), filtered and concentrated in vacuo. The residue was suspended in diethyl ether and concentrated in vacuo two times to afford 49.8 g (99%) of the title compound.

Mass Spectrum: M−1=276.

Preparation SM3

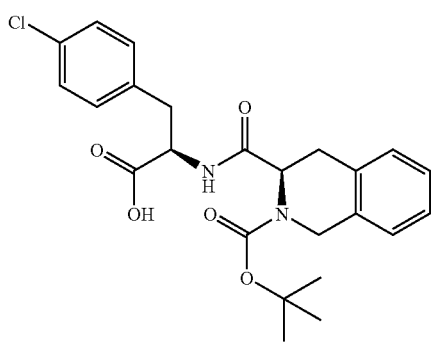

3-[1-Carboxy-2-(4-chloro-phenyl)-ethylcarbamoyl]-
3,4-dihydro-1H-isoquinoline-2-carboxylic acid tert-
butyl ester A. 3-[2-(4-Chloro-phenyl)-1-methoxycarbonyl-ethylcarbamoyl]-3,4-dihydro-1H-isoquinoline-2-carboxylic acid tert-butyl ester: To a 0° C. solution of D-4-chlorophenylalanine methyl ester (23.8 g, 111.0 mmol), Boc-D-1,2,3,4-tetrahydroisoquinoline carboxylic acid (30.8 g,111.0) and 4-dimethylaminopyridine (75 mg, 0.61 mmol) in 200 mL of dichloromethane is added 1-(3-dimethylaminopropyl)-3-ethylcarbodiimide hydrochloride 30.8 g, 111.0 mmol) and the mixture stirred for 20 min. Remove ice bath and stir at room temperature for 4 hr. Wash 4 times with 200 mL each of water. The combined aqueous portions are extracted two times with 200 mL of dichloromethane. The combined organic portions are washed once with brine, dried (MgSO₄), filtered and concentrated in vacuo. Chromatography (silica gel, 35% ethyl acetate/hexanes) of the residue affords 43.0 g (83%) of the title compound.

Elecrospray Mass Spectrum: M+1=473.

B. To a 0° C. solution of material from part A (43.0 g, 91.0 mmol) in 170 mL of methanol was added dropwise 1N sodium hydroxide (227.0 mL, 227.0 mmol). After 20 min the ice bath is removed and the mixture is stirred at room temperature for 3 hr. The mixture is concentrated in vacuo, and the residue is suspended in 200 mL of water. Adjust to pH 1 with 5 N hydrochloric acid and extract aqueous four times with 200 mL each of ethyl acetate. The combined organics are dried (MgSO₄), filtered and concentrated in vacuo to afford 39.0 g (93%) of the title compound.

Elecrospray Mass Spectrum: M+1=459.

EXAMPLE S1

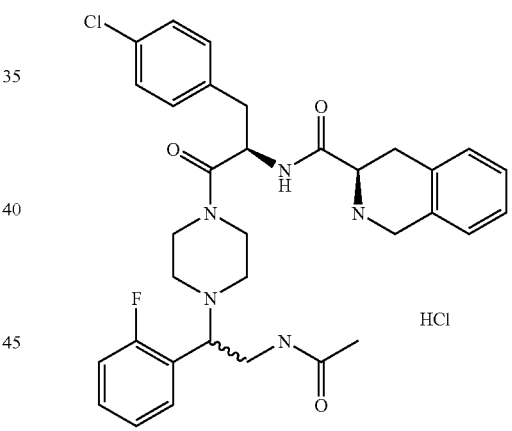

1,2,3,4-Tetrahydro-isoquinoline-3-carboxylic acid
[2-{4-[2-acetylamino-1-(2-fluoro-phenyl)-ethyl]-
piperazine-1-yl}-1-(4-chloro-benzyl)-2-oxo-ethyl]-
amide hydrochloride A. 4-[2-Acetylamino-1-(2-fluoro-phenyl)-ethyl]-piperazine-1-carboxylic acid tert-butyl ester: To a solution of 0.25 g (0.77 mmol) of 4-[2-Amino-1-(2-fluoro-phenyl)-ethyl]-piperazine-1-carboxylic acid tert-butyl ester and 0.12 mL (0.85 mmol) of triethylamine in 3 mL of dichloromethane is slowly added 0.06 mL (0.85 mmol) of acetyl chloride. After one hr, saturated sodium bicarbonate is added and the organic portion is separated. The aqueous portion is diluted with 3 mL of 1N sodium hydroxide and extracted four times with dichloromethane. The combined organics are dried (Na₂SO₄), filtered and concentrated in vacuo to afford 0.28 g (100%) of the title compound.

481

B. N-[2-(2-Fluoro-phenyl)-2-piperazin-1-yl-ethyl]-acetamide: To a solution of 0.28 g (0.77 mmol) of material from part A in 1 mL of dichloromethane is added 1 mL of trifluoroacetic acid. After stirring for one hr, the mixture is concentrated in vacuo. The residue is partitioned between 1N sodium hydroxide and dichloromethane. The organic portion is separated and the aqueous portion is extracted three times with dichloromethane. The combined organics are dried ($Na_2SO_4$), filtered and concentrated in vacuo to afford 0.15 g (73%) of the title compound.

C. 3-[2-{4-[2-Acetylamino-1-(2-fluoro-phenyl)-ethyl]-piperazin-1-yl}-1-(4-chloro-benzyl)-2-oxo-ethylcarbamoyl]-3,4-dihydro-1H-isoquinoline-2-carboxylic acid tert-butyl ester: To a mixture of 0.28 g (0.62 mmol) of product from Preparation SM3, 0.15 g (0.57 mmol) of material from part B and 0.24 g (0.62 mmol) of O-(7-azabenzotriazole-1-yl)-N,N,N',N'-tetramethyluronium hexafluorophosphate in 2 ml of dichlorormethane is added 0.11 mL (0.62 mmol) of N,N-diisopropylethylamine. The mixture is stirred for three hr and washed with 10% aqueous sodium bisulfate. After the organic portion is separated, the aqueous portion is saturated with sodium chloride and extracted three times with dichloromethane. The combined organics are dried ($Na_2SO_4$), filtered and concentrated in vacuo. Chromatography (Biotage, 5% ethanol, ethyl acetate) afforded 0.23 g (52%) of the title compound.

D. To a solution of 0.22 g (0.31 mmol) of material from part C in 1 mL of dichloromethane is added 0.5 mL of trifluoroacetic acid. After stirring for 1 hr, the mixture is concentrated in vacuo. The residue is dissolved in 5 mL of 1N hydrochloric acid and lyophilized. The resulting solid is subjected to reverse phase preparative HPLC and concentrated in vacuo. The residue is dissolved in 2 mL of 1 N hydrochloric acid and lyophilized to afford 89 mg (45%) of the title compound. Electrospray Mass Spectrum: M+1=606.

EXAMPLE S2

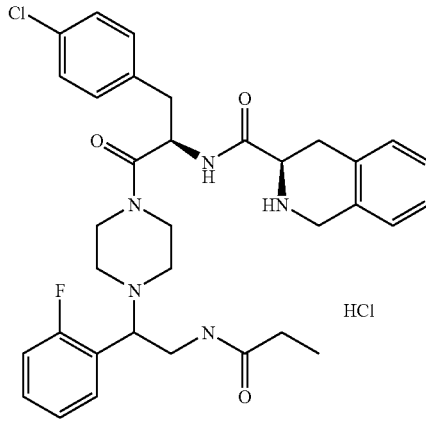

1,2,3,4-Tetrahydro-isoquinoline-3-carboxylic acid (1-(4-chloro-benzyl)-2-{4-[1-(2-fluoro-phenyl)-2-propionylamino-ethyl]-piperazin-1-yl}-2-oxo-ethyl)-amide hydrochloride A. 4-[1-(2-Fluoro-phenyl)-2-propionylamino-ethyl]-piperazine-1-carboxylic acid tert-butyl ester: To a solution of 0.25 g (0.77 mmol) of 4-[2-Amino-1-(2-fluoro-phenyl)-ethyl]-piperazine-1-carboxylic acid tert-butyl ester and 0.12 mL (0.85 mmol) of triethylamine in 3 mL of dichlorormethane is slowly added 0.07 mL (0.85 mmol) of acetyl chloride. After one hr, the mixture is diluted with 3 mL of 1N sodium hydroxide and extracted four times with dichloromethane. The combined organics are dried ($Na_2SO_4$), filtered and concentrated in vacuo to afford 0.29 g (99%) of the title compound.

B. N-[2-(2-Fluoro-phenyl)-2-piperazin-1-yl-ethyl]-propionamide: To a solution of 0.29 g (0.77 mmol) of material from part A in 1 mL of dichloromethane is added 1 mL of trifluoroacetic acid. After stirring for 30 min, the mixture is concentrated in vacuo. The residue is partitioned between 1N sodium hydroxide and dichloromethane. The organic portion is separated and the aqueous portion is extracted three times with dichloromethane. The combined organics are dried ($Na_2SO_4$), filtered and concentrated in vacuo to afford 0.17 g (77%) of the title compound.

C. 3-(1-(4-Chloro-benzyl)-2-{4-[1-(2-fluoro-phenyl)-2-propionylamino-ethyl]-piperazin-1-yl}-2-oxo-ethylcarbamoyl)-3,4-dihydro-1H-isoquinoline-2-carboxylic acid tert-butyl ester: To a mixture of 0.30 g (0.65 mmol) of the product from Preparation SM3, 0.17 g (0.59 mmol) of material from part B and 0.25 g (0.65 mmol) of 0-(7-azabenzotriazole-1-yl)-N,N,N',N'-tetramethyluronium hexafluorophosphate in 2 ml of dichlorormethane is added 0.11 mL (0.62 mmol) of N,N-diisopropylethylamine. The mixture is stirred for three hr and washed with 10% aqueous sodium bisulfate. After the organic portion is separated, the aqueous portion is saturated with sodium chloride and extracted three times with dichloromethane. The combined organics are dried ($Na_2SO_4$), filtered and concentrated in vacuo. Chromatography (Biotage, 5% ethanol, ethyl acetate) of the residue affords a mixture which is chromatographed again (Biotage, 0.25% $NH_4OH$/2.25% methanol/dichloromethane) affords 0.23 g (53%) of the title compound.

D. To a solution of 0.21 g (0.29 mmol) of material from part C in 1 mL of dichlorormethane is added 0.5 mL of trifluoroacetic acid. After stirring for 30 min, the mixture is concentrated in vacuo. The residue is dissolved in 2.5 mL of 1N hydrochloric acid and lyophilized. The resulting solid is chromatographed (Biotage, 2% (9:1 methanol:$NH_4OH$)/dichloromethane to 100% methanol) and concentrated in vacuo. The residue is dissolved in dichloromethane, filtered through celite and concentrated in vacuo. The residue is dissolved in 2 mL of 1 N hydrochloric acid and lyophilized to afford 73 mg (38%) of the title compound.

Electrospray Mass Spectrum: M+1=620.

EXAMPLE S3

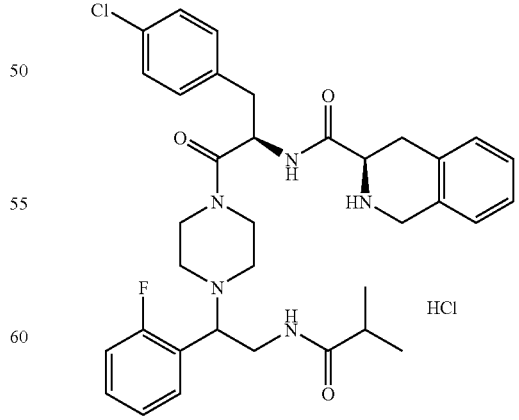

1,2,3,4-Tetrahydro-isoquinoline-3-carboxylic acid (1-(4-chloro-benzyl)-2-{4-[1-(2-fluoro-phenyl)-2-isobutyrylamino-ethyl]-piperazin-1-yl}-2-oxo-ethyl)-amide hydrochloride

483

A. 4-[1-(2-Fluoro-phenyl)-2-isobutyrylamino-ethyl]-piperazine-1-carboxylic acid tert-butyl ester: To a solution of 0.25 g (0.77 mmol) of 4-[2-Amino-1-(2-fluoro-phenyl)-ethyl]-piperazine-1-carboxylic acid tert-butyl ester and 0.12 mL (0.85 mmol) of triethylamine in 3 mL of dichlorormethane is slowly added 0.09 mL (0.85 mmol) of acetyl chloride. After one hr, the mixture is diluted with 3 mL of 1N sodium hydroxide and extracted four times with dichloromethane. The combined organics are dried ($Na_2SO_4$), filtered and concentrated in vacuo to afford 0.26 g (86%) of the title compound B. N-[2-(2-Fluoro-phenyl)-2-piperazin-1-yl-ethyl]-isobutyramide: To a solution of 0.25 g (0.64 mmol) of material from part A in 2 mL of dichloromethane is added 1 mL of trifluoroacetic acid. After stirring for 20 min, the mixture is concentrated in vacuo. The residue is partitioned between 1N sodium hydroxide and dichloromethane. The organic portion is separated and the aqueous portion is extracted three times with dichloromethane. The combined organics are dried ($Na_2SO_4$), filtered and concentrated in vacuo to afford 0.15 g (60%) of the title compound.

C. 3-(1-(4-Chloro-benzyl)-2-{4-[1-(2-fluoro-phenyl)-2-isobutyrylamino-ethyl]-piperazin-1-yl}-2-oxo-ethylcarbamoyl)-3,4-dihydro-1H-isoquinoline-2-carboxylic acid tert-butyl ester: To a mixture of 0.26 g (0.56 mmol) of product from Preparation SM3, 0.15 g (0.51 mmol) of material from part B and 0.21 g (0.56 mmol) of O-(7-azabenzotriazole-1-yl)-N,N,N',N'-tetramethyluronium hexafluorophosphate in 2 ml of dichlorormethane is added 0.10 mL (0.56 mmol) of N,N-diisopropylethylamine. The mixture is stirred for 16 hr and washed with 10% aqueous sodium bisulfate. After the organic portion is separated, the aqueous portion is saturated with sodium chloride and extracted three times with dichloromethane. The combined organics are dried ($Na_2SO_4$), filtered and concentrated in vacuo. Chromatography (Biotage, 5% ethanol, ethyl acetate) affords 0.17 g (42%) of the title compound.

D. To a solution of 0.17 g (0.23 mmol) of material from part C in 1 mL, of dichlorormethane is added 0.5 mL of trifluoroacetic acid. After stirring for one hr, the mixture is concentrated in vacuo. The residue is dissolved in 2.5 mL of 1N hydrochloric acid and lyophilized. The resulting solid is chromatographed (Reverse phase preparative HPLC) and concentrated in vacuo. The residue is dissolved in 2 mL of 1 N hydrochloric acid and lyophilized to afford 90mg (58%) of the title compound.

Electrospray Mass Spectrum: M+1=634.

EXAMPLE S4

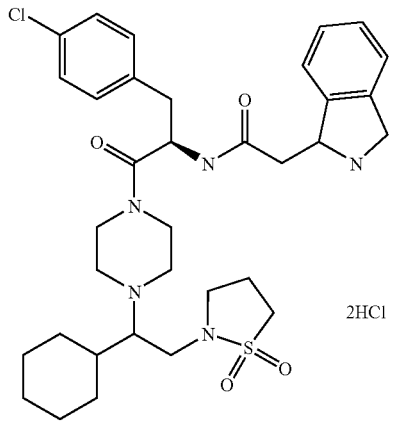

N-(1-(4-Chloro-benzyl)-2-{4-[1-cyclohexyl-2-(1,1-dioxo-1$\square^6$-isothiazolidin-2-yl)-ethyl]-piperazin-1-yl}-2-oxo-ethyl)-2-(2,3-dihydro-1H-isoindol-1-yl)-acetamide dihydrochloride

484

A. To a 0° C. solution of 4-(2-Amino-1-cyclohexyl-ethyl)-piperazine-1-carboxylic acid tert-butyl ester and 0.15 mL (1.06 mmol) of triethylamine in 3 mL of dichlorormethane is added 0.13 mL (1.06 mmol) of 3-chloropropanesulfonyl chloride. The cooling bath is removed and the mixture is stirred for 16 hr. The mixture is washed once with 10% aqueous sodium bisulfate and the organic portion is separated. The aqueous portion is extracted three times with dichloromethane. The combined organics are dried ($Na_2SO_4$), filtered and concentrated in vacuo. Chromatography (Silica gel, 25% ethyl acetate/hexanes) of the residue affords 0.25 g (57%) of the title compound.

Mass Spectrum: M-1=450.

B. 4-[1-Cyclohexyl-2-(1,1-dioxo-1$\lambda^6$-isothiazolidin-2-yl)-ethyl]-piperazine-1-carboxylic acid tert-butyl ester: To a solution of 0.24 g (0.53 mmol) of material from part A in 2 mL of tetrahydrofuran is added 0.80 mL (0.80 mmol) of 1M sodium bis(trimethylsilyl)amide in tetrahydrofuran. The mixture is srirred for 16 hr at room temperature then heated to reflux for 1 hr. The mixture is cooled, diluted with ethyl acetate and washed with water. The organic portion is separated and the aqueous portion is extracted twice with ethyl acetate. The combined organics are dried (MgSO4), filtered and concentrated in vacuo. Chromatography (Silica gel, 60% ethyl acetate/hexane) of the residue affords 0.10 g (45%) of the title compound.

Mass Spectrum: M+1=416.

C. 1-[1-Cyclohexyl-2-(1,1-dioxo-1$\lambda^6$-isothiazolidin-2-yl)-ethyl]-piperazine: To a solution of 0.10 g (0.23 mmol) of material from part B in 1 mL of dichloromethane is added 0.5 mL of trifluoroacetic acid and the mixture is stirred for 1 hr and concentrated in vacuo. The residue is partitioned between 1N sodium hydroxide and dichloromethane. The organic portion is separated and the aqueous portion is extracted twice with dichloromethane. The combined organics are dried ($Na_2SO_4$), filtered and concentrated in vacuo to afford 76 mg (100%) of the title compound.

Mass Spectrum: M+1=328.

D. 1-[(1-(4-Chloro-benzyl)-2-{4-[1-cyclohexyl-2-(1,1-dioxo-1$\lambda^6$-isothiazolidin-2-yl)-ethyl]-piperazin-1-yl}-2-oxo-ethylcarbamoyl)-methyl]-1,3-dihydro-2-isoindole-2-carboxylic acid tert-butyl ester: To a suspension of 0.074 g (0.23 mmol) of material from part C, 0.11 g (0.23 mmol) of 1-{[1-Carboxy-2-(4-chloro-phenyl)-ethylcarbamoyl]-methyl}-1,3-dihydro-isoindole-2-carboxylic acid tert-butyl ester and 0.24 g (0.62. mmol) of O-(7-azabenzotriazol-1-yl)-N,N,N',N'-tetramethyluronuim hexafluorophosphate in 2 mL of dichloromethane is added 0.11 mL (0.62 mmol) of N,N-diisopropylethylamine. After 3 hr the mixture is washed once with 10% aqueous sodium bisulfate. The organic portion is separated and the aqueous potion is saturated by addition of sodium chloride. The aqueous portion is extracted three times with dichloromethane. The combined organic portions are dried ($Na_2SO_4$), filtered and concentrated in vacuo. Chromatography (Silica gel, 75% ethyl acetate/hexane) of the residue affords 0.10 g (56%) of the title compound.

Mass Spectrum: M+1=756.

E. To a solution of 0.10 g (0.13 mmol) of material from part D in 1 mL of dichloromethane is added 0.5 mL of trifluoroacetic acid. After 1 hr the mixture is concentrated in vacuo. Chromatography (Silica gel, 0.2% ammonium hydroxide/1.8% methanol/dichloromethane) affords a solid which is dissolved in 5 ml of dichloromethane. To this solution is added 1 mL of 2M hydrogen chloride in diethyl ether and the mixture is concentrated in vacuo. The residue is suspended in diethyl ether, filtered and dried in vacuo to afford 70 mg (74%) of the title compound.

Mass Spectrum: M+1=656.

Preparations of Other Non-glycinic A-Domain

Preparation NA1

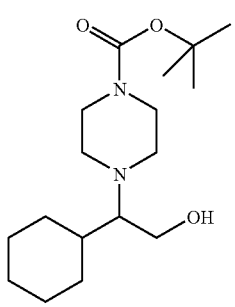

4-(1-Cyclohexyl-2-hydroxy-ethyl)-piperazine-1-carboxylic acid tert-butyl ester

Step I: Preparation of Bromo-cyclohexyl-acetic acid methyl ester

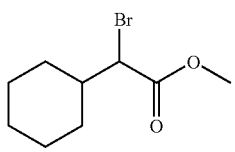

Method A

A mixture of cyclohexylacetic acid (25.0 g, 175.8 mmol) and $SOCl_2$ (51.3 mL, 703.2 mmol) in $CCl_4$ (25 mL) was heated at 65° C. for 30 min. Then, a suspension of NBS (37.5 g, 211.0 mmol) in $CCl_4$ (100 mL) was added, followed by addition of HBr (48%) (15 drops). Reaction was heated at 85° C. for 2 h and then cooled down to room temperature. Mixture was poured carefully onto cold MeOH (400 mL) and stirred for 15 min. Volatiles were evaporated under reduced pressure and the residue was taken into EtOAc. The resulting solution was washed with $H_2O$ and brine, dried ($Na_2SO_4$) and evaporated under reduced pressure. Residue was purified by column chromatography (hexane-EtOAc 30:1) to give the a-bromoester (95%) as a pale yellow oil. MS m/z 235.1 ($M^+$+1).

Method B

To a solution of methyl cyclohexylacetate (14.0 mL, 85.1 mmol) in anhydrous THF (140 mL) under nitrogen atmosphere at −78° C., a 1.0 M solution of LiHMDS in THF (93.6 mL, 93.6 mmol) was added. Reaction was stirred for 30 min and a solution of chlorotrimethylsilane (19.4 mL, 153.2 mmol) in anhydrous THF (140 mL) was added via cannula at −78° C. After 30 min., NBS (17.6 g, 98.9 mmol) was added in one portion and the reaction mixture was allowed to react at room temperature for 3.5 h. Reaction was quenched with a saturated aqueous solution of $NH_4Cl$ (100 mL) and diluted with EtOAc (500 mL). The layers were separated and the aqueous phase was extracted with EtOAc (100 mL). The combined organic layers was dried ($MgSO_4$), filtered and concentrated under reduced pressure. The residue was purified by column chromatography (hexane-EtOAc 9:1) to afford an inseparable 1:1.4 mixture of starting material and α-bromoester respectively (14.6 g). MS m/z 235.1 ($M^+$+1).

Step II: Preparation of 4-(Cyclohexyl-methoxycarbonyl-methyl)-piperazine-1-carboxylic acid tert-butyl ester

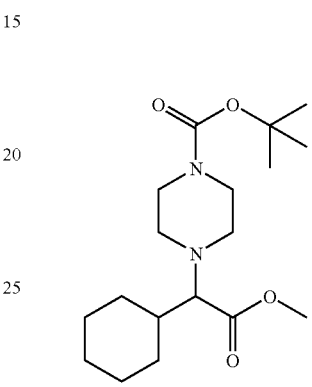

To a solution the product of Step I (25.0 g, 106.3 mmol) in anhydrous $CH_3CN$ (500 mL), $K_2CO_3$ (29.3 g, 212.0 mmol), N-Boc-piperazine (20.8 g, 111.6 mmol), and a catalytic amount of $nBu_4NI$ (7.85 g, 21.3 mmol) were added. Mixture was heated under reflux for 48 h and then cooled to room temperature. Reaction was diluted with EtOAc, washed with $H_2O$ and brine, dried ($Na_2SO_4$) and evaporated under reduced pressure. The residue was purified by column chromatography (hexane-EtOAc 9:1) to afford the title compound (34%) as a white solid. MS m/z 341.2 ($M^+$+1).

Step III: Preparation of 4-(1-Cyclohexyl-2-hydroxy-ethyl)-piperazine-1-carboxylic acid tert-butyl ester

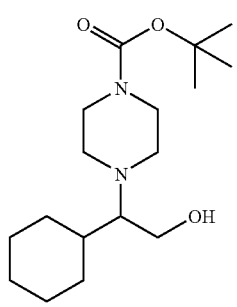

To an ice cooled solution of the product of Step II (9.75 g, 28.7 mmol) in THF (200 mL) under nitrogen, LAH (2.18 g, 57.4 mmol) was added portionwise. Mixture was allowed to react at room temperature for 20 minutes. Reaction was cooled to 0° C., and $H_2O$ (1.6 mL) and 2N NaOH (7 mL) were carefully added. The mixture was stirred for 1 h and filtered through a pad of silica gel and Celite. Solvent was removed under reduced pressure to afford the title compound (96%) as a white solid. MS m/z 313.2 ($M^+$+1)

Preparation NA2

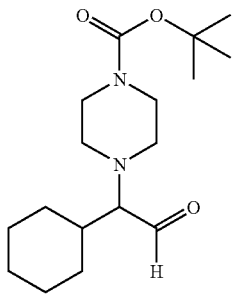

4-(1-Cyclohexyl-2-oxo-ethyl)-piperazine-1-carboxylic acid tert-butyl ester

To a solution of oxalyl chloride (1.61 mL, 18.8 mmol) in CH₂Cl₂ (150 mL) at −78° C. under nitrogen atmosphere, a solution of DMSO (2.8 mL, 39.25 mmol) was added dropwise and stirred for 10 min. To this mixture, a solution of the product of Preparation NA1 (4.9 g, 15.7 mmol) in CH₂Cl₂ (30 mL) was added dropwise and reaction was stirred at the same temperature for 30 minutes. Then, Et₃N (10.9 mL, 78.5 mmol) was added and mixture allowed to react at room temperature. After 30 min, reaction mixture was quenched with H₂O (100 mL), the layers were separated and the aqueous layer was extracted with CH₂Cl₂ (2×). The combined organic layers were dried (Na₂SO₄), filtered and evaporated to afford the title compound (82%) as a colorless oil. MS m/z 311.4 (M⁺+1)

Preparation NA3

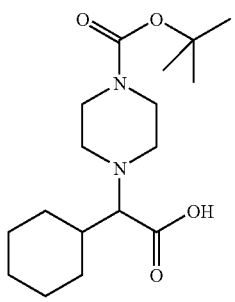

4-(Carboxy-cyclohexyl-methyl)-piperazine-1-carboxylic acid tert-butyl ester

To a solution of the product of Preparation NA1 (1.0 g, 3.21 mmol) in acetone (22 mL) at 0° C., Jones reagent (5.6 mL) was added. The reaction mixture was allowed to react at 0° C. for 1 h and 2.5 h at room temperature. Then, H₂O (20 mL) and isopropanol (20 mL) were added, and pH adjusted to 6–7 upon addition of 1N KOH. Resulting aqueous solution was extracted with EtOAc (4×) and the combined organic layers were dried (MgSO₄), filtered and concentrated under reduced pressure to afford the title compound (70%) as a solid. MS m/z 326.7 (M⁺+1)

Preparation NA4

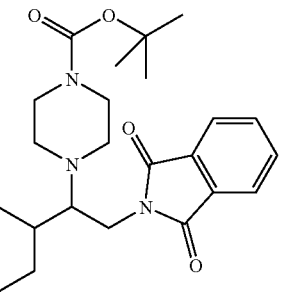

4-[(1-Cyclohexyl-2-(1,3-dioxo-1,3-dihydro-isoindol-2-yl)-ethyl)]-piperazine-1-carboxylic acid tert-butyl ester

Method A

To solution of the product of Preparation NA1 (5.0 g, 16.0 mmol), phthalimide (2.6 g, 17.6 mmol) and triphenylphosphine (4.6 g, 17.6 mmol) in anhydrous THF (80 mL) at 0° C., DEAD (2.8 mL, 17.6 mmol) was added dropwise. The mixture was stirred for 1 h and then the solvent was removed under reduced pressure. The residue obtained was purified by column chromatography (hexane/EtOAc 3:1) to afford the title compound (80%) as a solid. MS m/z 442.3 (M⁺+1)

Method B

Step I: Preparation of 4-[(1-Cyclohexyl-2-hydroxy-imino-ethyl)-piperazine-1-carboxylic acid tert-butyl ester

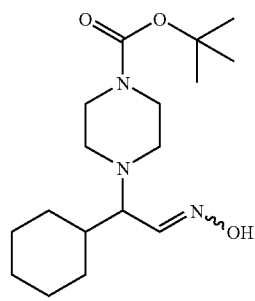

A mixture of the product of Preparation NA2 (1.0 g, 3.22 mmol), hydroxylamine hydrochloride (0.27 g, 3.86 mmol) and pyridine (0.62 mL, ;.72 mmol) in CH₂Cl₂ (20 mL) was stirred at room temperature for 16 h. The solvent was evaporated under reduced pressure and the residue purified by column chromatography (hexane-EtOAc 4:1) to afford the oxime (62%) as a white solid. MS m/z 326.4 (M⁺+1).

Step II: Preparation of 4-[(1-Cyclohexyl-2-(1,3-dioxo-1,3-dihydro-isoindol-2-yl)-ethyl)]-piperazine-1-carboxylic acid tert-butyl ester

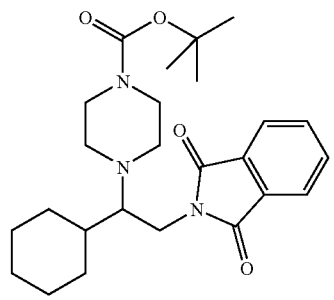

To a solution of NiCl$_2$·6H$_2$O (402 mg, 1.69 mmol) in MeOH (20 mL), NaBH$_4$ (64 mg, 1.69 mmol)) was added. To the resulting black solution, a solution of the product of Step I (550 mg, 1.69 mmol) in MeOH (5 mL) was added, followed by NaBH$_4$ (351 mg, 9.3 mmol) portionwise. The mixture was stirred for 5 min and filtered through celite. The solution was diluted with EtOAc and washed with a 4% aqueous solution of NH$_4$OH, dried, filtered and evaporated to afford the primary amine. A solution of this crude and phthalic anhydride (243 mg, 1.64 mmol) in CHCl$_3$ (10 mL) was heated at 70° C. for 2 h. The solvent was evaporated and the residue purified by column chromatography (hexane-EtOAc 5:1) to afford the title compound (15%) as a solid. MS m/z 442.3 (M$^+$+1) Enantiomers of this product were separated by chiral HPLC (CHIRALPAK AD 20 μm, 100% methanol/DMEA 0.1% isocratic mode, 1 mL/min). Isomer 1 t=8.5 min; Isomer 2 t=10.4 min.

Preparation NA5

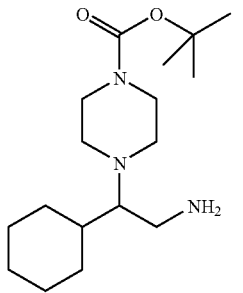

4-(2-Amino-1-cyclohexyl-ethyl)-piperazine-1-carboxylic acid tert-butyl ester

Method A

A solution of the product of Preparation NA4 (3.0 g, 6.79 mmol) in a 0.2N solution hydrazine monohydrate in MeOH (0.51 L) (0.2 M) was refluxed for 3 hours. Solvent was removed under reduced pressure and the residue was dissolved in CHCl$_3$. The insoluble materials were filtered off and the filtrated was concentrated to dryness to afford the title compound (99%) as yellow oil. MS m/z 312.2 (M$^+$+1). Enantiomer I was obtained from Isomer 1 of Preparation NA4. Enantiomer II was obtained from Isomer 2 of Preparation NA4.

Method B

Step I: Preparation of 4-[(1-Cyclohexyl-2-nitro-ethyl)]-piperazine-1-carboxylic acid tert-butyl ester

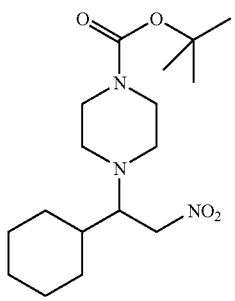

To a solution of (2-nitrovinyl)-cyclohexane (2.63 g, 16.94 mmol), prepared as in *J. Org. Chem.* 1993, 58, 3850, in dry CH$_2$Cl$_2$ (22 mL), N-Boc piperazine (2.63 g, 14.12 mmol) was added at room temperature and reaction stirred overnight. Solvent was removed under reduced pressure to afford the adduct product (99%) as an oil. MS m/z 342.4 (M$^+$+1).

Step II: Preparation of 4-[(2-amino-1-Cyclohexyl-ethyl)]-piperazine-1-carboxylic acid tert-butyl ester

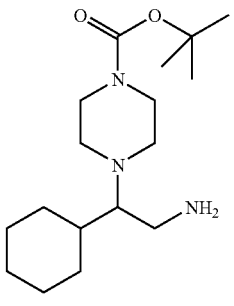

Samarium powder 40 mesh (10.72 g, 71.3 mmol) and 1,2-diiodoethane (18.67 g, 66.24 mmol) were placed in a flame dried 1000 mL round bottom flask. The flask was purged of nitrogen by a triple evacuated fill process. Dry THF (100 mL) was added and the mixture was stirred for 1 h. Then, it was diluted with additional dry THF (200 mL) and stirred for 1 h and 45 min. To this mixture, a solution of the Step I product (3.5 g, 10.19 mmol) in anhydrous THF (60 mL) and MeOH (30 mL) was added via cannula and reaction stirred at room temperature overnight. A solution of oxalic acid dihydrate (15.4 g, 122.3 mmol) in H$_2$O (125 mL) was added to quench the reaction and the resulting suspension was diluted with H$_2$O (400 mL) and filtered through celite. Organic solvents were removed under reduced pressure and the aqueous solution was neutralized with NaOH (9.78 g, 244.6 mmol) and extracted with EtOAc (3×600 mL). The combined organic layers were washed with brine, dried (MgSO$_4$), filtered and concentrated under reduced pressure. The crude was purified by a C18 cartridge to afford the title compound (14%). MS m/z 312.2 (M$^+$+1)

Preparation NA6

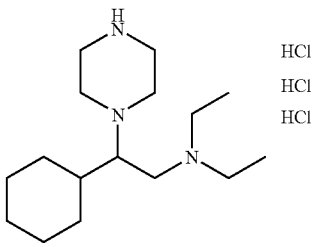

(2-Cyclohexyl-2-piperazin-1-yl-ethyl)-diethyl-amine trihydrochloride salt

Method A

To a solution of the product of Preparation NA2 (2.4 g, 7.73 mmol) in dry 1,2-dichloroethane (75 mL), diethylamine was added at room temperature. Mixture was stirred for 15 min and then sodium triacetoxyborohydride (2.46 g, 11.6 mmol) was added. Reaction mixture was stirred at room temperature overnight and then quenched with a saturated aqueous solution of NaHCO$_3$. Layers were separated and aqueous phase was extracted with EtOAc (3×). The combined organic layers were dried (MgSO$_4$), filtered and concentrated under reduced pressure. Residue was purified by column chromatography (EtOAc, then EtOAc-MeOH-Et$_3$N 90:5:5) to give the N-Boc protected product as an oil. Enantiomers of this N-Boc protected product could be separated by chiral HPLC (CHIRALPAK AD (4.6×250 mm), hexane-TFA 0.05%/isopropanol (9:1) isocratic mode, 1 mL/min). Isomer 1 t=7.12 min; Isomer 2 t=7.59 min. A solution of N-Boc derivative (178 mg, 0.48 mmol) in 1N HCl/EtOAc (10 mL) was stirred overnight at room temperature. Solvent was removed under reduced pressure and residue washed with Et$_2$O to afford the title compound (80%) a white solid. MS m/z 268.4 (M$^+$+1).

Method B

To a solution of the product of Preparation NA5 (0.75 g, 2.41 mmol) in anhydrous DMF (10 mL), K$_2$CO$_3$ (1.66 g, 12.05 mmol) and bromoethane (0.54 mL, 7.23 mmol) were added. Reaction was stirred at room temperature for 60 hours. Mixture was diluted with EtOAc and washed with brine, dried (Na$_2$SO$_4$), filtered and evaporated. The residue was purified by column chromatography (EtOAc, then EtOAc-MeOH-Et$_3$N 90:5:5) to afford the N-Boc protected product as a yellow oil (MS m/z 368.4, M$^+$+1). A solution of the N-Boc derivative (551 mg, 1.5 mmol) in 1N HCl/EtOAc (25 mL) was stirred for 2 h at room temperature. Solvent was removed under reduced pressure and residue washed with Et$_2$O to afford the title compound (62%) a pale yellow solid. MS m/z 268.3 (M$^+$+1). Enantiomer A was obtained from Enantiomer I of Preparation NA5. Enantiomer B was obtained from Enantiomer II of Preparation NA5.

Preparation NA7

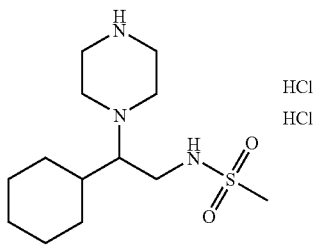

N-(2-Cyclohexyl1-2-piperazin-1-yl-ethyl)-methane-sulfonamide dihydrochloride salt

Method A

To a solution of the product of Preparation NA2 (2.82 g,. 9.08 mmol) in dry 1,2-dichloroethane (50 mL), MeSO$_2$NH$_2$ (0.95 g, 9.99 mmol), sodium triacetoxyborohydride (3.85 g, 18.16 mmol) and Et$_3$N (2.5 mL, 18.16 mmol) were added. Mixture was stirred overnight at room temperature and then AcOH (1.3 mL, 22.7 mmol), sodium triacetoxyborohydride (1.93 g, 9.08 mmol) were added. Reaction mixture was stirred at room temperature for 24 hours and then diluted with CH$_2$Cl$_2$ (50 mL). Mixture was washed with brine, dried (Na$_2$SO$_4$), filtered and evaporated. The residue was purified by column chromatography (hexane-EtOAc 3:1) to afford the N-Boc protected product as a pale yellow oil (MS m/z 390.6 (M$^+$1)). Enantiomers of this N-Boc protected product could be separated by chiral HPLC (CHIRALPAK AD (4.6×250 mm), hexane-TFA 0.05%/isopropanol (9:1) isocratic mode, 1 mL/min). Isomer 1 t=10.9 min; Isomer 2 t=11.9 min. A solution of N-Boc derivative (195 mg, 0.50 mmol) in 1N HCl/EtOAc (20 mL) was stirred for 2 h at room temperature. Solvent was removed under reduced pressure and residue washed with Et$_2$O to afford the title compound (14%) as a pale yellow solid. MS m/z 290.6 (M$^+$1).

Method B

To a solution of the product of Preparation NA5 (1.08 g, 3.47 mmol) in anhydrous CH$_2$Cl$_2$ (25 mL) under nitrogen at 0° C., Et$_3$N (0.97 mL, 6.95 mmol) and MeSO$_2$Cl (0.27 mL, 3.47 mmol) were added. After 30 minutes at room temperature, solvent was removed under reduced pressure and the residue was purified by column chromatography (hexane-EtOAc 1:1) to afford the N-Boc protected product as an oil. A solution of the N-Boc derivative (0.18 g, 0.46 mmol) in 1N HCl/EtOAc (20 mL) was stirred at room temperature overnight. A white solid appeared. Solvent was removed under reduced pressure and the solid washed twice with Et$_2$O to afford the title compound (70%) as a white solid. MS m/z 290.6 (M$^+$+1). Enantiomer A was obtained from Enantiomer I of Preparation NA5. Enantiomer B was obtained from Enantiomer II of Preparation NA5.

Preparation NA8

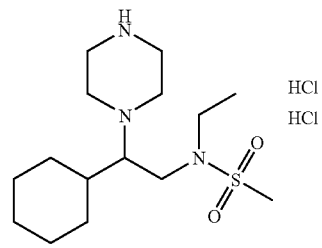

N-(2-Cyclohexyl-2-piperazin-1-yl-ethyl)-N-ethyl-methanesulfonamide dihydrochloride salt

Method A

Step I: Preparation of 4-(1-cyclohexyl-2-ethylamino-ethyl)-piperazine-1-carboxylic acid tert-butyl ester

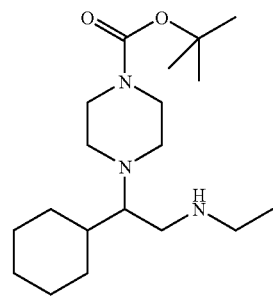

To a solution of the product of Preparation NA2 (1.48 g, 4.8 mmol) in 1,2-dichloroethane (10 mL) at room temperature was added EtNH₂ (70% in H₂O, 0.3 mL, 5.7 mmol). After 10 min, sodium triacetoxyborohydride (1.5 g, 7.2 mmol) was added. Reaction was stirred for 30 min and then quenched with a saturated aqueous solution of NaHCO₃ (2 mL) and diluted with EtOAc (20 mL). Mixture was filtered through Celite and solvent was removed under reduced pressure. Residue was purified by column chromatography (EtOAc, then EtOAc-MeOH-Et₃N 90:5:5) to give the N-Boc protected product (99%) as an oil. MS m/z 340.3 (M⁺+1)

Step II: Preparation of N-(2-Cyclohexyl-2-piperazin-1-yl-ethyl)-N-ethyl-methanesulfonamide dihydrochloride salt

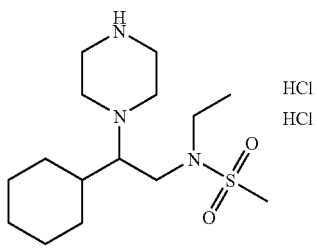

To a solution of the product of Step I (1.5 g, 4.5 mmol) in anhydrous CH₂Cl₂ (15 mL) under nitrogen at 0° C., Et₃N (1.28 mL, 9.16 mmol) and MeSO₂Cl (0.7 mL, 9.16 mmol) were added. After 10 minutes solvent was removed under reduced pressure and the crude obtained was suspended in a mixture hexane/EtOAc (2:1). The insoluble solids were filtered off and the filtrate concentrated. Residue was purified by column chromatography (hexane-EtOAc 2:1) to afford the N-Boc protected product as an oil. MS m/z 418.3 (M⁺+1). Enantiomers of this N-Boc protected product could be separated by chiral HPLC (CHIRALPAK AD 20 μm, Hexane/isopropanol (7:3), isocratic mode, 1 mL/min). Isomer 1 t=4.18 min; Isomer 2 t=4.67 min. A solution of N-Boc derivative (1.5 g, 4.5 mmol) in 1N HCl/EtOAc (50 mL) was stirred at room temperature overnight. A white solid appeared. Solvent was removed under reduced pressure and the solid washed twice with EtOAc to afford the title compound (75%) a white solid. MS m/z 318.3 (M⁺+1).

Method B

Enantiomer A was obtained from Enantiomer I of Preparation NA5. Enantiomer B was obtained from Enantiomer II of Preparation NA5.

Step I: Preparation of 4-(2-Acetylamino-1-cyclohexyl-ethyl)-piperazine-1-carboxylic acid tert-butyl ester

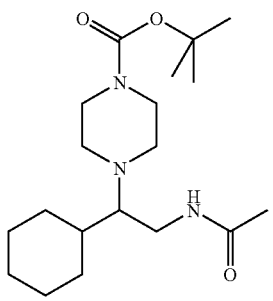

To a solution of the product of Preparation NA5 (2.1 g, 6.78 mmol) in anhydrous CH₂Cl₂, pyridine (1.1 mL, 13.5 mmol) and Ac₂O (0.83 mL, 8.1 mmol) were added. The mixture was stirred for 2 h at room temperature. Then, the mixture was diluted with CH₂Cl₂ (20 mL) and washed with water, 1N HCl, and brine. The organic phase was dried (Na₂SO₄), filtered and evaporated to afford the title compound (63%) as an oil. MS m/z 354.2 (M⁺+1)

Step II: Preparation of 4-(1-cyclohexyl-2-ethylamino-ethyl)-piperazine-1-carboxylic acid tert-butyl ester

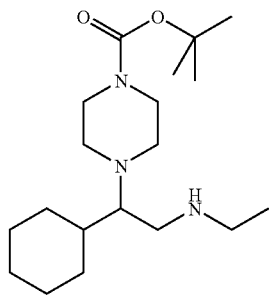

To a solution of the product of Step I (397 mg, 1.12 mmol) in anhydrous THF (5.1 mL), a 1M solution of BH₃-THF complex in THF (3.4 mL, 3.4 mmol) was added. The mixture was heated at 60° C. for 1 h and then cooled to room temperature. Then, MeOH (1.5 mL) and DIPEA (0.760 mL) were added. To this mixture, a solution of iodine (562 mg, 2.24 mmol) in anhydrous THF (2.6 mL) was cautiously added and stirred at room temperature for 30 min. The reaction was diluted with EtOAc (75 mL) and the organic phase was washed with 1N Na₂S₂O₃ and H₂O, dried (MgSO₄), filtered and concentrated under reduced pressure. The residue was purified through a SCX column to afford the title compound (86%) as an oil. MS m/z 340.3 (M⁺+1).

Step III: Preparation of N-(2-Cyclohexyl-2-piperazin-1-yl-ethyl)-N-ethyl-methanesulfonamide dihydrochloride salt

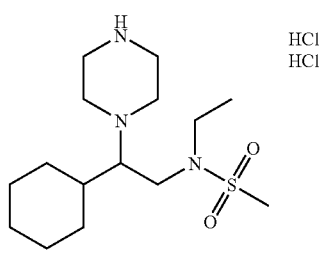

Following the general procedure described in Step II of Method A in Preparation NA8, and using the product of Step II as starting material, the title compound was prepared. MS m/z 318.3 (M$^+$+1). Enantiomer A was obtained from Enantiomer I of Preparation NA5. Enantiomer B was obtained from Enantiomer II of Preparation NA5.

Preparation NA9

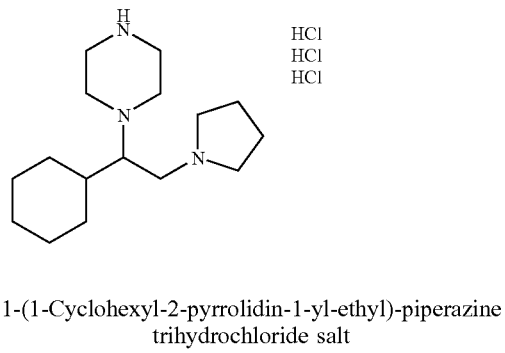

1-(1-Cyclohexyl-2-pyrrolidin-1-yl-ethyl)-piperazine trihydrochloride salt

Following the general procedure described in Method A of Preparation NA6, using pyrrolidine and the product of Preparation NA19 as starting materials, the title compound was prepared (19%). MS m/z 266.0 (M$^+$+1)

Preparation NA10

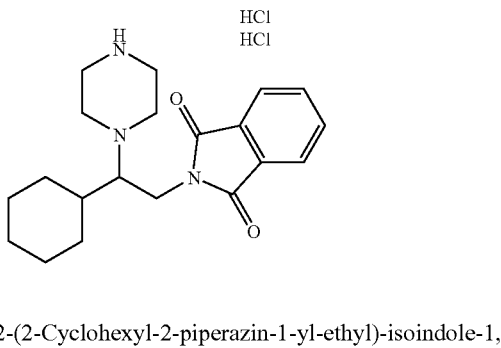

2-(2-Cyclohexyl-2-piperazin-1-yl-ethyl)-isoindole-1,3-dione dihydrochloride salt A solution of the product of Preparation NA4 (0.5 g, 1.13 mmol) in 1N HCl/EtOAc (25 mL) was stirred at room temperature for 5 h. Solvent was removed under reduced pressure and solid washed twice with Et$_2$O to afford the title compound (96%) a white solid. MS m/z 342.3 (M$^+$+1)

Preparation NA11

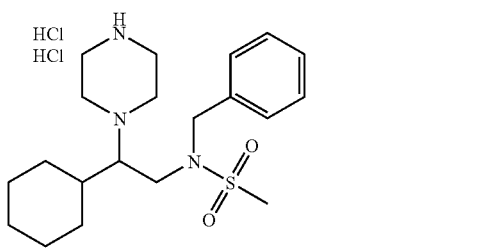

N-Benzyl-N-(2-cyclohexyl-2-piperazin-1-yl-ethyl)-methanesulfonamide dihydrochloride salt Following the general procedure described in Method A of Preparation NA8, using benzylamine and the product of Preparation NA2 in Step I as starting materials, the title compound was prepared (12%). MS m/z 380.6 (M$^+$+1)

Preparation NA12

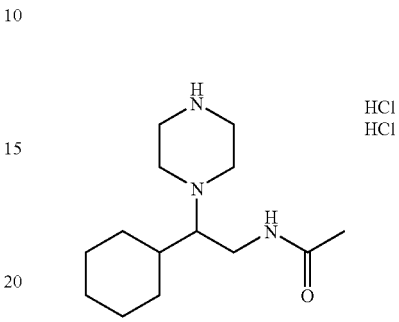

N-(2-Cyclohexyl-2-piperazin-1-yl-ethyl)-acetamide dihydrochloride salt

To a solution of the product of Preparation NA5 (2.1 g, 6.78 mmol) in anhydrous CH$_2$Cl$_2$ (20 mL), pyridine (1.1 mL, 13.5 mmol) and Ac$_2$O (0.83 mL, 8.1 mmol) were added. The mixture was stirred for 2 h at room temperature. Then, the mixture was diluted with CH$_2$Cl$_2$ (20 mL) and washed with water, 1N HCl, and brine. The organic phase was dried (Na$_2$SO$_4$), filtered and evaporated to afford the N-Boc protected amide as an oil. MS m/z 354.2 (M$^+$+1). A solution of the N-Boc derivative (0.5 g, 1.4 mmol) in 1N HCl/EtOAc (25 mL) was stirred at room temperature for 5 h. Solvent was removed under reduced pressure and solid washed twice with Et$_2$O to afford the title compound (59%) as a white solid. MS m/z 254.3 (M$^+$+1).

Preparation NA13

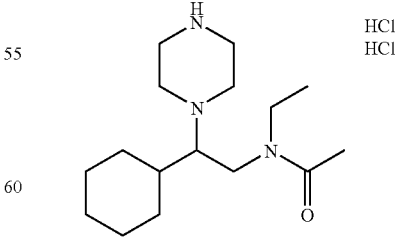

N-(2-Cyclohexyl-2-piperazin-1-yl-ethyl)-N-ethyl-acetamide dihydrochloride salt

To a solution of the product of Step II of Method B in Preparation NA8 (325 mg, 0.96 mmol) in anhydrous pyridine (1.8 mL) at room temperature, Ac₂O (1.8 mL) was added. The mixture was stirred for 1 h at 65° C. and then cooled to room temperature. The mixture was diluted with EtOAc (40 mL) and washed with a saturated aqueous solution of NaHCO₃, H₂O, and brine. The organic phase was dried (MgSO₄), filtered and concentrated under reduced pressure The residue was purified by column chromatography (hexane-EtOAc 1:1) to afford the N-Boc protected amide as an oil. A solution of the N-Boc derivative (109 mg, 0.29 mmol) in 1N HCl/EtOAc (20 mL) was stirred at room temperature overnight. Solvent was removed under reduced pressure and solid washed twice with Et₂O to afford the title compound (30%) as a white solid. MS m/z 282.3 (M⁺+1).

Enantiomer A was obtained from Enantiomer A of Step II of Method B in Preparation NA8. Enantiomer B was obtained from enantiomer B of Step II of Method B in Preparation NA8.

Preparation NA14

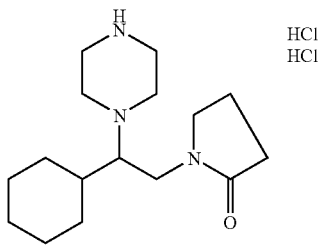

1-(2-Cyclohexyl-2-piperazin-1-yl-ethyl)-pyrrolidin-2-one dihydrochloride salt

Enantiomer A was obtained from Enantiomer I of Preparation NA5. Enantiomer B was obtained from Enantiomer II of Preparation NA5.

Step I: Preparation of 4-[2-(4-Chloro-butyrylamino)-1-cyclohexyl-ethyl]-piperazine-1-carboxylic acid tert-butyl ester

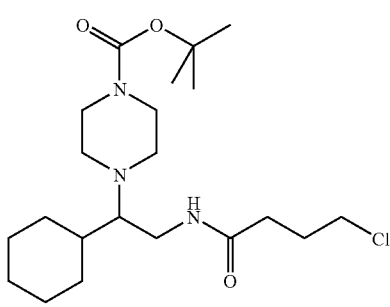

To a solution of the product of Preparation NA5 (1.0 g, 3.21 mmol) in CH₂Cl₂ (18 EL) and DMF (4.4 mL), DIPEA (2.8 mL, 16.05 mmol), 4-chlorobutyric acid (0.381 mL, 3.85 mmol), HOAT (546 mg, 4.01 mmol), and HATU (1.52 mg, 4.01 mmol) were added at room temperature. The mixture was stirred overnight at room temperature. Then, H₂O was added and the layers were separated. The aqueous phase was extracted with CH₂Cl₂ and the combined organic layers were dried (MgSO₄), filtered and concentrated under reduced pressure. The crude was purified by column chromatography (hexane-EtOAc 7:3) to afford the title compound (69%) as an oil. MS m/z 416.2 (M⁺+1).

Step II: Preparation of 1-(2-Cyclohexyl-2-piperazin-1-yl-ethyl)-pyrrolidin-2-one dihydrochloride salt

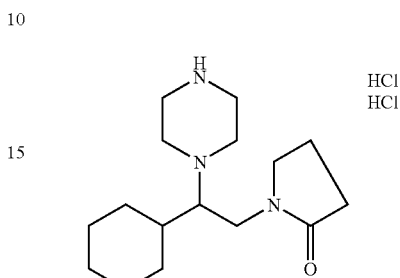

To a solution of the product of Step I (538 mg, 1.29 mmol), in anhydrous THF (7.7 mL) at 0° C., potassium tert-butoxide (145 mg, 1.29 mmol) was added. After stirring for 1.5 h, additional potassium tert-butoxide (145 mg, 1.29 mmol) was added and mixture stirred for 30 min. Reaction was quenched with H₂O and aqueous layer extracted with EtOAc. The combined organic phase was dried (MgSO₄), filtered and evaporated. The residue was purified by column chromatography (hexane/EtOAc 1:1) to afford the N-Boc protected product as an oil. A solution of the N-Boc derivative (266 mg, 0.70 mmol) in 1N HCl/EtOAc (25 mL) was stirred at room temperature overnight. Solvent was removed under reduced pressure and solid washed twice with Et₂O to afford the title compound (54%) as a white solid. MS m/z 280.2 (M⁺+1).

Preparation NA15

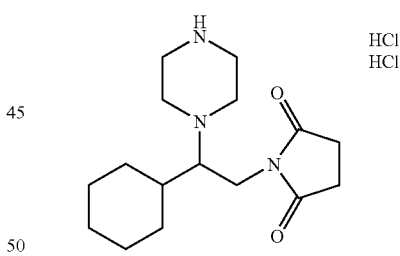

1-(2-Cyclohexyl-2-piperazin-1-yl-ethyl)-pyrrolidin-2,5-dione dihydrochloride salt Method A To a solution of the product of Preparation NA1 (300 mg, 0.96 mmol) in anhydrous THF (4.8 mL) at 0° C., succinimide (105 mg, 1.06 mmol) and triphenylphosphine (278 mg, 1.06 mmol) were added. Then, DEAD (0.167 mL, 1.06 mmol) was added dropwise at 0° C. and the reaction was stirred at 0° C. for 1 h and at room temperature overnight. The mixture was concentrated under reduced pressure and the residue purified by column chromatography (hexane/EtOAc 1:1) to afford the N-Boc protected product as an oil. A solution of the N-Boc derivative (291 mg, 0.74 mmol) in 1N HCl/EtoAc (20 mL) was stirred at room temperature overnight. Solvent was removed under reduced pressure and solid washed twice with Et$_2$O to afford the title compound (77%) as a white solid. MS m/z 293.9 (M$^+$+1)

Method B

Enantiomer A was obtained from Enantiomer I of Preparation NA5. Enantiomer B was obtained from Enantiomer II of Preparation NA5.

To a solution of the product of Preparation NA5 (0.641 g, 2.05 mmol) in CHCl$_3$ (2 mL) and succinic anhydride (205 mg, 2.05 mmol) were added at room temperature. The mixture was stirred under reflux for 1 hour and then it was heated at 120° C. for another 2 hours. The crude was purified by column chromatography (hexane/EtOAc 1:1) to afford 645 mg (83%) of the N-Boc protected product as white solid. A solution of the N-Boc derivative (645 mg, 1.64 mmol) in 1N HCl/EtOAc (25 mL) was stirred at room temperature overnight. Solvent was removed under reduced to afford the title compound as a white solid. MS m/z 293.9 (M$^+$+1)

Preparation NA16

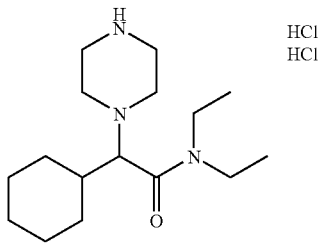

2-Cyclohexyl-N,N-diethyl-2-piperazin-1-yl-acetamide dihydrochloride salt

To a solution of the product of Preparation NA3 (300 mg, 0.92 mmol) in CH$_2$Cl$_2$ (4.8 mL) and DMF (1 mL) at room temperature, DIPEA (0.8 mL, 4.6 mmol), diethylamine (0.114 mL, 1.10 mmol) and HOBT (155 mg, 1.15 mmol) were added and the mixture stirred for 5 min. Then, EDCI (220 mg, 1.15 mmol) was added and the reaction stirred overnight at room temperature. Then, H$_2$O (10 mL) was added and mixture diluted with CH$_2$Cl$_2$ (10 mL). The layers were separated and the aqueous phase was extracted with CH$_2$Cl$_2$. The combined organic layers were dried (MgSO$_4$), filtered and evaporated under reduced pressure. The residue was purified by column chromatography (hexane/EtOAc 7:3) to afford the N-Boc protected amide as an oil. Enantiomers of this N-Boc protected product could be separated by chiral HPLC (CHIRALPAK AD (4.6×250mm), hexane-TFA 0.05%/isopropanol (20:1) isocratic mode, 1 mL/min). Isomer 1 t=7.59 min; Isomer 2 t=8.8l1min. A solution of the N-Boc derivative (203 mg, 0.53 mmol) in 1N HCl/EtOAc (20 mL) was stirred at room temperature overnight. Solvent was removed under reduced pressure and solid washed twice with Et$_2$O to afford the title compound (58%) as a white solid. MS m/z 281.9 (M$^+$+1).

Preparation NA17

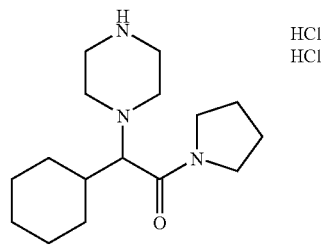

2-Cyclohexyl-2-piperazin-1-yl-1-pyrrolidin-1-yl-ethanone dihydrochloride salt

Following the general procedure described in Preparation NA16, and using pyrrolidine and the product of Preparation NA3 as starting materials, the title compound was prepared (40%). MS m/z 279.8 (M$^+$+1).

Preparation NA18

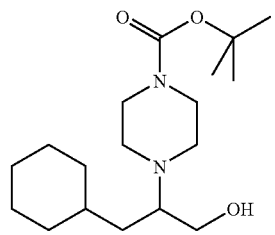

4-(1-Cyclohexylmethyl-2-hydroxy-ethyl)-piperazine-1-carboxylic acid tert-butyl ester Following the general procedure described in Preparation NA1, and using 3-cyclohenxylpropionic acid as starting material, the title compound was prepared (49%). MS m/z 327.2 (M$^+$+1)

Preparation NA19

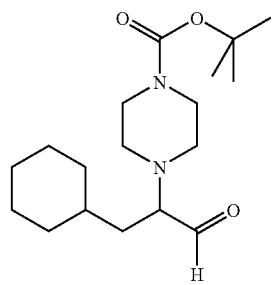

4-(1-Cyclohexylmethyl-2-oxo-ethyl)-piperazine-1-carboxylic acid tert-butyl ester Following the general procedure described in Preparation NA2, and using the product of Preparation NA18 as starting material, the title compound was prepared (95%). MS m/z 325.4 (M$^+$+1)

Preparation NA20

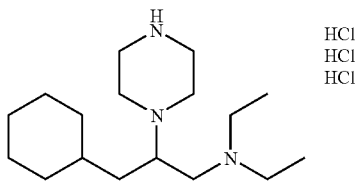

(2-Cyclohexylmethyl-2-piperazin-1-yl-ethyl)-di-
ethyl-amine trihydrochloride salt Following the general procedure described in Method A of Preparation NA6, using diethylamine and the product of Preparation NA19 as starting materials, the title compound was prepared (68%). MS m/z 282.3 (M$^+$+1).

Preparation NA21

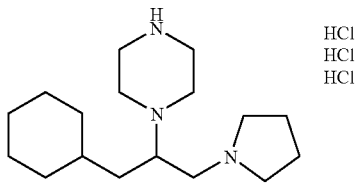

1-(1-Cyclohexylmethyl-2-pyrrolidin-1-yl-ethyl)-
piperazine trihydrochloride salt Following the general procedure described in Method A of Preparation NA6, using pyrrolidine and the product of Preparation NA19 as starting materials, the title compound was prepared (76%). MS m/z 280.4 (M$^+$+1).

Preparation NA22

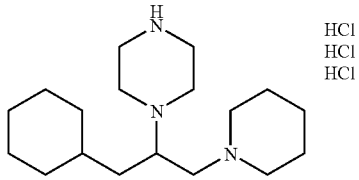

1-(1-Cyclohexylmethyl-2-piperidin-1-yl-ethyl)-pip-
erazine trihydrochloride salt Following the general procedure described in Method A of Preparation NA6, using piperidine and the product of Preparation NA19 as starting materials, the title compound was prepared (70%). MS m/z 294.2 (M$^+$+1).

Preparation NA23

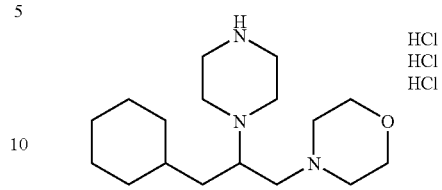

4-(3-Cyclohexyl-2-piperazin-1-yl-propyl)-morpho-
line trihydrochloride salt

Following the general procedure described in Method A of Preparation NA6, using morpholine and the product of Preparation NA19 as starting materials, the title compound was prepared (65%). MS m/z 296.6 (M$^+$+1).

Preparation NA24

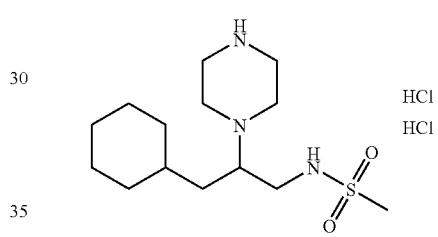

N-(3-Cyclohexyl-2-piperazin-1-yl-propyl)-methane-
sulfonamide dihydrochloride salt Step I: Preparation of 4-[(1-Cyclohexylmethyl-2-
hydroxyimino-ethyl)-piperazine-1-carboxylic acid
tert-butyl ester

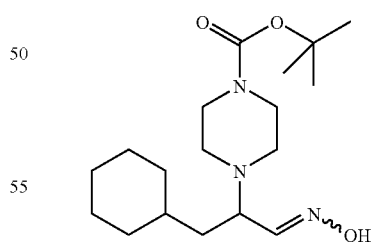

Following the procedure described in Step I of Method B in Preparation NA4, using the product of Preparation NA19 as starting materials, the title compound was prepared (46%). MS m/z 340.3 (M$^+$+1).

Step II: Preparation of N-(3-Cyclohexyl-2-piper-
azin-1-yl-propyl)-methanesulfonamide dihydrochlo-
ride salt

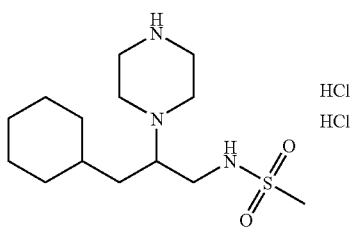

To a solution of NiCl$_2$·6H$_2$O (533 mg, 2.24 mmol) in MeOH (25 mL), NaBH$_4$ (85 mg, 2.24 mmol) was added. To the resulting black solution, a solution of the product of Step I (760 mg, 2.24 mmol) in MeOH (10 mL) was added, followed by NaBH$_4$ (465 mg, 12.3 mmol) portionwise. The mixture was stirred for 5 min and filtered through celite. The solution was diluted with EtOAc and washed with a 5% aqueous solution of NH$_4$OH, dried, filtered and evaporated to afford the primary amine. To a solution of this amine (676 mg, 2.08 mmol) in anhydrous CH$_2$Cl$_2$ (20 mL) under nitrogen at 0° C., Et$_3$N (0.43 mL, 3.12 mmol) and MeSO$_2$Cl (0.24 mL, 3.12 mmol) were added. After 30 minutes at room temperature, solvent was removed under reduced pressure and the residue was purified by column chromatography (hexane-EtOAc 1:1) to afford the N-Boc protected product as an oil. A solution of the N-Boc derivative (440 mg, 1.09 mmol) in 1N HCl/EtOAc (25 mL) was stirred at room temperature for 2 h. A white solid appeared. Solvent was removed under reduced pressure and the solid washed twice with Et$_2$O to afford the title compound as a solid (35%). MS m/z 304.6 (M$^+$+1).

Preparation NA25

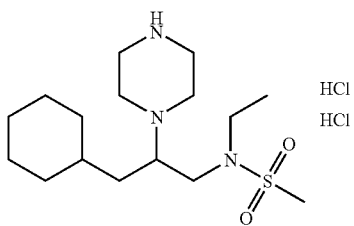

N-(3-Cyclohexyl-2-piperazin-1-yl-propyl)-N-ethyl-methanesulfonamide dihydrochloride salt Following the general procedure described in Method A of Preparation NA8, using ethylamine and the product of Preparation NA19 as starting materials, the title compound was prepared (59%). MS m/z 332.3 (M$^+$+1)

Preparation NA26

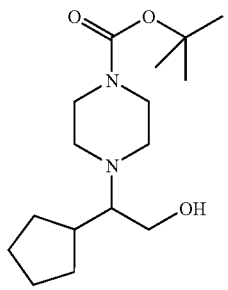

4-(1-Cyclopentyl-2-hydroxy-ethyl)-piperazine-1-carboxylic acid tert-butyl ester

Following the general procedure described in Preparation NA1, and using cyclopentylacetic acid as starting material, the title compound was prepared (16%). MS m/z 299.2 (M$^+$+1)

Preparation NA27

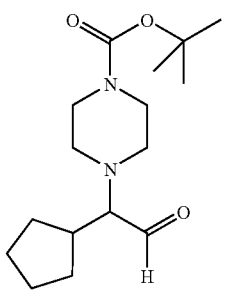

4-(1-Cyclopentyl-2-oxo-ethyl)-piperazine-1-carboxylic acid tert-butyl ester

Following the general procedure described in Preparation NA2, and using the product of Preparation NA26 as starting material, the title compound was prepared (99%). MS m/z 297.3 (M$^+$+1)

Preparation NA28

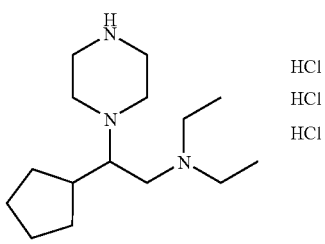

(2-Cyclopentyl-2-piperazin-1-yl-ethyl)-diethyl-amine trihydrochloride salt

Following the general procedure described in Preparation NA6, and using the product of Preparation NA27 as starting material, this intermediate was prepared (86%). MS m/z 254.3 (M$^+$+1)

Preparation NA29

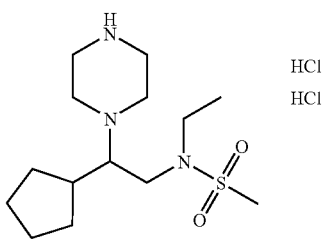

N-(2-Cyclopentyl-2-piperazin-1-yl-ethyl)-N-ethyl-methanesulfonamide dihydrochloride salt Following the general procedure described in Preparation NA8, and using the product of Preparation NA27 as starting material, the title compound was prepared (24%). MS m/z 304.2 (M⁺+1).

Preparation NA30

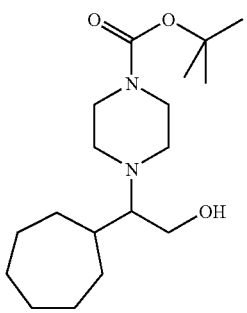

4-(1-Cycloheptyl-2-hydroxy-ethyl)-piperazine-1-carboxylic acid tert-butyl ester

Following the general procedure described in Preparation NA1, and using cycloheptylacetic acid as starting material, the title compound was prepared (40%). MS m/z 327.4 (M⁺+1).

Preparation NA31

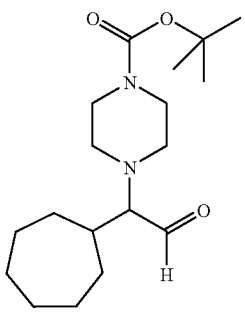

4-(1-Cycloheptyl-2-oxo-ethyl)-piperazine-1-carboxylic acid tert-butyl ester

Following the general procedure described in Preparation NA2, and using the product of Preparation NA30 as starting material, the title compound was prepared (91%). MS m/z 325.4 (M⁺+1).

Preparation NA32

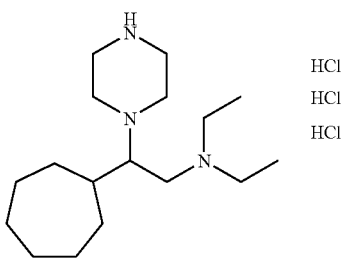

(2-Cycloheptyl-2-piperazin-1-yl-ethyl)-diethyl-amine trihydrochloride salt

Following the general procedure described in Preparation NA6, and using the product of Preparation NA31 as starting material, the title compound was prepared (44%). MS m/z 282.6 (M⁺+1).

Preparation NA33

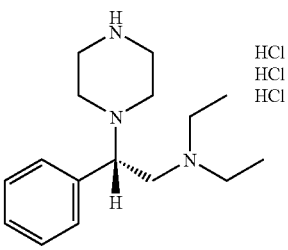

(2S)-Diethyl-(2-phenyl-2-piperazin-1-yl-ethyl)-amine trihydrochloride salt

Step I: Preparation of (2R)-2-Diethylamino-2-phenyl-ethanol

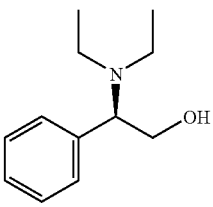

To a solution of (R)-phenylglycinol (0.5 g, 3.6 mmol) in THF (15 mL) under nitrogen atmosphere, Na₂CO₃ (1.14 g, 10.8 mmol), tetrabutylammonium iodide (0.66 g, 1.8 mmol) and ethyl iodide (0.6 mmol, 7.3 mmol) were added. The reaction was stirred under reflux for 24 hours. The resulting mixture was cooled to room temperature and the solids filtered off. The filtrated was concentrated under reduced pressure and the residue was dissolved in EtOAc, washed with H₂O, dried (Na₂SO₄), filtered and evaporated under reduced pressure. The crude product was purified by column chromatography (EtOAc-MeOH-Et₃N 90:5:5) to afford the title compound (96%). MS m/z 194.2 (M⁺+1)

Step II: Preparation of (2S)-Diethyl-(2-phenyl-2-piperazin-1-yl-ethyl)-amine trihydrochloride salt

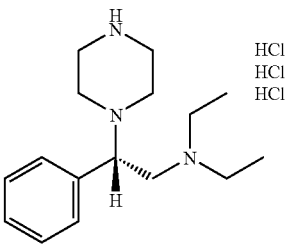

To a solution of the product of Step I (0.68 g, 3.5 mmol) in anhydrous Et$_2$O (10 mL) under nitrogen atmosphere, Et$_3$N (1.4 mL, 10.5 mmol) was added. The mixture was cooled to 0° C. and methanesulfonyl chloride (0.4 mL, 4.9 mmol) was added dropwise. The mixture was allowed to react at room temperature and stirred for 30 min. Then, N-Boc-piperazine (1.3 g, 7.2 mmol) was added and the reaction was stirred at room temperature overnight. The mixture was diluted with EtOAc (10 mL) and washed with H$_2$O (5 mL). The phases were separated and the organic layer was dried (Na$_2$SO$_4$), filtered and evaporated under reduced pressure. The residue was purified by medium pressure chromatography (EtOAc-MeOH-Et$_3$N 90:5:5) to afford the N-Boc protected product in >98% ee. (determined by chiral HPLC Chiralpak AD, Hexane-TFA 0.05%, 1 mL/min, t=9.748). A solution of the N-Boc derivative (0.68 g, 1.88 mmol) in 1N HCl/EtOAc (25 mL) was stirred overnight at room temperature. Solvent was removed under reduced pressure and residue washed with Et$_2$O to afford the title compound (52%) a white solid. MS m/z 262.2 (M$^+$+1).

Preparation NA34

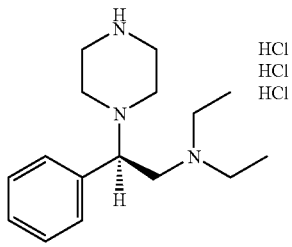

(2R)-Diethyl-(2-phenyl-2-piperazin-1-yl-ethyl)-amine trihydrochloride salt

Following the general procedure described in Preparation NA37, and using (S)-phenylglycinol as starting material, the title compound was prepared. MS m/z 262.2 (M$^+$+1).

Preparation NA35

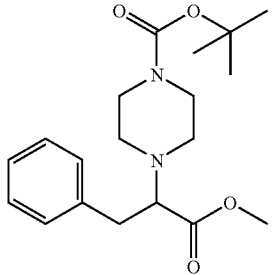

4-(1-Methoxycarbonyl-2-phenyl-ethyl)-piperazine-1-carboxylic acid tert-butyl ester Step I: Preparation of 3-Bromo-4-phenyl-butyric acid methyl ester

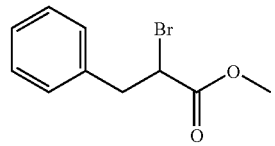

Following the general procedure described in Method A of Step I in Preparation NA1, using 3-phenylpropionic acid as starting material, the title compound was prepared (37%). MS m/z 243.0 (M$^+$+1).

Step II: Preparation of 4-(1-Methoxycarbonyl-2-phenyl-ethyl)-piperazine-1-carboxylic acid tert-butyl ester

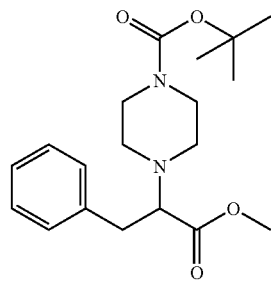

Following the general procedure described in Step II of Preparation NA1, using the product of Step I as starting material, the title compound was prepared (24%). MS m/z 349.2 (M$^+$+1).

Preparation NA36

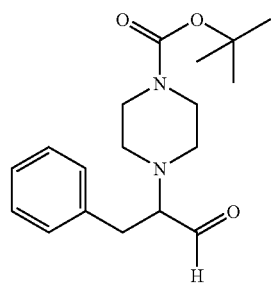

4-(1-Formyl-2-phenyl-ethyl)-piperazine-1-carboxylic acid tert-butyl ester

To a solution of the product of Preparation NA39 (infra) (2.41 g, 6.92 mmol) in CH$_2$Cl$_2$ (40 mL) at −78° C. under nitrogen atmosphere, a 1M solution of DIBAL-H in toluene (17.3 mL, 17.3 mmol) was added. Reaction was stirred for 1 hour (h) at −78° C. and quenched with a saturated aqueous solution of sodium tartrate. Mixture was stirred for 1 hour and layers separated. Aqueous layer was extracted with CH$_2$Cl$_2$, dried (Na$_2$SO$_4$), filtered and evaporated. The residue was purified by column chromatography (hexane-EtOAc 5:1) to afford the title compound as a pale yellow oil (56%). MS m/z 319.4 (M$^+$+1).

Preparation NA37

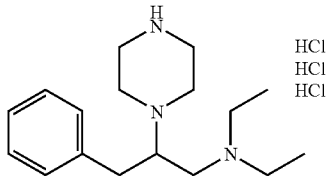

Diethyl-(3-phenyl-2-piperazin-1-yl-propyl)-amine trihydrochloride salt

Following the general procedure described in Method A of Preparation NA6, using diethylamine and the product of Preparation NA40 as starting materials, the title compound was prepared (41%). MS m/z 276.5 (M$^+$+1).

Preparation NA38

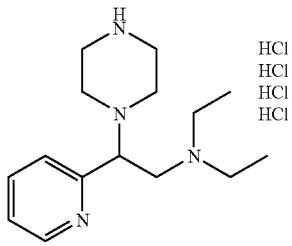

Diethyl-(2-piperazin-1-yl-2-pyridin-2-yl-ethyl)-amine tretrahydrochloride salt

Step I: Preparation of 4–7(Ethoxycarbonyl-pyridin-2-yl-methyl)-piperazine-1-carboxylic acid tert-butyl ester

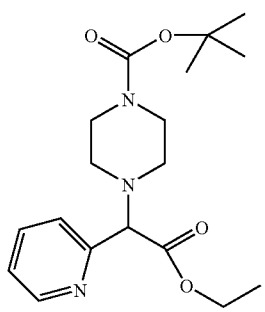

To a solution of ethyl 2-pyridylacetate (3.0 g, 18.16 mmol) in CCl$_4$ (26 mL), NBS (3.56 g, 20.0 mmol), AIBN (149 mg, 0.91 mmol) were added at room temperature. The reaction mixture was allowed to stir under reflux for 5 hours. The resulting brown suspension was cooled to room temperature and water and CH$_2$Cl$_2$ were added. The layers were separated and the organic layer was washed with water. Then it was dried (MgSO$_4$), filtered and concentrated under reduced pressure to afford the bromide derivative as brown oil. To a solution of this product (3.69 g, 15.12 mmol) in anhydrous CH$_3$CN (36 mL), K$_2$CO$_3$ (4.19 g, 30.24 mmol), N-Boc-piperazine (3.09 g, 16.63 mmol), and a catalytic amount of nBu$_4$NI (559 mg, 1.51 mmol) were added. The mixture was heated under reflux overnight and then cooled to room temperature. Reaction was diluted with EtOAc, washed with H$_2$O and brine, dried (MgSO$_4$) and evaporated under reduced pressure. The residue was purified by column chromatography (hexane-EtOAc 1:1) to afford the title compound (17%) as a yellow oil. MS m/z 350.4 (M$^+$+1).

Step II: Preparation of 4-(2-Oxo-1-pyridin-2-yl-ethyl)-piperazine-1-carboxylic acid tert-butyl ester

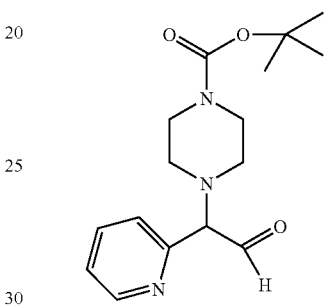

To a solution of product from Step I (803 mg, 2.3 mmol) in dry CH$_2$Cl$_2$ (5.4 mL) at −78° C., under N$_2$ atmosphere, a 1.0 M solution of DIBAL-H in toluene (5.8 mL, 5.8 mmol) was added dropwise. The reaction mixture was allowed to stir at this temperature for about 30 minutes. Then it was quenched with MeOH (1mL) slowly. Then EtOAc (50 mL) and a saturated solution of sodium tartrate (50 mL) were added. After stirring at RT for 1 hour the layers were separated and the aqueous phase was extracted with EtOAc. The combined organic phase was dried over MgSO4, filtered and concentrated in vacuo to afford the title compound as an oil. MS m/z 306.4 (M$^+$+1).

Step III: Preparation of Diethyl-(2-piperazin-1-yl-2-pyridin-2-yl-ethyl)-amine tretrahydrochloride salt

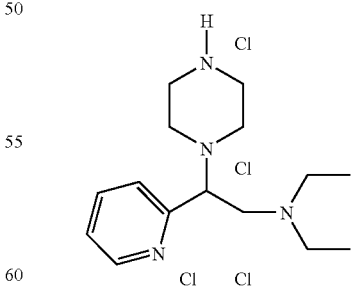

To a solution of product from Step II (624 mg, 2.05 mmol) in dry 1,2-dichloroethane (7.2 mL), diethylamine (0.254 mL, 2.46 mmol) was added at room temperature. The mixture was stirred for 15 min and then sodium triacetoxyborohydride (652 mg, 3.08 mmol) was added. Reaction mixture was stirred at room temperature overnight and then quenched with a saturated aqueous solution of NaHCO$_3$. Layers were separated and aqueous phase was extracted with EtOAc (3×). The combined organic layers were dried (MgSO$_4$), filtered and concentrated under reduced pressure. Residue was purified by column chromatography (EtOAc, then EtOAc-MeOH-Et$_3$N 90:5:5) to give the N-Boc protected product as an oil. A solution of N-Boc derivative (208 mg, 0.57 mmol) in saturated HCl(g)/MeOH (10 mL) was stirred overnight at room temperature. Solvent was removed under reduced pressure to afford the title compound (26%) as a white solid. MS m/z 263.4 (M$^+$+1).

Preparation NA39

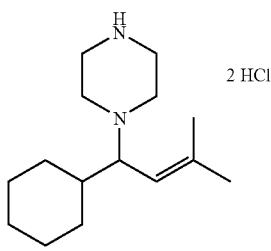

1-(1-Cyclohexyl-3-methyl-but-2-enyl)-piperazine dihydrochloride salt

Step I: Preparation of 4-(1-Cyclohexyl-3-methyl-but-2-enyl)-piperazine-1-carboxylic acid tert-butyl ester

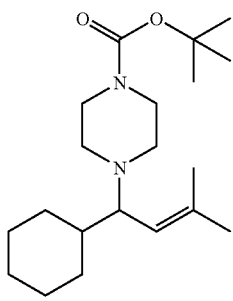

To a solution of isopropyltriphenylphosphonium iodide (709 mg, 1.79 mmol) cooled at −78° C. was added n-butyllithium (0.98 mL, 1.57 mtnol, 1.6 M in hexanes) and stirred for 1 hour while warming to 0° C. The mixture was added to a solution of product of Preparation NA2 (443 mg, 1.43 mmol) at −78° C. and stirred at 23° C. for 2 hours. The reaction was diluted with EtOAC and washed with brine, the combined organic phase was dried (Na$_2$SO$_4$), dried, and evaporated. The residue was purified by flash chromatography (hexane-EtOAc 15:1) to afford the title compound (385 mg). MS m/z 337.3 (M$^+$+1).

Step II: Preparation of 1-(1-Cyclohexyl-3-methyl-but-2-enyl)-piperazine dihydrochloride salt

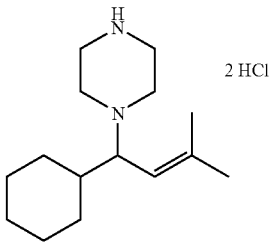

A solution of the N-Boc derivative (250 mg, 0.74 mmol) in 1N HCl/EtOAc (25 mL) was stirred at room temperature overnight. Solvent was removed under reduced pressure and solid washed twice with Et$_2$O to afford the title compound as a white solid. MS m/z 237.3 (M$^+$+1).

Preparation NA40

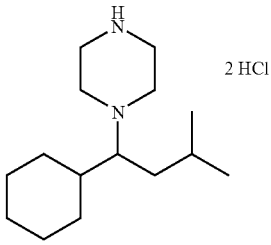

1-(1-Cyclohexyl-3-methyl-butyl)-piperazine dihydrochloride salt

Step I: Preparation of 4-(Cyano-cyclohexyl-methyl)-piperazine-1-carboxylic tert-butyl ester

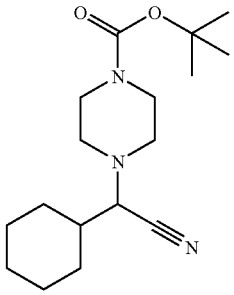

To a solution of KCN (1.61 g, 24.8 mmol) in H$_2$O (15 mL) N-Boc-piperazine (4.6 g, 24.6 mmol) was added and the mixture cooled to 0° C. Then 1M aqueous HCl (23.9 mL, 23.9 mmol) wan added followed by cyclohexanecarboxaldehyde (2.0 mL, 16.5 mmol) and the mixture stirred for 20 h. It was poured over Et$_2$O and the aqueous phase extracted with Et$_2$O, dried (MgSO$_4$), and evaporated. The crude was purified by flash chromatography (hexane-EtOAc 4:1→3:1) to afford 4.2 g of the title compound.

Step II: Preparation of 4-(1-Cyclohexyl-3-methyl-butyl)-piperazine-1-carboxylic acid tert-butyl ester

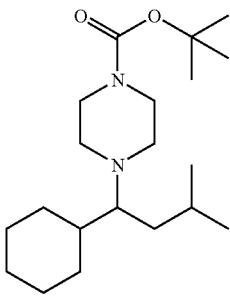

A solution of product from Step I (750 mg, 2.44 mmol) in THF (15 mL) and isobutylmagnesium bromide (6.1 mL, 12.2 mmol, 2 M in THF) was heated at 70° C. for 24 h. The reaction was quenched with EtOAc and washed with brine, dried (Na$_2$SO$_4$), and evaporated. Final purification by flash chromatography (hexane-EtOAc 25:1) afforded, 406 mg of the title compound. MS m/z 339.3 (M$^+$+1).

Step III: Preparation of 1-(1-Cyclohexyl-3-methyl-butyl)-piperazine dihydrochloride salt

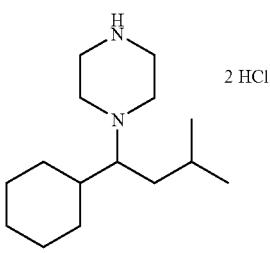

A solution of the product from Step II (406 mg, 1.21 mmol) in 1N HCl/EtOAc (25 mL) was stirred at room temperature overnight. Solvent was removed under reduced pressure and solid washed twice with Et$_2$O to afford the title compound as a white solid. MS m/z 239.3 (M$^+$+1).

Preparation NA41

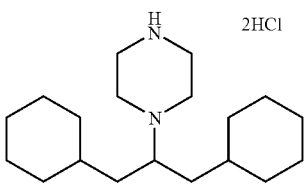

1-(2-Cyclohexyl-1-cyclohexylmethyl-ethyl)-piperazine dihydrochloride salt

Step I: Preparation of 4-(1-Cyano-2-cyclohexyl-ethyl)-piperazine-1-carboxylic acid tert-butyl ester

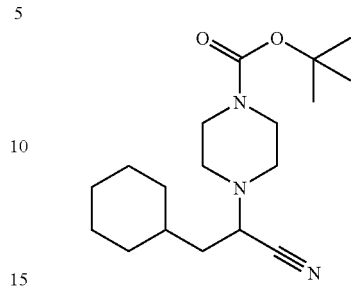

A solution of cyclohexaneacetaldehyde (8.45 g, 66.96 mmol) and TMSCN (17.9 mL, 133.92 mmol) in MeOH was stirred for 2 h at 23° C. and N-BOC-piperazine (13.72 g, 73.66 mmol) was added. After 24 the solvent was evaporated to give the title compound.

Step II: Preparation of 4-(2-Cyclohexyl-1-cyclohexylmethyl-ethyl)-piperazine-1-carboxylic acid tert-butyl ester

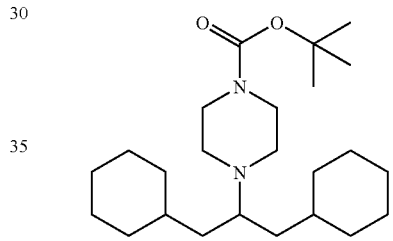

A solution of 4-(1-cyano-2-cyclohexyl-ethyl)-piperazine-1-carboxylic acid tert-butyl ester (1.81, 5.65 mmol) in THF (20 mL) and cyclohexylmethylmagnesium bromide (1.51 g, 22.60 mmol, 0.4 M in Et$_2$O) was stirred at 23° C. for 24 h. The reaction was quenched with EtOAc and washed with brine, dried (Na$_2$SO$_4$), and evaporated. Final purification by flash chromatography (hexane-EtOAc 15:1) afforded 1020 mg of the title compound. MS m/z 393.3 (M$^+$+1).

Step III: Preparation of 1-(2-Cyclohexyl-1-cyclohexylmethyl-ethyl)-piperazine dihydrochloride salt

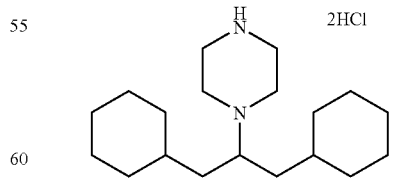

A solution of the N-Boc derivative (1020 mg, 2.60 mmol) in 1N HCl/EtOAc (25 mL) was stirred at room temperature overnight. Solvent was removed under reduced pressure and solid washed twice with Et$_2$O to afford the title compound as a white solid. MS m/z 293.3 (M$^+$+1).

Preparation NA42

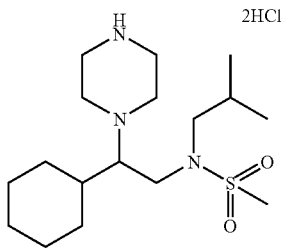

N-(2-Cyclohexyl-2-piperazine-1-yl-ethyl)-N-isobutyl-methanesulfonamide dihydrochloride salt Enantiomer A was obtained from Enantiomer I of Preparation NA5. Enantiomer B was obtained from Enantiomer II of Preparation NA5.

Step I: Preparation of 4-(1-Cyclohexyl-2-isobutyrylamino-ethyl)-piperazine-1-carboxylic acid tert-butyl ester

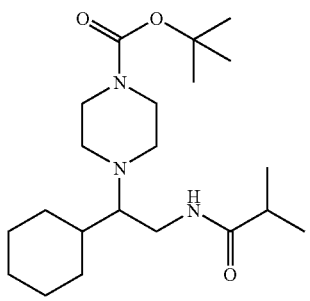

To a solution of the product of Preparation NA5 (1.0 g, 3.21 mmol) in $CH_2Cl_2$ (10 mL) was added isobutyryl chloride (0.4 ml, 3.85 mmol) and pyridine (0.39 mL, 4.82 mmol) at 0° C. and stirring for 1 hour while warming to 23° C. The mixture was diluted with $CH_2Cl_2$ and washed with brine, dried ($Na_2SO_4$), and evaporated to give the title product as an oil. MS m/z 382.3 ($M^+$+1).

Step II: Preparation of 4-(1-Cyclohexyl-2-isobutylamino-ethyl)-piperazine-1-carboxylic acid tert-butyl ester

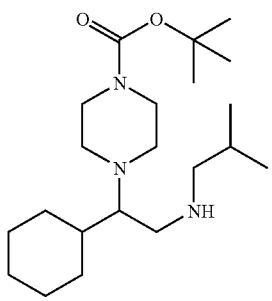

A solution of the product from Step I (1.23 g, 3.21 mmol) and borane-tetrahydrofurane complex (9.6 mL, 9.63 mmol, 1 M in THF) in THF (20 mL) was heated at 60° C. for 1 hour. The mixture was allowed to cool to ambient temperature followed by addition of MeOH (5 mL) and DIPEA (7.5 mL). Next, iodine (1.62 g, 6.42 mmol) in THF (10 mL) was added and the mixture stirred for 30 min. The mixture was diluted with EtOAc and successively washed with 10% aqueous $Na_2S_2O_5$ and brine, dried ($Na_2SO_4$), and evaporated. The residue was purified by flash chromatography (hexane:EtOAc 1:1→EtOAc→EtOAc:MeOH:$NEt_3$ 90:5:5) to afford the title compound (904 mg) as a yellow oil. MS m/z 368.3 ($M^+$+1).

Step III: Preparation of 4-[1-Cyclohexyl-2-(isobutyl-methanesulfonyl-amino)-ethyl]-piperazine-1-carboxylic acid tert-butyl ester

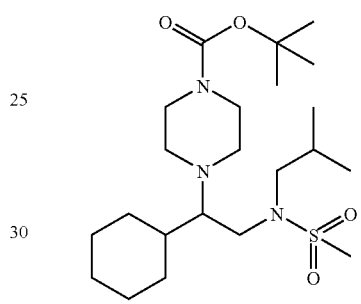

To a solution of the product from Step II (450 mg, 1.2 mmol) in $CH_2Cl_2$ (5 mL) was added TEA (0.35 mL, 2.44 mmol) and methanesulfonyl chloride (0.14 mL, 1.83 mmol). After stirring was 30 min at 23° C. the reaction was diluted with $CH_2Cl_2$ and washed with brine, dried ($Na_2SO_4$), and evaporated to give the title product as an oil. MS m/z 446.3 ($M^+$+1).

Step IV: Preparation of N-(2-Cyclohexyl-2-piperazin-1-yl-ethyl)-N-isobutyl-methanesulfonamide dihydrochloride salt

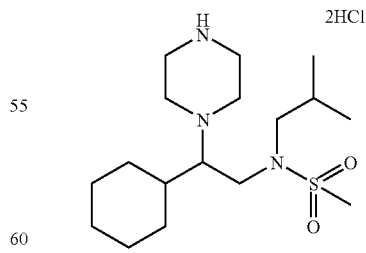

A solution of the product from Step III (446 mg, 1.22 mmol) in 1N HCl/EtOAc (25 mL) was stirred at room temperature overnight. Solvent was removed under reduced pressure and solid washed twice with $Et_2O$ to afford the title compound as a white solid. MS m/z 346.3 ($M^+$+1).

Preparation NA43

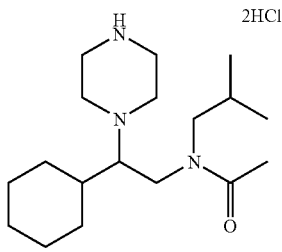

N-(2-Cyclohexyl-2-piperazine-1-yl-ethyl)-N-isobutyl-acetamide dihydrochloride salt Enantiomer A was obtained from Enantiomer I of Preparation NA5. Enantiomer B was obtained from Enantiomer II of Preparation NA5.

Step I: Preparation of 4-[2-(Acetyl-isobutyl-amino)-1-cyclohexyl-ethyl]-piperazine-1-carboxylic acid tert-butyl ester

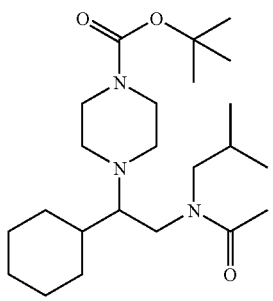

To a solution of the product from Step II of Preparation NA42 (450 mg, 1.22 mmol) in CH$_2$Cl$_2$ (5 mL) was added at 0° C. acetyl chloride (0.1 mL, 1.46 mmol) and pyridine (0.15 mL, 1.83 mmol). The cold bath was removed and the reaction was stirred for 1 hour at 23° C. The reaction mixture was diluted with CH$_2$Cl$_2$ and washed with brine, dried (Na$_2$SO$_4$), and evaporated to the title compound (500 mg). MS m/z 410.3 (M$^+$+1).

Step II: Preparation of N-(2-Cyclohexyl-2-piperazin-1-yl-ethyl)-N-isobutyl-acetamide dihydrochloride salt

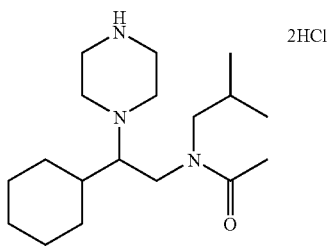

A solution of the product from Step I (500 mg, 1.2.1 mmol) in 1N HCl/EtOAc (25 mL) was stirred at room temperature overnight. Solvent was removed under reduced pressure and solid washed twice with Et$_2$O to afford the title compound as a white solid. MS m/z 310.3 (M$^+$+1).

Preparation NA44

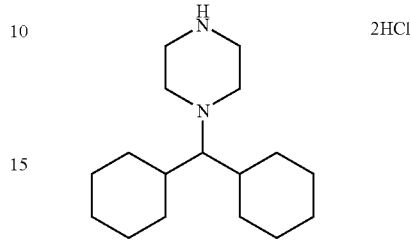

1-Dicyclohexylmethyl-piperazine dihydrochloride salt

Step I: Preparation of 4-Dicyclohexylmethyl-piperazine-1-carboxylic acid tert-butyl ester

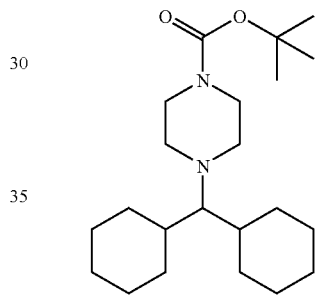

A solution of product from Step I of Preparation NA40 (1.0 g, 3.25 mmol) in THF (30 mL). and cyclohexylmagnesium chloride (8.1 mL, 16.3 mmol, 2 M in THF) was heated at 70° C. for 72 h. After cooling to 0° C., the reaction was quenched with a saturated aqueous solution of NH$_4$Cl and extracted with EtOAc washed with brine, dried (Na$_2$SO$_4$), and evaporated. Final purification by flash chromatography (hexane-EtoAc 15:1) afforded 205 mg of the title compound. MS m/z 364.9 (M$^+$+1).

Step II: Preparation of 1-Dicyclohexylmethyl-piperazine dihydrochloride salt

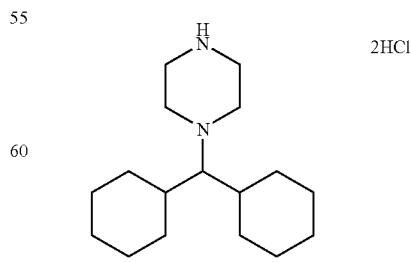

A solution of the product from Step I (200 mg, 0.55 mmol) in 1N HCl/EtOAc (5.5 mL) was stirred at room temperature overnight. Solvent was removed under reduced pressure and solid washed twice with Et$_2$O to afford the title compound as a white solid. MS m/z 264.9 (M$^+$+1).

EXAMPLE N1

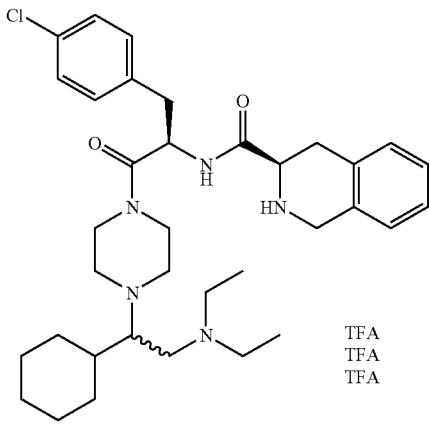

1,2,3,4-Tetrahydro-isoquinoline-3-carboxylic acid {1-(4-chloro-benzyl)-2-[4-(1-cyclohexyl-2-diethy-lamino-ethyl)-piperazin-1-yl]-2-oxo-ethyl}-amide tri(trifluoroacetate) salt.

A mixture of the racemic A domain compound of Preparation NA6 (180 mg, 0.48 mmol, 1 eq.), the BC domain combination of Preparation BC1 (273 mg, 0.58 mmol, 1.2 eq.), HOAT (82 mg, 0.60 mmol, 1.25 eq.), HATU (228 mg, 0.60 mmol, 1.25 eq.) and DIPEA (0.83 mL, 4.8 mmol, 10 eq.) was stirred in CH$_2$Cl$_2$/DMF (4:1, v:v) (3.0 mL) at room temperature overnight. Extractive work up with EtOAc yielded the crude product that was purified by column chromatography. A solution of the N-Boc protected product in methylene chloride/TFA (1:1, v:v) was stirred at room temperature for 2 hours. Solvent was evaporated and residue washed with Et$_2$O to afford the title compound (51). MS m/z 608.6 (M$^+$+1).

EXAMPLE N2

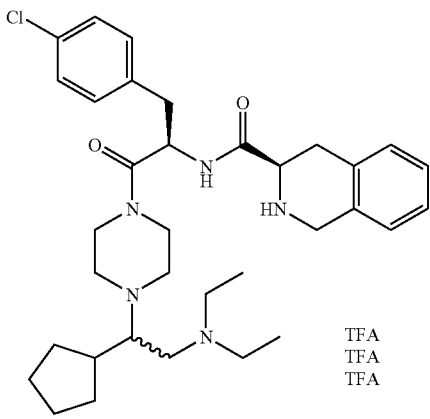

1,2,3,4-Tetrahydro-isoquinoline-3-carboxylic acid {1-(4-chloro-benzyl)-2-[4-(1-cyclopentyl-2-diethy-lamino-ethyl)-piperazin-1-yl]-2-oxo-ethyl}-amide tri(trifluoroacetate) salt According to the procedure described in Example N1, this compound was prepared from the racemic A domain of Preparation NA28 and the BC domain combination of Preparation BC1. MS m/z 594.4 (M$^+$+1).

EXAMPLE N3

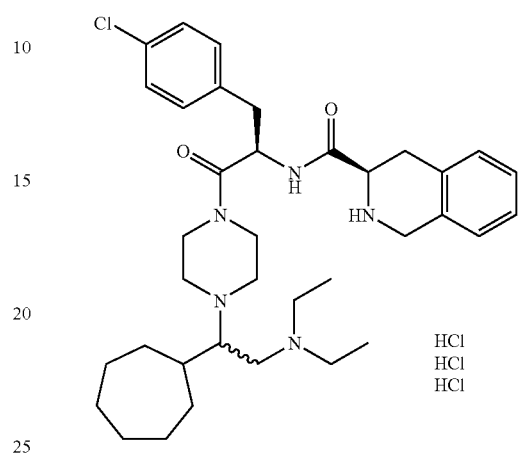

1,2,3,4-Tetrahydro-isoquinoline-3-carboxylic acid {1-(4-chloro-benzyl)-2-[4-(1-cycloheptyl-2-diethy-lamino-ethyl)-piperazin-1-yl]-2-oxo-ethyl}-amide trihydrochloride salt A mixture of the racemic A domain compound of Preparation NA32 (421 mg, 1.07 mmol, 1 eq.), the BC domain combination of Preparation BC1 (567 mg, 1.23 mmol, 1.2 eq.), HOAT (183 mg, 1.34 mmol, 1.25 eq.), HATU (510 mg, 1.34 mmol, 1.25 eq.) and DIPEA (1.87 mL, 10.7 mmol, 10 eq.) was stirred in CH$_2$Cl$_2$/DMF (4:1, v:v) (7.5 mL) at room temperature overnight. Extractive work up with EtOAc yielded the crude product that was purified by column chromatography. A solution of the N-Boc protected product in 1N HCl/EtOAc was stirred at room overnight. Solvent was evaporated and residue washed with Et$_2$O to afford the title compound (79%). MS m/z 622.5 (M$^+$+1).

EXAMPLE N4

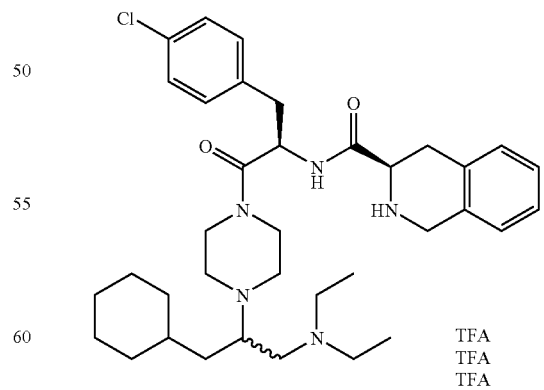

1,2,3,4-Tetrahydro-isoquinoline-3-carboxylic acid {1-(4-chloro-benzyl)-2-[4-(1-cyclohexyl-2-diethy-lamino-ethyl)-piperazin-1-yl]-2-oxo-ethyl}-amide tri(trifluoroacetate) salt According to the procedure described in Example N1, this compound was prepared from the racemic A domain of Preparation NA20 and the BC domain combination of Preparation BC1. MS m/z 622.4 (M$^+$+1)

EXAMPLE N5

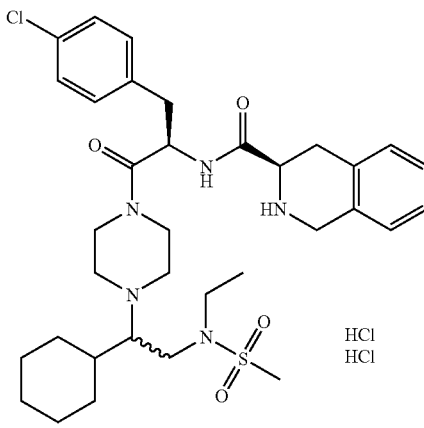

1,2,3,4-Tetrahydro-isoquinoline-3-carboxylic acid (1-(4-chloro-benzyl)-2-{4-[1-cyclohexyl-2-(ethyl-methanesulfonyl-amino)-ethyl]-piperazin-1-yl}-2-oxo-ethyl)-amide dihydrochloride salt According to the procedure described in Example N3, this compound was prepared from the racemic A domain of Preparation NA8 and the BC domain combination of Preparation BC1. MS m/z 658.3 (M$^+$+1)

EXAMPLE N6

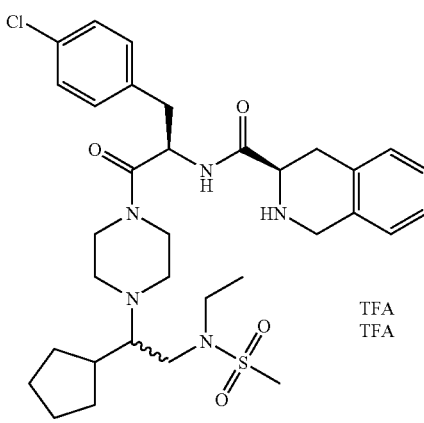

1,2,3,4-Tetrahydro-isoquinoline-3-carboxylic acid (1-(4-chloro-benzyl)-2-{4-[1-cyclopentyl-2-(ethyl-methanesulfonyl-amino)-ethyl]-piperazin-1-yl}-2-oxo-ethyl)-amide dihydrochloride salt According to the procedure described in Example N1, this compound was prepared from the racemic A domain of Preparation NA29 and the BC domain combination of Preparation BC1. MS m/z 644.4 (M$^+$+1)

EXAMPLE N6

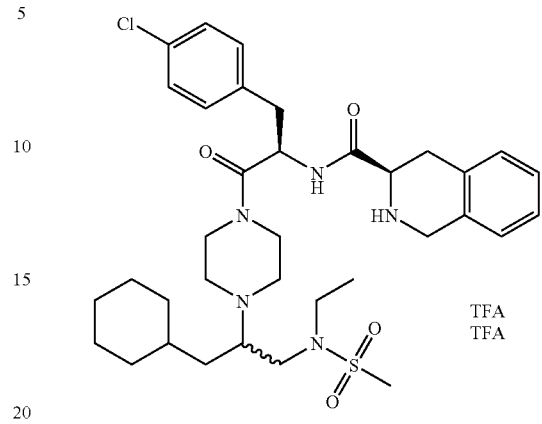

1,2,3,4-Tetrahydro-isoquinoline-3-carboxylic acid (1-(4-chloro-benzyl)-2-{4-[1-cyclohexylmethyl-2-(ethyl-methanesulfonyl-amino)-ethyl]-piperazin-1-yl}-2-oxo-ethyl)-amide dihydrochloride salt According to the procedure described in Example N1, this compound was prepared from the racemic A domain of Preparation NA25 and the BC domain combination of Preparation BC1. MS m/z 672.3 (M$^+$+1)

EXAMPLE N7

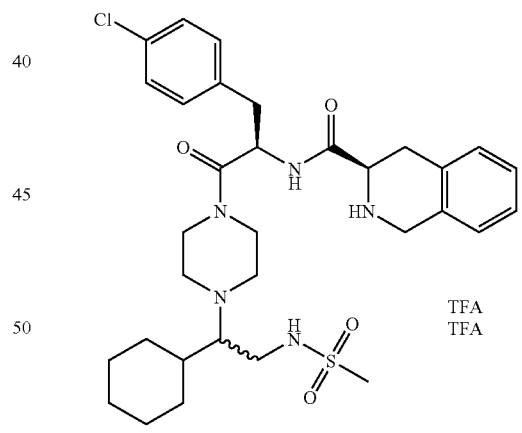

1,2,3,4-Tetrahydro-isoquinoline-3-carboxylic acid {1-(4-chloro-benzyl)-2-[4-[1-cyclohexyl-2-methane-sulfonylamino-ethyl)-piperazin-1-yl]-2-oxo-ethyl}-amide di(trifluoroacetate) salt According to the procedure described in Example N1, this compound was prepared from the racemic A domain of Preparation NA7 and the BC domain combination of Preparation BC1. MS m/z 630.2 (M$^+$+1)

EXAMPLE N8

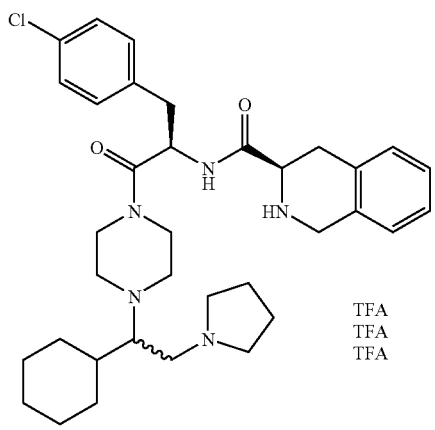

1,2,3,4-Tetrahydro-isoquinoline-3-carboxylic acid {1-(4-chloro-benzyl)-2-[4-(1-cyclohexyl-2-pyrrolidin-1-yl-ethyl)-piperazin-1-yl]-2-oxo-ethyl}-amide tri(trifluoroacetate) salt According to the procedure described in Example N1, this compound was prepared from the racemic A domain of Preparation NA9 and the BC domain combination of Preparation BC1. MS m/z 606.4 (M$^+$+1)

EXAMPLE N9

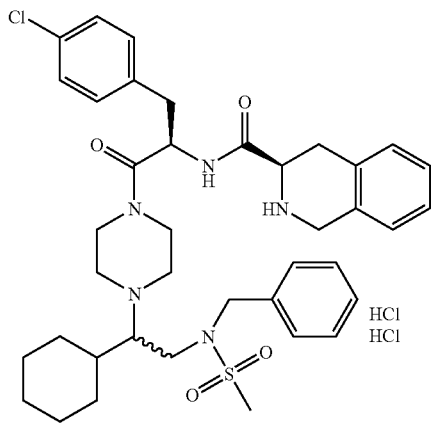

1,2,3,4-Tetrahydro-isoquinoline-3-carboxylic acid [2-{4-[2-(benzyl-methanesulfonyl-amino)-1-cyclohexyl-ethyl]-piperazin-1-yl}-1-(4-chloro-benzyl)-2-oxo-ethyl]-amide dihydrochloride salt According to the procedure described in Example N3, this compound was prepared from the racemic A domain of Preparation NA11 and the BC domain combination of Preparation BC1. MS m/z 720.4 (M$^+$+1)

EXAMPLE N10

1,2,3,4-Tetrahydro-isoquinoline-3-carboxylic acid (1-(4-chloro-benzyl)-2-{4-[1-cyclohexyl-2-(1,3-dioxo-1,3-dihydro-isoindol-2-yl)-ethyl]-piperazin-1-yl}-2-oxo-ethyl)-amide di(trifluoroacetate) salt According to the procedure described in Example N1, this compound was prepared from the racemic A domain of Preparation NA10 and the BC domain combination of Preparation BC1. MS m/z 682.4 (M$^+$+1)

EXAMPLE N11

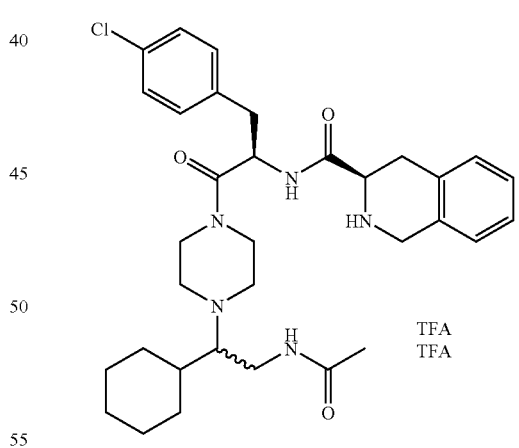

1,2,3,4-Tetrahydro-isoquinoline-3-carboxylic acid [2-[4-[(2-acetylamino-1-cyclohexyl-ethyl)-piperazin-1-yl]-1-(4-chloro-benzyl)-2-oxo-ethyl]-amide di(trifluoroacetate) salt According to the procedure described in Example N1, this compound was prepared from the racemic A domain of Preparation NA12 and the BC domain combination of Preparation BC1. MS m/z 594.3 (M$^+$+1)

EXAMPLE N12

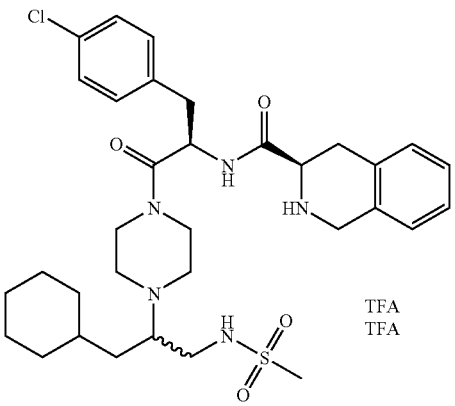

1,2,3,4-Tetrahydro-isoquinoline-3-carboxylic acid {1-(4-chloro-benzyl)-2-[4-[1-cyclohexylmethyl-2-methanesulfonylamino-ethyl]-piperazin-1-yl]-2-oxo-ethyl}-amide di(trifluoroacetate) salt According to the procedure described in Example N1, this compound was prepared from the racemic A domain of Preparation NA24 and the BC domain combination of Preparation BC1. MS m/z 644.3 (M$^+$+1)

EXAMPLE N13

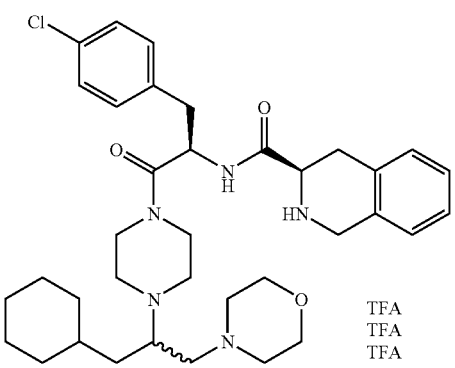

1,2,3,4-Tetrahydro-isoquinoline-3-carboxylic acid {1-(4-chloro-benzyl)-2-[4-[1-cyclohexylmethyl-2-morpholin-4-yl-ethyl]-piperazin-1-yl]-2-oxo-ethyl}-amide tri (trifluoroacetate) salt According to the procedure described in Example N1, this compound was prepared from the racemic A domain of Preparation NA23 and the BC domain combination of Preparation BC1. MS m/z 636.4 (M$^+$+1)

EXAMPLE N14

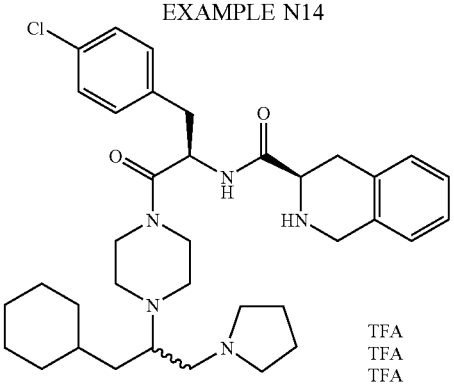

1,2,3,4-Tetrahydro-isoquinoline-3-carboxylic acid {1-(4-chloro-benzyl)-2-[4-[1-cyclohexylmethyl-2-pyrrolidin-1-yl-ethyl]-piperazin-1-yl]-2-oxo-ethyl}-amide tri (trifluoroacetate) salt According to the procedure described in Example N1, this compound was prepared from the racemic A domain of Preparation NA21 and the BC domain combination of Preparation BC1. MS m/z 620.4 (M$^+$+1)

EXAMPLE N15

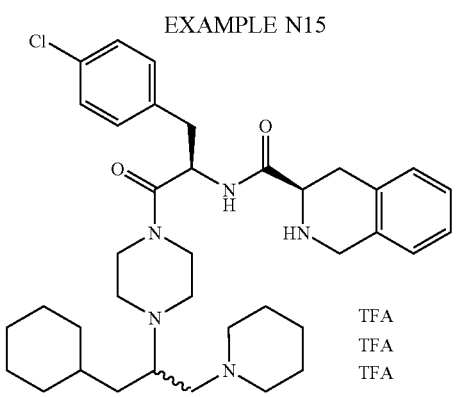

1,2,3,4-Tetrahydro-isoquinoline-3-carboxylic acid {1-(4-chloro-benzyl)-2-[4-[1-cyclohexylmethyl-2-piperidin-1-yl-ethyl]-piperazin-1-yl]-2-oxo-ethyl}-amide tri (trifluoroacetate) salt According to the procedure described in Example N1, this compound was prepared from the racemic A domain of Preparation NA22 and from the BC domain combination of Preparation BC1. MS m/z 634.4 (M$^+$+1)

EXAMPLE N16

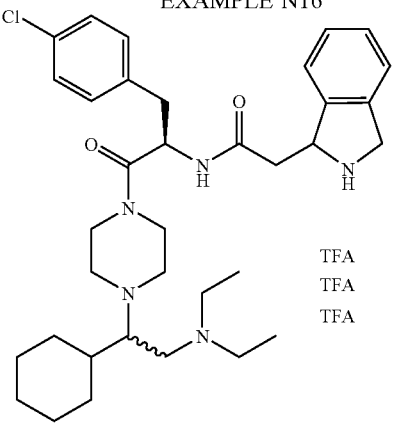

N-{1-(4-chloro-benzyl)-2-[4-(1-cyclohexyl-2-diethylamino-ethyl)-piperazin-1-yl]-2-oxo-ethyl}-2-(2,3-dihydro-1H-isoindol-1-yl)-acetamide tri(trifluoroacetate) salt According to the procedure described in Example N1, this compound was prepared from the racemic A domain of Preparation NA6 and from the BC domain combination of Preparation BC2. MS m/z 608.4 (M++1)

EXAMPLE N17

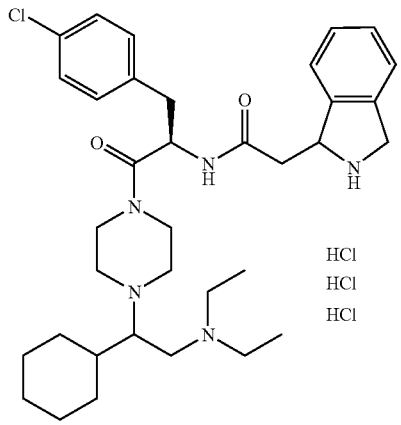

N-{1-(4-chloro-benzyl)-2-[4-(1-cyclohexyl-2-di-ethylamino-ethyl)-piperazin-1-yl]-2-oxo-ethyl}-2-(2,3-dihydro-1H-isoindol-1-yl)-acetamide trihydrochloride salt A mixture of the A domain compound of preparation NA6 (Isomer 1 of Method A) (441 mg, 1.17 mmol, 1 eq.), the BC domain combination of Preparation BC2 (644 mg, 1.40 mmol, 1.2 eq.), HOAT (199 mg, 1.46 mmol, 1.25 eq.), HATU (555 mg, 1.46 mmol, 1.25 eq.) and DIPEA (2.03 mL, 11.7 mmol, 10 eq.) was stirred in CH$_2$Cl$_2$/DMF (4:1, v:v) (7.5 mL) at room temperature overnight. Reaction mixture was diluted with water and aqueous layer was extracted with CH$_2$Cl$_2$. Combined organic layers were dried (MgSO$_4$), filtered and concentrated to give a crude product that was purified by column chromatography. A solution of the N-BOC protected product in CH$_2$Cl$_2$/TFA (1:1, v:v) was stirred at room temperature for 30 min. Solvent was evaporated and residue washed with Et$_2$O and taken into 0.1N HCl (10 eq.). Solution was solidified at −78° C. and the solid lyophilized to afford the title compound (331 mg). MS m/z 608.4 (M++1).

EXAMPLE N18

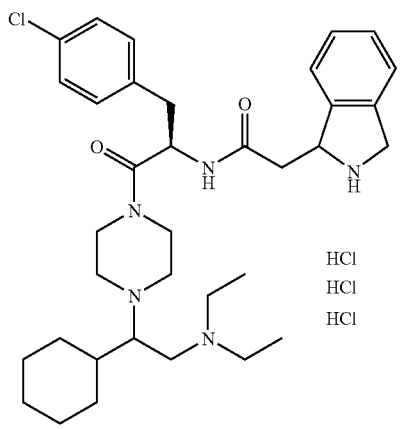

N-{1-(4-chloro-benzyl)-2-[4-(1-cyclohexyl-2-diethylamino-ethyl)-piperazin-1-yl]-2-oxo-ethyl}-2-(2,3-dihydro-1H-isoindol-1-yl)-acetamide trihydrochloride salt According to the procedure described in Example N17, this compound was prepared from the A domain of preparation NA6 (Isomer 2 of Method A) and from the BC domain combination of Preparation BC2. MS m/z 608.4 (M++1)

EXAMPLE N19

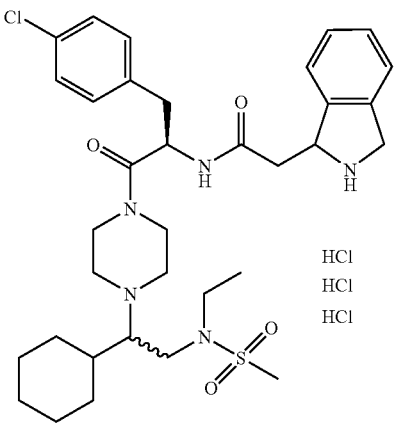

N-{1-(4-chloro-benzyl)-2-{4-[1-cyclohexyl-2-(ethyl-methanesulfonyl-amino)-ethyl]-piperazin-1-yl}-2-oxo-ethyl)-2-(2,3-dihydro-1H-isoindol-1-yl)-acetamide dihydrochloride salt According to the procedure described in Example N17, this compound was prepared from the racemic A domain of preparation NA8 and from the BC domain combination of Preparation BC2. MS m/z 658.3 (M++1)

EXAMPLE N20

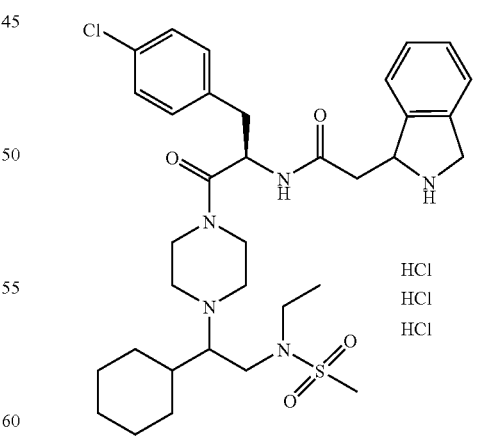

N-{1-(4-chloro-benzyl)-2-{4-[1-cyclohexyl-2-(ethyl-methanesulfonyl-amino)-ethyl]-piperazin-1-yl}-2-oxo-ethyl)-2-(2,3-dihydro-1H-isoindol-1-yl)-acetamide dihydrochloride salt According to the procedure described in Example N17, this compound was prepared from the A domain of prepration A8 (Isomer 1 of Method A) and from the BC domain combination of Preparation BC2. MS m/z 658.3 (M$^+$+1)

EXAMPLE N21

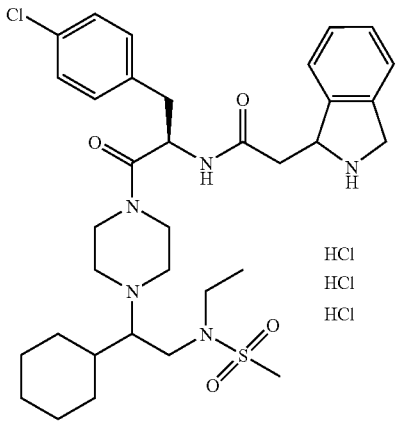

HCl
HCl
HCl

N-{1-(4-chloro-benzyl)-2-{4-[1-cyclohexyl-2-(ethyl-methanesulfonyl-amino)-ethyl]-piperazin-1-yl}-2-oxo-ethyl}-2-(2,3-dihydro-2H-isoindol-1-yl)-acetamide dihydrochloride salt According to the procedure described in Example N17, this compound was prepared from the A domain of preparation NA8 (Isomer 2 of Method A) and from the BC domain combination of Preparation BC2. MS m/z 658.3 (M$^+$+1)

EXAMPLE N22

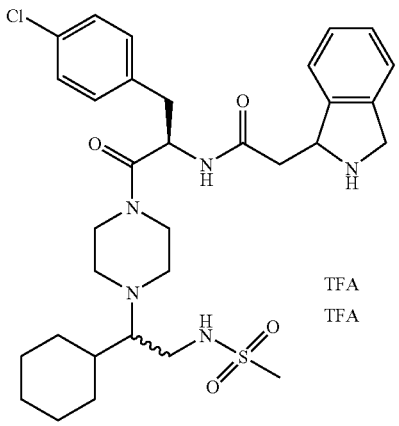

TFA
TFA

N-{1-(4-chloro-benzyl)-2-[4-(1-cyclohexyl-2-methanesulfonylamino-ethyl)-piperazin-1-yl]-2-oxo-ethyl}-2-(2,3-dihydro-1H-isoindol-1-yl)-acetamide di(trifluoroacetate) salt According to the procedure described in Example N1, this compound was prepared from the racemic A domain of preparation NA7 and from the BC domain combination of Preparation BC2. MS m/z 630.3 (M$^+$+1)

EXAMPLE N23

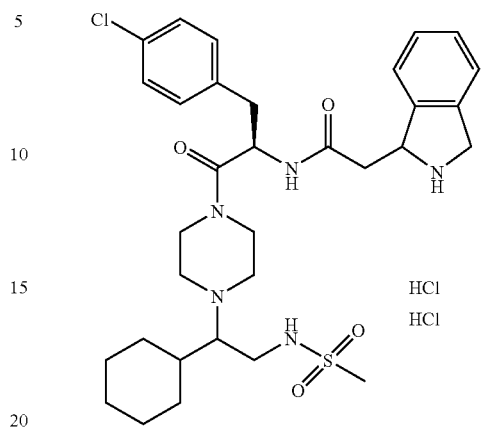

HCl
HCl

N-{1-(4-chloro-benzyl)-2-[4-(1-cyclohexyl-2-methanesulfonylamino-ethyl)-piperazin-1-yl]-2-oxo-ethyl}-2-(2,3-dihydro-1H-isoindol-1-yl)-acetamide di(trifluoroacetate) salt According to the procedure described in Example N17, this compound was prepared from the A domain of Preparation NA7 (Enantiomer A of Method B) and from the BC domain combination of Preparation BC2. MS m/z 630.3 (M$^+$+1)

EXAMPLE 24

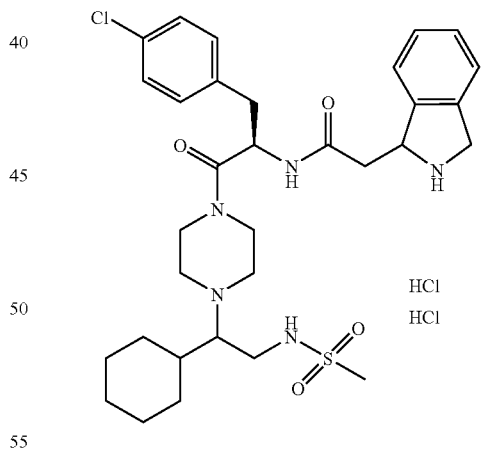

HCl
HCl

N-{1-(4-chloro-benzyl)-2-[4-(1-cyclohexyl-2-methanesulfonylamino-ethyl)-piperazin-1-yl]-2-oxo-ethyl}-2-(2,3-dihydro-1H-isoindol-1-yl)-acetamide di(trifluoroacetate) salt According to the procedure described in Example N17, this compound was prepared from the A domain of Preparation NA7 (Enantiomer B of Method B) and from the BC domain combination of Preparation BC2. MS m/z 658.3 (M$^+$+1)

EXAMPLE N25

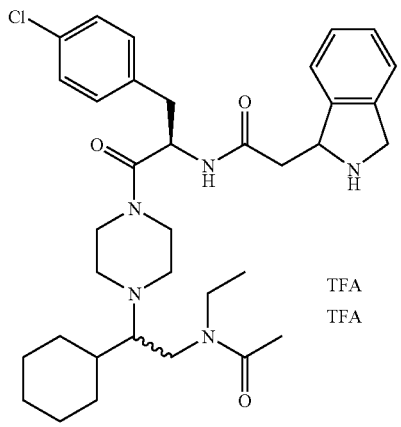

TFA
TFA

N-[2-{4-(Acethyl-ethyl-amino)-1-cyclohexyl-ethyl]-
piperazin-1-yl}-1-(4-chloro-benzyl)-2-oxo-ethyl]-2-
(2,3-dihydro-1H-isoindol-1-yl)-acetamide di(trifluo-
roacetate) salt According to the procedure described in Example N1, this compound was prepared from the racemic A domain of Preparation NA13 and from the BC domain combination of Preparation BC2. MS m/z 622.4 (M$^+$+1)

EXAMPLE N26

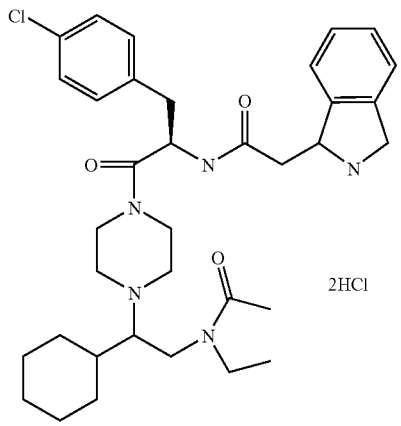

2HCl

N-[2-{4-(Acethyl-ethyl-amino)-1-cyclohexyl-ethyl]-
piperazin-1-yl}-1-(4-chloro-benzyl)-2-oxo-ethyl]-2-
(2,3-dihydro-1H-isoindol-1-yl)-acetamide dihydro-
chloride salt According to the procedure described in Example N17, this compound was prepared from the A domain of Preparation NA13 (Enantiomer A) and from the BC domain combination of Preparation BC2. MS m/z 622.4 (M$^+$+1)

EXAMPLE N27

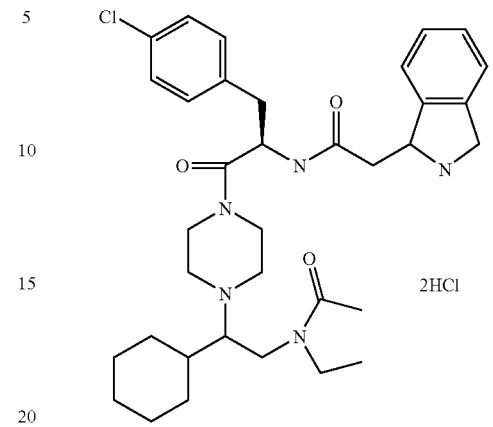

2HCl

N-[2-{4-(Acethyl-ethyl-amino)-1-cyclohexyl-ethyl]-
piperazin-1-yl}-1-(4-chloro-benzyl)-2-oxo-ethyl]-2-
(2,3-dihydro-1H-isoindol-1yl)-acetamide dihydro-
chloride salt According to the procedure described in Example N17, this compound was prepared from the A domain of Preparation NA13 (Enantiomer B) and from the BC domain combination of Preparation BC2. MS m/z 622.4 (M$^+$+1)

EXAMPLE N28

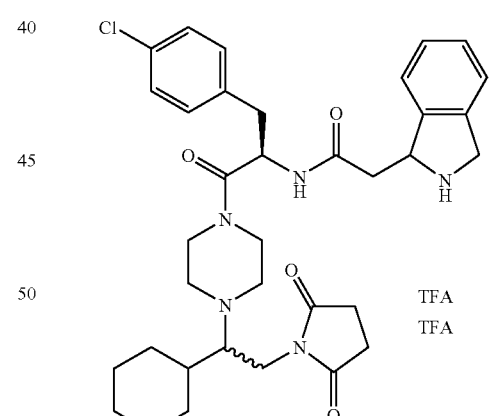

TFA
TFA

N-(1-(4-chloro-benzyl)2-{4-[1-cyclohexyl-2-(2,5-
dioxo-pyrrolidin-yl)-ethyl]-piperazin-1-yl}-2-oxo-
ethyl]-2-(2,3-dihydro-1H-isoindol-1-yl)-acetamide
di(trifluoroacetate) salt According to the procedure described in Example N1, this compound was prepared from the racemic A domain of Preparation NA15 and from the BC domain combination of Preparation BC2. MS m/z 634.3 (M$^+$+1)

EXAMPLE N29

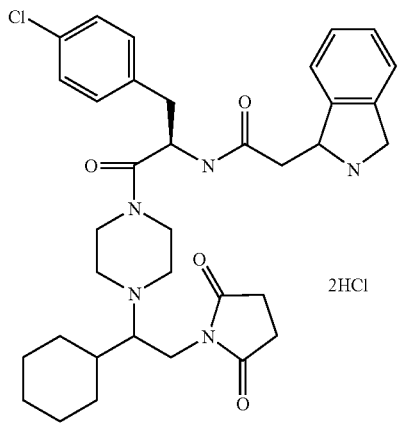

2HCl

N-(1-(4-chloro-benzyl)2-{4-[1-cyclohexyl-2-(2,5-dioxo-pyrrolidin-yl)-ethyl]-piperazin-1-yl}-2-oxo-ethyl]-2-(2,3-dihydro-1H-isoindol-1-yl)-acetamide dihydrochloride salt According to the procedure described in Example N17, this compound was prepared from the A domain of Preparation of A15 (Enantiomer A of Method B) and from the BC domain combination of Preparation BC2. MS m/z 634.3 ($M^+$+1)

EXAMPLE N30

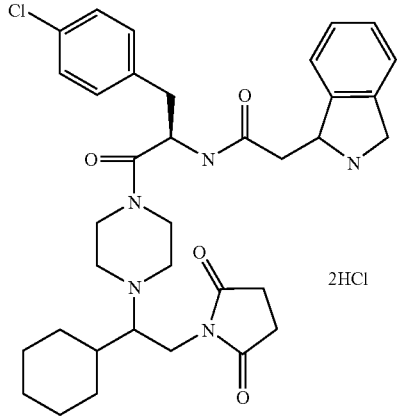

2HCl

N-(1-(4-chloro-benzyl)2-{4-[1-cyclohexyl-2-(2,5-dioxo-pyrrolidin-yl)-ethyl]-piperazin-1-yl}-2-oxo-ethyl]-2-(2,3-dihydro-1H-isoindol-1-yl)-acetamide dihydrochloride salt According to the procedure described in Example N17, this compound was prepared from the A domain of Preparation NA15 (Enantiomer B of Method B) and from the BC domain combination of Preparation BC2. MS m/z 634.3 ($M^+$+1)

EXAMPLE N31

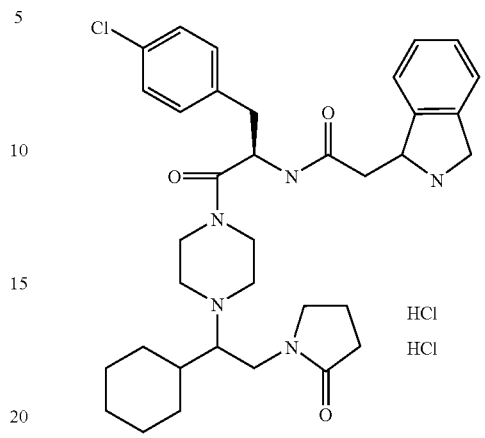

HCl
HCl

N-(1-(4-chloro-benzyl)2-{4-[1-cyclohexyl-2-(2-oxo-pyrrolidin-yl)-ethyl]-piperazin-1-yl}-2-oxo-ethyl]-2-(2,3-dihydro-1H-isoindol-1-yl)-acetamide dihydrochloride salt According to the procedure described in Example N17, this compound was prepared from the A domain of Preparation NA14 (Enantiomer A) and from the BC domain combination of Preparation BC2. MS m/z 620.2 ($M^+$+1)

EXAMPLE N32

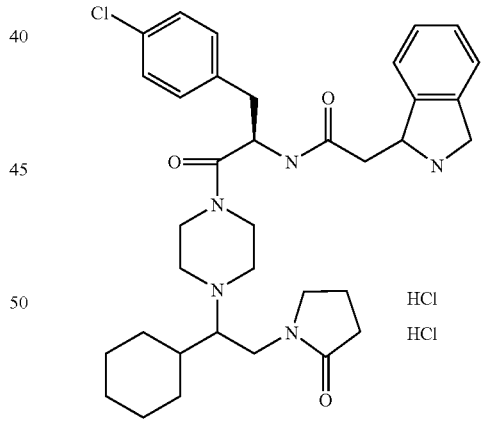

HCl
HCl

N-(1-(4-chloro-benzyl)2-{4-[1-cyclohexyl-2-(2-oxo-pyrrolidin-yl)-ethyl]-piperazin-1-yl}-2-oxo-ethyl]-2-(2,3-dihydro-1H-isoindol-1-yl)-acetamide dihydrochloride salt According to the procedure described in Example N17, this compound was prepared from the A domain of Preparation NA14 (Enantiomer B) and from the BC domain combination of Preparation BC2. MS m/z 620.2 ($M^+$+1)

EXAMPLE N33

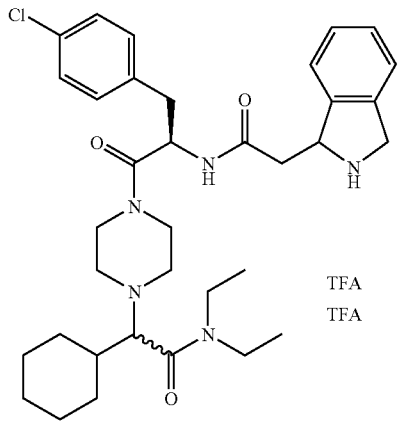

TFA
TFA

2-{4-[3-(4-Chloro-benzyl)2-(2-2,3-dihydro-1H-isoindol-1-yl-acetylamino)-propionyl]-piperazin-1-yl}-3-cyclohexyl-N,N-diethyl-propionamide di(trifluoroacetate) salt According to the procedure described in Example N1, this compound was prepared from the racemic A domain of Preparation NA16 and from the BC domain combination of Preparation BC2. MS m/z 622.4 (M$^+$+1)

EXAMPLE N34

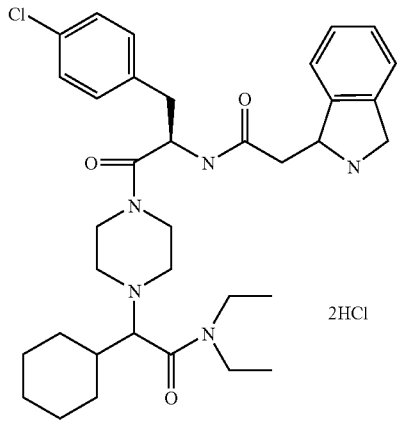

2HCl

2-{4-[3-(4-Chloro-benzyl)2-(2-2,3-dihydro-1H-isoindol-1-yl-acetylamino)-propionyl]-piperazin-1-yl}-3-cyclohexyl-N,N-diethyl-propionamide dihydrochloride salt According to the procedure described in Example N17, this compound was prepared from the A domain of Preparation NA16 (Enantiomer A) and from the BC domain combination of Preparation BC2. MS m/z 622.4 (M$^+$+1)

EXAMPLE N35

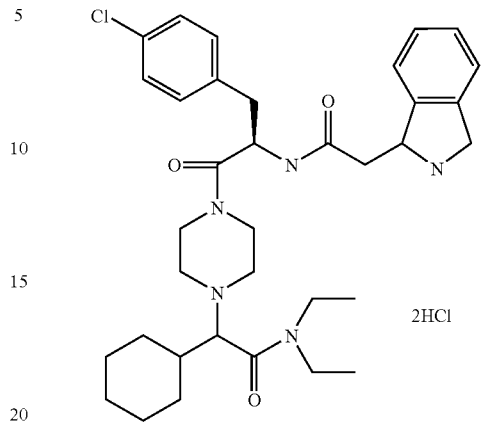

2HCl

2-{4-[3-(4-Chloro-benzyl)2-(2-2,3-dihydro-1H-isoindol-1-yl-acetylamino)-propionyl]-piperazin-1-yl}-3-cyclohexyl-N,N-diethyl-propionamide dihydrochloride salt According to the procedure described in Example N17, this compound was prepared from the A domain of Preparation NA16 (Enantiomer B) and from the BC domain combination of Preparation BC2. MS m/z 622.4 (M$^+$+1)

EXAMPLE N36

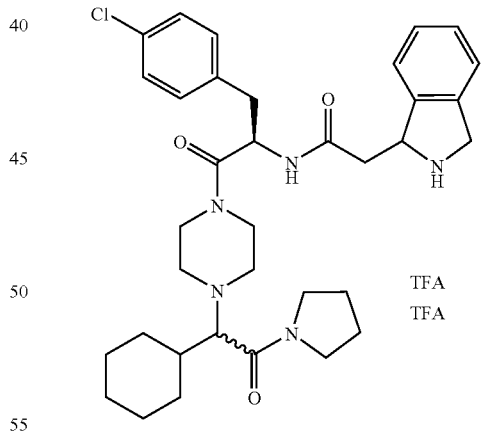

TFA
TFA

N-(1-(4-chloro-benzyl)2-[4-(1-cyclohexyl-2-oxo-2-pyrrolidin-yl-ethyl)-piperazin-1-yl]-2-oxo-ethyl}-2-(2,3-dihydro-1H-isoindol-1-yl)-acetamide di(trifluoroacetate) salt According to the procedure described in Example N1, this compound was prepared from the racemic A domain of Preparation NA17 and from the BC domain combination of Preparation BC2. MS m/z 620.4 (M$^+$+1)

EXAMPLE N37

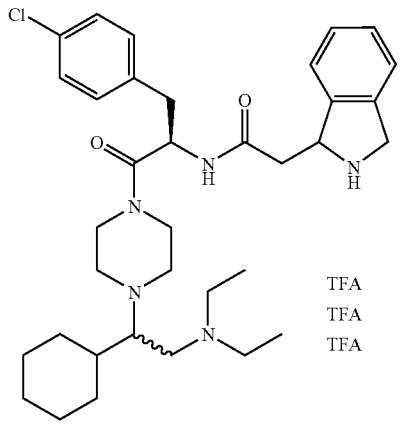

N-{1-(4-chloro-benzyl)-2-[4-(1-cyclohexylmethyl-2-diethylamino-ethyl)-piperazin-1-yl]-2-oxo-ethyl}-2-(2,3-dihydro-1H-isoindol-1-yl)-acetamide tri(trifluoroacetate) salt According to the procedure described in Example N1, this compound was prepared from the racemic A domain of Preparation NA20 and from the BC domain combination of Preparation BC2. MS m/z 622.4 (M$^+$+1)

EXAMPLE N38

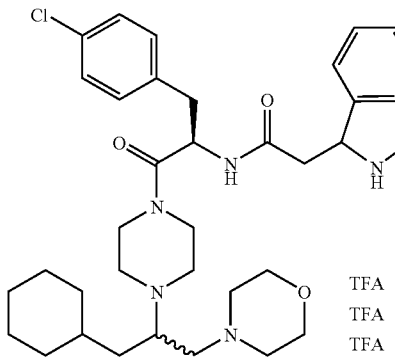

N-{1-(4-chloro-benzyl)-2-[4-(1-cyclohexylmethyl-2-morpholine-4-yl-ethyl)-piperazin-1-yl]-2-oxo-ethyl}-2-(2,3-dihydro-1H-isoindol-1-yl)-acetamide tri(trifluoroacetate) salt According to the procedure described in Example N1, this compound was prepared from the racemic A domain of Preparation NA23 and from the BC domain combination of Preparation BC2. MS m/z 636.4 (M$^+$+1)

EXAMPLE N39

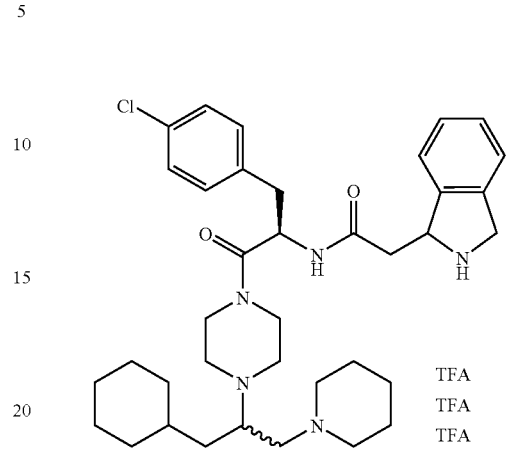

N-{1-(4-chloro-benzyl)-2-[4-(1-cyclohexylmethyl-2-piperidin-1-yl-ethyl)-piperazin-1-yl]-2-oxo-ethyl}-2-(2,3-dihydro-1H-isoindol-1-yl)-acetamide tri(trifluoroacetate) salt According to the procedure described in Example N1, this compound was prepared from the racemic A domain of Preparation NA22 and from the BC domain combination of Preparation BC2. MS m/z 634.4 (M$^+$+1)

EXAMPLE N40

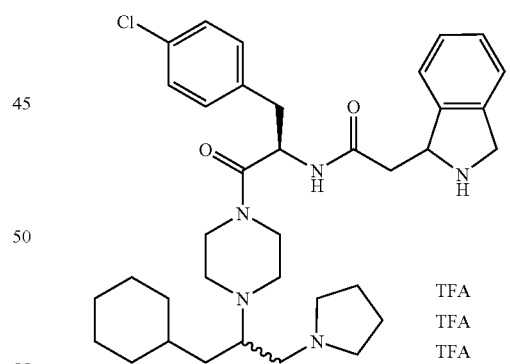

N-{1-(4-chloro-benzyl)-2-[4-(1-cyclohexylmethyl-2-pyrrolidin-1-yl-ethyl)-piperazin-1-yl]-2-oxo-ethyl}-2-(2,3-dihydro-1H-isoindol-1-yl)-acetamide tri(trifluoroacetate) salt According to the procedure described in Example N1, this compound was prepared from the racemic A domain of Preparation NA21 and from the BC domain combination of Preparation BC2. MS m/z 620.4 (M$^+$+1)

EXAMPLE N41

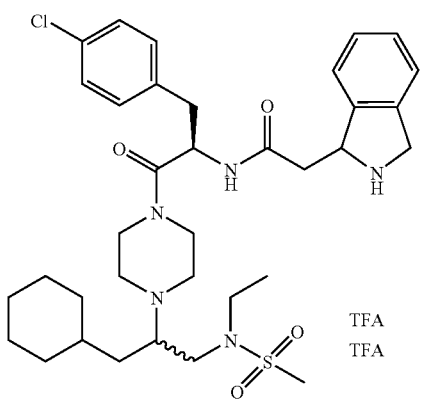

N-{1-(4-chloro-benzyl)-2-(4-[1-cyclohexylmethyl-2-
(ethyl-methanesulfonyl-amino)-ethyl]-piperazin-1-
yl}-2-oxo-ethyl)-2-(2,3-dihydro-1H-isoindol-1-yl)-
acetamide dihydrochloride salt According to the procedure described in Example N1, this compound was prepared from the racemic A domain of Preparation NA25 and from the BC domain combination of Preparation BC2. MS m/z 672.3 (M$^+$+1)

EXAMPLE N42

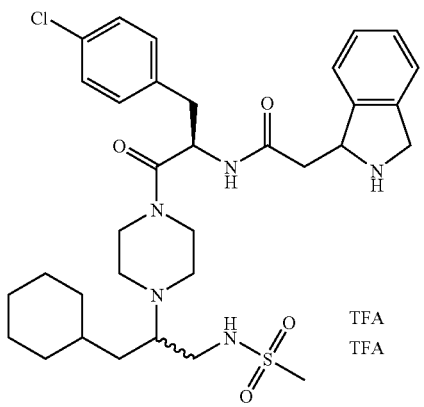

N-{1-(4-chloro-benzyl)-2-[4-(1-cyclohexylmethyl-2-
methanesulfonylamino-ethyl)-piperazin-1-yl]-2-oxo-
ethyl}-2-(2,3-dihydro-1H-isoindol-1-yl)-acetamide
di(trifluoroacetate) salt According to the procedure described in Example N1, this compound was prepared from the racemic A domain of Preparation NA24 and from the BC domain combination of Preparation BC2. MS m/z 644.4 (M$^+$+1)

EXAMPLE N43

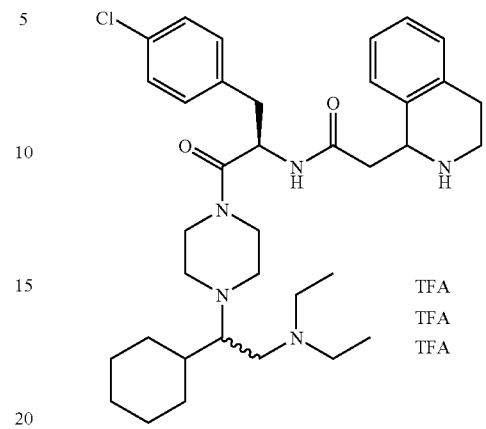

N-{1-(4-chloro-benzyl)-2-[4-(1-cyclohexyl-2-diethy-
lamino-ethyl)-piperazin-1-yl]-2-oxo-ethyl}-2-(1,2,3,
4-tetrahydro-isoquinolin-1-yl)-acetamide tri(trifluo-
roacetate) salt According to the procedure described in Example N1, this compound was prepared from the racemic A domain of Preparation NA6 and from the BC domain combination of Preparation BC13. MS m/z 622.4 (M$^+$+1).

EXAMPLE N44

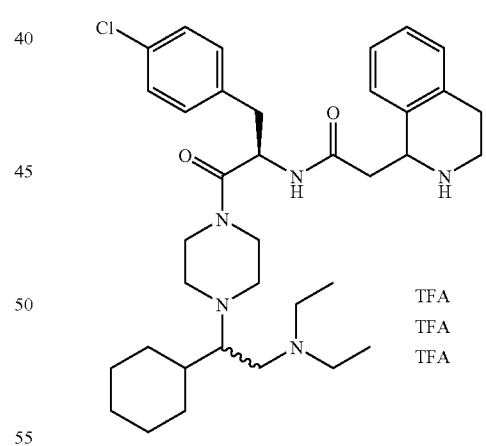

N-{1-(4-chloro-benzyl)-2-[4-(1-cyclohexyl-2-diethy-
lamino-ethyl)-piperazin-1-yl]-2-oxo-ethyl}-2-(1,2,3,
4-tetrahydro-isoquinolin-1-yl)-acetamide tri(trifluo-
roacetate) salt According to the procedure described in Example N1, this compound was prepared from the racemic A domain of Preparation NA6 and from the BC domain combination of Preparation BC12. MS m/z 622.4 (M$^+$+1)

EXAMPLE N45

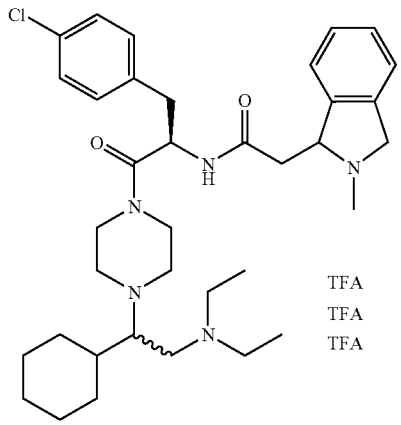

TFA
TFA
TFA

N-{1-(4-chloro-benzyl)-2-[4-(1-cyclohexyl-2-diethylamino-ethyl)-piperazin-1-yl]-2-oxo-ethyl}-2-(2-methyl-2,3-dihydro-1H-isoindol-1-yl)-acetamide tri(trifluoroacetate) salt According to the procedure described in Example N1, this compound was prepared from the racemic A domain of Preparation NA6 and from the BC domain combination of Preparation BC14. MS m/z 622.4 (M$^+$+1)

EXAMPLE N46

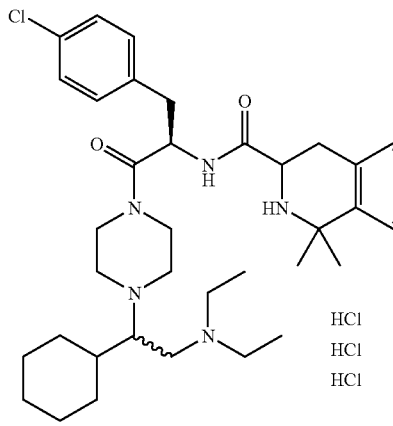

HCl
HCl
HCl 1,1-Dimethyl-1,2,3,4-tetrahydro-isoquinoline-3-carboxylic acid {1-(4-chloro-benzyl)-2-[4-(1-cyclohexyl-2-diethylamino-ethyl)-piperazin-1-yl]-2-oxoethyl}-amide trihydrochloride salt According to the procedure described in Example N17, this compound was prepared from the racemic A domain of Preparation NA6 and from the BC domain combination of Preparation BC11 (Diastereomer 1). MS m/z 636.2 (M$^+$+1)

EXAMPLE N47

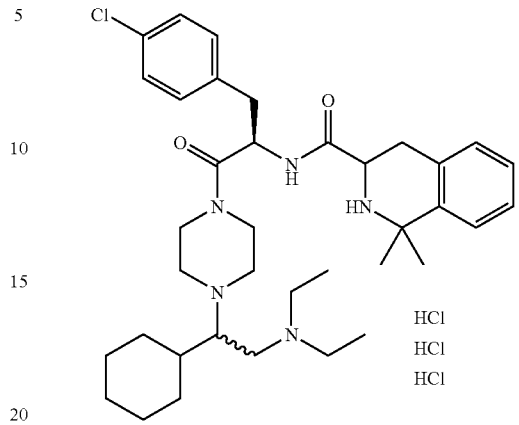

HCl
HCl
HCl 1,1-Dimethyl-1,2,3,4-tetrahydro-isoquinoline-3-carboxylic acid {1-(4-chloro-benzyl)-2-[4-(1-cyclohexyl-2-diethylamino-ethyl)-piperazin-1-yl]-2-oxoethyl}-amide trihydrochloride salt According to the procedure described in Example N17, this compound was prepared from the racemic A domain of Preparation NA6 and from the BC domain combination of Preparation BC11 (Diastereomer 2). MS m/z 636.2 (M$^+$+1)

EXAMPLE N48

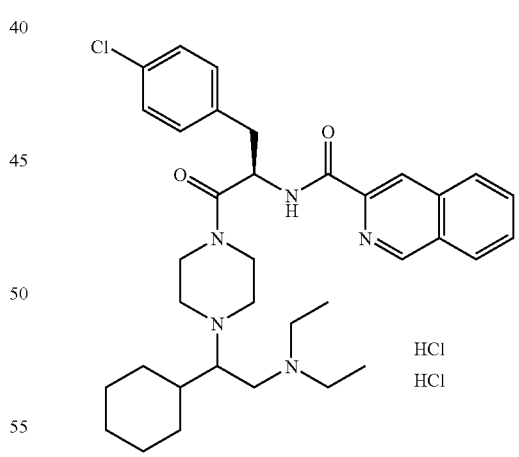

HCl
HCl

Isoquinoline-3-carboxylic acid {1-(4-chloro-benzyl)-2-[4-(1-cyclohexyl-2-diethylamino-ethyl)-piperazin-1-yl]-2-oxo-ethyl}-amide dihydrochloride salt According to the procedure described in Example N3, this compound was prepared from the A domain of Preparation NA6 (Enantiomer B Method B) and from the BC domain combination of Preparation BC15. MS m/z 604.3 (M$^+$+1)

EXAMPLE N49

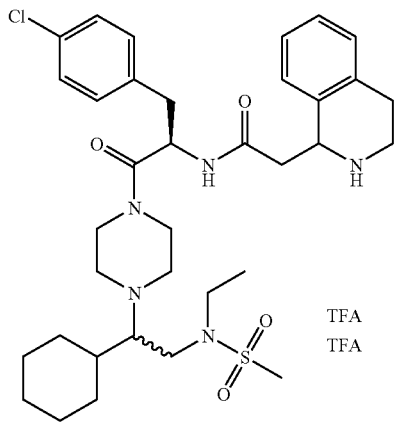

N-{1-(4-chloro-benzyl)-2-[4-(1-cyclohexyl-2-(ethyl-methanesulfonyl-amino)-ethyl]-piperazin-1-yl]-2oxo-ethyl}-2-(1,2,3,4-tetrahydro-isoquinolin-1-yl)-acetamide di(trifluoroacetate) salt According to the procedure described in Example N1, this compound was prepared from the racemic A domain of Preparation NA8 and from the BC domain combination of Preparation BC12. MS m/z 672.3 (M⁺+1)

EXAMPLE 50

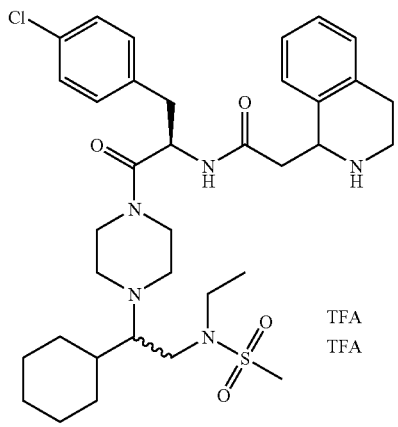

N-{1-(4-chloro-benzyl)-2-[4-(1-cyclohexyl-2-(ethyl-methanesulfonyl-amino)-ethyl]-piperazin-1-yl]-2-oxo-ethyl}-2-(1,2,3,4-tetrahydro-isoquinolin-1-yl)-acetamide di(trifluoroacetate) salt According to the procedure described in Example N1, this compound was prepared from the racemic A domain of Preparation NA8 and from the BC domain combination of Preparation BC13. MS m/z 672.3 (M⁺+1)

EXAMPLE N51

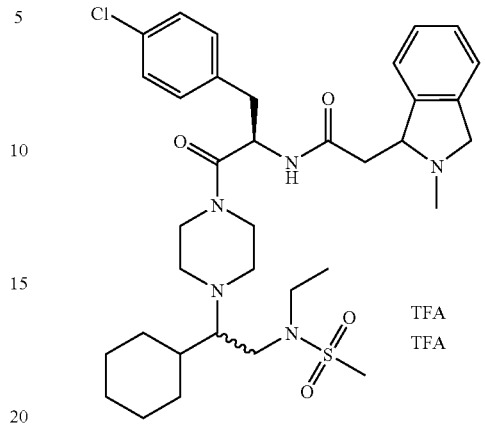

N-{1-(4-chloro-benzyl)-2-{4-[1-cyclohexyl-2-(ethyl-methanesulfonyl-amino)-ethyl]-piperazin-1-yl}-2-oxo-ethyl)-2-(2-methyl-2,3-dihydro-1H-isoindol-1-yl)-acetamide di(trifluoroacetate) salt According to the procedure described in Example N1, this compound was prepared from the racemic A domain of Preparation NA8 and from the BC domain combination of Preparation BC14. MS m/z 672.3 (M⁺+1)

EXAMPLE N52

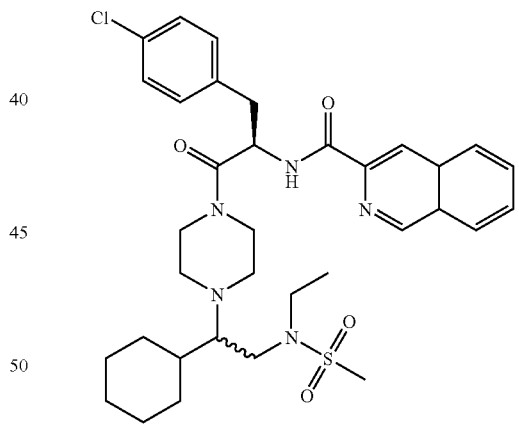

Isoquinoline-3-carboxylic acid {1-(4-chloro-benzyl)-2-{4-[1-cyclohexyl-2-(ethyl-methanesulfonyl-amino)-ethyl]-piperazin-1-yl}-2-oxo-ethyl}-amide A mixture of the racemic A domain compound of Preparation NA8 (1 eq.), the BC domain combination of Preparation BC15 (1.2 eq.), HOAT (1.25 eq.), HATU (1.25 eq.) and DIPEA (10 eq.) was stirred in CH$_2$Cl$_2$/DMF (4:1, v:v) at room temperature overnight. Reaction mixture was diluted with water and aqueous layer was extracted with CH$_2$Cl$_2$. Combined organic layers were dried (MgSO$_4$), filtered and concentrated to give a crude product that was purified by column chromatography. MS m/z 654.2 (M⁺+1)

EXAMPLE N53

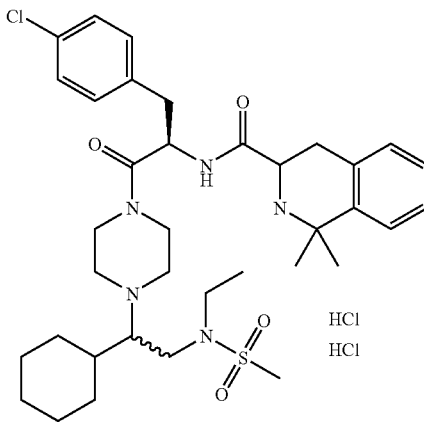

1,1-Dimethyl-1,2,3,4-Tetrahydro-isoquinoline-3-carboxylic acid (1-(4-chloro-benzyl)-2-{4-[1-cyclohexylmethyl-2-(ethyl-methanesulfonyl-amino)-ethyl]-piperazin-1-yl}-2-oxo-ethyl)-amide dihydrochloride salt According to the procedure described in Example N17, this compound was prepared from the A domain of Preparation NA8 (Enantiomer B of Method B) and from the BC domain combination of Preparation BC11 (Diasteromer 2). MS m/z 686.3 (M$^+$+1)

EXAMPLE N54

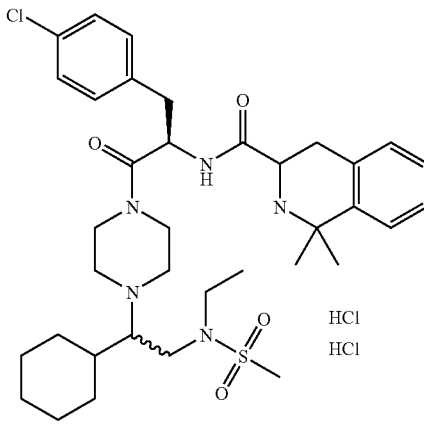

1,1-Dimethyl-1,2,3,4-Tetrahydro-isoquinoline-3-carboxylic acid (1-(4-chloro-benzyl)-2-{4-[1-cyclohexylmethyl-2-(ethyl-methanesulfonyl-amino)-ethyl]-piperazin-1-yl}-2-oxo-ethyl)-amide dihydrochloride salt According to the procedure described in Example N17, this compound was prepared from the A domain of Preparation NA8 (Enantiomer A of Method B) and from the BC domain combination of Preparation BC11 (Diasteromer 1). MS m/z 686.3 (M$^+$+1)

EXAMPLE N55

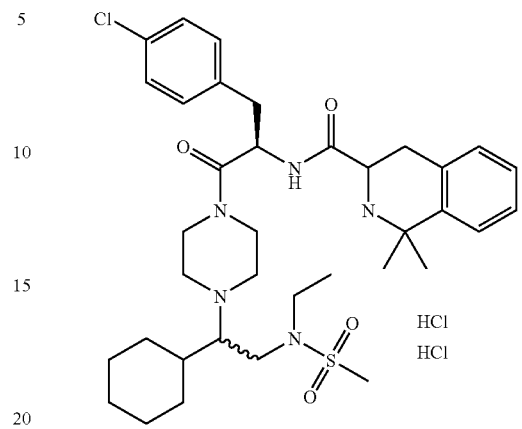

1,1-Dimethyl-1,2,3,4-Tetrahydro-isoquinoline-3-carboxylic acid (1-(4-chloro-benzyl)-2-{4-[1-cyclohexylmethyl-2-(ethyl-methanesulfonyl-amino)-ethyl]-piperazin-1-yl}-2-oxo-ethyl)-amide dihydrochloride salt According to the procedure described in Example N17, this compound was prepared from the A domain of Preparation NA8 (Enantiomer B of Method B) and from the BC domain combination of Preparation BC11 (Diasteromer 1). MS m/z 686.3 (M$^+$+1)

EXAMPLE N56

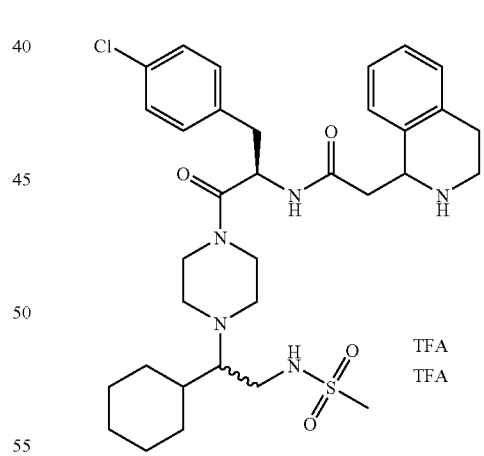

N-{1-(4-chloro-benzyl)-2-[4-(1-cyclohexyl-2-methanesulfonyl-amino-ethyl]-piperazin-1-yl]-2-oxo-ethyl}-2-(1,2,3,4-tetrahydro-isoquinolin-1-yl)-acetamide di(trifluoroacetate) salt According to the procedure described in Example N1, this compound was prepared from the racemic A domain of Preparation NA7 and from the BC domain combination of Preparation BC12. MS m/z 644.3 (M$^+$+1)

EXAMPLE N57

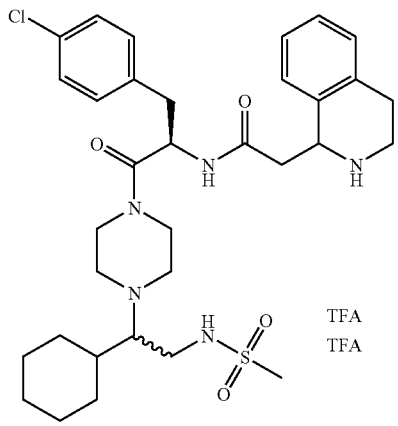

N-{1-(4-chloro-benzyl)-2-[4-(1-cyclohexyl-2-meth-anesulfonyl-amino-ethyl]-piperazin-1-yl]-2-oxo-ethyl}-2-(1,2,3,4-tetrahydro-isoquinolin-1-yl)-acetamide di(trifluoroacetate) salt According to the procedure described in Example N1, this compound was prepared from the racemic A domain of Preparation NA7 and from the BC domain combination of Preparation BC13 (Diasteromer 2). MS m/Z 644.3 (M$^+$+1)

EXAMPLE N58

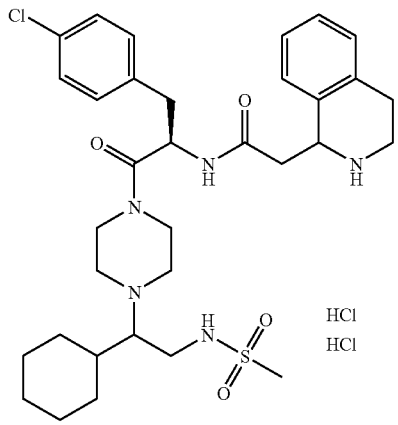

N-{1-(4-chloro-benzyl)-2-[4-(1-cyclohexyl-2-meth-anesulfonyl-amino-ethyl]-piperazin-1-yl]-2-oxo-ethyl}-2-(1,2,3,4-tetrahydro-isoquinolin-1-yl)-acetamide di(trifluoroacetate) salt According to the procedure described in Example N17, this compound was prepared from the A domain of Preparation NA7 (Enantiomer A of Method B) and from the BC domain combination of Preparation BC13. MS m/z 644.3 (M$^+$+1)

EXAMPLE N59

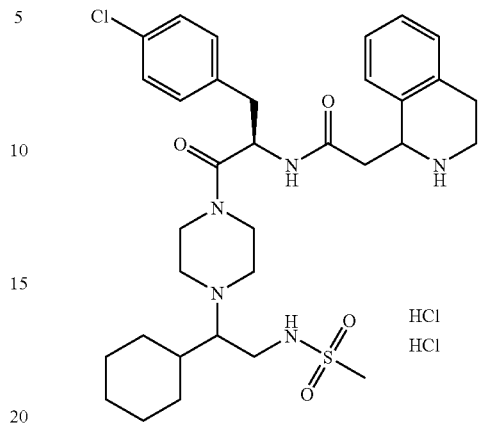

N-{1-(4-chloro-benzyl)-2-[4-(1-cyclohexyl-2-meth-anesulfonyl-amino-ethyl]-piperazin-1-yl]-2-oxo-ethyl}-2-(1,2,3,4-tetrahydro-isoquinolin-1-yl)-acetamide di(trifluoroacetate) salt According to the procedure described in Example N17, this compound was prepared from the A domain of Preparation NA7 (Enantiomer B of Method B) and from the BC domain combination of Preparation BC13. MS m/z 644.3 (M$^+$+1)

EXAMPLE N60

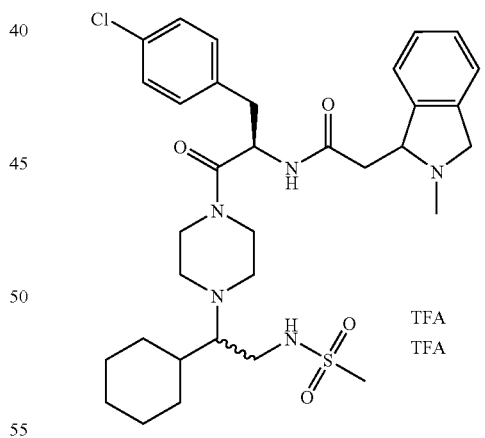

N-{1-(4-chloro-benzyl)-2-{4-[1-cyclohexyl-2-meth-anesulfonyl-amino-ethyl]-piperazin-1-yl}-2-oxo-ethyl)-2-(2-methyl-2,3-dihydro-1H-isoindol-1-yl)-acetamide di(trifluoroacetate) salt According to the procedure described in Example N1, this compound was prepared from the racemic A domain of Preparation NA7 and from the BC domain combination of Preparation BC14. MS m/z 644.3 (M$^+$+1)

EXAMPLE N61

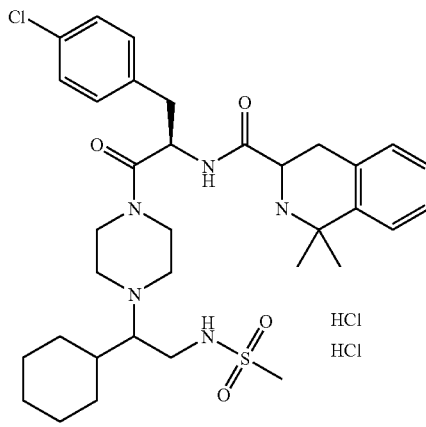

1,1-Dimethyl-1,2,3,4-tetrahydro-isoquinoline-3-carboxylic acid {1-(4-chloro-benzyl)-2-[4-[1-cyclohexyl-2-methanesulfonylamino-ethyl)-piperazin-1-yl]-2-oxo-ethyl}-amide dihydrochloride salt According to the procedure described in Example N17, this compound was prepared from the A domain of Preparation NA7 (Enantiomer A of Method B) and from the BC domain combination of Preparation BC11 (Diasteromer 1). MS m/z 658.3 (M$^+$+1)

EXAMPLE N62

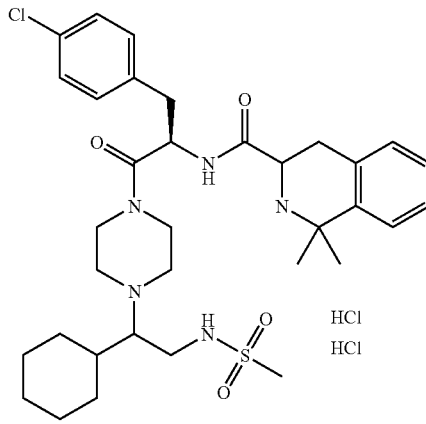

1,1-Dimethyl-1,2,3,4-tetrahydro-isoquinoline-3-carboxylic acid {1-(4-chloro-benzyl)-2-[4-[1-cyclohexyl-2-methanesulfonylamino-ethyl)-piperazin-1-yl]-2-oxo-ethyl}-amide dihydrochloride salt According to the procedure described in Example N21, this compound was prepared from the A domain of Preparation NA7 (Enantiomer B of Method B) and from the BC domain combination of Preparation BC11 (Diasteromer 1). MS m/z 658.3 (M$^+$+1)

EXAMPLE N63

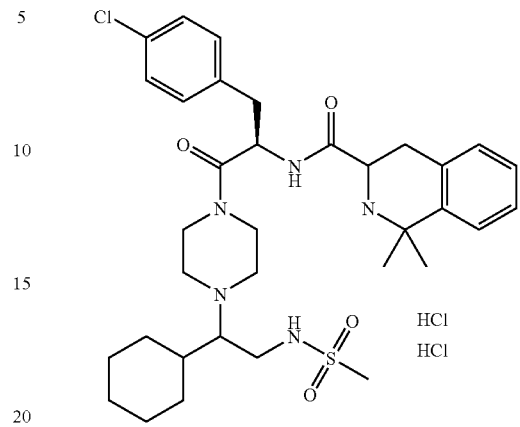

1,1-Dimethyl-1,2,3,4-tetrahydro-isoquinoline-3-carboxylic acid {1-(4-chloro-benzyl)-2-[4-[1-cyclohexyl-2-methanesulfonylamino-ethyl)-piperazin-1-yl]-2-oxo-ethyl}-amide dihydrochloride salt According to the procedure described in Example N17, this compound was prepared from the A domain of Preparation NA7 (Enantiomer A of Method B) and from the BC domain combination of Preparation BC11 (Diasteromer 2). MS m/z 658.3 (M$^+$+1)

EXAMPLE N64

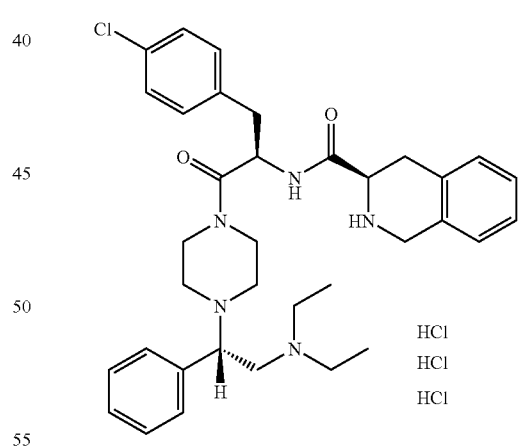

1,2,3,4-Tetrahydro-isoquinoline-3-carboxylic acid {1-(4-chloro-benzyl)-2-[4-(1-diethylamino-1-phenyl-ethyl)-piperazin-1-yl]-2-oxo-ethyl}-amide trihydrochloride salt According to the procedure described in Example N3, this compound was prepared from the A domain of Preparation NA33 and from the BC domain combination of Preparation BC1. MS m/z 602.3 (M$^+$+1)

EXAMPLE N65

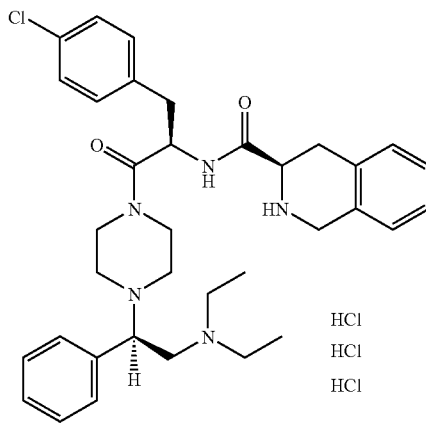

1,2,3,4-Tetrahydro-isoquinoline-3-carboxylic acid {1-(4-chloro-benzyl)-2-[4-(1-diethylamino-1-phenyl-ethyl)-piperazin-1-yl]-2-oxo-ethyl}-amide trihydrochloride salt According to the procedure described in Example N3, this compound was prepared from the A domain of Preparation NA34 and from the BC domain combination of Preparation BC1. MS m/z 602.3 (M$^+$+1)

EXAMPLE N66

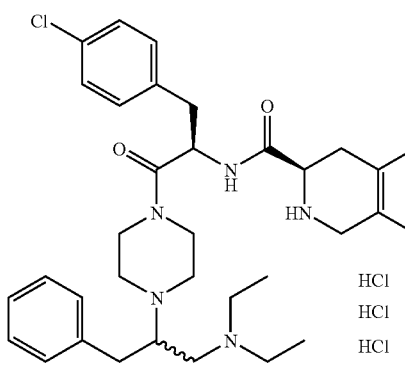

1,2,3,4-Tetrahydro-isoquinoline-3-carboxylic acid [2-[4-(1-benzyl-2-diethylamino-ethyl)-piperazin-1-yl]-1-(4-chloro-benzyl)-2-oxo-ethyl]-amide trihydrochloride salt According to the procedure described in Example N3, this compound was prepared from the racemic A domain of Preparation NA37 and from the BC domain combination of Preparation BC1. MS m/z 616.3 (M$^+$+1)

EXAMPLE N67

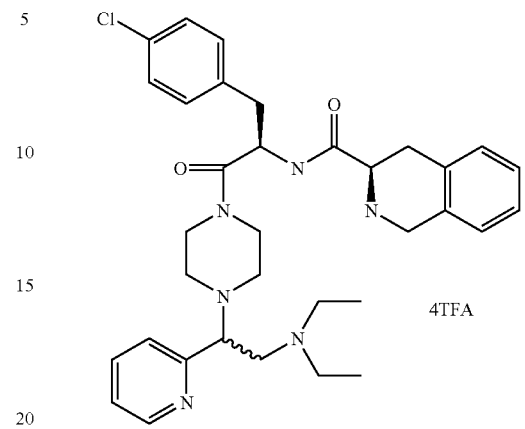

1,2,3,4-Tetrahydro-isoquinoline-3-carboxylic acid {1-(4-chloro-benzyl)-2-[4-(2-diethylamino-1-pyridin-2-yl-ethyl)-piperazin-1-yl]-2-oxo-ethyl}-amide tetrahydrochloride salt According to the procedure described in Example N1, this compound was prepared from the racemic A domain of preparation NA38 and from the BC domain combination of Preparation BC1. MS m/z 603.6 (M$^+$+1)

EXAMPLE N68

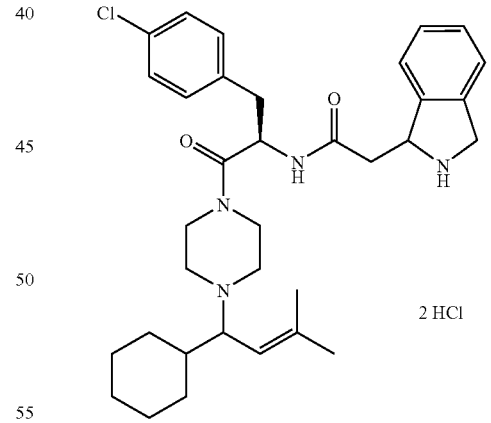

N-{1-(4-Chloro-benzyl)-2-[4-(1-cyclohexyl-3-methyl-but-2-enyl)-piperazin-1-yl]-2-oxo-ethyl}-2-(2,3-dihydro-1H-isoindol-1-yl)-acetamide dihydrochloride salt.

According to the procedure described in Example N17, this compound was prepared from the racemic A domain of preparation NA39 and from the BC domain combination of Preparation BC2. MS m/z 577.3 (M$^+$+1)

EXAMPLE N69

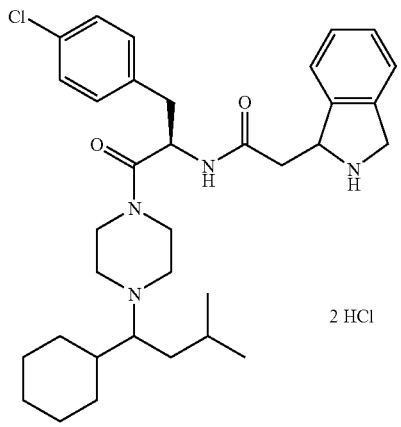

N-{1-(4-Chloro-benzyl)-2-[4-(1-cyclohexyl-3-methyl-butyl)-piperazin-1-yl]-2-oxo-ethyl}-2-(2,3-dihydro-1H-isoindol-1-yl)-acetamide dihydrochloride salt According to the procedure described in Example N17, this compound was prepared from the racemic A domain of preparation NA40 and from the BC domain combination of Preparation BC2. MS m/z 579.4 (M$^+$+1)

EXAMPLE N70

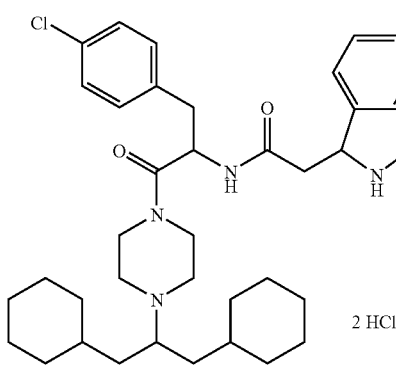

N-{1-(4-Chloro-benzyl)-2-[4-(2-cyclohexyl-1-cyclohexylmethyl-ethyl)-piperazin-1-yl]-2-oxo-ethyl}-2-(2,3-dihydro-1H-isoindol-1-yl)-acetamide dihydrochloride salt According to the procedure described in Example N17, this compound was prepared from the A domain of preparation NA41 and from the BC domain combination of Preparation BC2. MS m/z 633.4 (M$^+$+1)

EXAMPLE N71

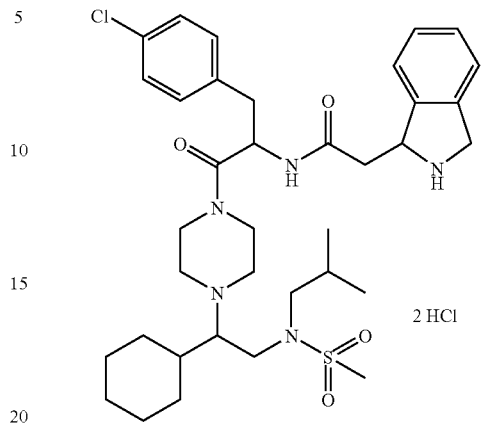

N-(1-(4-Chloro-benzyl)-2-{4-[1-cyclohexyl-2-(isobutyl-methanesulfonyl-amino)-ethyl]-piperazin-1-yl}-2-oxo-ethyl)-2-(2,3-dihydro-1H-isoindol-1-yl)-acetamide dihydrochloride salt According to the procedure described in Example N17, this compound was prepared from the A domain of preparation NA42 (Enantiomer A) and from the BC domain combination of Preparation BC2. MS m/z 686.3 (M$^+$+1)

EXAMPLE N72

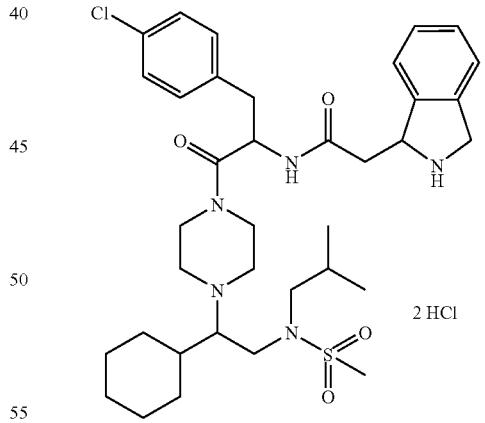

N-(1-(4-Chloro-benzyl)-2-{4-[1-cyclohexyl-2-(isobutyl-methanesulfonyl-amino)-ethyl]-piperazin-1-yl}-2-oxo-ethyl)-2-(2,3-dihydro-1H-isoindol-1-yl)-acetamide dihydrochloride salt According to the procedure described in Example N17, this compound was prepared from the A domain of Preparation NA42 (Enantiomer B) and from the BC domain combination of Preparation BC2. MS m/z 686.3 (M$^+$+1)

EXAMPLE N73

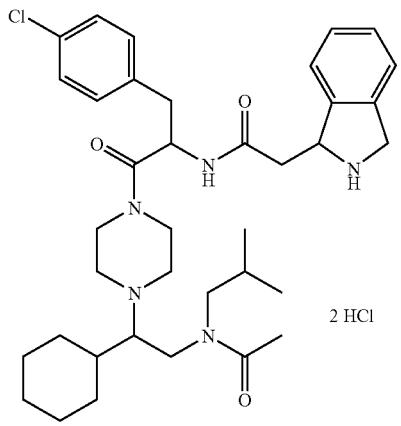

N-[2-{4-[2-(Acetyl-isobutyl-amino)-1-cyclohexyl-ethyl]-piperazin-1-yl}-1-(4-chloro-benzyl)-2-oxo-ethyl]-2-(2,3-dihydro-1H-isoindol-1-yl)-acetamide dihydrochloride salt According to the procedure described in Example N17, this compound was prepared from the A domain of Preparation NA43 (Enantiomer A) and from the BC domain combination of Preparation BC2. MS m/z 650.4 (M$^+$+1)

EXAMPLE N74

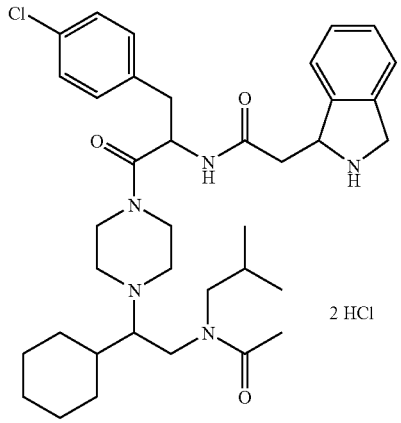

N-[2-{4-[2-(Acetyl-isobutyl-amino)-1-cyclohexyl-ethyl]-piperazin-1-yl}-1-(4-chloro-benzyl)-2-oxo-ethyl]-2-(2,3-dihydro-1H-isoindol-1-yl)-acetamide dihydrochloride salt According to the procedure described in Example N17, this compound was prepared from the A domain of Preparation NA43 (Enantiomer B) and from the BC domain combination of Preparation BC2. MS m/z 650.4 (M$^+$+1)

EXAMPLE N75

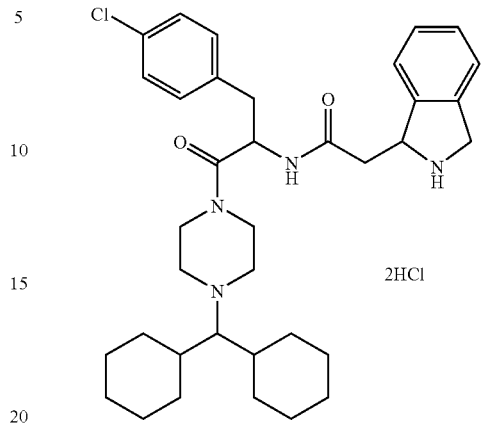

N-[1-(4-Chloro-benzyl)-2-(4-dicyclohexylmethyl-piperazin-1-yl)-2-oxo-ethyl]-2-(2,3-dihydro-1H-isoindol-1-yl)-acetamide dihydrochloride salt.

According to the procedure described in Example N17, this compound was prepared from the A domain of Preparation NA44 and from the BC domain combination of Preparation BC2. MS m/z 605.3 (M$^+$+1)

EXAMPLE 76

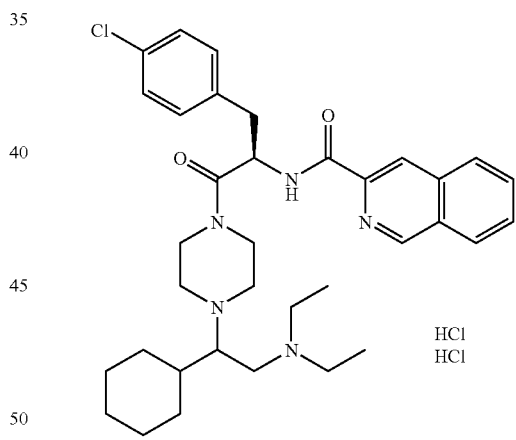

Isoquinoline-3-carboxylic acid {1-(4-chloro-benzyl)-2-[4-(1-cyclohexyl-2-diethylamino-ethyl)-piperazin-1-yl]-2-oxo-ethyl}-amide dihydrochloride salt A mixture of the racemic A domain compound of Preparation A6 (Enantiomer A, Method B) (1 eq.), the BC domain combination of example BC15 (1.2 eq.), HOAT (1.25 eq.), HATU (1.25 eq.) and DIPEA (10 eq.) was stirred in CH$_2$Cl$_2$/DMF (4:1, v:v) at room temperature overnight. Extractive work up with EtOAc yielded the crude product that was purified by column chromatography. A solution of the N-Boc protected product in 1N HCl/EtOAc was stirred at room overnight. Solvent was evaporated and residue washed with Et$_2$O to afford the title compound (79%). MS m/z 604.3 (M$^+$+1).

EXAMPLE 77

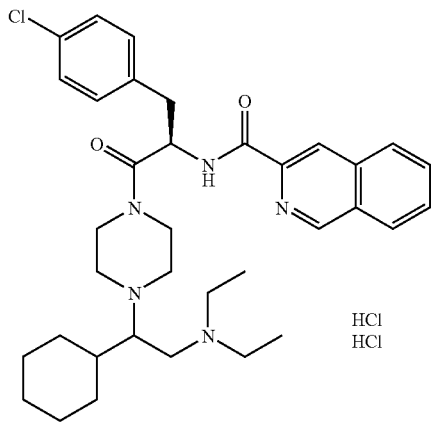

Isoquinoline-3-carboxylic acid {1-(4-chloro-benzyl)-2-[4-(1-cyclohexyl-2-diethylamino-ethyl)-piperazin-1-yl]-2-oxo-ethyl}-amide dihydrochloride salt According to the procedure described in Example N76, this compound was prepared from the A domain of Preparation A6 (Enantiomer B, Method B) and from the BC domain combination of Example BC15. MS m/z 604.3 (M$^+$+1)

EXAMPLE N78

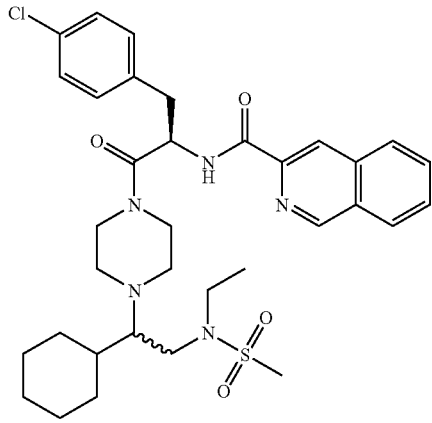

Isoquinoline-3-carboxylic acid {1-(4-chloro-benzyl)-2-{4-[1-cyclohexyl-2-(ethyl-methanesulfonyl-amino)-ethyl]-piperazin-1-yl}-2-oxo-ethyl}-amide A mixture of the racemic A domain compound of Preparation A8 (1 eq.), the BC domain combination of example BC15 (1.2 eq.), HOAT (1.25 eq.) HATU (1.25 eq.) and DIPEA (10 eq.) was stirred in CH$_2$Cl$_2$/DMF (4:1, v:v) at room temperature overnight. Reaction mixture was diluted with water and aqueous layer was extracted with CH$_2$Cl$_2$. Combined organic layers were dried (MgSO$_4$), filtered and concentrated to give a crude product that was purified by column chromatography. MS m/z 654.2 (M$^+$+1)

EXAMPLE 79

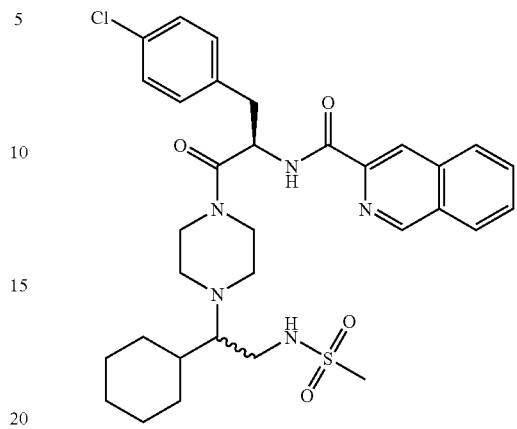

Isoquinoline-3-carboxylic acid {1-(4-chloro-benzyl)-2-{4-[1-cyclohexyl-2-(ethyl-methanesulfonyl-amino)-ethyl]-piperazin-1-yl}-2-oxo-ethyl}-amide According to the procedure described in Example N78, this compound was prepared from the A domain of Preparation A7 and from the BC domain combination of Example BC15. MS m/z 626.0 (M$^+$+1)

EXAMPLE N80

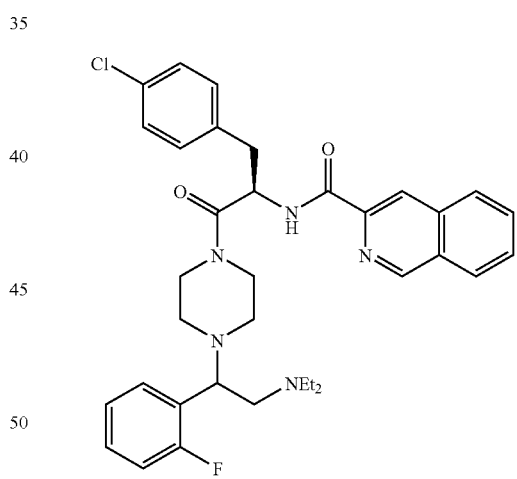

Isoquinoline-3-carboxylic acid (1-(4-chloro-benzyl)-2-{4-[2-diethylamino-1-(2-fluoro-phenyl)-ethyl]-piperazin-1-yl}-2-oxo-ethyl)-amide To the "A-B" piece (Compound #707, Table XIV) (1 eq.), the commercially available isoquinoline-3-carboxylic acid hydrate (1 eq.), EDC (1 eq.) and HOBT (1 eq.) was added MeCl$_2$ (to make the a 0.5 M solution). NMM (3 eq.) was then added and the reaction was allowed to stir at room temperature for 4 h. The reaction mixture was then concentrated to dryness. The resulting reside was taken up in EtOAc and washed with sat. NaHCO$_3$ and brine. The organic phase was collected and concentrated to dryness.

The crude material was further purified by column chromatography (silica gel 60 mesh, eluting with a gradient of 100% EtOAc to 5% MeOH/5% TEA in EtOAc) yielding the pure free base of the title compound at a yield of 80%. The HCl salt of the title compound can be obtained by taking the free base up in 1N HCl and lyophillizing overnight. MS (ES) 616.3 [M+1]

EXAMPLE 81

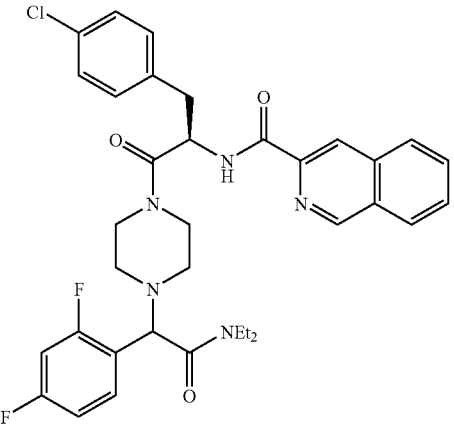

Isoquinoline-3-carboxylic acid (1-(4-chloro-benzyl)-2-{4-[diethylcarbamoyl-(2,4-difluoro-phenyl)-methyl]-piperazin-1-yl}-2-oxo-ethyl)-amide According to the procedure described in Example 80, the title compound was prepared from the "A-B" piece (compound of Preparation G8) and the commercially available isoquinoline-3-carboxylic acid hydrate.
MS (ES) 648.3 [M+1]

What is claimed is:
1. A compound of formula I

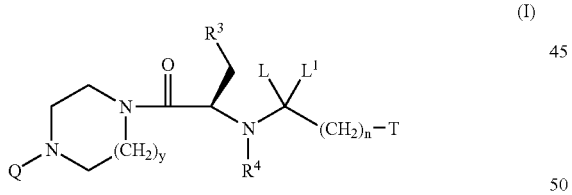

(I)

or a pharmaceutically acceptable salt or stereoisomer thereof, wherein
L and $L^1$ are both hydrogen, or combine together to form an oxo group;
$R^3$ is phenyl;
wherein the phenyl is optionally substituted with one to three substituents independently selected from the group consisting of:
cyano, perfluoroalkoxy, halo, $C_1$–$C_8$ alkyl, (D)$C_3$–$C_7$ cycloalkyl, $C_1$–$C_4$ alkoxy, $C_1$–$C_4$ haloalkyl;
$R^4$ is hydrogen, $C_1$–$C_8$ alkyl, $C_3$–$C_8$ alkenyl, C(O)$C_1$–$C_8$ alkyl, or (D)phenyl;
Q is: —C($R^{a1}$) ($R^{a2}$) ($R^{a3}$)
Wherein $R^{a1}$ is $C_1$–$C_8$ alkyl, $C_2$–$C_8$ alkenyl, $C_2$–$C_8$ alkynyl, $C_1$–$C_8$ alkoxy, $C_3$–$C_8$ cycloalkyl, (D)$C_3$–$C_7$ cycloalkyl, (D)heterocyclic, (D)phenyl, aryl, and wherein $C_1$–$C_8$ alkyl, $C_2$–$C_8$ alkenyl, $C_2$–$C_8$ alkynyl, and (D)$C_3$–$C_7$ cycloalkyl, heterocyclic, phenyl, and aryl are each optionally substituted with one to five substituents independently selected from R;

R is:
hydroxy,
halo,
$C_1$–$C_8$ alkyl,
$C_2$–$C_8$ alkenyl,
$C_1$–$C_8$ alkoxy,
$C_1$–$C_4$ haloalkyl,
(D)C(O)$C_1$–$C_4$ alkyl,
(D)C(O)O$C_1$–$C_4$ alkyl,
$(CH_2)_m N(R^8)_2$,
$(CH_2)_m NR^8 C(O)C_1$–$C_4$ alkyl,
$(CH_2)_m NR^8 SO_2(C_1$–$C_4$ alkyl),
(D)O$C_1$–$C_4$ alkyl,
(D)S$C_1$–$C_4$ alkyl, or
(D)SO$_2$N$(R^8)_2$;
$R^{a2}$ is
$C_1$–$C_8$ alkyl,
$C_2$–$C_8$ alkenyl,
$C_2$–$C_8$ alkynyl,
(D)$C_3$–$C_7$ cycloalkyl,
phenyl,
aryl,
$(CH_2)_m N(R^8)_2$,
$(CH_2)_m NR^8 C(O)C_1$–$C_4$ alkyl,
$(CH_2)_m NR^8 C(O)OC_1$–$C_4$ alkyl,
$(CH_2)_m NR^8 SO_2(C_1$–$C_4$ alkyl),
$(CH_2)_m OC_1$–$C_4$ alkyl,
$(CH_2)_m OC(O)C_1$–$C_4$ alkyl,
CON$(R^8)_2$,
wherein for the group or subgroup —N$(R^8)_2$, each $R^8$ may combine with the other to form a 5, 6, or 7-membered saturated or unsaturated, optionally substituted nitrogen containing heterocycle;
$R^{a3}$ is selected from the group consisting of hydrogen, methyl, ethyl and propyl; each $R^8$ is independently:
hydrogen,
$C_1$–$C_8$ alkyl,
$C_2$–$C_8$ alkenyl,
(D)$C_3$–$C_7$ cycloalkyl,
phenyl, or
aryl
T is:

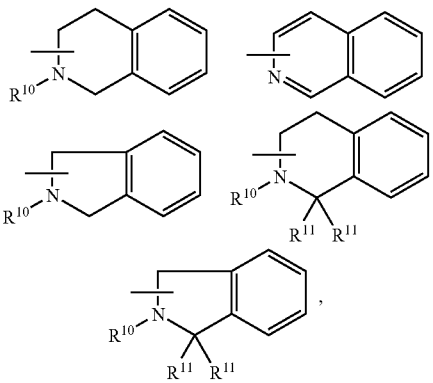

$R^{10}$ is hydrogen, $(C_1–C_8)$alkyl, $C_3–C_8$ alkenyl, $C(O)$ $C_1–C_8$ alkyl, $C_2–C_8$ alkynyl, phenyl,
$R^{11}$ is independently hydrogen or $(C_1–C_8)$ alkyl;
D is a bond or $C_1–C_4$ alkyl;
y is 1;
m is 1–4;
n is 0–8;
p is 0–4; and
q is 0–1.

2. A compound of formula II:

(II)

or a pharmaceutically acceptable salt, or stereoisomer thereof, wherein L and $L^1$ are both hydrogen, or combine together to form an oxo group;
$R^1$ is selected from the group consisting of:
  hydrogen,
  halo,
  $C_1–C_8$ alkyl,
  $C_1–C_4$ haloalkyl
  $C_2–C_8$ alkenyl,
  $(D)N(R^8)_2$,
  $(D)NR^8C(O)C_1–C_4$ alkyl,
  $(D)OC_1–C_4$ alkyl,
  wherein for the group or subgroup $—N(R^8)_2$, each $R^8$ may combine with the other to form a 5, 6, or 7-membered saturated or unsaturated, optionally substituted nitrogen containing heterocycle;
$R^{3'}$ is phenyl, optionally substituted with one to three substituents independently selected from the group consisting of: cyano, halo, $C_1–C_8$ alkyl, $(D)C_3–C_7$ cycloalkyl, $C_1–C_4$ alkoxy, $C_1–C_4$ haloalkyl and perfluoroalkoxy;
$R^4$ is hydrogen, $C_1–C_8$ alkyl, $C_3–C_8$ alkenyl, or $(D)$phenyl;
$R^{a2}$ is:
  $C_1–C_8$ alkyl,
  $C_2–C_8$ alkenyl,
  $C_2–C_8$ alkynyl,
  $(D)C_3–C_7$ cycloalkyl,
  phenyl,
  aryl,
  $(CH_2)_mN(R^8)_2$,
  $(CH_2)_mNR^8C(O)C_1–C_4$ alkyl,
  $(CH_2)_mNR^8C(O)OC_1–C_4$ alkyl,
  $(CH_2)_mNR^8SO_2(C_1–C_4$ alkyl$)$,
  $(CH_2)_mOC_1–C_4$ alkyl,
  $(CH_2)_mOC(O)C_1–C_4$ alkyl,
  $CON(R^8)_2$,
  wherein for the group or subgroup $—N(R^8)_2$, each $R^8$ may combine with the other to form a 4, 5, 6, or 7-membered saturated or unsaturated, optionally substituted nitrogen containing heterocycle;

$R^{a3}$ is selected from the group consisting of hydrogen, methyl, ethyl and propyl;
T' is:

each $R^8$ is independently:
  hydrogen,
  $C_1–C_8$ alkyl,
  $C_2–C_8$ alkenyl,
  $(D)C_3–C_7$ cycloalkyl,
  phenyl,
  aryl or
$R^{10}$ is hydrogen, $(C_1–C_8)$alkyl, $C_3–C_8$ alkenyl, $C_2–C_8$ alkynyl, phenyl,
$R^{11}$ is independently hydrogen, $(C_1–C_8)$alkyl, or phenyl, aryl;
D is a bond or $C_1–C_4$ alkyl;
y is 1;
u is 0, 1, or 2;
m is 1–4;
n is 0–8;
p is 0–4; and
q is 0–1.

3. The compound of claim 1, wherein the $C_3–C_7$ cycloalkyl is cyclohexyl, cyclopentyl, or cycloheptane.

4. The compound of claim 1, wherein the heterocyclyl is 5- or 6-membered ring containing at least one nitrogen and 0 to 3 atoms selected from O, or S wherein the nitrogen is substituted with a substituent selected from the group consisting of hydrogen, $C_1–C_8$ alkyl, $C_3–C_7$ cycloalkyl, phenyl and benzyl.

5. The compound of claim 1, wherein the heterocyclyl is piperidinyl, pyrrolidinyl, pyrrolinyl, isoxazolyl, oxazolyl, thiazoyl, triazolyl, tetrazolyl, thiadiazolyl, or oxadiazolyl.

6. The compound of claim 1, wherein R is independently at each occurrence: $C_1–C_8$ alkyl, $C_1–C_8$ alkoxy, $(CH_2)_mN(R^8)_2$, where $R^8$ independently at each occurrence is hydrogen, $C_1–C_8$ alkyl, or phenyl.

7. The compound of claim 1 or 2, wherein $R^3$ is phenyl optionally para-substituted with chloro, bromo, or methyl.

8. The compound of claim 1 or 2, wherein $R^3$ is phenyl para-substituted with chloro.

9. The compound of claim 8, wherein $R^4$ is hydrogen.

10. The compound of claim 1, wherein T is

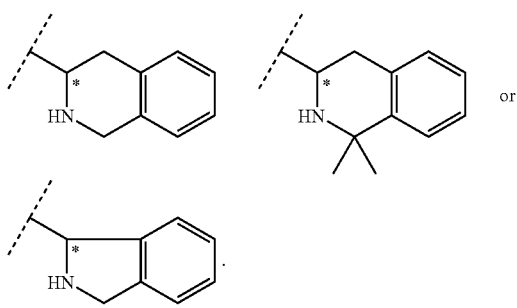

11. The compound of any one of claims 1 or 2 wherein L and L¹ are each hydrogen; and T is a moiety of the formula:

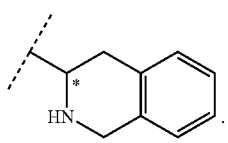

12. The compound of claim 10 wherein the carbon atom marked with * has the R configuration.

13. A compound according to claim 2 wherein T' is selected from the group consisting of:

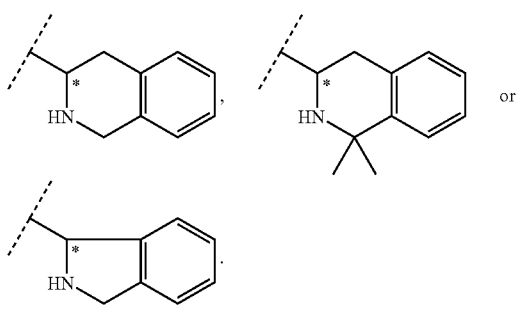

where * denotes a chiral carbon atom which has a R configuration.

14. A compound according to claim 1 or 2 or 3 wherein $R^{a3}$ is hydrogen.

15. A compound according to claim 1 wherein T is

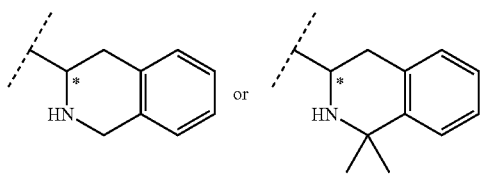

$R^3$ is 4-chlorophenylmethyl,
$R^4$ is hydrogen,
$R^{a3}$ is hydrogen, and
$R^{a1}$ is selected from the group consisting of: n-butyl, isobutyl, trifluoromethylphenyl, 4-methylphenyl, cyclopentyl, cyclohexyl, cycloheptyl, 2-fluorophenyl, 2-chlorophenyl, phenyl, and benzyl.

16. A compound according to claim 15 wherein $R^{a2}$ is a group selected from the group consisting of: cyclohexyl, methylcyclohexyl, isopropyl, isobutyl, N-methylmethanesulfonamido, N,N-diethylmethylamino, N-methylpyrrolidinyl, N-benzylmethansulfonylamido, N-methylphthalimido, methylacetamido, N-methylmorpholino, N-methylpiperidinyl, N-methyacetamido, N-methylmaleimido, 2-oxo-N-methylpyrrolidinyl, carboxy-N,N-diethylamino, N-ethylmethanesulfonylamido, N-isobutylmethanesulfonylamido, and N-isobutyl,N-carboxymethylamine.

17. A compound according to claim 1 wherein T is

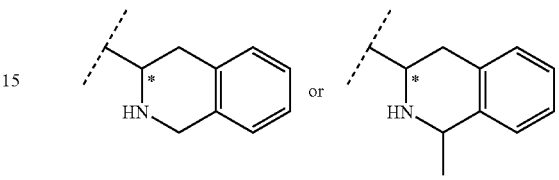

$R^3$ is 4-chlorophenylmethyl,
$R^4$ is hydrogen,
$R^{a3}$ is hydrogen, and
$R^{a1}$ is selected from the group consisting of: n-butyl, isobutyl, trifluoromethylphenyl, 4-methylphenyl, cyclopentyl, cyclohexyl, cycloheptyl, 2-fluorophenyl, 2-chlorophenyl, phenyl, and benzyl.

18. A compound according to claim 17 wherein $R^{a2}$ is a group selected from the group consisting of:cyclohexyl, methylcyclohexyl, isopropyl, isobutyl, N-methylmethanesulfonamido, N,N-diethylmethylamino, N-methylpyrrolidinyl, N-benzylmethansulfonylamido, N-methylphthalimido, methylacetamido, morpholino, N-methylpiperidinyl, N-methyacetamido, N-methylmaleimido, 2-oxo-N-methylpyrrolidinyl, carboxy-N,N-diethylamino, N-ethylmethanesulfonylamido, N-isobutylmethanesulfonamido, and N-isbutyl, N-carboxymethylamine.

19. The compound of claim 10 wherein the carbon atom marked with * has the S configuration.

20. A pharmaceutical composition comprising a compound of claims 1 and a pharmaceutical carrier.

21. The pharmaceutical composition of claim 20 further comprising a second active ingredient selected from the group consisting of an insulin sensitizer, insulin mimetic, sulfonylurea, alpha-glucosidase inhibitor, HMG-CoA reductase inhibitor, sequestrant cholesterol lowering agent, beta 3 adrenergic receptor agonist, neuropeptide Y antagonist, and phosphodiester V inhibitor.

22. A compound selected from the group consisting of:

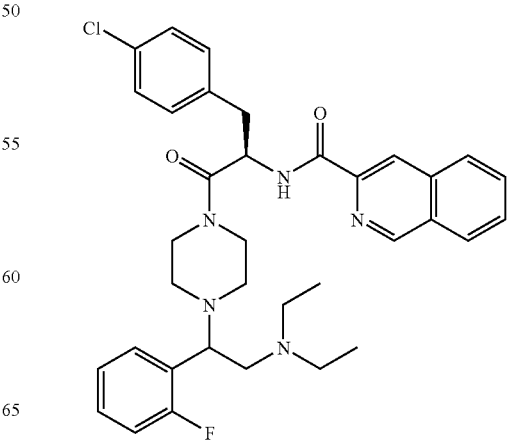

"A" isomer#2
Isoquinoline-3-carboxylic acid (1-(4-chloro-benzyl)-2-{4-[2-diethylamino-1-(2-fluoro-phenyl)-ethyl]-piperazin-1-yl}-2-oxo-ethyl)-amide,

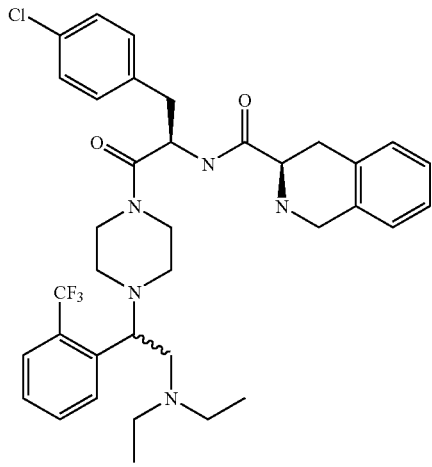

1,2,3,4-Tetrahydro-isoquinoline-3-carboxylic acid (1-(4-chloro-benzyl)-2-{4-[2-diethylamino-1-(2-trifluorom-ethyl-phenyl)-ethyl]-piperazin-1-yl}-2-oxo-ethyl)-amide,

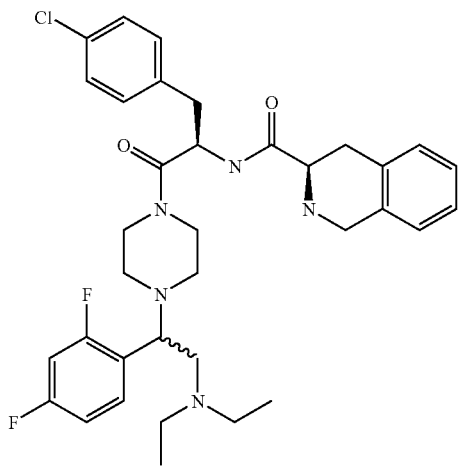

1,2,3,4-Tetrahydro-isoquinoline-3-carboxylic acid (1-(4-chloro-benzyl)-2-{4-[2-diethylamino-1-(2,4-difluoro-phenyl)-ethyl]-piperazin-1-yl}-2-oxo-ethyl)-amide,

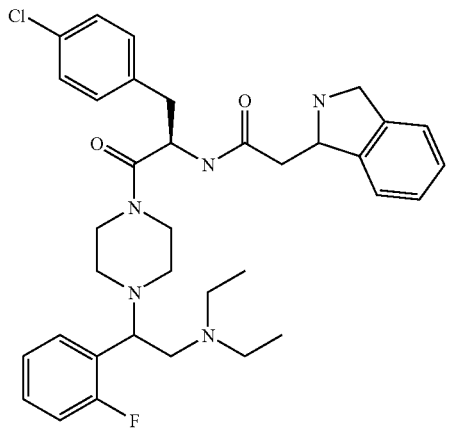

"A" isomer#2

N-(1-(4-Chloro-benzyl)-2-{4-[2-diethylamino-1-(2-fluoro-phenyl)-ethyl]-piperazin-1-yl}-2-oxo-ethyl)-2-(2,3dihydro-1H-isoindol-1-yl)-acetamide,

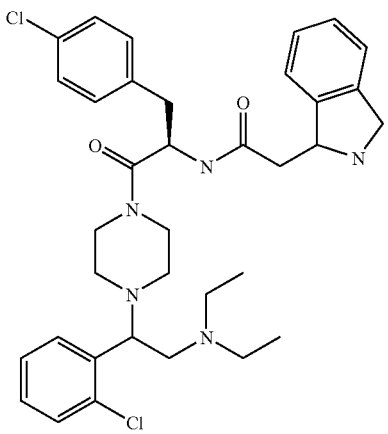

"A" isomer#2

N-(1-(4-Chloro-benzyl)-2-{4-[1-(2-chloro-phenyl)-2-diethylamino-ethyl]-piperazin-1-yl}-2-oxo-ethyl)-2-(2,3-dihydro-1H-isoindol-1-yl)-acetamide,

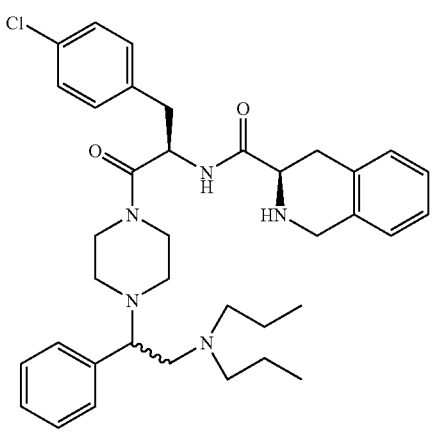

1,2,3,4-Tetrahydro-isoquinoline-3-carboxylic acid {1-(4-chloro-benzyl)-2-[4-(2-dipropylamino-1-phenyl-ethyl)-piperazin-1-yl]-2-oxo-ethyl}-amide,

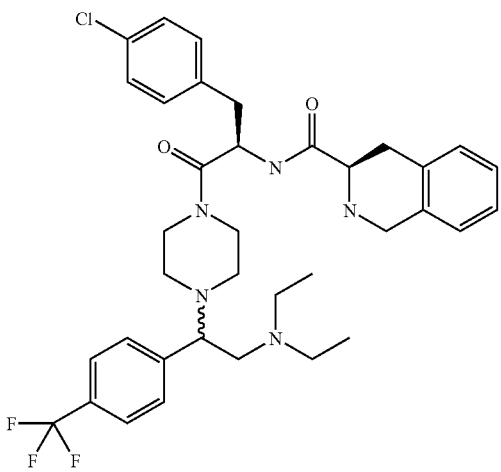

1,2,3,4-Tetrahydro-isoquinoline-3-carboxylic acid (1-(4-chloro-benzyl)-2-{4-[2-diethylamino-1-(4-trifluoromethyl-phenyl)-ethyl]-piperazin-1-yl}-2-oxo-ethyl)-amide,

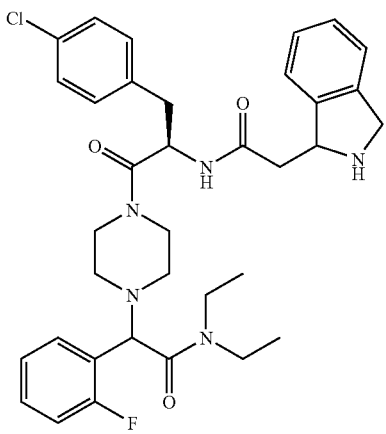

"A" isomer #2
2-{4-[3-(4-Chloro-phenyl)-2-(2-2,3-dihydro-1H-isoindol-1-yl-acetylamino)-propionyl]-piperazin-1-yl}-N,N-diethyl-2-(2-fluoro-phenyl)-acetamide,

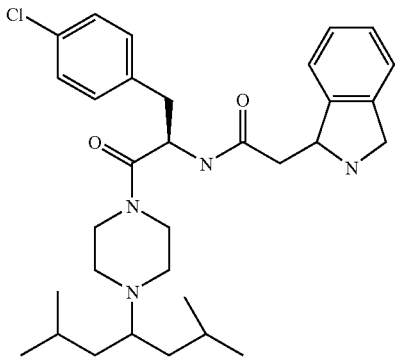

N-{1-(4-Chloro-benzyl)-2-[4-(1-isobutyl-3-methyl-butyl)-piperazin-1-yl]-2-oxo-ethyl}-2-(2,3-dihydro-1H-isoindol-1-yl)-acetamide,

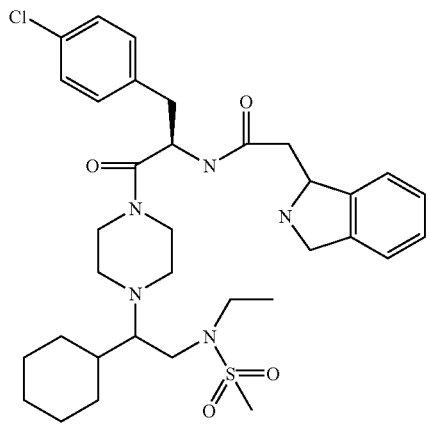

N-(1-(4-Chloro-benzyl)-2-{4-[1-cyclohexyl-2-(ethyl-methanesulfonyl-amino)-ethyl]-piperazin-1-yl}-2-oxo-ethyl)-2-(2,3-dihydro-1H-isoindol-1-yl)-acetamide,

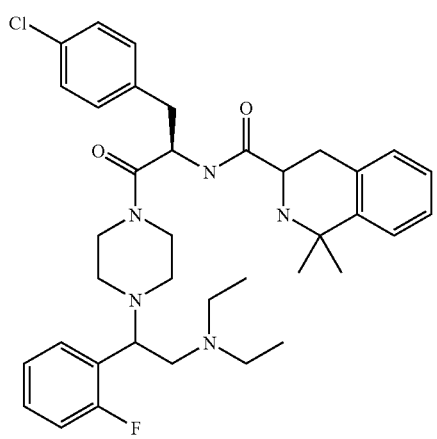

"A" isomer#2, "C" isomer#2
1,1-Dimethyl-1,2,3,4-tetrahydro-isoquinoline-3-carboxylic acid (1-(4-chloro-benzyl)-2-{4-[2-diethylamino-1-(2-fluoro-phenyl)-ethyl]-piperazin-1-yl}-2-oxo-ethyl)-amide,

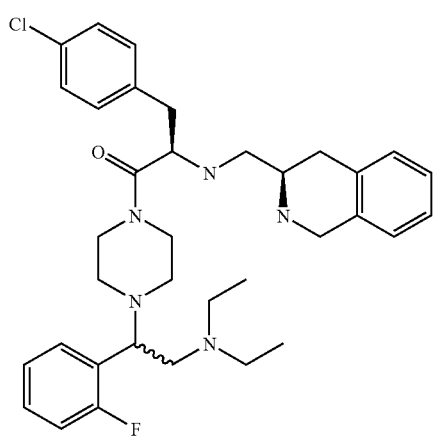

3-(4-Chloro-phenyl)-1-{4-[2-diethylamino-1-(2-fluoro-phenyl)-ethyl]-piperazin-1-yl}-2-[(1,2,3,4-tetrahydro-isoquinolin-3-ylmethyl)-amino]-propan-1-one,

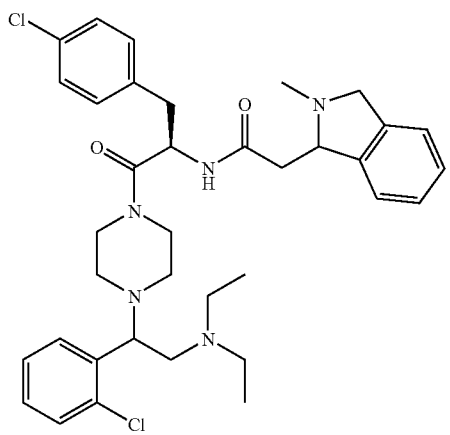

"A" isomer#2, "C" isomer#2
N-(1-(4-Chloro-benzyl)-2-{4-[1-(2-chloro-phenyl)-2-di-
ethylamino-ethyl]-piperazin-1-yl}-2-oxo-ethyl)-2-(2-
methyl-2,3-dihydro-1H-isoindol-1-yl)-acetamide,

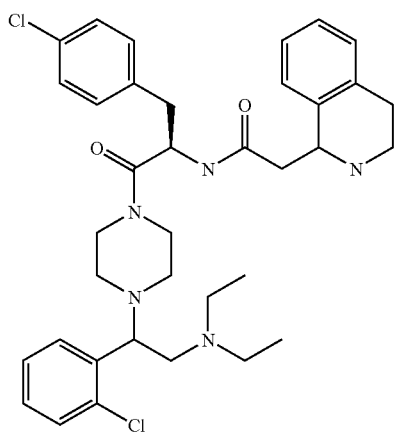

"A" isomer#2, "C" isomer#2
N-(1-(4-Chloro-benzyl)-2-{4-[1-(2-chloro-phenyl)-2-di-
ethylamino-ethyl]-piperazin-1-yl}-2-oxo-ethyl)-2-(1,2,
3,4-tetrahydro-isoquinolin-1-yl)-acetamide,

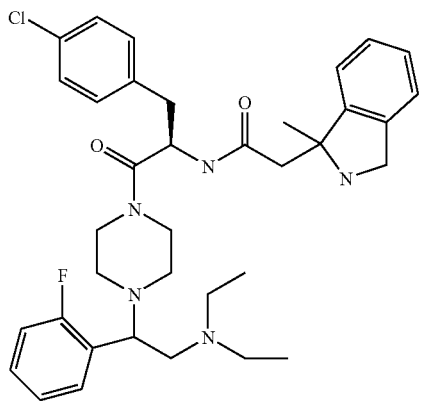

"A" isomer#2, "C" isomer#1
N-(1-(4-Chloro-benzyl)-2-{4-[2-diethylamino-1-(2-
fluoro-phenyl)-ethyl]-piperazin-1-yl}-2-oxo-ethyl)-2-
(1-methyl-2,3-dihydro-1H-isoindol-1-yl)-acetamide,

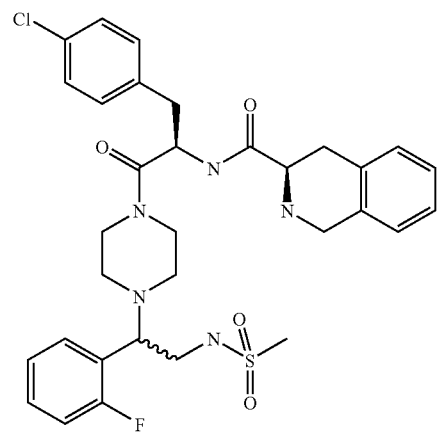

1,2,3,4-Tetrahydro-isoquinoline-3-carboxylic acid (1-(4-
chloro-benzyl)-2-{4-[1-(2-fluoro-phenyl)-2-methane-
sulfonylamino-ethyl]-piperazin-1-yl}-2-oxo-ethyl)-
amide,

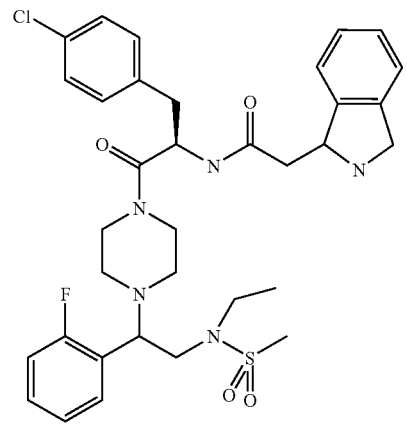

"A" isomer#2, "C" isomer#2
N-(1-(4-Chloro-benzyl)-2-{4-[2-(ethyl-methanesulfony-
lamino)-1-(2-fluoro-phenyl)-ethyl]-piperazin-1-yl}-2-
oxo-ethyl)-2-(2,3-dihydro-1H-isoindol-1-yl)-aceta-
mide,

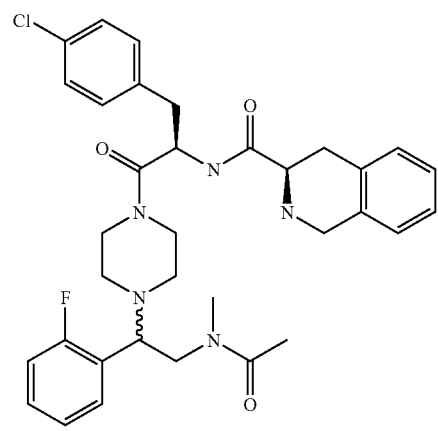

1,2,3,4-Tetrahydro-isoquinoline-3-carboxylic acid [2-{4-
[2-(acetyl-methyl-amino)-1-(2-fluoro-phenyl)-ethyl]-
piperazin-1-yl}-1-(4-chloro-benzyl)-2-oxo-ethyl]-
amide,

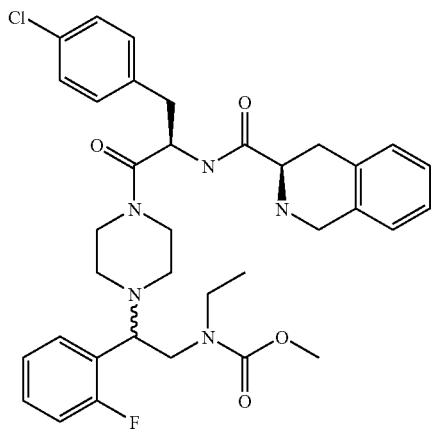

[2-(4-{3-(4-Chloro-phenyl)-2-[(1,2,3,4-tetrahydro-isoquinoline-3-carbonyl)-amino]-propionyl}-piperazin-1-yl)-2-(2-fluoro-phenyl)-ethyl]-ethyl-carbamic acid methyl ester,

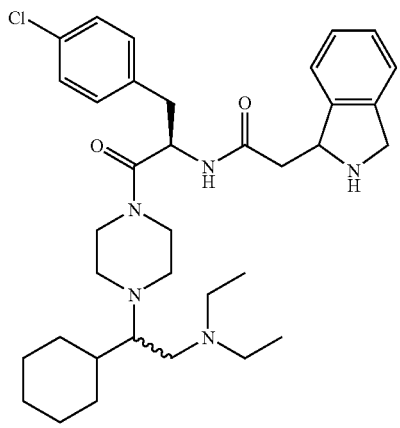

N-{1-(4-chloro-benzyl)-2-[4-(1-cyclohexyl-2-diethylaminoethyl)-piperazin-1-yl]-2-oxo-ethyl}-2-(2,3-dihydro-1H-isoindol-1-yl)-acetamide,

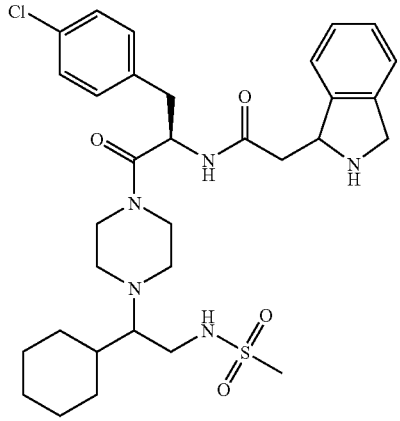

"C" isomer#2
N-{1-(4-chloro-benzyl)-2-[4-(1-cyclohexyl-2-methanesulfonylamino-ethyl)-piperazin-1-yl]-2-oxo-ethyl}-2-(2,3-dihydro-1H-isoindol-1-yl)-acetamide, and

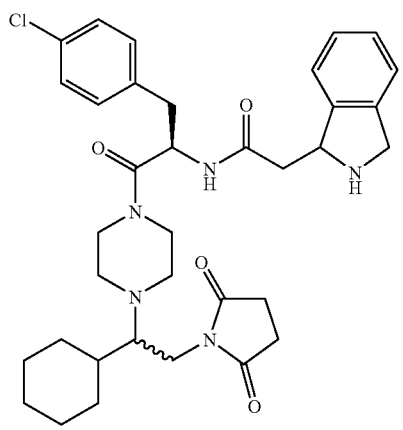

"C" isomer#2
N-(1-(4-chloro-benzyl)2-{4-[1-cyclohexyl-2-(2,5-dioxo-pyrrolidin-yl)-ethyl]-piperazin-1-yl}-2-oxo-ethyl]-2-(2,3-dihydro-1H-isoindol-1-yl)-acetamide, and a pharmaceutically acceptable salt, and stereoisomer thereof.

23. A method of treating obesity in a mammal comprising the administration of a therapeutically effective amount of the compound of formula I as recited in claim 1.

24. A process for preparing a compound of formula I

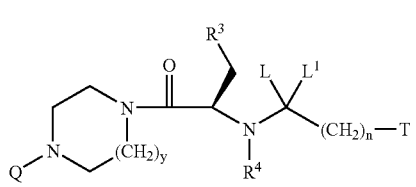

(I)

or a pharmaceutically acceptable salts or stereoisomers thereof, wherein
—CLL'—(CH$_2$)$_n$—T is:

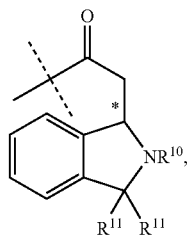

wherein R$^{10}$ is a CBz or Boc protecting group, hydrogen, (C$_1$–C$_8$) alkyl, C$_3$–C$_8$ alkenyl, C(O)C$_1$–C$_8$ alkyl, C$_2$–C$_8$ alkynyl, phenyl, aryl, or heteroaryl;

R$^3$ is: phenyl, aryl or thienyl;

wherein phenyl, aryl and thienyl are optionally substituted with one to three substituents independently selected from the group consisting of:

cyano, perfluoroalkoxy, halo, C$_1$–C$_8$ alkyl, (D)C$_3$–C$_7$ cycloalkyl, C$_1$–C$_4$ alkoxy, C$_1$–C$_4$ haloalkyl;

$R^4$ is hydrogen, $C_1$–$C_8$ alkyl, $C_3$–$C_8$ alkenyl, $C(O)C_1$–$C_8$ alkyl, or (D)phenyl;

Q is: —$C(R^{a1})(R^{a2})(R^{a3})$

Wherein $R^{a1}$ is $C_1$–$C_8$ alkyl, $C_2$–$C_8$ alkenyl, $C_2$–$C_8$ alkynyl, $C_3$–$C_8$alkoxy, (D)$C_3$–$C_7$ cycloalkyl, (D)heterocyclic, (D)phenyl, or aryl, and wherein $C_1$–$C_8$ alkyl, $C_2$–$C_8$ alkenyl, $C_2$–$C_8$ alkynyl, (D)$C_3$–$C_7$ cycloalkyl, heterocyclic, phenyl, and aryl, are each optionally substituted with one to five substituents independently selected from R;

R is:
hydroxy,
halo,
$C_1$–$C_8$ alkyl,
$C_2$–$C_8$ alkenyl,
$C_1$–$C_8$ alkoxy,
$C_1$–$C_4$ haloalkyl,
(D)$C(O)C_1$–$C_4$ alkyl,
(D)$C(O)OC_1$–$C_4$ alkyl,
$(CH_2)_mN(R^8)_2$,
$(CH_2)_mNR^8C(O)C_1$–$C_4$ alkyl,
$(CH_2)_mNR^8SO_2(C_1$–$C_4$ alkyl),
(D)$OC_1$–$C_4$ alkyl,
(D)$SC_1$–$C_4$ alkyl, or
(D)$SO_2N(R^8)_2$;

$R^{a2}$ is
$C_1$–$C_8$ alkyl,
$C_2$–$C_8$ alkenyl,
$C_2$–$C_8$ alkynyl,
(D)$C_3$–$C_7$ cycloalkyl,
phenyl,
aryl,
$(CH_2)_mN(R^8)_2$,
$(CH_2)_mNR^8C(O)C_1$–$C_4$ alkyl,
$(CH_2)_mNR^8C(O)O\ C_1$–$C_4$ alkyl,
$(CH_2)_mNR^8SO_2(C_1$–$C_4$ alkyl),
$(CH_2)_mOC_1$–$C_4$ alkyl,
$(CH_2)_mOC(O)C_1$–$C_4$ alkyl,
$CON(R^8)_2$, wherein for the group or subgroup —$N(R^8)_2$, each $R^8$ may combine with the other to form a 5, 6, or 7-membered saturated or unsaturated, optionally substituted nitrogen containing heterocycle;

$R^{a3}$ is selected from the group consisting of hydrogen, methyl, ethyl and propyl;

each $R^8$ is independently:
hydrogen,
$C_1$–$C_8$ alkyl,
$C_2$–$C_8$ alkenyl,
(D)$C_3$–$C_7$ cycloalkyl,
phenyl, or
aryl $R^{11}$ is independently hydrogen or $(C_1$–$C_8)$alkyl;
D is a bond or $C_1$–$C_4$ alkyl;
y is 1;
m is 1–4;
n is 0–8; and
p is 0–4;
comprising the steps of:

a) reacting a compound having a structural formula 1

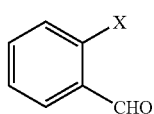
(1)

with $CH_2CH$=$C(O)OR^a$ wherein $R^a$ is hydrogen or $C_1$–$C_8$ alkyl and X is halo, in the presence of a catalyst and a base in a suitable organic solvent to give the compound of formula 2

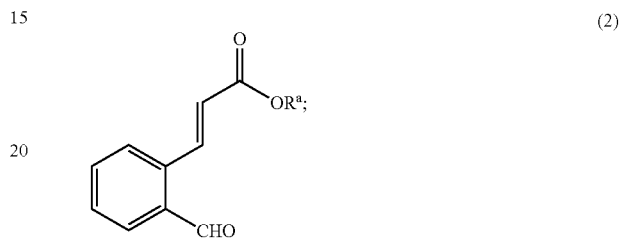
(2)

b) reductively aminating the compound of formula 2 in the presence of amine to give a compound of formula 3

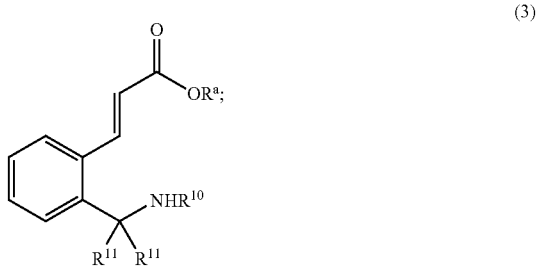
(3)

c) cyclizing the compound of formula 3 by Michael addition to give a compound of formula 4 or stereoisomers thereof

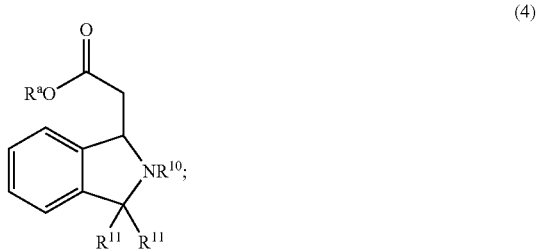
(4)

d) coupling the compound of formula 4 or stereoisomers thereof wherein $R^a$ is H, with a compound of formula 5

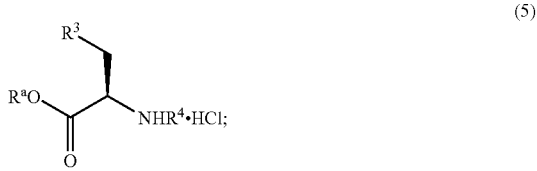
(5)

wherein R$^a$ is C$_1$–C$_8$ alkyl, to give a compound of formula 6

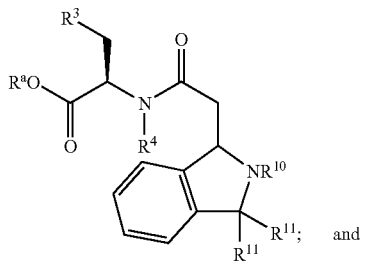
(6)

e) coupling the compound of formula 6 wherein R$^a$ is H, with a compound having a structural formula:

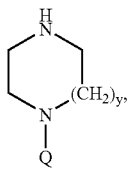

to afford the compound of formula 1.

25. The process of claim 24, wherein CH$_2$CH=C(O)OR$^a$ in Step (a) is methylacrylate.

26. The process of claim 25, wherein the catalyst in Step (a) is selected from the group consisting of: Pd(Ph$_3$P)$_2$Cl$_2$, Pd(Ph$_3$P)$_4$Cl$_2$, Pd(Ph$_3$P)$_4$, Pd(Ph$_3$P)$_2$Cl$_2$/CuI, Pd(OAc)$_2$/Ph$_3$P-Bu$_4$NBr, Pd(Ph$_3$P)$_4$Cl$_2$/H$_2$ and Pd(OAc)$_2$/P(O-tol)$_3$; and wherein the base in Step (a) is N(R)$_3$ wherein R is hydrogen or C$_1$–C$_8$ alkyl.

27. The process of claim 26, wherein the amine in Step (b) is selected from the group consisting of: benzylamine, alpha-methylbenzylamine and BocNH$_2$.

28. The process of claim 27, wherein the Step (b) further comprises reducing an intermediate imine compound in the presence of reducing agent, the reducing agent being selected from the group consisting of: NaCNBH$_3$, Na(OAc)$_3$BH, NaBH$_4$/H+, and a combination of Et$_3$SiH and TFA in CH$_3$CN or CH$_2$Cl$_2$.

29. The process of claim 24, wherein the stereoisomer of compound of formula (7) in Step (c) is a compound of formula 7a:

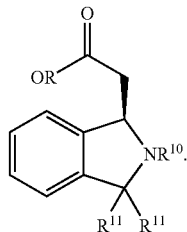
(7a)

30. The process of claim 29, wherein the compound of formula 7a is prepared by asymmetric hydrogenation of a compound having structural formula:

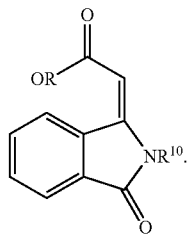

31. The process of claim 24, wherein the Michael addition in Step (c) is carried out under basic workup condition.

32. The process of claim 24, wherein the Step (e) further comprises deprotecting or protecting of the compound of formula (4) at NR$^{10}$.

* * * * *